US012624089B2

(12) United States Patent
Igawa et al.

(10) Patent No.: US 12,624,089 B2
(45) Date of Patent: *May 12, 2026

(54) ANTIGEN-BINDING MOLECULE FOR PROMOTING DISAPPEARANCE OF ANTIGEN VIA FCγRIIB

(71) Applicant: Chugai Seiyaku Kabushiki Kaisha, Tokyo (JP)

(72) Inventors: Tomoyuki Igawa, Shizuoka (JP); Atsuhiko Maeda, Shizuoka (JP); Yuki Iwayanagi, Shizuoka (JP); Kenta Haraya, Shizuoka (JP); Hitoshi Katada, Shizuoka (JP); Shojiro Kadono, Kanagawa (JP); Futa Mimoto, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 875 days.

This patent is subject to a terminal disclaimer.

(21) Appl. No.: 17/854,023

(22) Filed: Jun. 30, 2022

(65) Prior Publication Data

US 2023/0140797 A1 May 4, 2023

Related U.S. Application Data

(62) Division of application No. 14/379,825, filed as application No. PCT/JP2013/054461 on Feb. 22, 2013, now abandoned.

(30) Foreign Application Priority Data

| Feb. 24, 2012 | (WO) | ................. | PCT/JP2012/054624 |
| Aug. 24, 2012 | (JP) | ................................ | 2012-185866 |
| Sep. 28, 2012 | (WO) | ................. | PCT/JP2012/075092 |

(51) Int. Cl.

| *C07K 16/00* | (2006.01) |
| *A61K 39/395* | (2006.01) |
| *C07K 16/28* | (2006.01) |
| *C07K 16/30* | (2006.01) |
| *A61K 39/00* | (2006.01) |
| *C07K 1/00* | (2006.01) |

(52) U.S. Cl.
CPC .......... *C07K 16/00* (2013.01); *C07K 16/2866* (2013.01); *C07K 16/303* (2013.01); *A61K 2039/505* (2013.01); *C07K 2317/41* (2013.01); *C07K 2317/52* (2013.01); *C07K 2317/524* (2013.01); *C07K 2317/526* (2013.01); *C07K 2317/71* (2013.01); *C07K 2317/72* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 4,689,299 | A | 8/1987 | Insel et al. |
| 4,801,687 | A | 1/1989 | Ngo |
| 5,585,089 | A | 12/1996 | Queen et al. |
| 5,827,733 | A | 10/1998 | Lee et al. |
| 5,994,524 | A | 11/1999 | Matsushima et al. |
| 6,024,956 | A | 2/2000 | Matsushima et al. |
| 6,025,158 | A | 2/2000 | Gonzalez et al. |
| 6,074,642 | A | 6/2000 | Wang et al. |
| 6,096,506 | A | 8/2000 | Lee et al. |
| 6,165,745 | A | 12/2000 | Ward et al. |
| 6,245,894 | B1 | 6/2001 | Matsushima et al. |
| 6,458,355 | B1 | 10/2002 | Hsei et al. |
| 6,737,056 | B1 | 5/2004 | Presta |
| 6,821,505 | B2 | 11/2004 | Ward |
| 7,247,302 | B1 | 7/2007 | Rosok et al. |
| 7,261,893 | B2 | 8/2007 | Geertruida et al. |
| 7,282,568 | B2 | 10/2007 | Teeling et al. |
| 7,317,091 | B2 | 1/2008 | Lazar et al. |
| 7,320,789 | B2 | 1/2008 | Aghajanian et al. |
| 7,371,826 | B2 | 5/2008 | Presta |
| 7,632,499 | B2 | 12/2009 | Davies et al. |
| 7,632,924 | B2 | 12/2009 | Cho et al. |
| 7,662,925 | B2 | 2/2010 | Lazar et al. |
| 7,670,600 | B2 | 3/2010 | Dall'Acqua et al. |
| 7,785,791 | B2 | 8/2010 | Presta |

(Continued)

FOREIGN PATENT DOCUMENTS

| AU | 2010206050 | 8/2010 |
| AU | 2011244851 | 11/2011 |

(Continued)

OTHER PUBLICATIONS

Patton et al. Journal of Immunological Methods, 2005, 304;1-2:189-195. (Year: 2005).*
Ito et al. FEBS Lett. 1992, 309(1):85-88. (Year: 1992).*
U.S. Appl. No. 18/052,258, Igawa et al., filed Nov. 3, 2022.
U.S. Appl. No. 18/052,258, filed Nov. 3, 2022, Igawa et al.
Perrakis et al., "AI revolutions in biology," EMBO Rep, Nov. 4, 2021, 22(11):e54046, 6 pages.
Xu, editor, Part III "Medicated Bath for Common Disease—Correct Medicated Bath Can Treat Various Diseases," Chinese Medicated Bath Encyclopedia, Golden Shield Press, Beijing, Oct. 3, 20131, p. 177.

(Continued)

*Primary Examiner* — Chun W Dahle
(74) *Attorney, Agent, or Firm* — Fish & Richardson P.C.

(57) ABSTRACT

The present invention provides antigen-binding molecules containing (i) an antigen-binding domain whose antigen-binding activity varies depending on ion concentration conditions, (ii) an FcγR-binding domain having Fcγ RIIb-selective binding activity, and (iii) an FcRn-binding domain having FcRn-binding activity under an acidic pH range condition, and methods of decreasing plasma antigen concentration as compared to before administering the molecule, which include the step of administering the molecule.

12 Claims, 45 Drawing Sheets

Specification includes a Sequence Listing.

(56) References Cited

U.S. PATENT DOCUMENTS

| | | | |
|---|---|---|---|
| 7,807,159 B2 | 10/2010 | Chin et al. | |
| 7,820,800 B2 | 10/2010 | Rossi et al. | |
| 7,888,486 B2 | 2/2011 | Walsh et al. | |
| 7,951,917 B1 | 5/2011 | Arathoon et al. | |
| 7,960,512 B2 | 6/2011 | Stavenhagen et al. | |
| 8,147,829 B2 | 4/2012 | Hariharan et al. | |
| 8,188,231 B2 | 5/2012 | Lazar et al. | |
| 8,323,962 B2 | 12/2012 | Dall Acqua et al. | |
| 8,329,867 B2 | 12/2012 | Lazar et al. | |
| 8,367,805 B2 | 2/2013 | Chamberlain et al. | |
| 8,415,459 B2 | 4/2013 | Vallie et al. | |
| 8,524,867 B2 | 9/2013 | Bernett et al. | |
| 8,562,991 B2 | 10/2013 | Igawa et al. | |
| 8,568,726 B2 | 10/2013 | Beaumont et al. | |
| 8,592,562 B2 | 11/2013 | Kannan et al. | |
| 8,604,174 B2 | 12/2013 | Babcook et al. | |
| 8,637,641 B2 | 1/2014 | Dahiyat et al. | |
| 8,679,490 B2 | 3/2014 | Dennis et al. | |
| 8,735,545 B2 * | 5/2014 | Lazar | C07K 16/18 |
| | | | 530/387.3 |
| 8,753,629 B2 | 6/2014 | Lazar et al. | |
| 8,802,823 B2 | 8/2014 | Lazar et al. | |
| 8,999,343 B2 | 4/2015 | Han et al. | |
| 9,029,515 B2 | 5/2015 | Pons et al. | |
| 9,051,373 B2 | 6/2015 | Lazar et al. | |
| 9,079,949 B1 | 7/2015 | Andrien, Jr. et al. | |
| 9,107,861 B1 | 8/2015 | Andrien, Jr. et al. | |
| 9,315,577 B2 | 4/2016 | Foltz et al. | |
| 9,605,061 B2 | 3/2017 | Lazar et al. | |
| 9,765,135 B2 | 9/2017 | Ruike | |
| 9,890,218 B2 | 2/2018 | Mimoto et al. | |
| 9,969,800 B2 | 5/2018 | Igawa et al. | |
| 10,000,560 B2 | 6/2018 | Ruike et al. | |
| 10,024,867 B2 | 7/2018 | Igawa | |
| 10,253,100 B2 | 4/2019 | Igawa et al. | |
| 10,472,623 B2 | 11/2019 | Igawa et al. | |
| 10,519,229 B2 | 12/2019 | Igawa et al. | |
| 10,618,965 B2 | 4/2020 | Igawa et al. | |
| 10,738,111 B2 | 8/2020 | Ruike et al. | |
| 10,766,960 B2 | 9/2020 | Igawa et al. | |
| 10,919,953 B2 * | 2/2021 | Katada | A61P 29/00 |
| 11,053,308 B2 | 7/2021 | Kakiuchi et al. | |
| 11,180,548 B2 | 11/2021 | Igawa et al. | |
| 11,267,868 B2 * | 3/2022 | Mimoto | A61P 3/10 |
| 11,359,009 B2 | 6/2022 | Ruike et al. | |
| 11,454,633 B2 | 9/2022 | Ruike et al. | |
| 11,718,678 B2 | 8/2023 | Igawa et al. | |
| 11,780,912 B2 | 10/2023 | Kakiuchi et al. | |
| 11,820,793 B2 * | 11/2023 | Igawa | A61P 37/02 |
| 11,827,699 B2 | 11/2023 | Igawa et al. | |
| 2002/0082396 A1 | 6/2002 | Matsushima et al. | |
| 2003/0077283 A1 | 4/2003 | Ye | |
| 2004/0001822 A1 | 1/2004 | Levanon et al. | |
| 2004/0001839 A1 | 1/2004 | Levanon et al. | |
| 2004/0002450 A1 | 1/2004 | Lazarovits et al. | |
| 2004/0110226 A1 | 6/2004 | Lazar et al. | |
| 2004/0132101 A1 | 7/2004 | Lazar et al. | |
| 2005/0032114 A1 | 2/2005 | Hinton et al. | |
| 2005/0260213 A1 | 11/2005 | Koenig et al. | |
| 2006/0134709 A1 | 6/2006 | Stavenhagen et al. | |
| 2006/0141456 A1 | 6/2006 | Edwards et al. | |
| 2006/0275283 A1 | 12/2006 | van Vlijmen et al. | |
| 2007/0009523 A1 | 1/2007 | Presta et al. | |
| 2007/0148164 A1 | 6/2007 | Farrington et al. | |
| 2007/0190056 A1 | 8/2007 | Kambadur et al. | |
| 2007/0224188 A1 | 9/2007 | Allan et al. | |
| 2007/0231329 A1 | 10/2007 | Lazar et al. | |
| 2007/0237767 A1 | 10/2007 | Lazar et al. | |
| 2007/0248602 A1 | 10/2007 | Lazar et al. | |
| 2007/0253951 A1 | 11/2007 | Ng et al. | |
| 2007/0269371 A1 | 11/2007 | Krummen et al. | |
| 2008/0044417 A1 | 2/2008 | Johnson et al. | |
| 2008/0050370 A1 | 2/2008 | Glaser et al. | |
| 2008/0051563 A1 | 2/2008 | Lazar et al. | |
| 2008/0089892 A1 | 4/2008 | Allan et al. | |
| 2008/0138349 A1 | 6/2008 | Stavenhagen et al. | |
| 2008/0181890 A1 | 7/2008 | Lazar et al. | |
| 2008/0199471 A1 | 8/2008 | Bernett et al. | |
| 2009/0035836 A1 | 2/2009 | Datta et al. | |
| 2009/0041770 A1 | 2/2009 | Chamberlain et al. | |
| 2009/0053211 A9 | 2/2009 | Lazar et al. | |
| 2009/0053240 A1 | 2/2009 | Lazar et al. | |
| 2009/0076251 A1 | 3/2009 | Koenig et al. | |
| 2009/0136485 A1 | 5/2009 | Chu et al. | |
| 2009/0142340 A1 | 6/2009 | Lazar | |
| 2009/0324589 A1 | 12/2009 | Igawa et al. | |
| 2010/0093979 A1 | 4/2010 | Lazar | |
| 2010/0098730 A1 | 4/2010 | Lowman et al. | |
| 2010/0099147 A1 | 4/2010 | Hariharan et al. | |
| 2010/0129365 A1 | 5/2010 | Kim et al. | |
| 2010/0183621 A1 | 7/2010 | Jure-Kunkel et al. | |
| 2010/0184959 A1 | 7/2010 | Guler-Gane et al. | |
| 2010/0216187 A1 | 8/2010 | Lasters et al. | |
| 2010/0249482 A1 | 9/2010 | Chung et al. | |
| 2010/0292443 A1 | 11/2010 | Sabbadini et al. | |
| 2010/0298542 A1 | 11/2010 | Igawa et al. | |
| 2010/0331527 A1 | 12/2010 | Davis et al. | |
| 2011/0021755 A1 | 1/2011 | Lazar et al. | |
| 2011/0059093 A1 | 3/2011 | Bohrmann et al. | |
| 2011/0105724 A1 | 5/2011 | Clegg et al. | |
| 2011/0111406 A1 * | 5/2011 | Igawa | C07K 16/2866 |
| | | | 435/69.6 |
| 2011/0135662 A1 | 6/2011 | Finney et al. | |
| 2011/0223658 A1 | 9/2011 | Beliard et al. | |
| 2011/0229489 A1 | 9/2011 | Pons et al. | |
| 2012/0009188 A1 | 1/2012 | Behrens et al. | |
| 2012/0093818 A1 | 4/2012 | Jackson et al. | |
| 2012/0149876 A1 | 6/2012 | Kreudenstein et al. | |
| 2012/0189639 A1 | 7/2012 | Schebye et al. | |
| 2012/0237498 A1 | 9/2012 | Ahrens et al. | |
| 2012/0244578 A1 | 9/2012 | Kannan et al. | |
| 2012/0301488 A1 | 11/2012 | Zhang et al. | |
| 2012/0303083 A1 | 11/2012 | Agnetti et al. | |
| 2012/0321620 A1 | 12/2012 | Chu et al. | |
| 2013/0011866 A1 | 1/2013 | Igawa et al. | |
| 2013/0085074 A1 | 4/2013 | Walker et al. | |
| 2013/0085265 A1 | 4/2013 | Jackson et al. | |
| 2013/0131319 A1 | 5/2013 | Igawa et al. | |
| 2013/0142788 A1 | 6/2013 | Ashman et al. | |
| 2013/0209489 A1 | 8/2013 | Han et al. | |
| 2013/0247234 A1 | 9/2013 | McWhirter et al. | |
| 2013/0259876 A1 | 10/2013 | Murphy et al. | |
| 2013/0302399 A1 | 11/2013 | Feldhaus et al. | |
| 2013/0303396 A1 | 11/2013 | Igawa et al. | |
| 2013/0336963 A1 | 12/2013 | Igawa et al. | |
| 2014/0044730 A1 | 2/2014 | Yancopoulos et al. | |
| 2014/0082760 A1 | 3/2014 | McWhirter et al. | |
| 2014/0086916 A1 | 3/2014 | Zha | |
| 2014/0093496 A1 | 4/2014 | Mimoto et al. | |
| 2014/0105889 A1 | 4/2014 | Igawa et al. | |
| 2014/0112926 A1 | 4/2014 | Liu | |
| 2014/0127209 A1 | 5/2014 | Grabstein et al. | |
| 2014/0199294 A1 | 7/2014 | Mimoto et al. | |
| 2014/0227292 A1 | 8/2014 | Flanagan et al. | |
| 2014/0234340 A1 | 8/2014 | Igawa et al. | |
| 2014/0255398 A1 | 9/2014 | Igawa et al. | |
| 2014/0271459 A1 | 9/2014 | Dutzar et al. | |
| 2014/0294833 A1 | 10/2014 | Desjarlais et al. | |
| 2014/0335089 A1 | 11/2014 | Igawa et al. | |
| 2014/0356371 A1 | 12/2014 | Swergold et al. | |
| 2014/0363426 A1 | 12/2014 | Moore et al. | |
| 2014/0363428 A1 | 12/2014 | Igawa et al. | |
| 2015/0050269 A1 | 2/2015 | Igawa et al. | |
| 2015/0056182 A1 | 2/2015 | Igawa et al. | |
| 2015/0079088 A1 | 3/2015 | Lowman et al. | |
| 2015/0166636 A1 | 6/2015 | Igawa et al. | |
| 2015/0166654 A1 | 6/2015 | Igawa et al. | |
| 2015/0203577 A1 | 7/2015 | Igawa et al. | |
| 2015/0210763 A1 | 7/2015 | Kuramochi et al. | |
| 2015/0252107 A1 | 9/2015 | Stevis et al. | |
| 2015/0299296 A1 | 10/2015 | Katada et al. | |
| 2015/0299313 A1 | 10/2015 | Igawa et al. | |
| 2015/0344570 A1 | 12/2015 | Igawa et al. | |
| 2015/0353630 A1 | 12/2015 | Igawa et al. | |

(56) References Cited

U.S. PATENT DOCUMENTS

| | | |
|---|---|---|
| 2016/0039912 A1 | 2/2016 | Mimoto et al. |
| 2016/0046693 A1 | 2/2016 | Igawa et al. |
| 2016/0053023 A1 | 2/2016 | Rosenthal et al. |
| 2016/0090425 A1 | 3/2016 | Rosenthal et al. |
| 2016/0200807 A1 | 7/2016 | Ruike et al. |
| 2016/0229908 A1 | 8/2016 | Igawa et al. |
| 2016/0229915 A1 | 8/2016 | Igawa et al. |
| 2016/0244526 A1 | 8/2016 | Igawa et al. |
| 2016/0326237 A1 | 11/2016 | Rosenthal et al. |
| 2017/0022270 A1 | 1/2017 | Igawa et al. |
| 2017/0181987 A1 | 6/2017 | Camilla et al. |
| 2018/0155451 A1 | 6/2018 | Mimoto et al. |
| 2018/0282719 A1 | 10/2018 | Igawa et al. |
| 2019/0112393 A1 | 4/2019 | Igawa et al. |
| 2019/0185557 A1 | 6/2019 | Igawa et al. |
| 2019/0218309 A1 | 7/2019 | Igawa et al. |
| 2019/0233525 A1 | 8/2019 | Igawa et al. |
| 2019/0359704 A1 | 11/2019 | Igawa et al. |
| 2020/0199241 A1 | 6/2020 | Igawa et al. |
| 2021/0079379 A1 | 3/2021 | Igawa et al. |
| 2021/0122812 A1 | 4/2021 | Igawa et al. |
| 2021/0261648 A1 | 8/2021 | Katada et al. |
| 2021/0324099 A1 | 10/2021 | Igawa et al. |
| 2022/0389118 A1 | 12/2022 | Igawa et al. |
| 2022/0411483 A1 | 12/2022 | Mimoto et al. |
| 2023/0140797 A1* | 5/2023 | Igawa .................... C07K 16/00 |
| | | 435/69.6 |
| 2023/0174655 A1 | 6/2023 | Mimoto et al. |
| 2023/0220083 A1 | 7/2023 | Igawa et al. |
| 2023/0257470 A1 | 8/2023 | Igawa et al. |
| 2023/0272099 A1 | 8/2023 | Sakurai et al. |
| 2023/0416371 A1 | 12/2023 | Katada et al. |
| 2024/0043515 A1 | 2/2024 | Katada et al. |
| 2024/0117059 A1 | 4/2024 | Igawa et al. |
| 2024/0279325 A1 | 8/2024 | Igawa et al. |

FOREIGN PATENT DOCUMENTS

| | | |
|---|---|---|
| AU | 2012222252 | 10/2013 |
| AU | 2014250434 | 10/2015 |
| AU | 2015227424 | 10/2015 |
| CA | 2 721 052 | 10/2009 |
| CA | 2 794 860 | 10/2011 |
| CA | 2 815 266 | 5/2012 |
| CA | 2 827 923 | 8/2012 |
| CA | 2 831 770 | 10/2012 |
| CA | 2 908 350 | 10/2014 |
| CN | 1156460 | 8/1997 |
| CN | 1291198 | 4/2001 |
| CN | 1763097 | 4/2006 |
| CN | 1867583 A | 11/2006 |
| CN | 101001873 | 7/2007 |
| CN | 101014619 | 8/2007 |
| CN | 101098890 | 1/2008 |
| CN | 101124245 A | 2/2008 |
| CN | 101230102 | 7/2008 |
| CN | 101277976 | 10/2008 |
| CN | 101282992 | 10/2008 |
| CN | 100455598 | 1/2009 |
| CN | 101479381 | 7/2009 |
| CN | 101511871 | 8/2009 |
| CN | 101932593 | 12/2010 |
| CN | 102056946 | 5/2011 |
| CN | 102149729 | 8/2011 |
| CN | 102325793 | 1/2012 |
| CN | 102918057 | 2/2013 |
| CN | 102993304 | 3/2013 |
| CN | 103097415 | 5/2013 |
| CN | 103221426 | 7/2013 |
| CN | 103492565 | 1/2014 |
| CN | 103827300 | 5/2014 |
| CN | 103975060 | 8/2014 |
| CN | 102633880 | 2/2015 |
| CN | 107108726 | 8/2017 |

| | | |
|---|---|---|
| CO | 07124506 | 11/2007 |
| CO | 11080753 | 6/2011 |
| CO | 13047993 | 3/2013 |
| CO | 15075851 | 4/2015 |
| EA | 004317 | 2/2004 |
| EA | 2008/01027 | 10/2008 |
| EP | 0 091 539 A | 10/1983 |
| EP | 1 509 770 A | 3/2005 |
| EP | 0 770 628 B | 9/2006 |
| EP | 1 787 998 A | 5/2007 |
| EP | 1 992 692 A | 11/2008 |
| EP | 2 006 381 A | 12/2008 |
| EP | 2 189 526 A | 5/2010 |
| EP | 2 196 541 A | 6/2010 |
| EP | 2 202 245 A | 6/2010 |
| EP | 2 206 775 A | 7/2010 |
| EP | 2 275 443 A | 1/2011 |
| EP | 2 314 618 A | 4/2011 |
| EP | 2 366 713 A | 9/2011 |
| EP | 2 368 911 A | 9/2011 |
| EP | 2 409 990 A | 1/2012 |
| EP | 2 431 393 A | 3/2012 |
| EP | 2 471 813 A | 7/2012 |
| EP | 2 543 730 A | 1/2013 |
| EP | 2 552 955 A | 2/2013 |
| EP | 2 647 706 A | 10/2013 |
| EP | 2 679 681 A | 1/2014 |
| EP | 2 698 431 A | 2/2014 |
| EP | 2 728 002 A | 5/2014 |
| EP | 2 760 890 A | 8/2014 |
| EP | 2 762 166 A | 8/2014 |
| EP | 2 762 493 A | 8/2014 |
| EP | 2 762 564 A | 8/2014 |
| EP | 2 765 192 A | 8/2014 |
| EP | 2 818 183 A | 12/2014 |
| EP | 2 853 898 A | 4/2015 |
| EP | 2 889 377 A | 7/2015 |
| EP | 2 940 043 A | 11/2015 |
| EP | 2 940 135 A | 11/2015 |
| EP | 3 042 912 A | 7/2016 |
| EP | 3 156 072 A | 4/2017 |
| EP | 3 240 804 A | 11/2017 |
| JP | H01-144991 | 6/1989 |
| JP | H02-501112 | 4/1990 |
| JP | H02-163085 | 6/1990 |
| JP | H08-217799 | 8/1996 |
| JP | 2638680 | 8/1997 |
| JP | 2003-512019 | 4/2003 |
| JP | 2005-510212 | 4/2005 |
| JP | 2006-512407 | 4/2006 |
| JP | 2006-517525 | 7/2006 |
| JP | 2006-519583 | 8/2006 |
| JP | 2006-524039 | 10/2006 |
| JP | 3865418 | 1/2007 |
| JP | 2007-252368 | 10/2007 |
| JP | 2007-532139 | 11/2007 |
| JP | 2008-503720 | 2/2008 |
| JP | 2008-505174 | 2/2008 |
| JP | 2008-510466 | 4/2008 |
| JP | 2008-511292 | 4/2008 |
| JP | 2008-519860 | 6/2008 |
| JP | 2009-511067 | 3/2009 |
| JP | 2009-541352 | 11/2009 |
| JP | 2010-500020 | 1/2010 |
| JP | 2010-079667 | 3/2010 |
| JP | 2010-081866 | 4/2010 |
| JP | 2010-514460 | 5/2010 |
| JP | 2010-250830 | 11/2010 |
| JP | 2011-504096 | 2/2011 |
| JP | 2011-507963 | 3/2011 |
| JP | 2011-184418 | 9/2011 |
| JP | 2012-505833 | 3/2012 |
| JP | 2012-512641 | 6/2012 |
| JP | 4961501 | 6/2012 |
| JP | 5048866 | 10/2012 |
| JP | 2013-518606 | 5/2013 |
| JP | 2013-521772 | 6/2013 |
| JP | 2013-528354 | 7/2013 |
| JP | 2013-531486 | 8/2013 |

(56) References Cited

FOREIGN PATENT DOCUMENTS

| | | |
|---|---|---|
| JP | 2013-537425 | 10/2013 |
| JP | 2014-055145 | 3/2014 |
| JP | 2014-514345 | 6/2014 |
| JP | 2014-528906 | 10/2014 |
| JP | 2016-026190 | 2/2016 |
| JP | 2016-505240 | 2/2016 |
| JP | 2017-535244 | 11/2017 |
| JP | 2018-517674 | 7/2018 |
| JP | 6433297 | 12/2018 |
| JP | 2019-523295 | 8/2019 |
| KR | 10-0261941 | 7/2000 |
| KR | 10-2011-0004435 | 1/2011 |
| KR | 10-2011-0103431 | 9/2011 |
| KR | 10-2012-0035192 | 4/2012 |
| KR | 10-2014-0005864 | 1/2014 |
| KR | 10-2014-0069332 | 6/2014 |
| RU | 2236222 | 9/2004 |
| RU | 2004/128259 | 8/2005 |
| RU | 2005/112742 | 1/2006 |
| RU | 2318829 | 3/2008 |
| RU | 2006/142852 | 6/2008 |
| RU | 2337107 | 10/2008 |
| RU | 2007/121679 | 12/2008 |
| RU | 2360925 | 7/2009 |
| RU | 2367667 | 9/2009 |
| RU | 2390527 | 5/2010 |
| RU | 2398777 | 9/2010 |
| RU | 2009/112723 | 10/2010 |
| RU | 2422460 | 6/2011 |
| RU | 2434882 | 11/2011 |
| RU | 2010/150931 | 6/2012 |
| SG | 183867 | 10/2012 |
| SG | 192945 | 9/2013 |
| TW | 416960 | 1/2001 |
| TW | 2010/00127 | 1/2010 |
| TW | 2011/16625 | 5/2011 |
| TW | 2012/02419 | 1/2012 |
| TW | 2016/43190 | 12/2016 |
| TW | 2017/12032 | 4/2017 |
| TW | I605057 | 11/2017 |
| TW | 2018/08331 | 3/2018 |
| TW | 2018/08992 | 3/2018 |
| TW | 2018/19409 | 6/2018 |
| TW | I656133 | 4/2019 |
| TW | 2020/39553 | 11/2020 |
| WO | WO 83/03678 | 10/1983 |
| WO | WO 88/04692 | 6/1988 |
| WO | WO 91/12023 | 8/1991 |
| WO | WO 91/13631 | 9/1991 |
| WO | WO 92/07084 | 4/1992 |
| WO | WO 94/21681 | 9/1994 |
| WO | WO 95/02187 | 1/1995 |
| WO | WO 95/14710 | 6/1995 |
| WO | WO 95/29697 | 11/1995 |
| WO | WO 96/02576 | 2/1996 |
| WO | WO 97/34631 | 9/1997 |
| WO | WO 98/05787 | 2/1998 |
| WO | WO 99/40117 | 8/1999 |
| WO | WO 99/51642 | 10/1999 |
| WO | WO 99/58572 | 11/1999 |
| WO | WO 00/15214 | 3/2000 |
| WO | WO 00/42072 | 7/2000 |
| WO | WO 01/70968 | 9/2001 |
| WO | WO 02/09641 | 2/2002 |
| WO | WO 02/060919 | 8/2002 |
| WO | WO 03/027248 | 4/2003 |
| WO | WO 03/057881 | 7/2003 |
| WO | WO 03/070760 | 8/2003 |
| WO | WO 03/074679 | 9/2003 |
| WO | WO 03/105757 | 12/2003 |
| WO | WO 03/107009 | 12/2003 |
| WO | WO 2004/007553 | 1/2004 |
| WO | WO 2004/024890 | 3/2004 |
| WO | WO 2004/029207 | 4/2004 |
| WO | WO 2004/035752 | 4/2004 |
| WO | WO 2004/037861 | 5/2004 |
| WO | WO 2004/039826 | 5/2004 |
| WO | WO 2004/058797 | 7/2004 |
| WO | WO 2004/063351 | 7/2004 |
| WO | WO 2004/092219 | 10/2004 |
| WO | WO 2004/099249 | 11/2004 |
| WO | WO 2004/108157 | 12/2004 |
| WO | WO 2005/023193 | 3/2005 |
| WO | WO 2005/037867 | 4/2005 |
| WO | WO 2005/047307 | 5/2005 |
| WO | WO 2005/047327 | 5/2005 |
| WO | WO 2005/056606 | 6/2005 |
| WO | WO 2005/056759 | 6/2005 |
| WO | WO 2005/059106 | 6/2005 |
| WO | WO 2005/066204 | 7/2005 |
| WO | WO 2005/070963 | 8/2005 |
| WO | WO 2005/077981 | 8/2005 |
| WO | WO 2005/092925 | 10/2005 |
| WO | WO 2005/094446 | 10/2005 |
| WO | WO 2005/115452 | 12/2005 |
| WO | WO 2005/123780 | 12/2005 |
| WO | WO 2006/004663 | 1/2006 |
| WO | WO 2006/015371 | 2/2006 |
| WO | WO 2006/016644 | 2/2006 |
| WO | WO 2006/019447 | 2/2006 |
| WO | WO 2006/020114 | 2/2006 |
| WO | WO 2006/023403 | 3/2006 |
| WO | WO 2006/023420 | 3/2006 |
| WO | WO 2006/031370 | 3/2006 |
| WO | WO 2006/036291 | 4/2006 |
| WO | WO 2006/047350 | 5/2006 |
| WO | WO 2006/050166 | 5/2006 |
| WO | WO 2006/053301 | 5/2006 |
| WO | WO 2006/071877 | 7/2006 |
| WO | WO 2006/076594 | 7/2006 |
| WO | WO 2006/083182 | 8/2006 |
| WO | WO 2006/083183 | 8/2006 |
| WO | WO 2006/085938 | 8/2006 |
| WO | WO 2006/085967 | 8/2006 |
| WO | WO 2006/088478 | 8/2006 |
| WO | WO 2006/088494 | 8/2006 |
| WO | WO 2006/102095 | 9/2006 |
| WO | WO 2006/105338 | 10/2006 |
| WO | WO 2006/106905 | 10/2006 |
| WO | WO 2006/113643 | 10/2006 |
| WO | WO 2006/116260 | 11/2006 |
| WO | WO 2006/116269 | 11/2006 |
| WO | WO 2006/130834 | 12/2006 |
| WO | WO 2006/133486 | 12/2006 |
| WO | WO 2007/001422 | 1/2007 |
| WO | WO 2007/008943 | 1/2007 |
| WO | WO 2007/012614 | 2/2007 |
| WO | WO 2007/021841 | 2/2007 |
| WO | WO 2007/022520 | 2/2007 |
| WO | WO 2007/024249 | 3/2007 |
| WO | WO 2007/024535 | 3/2007 |
| WO | WO 2007/041635 | 4/2007 |
| WO | WO 2007/044411 | 4/2007 |
| WO | WO 2007/044616 | 4/2007 |
| WO | WO 2007/047112 | 4/2007 |
| WO | WO 2007/047578 | 4/2007 |
| WO | WO 2007/084253 | 7/2007 |
| WO | WO 2007/092772 | 8/2007 |
| WO | WO 2007/114319 | 10/2007 |
| WO | WO 2007/114325 | 10/2007 |
| WO | WO 2007/150015 | 12/2007 |
| WO | WO 2007/150016 | 12/2007 |
| WO | WO 2008/002933 | 1/2008 |
| WO | WO 2008/017963 | 2/2008 |
| WO | WO 2008/022152 | 2/2008 |
| WO | WO 2008/030706 | 3/2008 |
| WO | WO 2008/031056 | 3/2008 |
| WO | WO 2008/036688 | 3/2008 |
| WO | WO 2008/091798 | 7/2008 |
| WO | WO 2008/091954 | 7/2008 |
| WO | WO 2008/092117 | 7/2008 |
| WO | WO 2008/098115 | 8/2008 |
| WO | WO 2008/121160 | 10/2008 |
| WO | WO 2008/130969 | 10/2008 |

(56) References Cited

FOREIGN PATENT DOCUMENTS

| | | |
|---|---|---|
| WO | WO 2008/143954 | 11/2008 |
| WO | WO 2008/150494 | 12/2008 |
| WO | WO 2009/000098 | 12/2008 |
| WO | WO 2009/000099 | 12/2008 |
| WO | WO 2009/008529 | 1/2009 |
| WO | WO 2009/026117 | 2/2009 |
| WO | WO 2009/032145 | 3/2009 |
| WO | WO 2009/032782 | 3/2009 |
| WO | WO 2009/041062 | 4/2009 |
| WO | WO 2009/041643 | 4/2009 |
| WO | WO 2009/053358 | 4/2009 |
| WO | WO 2009/058346 | 5/2009 |
| WO | WO 2009/058492 | 5/2009 |
| WO | WO 2009/062083 | 5/2009 |
| WO | WO 2009/086320 | 7/2009 |
| WO | WO 2009/089846 | 7/2009 |
| WO | WO 2009/095235 | 8/2009 |
| WO | WO 2009/125825 | 10/2009 |
| WO | WO 2009/131702 | 10/2009 |
| WO | WO 2009/137880 | 11/2009 |
| WO | WO 2009/139822 | 11/2009 |
| WO | WO 2009/155513 | 12/2009 |
| WO | WO 2010/015608 | 2/2010 |
| WO | WO 2010/033736 | 3/2010 |
| WO | WO 2010/035769 | 4/2010 |
| WO | WO 2010/045193 | 4/2010 |
| WO | WO 2010/058860 | 5/2010 |
| WO | WO 2010/070094 | 6/2010 |
| WO | WO 2010/077854 | 7/2010 |
| WO | WO 2010/081173 | 7/2010 |
| WO | WO 2010/085682 | 7/2010 |
| WO | WO 2010/106180 | 9/2010 |
| WO | WO 2010/106812 | 9/2010 |
| WO | WO 2010/107109 | 9/2010 |
| WO | WO 2010/107110 | 9/2010 |
| WO | WO 2010/136831 | 12/2010 |
| WO | WO 2010/151338 | 12/2010 |
| WO | WO 2010/151792 | 12/2010 |
| WO | WO 2011/008517 | 1/2011 |
| WO | WO 2011/021009 | 2/2011 |
| WO | WO 2011/043643 | 4/2011 |
| WO | WO 2011/044368 | 4/2011 |
| WO | WO 2011/091078 | 7/2011 |
| WO | WO 2011/100271 | 8/2011 |
| WO | WO 2011/107989 | 9/2011 |
| WO | WO 2011/108714 | 9/2011 |
| WO | WO 2011/111007 | 9/2011 |
| WO | WO 2011/120134 A1 | 10/2011 |
| WO | WO 2011/122011 | 10/2011 |
| WO | WO 2011/150008 | 12/2011 |
| WO | WO 2011/151432 | 12/2011 |
| WO | WO 2012/016227 | 2/2012 |
| WO | WO 2012/024242 | 2/2012 |
| WO | WO 2012/033953 | 3/2012 |
| WO | WO 2012/044831 | 4/2012 |
| WO | WO 2012/058768 | 5/2012 |
| WO | WO 2012/073992 | 6/2012 |
| WO | WO 2012/093704 | 7/2012 |
| WO | WO 2012/115241 | 8/2012 |
| WO | WO 2012/125850 | 9/2012 |
| WO | WO 2012/132067 | 10/2012 |
| WO | WO 2012/133782 | 10/2012 |
| WO | WO 2012/151199 | 11/2012 |
| WO | WO 2012/151481 | 11/2012 |
| WO | WO 2013/002362 | 1/2013 |
| WO | WO 2013/004842 | 1/2013 |
| WO | WO 2013/012733 | 1/2013 |
| WO | WO 2013/046704 | 4/2013 |
| WO | WO 2013/046722 | 4/2013 |
| WO | WO 2013/047729 | 4/2013 |
| WO | WO 2013/047748 | 4/2013 |
| WO | WO 2013/047752 | 4/2013 |
| WO | WO 2013/063702 | 5/2013 |
| WO | WO 2013/081143 | 6/2013 |
| WO | WO 2013/125667 | 8/2013 |
| WO | WO 2013/138680 | 9/2013 |
| WO | WO 2013/138681 | 9/2013 |
| WO | WO 2013/152001 | 10/2013 |
| WO | WO 2013/166099 | 11/2013 |
| WO | WO 2013/180200 | 12/2013 |
| WO | WO 2013/180201 | 12/2013 |
| WO | WO 2013/186719 | 12/2013 |
| WO | WO 2013/192240 | 12/2013 |
| WO | WO 2014/006217 | 1/2014 |
| WO | WO 2014/028354 | 2/2014 |
| WO | WO 2014/030728 | 2/2014 |
| WO | WO 2014/030750 | 2/2014 |
| WO | WO 2014/043344 | 3/2014 |
| WO | WO 2014/066744 | 5/2014 |
| WO | WO 2014/071206 | 5/2014 |
| WO | WO 2014/074532 | 5/2014 |
| WO | WO 2014/100689 | 6/2014 |
| WO | WO 2014/104165 | 7/2014 |
| WO | WO 2014/114651 | 7/2014 |
| WO | WO 2014/140366 | 9/2014 |
| WO | WO 2014/144080 | 9/2014 |
| WO | WO 2014/144577 | 9/2014 |
| WO | WO 2014/144903 | 9/2014 |
| WO | WO 2014/145159 | 9/2014 |
| WO | WO 2014/145806 | 9/2014 |
| WO | WO 2014/150983 | 9/2014 |
| WO | WO 2014/163101 | 10/2014 |
| WO | WO 2014/164959 | 10/2014 |
| WO | WO 2014/182676 | 11/2014 |
| WO | WO 2014/184384 | 11/2014 |
| WO | WO 2014/186599 | 11/2014 |
| WO | WO 2014/190441 | 12/2014 |
| WO | WO 2015/022658 | 2/2015 |
| WO | WO 2015/034000 | 3/2015 |
| WO | WO 2015/042250 | 3/2015 |
| WO | WO 2015/077491 | 5/2015 |
| WO | WO 2015/083764 | 6/2015 |
| WO | WO 2015/111008 | 7/2015 |
| WO | WO 2015/134894 | 9/2015 |
| WO | WO 2015/162590 | 10/2015 |
| WO | WO 2015/190538 | 12/2015 |
| WO | WO 2016/000813 | 1/2016 |
| WO | WO 2016/073853 | 5/2016 |
| WO | WO 2016/073879 | 5/2016 |
| WO | WO 2016/073906 | 5/2016 |
| WO | WO 2016/092439 | 6/2016 |
| WO | WO 2016/098356 | 6/2016 |
| WO | WO 2016/098357 | 6/2016 |
| WO | WO 2016/125495 | 8/2016 |
| WO | WO 2016/164358 | 10/2016 |
| WO | WO 2016/168613 | 10/2016 |
| WO | WO 2016/170176 | 10/2016 |
| WO | WO 2016/194992 | 12/2016 |
| WO | WO 2017/046994 | 3/2017 |
| WO | WO 2017/049011 | 3/2017 |
| WO | WO 2017/091719 | 6/2017 |
| WO | WO 2017/104783 | 6/2017 |
| WO | WO 2017/110981 | 6/2017 |
| WO | WO 2017/120523 | 7/2017 |
| WO | WO 2017/217525 | 12/2017 |
| WO | WO 2017/218592 | 12/2017 |
| WO | WO 2018/025982 | 2/2018 |
| WO | WO 2018/169993 | 9/2018 |
| WO | WO 2019/098212 | 5/2019 |
| WO | WO 2019/198807 | 10/2019 |
| WO | WO 2020/032230 | 2/2020 |
| WO | WO 2020/209318 | 10/2020 |
| WO | WO 2020/230834 | 11/2020 |
| WO | WO 2021/075479 | 4/2021 |
| WO | WO 2021/162020 | 8/2021 |
| WO | WO 2022/044248 | 3/2022 |
| WO | WO 2022/045276 A1 | 3/2022 |
| WO | WO 2022/220275 A1 | 10/2022 |

OTHER PUBLICATIONS

Katagiri et al., "Effects of SA237, a humanized anti-interleukin-6 receptor monoclonal antibody, on pre- and postnatal development in

(56) References Cited

OTHER PUBLICATIONS cynomolgus monkey," Birth Defects Res, Jul. 3, 2017, 109(11):843-856.

U.S. Appl. No. 17/798,686, Sakurai et al., filed Aug. 10, 2011.

U.S. Appl. No. 17/798,686, filed Aug. 10, 2022, Sakurai et al.

U.S. Appl. No. 18/298,743, Igawa et al., filed Apr. 11, 2023.

U.S. Appl. No. 18/298,743, filed Apr. 11, 2023, Igawa et al.

Yu et al., "How to select IgG subclasses in developing anti-tumor therapeutic antibodies," J Hematol Oncol, May 5, 2020, 13(1):45, 10 pages.

U.S. Appl. No. 18/286,471, Koga, filed Oct. 11, 2023.

U.S. Appl. No. 18/286,471, filed Oct. 11, 2023, Koga.

Li et al., "Characterization of a humanized anti-CD3 antibody containing mutated constant region," Chinese Journal of Microbiology and Immunology, Aug. 23, 2003, (8):584-587 (with English abstract).

Morris et al., "Signaling through the Inhibitory Fc Receptor FcγRIIB Induces CD8+ T Cell Apoptosis to Limit T Cell Immunity," Immunity, Jan. 14, 2020, 52(1):136-150.

U.S. Appl. No. 14/347,034, filed Mar. 25, 2014, Igawa et al.

U.S. Appl. No. 14/347,187, filed Mar. 25, 2014, Igawa et al.

U.S. Appl. No. 14/347,321, filed Mar. 26, 2014, Igawa et al.

U.S. Appl. No. 14/361,013, filed May 28, 2014, Igawa et al.

U.S. Appl. No. 14/404,051, filed Nov. 26, 2014, Igawa et al.

U.S. Appl. No. 14/423,269, filed Feb. 23, 2015, Katada et al.

U.S. Appl. No. 15/210,360, filed Jul. 14, 2016, Igawa et al.

U.S. Appl. No. 15/210,353, filed Jul. 14, 2016, Igawa et al.

U.S. Appl. No. 15/495,026, filed Apr. 24, 2017, Igawa et al.

U.S. Appl. No. 15/860,163, filed Jan. 2, 2018, Mimoto et al.

U.S. Appl. No. 15/952,945, filed Apr. 13, 2018, Igawa et al.

U.S. Appl. No. 15/963,449, filed Apr. 26, 2018, Ruike et al.

U.S. Appl. No. 15/963,455, filed Apr. 26, 2018, Ruike et al.

U.S. Appl. No. 15/976,288, filed May 10, 2018, Igawa et al.

U.S. Appl. No. 15/977,757, filed May 11, 2018, Igawa et al.

U.S. Appl. No. 16/028,140, filed Jul. 5, 2018, Igawa et al.

U.S. Appl. No. 16/065,192, filed Jun. 22, 2018, Ruike et al.

U.S. Appl. No. 16/108,897, filed Aug. 22, 2018, Igawa et al.

U.S. Appl. No. 16/264,735, filed Feb. 1, 2019, Igawa et al.

U.S. Appl. No. 16/323,142, filed Feb. 4, 2019, Kakiuchi et al.

U.S. Appl. No. 16/697,310, filed Nov. 27, 2019, Igawa et al.

U.S. Appl. No. 16/763,134, filed May 11, 2020, Feng et al.

U.S. Appl. No. 16/889,066, filed Jun. 1, 2020, Ruike et al.

U.S. Appl. No. 17/028,210, filed Sep. 22, 2020, Katada et al.

U.S. Appl. No. 17/046,395, filed Oct. 9, 2020, Fukuzawa et al.

U.S. Appl. No. 17/144,342, filed Jan. 8, 2021, Igawa et al.

U.S. Appl. No. 61/313,102, filed Mar. 11, 2010, Pons.

"Blog entry," Thunder's Place, Jun. 1, 2014, retrieved from the Internet on May 23, 2018: https://www.thundersplace.org/male-supplements/the-chemical-pe thread-7.html92.

"Mouse GDF-8/Myostatin Propeptide Antibody," R&D Catalogue AF 1539, Feb. 6, 2018, XP055478493, retrieved from the Internet on May 25, 2018: https://resources.rndsystems.com/pdfs/datasheets/af1539.pdf.

"Polyclonal human pro-Myostatin (aa 79-92) antibody," Immun Diagnostik Antibodies catalogue, Jun. 30, 2016, retrieved from the Internet on May 24, 2018: https://www.immundiagnostik.com/fileadmin/pdf/AK3004.pdf.

"Rabbit Antibody to Human pro-Myostatin (amino acids 79-92)," Meridian Life Science Inc., Nov. 13, 2015, XP055478289, retrieved from the Internet on May 24, 2018: https://meridianlifescience.com/biospecs/K24340R.pdf.

Abe et al., "Effect of $\beta_2$-microglobulin adsorption column on dialysis-related amyloidosis," Kidney Int, Oct. 2003, 64(4):1522-1528. doi: 10.1046/j.1523-1755.2003.00235.x.

Akbarzadeh-Sharbaf et al., "In silico design, construction and cloning of Trastuzumab humanized monoclonal antibody: A possible biosimilar for Herceptin," Adv Biomed Res, Jan.-Mar. 2012, 1(1):1-6. doi: 10.4103/ 2277-9175. 98122. Epub Jul. 6, 2012.

"Alexa Fluor® 488 anti-ß-Amyloid, 1-16 Antibody 6E10," Catalog 803013, Biolegend, Sep. 10, 2018, 3 pages, <https://www.biolegend.com/en-us/global-elements/pdf-popup/alexa-fluor-488-antibeta-amyloid--1-16-antibody-10833?filename=Alexa%20Fluorreg%20488%20anti-beta-Amyloid%201-16%20Antibody.pdf&pdfgen=true>.

Alignment of constant region sequences from WO 2009/125825 (SEQ IDs 28-32), 1 page (document submitted in EPO opposition proceedings and posted by EPO on Feb. 2, 2018).

Alignment of the amino acid sequences of the Fc regions of antibodies exemplified in EP 2 275 443, 1 page (document submitted in EPO opposition proceedings and posted by EPO on Feb. 2, 2018).

Alignment of variable heavy and light chain amino acid sequences from WO 2009/125825, 2 pages (document submitted in EPO opposition proceedings and posted by EPO on Feb. 2, 2018).

Alignment sequences 1047 and 30, Jan. 26, 2021, 1 page (document cited in the office action dated Feb. 2, 2021 for EP 15869566.8).

Alignment sequences 472 and 24, Jan. 26, 2021, 1 page (document cited in the office action dated Feb. 2, 2021 for EP 15869566.8).

Alley et al., "Antibody-drug conjugates: targeted drug delivery for cancer," Curr Opin Chem Biol, Aug. 2010, 14(4):529-537. doi: 10.1016/j.cbpa.2010.06.170. Epub Jul. 17, 2010.

Amigorena et al., "Cytoplasmic domain heterogeneity and functions of IgG Fc receptors in B lymphocytes," Science, Jun. 26, 1992, 256(5065):1808-1812.

Amigorena et al., "FcγRII expression in resting and activated B lymphocytes," Eur J Immunol, Aug. 1989, 19(8):1379-1385.

"Antibodies," downloaded from the Internet on Jul. 11, 2018, www.bioinf.org.uk: Dr. Andrew C.R. Martin's Group, 9 pages.

Annotated amino acid sequence of the variable heavy (VH) and variable light (VL) domains of the monoclonal antibodies bevacizumab/Avastin, adalimumab/Humira, omalizumab/Xolair, and rituximab/Mabthera, Jul. 2019, 10 pages (document submitted by Opponent 1 to the EPO with the written submission to attend oral proceedings on Sep. 6, 2019 in EP 11714860.1).

"Anti-Glial Fibrillary Acidic Protein (GFAP) Mouse mAb (G-A-5)," IF03L, Millipore Sigma, Aug. 27, 2007, 3 pages, <https://www.emdmillipore.com/US/en/product/Anti-Glial-Fibrillary-Acidic-Protein-GFAP-Mouse-mAb-G-A-5,EMD_BIOIF03L#anchor_PDS>.

"Anti-Huntingtin antibody [EPR5526] ab109115," Abcam, 11 pages, retrieved from the Internet on Apr. 13, 2020, <https://www.abcam.com/huntingtin-antibody-epr5526-ab109115.pdf>.

Araujo et al., "Increased rheumatoid factor interference observed during immunogenicity assessment of an Fc-engineered therapeutic antibody," J Pharm Biomed Anal, Jul. 15, 2011, 55(5):1041-1049. doi: 10.1016/j.jpba.2011.03.008. Epub Mar. 11, 2011.

Arici, "Local Cytokines in Endometrial Tissue: The Role of Interleukin-8 in the Pathogenesis of Endometriosis," Ann NY Acad Sci, Mar. 2002, 955:101-109, discussion 118:396-406.

Arlaud et al., "A Study on the Structure and Interactions of the C1 Sub-Components C1r and C1s in the Fluid Phase," Biochim Biophys Acta, Nov. 6, 1980, 616(1):105-115.

Armour et al., "Differential binding to human FcγRIIa and FcγRIIb receptors by human IgG wildtype and mutant antibodies," Mol Immunol, Dec. 2003, 40(9):585-593.

Arnoux et al., "Metformin reverses early cortical network dysfunction and behavior changes in Huntington's disease," Elife, Sep. 4, 2018, 7:e38744, 32 pages. doi: 10.7554/eLife.38744.

Ascierto et al., "Clinical Experiences With Anti-CD137 and Anti-PD1 Therapeutic Antibodies," Semin Oncol, Oct. 2010, 37(5):508-516. doi: 10.1053/j.seminoncol.2010.09.008.

Atherton et al., "Acid-base balance: maintenance of plasma pH," Anaesthesia & Intensive Care Medicine, 2009, 10(11):557-561 (abstract only).

Baeuerle et al., "BiTE: Teaching antibodies to engage T-cells for cancer therapy," Curr Opin Mol Ther, Feb. 2009, 11(1):22-30.

Bayry et al., "Immuno affinity purification of foot and mouth disease virus type specific antibodies using recombinant protein adsorbed to polystyrene wells," J Virol Methods, Aug. 1999, 81(1-2):21-30.

Becker et al., "Prevention of postoperative abdominal adhesions by a sodium hyaluronate-based bioresorbable membrane: a prospective, randomized, double-blind multicenter study," J Am Coll Surg, Oct. 1996, 183(4):297-306.

(56) References Cited

OTHER PUBLICATIONS

Beringhelli et al., "pH and ionic strength dependence of protein (un)folding and ligand binding to bovine beta-lactoglobulins A and B," Biochemistry, Dec. 24, 2002, 41(51):15415-15422.

Biasini et al., "Immunopurification of pathological prion protein aggregates," PLoS One, Nov. 12, 2009, 4(11):e7816, 8 pages. doi: 10.1371/journal.pone.0007816.

Bjellqvist et al., "The focusing positions of polypeptides in immobilized pH gradients can be predicted from their amino acid sequences," Electrophoresis, Oct. 1993, 14(10):1023-1031.

Blank et al., "Decreased transcription of the human FCGR2B gene mediated by the -343 G/C promoter polymorphism and association with systemic lupus erythematosus," Hum Genet, Jul. 2005, 117(2-3):220-227. Epub May 14, 2005.

Bogdanovich et al., "Functional improvement of dystrophic muscle by myostatin blockade," Nature, Nov. 28, 2002, 420(6914):418-421.

Bonvin et al., "De novo isolation of antibodies with pH-dependent binding properties," mAbs, 2015, 7(2):294-302.

Bork, "Powers and Pitfalls in Sequence Analysis: The 70% Hurdler," Genome Res, Apr. 2000, 10(4):398-400.

Borrok et al., "pH-dependent Binding Engineering Reveals an FcRn Affinity Threshold That Governs IgG Recycling," J Biol Chem, Feb. 13, 2015, 290(7):4282-4290. doi: 10.1074/jbc.M114.603712. Epub Dec. 23, 2014.

Boruchov et al., "Activating and inhibitory IgG Fc receptors on human DCs mediate opposing functions," J Clin Invest, Oct. 2005, 115(10):2914-2923. Epub Sep. 15, 2005.

Boumpas et al., "A short course of BG9588 (anti-CD40 ligand antibody) improves serologic activity and decreases hematuria in patients with proliferative lupus glomerulonephritis," Arthritis Rheum, Mar. 2003, 48(3):719-727.

Bowie et al., "Deciphering the Message in Protein Sequences: Tolerance to Amino Acid Substitutions," Science, Mar. 16, 1990, 247(4948):1306-1310.

Breitbart et al., "Highly Specific Detection of Myostatin Prodomain by an Immunoradiometric Sandwich Assay in Serum of Healthy Individuals and Patients," PLoS One, Nov. 15, 2013, 8(11):e80454, 10 pages. doi: 10.1371/journal.pone.0080454. eCollection 2013.

Brown et al., "Tolerance to Single, but Not Multiple, Amino Acid Replacements in Antibody $V_H$ CDR2," J Immunol, May 1, 1996, 156(9):3285-3291.

Bruhns et al., "Specificity and affinity of human Fcγ receptors and their polymorphic variants for human IgG subclasses," Blood, Apr. 16, 2009, 113(16):3716-3725. doi: 10.1182/blood-2008-09-179754. Epub Nov. 18, 2008.

Bruhns, "Properties of mouse and human IgG receptors and their contribution to disease models," Blood, Jun. 14, 2012, 119(24):5640-5649. doi: 10.1182/blood-2012-01-380121. Epub Apr. 25, 2012.

Buckler, Section 2.4 "Library Selection," vol. 4—Molecular Medicine and Medicinal Chemistry, Antibody Drug Discovery, edited by Clive R. Wood, London: Imperial College Press, 2012, pp. 49-57.

Bulun, "Endometriosis," New Eng J Med, Jan. 2009, 360(3):268-279.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J Cell Biol, Nov. 1990, 111(5 Pt 1):2129-2138.

Burmeister et al., "Crystal structure of the complex of rat neonatal Fc receptor with Fc," Nature, Nov. 24, 1994, 372(6504):379-383.

Cartron et al., "Therapeutic activity of humanized anti-CD20 monoclonal antibody and polymorphism in IgG Fc receptor FcγRIIIa gene," Blood, Feb. 1, 2002, 99(3):754-758.

Cemerski et al., "Suppression of mast cell degranulation through a dual-targeting tandem IgE-IgG Fc domain biologic engineered to bind with high affinity to FcγRIIb," Immunol Lett, Mar. 30, 2012, 143(1):34-43. doi: 10.1016/j.imlet.2012.01.008. Epub Jan. 25, 2012.

Chaparro-Riggers et al., "Increasing Serum Half-life and Extending Cholesterol Lowering in vivo by Engineering Antibody with pH-sensitive Binding to PCSK9," J Biol Chem, Mar. 30, 2012, 287(14):11090-11097. doi: 10.1074/jbc.M111.319764. Epub Jan. 31, 2012.

Chen et al., "Association of a transmembrane polymorphism of Fcγ receptor IIb (FCGR2B) with systemic lupus erythematosus in Taiwanese patients," Arthritis Rheum, Dec. 2006, 54(12):3908-3917.

Chen et al., "Enhancement and destruction of antibody function by somatic mutation: unequal occurrence is controlled by V gene combinatorial associations," EMBO J, Jun. 15, 1995, 14(12):2784-2794.

Chu et al., "Inhibition of B cell receptor-mediated activation of primary human B cells by coengagement of CD19 and FcγRIIb with Fc-engineered antibodies," Mol Immunol, Sep. 2008, 45(15):3926-3933. doi: 10.1016/j.molimm.2008.06.027. Epub Aug. 8, 2008.

Chu et al., "Reduction of total IgE by targeted coengagement of IgE B-cell receptor and FcγRIIb with Fc-engineered antibody," J Allergy Clin Immunol, Apr. 2012, 129(4):1102-1115. doi: 10.1016/j.jaci. 2011.11.029. Epub Jan. 16, 2012.

Chuntharapai et al., "Isotype-dependent inhibition of tumor growth in vivo by monoclonal antibodies to death receptor 4," J Immunol, Apr. 15, 2001, 166(8):4891-4898.

Claims as granted for EP 2 275 443, 6 pages (document submitted in EPO opposition proceedings).

Clark, "An alignment of IgG sequences from Human, Mouse and Rat," Part II Immunoglobulin lectures (v4), pp. 5(i)-(ii), retrieved from the Internet on Jul. 25, 2014: http://www.path.cam.ac.uk/~mrc7/lecturenotes/handoutla.pdf.

Clark, "IgG effector mechanisms," Chem Immunol, 1997, 65:88-110.

Clarkson et al., "Blockade of clearance of immune complexes by an anti-Fcγ receptor monoclonal antibody," J Exp Med, Aug. 1, 1986, 164(2):474-489.

Clynes et al., "Fc receptors are required in passive and active immunity to melanoma," Proc Natl Acad Sci USA, Jan. 20, 1998, 95(2):652-656.

Clynes et al., "Inhibitory Fc receptors modulate in vivo cytotoxicity against tumor targets," Nat Med, 2000, 6(4):443-446.

Colman, "Effects of amino acid sequence changes on antibody-antigen interactions," Res Immunol, Jan. 1994, 145(1):33-36.

Cooper et al., "Variable domain-identical antibodies exhibit IgG subclass-related differences in affinity and kinetic constants as determined by surface plasmon resonance," Mol Immunol, Jun. 1994, 31(8):577-584.

Cunningham et al., "The Covalent Structure of a Human γG-Immunoglobulin. VII. Amino Acid Sequence of Heavy-Chain Cyanogen Bromide Fragments $H_1$-$H_4$," Biochemistry, Aug. 4, 1970, 9(16):3161-3170.

Dagbay et al., "Structural basis of specific inhibition of extracellular activation of pro- or latent myostatin by the monoclonal antibody SRK-015," J Biol Chem, Apr. 17, 2020, 295(16):5404-5418.

Dall'Acqua et al., "Increasing the affinity of a human IgGl for the neonatal Fc receptor: biological consequences," J Immunol, Nov. 1, 2002, 169(9):5171-5180.

Dall'Acqua et al., "Properties of human IgG1s engineered for enhanced binding to the neonatal Fc receptor (FcRn)," J Biol Chem, Aug. 18, 2006, 281(33):23514-23524. Epub Jun. 21, 2006.

Datta-Mannan et al., "Humanized IgG1 Variants with Differential Binding Properties to the Neonatal Fc Receptor: Relationship to Pharmacokinetics in Mice and Primates," Drug Metab Dispos, Jan. 2007, 35(1):86-94. Epub Oct. 18, 2006.

Datta-Mannan et al., "Monoclonal antibody clearance. Impact of modulating the interaction of IgG with the neonatal Fc receptor," J Biol Chem, Jan. 19, 2007, 282(3):1709-1717. Epub Nov. 29, 2006.

Davda et al., "Properties of a general PK/PD model of antibody-ligand interactions for therapeutic antibodies that bind to soluble endogenous targets," mAbs, Sep./Oct. 2010, 2(5):576-588. doi: 10.4161/mabs.2.5.12833. Epub Sep. 1, 2010.

Davis et al., "SEEDbodies: fusion proteins based on strand-exchange engineered domain (Seed) $C_H3$ heterodimers in an Fc analogue platform for asymmetric binders or immunofusions and bispecific antibodies," Protein Eng Des Sel, Apr. 2010, 23(4):195-202. doi: 10.1093/protein/gzp094. Epub Feb. 4, 2010.

(56) References Cited

OTHER PUBLICATIONS

Davydov, "Omalizuman (Xolair) for Treatment of Asthma," Am Fam Physician, Jan. 15, 2005, 71(2):341-342.

De Bono et al., "ING-1, a monoclonal antibody targeting Ep-CAM in patients with advanced adenocarcinomas," Clin Cancer Res, Nov. 15, 2004, 10(22):7555-7565.

De Felice et al., "Formation of amyloid aggregates from human lysozyme and its disease-associated variants using hydrostatic pressure," FASEB J, Jul. 2004, 18(10):1099-1101. doi: 10.1096/fj.03-1072fje; PMID 15155566.

De Groot et al., "Reducing risk, improving outcomes: bioengineering less immunogenic protein therapeutics," Clin Immunol, May 2009, 131(2):189-201. doi: 10.1016/j.clim.2009.01.009. Epub Mar. 6, 2009.

Decision of the Opposition Division dated Dec. 19, 2019 in EP 2 552 955, 18 pages (document submitted by Patentee (Chugai Seiyaku Kabushiki Kaisha) in the grounds of appeal on Apr. 28, 2020 in EP 2 552 955).

Declaration of Nimish Gera, Ph.D., CV and Exhibits, dated Sep. 1, 2016, 24 pages (document submitted by Alexion Pharmaceuticals, Inc. in the EPO opposition proceedings of EP 2 275 443).

Declaration of Muramatsu Hiroyasu, dated Oct. 21, 2020, 5 pages (document cited in the office action dated Feb. 2, 2021 for EP 15869566.8).

Deng et al., "Pharmacokinetics of humanized monoclonal anti-tumor necrosis factor-α antibody and its neonatal Fc receptor variants in mice and cynomolgus monkeys," Drug Metab Dispos, Apr. 2010, 38(4):600-605. doi: 10.1124/dmd.109.031310. Epub Jan. 13, 2010.

Desai et al., "Fcγ receptor IIB on dendritic cells enforces peripheral tolerance by inhibiting effector T cell responses," J Immunol, May 15, 2007, 178(10):6217-6226.

Desjarlais et al., "Optimizing engagement of the immune system by anti-tumor antibodies: an engineer's perspective," Drug Discovery Today, Nov. 2007, 12(21-22):898-910. Epub Oct. 22, 2007.

Devanaboyina et al., "The effect of pH dependence of antibody-antigen interactions on subcellular trafficking dynamics," mAbs, Nov. 1, 2013, 5(6):851-859.

Dhodapkar et al., "Selective blockade of inhibitory Fcγ receptor enables human dendritic cell maturation with IL-12p70 production and immunity to antibody-coated tumor cells," Proc Natl Acad Sci USA, Feb. 2, 20052, 102(8):2910-2915. Epub Feb. 9, 2005.

Di Stefano et al., "Role of Interleukin-8 in the Pathogenesis and Treatment of COPD," Chest, Sep. 2004, 126(3):676-678. doi: 10.1378/chest.126.3.676.

Diamond et al., "Somatic mutation of the T15 heavy chain gives rise to an antibody with autoantibody specificity," Proc Natl Acad Sci USA, Sep. 1984, 81(18):5841-5844.

Donnez et al., "Current thinking on the pathogenesis of endometriosis," Gynecol Obstet Invest, Dec. 2002, 54(Suppl 1):52-58; post presentation discussion, pp. 59-62.

Dubrot et al., "Treatment with anti-CD137 mAbs causes intense accumulations of liver T cells without selective antitumor immunotherapeutic effects in this organ," Cancer Immunol Immunother, Aug. 2010, 59(8):1223-1233. doi: 10.1007/s00262-010-0846-9. Epub Mar. 25, 2010.

Duffau et al., "Platelet CD154 potentiates interferon-α secretion by plasmacytoid dendritic cells in systemic lupus erythematosus," Sci Transl Med, Sep. 1, 2010, 2(47):47ra63, 21 pages. doi: 10.1126/scitranslmed.3001001.

Dufner et al., "Harnessing phage and ribosome display for antibody optimization," Trends Biotechnol, Nov. 2006, 24(11):523-529. Epub Sep. 26, 2006.

Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-118.

Ejima et al., "Effective elution of antibodies by arginine and arginine derivatives in affinity col. chromatography," Anal Biochem, Oct. 15, 2005, 345(2):250-257.

EMA product information: Annexes to file of the tocilizumab preparation RoActemra (WC500054890), published by EMA on Jan. 8, 2010, 109 pages.

English translation of JP 2010-266121, 132 pages (priority document for EP 2 647 706), document submitted to EPO on May 25, 2020 by applicant during the examination procedure of EP 3 517 550.

English translation of JP 2011-217886, 365 pages (priority document for EP 2 647 706), document submitted to EPO on May 25, 2020 by applicant during the examination procedure of EP 3 517 550.

Epstein, "Non-randomness of amino-acid changes in the evolution of homologous proteins," Nature, Jul. 22, 1967, 215(5099):355-359.

Evidence for the publication date of Zalevsky et al., Nat Biotechnol, Feb. 2010, 28(2):157-159, 1 page (document submitted by Opponent 1 to the EPO with the written submission to attend oral proceedings on Sep. 6, 2019 in EP 11714860.1).

Examination Report No. 1 for AU 2013306700 issued on Jun. 7, 2018, 3 pages.

Experimental data characterizing the binding of rituximab to its antigen CD20 and to human FcRn, 6 pages (document submitted in EPO opposition proceedings and posted by EPO on Feb. 5, 2018).

Experimental information regarding off-rate of Xolair Fab for binding to human IgE at pH 7.4 and pH 5.5, 3 pages (document submitted in EPO opposition proceedings and posted by EPO on Feb. 2, 2018).

Expert Declaration by Dr. Madhusudan Natarajan, dated Dec. 19, 2018, 4 pages (document submitted in EPO opposition proceedings of EP 2 552 955 and posted by EPO on Feb. 5, 2018).

Expert Declaration of J. Boucneau, dated Sep. 6, 2019, 13 pages (document submitted by Opponent 1 to the EPO with the written submission to attend oral proceedings on Sep. 6, 2019 in EP 11714860.1).

Fan et al., "Self-Association of Human PCSK9 Correlates with Its LDLR-Degrading Activity," Biochemistry, Feb. 12, 2008, 47(6):1631-1639. doi: 10.1021/bi7016359. Epub Jan. 16, 2008.

Fillipovic, Biochemical Basis of Human Life, VLADOS, 2005:38-43 (with English translation).

Fillipovich, Biochemical Basis of Human Life, VLADOS, 2005:49-50 (with English translation).

Finlay et al., "Affinity Maturation of a Humanized Rat Antibody for Anti-RAGE Therapy: Comprehensive Mutagenesis Reveals a High Level of Mutational Plasticity Both Inside and Outside the Complementarity-Determining Regions," J Mol Biol, May 8, 2009, 388(3):541-558.

Flores et al., "Dominant Expression of the Inhibitory FcγRIIB Prevents Antigen Presentation by Murine Plasmacytoid Dendritic Cells," J Immunol, Dec. 1, 2009, 183(11):7129-7139. doi: 10.4049/jimmunol.0901169.

Floto et al., "Loss of function of a lupus-associated FcγRIIb polymorphism through exclusion from lipid rafts," Nat Med, Oct. 2005, 11(10):1056-1058. Epub Sep. 18, 2005.

Fournier et al., "Activation of human peripheral IgM+ B cells is transiently inhibited by BCR-independent aggregation of FcγRIIB," J Immunol, Oct. 15, 2008, 181(8):5350-5359.

Gary et al., Chapter 8 "Making Antibodies in Bacteria," Making and Using Antibodies: A Practical Handbook, CRC Press, Taylor & Francis Group, 2006, pp. 157-177.

"GD-IgAl (KM55) anti-human rat monoclonal antibody," Catalog No. 10777, IBL America, 6 pages, retrieved from the Internet on Apr. 13, 2020, <https://www.iblamerica.com/gd-iga1-km55-antihuman-rat-igg-moab/>.

GE Healthcare, Biacore Sensor Surface Handbook, BR-1005-71, Edition AB, 2005, pp. 1-100.

Ghetie et al., "Increasing the serum persistence of an IgG fragment by random mutagenesis," Nat Biotechnol, Jul. 1997, 15(7):637-640.

Ghetie et al., "Multiple Roles for the Major Histocompatibility Complex Class I—Related Receptor FcRn," Annu Rev Immunol, Apr. 2000, 18:739-766.

Giudice et al., "Endometriosis," Lancet, Nov. 2004, 364(9447):1789-1799.

(56)     References Cited

OTHER PUBLICATIONS

Goebl et al., "Neonatal Fc Receptor Mediates Internalization of Fc Transfected Human Endothelial Cells," Molecular Biology of the Cell, Dec. 2008, 19(12):5490-5505.

Goel et al., "Plasticity within the Antigen-Combining Site May Manifest as Molecular Mimicry in the Humoral Immune Response," J Immunol., Dec. 15, 2004, 173(12):7358-7367.

Gonzalez et al., "BMP-1/Tolloid-like Metalloproteases Process Endorepellin, the Angiostatic C-terminal Fragment of Perlecan," J Biol Chem, Feb. 25, 2005, 280(8):7080-7087. Epub Dec. 9, 2004.

Greenwood et al., "Structural motifs involved in human IgG antibody effector functions," Eur J Immunol, May 1993, 23(5):1098-1104.

Gunasekaran et al., "Enhancing antibody Fc heterodimer formation through electrostatic steering effects: applications to bispecific molecules and monovalent IgG," J Biol Chem, 2010, 285(25):19637-19646.

Guo, "Recurrence of endometriosis and its control," Hum Reprod Update, Jul.-Aug. 2009, 15(4):441-461. Epub Mar. 2009.

Gurbaxani et al., "Analysis of a family of antibodies with different half-lives in mice fails to find a correlation between affinity for FcRn and serum half-life," Mol Immunol, Mar. 2006, 43(9):1462-1473. Epub Sep. 1, 2005.

Haakenstad et al., "The disappearance kinetics and glomerular deposition of small-latticed soluble immune complexes," Immunology, Nov. 1982, 47(3):407-414.

Hamid et al., "Anti-programmed death-1 and anti-programmed death-ligand 1 antibodies in cancer therapy," Expert Opin Biol Ther, Jun. 2013, 13(6):847-861. doi: 10.1517/14712598.2013.770836. Epub Feb. 19, 2013.

Hamilton, "Molecular engineering: applications to the clinical laboratory," Clin Chem, Sep. 1993, 39(9):1988-1997.

Han et al., "Targeting the Myostatin Signaling Pathway to Treat Muscle Wasting Diseases," Curr Opin Support Palliat Care, Dec. 2011, 5(4):334-341. doi: 10.1097/SPC.0b013e32834bddf9.

Hanahan et al., "Hallmarks of Cancer: The Next Generation," Cell, Mar. 4, 2011, 144(5):646-674. doi: 10.1016/j.cell.2011.02.013.

Hanson et al., "Catalytic antibodies and their applications," Curr Opin Biotechnol, Dec. 2005, 16(6):631-636. Epub Oct. 21, 2005.

Haringman et al., "A randomized controlled trial with an anti-CCL2 (anti-monocyte chemotactic protein 1) monoclonal antibody in patients with rheumatoid arthritis," Arthritis Rheum, Aug. 2006, 54(8):2387-2392.

Harvey et al., Chapter 2 "Antigens and Receptors," pp. 11-23 and Chapter 11 "Lymphocyte Effector Functions," pp. 141-157, Lippincott's Illustrated Reviews: Immunology, $2^{nd}$ ed., Nov. 3, 20130.

Hasemann et al., "Mutational Analysis of Arsonate Binding by a $CRI_{A+}$ Antibody—$V_H$ and $V_L$ Junctional Diversity are Essential for Binding Activity," J Biol Chem, Apr. 25, 1991, 266(12):7626-7632.

Hebert, "The clearance of immune complexes from the circulation of man and other primates," Am J Dis, Mar. 1991, 17(3):352-361.

Heyman, "Feedback regulation by IgG antibodies," Immunol Lett, Aug. 5, 2003, 88(2):157-161.

Hill et al., "The Myostatin Propeptide and the Follistatin-related Gene are Inhibitory Binding Proteins of Myostatin in Normal Serum," J Biol Chem, Oct. 25, 2002, 277(43):40735-40741. Epub Aug. 22, 2002.

Hinton et al., "An engineered human IgGI antibody with longer serum half-life," J Immunol, Jan. 1, 2006, 176(1):346-356.

Hinton et al., "Engineered human IgG antibodies with longer serum half-lives in primates," J Biol Chem, Feb. 20, 2004, 279(8):6213-6216. Epub Dec. 29, 2003.

Hirose, "Visualization of intracellular calcium signaling," Nihon Yakurigaku Zasshi, May 2006, 127(5):362-367 (with English translation).

Hjelm et al., "Antibody-mediated regulation of the immune response," Scand J Immunol, Sep. 2006, 64(3):177-184.

Holash et al., "VEGF-Trap: a VEGF blocker with potent antitumor effects," Proc Natl Acad Sci USA, Aug. 20, 2002, 99(17):11393-11398. Epub Aug. 12, 2002.

Hoodless et al., "Mechanism and function of signaling by the TGF beta superfamily," Curr Top Microbiol Immunol, 1998, 228:235-272.

Hoogenboom, "Selecting and screening recombinant antibody libraries," Nat Biotechnol, Sep. 2005, 23(9):1105-1116.

Horn et al., "Analysis of the binding of pro-urokinase and urokinase-plasminogen activator inhibitor-1 complex to the low density lipoprotein receptor-related protein using a Fab fragment selected from a phage-displayed Fab library," J Biol Chem, May 19, 1995, 270(20):11770-11775.

Horton et al., "Potent in vitro and in vivo activity of an Fc-engineered anti-CD19 monoclonal antibody against lymphoma and leukemia," Cancer Res, Oct. 1, 2008, 68(19):8049-8057. doi: 10.1158/0008-5472. CAN-08-2268.

Houot et al., "Therapeutic effect of CD137 immunomodulation in lymphoma and its enhancement by $T_{reg}$ depletion," Blood, Oct. 15, 2009, 114(16):3431-3438. doi: 10.1182/blood-2009-05-223958. Epub Jul. 29, 2009.

Idusogie et al., "Engineered antibodies with increased activity to recruit complement," J Immunol, Feb. 15, 2001, 166(4):2571-2575.

Idusogie et al., "Mapping of the Clq binding site on rituxan, a chimeric antibody with a human IgG1 Fc," J Immunol, Apr. 15, 2000, 164(8):4178-4184.

Igawa et al., "Antibody Optimization Technologies for Developing Next Generation Antibody Therapeutics," Bio Industry, 2011, 28(7):15-21 (with English translation).

Igawa et al., "Antibody recycling by engineered pH-dependent antigen binding improves the duration of antigen neutralization," Nat Biotechnol, Nov. 2010, 28(11):1203-1207. doi: 10.1038/nbt.1691. Epub Oct. 17, 2010.

Igawa et al., "Reduced elimination of IgG antibodies by engineering the variable region," Protein Eng Des Sel, May 2010, 23(5):385-392. Epub Feb. 15, 2010.

Igawa et al., "Engineering the variable region of therapeutic IgG antibodies," mAbs, May-Jun. 2011, 3(3):243-252. Epub May 1, 2011.

Igawa et al., "Engineered Monoclonal Antibody with Novel Antigen-Sweeping Activity In Vivo," PLoS One, May 7, 2013, 8(5):e63236, 10 pages. doi: 10.1371/journal.pone.0063236.

Igawa et al., "pH-dependent antigen-binding antibodies as a novel therapeutic modality," Biochim Biophys Acta, Nov. 2014, 1844(11):1943-1950. doi: 10.1016/j.bbapap.2014.08.003. Epub Aug. 12, 2014.

Igawa et al., "Sweeping antibody as a novel therapeutic antibody modality capable of eliminating soluble antigens from circulation," Immunol Rev, Mar. 2016, 270(1):132-151.

Information Meeting on Antibody Engineering Technologies, Copyright © Chugai Pharmaceutical Co., Ltd., Dec. 18, 2012.

Irani et al., "Molecular properties of human IgG subclasses and their implications for designing therapeutic monoclonal antibodies against infectious diseases," Mol Immunol, Oct. 2015, 67(2 Pt A):171-182. doi: 10.1016/j.molimm.p2015.03.255. Epub Apr. 18, 2015.

Ishii et al., "FcRn, a critical regulator of antibody pharmacokinetics," Folia Pharmacol Jpn, Jun. 2010, 136(5):280-284.

Ito et al., "The His-probe method: effects of histidine residues introduced into the complementarity-determining regions of antibodies on antigen-antibody interactions at different pH values," FEBS Lett, 1992, 309:85-88.

Ito et al., "Molecular Designs of Antibodies and Peptides by Phage Display," Seibutsubutsuri, 2008, 48(5):294-298 (with English translation).

Iwabe et al., "Pathogenetic significance of increased levels of interleukin-8 in the peritoneal fluid of patients with endometriosis," Fertil Steril, May 1998, 69(5):924-930.

Jaeger, Clinical Immunology and Allergology, M.: Meditsina, $2^{nd}$ ed., 1990, 2:484-485 (with English translation).

Janeway et al., Chapter 3 "Structure of the Antibody Molecule and Immunoglobulin Genes," Immunobiology, The Immune System in Health and Disease, $3^{rd}$ ed., Garland Publishing Inc., 1997, pp. 3:1-3:11.

Jefferis et al., "Interaction sites on human IgG-Fc for FcγR: current models," Immunol Lett, Jun. 3, 2002, 82(1-2):57-65.

(56) References Cited

OTHER PUBLICATIONS

Jones et al., "Mutations in GFAP Disrupt the Distribution and Function of Organelles in Human Astrocytes," Cell Rep, Oct. 23, 2018, 25(4):947-958.e4. doi: 10.1016/j.celrep.2018.09.083.

Juszczak et al., "Ipilimumab: a novel immunomodulating therapy causing autoimmune hypophysitis: a case report and review," Eur J Endocrinol, 2012, 167(1):1-5. doi: 10.1530/EJE-12-0167. Epub Apr. 10, 2012.

Kabat et al., "Sequences of proteins of immunological interest," National Institutes of Health Publication No. 91-3242, 5$^{th}$ ed., 1991, vol. 1, pp. 679-687.

Kabat et al., "Sequences of Proteins of Immunological Interest," 1991, National Institute of Health Publication No. 91-3242, 5$^{th}$ ed., 1991, vol. 1, pp. 103 and 310.

Kakita et al., "Isolation of a Human Monoclonal Antibody with Strong Neutralizing Activity against Diphtheria Toxin," Infect Immun, Jun. 2006, 74(6):3682-3683.

Kamata et al., "Comparison of pH and Ionic Strength Dependence of Interactions between Monoclonal Antibodies and Bovine β-Lactoglobulin," Biosci Biotechnol Biochem, Jan. 1996, 60(1):25-29.

Kamei et al., "Quantitative methods for developing Fc mutants with extended half-lives," Biotechnol Bioeng, Dec. 20, 2005, 92(6):748-760.

Kanyavuz et al., "Breaking the law: unconventional strategies for antibody diversification," Nat Rev Immunol, Jun. 2019, 19(6):355-368. doi: 10.1038/s41577-019-0126-7.

Kedia et al., "Desmin forms toxic, seeding-competent amyloid aggregates that persist in muscle fibers," Proc Natl Acad Sci USA, Aug. 20, 2019, 116(34):16835-16840. doi: 10.1073/pnas.1908263116. Epub Aug. 1, 2019.

Kim et al., "Production of a Polyclonal Anti-Myostatin Antibody and the Effects of In Ovo Administration of the Antibody on Posthatch Broiler Growth and Muscle Mass," Poult Sci, Jun. 2007, 86(6):1196-1205.

Kim et al., "Antibody Engineering for the Development of Therapeutic Antibodies," Mol Cells, Aug. 31, 2005, 20(1):17-29.

Kim et al., "Production of a Monoclonal Anti-Myostatin Antibody and the Effects of In Ovo Administration of the Antibody on Posthatch Broiler Growth and Muscle Mass," Poult Sci, Jun. 2006, 85(6):1062-1071.

Kim et al., "Affinity Maturation of Monoclonal Antibodies by Multi-Site-Directed Mutagenesis," Methods Mol Biol, 2014, 1131:407-420. doi: 10.1007/978-1-62703-992-5_24.

King et al., "Applications and Engineering of Monoclonal Antibodies," Applications and Engineering of Monoclonal Antibodies, 1998, pp. 68-71.

King, "Preparation, structure and function of monoclonal antibodies," Applications and Engineering of Monoclonal Antibodies, 1998, pp. 2 and 13-14.

King et al., Applications and Engineering of Monoclonal Antibodies, 2005, pp. 1-236.

Kingsley et al., "The TGF-beta superfamily: new members, new receptors, and new genetic tests of function in different organisms," Genes Dev, Jan. 1994, 8(2):133-146.

Kipriyanov et al., "Review—Generation of Recombinant Antibodies," Mol Biotechnol, Sep. 1999, 12(2):173-201.

Kohrt et al., "Stimulation of natural killer cells with a CD137-specific antibody enhances trastuzumab efficacy in xenotransplant models of breast cancer," J Clin Invest, Mar. 1, 2012, 122(3):1066-1075. doi: 10.1172/JCI61226. Epub Feb. 13, 2012.

Kontermann et al., Chapter 4 "Mouse Immune Libraries for the Generation of ScFv Fragments Directed Against Human Cell Surface Antigens," 1:47-62 and Chapter 27 "Engineering of the Fc Region for Improved PK (FcRn Interaction)," 1:415-427, Antibody Engineering, 2010.

Kurki et al., "Desmin antibodies in acute infectious myopericarditis," APMIS, Jun. 1989, 97(6):527-532.

Lazar et al., "Engineered antibody Fc variants with enhanced effector function," Proc Natl Acad Sci USA, Mar. 2006, 103(11):4005-4010. Epub Mar. 6, 2006.

Lazar et al., "Transforming Growth Factor α: Mutation of Aspartic Acid 47 and Leucine 48 Results in Different Biological Activities," Mol Cell Biol, Mar. 1988, 8(3):1247-1252.

Lee et al., "Genetic analysis of the role of proteolysis in the activation of latent myostatin," PLoS One, Feb. 20, 2008, 3(2):e1628, 7 pages. doi: 10.1371/journal.pone.001628.

Lee et al., "Regulation of myostatin activity and muscle growth," Proc Natl Acad Sci U S A., Jul. 31, 2001;98(16):9306-11. Epub Jul. 17, 2001.

Lewis et al., "Differential responses of human tumor cell lines to anti-p185$^{HER2}$ monoclonal antibodies," Cancer Immunol Immunother, Sep. 1993, 37(4):255-263.

Li et al., "Apoptotic and antitumor activity of death receptor antibodies require inhibitory Fcγ receptor engagement," Proc Natl Acad Sci USA, Jul. 3, 2012, 109(27):10966-10971. doi: 10.1073/pnas.1208698109. Epub Jun. 20, 2012.

Li et al., "CD72 down-modulates BCR-induced signal transduction and diminishes survival in primary mature B lymphocytes," J Immunol, May 1, 2006, 176(9):5321-5328.

Li et al., "Inhibitory Fcγ receptor engagement drives adjuvant and anti-tumor activities of agonistic CD40 antibodies," Science, Aug. 19, 2011, 333(6045):1030-1034. doi: 10.1126/science.1206954.

Li et al., "Antitumor activities of agonistic anti-TNFR antibodies require differential FcγRIIB coengagement in vivo," Proc Natl Acad Sci USA, Nov. 26, 2013, 110(48):19501-19506. doi: 10.1073/pnas.1319502110. Epub Nov. 11, 2013.

Liang et al., "Immunity against a therapeutic xenoprotein/Fc construct delivered by gene transfer is reduced through binding to the inhibitory receptor FcγRIIb," J Gene Med, Sep. 2011, 13(9):470-477.

Liberti et al., "Antigenicity of polypeptides (poly-α-amino acids). Physicochemical studies of a calcium-dependent antigen-antibody reaction," Biochemistry, Apr. 27, 1971, 10(9):1632-1639.

Liu et al., "Asymmetrical Fc engineering greatly enhances antibody-dependent cellular cytotoxicity (ADCC) effector function and stability of the modified antibodies," J Biol Chem, Feb. 7, 2014, 289(6):3571-3590. doi: 10.1074/jbc.M113.513366. Epub Dec. 5, 2013.

Lloyd et al., "Modelling the human immune response: performance of a 10$^{11}$ human antibody repertoire against a broad panel of therapeutically relevant antigens," Protein Eng Des Sel, Mar. 2009, 22(3):159-168. doi: 10.1093/protein/gzn058. Epub Oct. 29, 2008.

Lutterbuese et al., "T cell-engaging BiTE antibodies specific for EGFR potently eliminate KRAS- and BRAF-mutated colorectal cancer cells," Proc Natl Acad Sci USA, 2010, 107(28):12605-12610. doi: 10.1073/pnas.1000976107. Epub Jun. 28, 2010.

Luttrell et al., "Reaction coupling of chelation and antigen binding in the calcium ion-dependent antibody binding of cyclic AMP," J Biol Chem, Nov. 15, 1991, 266(32):21626-21630.

Maccallum et al., "Antibody-antigen Interactions: Contact Analysis and Binding Site Topography," J Mol Biol, Oct. 11, 1996, 262:732-745.

Mackay et al., "Selective dysregulation of the FcγIIB receptor on memory B cells in SLE," J Exp Med, Sep. 4, 2006, 203(9):2157-2164. Epub Aug. 21, 2006.

Malbec et al., "Antibodies against growth factor receptors can inhibit the proliferation of transformed cells via a cis-interaction with inhibitory FcR," Immunol Lett, Mar. 30, 2012, 143(1):28-33.

Male et al., Chapter 3 "Antibodies," Immunology, Elsevier Ltd., 7$^{th}$ ed., 2006, pp. 59-86.

Manger et al., "Fcγ receptor IIa polymorphism in Caucasian patients with systemic lupus erythematosus: association with clinical symptoms," Arthritis Rheum, Jul. 1998, 41(7):1181-1189.

Mariuzza et al., "The Structural Basis of Antigen-Antibody Recognition," Annu Rev Biophys Chem, Jun. 1987, 16:139-159.

Martin et al., "Reviews Preclinical Safety and Immune-Modulating Effects of Therapeutic Monoclonal Antibodies to Interleukin-6 and Tumor Necrosis Factor-α in Cynomolgus Macaques," J Immunotoxicol, 2004, 1(3):131-139. doi: 10.1080/15476910490894904.

(56) References Cited

OTHER PUBLICATIONS

Marvin et al., "Recombinant approaches to IgG-like bispecific antibodies," Acta Pharmacol Sin, Jun. 2005, 26(6):649-658.

Matsumiya et al., "Structural comparison of fucosylated and nonfucosylated Fc fragments of human immunoglobulin G1," J Mol Biol, May 4, 2007, 368(3):767-779. Epub Feb. 22, 2007.

Matsumoto et al., "Functional analysis of activated C1s, a subcomponent of the first component of human complement, by monoclonal antibodies," J Immunol, Nov. 1, 1986, 137(9):2907-2912.

Matsunaga et al., "A pH-dependent conformational transition of Aβ peptide and physicochemical properties of the conformers in the glial cell," Biochem J, Feb. 1, 2002, 361(Pt 3):547-556.

Maurer et al., "Antigenicity of polypeptides (polyaamino acids): calcium-dependent and independent antibodies," J Immunol, Sep. 1970, 105(3):567-573.

Maxfield et al., "Endocytic Recycling," Nat Rev Mol Cell Biol, Feb. 2004, 5(2):121-132.

Maxwell et al., "Crystal structure of the human leukocyte Fc receptor, FcγRIIa," Nat Struct Biol, May 1999, 6(5):437-442.

Mazda et al., "Regulation of Muscle Homeostasis and Metabolism by the TGF-β Superfamily Cytokine, Myostatin/growth Differentiation Factor 8 (GDF8)," Journal of Kyoto Prefectural University of Medicine, 2013, 122(3):133-141.

Mccroskery et al., "Improved muscle healing through enhanced regeneration and reduced fibrosis in myostatin-null mice," J Cell Sci, Aug. 1, 2005, 118(Pt 15):3531-3541.

Mcpherron et al., "Double muscling in cattle due to mutations in the myostatin gene," Proc Natl Acad Sci USA, Nov. 11, 1997, 94(23):12457-12461.

Mcpherron et al., "Regulation of skeletal muscle mass in mice by a new TGF-beta superfamily member," Nature, May 1, 1997, 387(6628):83-90.

Medesan et al., "Comparative studies of rat IgG to further delineate the Fc:FcRn interaction site," Eur J Immunol, Jul. 1998, 28(7):2092-2100.

Mellman, "The importance of being acid: The role of acidification in intracellular membrane traffic," J Exp Biol, Nov. 1992, 172:39-45.

Mendez-Fernandez et al., "The inhibitory FcγRIIb modulates the inflammatory response and influences atherosclerosis in male apoE$^{-/-}$ mice," Atherosclerosis, Jan. 2011, 214(1):73-80. doi: 10.1016/j.atherosclerosis.2010.10.018.

Meulenbroek et al., Chapter 2.3 "Properties of human IgG subclasses," Human IgG Subclasses: Useful Diagnostic Markers for Immunocompetence, published online by Sanquin, Amsterdam, The Netherlands, retrieved from the Internet on Mar. 23 and 24, 2017: <http://ednieuw.home.xs4all.nl/IgGsubclasses/subk123.htm>, 8 pages.

Meyer et al., "Bevacizumab immune complexes activate platelets and induce thrombosis in FCGR2A transgenic mice," J Thromb Haemost, Jan. 2009, 7(1):171-181. doi: 10.1111/j.1538-7836.2008.03212.x. Epub Oct. 30, 2008.

Mi et al., "Targeting the neonatal fc receptor for antigen delivery using engineered fc fragments," J Immunol, Dec. 1, 2008, 181(11):7550-7561.

Mimoto et al., "Engineered antibody Fc variant with selectively enhanced FcγRIIb binding over both FcγRIIa$^{R131}$ and FcγRIIa$^{H131}$," Protein Eng Des Sel, Oct. 2013, 26(10):589-598. doi: 10.1093/protein/gzt022. Epub Jun. 5, 2013.

Mimoto et al., "Novel asymmetrically engineered antibody Fc variant with superior FcγR binding affinity and specificity compared with afucosylated Fc variant," mAbs, Mar.-Apr. 2013, 5(2):229-236. doi: 10.4161/mabs.23452. Epub Feb. 13, 2013.

Misawa et al., "Rapid and High-Sensitivity Cell-Based Assays of Protein—Protein Interactions Using Split Click Beetle Luciferase Complementation: An Approach to the Study of G-Protein-Coupled Receptors," Anal Chem, Mar. 15, 2010, 82(6):2552-2560. doi: 10.1021/ac100104q.

Molina et al., "Trastuzumab (Herceptin), a Humanized Anti-HER2 Receptor Monoclonal Antibody, Inhibits Basal and Activated HER2 Ectodomain Cleavage in Breast Cancer Cells," Cancer Res, Jun. 15, 2001, 61(12):4744-4749.

"Monoclonal Mouse Anti-Human Desmin (Concentrate) Clone D33," Code No. M0760, Agilent Dako, 3 pages, retrieved from the Internet on Apr. 13, 2020, <https://www.agilent.com/en/product//immunohistochemistry/antibodies controls/primaryantibodies/desmin-(concentrate)-76523>.

Montero-Julian et al., "Pharmacokinetic study of anti-interleukin-6 (IL-6) therapy with monoclonal antibodies: enhancement of IL-6 clearance by cocktails of anti-IL-6 antibodies," Blood, Feb. 15, 1995, 85(4):917-924.

Moore et al., "Engineered Fc variant antibodies with enhanced ability to recruit complement and mediate effector functions," mAbs, Mar.-Apr. 2010, 2(2):181-189.

Morgan et al., "The N-terminal end of the $C_H2$ domain of chimeric human IgGI anti-HLA-DR is necessary for C1q, FcγRI and FcγRIII binding," Immunology, Oct. 1995, 86(2):319-324.

Mortensen et al., "Structure and activation of C1, the complex initiating the classical pathway of the complement cascade," Proc Natl Acad Sci USA, Jan. 31, 2017, 114(5):986-991. doi: 10.1073/pnas.1616998114. Epub Jan. 19, 2017.

Muramatsu, "Latent myostatin specific elimination by sweeping antibody® is a novel therapeutic approach to improve muscle strength," Abstracts/Neuromuscular Disorders, 2019, 29(Supplement 1):S86, 1 page.

Murtaugh et al., "A Combinatorial Histidine Scanning Library Approach to Engineer Highly pH-Dependent Protein Switches," Protein Sci, Sep. 2011, 20(9):1619-1631. doi: 10.1002/pro.696. Epub Aug. 3, 2011.

Muta et al., "A 13-amino-acid motif in the cytoplasmic domain of FcγRIIB modulates B-cell receptor signaling," Nature, Mar. 3, 1994, 368(6466):70-73.

Nagaoka et al., "Single amino acid substitution in the mouse IgG1 Fc region induces drastic enhancement of the affinity to protein A," Protein Eng, Apr. 2003, 16(4):243-245. doi: 10.1093/proeng/gzg037.

Nakamura et al., "Fcγ receptor IIB-deficient mice develop Goodpasture's syndrome upon immunization with type IV collagen: a novel murine model for autoimmune glomerular basement membrane disease," J Exp Med, Mar. 6, 2000, 191(5):899-906.

Nam et al., "Current evidence for the management of rheumatoid arthritis with biological disease-modifying antirheumatic drugs: a systematic literature review informing the EULAR recommendations for the management of RA," Ann Rheum Dis, 2010, 69(6):976-986. doi: 10.1136/ard.2009.126573. Epub May 6, 2010.

Nicholas et al., "Regulation of the immune response. I. Reduction in ability of specific antibody to inhibit long-lasting IgG immunological priming after removal of the Fc fragment," J Exp Med, Jun. 1, 1969, 129(6):1183-1201.

Niebecker et al., "Safety of therapeutic monoclonal antibodies," Curr Drug Saf, Oct. 2010, 5(4):275-286.

Nimmerjahn et al., "Divergent immunoglobulin g subclass activity through selective Fc receptor binding," Science, 2005, 310(5753):1510-1512.

Nimmerjahn et al., "Fcγ receptors as regulators of immune responses," Nat Rev Immunol, Jan. 2008, 8(1):34-47.

Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease," Blood, 2008, 112(10):3959-3964. doi: 10.1182/blood-2008-05-155846. Epub Sep. 10, 2008.

O'Donovan et al., "EGFR and HER-2 Antagonists in Breast Cancer," Anticancer Res, May-Jun. 2007;27(3A):1285-1294.

Official Action dated Oct. 13, 2016 in EP Application No. 11714860.1 and submitted as evidence during EPO opposition proceedings, 3 pages.

Ohno et al., "Antigen-binding specificities of antibodies are primarily determined by seven residues of $V_H$," Proc Natl Acad Sci USA, May 1985, 82(9):2945-2949.

(56)          References Cited

OTHER PUBLICATIONS

Okabe, "Proprietary Innovative Antibody Engineering Technologies in Chugai Pharmaceutical," Information meeting on Antibody Engineering Technologies, Dec. 18, 2012, 78 pages.

Olferiev et al., "The role of activating protein 1 in the transcriptional regulation of the human FCGR2B promoter mediated by the -343 G → C polymorphism associated with systemic lupus erythematosus," J Biol Chem, Jan. 19, 2007, 282(3):1738-1746. Epub Nov. 27, 2006.

OriGene Technologies, Inc., AP02123SU-N, Polyclonal Antibody to Myostatin (79-92)—Serum, Mar. 19, 2013, https://ml.acris-antibodies.com/pdf/AP02123SU-N.pdf.

Pace et al., "How to measure and predict the molar absorption coefficient of a protein," Protein Sci, Nov. 1995, 4(11):2411-2423.

Pakula et al., "Genetic Analysis of Protein Stability and Function," Annu Rev Genet, 1989, 23:289-310.

Papista et al., "Dysfunctions of the IgA system: a common link between intestinal and renal diseases," Cell Mol Immunol, Mar. 2011, 8(2):126-134. doi: 10.1038/cmi.2010.69. Epub Jan. 31, 2011.

Patentee submission dated Jul. 16, 2015 (Response to Search Report filed on Jul. 16, 2015), 30 pages (document submitted by the Opponent on May 6, 2020 in the EPO opposition proceedings of EP 2 679 681).

Patton et al., "An acid dissociation bridging ELISA for detection of antibodies directed against therapeutic proteins in the presence of antigen," J Immunol Methods, Sep. 2005, 304(1-2):189-195.

Pavlou et al., "The therapeutic antibodies market to 2008," Eur J Pharm Biopharm, Apr. 2005, 59(3):389-396.

Perng et al., "Desmin Aggregate Formation by R120G αB-Crystallin Is Caused by Altered Filament Interactions and Is Dependent upon Network Status in Cells," Mol Biol Cell, May 2004, 15(5):2335-2346.

Petillot et al., "Analysis of the N-linked oligosaccharides of human C1s using electrospray ionisation mass spectrometry," FEBS Lett, Jan. 30, 1995, 358(3):323-328.

Petkova et al., "Enhanced half-life of genetically engineered human IgGI antibodies in a humanized FcRn mouse model: potential application in humorally mediated autoimmune disease," Int Immunol, 2006, 18(12):1759-1769. Epub Oct. 31, 2006.

Pirruccello-Straub, "Blocking extracellular activation of myostatin as a strategy for treating muscle wasting," Scientific Reports, Feb. 2, 2018, 8:2292, 15 pages.

Poosarla et al., "Computational de novo Design of Antibodies binding to a Peptide with High Affinity," Biotechn Bioeng, Jun. 2017, 114(6):1331-1342.

Popov et al., "The Stoichiometry and Affinity of the Interaction of Murine Fc Fragments with the MHC Class I-Related Receptor, FcRn," Mol Immunol, Apr. 1996, 33(6):521-530.

Presta et al., "Humanization of an Anti-Vascular Endothelial Growth Factor Monoclonal Antibody for the Therapy of Solid Tumors and Other Disorders," Cancer Res, Oct. 15, 1997, 57(20):4593-4599.

Presta, "Molecular engineering and design of therapeutic antibodies," Curr Opin Immunol, Aug. 2008, 20(4):460-470. doi : 10.1016/j.coi.2008. 06.012.

Prickett et al., "A calcium-dependent antibody for identification and purification of recombinant proteins," Biotechniques, Jun. 1989, 7(6):580-589.

Prieto et al., "CTLA-4 Blockade with Ipilimumab: Long-term Follow-up of 177 Patients with Metastatic Melanoma," Clin Cancer Res, Apr. 1, 2012, 18(7):2039-2047. doi: 10.1158/1078-0432.CCR-11-1823. Epub Jan. 23, 2012.

Product labelling information for Rituxan (Rituximab), dated Nov. 1997, 2 pages.

Proprietor's (Chugai Seiyaku Kabushiki Kaisha) submission dated Sep. 19, 2016 in EP11714860.1, 3 pages (document submitted by Opponent 1 to the EPO with the written submission to attend oral proceedings on Sep. 6, 2019 in EP 11714860.1).

Proprietor's (Chugai Seiyaku Kabushiki Kaisha) Response to the Summons to attend Oral Proceedings dated Sep. 5, 2016 in EP11714860.

1, 6 pages (document submitted by Opponent 1 to the EPO with the written submission to attend oral proceedings on Sep. 6, 2019 in EP 11714860.1).

Proprietor's (Chugai Seiyaku) Reply to the Communication pursuant to Rule 79(1) EPC dated Oct. 10, 2016 dated Feb. 20, 2017 in EP 2 275 443, 35 pages (document submitted by Opponent 5 to the EPO with the written submission to attend oral proceedings on Sep. 6, 2019 in EP 11714860.1).

Qiao et al., "Dependence of antibody-mediated presentation of antigen on FcRn," Proc Natl Acad Sci USA, Jul. 8, 2008, 105(27):9337-9342. Epub Jul. 1, 2008.

Radaev et al., "The role of Fc glycosylation and the binding of peptide inhibitors," J Biol Chem, May 11, 2001, 276(19):16478-16483. Epub Jan. 31, 2001.

Radaev et al., "The structure of a human type III Fcγ receptor in complex with Fc," J Biol Chem, May 11, 2001, 276(19):16469-16477. Epub Jan. 31, 2001.

Raghavan et al., "Analysis of the pH Dependence of the Neonatal Fc Receptor/immunoglobulin G Interaction Using Antibody and Receptor Variants," Biochemistry, Nov. 14, 1995, 34(45):14649-14657.

Rajpal et al., "A general method for greatly improving the affinity of antibodies by using combinatorial libraries," Proc Natl Acad Sci USA, Jun. 14, 2005, 102(24):8466-8471. Epub Jun. 6, 2005.

Ramos et al., "Evaluation of CA-125 and soluble CD-23 in patients with pelvic endometriosis: a case-control study," Rev Assoc Med Bras, Jan.-Feb. 2012, 58(1):26-32.

Rathanaswami et al., "Demonstration of an in vivo generated sub-picomolar affinity fully human monoclonal antibody to interleukin-8," Biochem Biophys Res Commun, 2005, 334(4):1004-1013.

Ravetch et al., "Immune inhibitory receptors," Science, Oct. 6, 2000, 290(5489):84-89.

Reichert et al., "Monoclonal antibody successes in the clinic," Nat Biotechnol, Sep. 2005, 23(9):1073-1078.

Reverberi et al., "Factors affecting the antigen-antibody reaction," Blood Transfus, Nov. 2007, 5(4):227-240. doi: 10.2450/2007.0047-07.

Rich et al., "A global study using affinity-based biosensors," Anal Biochem, Mar. 15, 2009, 386(2):194-216. doi: 10.1016/j.ab.2008. 11.021. Epub Nov. 27, 2008.

Richards et al., "Optimization of antibody binding to FcγRIIa enhances macrophage phagocytosis of tumor cells," Mol Cancer Ther, Aug. 2008, 7(8):2517-2527. doi: 10.1158/1535-7163.MCT-08-0201.

Riechelmann et al., "Phase I trial with the CD44v6-targeting immunoconjugate bivatuzumab mertansine in head and neck squamous cell carcinoma," Oral Oncol, Sep. 2008, 44(9):823-829. doi: 10.1016/j.oraloncology.2007.10.009. Epub Jan. 18, 2008.

Rivas et al., "Calcium-Linked Self-Association of Human Complement C1s," Biochemistry, Dec. 1, 1992, 31(47):11707-11712.

Robles-Carrillo et al., "Anti-CD40L immune complexes potently activate platelets in vitro and cause thrombosis in FCGR2A transgenic mice," J Immunol, Aug. 1, 2010, 185(3):1577-1583. doi: 10.4049/jimmunol.0903888. Epub Jun. 28, 2010.

Roitt et al., Chapter 3 "Antibodies," Immunology, M., Mir, 2000, pp. 97-113 (with what are believed to be corresponding pages from an English language edition of Immunology).

Roitt et al., "Overview: Antibody—a flexible adaptor," Immunology, M., Mir, 2000, p. 9 (what are believed to be corresponding pages from an English language edition of Immunology).

Roitt et al., Chapter 19 "Vaccination," Immunology, Moscow, Mir, 2000, pp. 373-374 (with English translation).

Rojas et al., "Formation, Distribution, and Elimination of Infliximab and Anti-Infliximab Immune Complexes in Cynomolgus Monkeys," J Pharmacol Exp Ther, May 2005, 313(2):578-585. Epub Jan. 12, 2005.

Roopenian et al., "FcRn: the neonatal Fc receptor comes of age," Nat Rev Immunol, 2007, 7(9):715-725. Epub Aug. 17, 2007.

Rossi et al., "Classical Complement Pathway Components C1r and C1s: Purification from Human Serum and in Recombinant Form and Functional Characterization," Methods Mol Biol, 2014, 1100:43-60. doi: 10.1007/978-1-62703-724-2_4.

(56) References Cited

OTHER PUBLICATIONS

Rudge et al., "VEGF Trap complex formation measures production rates of VEGF, providing a biomarker for predicting efficacious angiogenic blockade," 2007, 104(47):18363-18370. Epub Nov. 13, 2007.

Rudikoff et al., "Single amino acid substitution altering antigen-binding specificity," Proc Natl Acad Sci USA, Mar. 1982, 79(6):1979-1983.

Russo et al., "The CXCL8/IL-8 chemokine family and its receptors in inflammatory diseases," Expert Rev Clin Immunol, May 2014, 10(5):593-619. doi: 10.1586/1744666X.2014.894886. Epub Mar. 29, 2014.

Safdari et al., "Antibody humanization methods—a review and update," Biotechnol Genet Eng Rev, 2013, 29:175-186.

Salmon et al., "FcγRIIA alleles are heritable risk factors for lupus nephritis in African Americans," J Clin Invest, Mar. 1, 1996, 97(5):1348-1354.

Samuelsson et al., "Anti-inflammatory activity of IVIG mediated through the inhibitory Fc receptor," Science, 2001, 291(5503):484-486.

Satoh et al., "Non-fucosylated therapeutic antibodies as next-generation therapeutic antibodies," Expert Opin Biol Ther, Nov. 2006, 6(11):1161-1173.

Sazinsky et al., "Aglycosylated immunoglobulin G1 variants productively engage activating Fc receptor," Proc Natl Acad Sci USA, Dec. 23, 2008, 105(51):20167-20172. doi: 10.1073/pnas.0809257105. Epub Dec. 12, 2008.

Scappaticci et al., "Arterial thromboembolic events in patients with metastatic carcinoma treated with chemotherapy and bevacizumab," J Natl Cancer Inst, Aug. 15, 2007, 99(16):1232-1239. Epub Aug. 8, 2007.

Schabowsky et al., "A Novel Form of 4-1BBL Has Better Immunomodulatory Activity than an Agonistic Anti-4-1BB Ab without Ab Associated Severe Toxicity," Vaccine, Dec. 11, 2009, 28(2):512-522. doi: 1016/j.vaccine.2009.09.127. Epub Oct. 29, 2009.

Schlothauer et al., "Novel human IgG1 and IgG4 Fc-engineered antibodies with completely abolished immune effector functions," Protein Eng Des Sel, Oct. 2016, 29(10):457-466. doi: 10.1093/protein/gzw040. Epub Aug. 29, 2016.

Schroter et al., "A generic approach to engineer antibody pH-switches using combinatorial histidine scanning libraries and yeast display," mAbs, Jan./Feb. 2015, 7(1):138-151. doi: 10.4161/19420862.2014.985993.

Schulke et al., "The homodimer of prostate-specific membrane antigen is a functional target for cancer therapy," Proc Natl Acad Sci USA, Oct. 28, 2003, 100(22):12590-12595.

Schuster et al., "Signaling of human ciliary neurotrophic factor (CNTF) revisited: The interleukin-6 receptor can serve as an α-receptor for CTNF," J Biol Chem, Mar. 14, 2003, 278(11):9528-9535.

Schuster et al., "The human interleukin-6 (IL-6) receptor exists as a preformed dimer in the plasma membrane," FEBS Lett, Mar. 13, 2003, 538(1-3):113-116.

Seda et al., "B-cell receptor signalling and its crosstalk with other pathways in normal and malignant cells," Eur J Haematol, Mar. 2015, 94(3):193-205. doi: 10.1111/ejh.12427. Epub Sep. 13, 2014.

Shi et al., "TNT003, an inhibitor of the serine protease C1s, prevents complement activation induced by cold agglutinins," Blood, Jun. 26, 2014, 123(26):4015-4022. doi: 10.1182/blood-2014-02-556027. Epub Apr. 2, 2014.

Shields et al., "High resolution mapping of the binding site on human IgG1 for FcγRI, FcγRII, FcγRIII, and FcRn and design of IgGI variants with improved binding to the FcγR," J Biol Chem, Mar. 2, 2001, 276(9):6591-6604. Epub Nov. 28, 2000.

Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem, Jan. 31, 2003, 278(5):3466-3473. Epub Nov. 8, 2002.

Siberil et al., "Molecular aspects of human FcγR interactions with IgG: functional and therapeutic consequences," Immunol Lett, Aug. 15, 2006, 106(2):111-118. Epub Jun. 12, 2006.

Sigma product information for ACES buffer, 1 page (document submitted by Opponent 1 to the EPO with the written submission to attend oral proceedings on Sep. 6, 2019 in EP 11714860.1).

Sikkink et al., "Biochemical and aggregation analysis of Bence Jones proteins from different light chain diseases," Amyloid, Mar. 2008, 15(1):29-39.

Sims et al., "HMGB1 and RAGE in inflammation and cancer," Annu Rev Immunol, 2010, 28:367-388.

Singer et al., "The Genetic Molecules," Genes & Genomes, Moscow, Mir, 1998, 1:63-64 (with what are believed to be the corresponding pages from an English version of Genes & Genomes).

Singer et al., Chapter 3 "The Logic and Machinery of Gene Expression," Genes & Genomes, Moscow, Mir, 1998, pp. 115-188 (with what are believed to be the corresponding pages from an English version of Genes & Genomes).

Smith et al., "FcγRIIB in autoimmunity and infection: evolutionary and therapeutic implications," Nat Rev Immunol, May 2010, 10(5):328-443. doi: 10.1038/nri2762.

Sondermann et al., "Crystal structure of the soluble form of the human Fcγ-receptor IIb: a new member of the immunoglobulin superfamily at 1.7 Å resolution," EMBO J, Mar. 1, 1999, 18(5):1095-1103.

Sondermann et al., "Molecular Basis for Immune Complex Recognition: A Comparison of Fc-Receptor Structures," J Mol Biol, Jun. 8, 2001, 309(3):737-749.

Sondermann et al., "The 3.2-Å crystal structure of the human IgG1 Fc fragment-FcγRIII complex," Nature, Jul. 20, 2000, 406(6793):267-273.

Stavenhagen et al., "Enhancing the potency of therapeutic monoclonal antibodies via Fc optimization," Adv Enzyme Regul, 2008, 48:152-164.

Stepanov, Chapter 4 "Primary Structure of Protein," Molecular biology. Structure and functions of proteins, M.:Nauka, 2005, pp. 61-62 (with English translation).

Strohl, "Optimization of Fc-mediated effector functions of monoclonal antibodies," Curr Opin Biotechnol, Dec. 2009, 20(6):685-691.

Su et al., "Expression profile of FcγRIIb on leukocytes and its dysregulation in systemic lupus erythematosus," J Immunol, Mar. 2007, 178(5):3272-3280.

Summers et al., "Fine-tuning of dendritic cell biology by the TNF superfamily," Nat Rev Immunol, Apr. 10, 2012, 12(5):339-351. doi: 10.1038/nri3193.

Supplementary data provided by opponent for EP Application No. 11714860.1, 3 pages (document submitted in EPO opposition proceedings and posted by EPO on Feb. 20, 2018).

Suzuki et al., "IgA nephropathy and IgA vasculitis with nephritis have a shared feature involving galactose-deficient IgA1-oirented pathogenesis," Kidney Int, Mar. 2018, 93(3):700-705. doi: 10.1016/j.kint.2017.10.019. Epub Jan. 10, 2018.

Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," J Immunol, Feb. 15, 2010, 184(4):1968-1976. doi: 10.4049/jimmunol.0903296. Epub Jan. 18, 2010.

Szlama et al., "Latent myostatin has significant activity and this activity is controlled more efficiently by WFIKKNI than by WFIKKN2," FEBS J, Aug. 2013, 280(16):3822-3839. doi: 10.1111/febs.12377. Epub Jul. 5, 2013.

Table summarizing alleged lack of novelty over WO 2009/086320A, Jul. 9, 2009, 4 pages (document submitted by Opponent 1 to the EPO with the written submission to attend oral proceedings on Sep. 6, 2019 in EP 11714860.1).

Tackenberg et al., "Impaired inhibitory Fcγ receptor IIB expression on B cells in chronic inflammatory demyelinating polyneuropathy," Proc Natl Acad Sci USA, Mar. 24, 2009, 106(12):4788-4792. doi: 10.1073/pnas.0807319106.

(56) References Cited

OTHER PUBLICATIONS

Takeuchi et al., "The Japanese experience with biologic therapies for rheumatoid arthritis," Nat Rev Rheumatol, 2010, 6(11):644-652. doi: 10.1038/nrrheum.2010.154. Epub Sep. 28, 2010.

Tanabe et al., "Characterization of the Monoclonal Antibodies Against Human Protein C Specific for Calcium Ion-induced Conformers," Japanese Journal of Thrombosis and Hemostasis, 1992, 3(1):29-35.

Tanzi et al., "Twenty years of the Alzheimer's disease amyloid hypothesis: a genetic perspective," Cell, Feb. 2005, 120(4):545-555. doi: 10.1016/j.cell.2005.02.008; PMID 15734686.

Tarantul, "Antibodies," Explanatory Biotechnological Dictionary— Russian-English, Moscow, Languages of Slavic Cultures, 2009, p. 72 (with English translation).

Torres et al., "The immunoglobulin constant region contributes to affinity and specificity," Trend Immunol, 2008, 29(2):91-97.

Travis et al., "Isolation of Albumin from Whole Human Plasma and Fractionation of Albumin-Depleted Plasma," Biochem J, Aug. 1, 1976, 157(2):301-306.

Trinh et al., "Ipilimumab in the treatment of melanoma," Expert Opin Biol Ther, Jun. 2012, 12(6):773-782. doi: 10.1517/14712598. 2012.675325. Epub Apr. 14, 2012.

Vaccaro et al., "Divergent activities of an engineered antibody in murine and human systems have implications for therapeutic antibodies," Proc Natl Acad Sci USA, Dec. 5, 2006, 103(49):18709-18714. Epub Nov. 20, 2006.

Vaccaro et al., "Engineering the Fc region of immunoglobulin G to modulate in vivo antibody levels," Nat Biotechnol, Oct. 2005, 23(10):1283-1288. Epub Sep. 25, 2005.

Vajdos et al., "Comprehensive Functional Maps of the Antigen-binding Site of an Anti-ErbB2 Antibody Obtained with Shotgun Scanning Mutagenesis," J Mol Biol, Jul. 5, 2002, 320(2):415-428.

Vercellini et al., "Postoperative oral contraceptive exposure and risk of endometrioma recurrence," Am J Obstet Gynecol, May 2008, 198(5):504. Epub Feb. 2008.

Veri et al., "Monoclonal antibodies capable of discriminating the human inhibitory Fcγ-receptor IIB (CD32B) from the activating Fcγ-receptor IIA (CD32A): biochemical, biological and functional characterization," Immunology, 2007, 121(3):392-404.

Veri et al., "Therapeutic control of B cell activation via recruitment of Fcγ receptor IIb (CD32B) inhibitory function with a novel bispecific antibody scaffold," Arthritis Rheum, Jul. 2010, 62(7):1933-1943. doi: 10.1002/art.27477.

Vinay et al., "4-1BB signaling beyond T cells," Cell Mol Immunol, Jul. 2011, 8(4):281-284. doi: 10.1038/cmi.2010.82. Epub Jan. 10, 2011.

Vidarsson et al., "IgG subclasses and allotypes: from structure to effector functions," Front Immunol, Oct. 20, 2014, 5:520. doi: 10.3389/ fimmu.2014.00520. eCollection 2014.

Waelbroeck et al., "The pH Dependence of Insulin Binding," J Biol Chem, Jul. 25, 1982, 257(14):8284-8291.

Wagner et al., "Loss of myostatin attenuates severity of muscular dystrophy in mdx mice," Ann Neurol, Dec. 2002, 52(6):832-836.

Wang et al., "HMG-1 as a late mediator of endotoxin lethality in mice," Science, 1999, 285(5425):248-251.

Wang et al., "Monoclonal Antibodies with Identical Fc Sequences Can Bind to FcRn Differentially with Pharmacokinetic Consequences," Drug Metabolism and Disposition, Sep. 2011, 39(9):1469-1477.

Wang et al., "Molecular Basis of Assembly and Activation of Complement Component C1 in Complex with Immunoglobulin G1 and Antigen," Mol Cell, Jul. 7, 2016, 63(1):135-145. doi: 10.1016/ j.molcel.2016.05.016. Epub Jun. 16, 2016.

Ward et al., "Evidence to support the cellular mechanism involved in serum IgG homeostasis in humans," Int Immunol, Feb. 2003, 15(2):187-195.

Ward et al., "A calcium-binding monoclonal antibody that recognizes a non-calcium-binding epitope in the short consensus repeat units (SCRs) of complement C1r," Mol Immunol, Jan. 1992, 29(1):83-93.

Warmerdam et al., "Molecular basis for a polymorphism of human Fcγ receptor II (CD32)," J Exp Med, Jul. 1990, 172(1):19-25.

Warmerdam et al., "The human low affinity immunoglobulin G Fc receptor IIC gene is a result of an unequal crossover event," J Biol Chem, Apr. 5, 1993, 268(10):7346-7349.

Warncke et al., "Different adaptations of IgG effector function in human and nonhuman primates and implications for therapeutic antibody treatment," J Immunol, May 1, 2012, 188(9):4405-4411. doi: 10.4049/jimmunol. 1200090. Epub Mar. 28, 2012.

Weiner et al., "Monoclonal antibodies: versatile platforms for cancer immunotherapy," Nat Rev Immunol, 2010, 10(5):317-327. doi: 10.1038/nri2744.

Weiss et al., "Rapid mapping of protein functional epitopes by combinatorial alanine scanning," Proc Natl Acad Sci USA, Aug. 1, 2000, 97(16):8950-8954.

Welch et al., "Adalimumab (Humira) for the Treatment of Rheumatoid Arthritis," Am Fam Physician, Dec. 15, 2008, 78(12):1406-1408.

Wenink et al., "The inhibitory FcγIIb receptor dampens TLR4-mediated immune responses and is selectively up-regulated on dendritic cells from rheumatoid arthritis patients with quiescent disease," J Immunol, Oct. 1, 2009, 183(7):4509-4520. doi: 10.4049/ jimmunol.0900153. Epub Sep. 4, 2009.

Wernersson et al., "IgG-mediated enhancement of antibody responses is low in Fc receptor gamma chain-deficient mice and increased in Fc gamma RII-deficient mice," J Immunol, Jul. 15, 1999, 163(2):618-622.

Whittemore et al., "Inhibition of myostatin in adult mice increases skeletal muscle mass and strength," Biochem Biophys Res Commun, Jan. 24, 2003, 300(4):965-971.

Wilson et al., "An Fcγ receptor-dependent mechanism drives antibody-mediated target-receptor signaling in cancer cells," Cancer Cell, Jan. 18, 2011, 19(1):101-113. doi: 10.1016/j.ccr.2010.11.012.

Wolfman et al., "Activation of latent myostatin by the BMP-1/ tolloid family of metalloproteinases," Proc Natl Acad Sci USA, Dec. 23, 2003, 100(26):15842-15846. Epub Dec. 11, 2003.

Wu et al., "Development of motavizumab, an ultra-potent antibody for the prevention of respiratory syncytial virus infection in the upper and lower respiratory tract," J Mol Biol, May 4, 2007, 368(3):652-665. Epub Feb. 20, 2007.

Wu et al., "Humanization of a murine monoclonal antibody by simultaneous optimization of framework and CDR residues," J Mol Biol, Nov. 19, 1999, 294(1):151-162.

Wu et al., "Structure-based engineering of a monoclonal antibody for improved solubility," Protein Eng Des Sel, Aug. 2010, 23(8):643-651. doi:10.1093/protein/gzq037. Epub Jun. 11, 2010.

Xiao et al., "Pharmacokinetics of anti-hepcidin monoclonal antibody Ab 12B9m and hepcidin in cynomolgus monkeys," AAPS J, 2010, 12(4):646-657. doi: 10.1208/s12248-010-9222-0. Epub Aug. 25, 2010.

Xolair (omalizumab) Prescribing Information, Jul. 2016, 27 pages, https://www.gene.com/download/pdf/xolair_prescribing.pdf.

Xu et al., "FcγRs modulate cytotoxicity of anti-Fas antibodies: implications for agonistic antibody-based therapeutics," J Immunol, Jul. 2003, 171(2):562-568.

Yada et al., Chapter 2 "Antigens and Receptors," pp. 11-23 and Chapter 11 "Lymphocyte Effector Receptors," pp. 141-157, Lippincott's Illustrated Reviews: Immunology, 2nd ed., Nov. 30, 2013 (with what are believed to be the corresponding pages from an English version of Lippincott's Illustrated Reviews: Immunology).

Yang et al., "Dataset of the binding kinetic rate constants of anti-PCSK9 antibodies obtained using the Biacore T100, Protean XPR36, Octet RED384, and IBIS MX96 biosensor platforms," Data Brief, Jul. 27, 2016, 8:1173-1183. doi : 10.1016/J.dib.2016.07.044. eCollection Sep. 2016.

Yang et al., "Maximizing in vivo target clearance by design of pH-dependent target binding antibodies with altered affinity to FcRn," mAbs, Oct. 2017, 9(7):1105-1117. doi: 10.1080/19420862. 2017.1359455. Epub Aug. 8, 2017.

Yang et al., "Comparison of biosensor platforms in the evaluation of high affinity antibody-antigen binding kinetics," Anal Biochem, Sep. 1, 2016, 508:78-96. doi: 10.1016/j.ab.2016.06.024. Epub Jun. 27, 2016.

(56)　　　　　　References Cited

OTHER PUBLICATIONS

Yarilin, Fundamentals of Immunology, M:Medicina, 1999, pp. 169-172 and 354-358 (with English translation).
Yarilin, Fundamentals of Immunology, M: Medicina, 1999, pp. 175, 182 (with English translation).
Yarilin, Chapter 3 "Molecular and cellular basis of adaptive immunity," Fundamentals of Immunology, M.:Medicina, 1999, pp. 172-174 (with English translation).
Yarilin, Chapter 3 "Molecular and cellular basis of adaptive immunity," Fundamentals of Immunology, M.:Medicina, 1999, pp. 181-184 (with English translation).
Yarmush et al., "Immunoadsorption: strategies for antigen elution and production of reusable adsorbents," Biotechnol Prog, May-Jun. 1992, 8(3):168-178.
Yeung et al., "A Therapeutic Anti-VEGF Antibody with Increased Potency Independent of Pharmocaokinetic Half-life," Cancer Res, Apr. 15, 2010, 70(8):3269-3277. doi: 10.1158/0008-5472.CAN-09-4580. Epub Mar. 30, 2010.
Yeung et al., "Engineering human IgG1 affinity to human neonatal Fc receptor: impact of affinity improvement on pharmacokinetics in primates," J Immunol, Jun. 15, 2009, 182(12):7663-7671. doi: 10.4049/jimmunol.0804182.
Ying et al., "Large Yellow Croaker MSTN-1 Prodomain Prokaryotic Expression, Polyclonal Antibody Preparation and Antibody Function Identification," Chinese Journal of Cell Biology, Oct. 2014, 36(10):1344-1349.
Yuasa et al., "Deletion of fcγ receptor IIB renders H-2$^b$ mice susceptible to collagen-induced arthritis," J Exp Med, Jan. 1999, 189(1):187-194.
Zalevsky et al., "Enhanced antibody half-life improves in vivo activity," Nat Biotechnol, Feb. 2010, 28(2):157-159. doi: 10.1038/nbt.1601. Epub Jan. 17, 2010.
Zalevsky et al., "The impact of Fc engineering on an anti-CD19 antibody: increased Fcγ receptor affinity enhances B-cell clearing in nonhuman primates," Blood, 2009, 113(16):3735-3743. Epub Dec. 24, 2008.
Zhang et al., "Effective therapy for a murine model of human anaplastic large-cell lymphoma with the anti-CD30 monoclonal antibody, HeFi-1, does not require activating Fc receptors," Blood, Jul. 15, 2006, 108(2):705-710. Epub Mar. 21, 2006.
Zhang et al., "Immune complex/Ig negatively regulate TLR4-triggered inflammatory response in macrophages through FcγRIIb-dependent PGE2 production," J Immunol, Jan. 1, 2009, 182(1):554-562.
Zheng et al., "Translational pharmacokinetics and pharmacodynamics of an FcRn-variant anti-CD4 monoclonal antibody from preclinical model to phase I study," Clin Pharmacol Ther, 2011, 89(2):283-290. doi: 10.1038/clpt.2010.311. Epub Dec. 29, 2010.
Zimmers et al., "Induction of cachexia in mice by systemically administered myostatin," Science, May 24, 2002, 296(5572):1486-1488.
International Search Report and Written Opinion for App. Ser. No. PCT/JP2012/054624, mailed Apr. 3, 2013, 7 pages.
International Preliminary Report on Patentability for App. Ser. No. PCT/JP2012/054624, dated Aug. 27, 2013, 7 pages.
USPTO Restriction Requirement in U.S. Appl. No. 14/347,321, dated Dec. 17, 2015, 10 pages.
Fish & Richardson P.C., Reply to Restriction Requirement dated Dec. 17, 2015 in U.S. Appl. No. 14/347,321, filed Feb. 16, 2016, 3 pages.
USPTO Office Action in U.S. Appl. No. 14/347,321, dated May 2, 2016, 35 pages.
Fish & Richardson P.C., Reply to Office Action dated May 2, 2016 in U.S. Appl. No. 14/347,321, filed Nov. 2, 2016, 35 pages.
USPTO Final Office Action in U.S. Appl. No. 14/347,321, dated Jan. 9, 2017, 61 pages.
International Search Report for App. Ser. No. PCT/JP2012/075092, mailed Dec. 25, 2012, 4 pages.
International Preliminary Report on Patentability for App. Ser. No. PCT/JP2012/075092, dated Apr. 1, 2014, 10 pages.

International Search Report for App. Ser. No. PCT/JP2013/054461, mailed May 7, 2013, 7 pages.
International Preliminary Report on Patentability for App. Ser. No. PCT/JP2013/054461, dated Aug. 26, 2014, 6 pages.
International Search Report for App. Ser. No. PCT/JP2013/072507, mailed Oct. 29, 2013, 4 pages.
International Preliminary Report on Patentability for App. Ser. No. PCT/JP2013/072507, dated Feb. 24, 2015, 6 pages.
International Search Report for App. Ser. No. PCT/JP2014/059706, dated Jul. 15, 2014, 4 pages.
International Preliminary Report on Patentability for App. Ser. No. PCT/JP2014/059706, dated Oct. 6, 2015, 10 pages.
International Preliminary Report on Patentability for App. Ser. No. PCT/JP2012/066665, dated Jan. 16, 2014, 10 pages.
International Search Report and Written Opinion for App. Ser. No. PCT/JP2012/066665, mailed Sep. 25, 2012, 10 pages.
International Search Report for App. Ser. No. PCT/JP2013/084809, mailed Apr. 1, 2014, 4 pages.
International Preliminary Report on Patentability for App. Ser. No. PCT/JP2013/084809, dated Jun. 30, 2015, 7 pages.
USPTO Final Office Action in U.S. Appl. No. 14/001,218, dated Jan. 29, 2018, 11 pages.
International Search Report for App. Ser. No. PCT/JP2016/003616, mailed Nov. 25, 2016, 4 pages.
USPTO Restriction Requirement in U.S. Appl. No. 14/423,269, dated May 4, 2017, 5 pages.
USPTO Non-Final Office Action in U.S. Appl. No. 14/423,269, dated Nov. 28, 2017, 58 pages.
USPTO Final Office Action in U.S. Appl. No. 14/423,269, dated Aug. 15, 2018, 25 pages.
USPTO Non-Final Office Action in U.S. Appl. No. 14/423,269, dated Oct. 2, 2019, 24 pages.
EUSPTO Notice of Allowance and Examiner-Initiated Interview Summary in U.S. Appl. No. 14/423,269, dated Jun. 5, 2020, 25 pages.
USPTO Restriction Requirement in U.S. Appl. No. 14/781,069, dated Dec. 7, 2017, 7 pages.
USPTO Non-Final Office Action in U.S. Appl. No. 14/781,069, dated Aug. 27, 2018, 59 pages.
USPTO Applicant-Initiated Interview Summary in U.S. Appl. No. 14/781,069, dated Feb. 26, 2019, 3 pages.
USPTO Final Office Action in U.S. Appl. No. 14/781,069, dated May 20, 2019, 29 pages.
USPTO Non-Final Office Action in U.S. Appl. No. 14/781,069, dated Mar. 13, 2020, 21 pages.
USPTO Final Office Action in U.S. Appl. No. 14/781,069, dated Nov. 9, 2020, 22 pages.
International Search Report for App. Ser. No. PCT/JP2015/006323, mailed Jul. 12, 2018, 23 pages.
International Search Report for App. Ser. No. PCT/JP2017/028346, mailed Oct. 31, 2017, 5 pages.
USPTO Non-final Office Action in U.S. Appl. No. 15/952,945, dated Sep. 20, 2018, 32 pages.
USPTO Final Office Action in U.S. Appl. No. 15/952,945, dated Jun. 3, 2019, 190 pages.
USPTO Non-Final Office Action in U.S. Appl. No. 15/952,951, dated Oct. 1, 2018, 12 pages.
USPTO Final Office Action in U.S. Appl. No. 15/952,951, dated Jun. 3, 2019, 67 pages.
USPTO Advisory Action in U.S. Appl. No. 15/952,951, dated Aug. 19, 2019, 5 pages.
USPTO Non-Final Office Action in U.S. Appl. No. 13/595,139, dated Nov. 14, 2012, 10 pages.
USPTO Non-Final Office Action in U.S. Appl. No. 13/595,139, dated Mar. 13, 2015, 12 pages.
USPTO Non-Final Office Action in U.S. Appl. No. 13/595,139, dated Aug. 3, 2015, 13 pages.
USPTO Final Office Action in U.S. Appl. No. 13/595,139, dated Feb. 12, 2016, 12 pages.
USPTO Non-Final Office Action in U.S. Appl. No. 13/595,139, dated Nov. 23, 2016, 11 pages.
USPTO Final Office Action in U.S. Appl. No. 13/595,139, dated May 30, 2017, 23 pages.

(56)　　　　　References Cited

OTHER PUBLICATIONS

USPTO Final Office Action in U.S. Appl. No. 13/595,139, dated Aug. 1, 2013, 8 pages.
USPTO Non-Final Office Action in U.S. Appl. No. 13/595,139, dated Sep. 26, 2018, 32 pages.
USPTO Restriction Requirement in U.S. Appl. No. 16/264,735, dated Nov. 16, 2020, 9 pages.
USPTO Non-Final Office Action in U.S. Appl. No. 16/264,735, dated Jun. 22, 2021, 119 pages.
USPTO Final Office Action in U.S. Appl. No. 16/264,735, dated Apr. 1, 2022, 26 pages.
Non-Final Office Action in U.S. Appl. No. 16/264,735, dated Jun. 9, 2023, 36 pages.
Bertolotti-Ciarlet et al., "Impact of methionine oxidation on the binding of human IgG1 to Fc Rn and Fcγ receptors," Mol Immunol, May 2009, 46(8-9):1878-1882.
Wang et al., "Recent advances in detection of k-ras gene mutations and target therapy of colorectal cancer," World Chinese Journal of Digestology, Jan. 2011, 19(1):62-67 (with English translation).
U.S. Appl. No. 18/657,893, filed May 8, 2024, Fukuzawa et al.
Kuznetsova, "Brackets in Text of Legal Document as a Linguo-Cognitive Phenomenon," Bulletin MGOU, Chapter: Russian philology, 2015, 3:37-43 (with English translation).
Singer et al., Chapter 1.3 "Structure of Proteins," Genes & Genomes, Moscow, Mir, 1998, pp. 63-66 (with what are believed to be the correspondence pages from an English version of Genes & Genomes).
U.S. Appl. No. 18/472,932, filed Sep. 22, 2023, Fukuzawa et al.
U.S. Appl. No. 18/480,730, filed Oct. 4, 2023, Igawa et al.
Lamm et al., "Microbial IgA protease removes IgA immune complexes from mouse glomeruli in vivo: potential therapy for IgA nephropathy," Am J Pathol, Jan. 2008, 172(1):31-36.
U.S. Appl. No. 18/929,733, Ruike et al., filed Oct. 29, 2024.
U.S. Appl. No. 18/929,733, filed Oct. 29, 2024, Ruike et al.
Bae et al., "Antibody-Aided Clearance of Extracellular α-Synuclein Prevents Cell-to-Cell Aggregate Transmission," J Neurosci, Sep. 26, 2012, 32(39):13454-13469.
Hoyer et al., "Dependence of α-Synuclein Aggregate Morphology on Solution Conditions," J Mol Biol, Sep. 13, 2002, 322(2):383-393.
Schulz-Schaeffer et al., "The synaptic pathology of α-synuclein aggregation in dementia with Lewy bodies, Parkinson's disease and Parkinson's disease dementia," Acta Neuropathol, Aug. 2010, 120(2):131-143.
U.S. Appl. No. 18/450,863, filed Aug. 16, 2023, Kakiuchi et al.
U.S. Appl. No. 18/022,342, Katada et al., filed Feb. 21, 2023.
U.S. Appl. No. 18/023,038, Katada et al., filed Feb. 24, 2023.
U.S. Appl. No. 18/022,342, filed Feb. 21, 2023, Katada et al.
U.S. Appl. No. 18/023,038, filed Feb. 24, 2023, Katada et al.
Attwood, "The Babel of Bioinformatics," Science, Oct. 20, 2000, 290(5491):471-473. doi: 10.1126/science.290.5491.471. PMID: 11183771.
Skolnick et al., "From genes to protein structure and function: novel applications of computational approaches in the genomic era," Trends Biotechnol, Jan. 2000, 18(1):34-39. doi: 10.1016/s0167-7799(99)01398-0. PMID: 10631780.
U.S. Appl. No. 18/533,360, filed Dec. 8, 2023, Igawa et al.
U.S. Appl. No. 16/889,066, Ruike et al., filed Jun. 1, 2020.
U.S. Appl. No. 16/763,134, Feng et al., filed May 11, 2020.
U.S. Appl. No. 15/963,455, Ruike et al., filed Apr. 26, 2018.
U.S. Appl. No. 13/637,415, Igawa et al., filed Feb. 4, 2013.
U.S. Appl. No. 15/050,145, Igawa et al., filed Feb. 22, 2016.
U.S. Appl. No. 15/210,353, Igawa et al., filed Jul. 14, 2016.
U.S. Appl. No. 15/210,360, Igawa et al., filed Jul. 14, 2016.
U.S. Appl. No. 15/495,026, Igawa et al., filed Apr. 24, 2017.
U.S. Appl. No. 17/046,395, Fukuzawa et al., filed Oct. 9, 2020.
U.S. Appl. No. 17/266,024, Igawa et al., filed Feb. 4, 2021.
U.S. Appl. No. 17/333,256, Kakiuchi et al., filed May 28, 2021.
U.S. Appl. No. 17/494,199, Igawa et al., filed Oct. 5, 2021.
U.S. Appl. No. 17/602,196, Wakabayashi et al., filed Oct. 7, 2021.
U.S. Appl. No. 17/610,204, Koga, filed Nov. 10, 2021.

U.S. Appl. No. 17/742,824, Ruike et al., filed May 12, 2022.
U.S. Appl. No. 17/768,053, Koga et al., filed Apr. 11, 2022.
U.S. Appl. No. 14/001,218, Mimoto et al., filed Aug. 23, 2013 (abandoned).
U.S. Appl. No. 17/846,672, Mimoto et al., filed Jun. 22, 2022.
U.S. Appl. No. 16/806,027, Igawa et al., filed Mar. 2, 2020.
U.S. Appl. No. 15/860,163, Mimoto et al., filed Jan. 2, 2018.
U.S. Appl. No. 14/347,034, Igawa et al., filed Mar. 25, 2014 (abandoned).
U.S. Appl. No. 15/230,904, Igawa et al., filed Aug. 8, 2016 (abandoned).
U.S. Appl. No. 16/028,140, Igawa et al., filed Jul. 5, 2018.
U.S. Appl. No. 14/347,321, Igawa et al., filed Mar. 26, 2014 (abandoned).
U.S. Appl. No. 15/977,757, Igawa et al., filed May 11, 2018 (abandoned).
U.S. Appl. No. 17/561,207, Igawa et al., filed Dec. 23, 2021.
U.S. Appl. No. 16/264,735, Igawa et al., filed Feb. 1, 2019.
U.S. Appl. No. 14/361,013, Igawa et al., filed May 28, 2014 (abandoned).
U.S. Appl. No. 16/108,897, Igawa et al., Aug. 22, 2018.
U.S. Appl. No. 14/379,825, Igawa et al., Aug. 20, 2014 (abandoned).
U.S. Appl. No. 14/404,051, Igawa et al., filed Nov. 26, 2014 (abandoned).
U.S. Appl. No. 17/144,342, Igawa et al., filed Jan. 8, 2021.
U.S. Appl. No. 17/671,185, Mimoto et al., filed Feb. 14, 2022.
U.S. Appl. No. 17/028,210, Katada et al., filed Sep. 22, 2020.
U.S. Appl. No. 14/379,825, filed Aug. 20, 2014, Igawa et al.
U.S. Appl. No. 16/539,765, filed Aug. 13, 2019, Igawa et al.
U.S. Appl. No. 17/266,024, filed Feb. 4, 2021, Igawa et al.
U.S. Appl. No. 17/333,256, filed May 28, 2021, Kakiuchi et al.
U.S. Appl. No. 17/494,199, filed Oct. 5, 2021, Igawa et al.
U.S. Appl. No. 17/602,196, filed Oct. 7, 2021, Wakabayashi et al.
U.S. Appl. No. 17/610,204, filed Nov. 10, 2021, Koga.
U.S. Appl. No. 17/561,207, filed Dec. 23, 2021, Igawa et al.
U.S. Appl. No. 17/671,185, filed Feb. 14, 2022, Mimoto et al.
U.S. Appl. No. 17/768,053, filed Apr. 11, 2022, Koga et al.
U.S. Appl. No. 17/742,824, filed May 12, 2022, Ruike et al.
U.S. Appl. No. 17/846,672, filed Jun. 22, 2022, Mimoto et al.
Abdiche et al., "Antibodies Targeting Closely Adjacent or Minimally Overlapping Epitopes Can Displace One Another," PLoS One, Jan. 6, 2017, 12(1):e0169535, 22 pages. doi: 10.1371/journal.pone.0169535.
Almitairi et al., "Structure of the C1r-C1s interaction of the C1 complex of complement activation," Proc Natl Acad Sci USA, 2018, 115(4):768-773. doi: 10.1073/pnas.1718709115.
Annex 1 accompanying Response to Statement of Grounds of Appeal of Opponent 2 (Alexion Pharmaceuticals, Inc.), dated Sep. 16, 2020, 29 pages (document submitted in EPO opposition proceedings of EP 2 552 955).
Application as filed for EP 2 698 431, 375 pages (document submitted during EPO opposition proceedings of EP 2 698 431 on Jun. 23, 2021).
Arduin et al., "Highly reduced binding to high and low affinity mouse Fc gamma receptors by L234A/L235A and N297A Fc mutations engineered into mouse IgG2a," Mol Immunol, Feb. 2015, 63(2):456-463.
Bally et al., "Identification of the C1q-binding Sites of Human C1r and C1s—A Refined Three-Dimensional Model of the C1 Complex of Complement," J Biol Chem, 2009, 284(29):19340-19348. doi: 10.1074/jbc.M109.004473.
Beranger et al., "IMGT Scientific Chart," Jun. 8, 2016, 7 pages.
Crowe et al., "Humanized monoclonal antibody CAMPATH-1H: myeloma cell expression of genomic constructs, nucleotide sequence of cDNA constructs and comparison of effector mechanisms of myeloma and Chinese hamster ovary cell-derived material," Clin Exp Immunol, Jan. 1992, 87(1):105-110.
Datta-Mannan et al., "FcRn Affinity-Pharmacokinetic Relationship of Five Human IgG4 Antibodies Engineered for Improved In Vitro FcRn Binding Properties in Cynomolgus Monkeys," Drug Metab Dispos, Aug. 2012, 40(8):1545-1555.

(56) References Cited

OTHER PUBLICATIONS

Decision of the Opposition Division in EP 2 275 443, dated Apr. 26, 2018, 29 pages (document submitted on Sep. 3, 2021 with response to EPO office action in EP 3 702 368).
Ellison et al., "Linkage and sequence homology of two human immunoglobulin γ heavy chain constant region genes," Proc Natl Acad Sci USA, Mar. 1982, 79(6):1984-1988.
English translation of PCT/JP2011/072550, 283 pages (corresponding to WO 2012/132067, which was cited in IDS filed on Jul. 18, 2022). The translation was submitted in the EPO opposition proceedings of EP 2 698 431 on Jun. 23, 2021.
English translation of PCT/JP2012/054624, 110 pages (corresponding to WO 2012/115241, which was cited in IDS filed on Jul. 18, 2022). The translation was submitted in the EPO opposition proceedings of EP 2 698 431 on Jun. 23, 2021.
EUTM register extract—Biacore, 4 pages (document downloaded on Aug. 26, 2020, submitted in EPO opposition proceedings of EP 2 552 955, and posted by EPO on Sep. 15, 2020).
Fillipovic, Biochemical Basis of Human Life, Moscow, Vlados, 2005, 407:49-50 and 70 (with English translation).
Fukuzawa et al., "Long lasting neutralization of C5 by SKY59, a novel recycling antibody, is a potential therapy for complement-mediated diseases," Sci Rep, Apr. 24, 2017, 7(1):1080. doi: 10.1038/s41598-017-01087-7.
Gal et al., "Early complement proteases: C1r, C1s and MASPs. A structural insight into activation and functions," Mol Immunol, 2009, 46(14):2745-2752. doi: 10.1016/j.molimm.2009.04.026.
Gershoni et al., "Epitope Mapping—The First Step in Developing Epitope-Based Vaccines," BioDrugs, 2007, 21(3):145-156.
Guidance on the use of International Nonproprietary Names (INNs) for Pharmaceutical Substances, World Health Organization, 2017, 54 pages (document submitted in EPO opposition proceedings of EP 2 552 955 and posted by EPO on Sep. 16, 2020).
Han et al., "Monoclonal antibodies: interspecies scaling with minimal preclinical information," Ther Deliv, Mar. 2011, 2(3):359-368.
Henne et al., "Anti-PCSK9 Antibody Pharmacokinetics and Low-Density Lipoprotein-Cholesterol Pharmacodynamics in Nonhuman Primates Are Antigen Affinity-Dependent and Exhibit Limited Sensitivity to Neonatal Fc Receptor-Binding Enhancement," J Pharmacol Exp Ther, Apr. 2015, 353(1):119-131. doi: 10.1124/jpet.114.221242. Epub Feb. 4, 2015.
Huang et al., "Fully Humanized Neutralizing Antibodies to Interleukin-8 (ABX-IL8) Inhibit Angiogenesis, Tumor Growth, and Metastasis of Human Melanoma," Am J Pathol, Jul. 2002, 161(1):125-134.
Huck et al., "Sequence of a human immunoglobulin gamma 3 heavy chain constant region gene: comparison with the other human Cγ genes," Nucleic Acids Res, Feb. 25, 1986, 14(4):1779-1789.
Jakubke et al., "Physicochemical properties," Amino Acids, Peptides and Proteins, Moscow, Mir, 1985, pp. 356-363 (with English translation).
James et al., "1.9 Å structure of the therapeutic antibody CAMPATH-1H fab in complex with a synthetic peptide antigen," J Mol Biol, Jun. 4, 1999, 289(2):293-301.
Jung et al., "Aglycosylated IgG variants expressed in bacteria that selectively bind FcγRI potentiate tumor cell killing by monocyte-dendritic cells," Proc Natl Acad Sci USA, Jan. 12, 2010, 107(2):604-609.
King et al., Applications and Engineering of Monoclonal Antibodies, 1998, pp. 27-75.
Lacroix et al., "Assembly and Enzymatic Properties of the Catalytic Domain of Human Complement Protease C1r," J Biol Chem, Sep. 28, 2001, 276(39):36233-36240. doi:10.1074/jbc.M105688200.
Lescar et al., "Crystal Structure of a Cross-reaction Complex between Fab F9.13.7 and Guinea Fowl Lysozyme," J Biol Chem, Jul. 28, 1995, 270(30):18067-18076.
Nakagawa et al., "Complement C1s activation in degenerating articular cartilage of rheumatoid arthritis patients: immunohistochemical studies with an active form specific antibody," Ann Rheum Dis, Mar. 1999, 58(3):175-181.

NCBI database: GenBank Accession No. AAC82527.1, Jun. 10, 2016, "immunoglobulin gamma-1 heavy chain constant region, partial [*Homo sapiens*]," (https://www.ncbi.nlm.nih.gov/protein/AAC82527.1).
NCBI database: GenBank Accession No. AAB59393.1, Aug. 1, 2016, "immunoglobulin gamma-2 heavy chain, partial [*Homo sapiens*]," (https://www.ncbi.nlm.nih.gov/protein/AAB59393.1).
NCBI database: GenBank Accession No. AAB59394.1, Aug. 1, 2016, "immunoglobulin gamma-4 heavy chain, partial [*Homo sapiens*]," (https://www.ncbi.nlm.nih.gov/protein/AAB59394.1).
NCBI database: GenBank Accession No. CAA27268.1, Jul. 25, 2016, "C gamma 3, partial [*Homo sapiens*]," (https://www.ncbi.nlm.nih.gov/protein/CAA27268.1).
Notice of Opposition by Opponent 1 (Ablynx N.V.), dated Feb. 2, 2018, 50 pages (document submitted in EPO opposition proceedings of EP 2 552 955).
Statement of Facts and Arguments in Support of Opposition by Opponent 2 (Alexion Pharmaceuticals, Inc.), dated Feb. 2, 2018, 39 pages (document submitted in EPO opposition proceedings of EP 2 552 955).
Opposition Statement of Opponent 5 (Shire Human Genetic Therapies, Inc.), dated Feb. 5, 2018, 70 pages (document submitted in EPO opposition proceedings of EP 2 552 955).
PCT/JP2011/001888, filed Mar. 30, 2011, 203 pages (corresponding to WO 2011/122011, which was cited in IDS filed on Jul. 18, 2020) (document cited in EPO opposition proceedings of EP 2 698 431 on Jun. 23, 2021).
Presta et al., "Engineering therapeutic antibodies for improved function," Biochem Soc Trans, Aug. 2002, 30(4):487-490.
Raso et al., "Antibodies Capable of Releasing Diphtheria Toxin in Response to the Low pH Found in Endosomes," J Biol Chem, Oct. 31, 1997, 272(44):27618-27622.
Rossi et al., "Baculovirus-mediated Expression of Truncated Modular Fragments from the Catalytic Region of Human Complement Serine Protease C1s," J Biol Chem, Jan. 9, 1998, 273(2):1232-1239. doi: 10.1074/jbc.273.2.1232.
Salfeld et al., "Isotype selection in antibody engineering," Nat Biotechnol, 2007, 25(12):1369-1372.
Response by Opponent 1 (Ablynx N.V.), dated Sep. 6, 2019, 57 pages (document submitted in EPO opposition proceedings of EP 2 552 955).
Final Written Submissions of Opponent 2 (Alexion Pharmaceuticals, Inc.), dated Sep. 6, 2019, 26 pages (document submitted in EPO opposition proceedings of EP 2 552 955).
Reply from Opponent 5 (Shire Human Genetic Therapies, Inc.), dated Sep. 6, 2019, 15 pages (document submitted in EPO opposition proceedings of EP 2 552 955).
Takahashi et al., "Structure of human immunoglobulin gamma genes: implications for evolution of a gene family," Cell, Jun. 1982, 29(2):671-679.
Tseng et al., "Probing the Structure of C1 with an Anti-C1s Monoclonal Antibody: The Possible Existence of Two Forms of Cl in Solution," Mol Immunol, 1997, 34(8-9):671-679. doi: 10.1016/s0161-5890(97)00039-4.
Wines et al., "The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A," J Immunol, May 15, 2000, 164(10):5313-5318.
Zwolak et al., "Rapid Purification of Human Bispecific Antibodies via Selective Modulation of Protein A Binding," Sci Rep, Nov. 14, 2017, 7(1):15521, 11 pages.
USPTO Restriction Requirement in U.S. Appl. No. 14/379,825, dated Dec. 22, 2016, 8 pages.
Fish & Richardson P.C., Reply to Restriction Requirement in U.S. Appl. No. 14/379,825, dated Jun. 21, 2017, 2 pages.
USPTO Non-Final Office Action in U.S. Appl. No. 14/379,825, dated Jul. 20, 2017, 18 pages.
Fish & Richardson P.C., Amendment and Reply to Action of Jul. 20, 2017 in U.S. Appl. No. 14/379,825, dated Jan. 22, 2018, 18 pages.
USPTO Final Office Action in U.S. Appl. No. 14/379,825, dated Apr. 2, 2018, 14 pages.
Fish & Richardson P.C., Amendment and Reply to Action of Apr. 2, 2018 in U.S. Appl. No. 14/379,825, dated Sep. 27, 2018, 20 pages.

(56) References Cited

OTHER PUBLICATIONS

USPTO Non-Final Office Action in U.S. Appl. No. 14/379,825, dated Nov. 1, 2018, 17 pages.
Fish & Richardson P.C., Amendment and Reply to Non-Final Action of Nov. 1, 2018 in U.S. Appl. No. 14/379,825, dated Apr. 30, 2019, 30 pages.
USPTO Final Office Action in U.S. Appl. No. 14/379,825, dated Jun. 14, 2019, 23 pages.
Fish & Richardson P.C., Amendment and Reply to Final Office Action of Jun. 14, 2019 in U.S. Appl. No. 14/379,825, dated Jul. 9, 2020, 29 pages.
USPTO Non-Final Office Action in U.S. Appl. No. 14/379,825, dated Nov. 4, 2020, 31 pages.
Fish & Richardson P.C., Amendment and Reply to Action of Nov. 4, 2020 in U.S. Appl. No. 14/379,825, dated Apr. 27, 2021, 24 pages.
USPTO Final Office Action in U.S. Appl. No. 14/379,825, dated Jun. 16, 2021, 35 pages.
USPTO Final Office Action in U.S. Appl. No. 15/952,951, dated Jul. 16, 2021, 15 pages.
USPTO Non-Final Office Action in U.S. Appl. No. 17/020,497, dated Jan. 29, 2021, 23 pages.
USPTO Non-Final Office Action in U.S. Appl. No. 17/020,497, dated Sep. 21, 2021, 21 pages.

* cited by examiner

FcgRIIb EXTRACELLULAR REGION

Fc CH2 DOMAIN A

Fc CH2 DOMAIN B

Fc CH3 DOMAIN A

Fc CH3 DOMAIN B

FcgRIIb EXTRACELLULAR REGION

Fc CH2 DOMAIN A

Fc CH2 DOMAIN B

BLACK   CRYSTAL STRUCTURE OF Fc(P238D)/FcγRIIb EXTRACELLULAR REGION COMPLEX
GRAY    MODEL STRUCTURE OF Fc(WT)/FcγRIIb EXTRACELLULAR REGION COMPLEX

BLACK   CRYSTAL STRUCTURE OF Fc(P238D)/FcγRIIb EXTRACELLULAR REGION COMPLEX
GRAY    MODEL STRUCTURE OF Fc(WT)/FcγRIIb EXTRACELLULAR REGION COMPLEX

FcgRllb or llla
EXTRACELLULAR REGION

P271

Fc
Chain B

BLACK   CRYSTAL STRUCTURE OF Fc(P238D)/FcγRllb EXTRACELLULAR REGION COMPLEX
GRAY    CRYSTAL STRUCTURE OF Fc(WT)/FcγRllla EXTRACELLULAR REGION COMPLEX (PDB code: 3SGJ)

FcγRIIb
EXTRACELLULAR REGION

Fc(P208)
CH2DOMAIN A

Fc(P208)
CH2DOMAIN B

Fc(P208)
CH3DOMAIN A

Fc(P208)
CH3DOMAIN B

THIN LINE:   Fc(Wt) CH2DOMAIN A
HEAVY LINE:   Fc(P208) CH2DOMAIN A

THIN LINE: X-RAY CRYSTAL STRUCTURE OF Fc(P238D)/FcγRIIb
EXTRACELLULAR REGION COMPLEX
HEAVY LINE: X-RAY CRYSTAL STRUCTURE OF Fc(P208)/FcγRIIb
EXTRACELLULAR REGION COMPLEX

THIN LINE : Fc(P208)
HEAVY LINE : FcγRIIb EXTRACELLULAR REGION

FcγRIIaR or FcγRIIb
EXTRACELLULAR REGION

Fc(P208)
CH2DOMAIN A

Fc(P208)
CH2DOMAIN B

Fc(P208)
CH3DOMAIN A

Fc(P208)
CH3DOMAIN B

BLACK: X-RAY CRYSTAL STRUCTURE OF Fc(P208)/FcγRIIaR
EXTRACELLULAR REGION COMPLEX
GRAY: X-RAY CRYSTAL STRUCTURE OF Fc(P208)/FcγRIIb
EXTRACELLULAR REGION COMPLEX

THIN LINE: Fc(P208)
HEAVY LINE: FcγRIIaR or FcγRIIb EXTRACELLULAR REGION
LEFT: X-RAY CRYSTAL STRUCTURE OF Fc(P208)/FcγRIIaR
      EXTRACELLULAR REGION COMPLEX
RIGHT: X-RAY CRYSTAL STRUCTURE OF Fc(P208)/FcγRIIb
      EXTRACELLULAR REGION COMPLEX

THIN LINE: Fc(P208)
HEAVY LINE: FcγRIIaR or FcγRIIb EXTRACELLULAR REGION

LEFT: X-RAY CRYSTAL STRUCTURE OF Fc(P208)/FcγRIIaR
EXTRACELLULAR REGION COMPLEX

RIGHT: X-RAY CRYSTAL STRUCTURE OF Fc(P208)/FcγRIIb
EXTRACELLULAR REGION COMPLEX

ANTIGEN-BINDING MOLECULE FOR PROMOTING DISAPPEARANCE OF ANTIGEN VIA FCγRIIB

CROSS-REFERENCE TO RELATED APPLICATIONS

This application is a divisional application of U.S. application Ser. No. 14/379,825, filed on Aug. 20, 2014, which is the National Stage of International Application No. PCT/JP2013/054461, filed on Feb. 22, 2013, which claims the benefit of International Application No. PCT/JP2012/054624, filed on Feb. 24, 2012, and Japanese Application No. 2012-185866, filed on Aug. 24, 2012, and International Application No. PCT/JP2012/075092, filed on Sep. 28, 2012. The contents of the foregoing U.S. application are incorporated by reference.

SEQUENCE LISTING

This application contains a Sequence Listing that has been submitted electronically as an ASCII text file named SequenceListing.txt. The ASCII text file, created on Jun. 28, 2022, is 204 kilobytes in size. The material in the ASCII text file is hereby incorporated by reference in its entirety.

TECHNICAL FIELD

The present invention provides uses of antigen-binding molecules for eliminating antigens from plasma; methods for eliminating antigens from plasma, which comprise administering antigen-binding molecules; pharmaceutical compositions comprising antigen-binding molecules that are capable of eliminating antigens from plasma; and methods for producing antigen-binding molecules for eliminating antigens from plasma.

BACKGROUND ART

Antibodies are drawing attention as pharmaceuticals as they are highly stable in plasma and have few side effects. At present, a number of IgG-type therapeutic antibodies are available on the market and many therapeutic antibodies are currently under development (Non-patent Documents 1 and 2). Meanwhile, various technologies applicable to second-generation therapeutic antibodies have been reported, including those that enhance effector function, antigen-binding ability, pharmacokinetics, and stability, and those that reduce the risk of immunogenicity (Non-patent Document 3). In general, the requisite dose of a therapeutic antibody is very high. This, in turn, has led to problems, such as high production cost, as well as the difficulty in producing subcutaneous formulations. In theory, the dose of a therapeutic antibody may be reduced by improving antibody pharmacokinetics or improving the affinity between antibodies and antigens.

Literature has reported methods for improving antibody pharmacokinetics using artificial substitution of amino acids in constant regions (Non-patent Documents 4 and 5). Similarly, affinity maturation has been reported as a technology for enhancing antigen-binding activity and/or antigen-neutralizing activity of an antibody (Non-patent Document 6). This technology enables enhancement of antigen-binding activity by introduction of amino acid mutations into the CDR region of a variable region or such. The enhancement of antigen-binding ability enables improvement of in vitro biological activity or reduction of dosage, and further enables improvement of in vivo efficacy (Non-patent Document 7).

The antigen-neutralizing capacity of a single antibody molecule having neutralizing activity depends on its affinity. Therefore, the affinity of antibodies has been enhanced using various methods in order to neutralize antigens with a small amount of antibodies (Non-patent Document 6). Furthermore, if the affinity of the antibody to the antigen could be made infinite by covalent binding to the antigen, a single antibody molecule could neutralize one antigen molecule (a divalent antibody can neutralize two antigen molecules). However, the stoichiometric neutralization reaction of one antibody molecule against one antigen molecule (one divalent antibody against two antigens) is the limit of such methods, and thus it is impossible to completely neutralize antigen with an amount of antibody smaller than the amount of antigen. That is, antigen-neutralizing effect by enhancing affinity has a limit (Non-patent Document 8). To sustain the neutralization effect of a neutralizing antibody for a certain period, the antibody must be administered at a dose higher than the amount of antigens produced in the body during the same period. With just the improvement of antibody pharmacokinetics or affinity maturation technology described above, there is thus a limitation in the reduction of the required antibody dose. Accordingly, in order to sustain the antigen-neutralizing effect for a target period with an amount of antibody smaller than the amount of antigen, a single antibody must neutralize multiple antigens. An antigen-binding molecule that binds to an antigen in a pH- and/or metal ion concentration-dependent manner has recently been reported as a novel method for achieving the above objective (Patent Documents 1 and 2). The ion concentration-dependent antigen-binding molecules, which strongly bind to an antigen under neutral pH and/or high calcium ion concentration conditions in plasma and dissociate from the antigen under acidic pH and/or low calcium ion concentration conditions in the endosome, can dissociate from the antigen in the endosome. When an ion concentration-dependent antigen-binding molecule dissociates from the antigen is recycled to the plasma by FcRn, it can bind to another antigen again. Thus, a single ion concentration-dependent antigen-binding molecule can bind to a number of antigens repeatedly.

On the other hand, the plasma retention of an antigen is very short compared to antibodies recycled via FcRn binding. However, even though the plasma retention of the antigen itself is short, when a typical antibody with such a long plasma retention binds to the antigen, the plasma retention of the antigen-antibody complex is prolonged similar to the antibody. Thus, normally, when an antibody is administered, the antigen bound by the antibody exists in the form of an antigen-antibody complex, which prolongs plasma retention of the antigen (antigen is not easily eliminated from plasma), and causes an increase of plasma antigen concentration. On the other hand, an ion concentration-dependent antigen-binding molecule can suppress increase in plasma antigen concentration by dissociating from the antigen in the endosome. However, this suppression of increase in plasma antigen concentration is affected by the balance with the amount of the antigens produced in vivo. Therefore, the possibility that administration of such ion concentration-dependent antigen-binding molecules may elevate the plasma antigen concentration as compared to before administration was considered (Patent Document 3).

Recently, antigen-binding molecules that bind to FcRn under neutral conditions were produced. Administration of an antigen-binding molecule that binds to an antigen in an ion concentration-dependent manner and binds to FcRn under neutral conditions revealed that the molecule can decrease the plasma antigen concentration as compared to before administration (Patent Document 3). While typical antibodies increase the plasma antigen concentration when administered, antigen-binding molecules having FcRn-binding activity under a neutral pH condition and antigen-binding molecules that bind to an antigen in an ion concentration-dependent manner and having FcRn-binding activity under a neutral pH condition can decrease the plasma antigen concentration when they are administered. Since such antigen-binding molecules can actively eliminate antigens from plasma via endocytosis that takes place as a result of binding to FcRn, these molecules are highly useful as pharmaceuticals.

On the other hand, besides FcRn, several Fcγ receptors (FcγRI, FcγRIIa, FcγRIIb, and FcγRIIIa) exist as receptors for IgG (Non-patent Document 9). Since binding activity of antibodies to activating Fcγ receptors play an important role in an antibody's cytotoxicity, antibodies targeting membrane antigens, whose cytotoxicities have been enhanced by enhancing their binding activity to activating Fcγ receptors have been developed to date (Non-patent Documents 10 and 11). Similarly, since binding activity to inhibitory Fcγ receptor (FcγRIIb) plays an important role in immunosuppression activity (Non-patent Documents 12, 13, and 14), agonistic activity (Non-Patent Documents 15 and 16), and such, antibodies targeting membrane antigens, which have enhanced binding activity to inhibitory Fcγ receptors, are being studied (Non-Patent Documents 17 and 18).

Effects of antibodies that bind to soluble antigens on FcγR binding have been examined mainly from the viewpoint of side effects. For example, it is known that the risk for thromboembolism increased in a group of patients who were administered bevacizumab, an antibody against VEGF (Non-patent Document 19). Similarly, thromboembolism has been observed in clinical development tests of antibodies against the CD40 ligand, and the clinical study was discontinued (Non-patent Document 20). FcγRIIa, an activating Fcγ receptor, is expressed on platelet cells, while an inhibitory Fcγ receptor FcγRIIb is not (Non-patent Document 21), and later studies using animal models and such have suggested that both of the administered antibodies aggregate platelets via binding to FcγRIIa on the platelets, and form blood clots as a result (Non-patent Documents 22 and 23). In patients with systemic lupus erythematosus which is an autoimmune disease, platelets are activated via an FcγRIIa-dependent mechanism, and platelet activation has been reported to correlate with the severity of symptoms (Non-patent Document 24). Furthermore, there are reports that when an antibody with enhanced FcγRIIb-binding is used as a pharmaceutical, a decrease in risk of antibody production can be expected (Non-Patent Document 25), and an antibody that binds to a membrane antigen, whose FcγRIIa-binding has been enhanced, enhances antibody-dependent cellular phagocytosis (ADCP) via macrophages and dendritic cells (Non-patent Document 26). However, the binding activity towards activating and/or inhibitory Fcγ receptors of antibodies targeting soluble antigens had not been known to have an effect on plasma kinetics of antibodies or antigens bound by the antibodies in the organisms administered with the antibodies.

PRIOR ART DOCUMENTS

Patent Documents

[Patent Document 1] WO2009/125825
[Patent Document 2] WO2012/073992
[Patent Document 3] WO2011/122011

Non-Patent Documents

[Non-patent Document 1] Janice M Reichert, Clark J Rosensweig, Laura B Faden & Matthew C Dewitz, Monoclonal antibody successes in the clinic., Nat. Biotechnol. (2005) 23, 1073-1078
[Non-patent Document 2] Pavlou A K, Belsey M J., The therapeutic antibodies market to 2008, Eur. J. Pharm. Biopharm., (2005) 59 (3), 389-396
[Non-patent Document 3] Kim S J, Park Y, Hong H J., Antibody engineering for the development of therapeutic antibodies., Mol. Cells, (2005) 20 (1), 17-29
[Non-patent Document 4] Hinton P R, Xiong J M, Johlfs M G, Tang M T, Keller S, Tsurushita N., An engineered human IgG1 antibody with longer serum half-life., J. Immunol. (2006) 176 (1), 346-356
[Non-patent Document 5] Ghetie V, Popov S, Borvak J, Radu C, Matesoi D, Medesan C, Ober R J, Ward E S., Increasing the serum persistence of an IgG fragment by random mutagenesis., Nat. Biotechnol. (1997) 15 (7), 637-640
[Non-patent Document 6] Rajpal A, Beyaz N, Haber L, Cappuccilli G, Yee H, Bhatt R R, Takeuchi T, Lerner R A, Crea R., A general method for greatly improving the affinity of antibodies by using combinatorial libraries., Proc. Natl. Acad. Sci. U.S.A. (2005) 102 (24), 8466-8471
[Non-patent Document 7] Wu H, Pfarr D S, Johnson S, Brewah Y A, Woods R M, Patel N K, White W I, Young J F, Kiener P A., Development of Motavizumab, an Ultra-potent Antibody for the Prevention of Respiratory Syncytial Virus Infection in the Upper and Lower Respiratory Tract., J. Mol. Biol. (2007) 368, 652-665
[Non-patent Document 8] Hanson C V, Nishiyama Y, Paul S., Catalytic antibodies and their applications., Curr. Opin. Biotechnol. (2005) 16 (6), 631-636
[Non-patent Document 9] Jefferis R, Lund J., Interaction sites on human IgG-Fc for FcgammaR: current models., Immunol. Lett. (2002) 82, 57-65
[Non-patent Document 10] Clynes, R., Yoshizumi, T., Moroi, Y., Houghton, A. N., and Ravetch, J. V., Fc Receptors are required for passive and active immunity to melanoma., Proc. Natl. Acad. Sci. U.S.A. (1998) 95, 652-656
[Non-patent Document 11] Clynes R A, Towers T L, Presta L G, Ravetch J V., Inhibitory Fc receptors modulate in vivo cytoxicity against tumor targets., Nat. Med. (2000) 6, 443-446
[Non-patent Document 12] Wernersson S, Karlsson M C, Dahlstrom J, Mattsson R, Verbeek J S, Heyman B., IgG-mediated enhancement of antibody responses is low in Fc receptor gamma chain-deficient mice and increased in Fc gamma RII-deficient mice., J. Immunol. (1999) 163 (2), 618-622
[Non-patent Document 13] Yuasa T, Kubo S, Yoshino T, Ujike A, Matsumura K, Ono M, Ravetch J V, Takai T., Deletion of fcgamma receptor IIB renders H-2(b) mice susceptible to collagen-induced arthritis., J. Exp. Med. (1999) 189 (1), 187-194

[Non-patent Document 14] Nakamura A, Yuasa T, Ujike A, Ono M, Nukiwa T, Ravetch J V, Takai T., Fcgamma receptor IIB-deficient mice develop Goodpasture's syndrome upon immunization with type IV collagen: a novel murine model for autoimmune glomerular basement membrane disease., J. Exp. Med. (2000) 191 (5), 899-906

[Non-patent Document 15] Li F, Ravetch J V., Inhibitory Fcγ receptor engagement drives adjuvant and anti-tumor activities of agonistic CD40 antibodies., Science (2011) 333 (6045), 1030-1034

[Non-patent Document 16] Wilson N S, Yang B, Yang A, Loeser S, Marsters S, Lawrence D, Li Y, Pitti R, Totpal K, Yee S, Ross S, Vernes J M, Lu Y, Adams C, Offringa R, Kelley B, Hymowitz S, Daniel D, Meng G, Ashkenazi A., An Fcγ receptor-dependent mechanism drives antibody-mediated target-receptor signaling in cancer cells., Cancer Cell (2011) 19 (1), 101-113

[Non-patent Document 17] Moore G L, Chen H, Karki S, Lazar G A., Engineered Fc variant antibodies with enhanced ability to recruit complement and mediate effector functions., Mol. Immunol. (2008) 45, 3926-3933

[Non-patent Document 18] Li F, Ravetch J V., Apoptotic and antitumor activity of death receptor antibodies require inhibitory Fcγ receptor engagement., Proc. Natl. Acad. Sci. USA. (2012) 109 (27), 10966-10971

[Non-patent Document 19] Scappaticci F A, Skillings J R, Holden S N, Gerber H P, Miller K, Kabbinavar F, Bergsland E, Ngai J, Holmgren E, Wang J, Hurwitz H., Arterial thromboembolic events in patients with metastatic carcinoma treated with chemotherapy and bevacizumab., J. Natl. Cancer Inst. (2007) 99 (16), 1232-1239

[Non-patent Document 20] Boumpas D T, Furie R, Manzi S, Illei G G, Wallace D J, Balow J E, Vaishnaw A, A short course of BG9588 (anti-CD40 ligand antibody) improves serologic activity and decreases hematuria in patients with proliferative lupus glomerulonephritis., Arthritis. Rheum. (2003) 48 (3), 719-727.

[Non-patent Document 21] Mackay M, Stanevsky A, Wang T, Aranow C, Li M, Koenig S, Ravetch J V, Diamond B., Selective dysregulation of the FcgammaIIB receptor on memory B cells in SLE., J. Exp. Med. (2006) 203 (9), 2157-2164

[Non-patent Document 22] Meyer T, Robles-Carrillo L, Robson T, Langer F, Desai H, Davila M, Amaya M, Francis J L, Amirkhosravi A., Bevacizumab immune complexes activate platelets and induce thrombosis in FCGR2A transgenic mice., J. Thromb. Haemost. (2009) 7 (1), 171-181

[Non-patent Document 23] Robles-Carrillo L, Meyer T, Hatfield M, Desai H, Davila M, Langer F, Amaya M, Garber E, Francis J L, Hsu Y M, Amirkhosravi A., Anti-CD40L immune complexes potently activate platelets in vitro and cause thrombosis in FCGR2A transgenic mice., J. Immunol. (2010) 185 (3), 1577-1583

[Non-patent Document 24] Duffau P, Seneschal J, Nicco C, Richez C, Lazaro E, Douchet I, Bordes C, Viallard J F, Goulvestre C, Pellegrin J L, Weil B, Moreau J F, Batteux F, Blanco P., Platelet CD154 potentiates interferon-alpha secretion by plasmacytoid dendritic cells in systemic lupus erythematosus., Sci. Transl. Med. (2010) 2 (47), 47-63

[Non-patent Document 25] Desai D D, Harbers S O, Flores M, Colonna L, Downie M P, Bergtold A, Jung S,

6

Clynes R., Fc gamma receptor JIB on dendritic cells enforces peripheral tolerance by inhibiting effector T cell responses., J. Immunol. (2007) 178 (10), 6217-6226

[Non-patent Document 26] Richards J O, Karki S, Lazar G A, Chen H, Dang W, Desjarlais J R., Optimization of antibody binding to FcgammaRIIa enhances macrophage phagocytosis of tumor cells., Mol. Cancer Ther. (2008) 7 (8) 2517-2527

SUMMARY OF THE INVENTION

Problems to be Solved by the Invention

The present invention was achieved in view of the above circumstances. As mentioned above, the binding activity towards activating and/or inhibitory Fcγ receptors of antibodies targeting soluble antigens had not been known to have an effect on plasma kinetics of antibodies or antigens bound by the antibodies in the organisms administered with the antibodies. More specifically, an objective of the present invention is to suppress increase in plasma concentration of an antigen bound by an antigen-binding molecule by administering the antigen-binding molecule that has a binding activity towards a pathogenic antigen present in a soluble form in plasma, and also has a desired binding activity towards activating and/or inhibitory Fcγ receptors. Another objective of the present invention is to optimize the binding activity towards activating and/or inhibitory Fcγ receptors of antigen-binding molecules against the disease-causing antigens present in a soluble form in plasma, and thereby optimize the suppression of the increase in plasma concentration of antigens bound by the antigen-binding molecules.

Means for Solving the Problems

Specifically, the present invention provides antigen-binding molecules comprising (i) an antigen-binding domain whose antigen-binding activity varies depending on ion concentration conditions, (ii) an FcγR-binding domain having FcγRIIb-selective binding activity, and (iii) an FcRn-binding domain having FcRn-binding activity under an acidic pH range condition, and methods for decreasing plasma concentration of the antigen as compared to before administering the antigen-binding molecule, which comprises the step of administering the molecule. Furthermore, the present invention provides agents for decreasing plasma concentration of the antigen, which comprise an antigen-binding molecule comprising (i) an antigen-binding domain whose antigen-binding activity varies depending on ion concentration conditions, (ii) an FcγR-binding domain having FcγRIIb-selective binding activity, and (iii) an FcRn-binding domain having FcRn-binding activity under an acidic pH range condition. The present invention also provides pharmaceutical compositions which comprise an antigen-binding molecule comprising (i) an antigen-binding domain whose antigen-binding activity varies depending on ion concentration conditions, (ii) an FcγR-binding_domain having FcγRIIb-selective binding activity, and (iii) an FcRn-binding domain having FcRn-binding activity under an acidic pH range condition. The present invention also provides uses of the antigen-binding molecule for decreasing plasma concentration of the antigen, wherein the molecule comprises (i) an antigen-binding domain whose antigen-binding activity varies depending on ion concentration conditions, (ii) an FcγR-binding domain having FcγRIIb-selective binding activity, and (iii) an FcRn-binding domain having FcRn-binding activity under an acidic pH range condition. In addition to the above, the present invention provides methods of producing and/or methods of screening for the antigen-binding molecules. Although it is not particularly intended to limit the invention, specifically, the following is provided as a non-limiting embodiment:

[1] use of an antigen-binding molecule for eliminating antigen from plasma, wherein the antigen-binding molecule comprises an antigen-binding domain whose antigen-binding activity varies depending on ion concentration conditions, and an Fc region in which the amino acid at position 238 is Asp and the amino acid at position 271 is Gly as indicated by EU numbering;

[2] the use of [1], wherein the Fc region has an amino acid substitution at at least one or more positions selected from the group consisting of 233, 234, 237, 264, 265, 266, 267, 268, 269, 272, 274, 296, 326, 327, 330, 331, 332, 333, 355, 356, 358, 396, 409, and 419 as indicated by EU numbering;

[3] the use of [2], wherein the amino acids of the Fc region include any one or more of the following amino acids indicated by EU numbering:

Asp at amino acid position 233;

Tyr at amino acid position 234;

Asp at amino acid position 237;

Ile at amino acid position 264;

Glu at amino acid position 265;

any one of Phe, Met, and Leu at amino acid position 266;

any one of Ala, Glu, Gly, and Gln at amino acid position 267;

any one of Asp, Glu, and Gln at amino acid position 268;

Asp at amino acid position 269;

any one of Asp, Phe, Ile, Met, Asn, Pro, and Gln at amino acid position 272;

Gln at amino acid position 274;

Asp or Phe at amino acid position 296;

Ala or Asp at amino acid position 326;

Gly at amino acid position 327;

Lys or Arg at amino acid position 330;

Ser at amino acid position 331;

Thr at amino acid position 332;

any one of Thr, Lys, and Arg at amino acid position 333;

Gln at amino acid position 355;

Glu at amino acid position 356;

Met at amino acid position 358;

any one of Asp, Glu, Phe, Ile, Lys, Leu, Met, Gln, Arg, and Tyr at amino acid position 396;

Arg at amino acid position 409; and

Glu at amino acid position 419;

[4] the use of any one of [1] to [3], wherein the antigen-binding domain is an antigen-binding domain whose antigen-binding activity varies depending on calcium ion concentration conditions;

[5] the use of [4], wherein the antigen-binding domain is an antigen-binding domain whose antigen-binding activity varies such that the antigen-binding activity under a low calcium ion concentration condition is lower than an antigen-binding activity under a high calcium ion concentration condition;

[6] the use of any one of [1] to [3], wherein the antigen-binding domain is an antigen-binding domain whose antigen-binding activity varies depending on pH conditions;

[7] the use of [6], wherein the antigen-binding domain is an antigen-binding domain whose antigen-binding activity varies such that the antigen-binding activity under an acidic pH range condition is lower than an antigen-binding activity under a neutral pH range condition;

[8] the use of any one of [1] to [7], wherein the antigen-binding domain is an antibody variable region;

[9] the use of any one of [1] to [8], wherein the Fc region is an Fc region in which the amino acid at position 238 is Asp and the amino acid at position 271 is Gly as indicated by EU numbering in the Fc region included in any one of SEQ ID NOs: 14, 15, 16, or 17;

[10] the use of any one of [1] to [8], wherein the FcRn-binding activity of the Fc region under an acidic pH range condition is enhanced compared to the FcRn-binding activity of the Fc region included in any one of SEQ ID NO: 14, 15, 16, or 17;

[11] the use of [10], wherein the Fc region with enhanced binding is an Fc region having an amino acid substitution at least one or more positions selected from the group consisting of 244, 245, 249, 250, 251, 252, 253, 254, 255, 256, 257, 258, 260, 262, 265, 270, 272, 279, 283, 285, 286, 288, 293, 303, 305, 307, 308, 309, 311, 312, 314, 316, 317, 318, 332, 339, 340, 341, 343, 356, 360, 362, 375, 376, 377, 378, 380, 382, 385, 386, 387, 388, 389, 400, 413, 415, 423, 424, 427, 428, 430, 431, 433, 434, 435, 436, 438, 439, 440, 442, and 447, as indicated by EU numbering, in the amino acid sequence of the Fc region included in any one of SEQ ID NO: 14, 15, 16, or 17;

[12] the use of [11], wherein the Fc region with enhanced binding comprises at least one or more amino acids selected from the group consisting of:

Leu at amino acid position 244;

Arg at amino acid position 245;

Pro at amino acid position 249;

Gln or Glu at amino acid position 250;

any one of Arg, Asp, Glu, and Leu at amino acid position 251;

any one of Phe, Ser, Thr, and Tyr at amino acid position 252;

Ser or Thr at amino acid position 254;

any one of Arg, Gly, Ile, and Leu at amino acid position 255;

any one of Ala, Arg, Asn, Asp, Gln, Glu, Pro, and Thr at amino acid position 256;

any one of Ala, Ile, Met, Asn, Ser, and Val at amino acid position 257;

Asp at amino acid position 258;

Ser at amino acid position 260;

Leu at amino acid position 262;

Lys at amino acid position 270;

Leu or Arg at amino acid position 272;

any one of Ala, Asp, Gly, His, Met, Asn, Gln, Arg, Ser, Thr, Trp, and Tyr at amino acid position 279;

any one of Ala, Asp, Phe, Gly, His, Ile, Lys, Leu, Asn, Pro, Gln, Arg, Ser, Thr, Trp, and Tyr at amino acid position 283;

Asn at amino acid position 285;

Phe at amino acid position 286;

Asn or Pro at amino acid position 288;

Val at amino acid position 293;

any one of Ala, Glu, Gln, and Met at amino acid position 307;

any one of Ile, Pro, and Thr at amino acid position 308;

Pro at amino acid position 309;

any one of Ala, Glu, Ile, Lys, Leu, Met, Ser, Val, and Trp at amino acid position 311;

any one of Ala, Asp, and Pro at amino acid position 312;

Ala or Leu at amino acid position 314;

Lys at amino acid position 316;

Pro at amino acid position 317;

Asn or Thr at amino acid position 318;

any one of Phe, His, Lys, Leu, Met, Arg, Ser, and Trp at amino acid position 332;

any one of Asn, Thr, and Trp at amino acid position 339;

Pro at amino acid position 341;

any one of Glu, His, Lys, Gln, Arg, Thr, or Tyr at amino acid position 343;

Arg at amino acid position 375;

any one of Gly, Ile, Met, Pro, Thr, and Val at amino acid position 376;

Lys at amino acid position 377;

any one of Asp, Asn, and Val at amino acid position 378;

any one of Ala, Asn, Ser, and Thr at amino acid position 380;

any one of Phe, His, Ile, Lys, Leu, Met, Asn, Gln, Arg, Ser, Thr, Val, Trp, and Tyr at amino acid position 382;

any one of Ala, Arg, Asp, Gly, His, Lys, Ser, and Thr at amino acid position 385;

any one of Arg, Asp, Ile, Lys, Met, Pro, Ser, and Thr at amino acid position 386;

any one of Ala, Arg, His, Pro, Ser, and Thr at amino acid position 387;

any one of Asn, Pro, and Ser at amino acid position 389;

Asn at amino acid position 423;

Asn at amino acid position 427;

any one of Leu, Met, Phe, Ser, and Thr at amino acid position 428;

any one of Ala, Phe, Gly, His, Ile, Lys, Leu, Met, Asn, Gln, Arg, Ser, Thr, Val, and Tyr at amino acid position 430;

His or Asn at amino acid position 431;

any one of Arg, Gln, His, Ile, Lys, Pro, and Ser at amino acid position 433;

any one of Ala, Gly, His, Phe, Ser, Trp, and Tyr at amino acid position 434;

any one of Arg, Asn, His, Ile, Leu, Lys, Met, and Thr at amino acid position 436;

any one of Lys, Leu, Thr, and Trp at amino acid position 438;

Lys at amino acid position 440; and

Lys at amino acid position 442 as indicated by EU numbering, in the amino acid sequence of the Fc region included in any one of SEQ ID NO: 14, 15, 16, or 17;

[13] the use of any one of [1] to [12], wherein the antigen-binding molecule is an antibody;

[14] a pharmaceutical composition comprising an antigen-binding molecule which comprises an antigen-binding domain whose antigen-binding activity varies depending on ion concentration conditions, and an Fc region in which the amino acid at position 238 is Asp and the amino acid at position 271 is Gly as indicated by EU numbering;

[15] the pharmaceutical composition of [14], wherein the Fc region has an amino acid substitution at at least one or more positions selected from the group consisting of 233, 234, 237, 264, 265, 266, 267, 268, 269, 272, 274, 296, 326, 327, 330, 331, 332, 333, 355, 356, 358, 396, 409, and 419 as indicated by EU numbering;

[16] the pharmaceutical composition of [15], wherein the amino acids of the Fc region include any one or more of the following amino acids indicated by EU numbering:

Asp at amino acid position 233;

Tyr at amino acid position 234;

Asp at amino acid position 237;

Ile at amino acid position 264;

Glu at amino acid position 265;

any one of Phe, Met, and Leu at amino acid position 266;

any one of Ala, Glu, Gly, and Gln at amino acid position 267;

any one of Asp, Glu, and Gln at amino acid position 268;

Asp at amino acid position 269;

any one of Asp, Phe, Ile, Met, Asn, Pro, and Gln at amino acid position 272;

Gln at amino acid position 274;

Asp or Phe at amino acid position 296;

Ala or Asp at amino acid position 326;

Gly at amino acid position 327;

Lys or Arg at amino acid position 330;

Ser at amino acid position 331;

Thr at amino acid position 332;

any one of Thr, Lys, and Arg at amino acid position 333;

Gln at amino acid position 355;

Glu at amino acid position 356;

Met at amino acid position 358;

any one of Asp, Glu, Phe, Ile, Lys, Leu, Met, Gln, Arg, and Tyr at amino acid position 396;

Arg at amino acid position 409; and

Glu at amino acid position 419;

[17] a method of producing an antigen-binding molecule, comprising the steps of (a) to (e) below:

(a) obtaining an antigen-binding domain whose antigen-binding activity varies depending on ion concentration conditions;

(b) obtaining a gene encoding the antigen-binding domain selected in step (a);

(c) operably linking the gene obtained in step (b) with a gene encoding an Fc region in which the amino acid at position 238 is Asp and the amino acid at position 271 is Gly as indicated by EU numbering;

(d) culturing host cells containing the gene operably linked in step (c); and (e) isolating an antigen-binding molecule from the culture solution obtained in step (d);

[18] the production method of [17], wherein the Fc region has an amino acid substitution at at least one or more positions selected from the group consisting of 233, 234, 237, 264, 265, 266, 267, 268, 269, 272, 274, 296, 326, 327, 330, 331, 332, 333, 355, 356, 358, 396, 409, and 419 as indicated by EU numbering;

[19] the production method of [18], wherein the amino acids of the Fc region include any one or more of the following amino acids indicated by EU numbering:

Asp at amino acid position 233;

Tyr at amino acid position 234;

Asp at amino acid position 237;

Ile at amino acid position 264;

Glu at amino acid position 265;

any one of Phe, Met, and Leu at amino acid position 266;

any one of Ala, Glu, Gly, and Gln at amino acid position 267;

any one of Asp, Glu, and Gln at amino acid position 268;

Asp at amino acid position 269;

any one of Asp, Phe, Ile, Met, Asn, Pro, and Gln at amino acid position 272;

Gln at amino acid position 274;

Asp or Phe at amino acid position 296;

Ala or Asp at amino acid position 326;

Gly at amino acid position 327;

Lys or Arg at amino acid position 330;

Ser at amino acid position 331;

Thr at amino acid position 332;

any one of Thr, Lys, and Arg at amino acid position 333;

Gln at amino acid position 355;

Met at amino acid position 356;

Met at amino acid position 358;

any one of Asp, Glu, Phe, Ile, Lys, Leu, Met, Gln, Arg, and Tyr at amino acid position 396;

Arg at amino acid position 409; and

Glu at amino acid position 419;

[20] a method of producing a pharmaceutical composition comprising an antigen-binding molecule, which comprises the steps of:

(a) obtaining an antigen-binding domain whose antigen-binding activity varies depending on ion concentration conditions;

(b) obtaining a gene encoding the antigen-binding domain selected in step (a);

(c) operably linking the gene obtained in step (b) with a gene encoding an Fc region in which the amino acid at position 238 (EU numbering) is Asp and the amino acid at position 271 (EU numbering) is Gly;

(d) culturing host cells containing the gene operably linked in step (c); and (e) isolating an antigen-binding molecule from the culture solution obtained in step (d);

[21] the production method of [20], wherein the Fc region has an amino acid substitution at least one or more positions selected from the group consisting of positions 233, 234, 237, 264, 265, 266, 267, 268, 269, 272, 274, 296, 326, 327, 330, 331, 332, 333, 355, 356, 358, 396, 409, and 419 (EU numbering);

[22] the production method of [21], wherein the amino acids of the Fc region include any one or more of the following amino acids indicated by EU numbering:

Asp at amino acid position 233;

Tyr at amino acid position 234;

Asp at amino acid position 237;

Ile at amino acid position 264;

Glu at amino acid position 265;

any one of Phe, Met, and Leu at amino acid position 266;

any one of Ala, Glu, Gly, and Gln at amino acid position 267;

any one of Asp, Glu, and Gln at amino acid position 268;

Asp at amino acid position 269;

any one of Asp, Phe, Ile, Met, Asn, Pro, and Gln at amino acid position 272;

Gln at amino acid position 274;

Asp or Phe at amino acid position 296;

Ala or Asp at amino acid position 326;

Gly at amino acid position 327;

Lys or Arg at amino acid position 330;

Ser at amino acid position 331;

Thr at amino acid position 332;

any one of Thr, Lys, and Arg at amino acid position 333;

Gln at amino acid position 355;

Glu at amino acid position 356;

Met at amino acid position 358;

any one of Asp, Glu, Phe, Ile, Lys, Leu, Met, Gln, Arg, and Tyr at amino acid position 396;

Arg at amino acid position 409; and

Glu at amino acid position 419;

[23] a method of eliminating an antigen from plasma, which comprises administering an effective amount of an antigen-binding molecule comprising an antigen-binding domain whose antigen-binding activity varies depending on ion concentration conditions, and an Fc region in which the amino acid at position 238 is Asp and the amino acid at position 271 is Gly as indicated by EU numbering;

[24] the method of [23], wherein the Fc region has an amino acid substitution at least one or more positions selected from the group consisting of 233, 234, 237, 264, 265, 266, 267, 268, 269, 272, 274, 296, 326, 327, 330, 331, 332, 333, 355, 356, 358, 396, 409, and 419 as indicated by EU numbering;

[25] the method of [24], wherein the amino acids of the Fc region include any one or more of the following amino acids indicated by EU numbering:

Asp at amino acid position 233;

Tyr at amino acid position 234;

Asp at amino acid position 237;

Ile at amino acid position 264;

Glu at amino acid position 265;

any one of Phe, Met, and Leu at amino acid position 266;

any one of Ala, Glu, Gly, and Gln at amino acid position 267;

any one of Asp, Glu, and Gln at amino acid position 268;

Asp at amino acid position 269;

any one of Asp, Phe, Ile, Met, Asn, Pro, and Gln at amino acid position 272;

Gln at amino acid position 274;

Asp or Phe at amino acid position 296;

Ala or Asp at amino acid position 326;

Gly at amino acid position 327;

Lys or Arg at amino acid position 330;

Ser at amino acid position 331;

Thr at amino acid position 332;

any one of Thr, Lys, and Arg at amino acid position 333;

Gln at amino acid position 355;

Glu at amino acid position 356;

Met at amino acid position 358;

any one of Asp, Glu, Phe, Ile, Lys, Leu, Met, Gln, Arg, and Tyr at amino acid position 396;

Arg at amino acid position 409; and

Glu at amino acid position 419;

[26] the method of any one of [23] to [25], wherein the antigen-binding domain is an antigen-binding domain whose antigen-binding activity varies depending on calcium ion concentration conditions;

[27] the method of [26], wherein the antigen-binding domain is an antigen-binding domain whose antigen-binding activity varies such that the antigen-binding activity under a low calcium ion concentration condition is lower than an antigen-binding activity under a high calcium ion concentration condition;

[28] the method of any one of [23] to [25], wherein the antigen-binding domain is an antigen-binding domain whose antigen-binding activity varies depending on pH conditions;

[29] the method of [28], wherein the antigen-binding domain is an antigen-binding domain whose antigen-binding activity varies such that the antigen-binding activity under an acidic pH range condition is lower than an antigen-binding activity under a neutral pH range condition;

[30] the method of any one of [23] to [29], wherein the antigen-binding domain is an antibody variable region;

[31] the method of any one of [23] to [30], wherein the aforementioned Fc region is the Fc region contained in any one of SEQ ID NOs: 14, 15, 16, or 17 in which the amino acid at position 238 is Asp and the amino acid at position 271 is Gly as indicated by EU numbering;

[32] the method of any one of [23] to [30], wherein the FcRn-binding activity of the Fc region under an acidic pH range condition is enhanced compared to the FcRn-binding activity of the Fc region contained in any one of SEQ ID NO: 14, 15, 16, or 17;

[33] the method of [32], wherein the Fc region with enhanced binding is an Fc region having an amino acid substitution at least one or more positions selected from the group consisting of positions 244, 245, 249, 250, 251, 252, 253, 254, 255, 256, 257, 258, 260, 262, 265, 270, 272, 279, 283, 285, 286, 288, 293, 303, 305, 307, 308, 309, 311, 312, 314, 316, 317, 318, 332, 339, 340, 341, 343, 356, 360, 362, 375, 376, 377, 378, 380, 382, 385, 386, 387, 388, 389, 400, 413, 415, 423, 424, 427, 428, 430, 431, 433, 434, 435, 436, 438, 439, 440, 442, and 447, as indicated by EU numbering, in the amino acid sequence of the Fc region contained in any one of SEQ ID NO: 14, 15, 16, or 17;

[34] the method of [33], wherein the Fc region with enhanced binding comprises at least one or more amino acids selected from the group consisting of:

Leu at amino acid position 244;

Arg at amino acid position 245;

Pro at amino acid position 249;

Gln or Glu at amino acid position 250;

any one of Arg, Asp, Glu, and Leu at amino acid position 251;

any one of Phe, Ser, Thr, and Tyr at amino acid position 252;

Ser or Thr at amino acid position 254;

any one of Arg, Gly, Ile, and Leu at amino acid position 255;

any one of Ala, Arg, Asn, Asp, Gln, Glu, Pro, and Thr at amino acid position 256;

any one of Ala, Ile, Met, Asn, Ser, and Val at amino acid position 257;

Asp at amino acid position 258;

Ser at amino acid position 260;

Leu at amino acid position 262;

Lys at amino acid position 270;

Leu or Arg at amino acid position 272;

any one of Ala, Asp, Gly, His, Met, Asn, Gln, Arg, Ser, Thr, Trp, and Tyr at amino acid position 279;

any one of Ala, Asp, Phe, Gly, His, Ile, Lys, Leu, Asn, Pro, Gln, Arg, Ser, Thr, Trp, and Tyr at amino acid position 283;

Asn at amino acid position 285;

Phe at amino acid position 286;

Asn or Pro at amino acid position 288;

Val at amino acid position 293;

any one of Ala, Glu, Gln, and Met at amino acid position 307;

any one of Ile, Pro, and Thr at amino acid position 308;

Pro at amino acid position 309;

any one of Ala, Glu, Ile, Lys, Leu, Met, Ser, Val, and Trp at amino acid position 311;

any one of Ala, Asp, and Pro at amino acid position 312;

Ala or Leu at amino acid position 314;

Lys at amino acid position 316;

Pro at amino acid position 317;

Asn or Thr at amino acid position 318;

any one of Phe, His, Lys, Leu, Met, Arg, Ser, and Trp at amino acid position 332;

any one of Asn, Thr, and Trp at amino acid position 339;

Pro at amino acid position 341;

any one of Glu, His, Lys, Gln, Arg, Thr, and Tyr at amino acid position 343;

Arg at amino acid position 375;

any one of Gly, Ile, Met, Pro, Thr, and Val at amino acid position 376;

Lys at amino acid position 377;

any one of Asp, Asn, or Val and amino acid position 378;

any one of Ala, Asn, Ser, and Thr at amino acid position 380;

any one of Phe, His, Ile, Lys, Leu, Met, Asn, Gln, Arg, Ser, Thr, Val, Trp, and Tyr at amino acid position 382;

any one of Ala, Arg, Asp, Gly, His, Lys, Ser, and Thr at amino acid position 385;

any one of Arg, Asp, Ile, Lys, Met, Pro, Ser, and Thr at amino acid position 386;

any one of Ala, Arg, His, Pro, Ser, and Thr at amino acid position 387;

any one of Asn, Pro, and Ser at amino acid position 389;

Asn at amino acid position 423;

Asn at amino acid position 427;

any one of Leu, Met, Phe, Ser, and Thr at amino acid position 428;

any one of Ala, Phe, Gly, His, Ile, Lys, Leu, Met, Asn, Gln, Arg, Ser, Thr, Val, and Tyr at amino acid position 430;

His or Asn at amino acid position 431;

any one of Arg, Gln, His, Ile, Lys, Pro, and Ser at amino acid position 433;

any one of Ala, Gly, His, Phe, Ser, Trp, and Tyr at amino acid position 434;

any one of Arg, Asn, His, Ile, Leu, Lys, Met, and Thr at amino acid position 436;

any one of Lys, Leu, Thr, and Trp at amino acid position 438;

Lys at amino acid position 440; and

Lys at amino acid position 442 as indicated by EU numbering, in the amino acid sequence of the Fc region contained in any one of SEQ ID NO: 14, 15, 16, or 17; and

[35] the method of any one of [23] to [34], wherein the antigen-binding molecule is an antibody.

In the present invention, the following phrases are used synonymously: "use of an antigen-binding molecule for eliminating antigen from plasma, wherein the antigen-binding molecule comprises an antigen-binding domain whose antigen-binding activity varies depending on ion concentration conditions, and an Fc region in which the amino acid at position 238 is Asp and the amino acid at position 271 is Gly as indicated by EU numbering"; "a method for treating a disease caused by an antigen, which comprises administering an antigen-binding molecule comprising an antigen-binding domain whose antigen-binding activity varies depending on ion concentration conditions, and an Fc region in which the amino acid at position 238 is Asp and the amino acid at position 271 is Gly as indicated by EU numbering"; "a pharmaceutical composition comprising an antigen-binding molecule which comprises an antigen-binding domain whose antigen-binding activity varies depending on ion concentration condition, and an Fc region in which the amino acid at position 238 is Asp and the amino acid at position 271 is Gly as indicated by EU numbering"; "use of an antigen-binding molecule in producing a pharmaceutical composition, wherein the antigen-binding molecule comprises an antigen-binding domain whose antigen-binding activity varies depending on ion concentration condition, and an Fc region in which the amino acid at position 238 is Asp and the amino acid at position 271 is Gly as indicated by EU numbering"; and "a process for producing a pharmaceutical composition, which comprises using an antigen-binding molecule comprising an antigen-binding domain whose antigen-binding activity varies depending on ion concentration condition, and an Fc region in which the amino acid at position 238 is Asp and the amino acid at position 271 is Gly as indicated by EU numbering".

MODE FOR CARRYING OUT THE INVENTION

Figure 1:
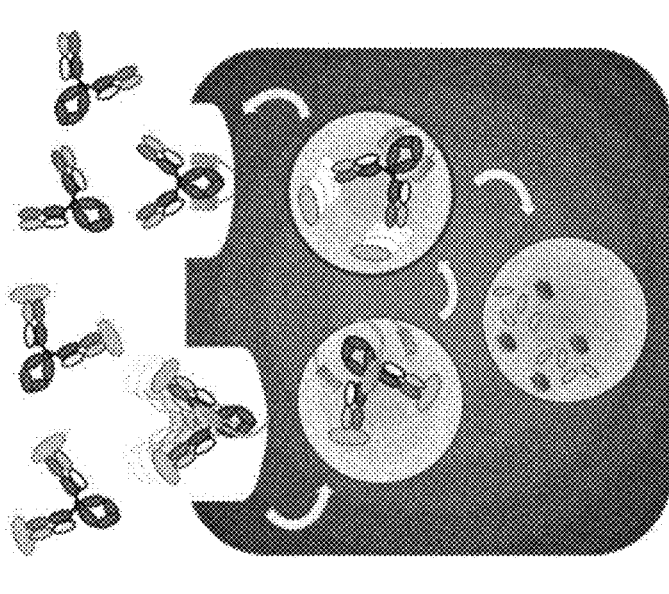
FIG. 1 shows a non-limiting action mechanism for the elimination of soluble antigen from plasma by administering an antibody that binds to an antigen in an ion concentration-dependent manner and whose Fcγ receptor binding is enhanced at a neutral pH as compared to existing neutralizing antibodies.
Figure 1:
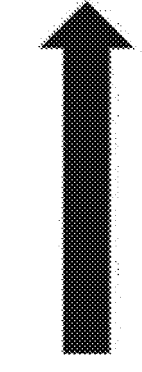
Figure 1:
Figure 1:
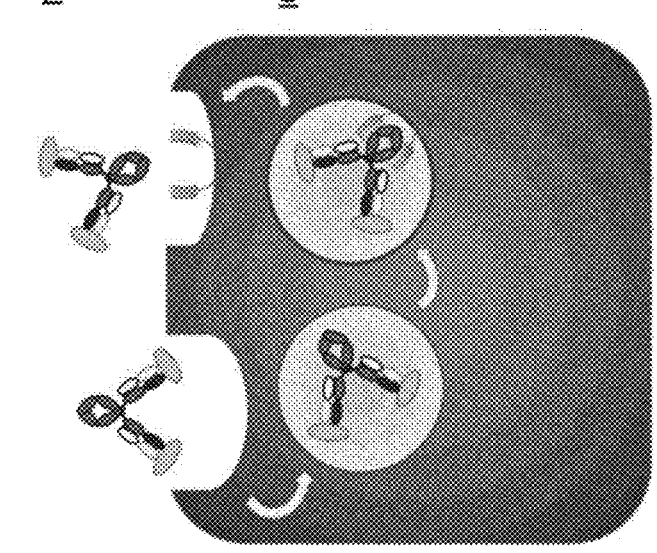

The definitions and detailed description below are provided to help the understanding of the present invention illustrated herein.

Amino Acids

Herein, amino acids are described in one- or three-letter codes or both, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

Alteration of Amino Acids

For amino acid alterations in the amino acid sequence of an antigen-binding molecule, known methods such as site-directed mutagenesis methods (Kunkel et al. (Proc. Natl. Acad. Sci. USA (1985) 82, 488-492)) and overlap extension PCR may be appropriately employed. Additions, deletions, and/or substitutions of an amino acid are added appropriately by these known methods. Substituting amino acid residues means substituting an amino acid residue with another amino acid residue for the purpose of altering aspects such as the following (a) to (c):

(a) backbone structure of a polypeptide in a helical structure region or a sheet structure region;

(b) charge or hydrophobicity at a target site; or (c) length of a side chain.

Amino acid residues are classified into the following groups based on the properties of side chains included in their structures:

(1) hydrophobic: norleucine, Met, Ala, Val, Leu, and Ile;

(2) neutral hydrophilic: Cys, Ser, Thr, Asn, and Gln:

(3) acidic: Asp and Glu;

(4) basic: His, Lys, and Arg;

(5) residues that affect the orientation of the chain: Gly and Pro; and (6) aromatic: Trp, Tyr, and Phe.

Substitution between amino acid residues within each of these groups is referred to as conservative substitution. On the other hand, substitution between amino acid residues from different amino acid groups is referred to as non-conservative substitution. Substitutions in the present invention may be conservative substitutions or non-conservative substitutions, or a combination of conservative and non-conservative substitutions. Furthermore, a plurality of known methods may be employed as amino acid alteration methods for substitution to non-native amino acids (Annu. Rev. Biophys. Biomol. Struct. (2006) 35, 225-249; and Proc. Natl. Acad. Sci. U.S.A. (2003) 100 (11), 6353-6357). For example, a cell-free translation system (Clover Direct (Protein Express)) containing a tRNA which has the non-native amino acid bound to a complementary amber suppressor tRNA of the UAG codon (amber codon), which is one of the stop codons, is suitably used.

Furthermore, an expression that uses one-letter amino-acid codes of the amino acid before alteration and the amino acid after the alteration before and after a number indicating a specific position, respectively, may be used appropriately as an expression for an amino acid alteration. For example, the alteration P238D, which is used when substituting an amino acid of the Fc region included in an antibody constant region, expresses substitution of Pro at position 238 (according to EU numbering) with Asp. That is, the number shows the position of the amino acid according to EU numbering, the one-letter amino-acid code written before the number shows the amino acid before substitution, and the one-letter amino-acid code written after the number shows the amino acid after substitution.

And/or

As used herein, the term "and/or" means a combination of the terms before and after the set phrase "and/or", and includes every combination where "and" and "or" are suitably combined. Specifically, for example, "the amino acids at positions 326, 328, and/or 428 are substituted" includes a variation of alterations of the following amino acids:

amino acid(s) at (a) position 326, (b) position 328, (c) position 428, (d) positions 326 and 328, (e) positions 326 and 428, (f) positions 328 and 428, and (g) positions 326, 328, and 428.

Antigens

Herein, "antigens" are not particularly limited in their structure, as long as they comprise epitopes to which antigen-binding domains bind. In other words, antigens can be inorganic or organic substances. Antigens include, for example, the molecules below: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAM8, ADAM9, ADAMTS, ADAMTS4, ADAMTS5, addressin, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic peptide, av/b3 integrin, Ax1, b2M, B7-1, B7-2, B7-H, B-lymphocyte stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, C5a, C10, CA125, CAD-8, calcitonin, cAMP, carcinoembryonic antigen (CEA), cancer associated antigen, cathepsin A, cathepsin B, cathepsin C/DPPI, cathepsin D, cathepsin E, cathepsin H, cathepsin L, cathepsin 0, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, Botulinum toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor associated antigen, DAN, DCC, DcR3, DC-SIGN, complement regulatory factor (Decay accelerating factor), des (1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast activation protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha1, GFR-alpha2, GFR-alpha3, GITR, glucagon, Glut4, glycoprotein IIb/IIa (GPIIb/IIIa), GM-CSF, gp130, gp72, GRO, growth hormone releasing hormone, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high molecular weight melanoma-associated antigen (HMW-MAA), HIV gp120, HIV MB gp 120 V3 loop, HLA, HLA-DR, HM1.24, HMFGPEM, HRG, Hrk, human cardiac myosin, human cytomegalovirus (HCMV), human growth hormone (HGH), HVEM, 1-309, TAP, ICAM, ICAM-1, ICAM-3, ICE, ICOS, IFNg, Ig, IgA receptor, IgE, IGF, IGF binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, inhibin, iNOS, insulin A chain, insulin B chain, insulin-like growth factor1, integrin alpha2, integrin alpha3, integrin alpha4, integrin alpha4/beta1, integrin alpha4/beta7, integrin alpha5 (alpha V), integrin alpha5/beta1, integrin alpha5/beta3, integrin alpha6, integrin beta1, integrin beta2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bp1, LBP, LDGF, LECT2, lefty, Lewis-Y antigen, Lewis-Y associated antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, METALLO-PROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mucl1), MUC18, Mullerian-inhibiting substance, Mug, MuSK, NAIP, NAP, NCAD, N-C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, Rheumatoid factor, RLIP76, RPA2, RSK, S100, SCF/KL, SDF-1, SER-INE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glyco-protein-72), TARC, TCA-3, T-cell receptor (for example, T-cell receptor alpha/beta), TdT, TECK, TEM1, TEM5, TEM7, TEM8, TERT, testis PLAP-like alkaline phosphatase, TfR, TGF, TGF-alpha, TGF-beta, TGF-beta Pan Specific, TGF-betaRI (ALK-5), TGF-betaRII, TGF-betaR-IIb, TGF-betaRIII, TGF-beta1, TGF-beta2, TGF-beta3, TGF-beta4, TGF-beta5, thrombin, thymus Ck-1, thyroid-stimulating hormone, Tie, TIMP, TIQ, tissue factor, TMEFF2, Tmpo, TMPRSS2, TNF, TNF-alpha, TNF-alpha-beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TSG, TSLP, tumor associated antigen CA125, tumor associated antigen expressing Lewis-Y associated carbohydrates, TWEAK, TXB2, Ung, uPAR, uPAR-1, urokinase, VCAM, VCAM-1, VECAD, VE-Cadherin, VE-cadherin-2, VEFGR-1 (fit-1), VEGF, VEGFR, VEGFR-3 (fit-4), VEGI, VIM, virus antigen, VLA, VLA-1, VLA-4, VNR integrin, von Willebrand factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, Aβ, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high molecular weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, and S1P; and receptors for hormone and growth factors.

While receptors are recited as examples of the above-mentioned antigens, when these receptors exist in soluble forms in biological fluids such as plasma, they can form complexes with the antigen-binding molecules of the present invention. Therefore, as long as the above-mentioned receptors exist in their soluble forms in biological fluids such as plasma, they may be used as antigens that may form complexes of the present invention by binding to an antigen-binding molecule of the present invention. An example of a non-limiting embodiment of such a soluble receptor is soluble IL-6R, which is a protein consisting of the amino acids at positions 1 to 357 in the IL-6R polypeptide sequence of SEQ ID NO: 1 as described in Mullberg et al. (J. Immunol. (1994) 152 (10), 4958-4968).

Soluble antigens are recited as examples of the above-mentioned antigens, and the solutions in which the antigens exist are not limited. Soluble antigens may exist in biological fluids, or more specifically in all fluids filling the space between tissues and cells or vessels in organisms. In a non-limiting embodiment, the antigens to which antigen-binding molecules of the present invention bind may be present in extracellular fluids. In vertebrates, extracellular fluid is a general term for plasma, interstitial fluid, lymph, compact connective tissue, cerebrospinal fluid, spinal fluid, puncture fluid, synovial fluid, or such components in the bone and cartilage, alveolar fluid (bronchoalveolar lavage fluid), peritoneal fluid, pleural fluid, pericardial fluid, cyst fluid, aqueous humor (hydatoid), or such transcellular fluids (various fluids in the glandular cavities and fluids in the digestive tract cavity and other body cavity fluids produced as a result of active transport/secretory activities of cells).

Epitope

"Epitope" means an antigenic determinant in an antigen, and refers to an antigen site to which the antigen-binding domain of an antigen-binding molecule disclosed herein binds. Thus, for example, the epitope can be defined according to its structure. Alternatively, the epitope may be defined according to the antigen-binding activity of an antigen-binding molecule that recognizes the epitope. When the antigen is a peptide or polypeptide, the epitope can be specified by the amino acid residues forming the epitope. Alternatively, when the epitope is a sugar chain, the epitope can be specified by its specific sugar chain structure.

A linear epitope is an epitope that contains an epitope whose primary amino acid sequence is recognized. Such a linear epitope typically contains at least three and most commonly at least five, for example, about 8 to 10 or 6 to 20 amino acids in its specific sequence.

In contrast to the linear epitope, "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance, site-specific spin labeling, and electron paramagnetic resonance, but are not limited thereto. See, for example, Epitope Mapping Protocols in Methods in Molecular Biology (1996), Vol. 66, Morris (ed.).

Binding Activity

Examples of a method for assessing the epitope binding by a test antigen-binding molecule containing an IL-6R antigen-binding domain are described below. According to the examples below, methods for assessing the epitope binding by a test antigen-binding molecule containing an antigen-binding domain for an antigen other than IL-6R, can also be appropriately conducted.

For example, whether a test antigen-binding molecule containing an IL-6R antigen-binding domain recognizes a linear epitope in the IL-6R molecule can be confirmed for example as mentioned below. A linear peptide comprising an amino acid sequence forming the extracellular domain of IL-6R is synthesized for the above purpose. The peptide can be synthesized chemically, or obtained by genetic engineering techniques using a region encoding the amino acid sequence corresponding to the extracellular domain in an IL-6R cDNA represented by SEQ ID NO: 2. Then, a test antigen-binding molecule containing an IL-6R antigen-binding domain is assessed for its binding activity towards a linear peptide comprising the amino acid sequence forming the extracellular domain. For example, an immobilized linear peptide can be used as an antigen by ELISA to evaluate the binding activity of the antigen-binding molecule towards the peptide. Alternatively, the binding activity towards a linear peptide can be assessed based on the level that the linear peptide inhibits the binding of the antigen-binding molecule to IL-6R-expressing cells. These tests can demonstrate the binding activity of the antigen-binding molecule towards the linear peptide.

Whether a test antigen-binding molecule containing an IL-6R antigen-binding domain recognizes a conformational epitope can be assessed as follows. IL-6R-expressing cells are prepared for the above purpose. A test antigen-binding molecule containing an IL-6R antigen-binding domain can be determined to recognize a conformational epitope when it strongly binds to IL-6R-expressing cells upon contact, but does not substantially bind to an immobilized linear peptide comprising an amino acid sequence forming the extracellular domain of IL-6R. Herein, "not substantially bind" means that the binding activity is 80% or less, generally 50% or less, preferably 30% or less, and particularly preferably 15% or less compared to the binding activity towards cells expressing human IL-6R.

Methods for assaying the binding activity of a test antigen-binding molecule containing an IL-6R antigen-binding domain towards IL-6R-expressing cells include, for example, the methods described in Antibodies: A Laboratory Manual (Ed Harlow, David Lane, Cold Spring Harbor Laboratory (1988) 359-420). Specifically, the assessment can be performed based on the principle of ELISA or fluorescence activated cell sorting (FACS) using IL-6R-expressing cells as antigen.

In the ELISA format, the binding activity of a test antigen-binding molecule containing an IL-6R antigen-binding domain towards IL-6R-expressing cells can be assessed quantitatively by comparing the levels of signal generated by enzymatic reaction. Specifically, a test polypeptide complex is added to an ELISA plate onto which IL-6R-expressing cells are immobilized. Then, the test antigen-binding molecule bound to the cells is detected using an enzyme-labeled antibody that recognizes the test antigen-binding molecule. Alternatively, when FACS is used, a dilution series of a test antigen-binding molecule is prepared, and the antibody binding titer for IL-6R-expressing cells can be determined to compare the binding activity of the test antigen-binding molecule towards IL-6R-expressing cells.

The binding of a test antigen-binding molecule towards an antigen expressed on the surface of cells suspended in buffer or the like can be detected using a flow cytometer. Known flow cytometers include, for example, the following devices:

FACSCanto™ II
FACSAria™
FAC SArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter).

Preferable methods for assaying the binding activity of a test antigen-binding molecule containing an IL-6R antigen-binding domain towards an antigen include, for example, the following method. First, IL-6R-expressing cells are reacted with a test antigen-binding molecule, and then this is stained with an FITC-labeled secondary antibody that recognizes the antigen-binding molecule. The test antigen-binding molecule is appropriately diluted with a suitable buffer to prepare the molecule at a desired concentration. For example, the molecule can be used at a concentration within the range of 10 μg/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to cells. That is, the binding activity of a test antigen-binding molecule, which is represented by the quantity of the test antigen-binding molecule bound, can be determined by measuring the Geometric Mean value.

Whether a test antigen-binding molecule containing an IL-6R antigen-binding domain shares a common epitope with another antigen-binding molecule can be assessed based on the competition between the two molecules for the same epitope. The competition between antigen-binding molecules can be detected by cross-blocking assay or the like. For example, the competitive ELISA assay is a preferred cross-blocking assay.

Specifically, in cross-blocking assay, the IL-6R protein immobilized to the wells of a microtiter plate is pre-incubated in the presence or absence of a candidate competitor antigen-binding molecule, and then a test antigen-binding molecule is added thereto. The quantity of test antigen-binding molecule bound to the IL-6R protein in the wells is indirectly correlated with the binding ability of a candidate competitor antigen-binding molecule that competes for the binding to the same epitope. That is, the greater the affinity of the competitor antigen-binding molecule for the same epitope, the lower the binding activity of the test antigen-binding molecule towards the IL-6R protein-coated wells.

The quantity of the test antigen-binding molecule bound to the wells via the IL-6R protein can be readily determined by labeling the antigen-binding molecule in advance. For example, a biotin-labeled antigen-binding molecule is measured using an avidin/peroxidase conjugate and appropriate substrate. In particular, cross-blocking assay that uses enzyme labels such as peroxidase is called competitive ELISA assay. The antigen-binding molecule can also be labeled with other labeling substances that enable detection or measurement. Specifically, radiolabels, fluorescent labels, and such are known.

When the candidate competitor antigen-binding molecule can block the binding by a test antigen-binding molecule containing an IL-6R antigen-binding domain by at least 20%, preferably at least 20 to 50%, and more preferably at least 50% compared to the binding activity in a control experiment conducted in the absence of the competitor antigen-binding molecule complex, the test antigen-binding molecule is determined to substantially bind to the same epitope bound by the competitor antigen-binding molecule, or compete for the binding to the same epitope.

When the structure of an epitope bound by a test antigen-binding molecule containing an IL-6R antigen-binding domain has already been identified, whether the test and control antigen-binding molecules share a common epitope can be assessed by comparing the binding activities of the two antigen-binding molecules towards a peptide prepared by introducing amino acid mutations into the peptide forming the epitope.

To measure the above binding activities, for example, the binding activities of test and control antigen-binding molecules towards a linear peptide into which a mutation is introduced are compared in the above ELISA format. Besides the ELISA methods, the binding activity towards the mutant peptide bound to a column can be determined by flowing test and control antigen-binding molecules in the column, and then quantifying the antigen-binding molecule eluted in the elution solution. Methods for adsorbing a mutant peptide to a column, for example, in the form of a GST fusion peptide, are known.

Alternatively, when the identified epitope is a conformational epitope, whether test and control antigen-binding molecules share a common epitope can be assessed by the following method. First, IL-6R-expressing cells and cells expressing IL-6R with a mutation introduced into the epitope are prepared. The test and control antigen-binding molecules are added to a cell suspension prepared by suspending these cells in an appropriate buffer such as PBS. Then, the cell suspensions are appropriately washed with a buffer, and an FITC-labeled antibody that recognizes the test and control antigen-binding molecules is added thereto. The fluorescence intensity and number of cells stained with the labeled antibody are determined using FACSCalibur (BD). The test and control antigen-binding molecules are appropriately diluted using a suitable buffer, and used at desired concentrations. For example, they may be used at a concentration within the range of 10 μg/ml to 10 ng/ml. The fluorescence intensity determined by analysis using the CELL QUEST Software (BD), i.e., the Geometric Mean value, reflects the quantity of labeled antibody bound to cells. That is, the binding activities of the test and control antigen-binding molecules, which are represented by the quantity of labeled antibody bound, can be determined by measuring the Geometric Mean value.

In the above method, whether an antigen-binding molecule does "not substantially bind to cells expressing mutant IL-6R" can be assessed, for example, by the following method. First, the test and control antigen-binding molecules bound to cells expressing mutant IL-6R are stained with a labeled antibody. Then, the fluorescence intensity of the cells is determined. When FACSCalibur is used for fluorescence detection by flow cytometry, the determined fluorescence intensity can be analyzed using the CELL QUEST Software. From the Geometric Mean values in the presence and absence of the polypeptide complex, the comparison value (ΔGeo-Mean) can be calculated according to the following formula to determine the ratio of increase in fluorescence intensity as a result of the binding by the antigen-binding molecule.

$$\Delta\text{Geo-Mean}=\text{Geo-Mean (in the presence of the poly-peptide complex)}/\text{Geo-Mean (in the absence of the polypeptide complex)}$$

The Geometric Mean comparison value (ΔGeo-Mean value for the mutant IL-6R molecule) determined by the above analysis, which reflects the quantity of a test antigen-binding molecule bound to cells expressing mutant IL-6R, is compared to the ΔGeo-Mean comparison value that reflects the quantity of the test antigen-binding molecule bound to IL-6R-expressing cells. In this case, the concentrations of the test antigen-binding molecule used to determine the ΔGeo-Mean comparison values for IL-6R-expressing cells and cells expressing mutant IL-6R are particularly preferably adjusted to be equal or substantially equal. An antigen-binding molecule that has been confirmed to recognize an epitope in IL-6R is used as a control antigen-binding molecule.

If the ΔGeo-Mean comparison value of a test antigen-binding molecule for cells expressing mutant IL-6R is smaller than the ΔGeo-Mean comparison value of the test antigen-binding molecule for IL-6R-expressing cells by at least 80%, preferably 50%, more preferably 30%, and particularly preferably 15%, then the test antigen-binding molecule "does not substantially bind to cells expressing mutant IL-6R". The formula for determining the Geo-Mean (Geometric Mean) value is described in the CELL QUEST Software User's Guide (BD biosciences). When the comparison shows that the comparison values are substantially equivalent, the epitope for the test and control antigen-binding molecules can be determined to be the same.

Antigen-Binding Domain

Herein, an "antigen-binding domain" may be of any structure as long as it binds to an antigen of interest. Such domains preferably include, for example:

antibody heavy-chain and light-chain variable regions; a module of about 35 amino acids called A domain which is contained in the in vivo cell membrane protein Avimer (WO 2004/044011, WO 2005/040229);

Adnectin containing the 10Fn3 domain which binds to the protein moiety of fibronectin, a glycoprotein expressed on cell membrane (WO 2002/032925);

Affibody which is composed of a 58-amino acid three-helix bundle based on the scaffold of the IgG-binding domain of Protein A (WO 1995/001937);

Designed Ankyrin Repeat proteins (DARPins) which are a region exposed on the molecular surface of ankyrin repeats (AR) having a structure in which a subunit consisting of a turn comprising 33 amino acid residues, two antiparallel helices, and a loop is repeatedly stacked (WO 2002/020565); Anticalins and such, which are domains consisting of four loops that support one side of a barrel structure composed of eight circularly arranged antiparallel strands that are highly conserved among lipocalin molecules such as neutrophil gelatinase-associated lipocalin (NGAL) (WO 2003/029462); and the concave region formed by the parallel-sheet structure inside the horseshoe-shaped structure constituted by stacked repeats of the leucine-rich-repeat (LRR) module of the variable lymphocyte receptor (VLR) which does not have the immunoglobulin structure and is used in the system of acquired immunity in jawless vertebrate such as lampery and hagfish (WO 2008/016854). Preferred antigen-binding domains of the present invention include, for example, those having antibody heavy-chain and light-chain variable regions. Preferred examples of antigen-binding domains include "single chain Fv (scFv)", "single chain antibody", "Fv", "single chain Fv 2 (scFv2)", "Fab", and "F(ab')2".

The antigen-binding domains of antigen-binding molecules of the present invention can bind to an identical epitope. Such epitope can be present, for example, in a protein comprising the amino acid sequence of SEQ ID NO: 1. Alternatively, each of the antigen-binding domains of antigen-binding molecules of the present invention can bind to a different epitope. Herein, the different epitope can be present in, for example, a protein comprising the amino acid sequence of SEQ ID NO: 1.

Specific

With regard to binding of antigen-binding molecules provided by the present invention to an antigen, the term "specific" means that one of the molecules that specifically binds to does not substantially bind to molecules other than its single or plurality of binding partner molecule(s). Herein, "does not substantially bind" refers to showing 80% or less, generally 50% or less, preferably 30% or less and particularly preferably 15% or less binding activity to molecules other than the binding partner molecules compared to the binding activity towards the partner molecule(s), as described in the above-mentioned section on binding activity. Furthermore, "specific" is also used when an antigen-binding domain is specific to a particular epitope among multiple epitopes in an antigen. When an epitope bound by an antigen-binding domain is contained in multiple different antigens, antigen-binding molecules containing the antigen-binding domain can bind to various antigens that have the epitope.

Neutralizing Activity

In a non-limiting embodiment of the present invention, a pharmaceutical composition comprising as an active ingredient an antigen-binding molecule having antigen-neutralizing activity is provided, wherein the antigen-binding molecule comprises (i) an antigen-binding domain whose antigen-binding activity varies depending on ion concentration conditions, (ii) an FcγR-binding domain having FcγRIIb-selective binding activity, and (iii) an FcRn-binding domain having FcRn-binding activity under an acidic pH range condition. Generally, neutralizing activity refers to activity of inhibiting the biological activity of a ligand, such as viruses and toxins, having biological activity on cells. Thus, substances having neutralizing activity refer to substances that bind to the ligand or the receptor to which the ligand binds, and inhibits the binding between the ligand and the receptor. Receptors blocked from binding with the ligand by the neutralizing activity will not be able to exhibit biological activity through this receptor. When the antigen-binding molecule is an antibody, such an antibody having neutralizing activity is generally called a neutralizing antibody. Neutralizing activity of a test substance may be measured by comparing the biological activity in the presence of a ligand between when the test substance is present and absent.

For example, major possible ligands for the IL-6 receptor preferably include IL-6 as shown in SEQ ID NO: 3. The IL-6 receptor, which is an I-type membrane protein with its amino terminus forming the extracellular domain, forms a heterotetramer with a gp130 receptor which has been induced to dimerize by IL-6 (Heinrich et al. (Biochem. J. (1998) 334, 297-314)). Formation of the heterotetramer activates Jak which is associated with the gp130 receptor. Jak undergoes autophosphorylation and phosphorylates the receptor. The phosphorylation site of the receptor and Jak serves as a binding site for SH2-carrying molecules belonging to the Stat family such as Stat3; MAP kinase; PI3/Akt; and other SH2-carrying proteins and adapters. Next, Stat bound to the gp130 receptor is phosphorylated by Jak. The phosphorylated Stat dimerizes and moves into the nucleus, and regulates the transcription of target genes. Jak or Stat can also be involved in signal cascades via receptors of other classes. Deregulated IL-6 signal cascades are observed in inflammation and pathological conditions of autoimmune diseases, and cancers such as prostate cancer and multiple myeloma. Stat3 which may act as an oncogene is constitutively activated in many cancers. In prostate cancer and multiple myeloma, there is a crosstalk between the signaling cascade via the IL-6 receptor and the signaling cascade via the epithelial growth factor receptor (EGFR) family members (Ishikawa et al. (J. Clin. Exp. Hematopathol. (2006) 46 (2), 55-66)).

Such intracellular signaling cascades are different for each cell type; therefore, appropriate target molecules can be determined for each target cell of interest, and are not limited to the above-mentioned factors. Neutralization activity can be evaluated by measuring the activation of in vivo signaling. Furthermore, the activation of in vivo signaling can be detected by using as an index the action of inducing the transcription of a target gene that exists downstream of the in vivo signaling cascade. Change in the transcription activity of the target gene can be detected by the principle of reporter assays. Specifically, a reporter gene such as green fluorescence protein (GFP) or luciferase is placed downstream of a promoter region or a transcription factor of the target gene, its reporter activity is measured, and thereby change in the transcription activity can be measured as the reporter activity. Commercially available kits for measuring the activation of in vivo signaling can be used appropriately (for example, Mercury Pathway Profiling Luciferase System (Clontech)).

Furthermore, for methods of measuring the activity of neutralizing receptors/ligands of the EGF receptor family and such, which normally act on signaling cascades that work toward promoting cell proliferation, the neutralization activity of antigen-binding molecules can be evaluated by measuring the proliferation activity of target cells. For example, when cells are promoted to proliferate by growth factors of the EGF family such as HB-EGF, the inhibitory effect on the proliferation of such cells based on the neutralizing activity of an anti-HB-EGF antibody can be suitably evaluated or measured by the following methods: For evaluating or measuring the cell proliferation inhibitory activity in vitro, a method of measuring the incorporation of [$^3$H]-labeled thymidine added to the medium by viable cells as an index of DNA replication ability is used. As more convenient methods, a dye exclusion method, in which the ability of a cell to exclude a dye such as trypan blue from the cell is measured under the microscope, and the MTT method are used. The latter method makes use of the ability of viable cells to convert MTT (3-(4,5-dimethylthiazol-2-yl)-2,5-diphenyl tetrazolium bromide), which is a tetrazolium salt, to a blue formazan product. More specifically, a test antibody is added as well as a ligand to the culture solution of a test cell, and after a certain period of time, the MTT solution is added to the culture solution, and this is left to stand for a while for incorporation of MTT into the cell. As a result, MTT, which is a yellow compound, is converted to a blue compound by the action of succinate dehydrogenase in the mitochondria of the cell. After dissolving this blue product for coloration, its absorbance is measured and used as an index for the number of viable cells. In addition to MTT, reagents such as MTS, XTT, WST-1, and WST-8 are also commercially available (Nacalai Tesque, and such) and can be suitably used. For measuring the activity, a binding antibody which is of the same isotype as the anti-HB-EGF antibody but does not have the cell proliferation inhibitory activity can be used as a control antibody in the same manner as the anti-HB-EGF antibody, and the activity can be determined when the anti-HB-EGF antibody shows stronger cell proliferation inhibitory activity than the control antibody.

Cells that can be preferably used for evaluating the activity include, for example, cells promoted to proliferate by HB-EGF such as the ovarian cancer cell line RMG-1, and mouse Ba/F3 cells which have been transformed by a vector for expressing a gene encoding hEGFR/mG-CSFR, which is a fusion protein in which the extracellular domain of human EGFR is fused in frame with the intracellular domain of the mouse G-CSF receptor. In this way, those skilled in the art can appropriately select cells to be used for evaluating the activity and use them to measure the cell proliferation activity as mentioned above.

Antibody

Herein, "antibody" refers to a natural immunoglobulin or an immunoglobulin produced by partial or complete synthesis. Antibodies can be isolated from natural sources such as naturally-occurring plasma and serum, or culture supernatants of antibody-producing hybridomas. Alternatively, antibodies can be partially or completely synthesized using techniques such as genetic recombination. Preferred antibodies include, for example, antibodies of an immunoglobulin isotype or subclass belonging thereto. Known human immunoglobulins include antibodies of the following nine classes (isotypes): IgG1, IgG2, IgG3, IgG4, IgA1, IgA2, IgD, IgE, and IgM. Of these isotypes, antibodies of the present invention include IgG1, IgG2, IgG3, and IgG4. A number of allotype sequences of human IgG1, human IgG2, human IgG3, and human IgG4 constant regions due to gene polymorphisms are described in "Sequences of proteins of immunological interest", NIH Publication No. 91-3242. Any of such sequences may be used in the present invention. In particular, for the human IgG1 sequence, the amino acid sequence at positions 356 to 358 as indicated by EU numbering may be DEL or EEM. Several allotype sequences due to genetic polymorphisms have been described in "Sequences of proteins of immunological interest", NIH Publication No. 91-3242 for the human Igκ (Kappa) constant region and human Igλ (Lambda) constant region, and any of the sequences may be used in the present invention.

Methods for producing an antibody with desired binding activity are known to those skilled in the art. Below is an example that describes a method for producing an antibody that binds to IL-6R (anti-IL-6R antibody). Antibodies that bind to an antigen other than IL-6R can also be produced according to the example described below.

Anti-IL-6R antibodies can be obtained as polyclonal or monoclonal antibodies using known methods. The anti-IL-6R antibodies preferably produced are monoclonal antibodies derived from mammals. Such mammal-derived monoclonal antibodies include antibodies produced by hybridomas or host cells transformed with an expression vector carrying an antibody gene by genetic engineering techniques. "Humanized antibodies" or "chimeric antibodies" are included in the monoclonal antibodies of the present invention.

Monoclonal antibody-producing hybridomas can be produced using known techniques, for example, as described below. Specifically, mammals are immunized by conventional immunization methods using an IL-6R protein as a sensitizing antigen. Resulting immune cells are fused with known parental cells by conventional cell fusion methods. Then, hybridomas producing an anti-IL-6R antibody can be selected by screening for monoclonal antibody-producing cells using conventional screening methods.

Specifically, monoclonal antibodies are prepared as mentioned below. First, the IL-6R gene whose nucleotide sequence is disclosed in SEQ ID NO: 2 can be expressed to produce an IL-6R protein shown in SEQ ID NO: 1, which will be used as a sensitizing antigen for antibody preparation. That is, a gene sequence encoding IL-6R is inserted into a known expression vector, and appropriate host cells are transformed with this vector. The desired human IL-6R protein is purified from the host cells or their culture supernatants by known methods. In order to obtain soluble IL-6R from culture supernatants, for example, a protein consisting of the amino acids at positions 1 to 357 in the IL-6R polypeptide sequence of SEQ ID NO: 1, such as described in Mullberg et al. (J. Immunol. (1994) 152 (10), 4958-4968), is expressed as a soluble IL-6R, instead of the IL-6R protein of SEQ ID NO: 1. Purified native IL-6R protein can also be used as a sensitizing antigen.

The purified IL-6R protein can be used as a sensitizing antigen for immunization of mammals. A partial IL-6R peptide may also be used as a sensitizing antigen. In this case, a partial peptide can be prepared by chemical synthesis based on the amino acid sequence of human IL-6R, or by inserting a partial IL-6R gene into an expression vector for expression. Alternatively, a partial peptide can be produced by degrading an IL-6R protein with a protease. The length and region of the partial IL-6R peptide are not limited to particular embodiments. A preferred region can be arbitrarily selected from the amino acid sequence at amino acid positions 20 to 357 in the amino acid sequence of SEQ ID NO: 1. The number of amino acids forming a peptide to be used as a sensitizing antigen is preferably at least five or more, six or more, or seven or more. More specifically, a peptide of 8 to 50 residues, more preferably 10 to 30 residues can be used as a sensitizing antigen.

For sensitizing antigen, alternatively it is possible to use a fusion protein prepared by fusing a desired partial polypeptide or peptide of the IL-6R protein with a different polypeptide. For example, antibody Fc fragments and peptide tags are preferably used to produce fusion proteins to be used as sensitizing antigens. Vectors for expression of such fusion proteins can be constructed by fusing in frame genes encoding two or more desired polypeptide fragments and inserting the fusion gene into an expression vector as described above. Methods for producing fusion proteins are described in Molecular Cloning 2nd ed. (Sambrook, J et al., Molecular Cloning 2nd ed., 9.47-9.58 (1989) Cold Spring Harbor Lab. Press). Methods for preparing IL-6R to be used as a sensitizing antigen, and immunization methods using IL-6R are specifically described in WO 2003/000883, WO 2004/022754, WO 2006/006693, and such.

There is no particular limitation on the mammals to be immunized with the sensitizing antigen. However, it is preferable to select the mammals by considering their compatibility with the parent cells to be used for cell fusion. In general, rodents such as mice, rats, and hamsters, rabbits, and monkeys are preferably used.

The above animals are immunized with a sensitizing antigen by known methods. Generally performed immunization methods include, for example, intraperitoneal or subcutaneous injection of a sensitizing antigen into mammals. Specifically, a sensitizing antigen is appropriately diluted with PBS (Phosphate-Buffered Saline), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein such as IL-6R; and there is no need to purify the antigen for immunization.

In order to prepare a monoclonal antibody of the present invention using DNA immunization, first, a DNA expressing an IL-6R protein is administered to an animal to be immunized. The IL-6R-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized. Antibodies that recognized IL-6R can also be produced by the methods described in WO 2003/104453.

After immunizing a mammal as described above, an increase in the titer of an IL-6R-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immune cells. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:

P3(P3x63Ag8.653) (J. Immunol. (1979) 123 (4), 1548-1550);

P3x63Ag8U.1 (Current Topics in Microbiology and Immunology (1978) 81, 1-7);

NS-1 (C. Eur. J. Immunol. (1976) 6 (7), 511-519);

MPC-11 (Cell (1976) 8 (3), 405-415);

SP2/0 (Nature (1978) 276 (5685), 269-270);

FO (J. Immunol. Methods (1980) 35 (1-2), 1-21);

S194/5.XX0.BU.1 (J. Exp. Med. (1978) 148 (1), 313-323);

R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immune cells to myeloma cells may be determined at one's own discretion, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) pre-warmed to about 37° C. is added thereto at a concentration of generally 30% to 60% (w/v). This is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Cells other than the desired hybridomas (non-fused cells) can be killed by continuing culture in the above HAT medium for a sufficient period of time (typically, the period is several days to several weeks). Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Cells other than the desired hybridomas (non-fused cells) can be killed by continuing culture in the above HAT medium for a sufficient period of time. Specifically, desired hybridomas can be selected by culture for generally several days to several weeks. Then, hybridomas producing the desired antibody are screened and singly cloned by conventional limiting dilution methods.

Desired antibodies can be preferably selected and singly cloned by screening methods based on known antigen/antibody reaction. For example, an IL-6R-binding monoclonal antibody can bind to IL-6R expressed on the cell surface. Such a monoclonal antibody can be screened by fluorescence activated cell sorting (FACS). FACS is a system that assesses the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, IL-6R-expressing cells are first prepared. Cells preferably used for screening are mammalian cells in which IL-6R is forcedly expressed. As control, the activity of an antibody to bind to cell-surface IL-6R can be selectively detected using non-transformed mammalian cells as host cells. Specifically, hybridomas producing an anti-IL-6R monoclonal antibody can be isolated by selecting hybridomas that produce an antibody which binds to cells forced to express IL-6R, but not to host cells.

Alternatively, the activity of an antibody to bind to immobilized IL-6R-expressing cells can be assessed based on the principle of ELISA. For example, IL-6R-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium, and stored in liquid nitrogen for a long period.

The above hybridomas are cultured by a conventional method, and desired monoclonal antibodies can be prepared from the culture supernatants. Alternatively, the hybridomas are administered to and grown in compatible mammals, and monoclonal antibodies are prepared from the ascites. The former method is suitable for preparing antibodies with high purity.

Antibodies encoded by antibody genes that are cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

For example, a cDNA encoding the variable region (V region) of an anti-IL-6R antibody is prepared from hybridoma cells expressing the anti-IL-6R antibody. For this purpose, total RNA is first extracted from hybridomas. Methods used for extracting mRNAs from cells include, for example:

the guanidine ultracentrifugation method (Biochemistry (1979) 18(24), 5294-5299), and the AGPC method (Anal. Biochem. (1987) 162(1), 156-159)

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Co.) or such. Furthermore, the SMART RACE cDNA Amplification Kit (Clontech) and the PCR-based 5'-RACE method (Proc. Natl. Acad. Sci. U.S.A. (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into *E. coli* or such. After colony selection, the desired recombinant vector can be prepared from the colony-forming *E. coli*. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA Amplification Kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip Mouse Monoclonal Antibody Isotyping Kit (Roche Diagnostics).

Specifically, for example, primers that allow amplification of genes encoding γ1, γ2a, γ2b, and γ3 heavy chains and κ and λ light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

PCR products thus amplified are used to reshape immunoglobulins composed of a combination of heavy and light chains. A desired antibody can be selected using the IL-6R-binding activity of a reshaped immunoglobulin as an indicator. For example, when the objective is to isolate an antibody against IL-6R, it is more preferred that the binding of the antibody to IL-6R is specific. An IL-6R-binding antibody can be screened, for example, by the following steps:

(1) contacting an IL-6R-expressing cell with an antibody comprising the V region encoded by a cDNA isolated from a hybridoma;

(2) detecting the binding of the antibody to the IL-6R-expressing cell; and (3) selecting an antibody that binds to the IL-6R-expressing cell.

Methods for detecting the binding of an antibody to IL-6R-expressing cells are known. Specifically, the binding of an antibody to IL-6R-expressing cells can be detected by the above-described techniques such as FACS. Immobilized samples of IL-6R-expressing cells are appropriately used to assess the binding activity of an antibody.

Preferred antibody screening methods that use the binding activity as an indicator also include panning methods using phage vectors. Screening methods using phage vectors are advantageous when the antibody genes are isolated from heavy-chain and light-chain subclass libraries from a polyclonal antibody-expressing cell population. Genes encoding the heavy-chain and light-chain variable regions can be linked by an appropriate linker sequence to form a single-chain Fv (scFv). Phages presenting scFv on their surface can be produced by inserting a gene encoding scFv into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the anti-IL-6R antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the anti-IL-6R antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, "chimeric antibody" means that the origin of the constant region is different from that of the variable region. Thus, in addition to mouse-human heterochimeric antibodies, human-human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA encoding a desired antibody constant region. A chimeric antibody expression vector is constructed by fusing in frame the two genes digested with the same combination of restriction enzymes.

To produce an anti-IL-6R monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. In the Examples described later, a peptide having the amino acid sequence MGWSCIILFLVATATGVHS (SEQ ID NO: 4) are used as a signal sequence. Meanwhile, other appropriate signal sequences may be attached. The expressed polypeptide is cleaved at the carboxyl terminus of the above sequence, and the resulting polypeptide is secreted to the outside of cells as a mature polypeptide. Then, appropriate host cells are transformed with the expression vector, and recombinant cells expressing the anti-IL-6R antibody-encoding DNA are obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors into which the H-chain and L-chain genes are respectively inserted. Alternatively, host cells can be transformed with a single expression vector into which DNAs encoding the H and L chains are inserted (see WO 1994/011523).

There are various known host cell/expression vector combinations for antibody preparation by introducing isolated antibody genes into appropriate hosts. All of these expression systems are applicable to isolation of the antigen-binding domains of the present invention. Appropriate eukaryotic cells used as host cells include animal cells, plant cells, and fungal cells. Specifically, the animal cells include, for example, the following cells.

(1) mammalian cells: CHO (Chinese hamster ovary cell line), COS (Monkey kidney cell line), myeloma (Sp2/O, NS0, and such), BHK (baby hamster kidney cell line), Hela, Vero, HEK293 (human embryonic kidney cell line with sheared adenovirus (Ad)5 DNA), Free-style293, PER.C6 cell (human embryonic retinal cell line transformed with the Adenovirus Type 5 (Ad5) E1A and E1B genes), and such (Current Protocols in Protein Science (May, 2001, Unit 5.9, Table 5.9.1));

(2) amphibian cells: Xenopus oocytes, or such; and
(3) insect cells: 49, sf21, Tn5, or such.

In addition, as a plant cell, an antibody gene expression system using cells derived from the Nicotiana genus such as Nicotiana tabacum is known. Callus cultured cells can be appropriately used to transform plant cells.

Furthermore, the following cells can be used as fungal cells:

yeasts: the Saccharomyces genus such as Saccharomyces serevisiae, and the Pichia genus such as Pichia pastoris; and filamentous fungi: the Aspergillus genus such as Aspergillus niger.

Furthermore, antibody gene expression systems that utilize prokaryotic cells are also known. For example, when using bacterial cells, E. coli cells, Bacillus subtilis cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat β-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Ebert, K. M. et al., Bio/Technology (1994) 12 (7), 699-702).

When an antigen-binding molecule described herein is administered to humans, an antigen-binding domain derived from a genetically recombinant antibody that has been artificially modified to reduce the heterologous antigenicity against human and such, can be appropriately used as the antigen-binding domain of the antigen-binding molecule. Such genetically recombinant antibodies include, for example, humanized antibodies. These modified antibodies are appropriately produced by known methods.

An antibody variable region used to produce the antigen-binding domain of an antigen-binding molecule described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced to another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Cancer Res. (1993) 53: 851-856).

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing an scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

In addition to the techniques described above, techniques of B cell cloning (identification of each antibody-encoding sequence, cloning and its isolation; use in constructing expression vector in order to prepare each antibody (IgG1, IgG2, IgG3, or IgG4 in particular); and such) such as described in Bernasconi et al. (Science (2002) 298: 2199-2202) or in WO 2008/081008 can be appropriately used to isolate antibody genes.

EU Numbering System and Kabat Numbering System

According to the methods used in the present invention, amino acid positions assigned to antibody CDR and FR are specified according to Kabat numbering (Sequences of Proteins of Immunological Interest (National Institute of Health, Bethesda, Md., 1987 and 1991)). Herein, when an antigen-binding molecule is an antibody or antigen-binding fragment, variable region amino acids are indicated according to Kabat numbering system, while constant region amino acids are indicated according to EU numbering system based on Kabat's amino acid positions.

Conditions of Ion Concentration

Conditions of Metal Ion Concentration

In one embodiment of the present invention, the ion concentration refers to a metal ion concentration. "Metal ions" refer to ions of group I elements except hydrogen such as alkaline metals and copper group elements, group II elements such as alkaline earth metals and zinc group elements, group III elements except boron, group IV elements except carbon and silicon, group VIII elements such as iron group and platinum group elements, elements belonging to subgroup A of groups V, VI, and VII, and metal elements such as antimony, bismuth, and polonium. Metal atoms have the property of releasing valence electrons to become cations. This is referred to as ionization tendency. Metals with strong ionization tendency are deemed to be chemically active.

In the present invention, preferred metal ions include, for example, calcium ion. Calcium ion is involved in modulation of many biological phenomena, including contraction of muscles such as skeletal, smooth, and cardiac muscles; activation of movement, phagocytosis, and the like of leukocytes; activation of shape change, secretion, and the like of platelets; activation of lymphocytes; activation of mast cells including secretion of histamine; cell responses mediated by catecholamine a receptor or acetylcholine receptor; exocytosis; release of transmitter substances from neuron terminals; and axoplasmic flow in neurons. Known intracellular calcium ion receptors include troponin C, calmodulin, parvalbumin, and myosin light chain, which have several calcium ion-binding sites and are believed to be derived from a common origin in terms of molecular evolution. There are also many known calcium-binding motifs. Such well-known motifs include, for example, cadherin domains, EF-hand of calmodulin, C2 domain of Protein kinase C, Gla domain of blood coagulation protein Factor IX, C-type lectins of asialoglycoprotein receptor and mannose-binding receptor, A domains of LDL receptors, annexin, thrombospondin type 3 domain, and EGF-like domains.

In the present invention, when the metal ion is calcium ion, the conditions of calcium ion concentration include low calcium ion concentration conditions and high calcium ion concentration conditions. "The antigen-binding activity of an antigen-binding domain contained in the antigen-binding molecule of the present invention varies depending on calcium ion concentration conditions" means that the antigen-binding activity of an antigen-binding domain contained in the antigen-binding molecule varies due to the difference in the conditions between low and high calcium ion concentrations. For example, the antigen-binding activity of an antigen-binding domain may be higher under a high calcium ion concentration condition than under a low calcium ion concentration condition. Alternatively, the antigen-binding activity of an antigen-binding domain may be, for example, higher under a low calcium ion concentration condition than under a high calcium ion concentration condition.

Herein, the high calcium ion concentration is not particularly limited to a specific value; however, the concentration may preferably be selected between 100 μM and 10 mM. In another embodiment, the concentration may be selected between 200 μM and 5 mM. In an alternative embodiment, the concentration may be selected between 400 μM and 3 mM. In still another embodiment, the concentration may be selected between 200 μM and 2 mM. Furthermore, the concentration may be selected between 400 μM and 1 mM. In particular, a concentration selected between 500 μM and 2.5 mM, which is close to the plasma (blood) concentration of calcium ion in vivo, is preferred.

Herein, the low calcium ion concentration is not particularly limited to a specific value; however, the concentration may preferably be selected between 0.1 μM and 30 μM. In another embodiment, the concentration may be selected between 0.2 μM and 20 μM. In still another embodiment, the concentration may be selected between 0.5 μM and 10 μM. In an alternative embodiment, the concentration may be selected between 1 μM and 5 μM. Furthermore, the concentration may be selected between 2 μM and 4 μM. In particular, a concentration selected between 1 μM and 5 μM, which is close to the concentration of ionized calcium in early endosomes in vivo, is preferred.

In the present invention, "the antigen-binding activity is lower under a low calcium ion concentration condition than under a high calcium ion concentration condition" means that the antigen-binding activity of an antigen-binding domain or antigen-binding molecule comprising the domain of the present invention is weaker at a calcium ion concentration selected between 0.1 μM and 30 μM than at a calcium ion concentration selected between 100 μM and 10 mM. Preferably, it means that the antigen-binding activity of an antigen-binding domain or antigen-binding molecule comprising the domain of the present invention is weaker at a calcium ion concentration selected between 0.5 μM and 10 μM than at a calcium ion concentration selected between 200 μM and 5 mM. It particularly preferably means that the antigen-binding activity at the calcium ion concentration in the early endosome in vivo is weaker than that at the in vivo plasma calcium ion concentration; and specifically, it means that the antigen-binding activity of an antigen-binding molecule is weaker at a calcium ion concentration selected between 1 μM and 5 μM than at a calcium ion concentration selected between 500 μM and 2.5 mM.

Whether the antigen-binding activity of an antigen-binding domain or antigen-binding molecule comprising the domain is changed depending on metal ion concentrations can be determined, for example, by the use of known measurement methods such as those described in the section "Binding Activity" above. For example, in order to confirm that the antigen-binding activity of an antigen-binding domain or antigen-binding molecule comprising the domain becomes higher under a high calcium ion concentration condition than under a low calcium ion concentration condition, the antigen-binding activity of the domain or the molecule under low and high calcium ion concentration conditions is compared.

In the present invention, the expression "the antigen-binding activity is lower under a low calcium ion concentration condition than under a high calcium ion concentration condition" can also be expressed as "the antigen-binding activity of an antigen-binding domain or antigen-binding molecule comprising the domain is higher under a high calcium ion concentration condition than under a low calcium ion concentration condition". In the present invention, "the antigen-binding activity is lower under a low calcium ion concentration condition than under a high calcium ion concentration condition" is sometimes written as "the antigen-binding activity is weaker under a low calcium ion concentration condition than under a high calcium ion concentration condition". Also, "the antigen-binding activity under a low calcium ion concentration condition is reduced to be lower than that under a high calcium ion concentration condition" may be written as "the antigen-binding activity under a low calcium ion concentration condition is made weaker than that under a high calcium ion concentration condition".

When determining the antigen-binding activity, the conditions other than calcium ion concentration can be appropriately selected by those skilled in the art, and are not particularly limited. For example, the activity can be determined at 37° C. in HEPES buffer. For example, Biacore (GE Healthcare) or such can be used for the determination. When the antigen is a soluble antigen, the antigen-binding activity of an antigen-binding domain or antigen-binding molecule comprising the domain can be assessed by flowing the antigen as an analyte over a chip onto which the antigen-binding domain or antigen-binding molecule comprising the domain is immobilized. When the antigen is a membrane antigen, the binding activity of an antigen-binding domain or antigen-binding molecule comprising the domain to the membrane antigen can be assessed by flowing the antigen-binding domain or antigen-binding molecule comprising the domain as an analyte over a chip onto which the antigen is immobilized.

As long as the antigen-binding activity of an antigen-binding molecule of the present invention is weaker under a low calcium ion concentration condition than under a high calcium ion concentration condition, the ratio of the antigen-binding activity between low and high calcium ion concentration conditions is not particularly limited. However, the ratio of the KD (dissociation constant) of the antigen-binding molecule for an antigen at a low calcium ion concentration condition with respect to the KD at a high calcium ion concentration condition, i.e., the value of KD (3 μM Ca)/KD (2 mM Ca), is preferably 2 or more, more preferably 10 or more, and still more preferably 40 or more. The upper limit of the KD (3 μM Ca)/KD (2 mM Ca) value is not particularly limited, and may be any value such as 400, 1000, or 10000 as long as the molecule can be produced by techniques known to those skilled in the art.

When the antigen is a soluble antigen, KD (dissociation constant) can be used to represent the antigen-binding activity. Meanwhile, when the antigen is a membrane antigen, apparent KD (apparent dissociation constant) can be used to represent the activity. KD (dissociation constant) and apparent KD (apparent dissociation constant) can be determined by methods known to those skilled in the art, for example, using Biacore (GE healthcare), Scatchard plot, or flow cytometer.

Alternatively, for example, the dissociation rate constant (kd) can also be preferably used as an index to represent the ratio of the antigen-binding activity of an antigen-binding domain or antigen-binding molecule comprising the domain of the present invention between low and high calcium concentration conditions. When the dissociation rate constant (kd) is used instead of the dissociation constant (KD) as an index to represent the binding activity ratio, the ratio of the dissociation rate constant (kd) between low and high calcium concentration conditions, i.e., the value of kd (low calcium concentration condition)/kd (high calcium concentration condition), is preferably 2 or more, more preferably 5 or more, still more preferably 10 or more, and yet more preferably 30 or more. The upper limit of the Kd (low calcium concentration condition)/kd (high calcium concentration condition) value is not particularly limited, and can be any value such as 50, 100, or 200 as long as the molecule can be produced by techniques known to those skilled in the art.

When the antigen is a soluble antigen, kd (dissociation rate constant) can be used to represent the antigen-binding activity. Meanwhile, when the antigen is a membrane antigen, apparent kd (apparent dissociation rate constant) can be used to represent the antigen-binding activity. The kd (dissociation rate constant) and apparent kd (apparent dissociation rate constant) can be determined by methods known to those skilled in the art, for example, using Biacore (GE healthcare) or flow cytometer. In the present invention, when the antigen-binding activity of an antigen-binding domain or antigen-binding molecule comprising the domain is determined at different calcium ion concentrations, it is preferable to use the same conditions except for the calcium concentrations.

The methods described in WO 2012/073992 (for example, paragraph 0200-0213) and such may be presented as examples of a method of screening for an antigen-binding molecule or an antigen-binding domain whose antigen-binding activity under low calcium ion concentration conditions is lower than under high calcium ion concentration conditions, which is an embodiment provided by the present invention.

Libraries

In an embodiment, an antigen-binding domain or antigen-binding molecule of the present invention can be obtained from a library that is mainly composed of a plurality of antigen-binding molecules whose sequences are different from one another and whose antigen-binding domains have at least one amino acid residue that alters the antigen-binding activity of the antigen-binding molecules depending on ion concentrations. The ion concentrations preferably include, for example, metal ion concentration and hydrogen ion concentration.

Herein, a "library" refers to a plurality of antigen-binding molecules or a plurality of fusion polypeptides containing antigen-binding molecules, or nucleic acids or polynucleotides encoding their sequences. The sequences of a plurality of antigen-binding molecules or a plurality of fusion polypeptides containing antigen-binding molecules in a library are not identical, but are different from one another.

Herein, the phrase "sequences are different from one another" in the expression "a plurality of antigen-binding molecules whose sequences are different from one another" means that the sequences of antigen-binding molecules in a library are different from one another. Specifically, in a library, the number of sequences different from one another reflects the number of independent clones with different sequences, and may also be referred to as "library size". The library size of a conventional phage display library ranges from $10^6$ to $10^{12}$. The library size can be increased up to $10^{14}$ by the use of known techniques such as ribosome display. However, the actual number of phage particles used in panning selection of a phage library is in general 10-10000 times greater than the library size. This excess multiplicity is also referred to as "the number of library equivalents", and means that there are 10 to 10,000 individual clones that have the same amino acid sequence. Thus, in the present invention, the phrase "sequences are different from one another" means that the sequences of independent antigen-binding molecules in a library, excluding library equivalents, are different from one another. More specifically, the above means that there are $10^6$ to $10^{14}$ antigen-binding molecules whose sequences are different from one another, preferably $10^7$ to $10^{12}$ molecules, more preferably $10^8$ to $10^{11}$, and particularly preferably $10^8$ to $10^{10}$ whose sequences are different from one another.

In the present invention, the phrase "a plurality of" in the expression "a library mainly composed of a plurality of antigen-binding molecules" generally refers to, in the case of, for example, antigen-binding molecules, fusion polypeptides, polynucleotide molecules, vectors, or viruses of the present invention, a group of two or more types of the substance. For example, when two or more substances are different from one another in a particular characteristic, this means that there are two or more types of the substance. Such examples may include, for example, mutant amino acids observed at specific amino acid positions in an amino acid sequence. For example, when there are two or more antigen-binding molecules of the present invention whose sequences are substantially the same or preferably the same except for flexible residues or except for particular mutant amino acids at hypervariable positions exposed on the surface, there is a plurality of antigen-binding molecules of the present invention. In another example, when there are two or more polynucleotide molecules whose sequences are substantially the same or preferably the same except for nucleotides encoding flexible residues or nucleotides encoding mutant amino acids of hypervariable positions exposed on the surface, there are a plurality of polynucleotide molecules in the present invention.

In addition, in the present invention, the phrase "mainly composed of" in the expression "a library mainly composed of a plurality of antigen-binding molecules" reflects the number of antigen-binding molecules whose antigen-binding activity varies depending on ion concentrations, among independent clones with different sequences in a library. Specifically, it is preferable that there are at least $10^4$ antigen-binding molecules having such binding activity in a library. More preferably, antigen-binding domains of the present invention can be obtained from a library containing at least $10^5$ antigen-binding molecules having such binding activity. Still more preferably, antigen-binding domains of the present invention can be obtained from a library containing at least $10^6$ antigen-binding molecules having such binding activity. Particularly preferably, antigen-binding domains of the present invention can be obtained from a library containing at least $10^7$ antigen-binding molecules having such binding activity. Yet more preferably, antigen-binding domains of the present invention can be obtained from a library containing at least $10^8$ antigen-binding molecules having such binding activity. Alternatively, this may also be preferably expressed as the ratio of the number of antigen-binding molecules whose antigen-binding activity varies depending on ion concentrations with respect to the number of independent clones having different sequences in a library. Specifically, antigen-binding domains of the present invention can be obtained from a library in which antigen-binding molecules having such binding activity account for 0.1% to 80%, preferably 0.5% to 60%, more preferably 1% to 40%, still more preferably 2% to 20%, and particularly preferably 4% to 10% of independent clones with different sequences in the library. In the case of fusion polypeptides, polynucleotide molecules, or vectors, similar expressions may be possible using the number of molecules or the ratio to the total number of molecules. In the case of viruses, similar expressions may also be possible using the number of virions or the ratio to total number of virions.

Amino Acids that Alter the Antigen-Binding Activity of Antigen-Binding Domains Depending on Calcium Ion Concentrations Antigen-binding domains or antigen-binding molecules of the present invention to be screened by the above-described screening methods may be prepared in any manner. For example, when the metal ion is calcium ion, it is possible to use preexisting antigen-binding domains or antigen-binding molecules, preexisting libraries (phage library, etc.), antibodies or libraries prepared from hybridomas obtained by immunizing animals or from B cells of immunized animals, antibodies or libraries obtained by introducing amino acids capable of chelating calcium (for example, aspartic acid and glutamic acid) or unnatural amino acid mutations into the above-described antibodies or libraries (calcium-chelatable amino acids (such as aspartic acid and glutamic acid), libraries with increased content of unnatural amino acids, libraries prepared by introducing calcium-chelatable amino acids (such as aspartic acid and glutamic acid) or unnatural amino acid mutations at particular positions, or the like.

Examples of the amino acids that alter the antigen-binding activity of antigen-binding molecules depending on ion concentrations as described above may be any types of amino acids as long as the amino acids form a calcium-binding motif. Calcium-binding motifs are well known to those skilled in the art and have been described in details (for example, Springer et al. (Cell (2000) 102, 275-277); Kawasaki and Kretsinger (Protein Prof (1995) 2, 305-490); Moncrief et al. (J. Mol. Evol. (1990) 30, 522-562); Chauvaux et al. (Biochem. J. (1990) 265, 261-265); Bairoch and Cox (FEBS Lett. (1990) 269, 454-456); Davis (New Biol. (1990) 2, 410-419); Schaefer et al. (Genomics (1995) 25, 638-643); Economou et al. (EMBO J. (1990) 9, 349-354); Wurzburg et al. (Structure. (2006) 14, 6, 1049-1058)). Specifically, any known calcium-binding motifs, including type C lectins such as ASGPR, CD23, MBR, and DC-SIGN, can be included in antigen-binding molecules of the present invention. Preferred examples of such preferred calcium-binding motifs also include, in addition to those described above, for example, the calcium-binding motif in the antigen-binding domain of SEQ ID NO: 5.

Furthermore, as amino acids that alter the antigen-binding activity of antigen-binding domains included in the antigen-binding molecules of the present invention depending on calcium ion concentration conditions, for example, amino acids having metal-chelating activity may also be preferably used. Examples of such metal-chelating amino acids include, for example, serine (Ser (S)), threonine (Thr (T)), asparagine (Asn (N)), glutamine (Gln (Q)), aspartic acid (Asp (D)), and glutamic acid (Glu (E)).

Positions in the antigen-binding domains at which the above-described amino acids are contained are not particularly limited to particular positions, and may be any positions within the heavy chain variable region or light chain variable region that forms an antigen-binding domain, as long as they alter the antigen-binding activity of antigen-binding molecules depending on calcium ion concentrations. In a non-limiting embodiment, antigen-binding domains of the present invention can be obtained from a library mainly composed of antigen-binding molecules whose sequences are different from one another and whose heavy chain antigen-binding domains contain amino acids that alter the antigen-binding activity of the antigen-binding molecules depending on calcium ion concentrations. In another non-limiting embodiment, antigen-binding domains of the present invention can be obtained from a library mainly composed of antigen-binding molecules whose sequences are different from one another and whose heavy chain CDR3 domains contain the above-mentioned amino acids. In still another embodiment, antigen-binding domains of the present invention can be obtained from a library mainly composed of antigen-binding molecules whose sequences are different from one another and whose heavy chain CDR3 domains contain the above-mentioned amino acids at positions 95, 96, 100a, and/or 101 as indicated according to the Kabat numbering system.

Meanwhile, in a non-limiting embodiment of the present invention, antigen-binding domains of the present invention can be obtained from a library mainly composed of antigen-binding molecules whose sequences are different from one another and whose light chain antigen-binding domains contain amino acids that alter the antigen-binding activity of antigen-binding molecules depending on calcium ion concentrations. In another non-limiting embodiment, antigen-binding domains of the present invention can be obtained from a library mainly composed of antigen-binding molecules whose sequences are different from one another and whose light chain CDR1 domains contain the above-mentioned amino acids. In still another embodiment, antigen-binding domains of the present invention can be obtained from a library mainly composed of antigen-binding molecules whose sequences are different from one another and whose light chain CDR1 domains contain the above-mentioned amino acids at positions 30, 31, and/or 32 as indicated according to the Kabat numbering system.

In another non-limiting embodiment, antigen-binding domains of the present invention can be obtained from a library mainly composed of antigen-binding molecules whose sequences are different from one another and whose light chain CDR2 domains contain the above-mentioned amino acid residues. In yet another non-limiting embodiment, the present invention provides libraries mainly composed of antigen-binding molecules whose sequences are different from one another and whose light chain CDR2 domains contain the above-mentioned amino acid residues at position 50 as indicated according to the Kabat numbering system.

In still another embodiment of the present invention, antigen-binding domains of the present invention can be obtained from a library mainly composed of antigen-binding molecules whose sequences are different from one another and whose light chain CDR3 domains contain the above-mentioned amino acid residues. In an alternative embodiment, antigen-binding domains of the present invention can be obtained from a library mainly composed of antigen-binding molecules whose sequences are different from one another and whose light chain CDR3 domains contain the above-mentioned amino acid residues at position 92 as indicated according to the Kabat numbering system.

Furthermore, in a different embodiment of the present invention, antigen-binding domains of the present invention can be obtained from a library mainly composed of antigen-binding molecules whose sequences are different from one another and in which two or three CDRs selected from the above-described light chain CDR1, CDR2, and CDR3 contain the aforementioned amino acid residues. Moreover, antigen-binding domains of the present invention can be obtained from a library mainly composed of antigen-binding molecules whose sequences are different from one another and whose light chains contain the aforementioned amino acid residues at any one or more of positions 30, 31, 32, 50, and/or 92 as indicated according to the Kabat numbering system.

In a particularly preferred embodiment, the framework sequences of the light chain and/or heavy chain variable region of an antigen-binding molecule preferably contain human germ line framework sequences. Thus, in an embodiment of the present invention, when the framework sequences are completely human sequences, it is expected that when such an antigen-binding molecule of the present invention is administered to humans (for example, to treat diseases), it induces little or no immunogenic response. In the above sense, the phrase "containing a germ line sequence" in the present invention means that a part of the framework sequences in the present invention is identical to a part of any human germ line framework sequences. For example, when the heavy chain FR2 sequence of an antigen-binding molecule in the present invention is a combination of heavy chain FR2 sequences of different human germ line framework sequences, such a molecule is also an antigen-binding molecule in the present invention "containing a germ line sequence".

Preferred examples of the frameworks include, for example, fully human framework region sequences currently known, which are included in the website of V-Base (http://vbase.mrc-cpe.cam.ac.uk/) or others. Those framework region sequences can be appropriately used as a germ line sequence contained in an antigen-binding molecule of the present invention. The germ line sequences may be categorized according to their similarity (Tomlinson et al. (J. Mol. Biol. (1992) 227, 776-798); Williams and Winter (Eur. J. Immunol. (1993) 23, 1456-1461); Cox et al. (Nat. Genetics (1994) 7, 162-168)). Appropriate germ line sequences can be selected from Vκ, which is grouped into seven subgroups; Vλ, which is grouped into ten subgroups; and VH, which is grouped into seven subgroups.

Fully human VH sequences preferably include, but are not limited to, for example, VH sequences of:
    subgroup VH1 (for example, VH1-2, VH1-3, VH1-8, VH1-18, VH1-24, VH1-45, VH1-46, VH1-58, and VH1-69);
    subgroup VH2 (for example, VH2-5, VH2-26, and VH2-70);
    subgroup VH3 (VH3-7, VH3-9, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-72, VH3-73, and VH3-74);
    subgroup VH4 (VH4-4, VH4-28, VH4-31, VH4-34, VH4-39, VH4-59, and VH4-61);

subgroup VH5 (VH5-51);
    subgroup VH6 (VH6-1); and
    subgroup VH7 (VH7-4 and VH7-81).
    These are also described in known documents (Matsuda et al. (J. Exp. Med. (1998) 188, 1973-1975)) and such, and thus persons skilled in the art can appropriately design antigen-binding molecules of the present invention based on the information of these sequences. It is also preferable to use other fully human frameworks or framework sub-regions.
Fully human Vκ sequences preferably include, but are not limited to, for example:
    A20, A30, L1, L4, L5, L8, L9, L11, L12, L14, L15, L18, L19, L22, L23, L24, O2, O4, O8, O12, O14, and O18 grouped into subgroup Vk1;
    A1, A2, A3, A5, A7, A17, A18, A19, A23, O1, and O11, grouped into subgroup Vk2;
    A11, A27, L2, L6, L10, L16, L20, and L25, grouped into subgroup Vk3;
    B3, grouped into subgroup Vk4;
    B2 (herein also referred to as Vk5-2), grouped into subgroup Vk5; and
    A10, A14, and A26, grouped into subgroup Vk6
        (Kawasaki et al. (Eur. J. Immunol. (2001) 31, 1017-1028); Schable and Zachau (Biol. Chem. Hoppe Seyler (1993) 374, 1001-1022); Brensing-Kuppers et al. (Gene (1997) 191, 173-181)).
Fully human Vλ sequences preferably include, but are not limited to, for example:
    V1-2, V1-3, V1-4, V1-5, V1-7, V1-9, V1-11, V1-13, V1-16, V1-17, V1-18, V1-19, V1-20, and V1-22, grouped into subgroup VL1;
    V2-1, V2-6, V2-7, V2-8, V2-11, V2-13, V2-14, V2-15, V2-17, and V2-19, grouped into subgroup VL1;
    V3-2, V3-3, and V3-4, grouped into subgroup VL3;
    V4-1, V4-2, V4-3, V4-4, and V4-6, grouped into subgroup VL4; and
    V5-1, V5-2, V5-4, and V5-6, grouped into subgroup VL5
        (Kawasaki et al. (Genome Res. (1997) 7, 250-261)).
    Normally, these framework sequences are different from one another at one or more amino acid residues. These framework sequences can be used in combination with "at least one amino acid residue that alters the antigen-binding activity of an antigen-binding molecule depending on ion concentration conditions" in the present invention. Other examples of the fully human frameworks used in combination with "at least one amino acid residue that alters the antigen-binding activity of an antigen-binding molecule depending on ion concentration conditions" in the present invention include, but are not limited to, for example, KOL, NEWM, REI, EU, TUR, TEI, LAY, and POM (for example, Kabat et al. (1991) supra; Wu et al. (J. Exp. Med. (1970) 132, 211-250)).
    Without being bound by a particular theory, one reason for the expectation that the use of germ line sequences precludes adverse immune responses in most individuals is believed to be as follows. As a result of the process of affinity maturation during normal immune responses, somatic mutation occurs frequently in the variable regions of immunoglobulin. Such mutations mostly occur around CDRs whose sequences are hypervariable, but also affect residues of framework regions. Such framework mutations do not exist on the germ line genes, and also they are less likely to be immunogenic in patients. On the other hand, the normal human population is exposed to most of the framework sequences expressed from the germ line genes. As a result of immunotolerance, these germ line frameworks are expected to have low or no immunogenicity in patients. To maximize the possibility of immunotolerance, variable region-encoding genes may be selected from a group of commonly occurring functional germ line genes.

Known methods such as site-directed mutagenesis (Kunkel et al. (Proc. Natl. Acad. Sci. USA (1985) 82, 488-492)) and overlap extension PCR can be appropriately employed to produce the antigen-binding molecules of the present invention in which the above-described variable region sequences, heavy or light chain variable region sequences, CDR sequences, or framework sequences contain amino acids that alter the antigen-binding activity of the antigen-binding molecules depending on calcium ion concentration conditions.

For example, a library which contains a plurality of antigen-binding molecules of the present invention whose sequences are different from one another can be constructed by combining heavy chain variable regions prepared as a randomized variable region sequence library with a light chain variable region selected as a framework sequence originally containing at least one amino acid residue that alters the antigen-binding activity of the antigen-binding molecule depending on calcium ion concentration conditions. As a non-limiting example, when the ion concentration is calcium ion concentration, such preferred libraries include, for example, those constructed by combining the light chain variable region sequence of SEQ ID NO: 5 (Vk5-2) and the heavy chain variable region produced as a randomized variable region sequence library.

Alternatively, a light chain variable region sequence selected as a framework region originally containing at least one amino acid residue that alters the antigen-binding activity of an antigen-binding domain or antigen-binding molecule as mentioned above can be design to contain various amino acid residues other than the above amino acid residues. In the present invention, such residues are referred to as flexible residues. The number and position of flexible residues are not particularly limited as long as the antigen-binding activity of the antigen-binding domain or antigen-binding molecule of the present invention varies depending on ion concentrations. Specifically, the CDR sequences and/or FR sequences of the heavy chain and/or light chain may contain one or more flexible residues. For example, when the ion concentration is calcium ion concentration, non-limiting examples of flexible residues to be introduced into the light chain variable region sequence of SEQ ID NO: 5 (Vk5-2) include the amino acid residues listed in Tables 1 or 2.

TABLE 1

| CDR | Kabat NUMBERING | AMINO ACID IN 70% OF THE TOTAL | | | |
|------|------|------|------|------|------|
| CDR1 | 28 | S: 100% | | | |
| | 29 | I: 100% | | | |
| | 30 | E: 72% | N: 14% | S: 14% | |
| | 31 | D: 100% | | | |
| | 32 | D: 100% | | | |
| | 33 | L: 100% | | | |
| | 34 | A: 70% | N: 30% | | |
| CDR2 | 50 | E: 100% | | | |
| | 51 | A: 100% | | | |
| | 52 | S: 100% | | | |
| | 53 | H: 5% | N: 25% | S: 45% | T: 25% |
| | 54 | L: 100% | | | |
| | 55 | Q: 100% | | | |
| | 56 | S: 100% | | | |
| CDR3 | 90 | Q: 100% | | | |
| | 91 | H: 25% | S: 15% | R: 15% | Y: 45% |
| | 92 | D: 80% | N: 10% | S: 10% | |
| | 93 | D: 5% | G: 10% | N: 25% | S: 50% | R: 10% |
| | 94 | S: 50% | Y: 50% | | |
| | 95 | P: 100% | | | |
| | 96 | L: 50% | Y: 50% | | |

(POSITION INDICATES Kabat NUMBERING)

TABLE 2

| CDR | Kabat NUMBERING | AMINO ACID IN 70% OF THE TOTAL | | | |
|------|------|------|------|------|------|
| CDR1 | 28 | S: 100% | | | |
| | 29 | I: 100% | | | |
| | 30 | E: 83% | S: 17% | | |
| | 31 | D: 100% | | | |
| | 32 | D: 100% | | | |
| | 33 | L: 100% | | | |
| | 34 | A: 70% | N: 30% | | |
| CDR2 | 50 | H: 100% | | | |
| | 51 | A: 100% | | | |
| | 52 | S: 100% | | | |
| | 53 | H: 5% | N: 25% | S: 45% | T: 25% |
| | 54 | L: 100% | | | |
| | 55 | Q: 100% | | | |
| | 56 | S: 100% | | | |
| CDR3 | 90 | Q: 100% | | | |
| | 91 | H: 25% | S: 15% | R: 15% | Y: 45% |

TABLE 2-continued

| CDR | Kabat NUMBERING | | AMINO ACID IN 70% OF THE TOTAL | | | |
|---|---|---|---|---|---|---|
| | 92 | D: 80% | N: 10% | S: 10% | | |
| | 93 | D: 5% | G: 10% | N: 25% | S: 50% | R: 10% |
| | 94 | S: 50% | Y: 50% | | | |
| | 95 | P: 100% | | | | |
| | 96 | L: 50% | Y: 50% | | | |

(POSITION INDICATES Kabat NUMBERING)

Herein, flexible residues refer to amino acid residue variations present at hypervariable positions at which several different amino acids are present on the light chain and heavy chain variable regions when the amino acid sequences of known and/or native antibodies or antigen-binding domains are compared. Hypervariable positions are generally located in the CDR regions. In an embodiment, the data provided by Kabat, Sequences of Proteins of Immunological Interest (National Institute of Health Bethesda Md.) (1987 and 1991) is useful to determine hypervariable positions in known and/or native antibodies. Furthermore, databases on the Internet (http://vbase.mrc-cpe.cam.ac.uk/, http://www.bioinf.org.uk/abs/index.html) provide the collected sequences of many human light chains and heavy chains and their locations. The information on the sequences and locations is useful to determine hypervariable positions in the present invention. According to the present invention, when a certain amino acid position has preferably about 2 to about 20 possible amino acid residue variations, preferably about 3 to about 19, preferably about 4 to about 18, preferably 5 to 17, preferably 6 to 16, preferably 7 to 15, preferably 8 to 14, preferably 9 to 13, and preferably 10 to 12 possible amino acid residue variations, the position is hypervariable. In some embodiments, a certain amino acid position may have preferably at least about 2, preferably at least about 4, preferably at least about 6, preferably at least about 8, preferably about 10, and preferably about 12 amino acid residue variations.

Alternatively, a library containing a plurality of antigen-binding molecules of the present invention whose sequences are different from one another can be constructed by combining heavy chain variable regions produced as a randomized variable region sequence library with light chain variable regions into which at least one amino acid residue that alters the antigen-binding activity of antigen-binding molecules depending on ion concentrations as mentioned above is introduced. When the ion concentration is calcium ion concentration, non-limiting examples of such libraries preferably include, for example, libraries in which heavy chain variable regions produced as a randomized variable region sequence library are combined with light chain variable region sequences in which a particular residue(s) in a germ line sequence such as SEQ ID NO: 6 (Vk1), SEQ ID NO: 7 (Vk2), SEQ ID NO: 8 (Vk3), or SEQ ID NO: 9 (Vk4) has been substituted with at least one amino acid residue that alters the antigen-binding activity of an antigen-binding molecule depending on calcium ion concentrations. Non-limiting examples of such amino acid residues include amino acid residues in light chain CDR1. Furthermore, non-limiting examples of such amino acid residues include amino acid residues in light chain CDR2. In addition, non-limiting examples of such amino acid residues also include amino acid residues in light chain CDR3.

Non-limiting examples of such amino acid residues contained in light chain CDR1 include those at positions 30, 31, and/or 32 in the CDR1 of light chain variable region as indicated by EU numbering. Furthermore, non-limiting examples of such amino acid residues contained in light chain CDR2 include an amino acid residue at position 50 in the CDR2 of light chain variable region as indicated by Kabat numbering. Moreover, non-limiting examples of such amino acid residues contained in light chain CDR3 include an amino acid residue at position 92 in the CDR3 of light chain variable region as indicated by Kabat numbering. These amino acid residues can be contained alone or in combination as long as they form a calcium-binding motif and/or as long as the antigen-binding activity of an antigen-binding molecule varies depending on calcium ion concentrations. Meanwhile, as troponin C, calmodulin, parvalbumin, and myosin light chain, which have several calcium ion-binding sites and are believed to be derived from a common origin in terms of molecular evolution, are known, the light chain CDR1, CDR2, and/or CDR3 can be designed to have their binding motifs. For example, it is possible to use cadherin domains, EF hand of calmodulin, C2 domain of Protein kinase C, Gla domain of blood coagulation protein Factor IX, C type lectins of asialoglycoprotein receptor and mannose-binding receptor, A domains of LDL receptors, annexin, thrombospondin type 3 domain, and EGF-like domains in an appropriate manner for the above purposes.

When heavy chain variable regions produced as a randomized variable region sequence library and light chain variable regions into which at least one amino acid residue that alters the antigen-binding activity of an antigen-binding molecule depending on ion concentration conditions has been introduced are combined as described above, the sequences of the light chain variable regions can be designed to contain flexible residues in the same manner as described above. The number and position of such flexible residues are not particularly limited to particular embodiments as long as the antigen-binding activity of antigen-binding molecules of the present invention varies depending on ion concentration conditions. Specifically, the CDR sequences and/or FR sequences of heavy chain and/or light chain can contain one or more flexible residues. When the ion concentration is calcium ion concentration, non-limiting examples of flexible residues to be introduced into the sequence of light chain variable region include the amino acid residues listed in Tables 1 and 2.

The preferred heavy chain variable regions to be combined include, for example, randomized variable region libraries. Known methods are combined as appropriate to produce a randomized variable region library. In a non-limiting embodiment of the present invention, an immune library constructed based on antibody genes derived from lymphocytes of animals immunized with a specific antigen, patients with infections, persons with an elevated antibody titer in blood as a result of vaccination, cancer patients, or auto immune disease patients, may be preferably used as a randomized variable region library.

In another non-limiting embodiment of the present invention, a synthetic library produced by replacing the CDR sequences of V genes in genomic DNA or functional reshaped V genes with a set of synthetic oligonucleotides containing sequences encoding codon sets of an appropriate length can also be preferably used as a randomized variable region library. In this case, since sequence diversity is observed in the heavy chain CDR3 sequence, it is also possible to replace the CDR3 sequence only. A criterion of giving rise to diversity in amino acids in the variable region of an antigen-binding molecule is that diversity is given to amino acid residues at surface-exposed positions in the antigen-binding molecule. The surface-exposed position refers to a position that is considered to be able to be exposed on the surface and/or contacted with an antigen, based on structure, ensemble of structures, and/or modeled structure of an antigen-binding molecule. In general, such positions are CDRs. Preferably, surface-exposed positions are determined using coordinates from a three-dimensional model of an antigen-binding molecule using a computer program such as the InsightII program (Accelrys). Surface-exposed positions can be determined using algorithms known in the art (for example, Lee and Richards (J. Mol. Biol. (1971) 55, 379-400); Connolly (J. Appl. Cryst. (1983) 16, 548-558)). Determination of surface-exposed positions can be performed using software suitable for protein modeling and three-dimensional structural information obtained from an antibody. Software that can be used for these purposes preferably includes SYBYL Biopolymer Module software (Tripos Associates). Generally or preferably, when an algorithm requires a user input size parameter, the "size" of a probe which is used in the calculation is set at about 1.4 Angstrom or smaller in radius. Furthermore, methods for determining surface-exposed regions and areas using software for personal computers are described by Pacios (Comput. Chem. (1994) 18 (4), 377-386; J. Mol. Model. (1995) 1, 46-53).

In another non-limiting embodiment of the present invention, a naive library, which is constructed from antibody genes derived from lymphocytes of healthy persons and whose repertoire consists of naive sequences, which are antibody sequences with no bias, can also be particularly preferably used as a randomized variable region library (Gejima et al. (Human Antibodies (2002) 11, 121-129); Cardoso et al. (Scand. J. Immunol. (2000) 51, 337-344)). Herein, an amino acid sequence comprising a naive sequence refers to an amino acid sequence obtained from such a naive library.

In one embodiment of the present invention, an antigen-binding domain of the present invention can be obtained from a library containing a plurality of antigen-binding molecules of the present invention whose sequences are different from one another, prepared by combining light chain variable regions constructed as a randomized variable region sequence library with a heavy chain variable region selected as a framework sequence that originally contains "at least one amino acid residue that alters the antigen-binding activity of an antigen-binding molecule depending on ion concentration conditions". When the ion concentration is calcium ion concentration, non-limiting examples of such libraries preferably include those constructed by combining light chain variable regions constructed as a randomized variable region sequence library with the sequence of heavy chain variable region of SEQ ID NO: 10 (6RL#9-IgG1) or SEQ ID NO: 11 (6KC4-1#85-IgG1). Alternatively, such a library can be constructed by selecting appropriate light chain variable regions from those having germ line sequences, instead of light chain variable regions constructed as a randomized variable region sequence library. Such preferred libraries include, for example, those in which the sequence of heavy chain variable region of SEQ ID NO: 10 (6RL#9-IgG1) or SEQ ID NO: 11 (6KC4-1#85-IgG1) is combined with light chain variable regions having germ line sequences.

Alternatively, the sequence of a heavy chain variable region selected as a framework sequence that originally contains "at least one amino acid residue that alters the antigen-binding activity of an antigen-binding molecule depending on ion concentration conditions" as mentioned above can be designed to contain flexible residues. The number and position of the flexible residues are not particularly limited as long as the antigen-binding activity of an antigen-binding molecule of the present invention varies depending on ion concentration conditions. Specifically, the CDR and/or FR sequences of heavy chain and/or light chain can contain one or more flexible residues. When the ion concentration is calcium ion concentration, non-limiting examples of flexible residues to be introduced into the sequence of heavy chain variable region of SEQ ID NO: 10 (6RL#9-IgG1) include all amino acid residues of heavy chain CDR1 and CDR2 and the amino acid residues of the heavy chain CDR3 except those at position(s) 95, 96, and/or 100a. Alternatively, non-limiting examples of flexible residues to be introduced into the sequence of heavy chain variable region of SEQ ID NO: 11 (6KC4-1#85-IgG1) include all amino acid residues of heavy chain CDR1 and CDR2 and the amino acid residues of the heavy chain CDR3 except those at amino acid position(s) 95 and/or 101.

Alternatively, a library containing a plurality of antigen-binding molecules whose sequences are different from one another can be constructed by combining light chain variable regions constructed as a randomized variable region sequence library or light chain variable regions having germ line sequences with heavy chain variable regions into which "at least one amino acid residue that alters the antigen-binding activity of an antigen-binding molecule depending on ion concentration conditions" has been introduced as mentioned above. When the ion concentration is calcium ion concentration, non-limiting examples of such libraries preferably include those in which light chain variable regions constructed as a randomized variable region sequence library or light chain variable regions having germ line sequences are combined with the sequence of a heavy chain variable region in which a particular residue(s) has been substituted with at least one amino acid residue that alters the antigen-binding activity of an antigen-binding molecule depending on calcium ion concentration conditions. Non-limiting examples of such amino acid residues include amino acid residues of the heavy chain CDR1. Further non-limiting examples of such amino acid residues include amino acid residues of the heavy chain CDR2. In addition, non-limiting examples of such amino acid residues also include amino acid residues of the heavy chain CDR3. Non-limiting examples of such amino acid residues of heavy chain CDR3 include the amino acid(s) at position(s) 95, 96, 100a, and/or 101 in the CDR3 of heavy chain variable region as indicated by the Kabat numbering. Furthermore, these amino acid residues can be contained alone or in combination as long as they form a calcium-binding motif and/or the antigen-binding activity of an antigen-binding molecule varies depending on calcium ion concentration conditions.

When light chain variable regions constructed as a randomized variable region sequence library or light chain variable regions having germ line sequence are combined with a heavy chain variable region into which at least one amino acid residue that alter the antigen-binding activity of an antigen-binding molecule depending on ion concentration conditions as mentioned above has been introduced, the sequence of the heavy chain variable region can also be designed to contain flexible residues in the same manner as described above. The number and position of flexible residues are not particularly limited as long as the antigen-binding activity of an antigen-binding molecule of the present invention varies depending on ion concentration conditions. Specifically, the heavy chain CDR and/or FR sequences may contain one or more flexible residues. Furthermore, randomized variable region libraries can be preferably used as amino acid sequences of CDR1, CDR2, and/or CDR3 of the heavy chain variable region other than the amino acid residues that alter the antigen-binding activity of an antigen-binding molecule depending on ion concentration conditions. When germ line sequences are used as light chain variable regions, non-limiting examples of such sequences include those of SEQ ID NO: 6 (Vk1), SEQ ID NO: 7 (Vk2), SEQ ID NO: 8 (Vk3), and SEQ ID NO: 9 (Vk4).

Any of the above-described amino acids that alter the antigen-binding activity of an antigen-binding molecule depending on calcium ion concentration conditions can be preferably used, as long as they form a calcium-binding motif. Specifically, such amino acids include electron-donating amino acids. Preferred examples of such electron-donating amino acids include serine, threonine, asparagine, glutamic acid, aspartic acid, and glutamic acid.

Condition of Hydrogen Ion Concentrations

In an embodiment of the present invention, the condition of ion concentrations refers to the condition of hydrogen ion concentrations or pH conditions. In the present invention, the concentration of proton, i.e., the nucleus of hydrogen atom, is treated as synonymous with hydrogen index (pH). When the activity of hydrogen ion in an aqueous solution is represented as aH+, pH is defined as −log 10aH+. When the ionic strength of the aqueous solution is low (for example, lower than $10^{-3}$), aH+ is nearly equal to the hydrogen ion strength. For example, the ionic product of water at 25° C. and 1 atmosphere is Kw=aH+aOH=$10^{-14}$, and therefore in pure water, aH+=aOH=$10^{-7}$. In this case, pH=7 is neutral; an aqueous solution whose pH is lower than 7 is acidic or whose pH is greater than 7 is alkaline.

In the present invention, when pH condition is used as the ion concentration condition, pH conditions include conditions of high hydrogen ion concentration or low pHs, i.e., an acidic pH range condition, and conditions of low hydrogen ion concentration or high pHs, i.e., a neutral pH range condition. "The antigen-binding activity of an antigen-binding domain contained in the antigen-binding molecule of the present invention varies depending on pH condition" means that the antigen-binding activity of an antigen-binding domain contained in an antigen-binding molecule varies due to the difference in conditions of a high hydrogen ion concentration or low pH (an acidic pH range) and a low hydrogen ion concentration or high pH (a neutral pH range). This includes, for example, the case where the antigen-binding activity of an antigen-binding molecule is higher under a neutral pH range condition than under an acidic pH range condition and the case where the antigen-binding activity of an antigen-binding molecule is higher under an acidic pH range condition than under a neutral pH range condition.

Herein, neutral pH range is not limited to a specific value and is preferably selected from between pH 6.7 and pH 10.0.

In another embodiment, the pH can be selected from between pH 6.7 and pH 9.5. In still another embodiment, the pH can be selected from between pH 7.0 and pH 9.0. In yet another embodiment, the pH can be selected from between pH 7.0 and pH 8.0. In particular, the preferred pH includes pH 7.4, which is close to the pH of plasma (blood) in vivo.

Herein, an acidic pH range is not limited to a specific value and is preferably selected from between pH 4.0 and pH 6.5. In another embodiment, the pH can be selected from between pH 4.5 and pH 6.5. In still another embodiment, the pH can be selected from between pH 5.0 and pH 6.5. In yet another embodiment, the pH can be selected from between pH 5.5 and pH 6.5. In particular, the preferred pH includes pH 5.8, which is close to the ionized calcium concentration in the early endosome in vivo.

In the present invention, "the antigen-binding activity under a condition of a high hydrogen ion concentration or low pH (an acidic pH range) is lower than that under a condition of a low hydrogen ion concentration or high pH (a neutral pH range)" means that the antigen-binding activity of antigen-binding domain or antigen-binding molecule comprising the domain of the present invention at a pH selected from between pH 4.0 and pH 6.5 is weaker than that at a pH selected from between pH 6.7 and pH 10.0; preferably means that the antigen-binding activity of an antigen-binding domain or antigen-binding molecule comprising the domain at a pH selected from between pH 4.5 and pH 6.5 is weaker than that at a pH selected from between pH 6.7 and pH 9.5; more preferably, means that the antigen-binding activity of an antigen-binding molecule at a pH selected from between pH 5.0 and pH 6.5 is weaker than that at a pH selected from between pH 7.0 and pH 9.0; still more preferably means that the antigen-binding activity of an antigen-binding molecule at a pH selected from between pH 5.5 and pH 6.5 is weaker than that at a pH selected from between pH 7.0 and pH 8.0; particularly preferably means that the antigen-binding activity at the pH in the early endosome in vivo is weaker than the antigen-binding activity at the pH of plasma in vivo; and specifically means that the antigen-binding activity of an antigen-binding molecule at pH 5.8 is weaker than the antigen-binding activity at pH 7.4.

Whether the antigen-binding activity of an antigen-binding domain or antigen-binding molecule comprising the domain has changed by the pH condition can be determined, for example, by the use of known measurement methods such as those described in the section "Binding Activity" above. For example, the binding activity is measured under different pH conditions using the measurement methods described above. For example, the antigen-binding activity of an antigen-binding domain or antigen-binding molecule comprising the domain is compared under the conditions of acidic pH range and neutral pH range to confirm that binding activity of the domain or the molecule changes to be higher under the condition of neutral pH range than that under the condition of acidic pH range.

Furthermore, in the present invention, the expression "the antigen-binding activity under a condition of high hydrogen ion concentration or low pH, i.e., under an acidic pH range condition, is lower than that under a condition of low hydrogen ion concentration or high pH, i.e., under a neutral pH range condition" can also be expressed as "the antigen-binding activity of an antigen-binding domain or antigen-binding molecule comprising the domain under a condition of low hydrogen ion concentration or high pH, i.e., under a neutral pH range condition, is higher than that under a condition of high hydrogen ion concentration or low pH, i.e., under an acidic pH range condition". In the present invention, "the antigen-binding activity under a condition of high hydrogen ion concentration or low pH, i.e., under an acidic pH range condition, is lower than that under a condition of low hydrogen ion concentration or high pH, i.e., under a neutral pH range condition" may be described as "the antigen-binding activity under a condition of high hydrogen ion concentration or low pH, i.e., under an acidic pH range condition, is weaker than the antigen-binding ability under a condition of low hydrogen ion concentration or high pH, i.e., under a neutral pH range condition". Alternatively, "the antigen-binding activity under a condition of high hydrogen ion concentration or low pH, i.e., under an acidic pH range condition, is reduced to be lower than that under a condition of low hydrogen ion concentration or high pH, i.e., under a neutral pH range condition" may be described as "the antigen-binding activity under a condition of high hydrogen ion concentration or low pH, i.e., under an acidic pH range condition, is reduced to be weaker than the antigen-binding ability under a condition of low hydrogen ion concentration or high pH, i.e., under a neutral pH range condition".

The conditions other than hydrogen ion concentration or pH for measuring the antigen-binding activity may be suitably selected by those skilled in the art and are not particularly limited. Measurements can be carried out, for example, at 37° C. using HEPES buffer. Measurements can be carried out, for example, using Biacore (GE Healthcare). When the antigen is a soluble antigen, the antigen-binding activity of antigen-binding domain or antigen-binding molecule comprising the domain can be determined by assessing the binding activity to the soluble antigen by flowing the antigen as an analyte into a chip immobilized with the antigen-binding domain or the antigen-binding molecule comprising the domain. When the antigen is a membrane antigen, the binding activity to the membrane antigen can be assessed by flowing the antigen-binding domain or the antigen-binding molecule comprising the domain as an analyte into a chip immobilized with the antigen.

As long as the antigen-binding activity of an antigen-binding molecule of the present invention at a condition of high hydrogen ion concentration or low pH, i.e., in an acidic pH range condition is weaker than that at a condition of low hydrogen ion concentration or high pH, i.e., in a neutral pH range condition, the ratio of the antigen-binding activity between that under a condition of high hydrogen ion concentration or low pH, i.e., under an acidic pH range condition, and under a condition of low hydrogen ion concentration or high pH, i.e., under a neutral pH range condition is not particularly limited, and the value of KD (pH 5.8)/KD (pH 7.4), which is the ratio of the dissociation constant (KD) for an antigen at a condition of high hydrogen ion concentration or low pH, i.e., in an acidic pH range condition to the KD at a condition of low hydrogen ion concentration or high pH, i.e., in a neutral pH range condition, is preferably 2 or more; more preferably the value of KD (pH 5.8)/KD (pH 7.4) is 10 or more; and still more preferably the value of KD (pH 5.8)/KD (pH 7.4) is 40 or more. The upper limit of KD (pH 5.8)/KD (pH 7.4) value is not particularly limited, and may be any value such as 400, 1000, or 10000, as long as the molecule can be produced by the techniques of those skilled in the art.

Alternatively, for example, the dissociation rate constant (kd) can be suitably used as an index for indicating the ratio of the antigen-binding activity of an antigen-binding domain or antigen-binding molecule comprising the domain of the present invention between that at a condition of high hydrogen ion concentration or low pH, i.e., in an acidic pH range condition and at a condition of low hydrogen ion concentration or high pH, i.e., in a neutral pH range condition. When kd (dissociation rate constant) is used as an index for indicating the binding activity ratio instead of KD (dissociation constant), the value of kd (in an acidic pH range condition)/kd (in a neutral pH range condition), which is the ratio of kd (dissociation rate constant) for the antigen at a condition of high hydrogen ion concentration or low pH, i.e., in an acidic pH range condition to kd (dissociation rate constant) at a condition of low hydrogen ion concentration or high pH, i.e., in a neutral pH range condition, is preferably 2 or more, more preferably 5 or more, still more preferably 10 or more, and yet more preferably 30 or more. The upper limit of kd (in an acidic pH range condition)/kd (in a neutral pH range condition) value is not particularly limited, and may be any value such as 50, 100, or 200, as long as the molecule can be produced by the techniques of those skilled in the art.

When the antigen is a soluble antigen, the dissociation rate constant (kd) can be used as the value for antigen-binding activity and when the antigen is a membrane antigen, the apparent dissociation rate constant (kd) can be used. The dissociation rate constant (kd) and apparent dissociation rate constant (kd) can be determined by methods known to those skilled in the art, and Biacore (GE healthcare), flow cytometer, and such may be used. In the present invention, when the antigen-binding activity of an antigen-binding domain or antigen-binding molecule comprising the domain is measured at different hydrogen ion concentrations, i.e., pHs, conditions other than the hydrogen ion concentration, i.e., pH, are preferably the same.

For example, an antigen-binding domain or antigen-binding molecule whose antigen-binding activity at a condition of high hydrogen ion concentration or low pH, i.e., in an acidic pH range condition is lower than that at a condition of low hydrogen ion concentration or high pH, i.e., in a neutral pH range condition, which is one embodiment provided by the present invention, can be obtained via screening of antigen-binding domains or antigen-binding molecules, comprising the following steps (a) to (c):

(a) obtaining the antigen-binding activity of an antigen-binding domain or antigen-binding molecule in an acidic pH range condition;

(b) obtaining the antigen-binding activity of an antigen-binding domain or antigen-binding molecule in a neutral pH range condition; and (c) selecting an antigen-binding domain or antigen-binding molecule whose antigen-binding activity in the acidic pH range condition is lower than that in the neutral pH range condition.

Alternatively, an antigen-binding domain or antigen-binding molecule whose antigen-binding activity at a condition of high hydrogen ion concentration or low pH, i.e., in an acidic pH range condition, is lower than that at a condition of low hydrogen ion concentration or high pH, i.e., in a neutral pH range condition, which is one embodiment provided by the present invention, can be obtained via screening of antigen-binding domains or antigen-binding molecules, or a library thereof, comprising the following steps (a) to (c):

(a) contacting an antigen-binding domain or antigen-binding molecule, or a library thereof, in a neutral pH range condition with an antigen;

(b) placing in an acidic pH range condition the antigen-binding domain or antigen-binding molecule bound to the antigen in step (a); and (c) isolating the antigen-binding domain or antigen-binding molecule dissociated in step (b).

An antigen-binding domain or antigen-binding molecule whose antigen-binding activity at a condition of high hydrogen ion concentration or low pH, i.e., in an acidic pH range condition is lower than that at a condition of low hydrogen ion concentration or high pH, i.e., in a neutral pH range condition, which is another embodiment provided by the present invention, can be obtained via screening of antigen-binding domains or antigen-binding molecules, or a library thereof, comprising the following steps (a) to (d):

(a) contacting in an acidic pH range condition an antigen with a library of antigen-binding domains or antigen-binding molecules;

(b) selecting the antigen-binding domain or antigen-binding molecule which does not bind to the antigen in step (a);

(c) allowing the antigen-binding domain or antigen-binding molecule selected in step (b) to bind with the antigen in a neutral pH range condition; and (d) isolating the antigen-binding domain or antigen-binding molecule bound to the antigen in step (c).

An antigen-binding domain or antigen-binding molecule whose antigen-binding activity at a condition of high hydrogen ion concentration or low pH, i.e., in an acidic pH range condition, is lower than that at a condition of low hydrogen ion concentration or high pH, i.e., in a neutral pH range condition, which is even another embodiment provided by the present invention, can be obtained by a screening method comprising the following steps (a) to (c):

(a) contacting in a neutral pH range condition a library of antigen-binding domains or antigen-binding molecules with a column immobilized with an antigen;

(b) eluting in an acidic pH range condition from the column the antigen-binding domain or antigen-binding molecule bound to the column in step (a); and (c) isolating the antigen-binding domain or antigen-binding molecule eluted in step (b).

An antigen-binding domain or antigen-binding molecule whose antigen-binding activity at a condition of high hydrogen ion concentration or low pH, i.e., in an acidic pH range condition, is lower than that at a condition of low hydrogen ion concentration or high pH, i.e., in a neutral pH range condition, which is still another embodiment provided by the present invention, can be obtained by a screening method comprising the following steps (a) to (d):

(a) allowing, in an acidic pH range condition, a library of antigen-binding domains or antigen-binding molecules to pass a column immobilized with an antigen;

(b) collecting the antigen-binding domain or antigen-binding molecule eluted without binding to the column in step (a);

(c) allowing the antigen-binding domain or antigen-binding molecule collected in step (b) to bind with the antigen in a neutral pH range condition; and (d) isolating the antigen-binding domain or antigen-binding molecule bound to the antigen in step (c).

An antigen-binding domain or antigen-binding molecule whose antigen-binding activity at a high hydrogen ion concentration or low pH, i.e., in an acidic pH range condition, is lower than that at a low hydrogen ion concentration or high pH, i.e., in a neutral pH range condition, which is yet another embodiment provided by the present invention, can be obtained by a screening method comprising the following steps (a) to (d):

(a) contacting an antigen with a library of antigen-binding domains or antigen-binding molecules in a neutral pH range condition;

(b) obtaining the antigen-binding domain or antigen-binding molecule bound to the antigen in step (a);

(c) placing in an acidic pH range condition the antigen-binding domain or antigen-binding molecule obtained in step (b); and (d) isolating the antigen-binding domain or antigen-binding molecule whose antigen-binding activity in step (c) is weaker than the standard selected in step (b).

The above-described steps may be repeated twice or more times. Thus, the present invention provides antigen-binding domains and antigen-binding molecules whose antigen-binding activity in an acidic pH range condition is lower than that in a neutral pH range condition, which are obtained by a screening method that further comprises the steps of repeating steps (a) to (c) or (a) to (d) in the above-described screening methods. The number of times that steps (a) to (c) or (a) to (d) is repeated is not particularly limited; however, the number is 10 or less in general.

In the screening methods of the present invention, the antigen-binding activity of an antigen-binding domain or antigen-binding molecule at a condition of a high hydrogen ion concentration or low pH, i.e., in an acidic pH range, is not particularly limited, as long as it is the antigen-binding activity at a pH of between 4.0 and 6.5, and includes the antigen-binding activity at a pH of between 4.5 and 6.6 as the preferred pH. The antigen-binding activity also includes that at a pH of between 5.0 and 6.5, and that at a pH of between 5.5 and 6.5 as another preferred pH. The antigen-binding activity also includes that at the pH in the early endosome in vivo as the more preferred pH, and specifically, that at pH 5.8. Meanwhile, the antigen-binding activity of an antigen-binding domain or antigen-binding molecule at a condition of a low hydrogen ion concentration or high pH, i.e., in a neutral pH range, is not particularly limited, as long as it is the antigen-binding activity at a pH of between 6.7 and 10, and includes the antigen-binding activity at a pH of between 6.7 and 9.5 as the preferred pH. The antigen-binding activity also includes that at a pH of between 7.0 and 9.5 and that at a pH of between 7.0 and 8.0 as another preferred pH. The antigen-binding activity also includes that at the pH of plasma in vivo as the more preferred pH, and specifically, that at pH 7.4.

The antigen-binding activity of an antigen-binding domain or antigen-binding molecule can be measured by methods known to those skilled in the art. Those skilled in the art can suitably determine conditions other than ionized calcium concentration. The antigen-binding activity of an antigen-binding domain or antigen-binding molecule can be assessed based on the dissociation constant (KD), apparent dissociation constant (KD), dissociation rate constant (kd), apparent dissociation rate constant (kd), and such. These can be determined by methods known to those skilled in the art, for example, using Biacore (GE healthcare), Scatchard plot, or FACS.

In the present invention, the step of selecting an antigen-binding domain or antigen-binding molecule whose antigen-binding activity at a condition of low hydrogen ion concentration or high pH, i.e., in a neutral pH range condition, is higher than that at a condition of high hydrogen ion concentration or low pH, i.e., in an acidic pH range condition, is synonymous with the step of selecting an antigen-binding domain or antigen-binding molecule whose antigen-binding activity at a condition of high hydrogen ion concentration or low pH, i.e., in an acidic pH range condition, is lower than that at a condition of low hydrogen ion concentration or high pH, i.e., in a neutral pH range condition.

As long as the antigen-binding activity at a condition of low hydrogen ion concentration or high pH, i.e., in a neutral pH range condition, is higher than that at a condition of high hydrogen ion concentration or low pH, i.e., in an acidic pH range condition, the difference between the antigen-binding activity at a condition of low hydrogen ion concentration or high pH, i.e., in a neutral pH range condition, and that at a condition of high hydrogen ion concentration or low pH, i.e., in an acidic pH range condition, is not particularly limited; however, the antigen-binding activity at a condition of low hydrogen ion concentration or high pH, i.e., in a neutral pH range condition, is preferably twice or more, more preferably 10 times or more, and still more preferably 40 times or more than that at a condition of high hydrogen ion concentration or low pH, i.e., in an acidic pH range condition.

Amino Acids that Alter the Antigen-Binding Activity of an Antigen-Binding Domain Depending on Hydrogen Ion Concentration Conditions The antigen-binding domain or antigen-binding molecule of the present invention to be screened by the above-described screening methods may be prepared in any manner. For example, conventional antigen-binding molecules, conventional libraries (phage library, etc.), antibodies or libraries prepared from B cells of immunized animals or from hybridomas obtained by immunizing animals, antibodies or libraries (libraries with increased content of amino acids with a side chain pKa of 4.0-8.0 (for example, histidine and glutamic acid) or unnatural amino acids, libraries introduced with amino acids with a side chain pKa of 4.0-8.0 (for example, histidine and glutamic acid) or unnatural amino acid mutations at specific positions, etc.) obtained by introducing amino acids with a side chain pKa of 4.0-8.0 (for example, histidine and glutamic acid) or unnatural amino acid mutations into the above-described antibodies or libraries may be used.

Methods for obtaining an antigen-binding domain or antigen-binding molecule whose antigen-binding activity at a low hydrogen ion concentration or high pH, i.e., in a neutral pH range condition, is higher than that at a high hydrogen ion concentration or low pH, i.e., in an acidic pH range condition, from an antigen-binding domains or antigen-binding molecules prepared from hybridomas obtained by immunizing animals or from B cells of immunized animals preferably include, for example, the antigen-binding molecule or antigen-binding molecule in which at least one of the amino acids of the antigen-binding domain or antigen-binding molecule is substituted with an amino acid with a side chain pKa of 4.0-8.0 (for example, histidine and glutamic acid) or an unnatural amino acid mutation, or the antigen-binding domain or antigen-binding molecule inserted with an amino acid with a side chain pKa of 4.0-8.0 (for example, histidine and glutamic acid) or unnatural amino acid, such as those described in WO 2009/125825.

The sites of introducing mutations of amino acids with a side chain pKa of 4.0-8.0 (for example, histidine and glutamic acid) or unnatural amino acids are not particularly limited, and may be any position as long as the antigen-binding activity in an acidic pH range becomes weaker than that in a neutral pH range (the value of KD (in an acidic pH range)/KD (in a neutral pH range) or kd (in an acidic pH range)/kd (in a neutral pH range) is increased) as compared to before substitution or insertion. For example, when the antigen-binding molecule is an antibody, antibody variable region and CDRs are suitable. Those skilled in the art can appropriately determine the number of amino acids to be substituted with or the number of amino acids with a side chain pKa of 4.0-8.0 (for example, histidine and glutamic acid) or unnatural amino acids to be inserted. It is possible to substitute with a single amino acid having a side chain pKa of 4.0-8.0 (for example, histidine and glutamic acid) or a single unnatural amino acid; it is possible to insert a single amino acid having a side chain pKa of 4.0-8.0 (for example, histidine and glutamic acid) or a single unnatural amino acid; it is possible to substitute with two or more amino acids having a side chain pKa of 4.0-8.0 (for example, histidine and glutamic acid) or two or more unnatural amino acids; and it is possible to insert two or more amino acids having a side chain pKa of 4.0-8.0 (for example, histidine and glutamic acid) or two or more unnatural amino acids. Alternatively, other amino acids can be deleted, added, inserted, and/or substituted concomitantly, aside from the substitution into amino acids having a side chain pKa of 4.0-8.0 (for example, histidine and glutamic acid) or unnatural amino acids, or the insertion of amino acids having a side chain pKa of 4.0-8.0 (for example, histidine and glutamic acid) or unnatural amino acids. Substitution into or insertion of amino acids with a side chain pKa of 4.0-8.0 (for example, histidine and glutamic acid) or unnatural amino acids can performed randomly by methods such as histidine scanning, in which the alanine of alanine scanning known to those skilled in the art is replaced with histidine. Antigen-binding molecules exhibiting a greater value of KD (in an acidic pH range)/KD (in a neutral pH range) or kd (in an acidic pH range)/kd (in a neutral pH range) as compared to before the mutation can be selected from antigen-binding domains or antibodies introduced with random insertions or substitution mutations of amino acids with a side chain pKa of 4.0-8.0 (for example, histidine and glutamic acid) or unnatural amino acids.

Preferred examples of antigen-binding molecules containing the mutation into amino acids with a side chain pKa of 4.0-8.0 (for example, histidine and glutamic acid) or unnatural amino acids as described above and whose antigen-binding activity in an acidic pH range is lower than that in a neutral pH range include, antigen-binding molecules whose antigen-binding activity in the neutral pH range after the mutation into amino acids with a side chain pKa of 4.0-8.0 (for example, histidine and glutamic acid) or unnatural amino acids is comparable to that before the mutation into amino acids with a side chain pKa of 4.0-8.0 (for example, histidine and glutamic acid) or unnatural amino acids. Herein, "an antigen-binding molecule after the mutation with amino acids having a side chain pKa of 4.0-8.0 (for example, histidine and glutamic acid) or unnatural amino acids has an antigen-binding activity comparable to that before the mutation with amino acids having a side chain pKa of 4.0-8.0 (for example, histidine and glutamic acid) or unnatural amino acids" means that, when taking the antigen-binding activity of an antigen-binding molecule before the mutation with amino acids having a side chain pKa of 4.0-8.0 (for example, histidine and glutamic acid) or unnatural amino acids as 100%, the antigen-binding activity of an antigen-binding molecule after the mutation with amino acids having a side chain pKa of 4.0-8.0 (for example, histidine and glutamic acid) or unnatural amino acids is at least 10% or more, preferably 50% or more, more preferably 80% or more, and still more preferably 90% or more. The antigen-binding activity after the mutation of amino acids with a side chain pKa of 4.0-8.0 (for example, histidine and glutamic acid) or unnatural amino acids at pH 7.4 may be higher than that before the mutation of amino acids with a side chain pKa of 4.0-8.0 (for example, histidine and glutamic acid) or unnatural amino acids at pH 7.4. If the antigen-binding activity of an antigen-binding molecule is decreased due to insertion of or substitution into amino acids with a side chain pKa of 4.0-8.0 (for example, histidine and glutamic acid) or unnatural amino acids, the antigen-binding activity can be made to be comparable to that before the insertion of or substitution into amino acids with a side chain pKa of 4.0-8.0 (for example, histidine and glutamic acid) or unnatural amino acids, by introducing a substitution, deletion, addition, and/or insertion of one or more amino acids of the antigen-binding molecule. The present invention also includes antigen-binding molecules whose binding activity has been adjusted to be comparable by substitution, deletion, addition, and/or insertion of one or more amino acids after substitution or insertion of amino acids with a side chain pKa of 4.0-8.0 (for example, histidine and glutamic acid) or unnatural amino acids.

In one embodiment of the present invention, a library containing multiple antigen-binding domains or antigen-binding molecules of the present invention whose sequences are different from one another can also be constructed by combining heavy chain variable regions, produced as a randomized variable region sequence library, with light chain variable regions introduced with "at least one amino acid residue that changes the antigen-binding activity of antigen-binding domain or antigen-binding molecule depending on the hydrogen ion concentration condition".

Such amino acid residues include, but are not limited to, for example, amino acid residues contained in the light chain CDR1. The amino acid residues also include, but are not limited to, for example, amino acid residues contained in the light chain CDR2. The amino acid residues also include, but are not limited to, for example, amino acid residues contained in the light chain CDR3.

The above-described amino acid residues contained in the light chain CDR1 include, but are not limited to, for example, amino acid residue(s) of position(s) 24, 27, 28, 31, 32, and/or 34 according to Kabat numbering in the CDR1 of light chain variable region. Meanwhile, the amino acid residues contained in the light chain CDR2 include, but are not limited to, for example, amino acid residue(s) of position

64

(s) 50, 51, 52, 53, 54, 55, and/or 56 according to Kabat numbering in the CDR2 of light chain variable region. Furthermore, the amino acid residues in the light chain CDR3 include, but are not limited to, for example, amino acid residues of position(s) 89, 90, 91, 92, 93, 94, and/or 95A according to Kabat numbering in the CDR3 of light chain variable region. Moreover, the amino acid residues can be contained alone or can be contained in combination of two or more amino acids as long as they allow the change in the antigen-binding activity of an antigen-binding molecule depending on the hydrogen ion concentration condition.

Even when the heavy chain variable region produced as a randomized variable region sequence library is combined with the above-described light chain variable region introduced with "at least one amino acid residue that changes the antigen-binding activity of an antigen-binding molecule depending on the hydrogen ion concentration condition", it is possible to design so that the flexible residues are contained in the sequence of the light chain variable region in the same manner as described above. The number and position of the flexible residues are not particularly limited to a specific embodiment, as long as the antigen-binding activity of antigen-binding domain or antigen-binding molecule of the present invention changes depending on the hydrogen ion concentration condition. Specifically, the CDR and/or FR sequences of heavy chain and/or light chain can contain one or more flexible residues. For example, flexible residues to be introduced into the sequences of the light chain variable regions include, but are not limited to, for example, the amino acid residues listed in Tables 3 and 4. Meanwhile, amino acid sequences of light chain variable regions other than the flexible residues and amino acid residues that change the antigen-binding activity of an antigen-binding domain or antigen-binding molecule depending on the hydrogen ion concentration condition suitably include, but are not limited to, germ line sequences such as Vk1 (SEQ ID NO: 6), Vk2 (SEQ ID NO: 7), Vk3 (SEQ ID NO: 8), and Vk4 (SEQ ID NO: 9).

TABLE 3

| POSITION | AMINO ACID | | | | | | | | |
|---|---|---|---|---|---|---|---|---|---|
| | CDR1 | | | | | | | | |
| 28 | S: 100% | | | | | | | | |
| 29 | I: 100% | | | | | | | | |
| 30 | N: 25% | S: 25% | R: 25% | H: 25% | | | | | |
| 31 | S: 100% | | | | | | | | |
| 32 | H: 100% | | | | | | | | |
| 33 | L: 100% | | | | | | | | |
| 34 | A: 50% | N: 50% | | | | | | | |
| | CDR2 | | | | | | | | |
| 50 | H: 100% | | | | OR | A: 25% | D: 25% | G: 25% | K: 25% |
| 51 | A: 100% | | | | | A: 100% | | | |
| 52 | S: 100% | | | | | S: 100% | | | |
| 53 | K: 33.3% | N: 33.3% | S: 33.3% | | | H: 100% | | | |
| 54 | L: 100% | | | | | L: 100% | | | |
| 55 | Q: 100% | | | | | Q: 100% | | | |
| 56 | S: 100% | | | | | S: 100% | | | |
| | CDR3 | | | | | | | | |
| 90 | Q: 100% | | | | OR | Q: 100% | | | |
| 91 | H: 100% | | | | | S: 33.3% | R: 33.3% | Y: 33.3% | |
| 92 | G: 25% | N: 25% | S: 25% | Y: 25% | | H: 100% | | | |
| 93 | H: 33.3% | N: 33.3% | S: 33.3% | | | H: 33.3% | N: 33.3% | S: 33.3% | |
| 94 | S: 50% | Y: 50% | | | | S: 50% | Y: 50% | | |
| 95 | P: 100% | | | | | P: 100% | | | |
| 96 | L: 50% | Y: 50% | | | | L: 50% | Y: 50% | | |

(Position indicates Kabat numbering)

65

TABLE 4

| CDR | POSITION | AMINO ACID | | | |
|---|---|---|---|---|---|
| CDR1 | 28 | S: 100% | | | |
| | 29 | I: 100% | | | |
| | 30 | H: 30% | N: 10% | S: 50% | R: 10% |
| | 31 | N: 35% | S: 65% | | |
| | 32 | H: 40% | N: 20% | Y: 40% | |
| | 33 | L: 100% | | | |
| | 34 | A: 70% | N: 30% | | |
| CDR2 | 50 | A: 25% | D: 15% | G: 25% | H: 30% K: 5% |
| | 51 | A: 100% | | | |
| | 52 | S: 100% | | | |
| | 53 | H: 30% | K: 10% | N: 15% | S: 45% |
| | 54 | L: 100% | | | |
| | 55 | Q: 100% | | | |
| | 56 | S: 100% | | | |
| CDR3 | 90 | Q: 100% | | | |
| | 91 | H: 30% | S: 15% | R: 10% | Y: 45% |
| | 92 | G: 20% | H: 30% | N: 20% | S: 15% Y: 15% |
| | 93 | H: 30% | N: 25% | S: 45% | |
| | 94 | S: 50% | Y: 50% | | |
| | 95 | P: 100% | | | |
| | 96 | L: 50% | Y: 50% | | |

(Position indicates Kabat numbering)

Any amino acid residue may be suitably used as the above-described amino acid residues that change the antigen-binding activity of an antigen-binding domain or antigen-binding molecule depending on the hydrogen ion concentration conditions. Specifically, such amino acid residues include amino acids with a side chain pKa of 4.0-8.0. Such electron-releasing amino acids preferably include, for example, naturally occurring amino acids such as histidine and glutamic acid, as well as unnatural amino acids such as histidine analogs (US2009/0035836), m-NO2-Tyr (pKa 7.45), 3,5-Br2-Tyr (pKa 7.21), and 3,5-I2-Tyr (pKa 7.38) (Bioorg. Med. Chem. (2003) 11 (17), 3761-3768). Particularly preferred amino acid residues include, for example, amino acids with a side chain pKa of 6.0-7.0. Such electron-releasing amino acid residues preferably include, for example, histidine.

The preferred heavy chain variable region that is used in combination includes, for example, randomized variable region libraries. Known methods are appropriately combined as a method for producing a randomized variable region library. In a non-limiting embodiment of the present invention, an immune library constructed based on antibody genes derived from animals immunized with specific antigens, patients with infection or persons with an elevated antibody titer in blood as a result of vaccination, cancer patients, or lymphocytes of autoimmune diseases may be suitably used as a randomized variable region library.

In another non-limiting embodiment of the present invention, in the same manner as described above, a synthetic library in which the CDR sequences of V genes from genomic DNA or functional reconstructed V genes are replaced with a set of synthetic oligonucleotides containing the sequences encoding codon sets of an appropriate length can also be suitably used as a randomized variable region library. In this case, the CDR3 sequence alone may be replaced because variety in the gene sequence of heavy chain CDR3 is observed. The basis for giving rise to amino acid variations in the variable region of an antigen-binding molecule is to generate variations of amino acid residues of surface-exposed positions of the antigen-binding molecule. The surface-exposed position refers to a position where an amino acid is exposed on the surface and/or contacted with an antigen based on the conformation, structural ensemble, and/or modeled structure of an antigen-binding molecule, and in general, such positions are the CDRs. The surface-exposed positions are preferably determined using the coordinates derived from a three-dimensional model of the antigen-binding molecule using computer programs such as InsightII program (Accelrys). The surface-exposed positions can be determined using algorithms known in the art (for example, Lee and Richards (J. Mol. Biol. (1971) 55, 379-400); Connolly (J. Appl. Cryst. (1983) 16, 548-558)). The surface-exposed positions can be determined based on the information on the three dimensional structure of antibodies using software suitable for protein modeling. Software which is suitably used for this purpose includes the SYBYL biopolymer module software (Tripos Associates). When the algorithm requires the input size parameter from the user, the "size" of probe for use in computation is generally or preferably set at about 1.4 angstrom or less in radius. Furthermore, a method for determining surface-exposed region and area using personal computer software is described by Pacios (Comput. Chem. (1994) 18 (4), 377-386; and J. Mol. Model. (1995) 1, 46-53).

In still another non-limiting embodiment of the present invention, a naive library constructed from antibody genes derived from lymphocytes of healthy persons and consisting of naive sequences, which are unbiased repertoire of antibody sequences, can also be particularly suitably used as a randomized variable region library (Gejima et al. (Human Antibodies (2002) 11, 121-129); and Cardoso et al. (Scand. J. Immunol. (2000) 51, 337-344)).

FcRn

Unlike Fcγ receptor belonging to the immunoglobulin superfamily, human FcRn is structurally similar to polypeptides of major histocompatibility complex (WIC) class I, exhibiting 22% to 29% sequence identity to class I WIC molecules (Ghetie el al., Immunol. Today (1997) 18 (12): 592-598). FcRn is expressed as a heterodimer consisting of soluble β or light chain (β2 microglobulin) complexed with transmembrane a or heavy chain. Like MHC, FcRn α chain comprises three extracellular domains (α1, α2, and α3) and its short cytoplasmic domain anchors the protein onto the cell surface. α1 and α2 domains interact with the FcRn-binding domain of the antibody Fc region (Raghavan et al., Immunity (1994) 1: 303-315).

FcRn is expressed in maternal placenta and york sac of mammals, and is involved in mother-to-fetus IgG transfer. In addition, in neonatal small intestine of rodents, where FcRn is expressed, FcRn is involved in transfer of maternal IgG across brush border epithelium from ingested colostrum or milk. FcRn is expressed in a variety of other tissues and endothelial cell systems of various species. FcRn is also expressed in adult human endothelia, muscular blood vessels, and hepatic sinusoidal capillaries. FcRn is believed to play a role in maintaining the plasma IgG concentration by mediating recycling of IgG to serum upon binding to IgG. Typically, binding of FcRn to IgG molecules is strictly pH dependent. The optimal binding is observed in an acidic pH range below 7.0.

Human FcRn whose precursor is a polypeptide having the signal sequence of SEQ ID NO: 12 (the polypeptide with the signal sequence is shown in SEQ ID NO: 13) forms a complex with human β2-microglobulin in vivo. Soluble human FcRn complexed with β2-microglobulin is produced by using conventional recombinant expression techniques. FcRn-binding domain of the present invention can be assessed for their binding activity to such a soluble human FcRn complexed with β2-microglobulin. Herein, unless otherwise specified, human FcRn refers to a form capable of binding to an FcRn-binding domain of the present invention. Examples include a complex between human FcRn and human β2-microglobulin.

Binding Activity of an FcRn-Binding Domain or Antigen-Binding Molecule Comprising the Domain to FcRn, Human FcRn In Particular The binding activity of an FcRn-binding domain contained in an antigen-binding molecule provided by the present invention to FcRn, human FcRn in particular, can be measured by methods known to those skilled in the art, as described in the section "Binding Activity" above. Those skilled in the art can appropriately determine the conditions other than pH. The binding activity of antigen-binding domain or antigen-binding molecule comprising the domain to human FcRn can be assessed based on the dissociation constant (KD), apparent dissociation constant (KD), dissociation rate (kd), apparent dissociation rate (kd), and such. These can be measured by methods known to those skilled in the art. For example, Biacore (GE healthcare), Scatchard plot, or flow cytometer may be used.

When the human FcRn-binding activity of an FcRn-binding domain or antigen-binding molecule comprising the domain of the present invention is measured, conditions other than the pH are not particularly limited, and can be appropriately selected by those skilled in the art. Measurements can be carried out, for example, at a condition of 37° C. using MES buffer, as described in WO 2009/125825. Alternatively, the human FcRn-binding activity of an FcRn-binding domain or antigen-binding molecule comprising the domain of the present invention can be measured by methods known to those skilled in the art, and may be measured by using, for example, Biacore (GE Healthcare) or such. The binding activity of an FcRn-binding domain or antigen-binding molecule comprising the domain of the present invention to human FcRn can be assessed by flowing, as an analyte, human FcRn, or an FcRn-binding domain or antigen-binding molecule comprising the domain into a chip immobilized with an FcRn-binding domain or antigen-binding molecule comprising the domain, or human FcRn.

In the present invention, the acidic pH range presented as the condition for having binding activity between FcRn and an antigen-binding molecule of the present invention or FcRn-binding domain in the molecule generally refers to pH 4.0 to pH 6.5. Preferably it refers to pH 5.5 to pH 6.5, and particularly preferably it refers to pH 5.8 to pH 6.0 which is close to the pH in an early endosome in vivo. The neutral pH range presented as the condition for having binding activity between FcRn and an antigen-binding molecule of the present invention or an FcRn-binding domain included in such a molecule generally refers to pH 6.7 to pH 10.0. Neutral pH range is preferably a range indicated by any pH value from pH 7.0 to pH 8.0, and is preferably selected from pH 7.0, 7.1, 7.2, 7.3, 7.4, 7.5, 7.6, 7.7, 7.8, 7.9, and 8.0, and is particularly preferably pH 7.4 which is close to the pH in plasma (in blood) in vivo. When evaluating the binding affinity between human FcRn and a human FcRn-binding domain or an antigen-binding molecule containing that domain at pH 7.4 is difficult due to low binding affinity, pH 7.0 can be used instead of pH 7.4. As temperature to be used in assay conditions, binding affinity between a human FcRn and human FcRn-binding domain or antigen-binding molecule comprising the domain may be assessed at any temperature from 10° C. to 50° C. Preferably, a temperature from 15° C. to 40° C. is used to determine the binding affinity between a human FcRn and human FcRn-binding domain or antigen-binding molecule comprising the domain. More preferably, any temperature from 20° C. to 35° C. such as any one of 20, 21, 22, 23, 24, 25, 26, 27, 28, 29, 30, 31, 32, 33, 34, and 35° C. is also equally used to determine the binding affinity between a human FcRn-binding domain or antigen-binding molecule comprising the domain and human FcRn. A temperature of 25° C. is a non-limiting example of an embodiment of the present invention.

FcRn-Binding Domain

Antigen-binding molecules of the present invention have an FcRn-binding domain having an activity to bind to FcRn under an acidic pH range condition. The FcRn-binding domain is not particularly limited as long as the antigen-binding molecules have an FcRn-binding activity in an acidic pH range, and it may be a domain that has direct or indirect binding activity to FcRn. Preferred examples of such an FcRn-binding domain include the Fc region of IgG immunoglobulin, albumin, albumin domain 3, anti-FcRn antibody described in Christianson et al. (mAbs (2012) 4 (2), 208-216), anti-FcRn peptide described in WO 2007/098420, anti-FcRn scaffold molecule, and such which have an activity to directly bind to FcRn, or molecules that bind to IgG or albumin, and such that have an activity to indirectly bind to FcRn. If the domain already has FcRn-binding activity in an acidic pH range, it may preferably be used as it is. If the domain does not have or has weak FcRn-binding activity in an acidic pH range, amino acids constituting an FcRn-binding domain in the antigen-binding molecule may be altered to confer FcRn-binding activity. Alternatively, amino acids may be altered in a domain already having FcRn-binding activity in an acidic pH range to increase the FcRn-binding activity in an acidic pH range. For amino acid alteration of the FcRn-binding domain, the alteration of interest can be identified by comparing the FcRn-binding activities in an acidic pH range before and after the amino acid alteration.

Fc Region

An Fc region contains the amino acid sequence derived from the heavy chain constant region of an antibody. An Fc region is a portion of the heavy chain constant region of an antibody, starting from the N terminal end of the hinge region, which corresponds to the papain cleavage site at an amino acid around position 216 according to the EU numbering system, and contains the hinge, CH2, and CH3 domains. While the Fc region may be obtained from human IgG1, it is not limited to a particular subclass of IgG. Examples of such a non-limiting embodiment of the Fc region include the Fc regions of human IgG1 (SEQ ID NO: 14), IgG2 (SEQ ID NO: 15), IgG3 (SEQ ID NO: 16), or IgG4 (SEQ ID NO: 17).

FcRn-Binding Domain Having Binding Activity to FcRn Under an Acidic pH Range Condition As described above, in a non-limiting embodiment of the present invention, an Fc region of a human IgG immunoglobulin is used as the FcRn-binding domain having binding activity to FcRn under an acidic pH range condition. An Fc region originally having FcRn-binding activity under an acidic pH range condition may be used as it is for this domain, and examples of such Fc regions include Fc regions of human IgGs (IgG1, IgG2, IgG3, or IgG4, and variants thereof). When an Fc region has weak or no FcRn-binding activity under an acidic pH range condition, Fc regions having desired FcRn-binding activity may be obtained by altering amino acids of the Fc region. Alternatively, Fc regions having desired or enhanced FcRn-binding activity under an acidic pH range condition may be suitably obtained by altering amino acids in the Fc region. Amino acid alterations of an Fc region that results in such desired binding activity may be determined by comparing the FcRn-binding activity under an acidic pH range condition before and after the amino acid alteration. For example, such amino acid alterations may be determined by methods described in the above-mentioned section "Binding activity of an FcRn-binding domain or antigen-binding molecule comprising the domain to FcRn, human FcRn in particular".

Alterations of the Fc region that enhance FcRn-binding activity under an acidic pH range condition are presented below as examples of a non-limiting embodiment of such alterations. Preferred Fc regions (starting Fc regions) of an IgG-type immunoglobulin for alteration include, for example, those of human IgGs (IgG1, IgG2, IgG3, and IgG4, and variants thereof). The origin of starting Fc regions is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In another embodiment, starting Fc regions can also be obtained from cynomolgus monkeys, marmosets, rhesus monkeys, chimpanzees, or humans. Starting Fc regions can be obtained preferably from human IgG1; however, they are not limited to any particular IgG subclass. This means that an Fc region represented by human IgG1 (SEQ ID NO: 14), IgG2 (SEQ ID NO: 15), IgG3 (SEQ ID NO: 16), or IgG4 (SEQ ID NO: 17) can be used appropriately as a starting Fc region, and herein also means that an Fc region of an arbitrary IgG class or subclass derived from any organisms described above can be preferably used as a starting Fc region. Examples of naturally-occurring IgG variants or modified forms are described in published documents (Curr. Opin. Biotechnol. (2009) 20 (6): 685-91; Curr. Opin. Immunol. (2008) 20 (4), 460-470; Protein Eng. Des. Sel. (2010) 23 (4): 195-202; WO 2009/086320; WO 2008/092117; WO 2007/041635; and WO 2006/105338); however, they are not limited to the examples.

Examples of alterations include those with one or more mutations, for example, mutations by substitution of different amino acid residues for amino acids of starting Fc regions, by insertion of one or more amino acid residues into starting Fc regions, or by deletion of one or more amino acids from starting Fc region. Preferably, the amino acid sequences of altered Fc regions comprise at least a part of the amino acid sequence of a non-native Fc region. Such variants necessarily have sequence identity or similarity less than 100% to their starting Fc region. In a preferred embodiment, the variants have amino acid sequence identity or similarity about 75% to less than 100%, more preferably about 80% to less than 100%, even more preferably about 85% to less than 100%, still more preferably about 90% to less than 100%, and most preferably about 95% to less than 100% to the amino acid sequence of their starting Fc region. In a non-limiting embodiment of the present invention, at least one amino acid is different between a modified Fc region of the present invention and its starting Fc region. Amino acid difference between a modified Fc region of the present invention and its starting Fc region can also be preferably specified based on amino acid differences at above-described particular amino acid positions according to EU numbering.

As long as the Fc region has an FcRn-binding activity under an acidic pH range condition or can increase the human FcRn-binding activity under an acidic pH range condition, amino acids at any position may be modified into other amino acids. When the antigen-binding molecule of the present invention contains the Fc region of human IgG1 as the FcRn-binding domain, it is preferable that the result-ing Fc region contains a modification that results in the effect of enhancing FcRn binding under an acidic pH range condition as compared to the binding activity of the starting human IgG1 Fc region. Amino acids that allow such modification include, for example, amino acid(s) at position(s) 252, 254, 256, 309, 311, 315, 433, and/or 434 according to EU numbering, and their combination amino acid(s) at position(s) 253, 310, 435, and/or 426 as described in WO 1997/034631. Favorable examples include amino acid(s) at position(s) 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447 as indicated by EU numbering as described in WO 2000/042072. Similarly, favorable examples of amino acids that allow such modification include, amino acid(s) at position(s) 251, 252, 254, 255, 256, 308, 309, 311, 312, 385, 386, 387, 389, 428, 433, 434, and/or 436 according to EU numbering as described in WO 2002/060919. Furthermore, amino acids that allow such modification include, for example, amino acid(s) at position(s) 250, 314, and 428 according to EU numbering as described in WO2004/092219. In addition, favorable examples of amino acids that allow such modification include amino acid(s) at position(s) 238, 244, 245, 249, 252, 256, 257, 258, 260, 262, 270, 272, 279, 283, 285, 286, 288, 293, 307, 311, 312, 316, 317, 318, 332, 339, 341, 343, 375, 376, 377, 378, 380, 382, 423, 427, 430, 431, 434, 436, 438, 440, and/or 442 as described in WO 2006/020114. Furthermore, favorable examples of amino acids that allow such modification include amino acid(s) at position(s) 251, 252, 307, 308, 378, 428, 430, 434, and/or 436 according to EU numbering as described in WO 2010/045193. Modification of these amino acids enhances FcRn binding of the Fc region of an IgG-type immunoglobulin under an acidic pH range condition.

When the Fc region of human IgG1 is comprised as the FcRn-binding domain, a non-limiting embodiment of the modification that results in the effect of enhancing FcRn binding under an acidic pH range condition as compared to the binding activity of the starting Fc region of human IgG1 includes at least one or more amino acid modifications selected from the group consisting of:

Arg or Leu for the amino acid at position 251;

Phe, Ser, Thr, or Tyr for the amino acid at position 252;

Ser or Thr for the amino acid at position 254;

Arg, Gly, Ile, or Leu for the amino acid at position 255;

Ala, Arg, Asn, Asp, Gln, Glu, or Thr for the amino acid at position 256;

Ile or Thr for the amino acid at position 308;

Pro for the amino acid at position 309;

Glu, Leu, or Ser for the amino acid at position 311;

Ala or Asp for the amino acid at position 312;

Ala or Leu for the amino acid at position 314;

Ala, Arg, Asp, Gly, His, Lys, Ser, or Thr for the amino acid at position 385;

Arg, Asp, Ile, Lys, Met, Pro, Ser, or Thr for the amino acid at position 386;

Ala, Arg, His, Pro, Ser, or Thr for the amino acid at position 387;

Asn, Pro, or Ser for the amino acid at position 389;

Leu, Met, Phe, Ser, or Thr for the amino acid at position 428;

Arg, Gln, His, Ile, Lys, Pro, or Ser for the amino acid at position 433;

His, Phe, or Tyr for the amino acid at position 434; and

Arg, Asn, His, Lys, Met, or Thr for the amino acid at position 436, as indicated by EU numbering. Mean-while, the number of amino acids to be modified is not particularly limited; and amino acid may be modified at only one site or amino acids may be modified at two or more sites.

When the Fc region of human IgG1 is comprised as the FcRn-binding domain, a non-limiting embodiment of the modification that results in the effect of enhancing FcRn binding in an acidic pH range condition as compared to the binding activity of the starting Fc region of human IgG1 may be modifications including Ile for the amino acid at position 308, Pro for the amino acid at position 309, and/or Glu for the amino acid at position 311 according to EU numbering. Another non-limiting embodiment of this modification may include Thr for the amino acid at position 308, Pro for the amino acid at position 309, Leu for the amino acid at position 311, Ala for the amino acid at position 312, and/or Ala for the amino acid at position 314. Furthermore, another non-limiting embodiment of this modification may include Ile or Thr for the amino acid at position 308, Pro for the amino acid at position 309, Glu, Leu, or Ser for the amino acid at position 311, Ala for the amino acid at position 312, and/or Ala or Leu for the amino acid at position 314. Another non-limiting embodiment of this modification may include Thr for the amino acid at position 308, Pro for the amino acid at position 309, Ser for the amino acid at position 311, Asp for the amino acid at position 312, and/or Leu for the amino acid at position 314.

When the Fc region of human IgG1 is comprised as the FcRn-binding domain, a non-limiting embodiment of the modification that results in the effect of enhancing FcRn binding under an acidic pH range condition as compared to the binding activity of the starting Fc region of human IgG1 may be modifications including Leu for the amino acid at position 251, Tyr for the amino acid at position 252, Ser or Thr for the amino acid at position 254, Arg for the amino acid at position 255, and/or Glu for the amino acid at position 256 according to EU numbering.

When the Fc region of human IgG1 is comprised as the FcRn-binding domain, a non-limiting embodiment of the modification that results in the effect of enhancing FcRn binding under an acidic pH range condition as compared to the binding activity of the starting Fc region of human IgG1 may be modifications including Leu, Met, Phe, Ser, or Thr for the amino acid at position 428, Arg, Gln, His, Ile, Lys, Pro, or Ser for the amino acid at position 433, His, Phe, or Tyr for the amino acid at position 434, and/or Arg, Asn, His, Lys, Met, or Thr for the amino acid at position 436 according to EU numbering. Another non-limiting embodiment of this modification may include His or Met for the amino acid at position 428, and/or His or Met for the amino acid at position 434.

When the Fc region of human IgG1 is comprised as the FcRn-binding domain, a non-limiting embodiment of the modification that results in the effect of enhancing FcRn binding under an acidic pH range condition as compared to the binding activity of the starting Fc region of human IgG1 may be modifications including Arg for the amino acid at position 385, Thr for the amino acid at position 386, Arg for the amino acid at position 387, and/or Pro for the amino acid at position 389 according to EU numbering. Another non-limiting embodiment of this modification may include Asp for the amino acid at position 385, Pro for the amino acid at position 386, and/or Ser for the amino acid at position 389.

Furthermore, when the Fc region of human IgG1 is comprised as the FcRn-binding domain, a non-limiting embodiment of the modification that results in the effect of enhancing FcRn binding under an acidic pH range condition as compared to the binding activity of the starting Fc region of human IgG1 include at least one or more amino acid modifications selected from the group consisting of:

Gln or Glu for the amino acid at position 250; and

Leu or Phe for the amino acid at position 428 according to EU numbering. The number of amino acids to be modified is not particularly limited; and amino acid may be modified at only one site or amino acids may be modified at two sites.

When the Fc region of human IgG1 is comprised as the FcRn-binding domain, a non-limiting embodiment of the modification that results in the effect of enhancing FcRn binding under an acidic pH range condition as compared to the binding activity of the starting Fc region of human IgG1 may be modifications including Gln for the amino acid at position 250, and/or Leu or Phe for the amino acid at position 428 according to EU numbering. Another non-limiting embodiment of this modification may include Glu for the amino acid at position 250, and/or Leu or Phe for the amino acid at position 428.

When the Fc region of human IgG1 is comprised as the FcRn-binding domain, a non-limiting embodiment of the modification that results in the effect of enhancing FcRn binding under an acidic pH range condition as compared to the binding activity of the starting Fc region of human IgG1 include at least two or more amino acid modifications selected from the group consisting of:

Asp or Glu for the amino acid at position 251;

Tyr for the amino acid at position 252;

Gln for the amino acid at position 307;

Pro for the amino acid at position 308;

Val for the amino acid at position 378;

Ala for the amino acid at position 380;

Leu for the amino acid at position 428;

Ala or Lys for the amino acid at position 430;

Ala, His, Ser, or Tyr for the amino acid at position 434; and

Ile for the amino acid at position 436, as indicated by EU numbering. The number of amino acids to be modified is not particularly limited; and amino acid may be modified at only two sites or amino acids may be modified at three or more sites.

When the Fc region of human IgG1 is comprised as the FcRn-binding domain, a non-limiting embodiment of the modification that results in the effect of enhancing FcRn binding under an acidic pH range condition as compared to the binding activity of the starting Fc region of human IgG1 may be modifications including Gln for the amino acid at position 307, and Ala or Ser for the amino acid at position 434 according to EU numbering. Another non-limiting embodiment of this modification may include Pro for the amino acid at position 308, and Ala for the amino acid at position 434. Furthermore, another non-limiting embodiment of this modification may include Tyr for the amino acid at position 252, and Ala for the amino acid at position 434. A different non-limiting embodiment of this modification may include Val for the amino acid at position 378, and Ala for the amino acid at position 434. Another different non-limiting embodiment of this modification may include Leu for the amino acid at position 428, and Ala for the amino acid at position 434. Another different non-limiting embodiment of this modification may include Ala for the amino acid at position 434, and Ile for the amino acid at position 436. Furthermore, another non-limiting embodiment of this modification may include Pro for the amino acid at position 308, and Tyr for the amino acid at position 434. In addition, another non-limiting embodiment of this modification may include Gln for the amino acid at position 307, and Ile for the amino acid at position 436.

When the Fc region of human IgG1 is comprised as the FcRn-binding domain, a non-limiting embodiment of the modification that results in the effect of enhancing FcRn binding under an acidic pH range condition as compared to the binding activity of the starting Fc region of human IgG1 may be modifications including any one of Gln for the amino acid at position 307, Ala for the amino acid at position 380, and Ser for the amino acid at position 434 according to EU numbering. Another non-limiting embodiment of this modification may include Gln for the amino acid at position 307, Ala for the amino acid at position 380, and Ala for the amino acid at position 434. Furthermore, another non-limiting embodiment of this modification may include Tyr for the amino acid at position 252, Pro for the amino acid at position 308, and Tyr for the amino acid at position 434. A different non-limiting embodiment of this modification may include Asp for the amino acid at position 251, Gln for the amino acid at position 307, and His for the amino acid at position 434.

When the Fc region of human IgG1 is comprised as the FcRn-binding domain, a non-limiting embodiment of the modification that results in the effect of enhancing FcRn binding under an acidic pH range condition as compared to the binding activity of the starting Fc region of human IgG1 include modification of at least two or more amino acids selected from the group consisting of:

Leu for the amino acid at position 238;
Leu for the amino acid at position 244;
Arg for the amino acid at position 245;
Pro for the amino acid at position 249;
Tyr for the amino acid at position 252;
Pro for the amino acid at position 256;
Ala, Ile, Met, Asn, Ser, or Val for the amino acid at position 257;
Asp for the amino acid at position 258;
Ser for the amino acid at position 260;
Leu for the amino acid at position 262;
Lys for the amino acid at position 270;
Leu or Arg for the amino acid at position 272;
Ala, Asp, Gly, His, Met, Asn, Gln, Arg, Ser, Thr, Trp, or Tyr for the amino acid at position 279;
Ala, Asp, Phe, Gly, His, Ile, Lys, Leu, Asn, Pro, Gln, Arg, Ser, Thr, Trp, or Tyr for the amino acid at position 283;
Asn for the amino acid at position 285;
Phe for the amino acid at position 286;
Asn or Pro for the amino acid at position 288;
Val for the amino acid at position 293;
Ala, Glu, or Met for the amino acid at position 307;
Ala, Ile, Lys, Leu, Met, Val, or Trp for the amino acid at position 311;
Pro for the amino acid at position 312;
Lys for the amino acid at position 316;
Pro for the amino acid at position 317;
Asn or Thr for the amino acid at position 318;
Phe, His, Lys, Leu, Met, Arg, Ser, or Trp for the amino acid at position 332;
Asn, Thr, or Trp for the amino acid at position 339;
Pro for the amino acid at position 341;
Glu, His, Lys, Gln, Arg, Thr, or Tyr for the amino acid at position 343;
Arg for the amino acid at position 375;
Gly, Ile, Met, Pro, Thr, or Val for the amino acid at position 376;
Lys for the amino acid at position 377;
Asp or Asn for the amino acid at position 378;

Asn, Ser, or Thr for the amino acid at position 380;
Phe, His, Ile, Lys, Leu, Met, Asn, Gln, Arg, Ser, Thr, Val, Trp, or Tyr for the amino acid at position 382;
Asn for the amino acid at position 423;
Asn for the amino acid at position 427;
Ala, Phe, Gly, His, Ile, Lys, Leu, Met, Asn, Gln, Arg, Ser, Thr, Val, or Tyr for the amino acid at position 430;
His or Asn for the amino acid at position 431;
Phe, Gly, His, Trp, or Tyr for the amino acid at position 434;
Ile, Leu, or Thr for the amino acid at position 436;
Lys, Leu, Thr, or Trp for the amino acid at position 438;
Lys for the amino acid at position 440; and
Lys for the amino acid at position 442 according to EU numbering. The number of amino acids to be modified is not particularly limited and amino acid at only two sites may be modified and amino acids at three or more sites may be modified.

When the Fc region of human IgG1 is comprised as the FcRn-binding domain, a non-limiting embodiment of the modification that results in the effect of enhancing FcRn binding under an acidic pH range condition as compared to the binding activity of the starting Fc region of human IgG1 may be modifications including Ile for the amino acid at position 257, and Ile for the amino acid at position 311 according to EU numbering. Another non-limiting embodiment of this modification may include Ile for the amino acid at position 257, and His for the amino acid at position 434. Another non-limiting embodiment of this modification may include Val for the amino acid at position 376, and His for the amino acid at position 434.

Fcγ Receptor

Fcγ receptor (FcγR) refers to a receptor capable of binding to the Fc region of monoclonal IgG1, IgG2, IgG3, or IgG4 antibodies, and includes all members belonging to the family of proteins substantially encoded by an Fcγ receptor gene. In humans, the family includes FcγRI (CD64) including isoforms FcγRIa, FcγRIb and FcγRIc; FcγRII (CD32) including isoforms FcγRIIa (including allotype H131 and R131), FcγRIIb (including FcγRIIb-1 and FcγRIIb-2), and FcγRIIc; and FcγRIII (CD16) including isoform FcγRIIIa (including allotype V158 and F158) and FcγRIIIb (including allotype FcγRIIIb-NA1 and FcγRIIIb-NA2); as well as all unidentified human FcγRs, FcγR isoforms, and allotypes thereof. However, Fcγ receptor is not limited to these examples. Without being limited thereto, FcγR includes those derived from humans, mice, rats, rabbits, and monkeys. FcγR may be derived from any organism. Mouse FcγR includes, without being limited to, FcγRI (CD64), FcγRII (CD32), FcγRIII (CD16), and FcγRIII-2 (FcγRIV, CD16-2), as well as all unidentified mouse FcγRs, FcγR isoforms, and allotypes thereof. Such preferred Fcγ receptors include, for example, human FcγRI (CD64), FcγRIIa (CD32), FcγRIIb (CD32), FcγRIIIa (CD16), and/or FcγRIIIb (CD16). The polynucleotide sequence and amino acid sequence of FcγRI are shown in SEQ ID NOs: 18 (NM_000566.3) and 19 (NP_000557.1), respectively; the polynucleotide sequence and amino acid sequence of FcγRIIa are shown in SEQ ID NOs: 20 (BCO20823.1) and 21 (AAH20823.1), respectively; the polynucleotide sequence and amino acid sequence of FcγRIIb are shown in SEQ ID NOs: 22 (BC146678.1) and 23 (AAI46679.1), respectively; the polynucleotide sequence and amino acid sequence of FcγRIIIa are shown in SEQ ID NOs: 24 (BC033678.1) and 25 (AAH33678.1), respectively; and the polynucleotide sequence and amino acid sequence of FcγRIIIb are shown in SEQ ID NOs: 26 (BC128562.1) and 27 (AAI28563.1), respectively (RefSeq accession number is shown in each parentheses). Whether an Fcγ receptor has binding activity to the Fc region of a monoclonal IgG1, IgG2, IgG3, or IgG4 antibody can be assessed by ALPHA screen (Amplified Luminescent Proximity Homogeneous Assay), surface plasmon resonance (SPR)-based BIACORE method, and others (Proc. Natl. Acad. Sci. USA (2006) 103(11), 4005-4010), in addition to the above-described FACS and ELISA formats.

In FcγRI (CD64) including FcγRIa, FcγRIb, and FcγRIc, and FcγRIII (CD16) including isoforms FcγRIIIa (including allotypes V158 and F158) and FcγRIIIb (including allotypes FcγRIIIb-NA1 and FcγRIIIb-NA2), α chain that binds to the Fc portion of IgG is associated with common γ chain having ITAM responsible for transduction of intracellular activation signal. Meanwhile, the cytoplasmic domain of FcγRII (CD32) including isoforms FcγRIIa (including allotypes H131 and R131) and FcγRIIc contains ITAM. These receptors are expressed on many immune cells such as macrophages, mast cells, and antigen-presenting cells. The activation signal transduced upon binding of these receptors to the Fc portion of IgG results in enhancement of the phagocytic activity and inflammatory cytokine production of macrophages, mast cell degranulation, and the enhanced function of antigen-presenting cells. Fcγ receptors having the ability to transduce the activation signal as described above are also referred to as activating Fcγ receptors.

Meanwhile, the intracytoplasmic domain of FcγRIIb (including FcγRIIb-1 and FcγRIIb-2) contains ITIM responsible for transduction of inhibitory signals. The crosslinking between FcγRIIb and B cell receptor (BCR) on B cells suppresses the activation signal from BCR, which results in suppression of antibody production via BCR. The crosslinking of FcγRIII and FcγRIIb on macrophages suppresses the phagocytic activity and inflammatory cytokine production. Fcγ receptors having the ability to transduce the inhibitory signal as described above are also referred to as inhibitory Fcγ receptors.

Binding Activity to the Fcγ Receptor

The binding activity of an FcγR-binding domain, which is included in an antigen-binding molecule of the present invention, to any of the human Fcγ receptors, FcγRI, FcγRIIa, FcγRIIb, FcγRIIIa, and/or FcγRIIIb, can be confirmed by the above-described FACS and ELISA format, as well as ALPHA Screen (Amplified Luminescent Proximity Homogeneous Assay), a BIACORE method using the surface plasmon resonance (SPR) phenomena, and such (Proc. Natl. Acad. Sci. USA (2006) 103 (11), 4005-4010).

ALPHA screen is performed by the ALPHA technology based on the principle described below using two types of beads: donor and acceptor beads. A luminescent signal is detected only when molecules linked to the donor beads interact biologically with molecules linked to the acceptor beads and when the two beads are located in close proximity. Excited by laser beam, the photosensitizer in a donor bead converts oxygen around the bead into excited singlet oxygen. When the singlet oxygen diffuses around the donor beads and reaches the acceptor beads located in close proximity, a chemiluminescent reaction within the acceptor beads is induced. This reaction ultimately results in light emission. If molecules linked to the donor beads do not interact with molecules linked to the acceptor beads, the singlet oxygen produced by donor beads do not reach the acceptor beads and chemiluminescent reaction does not occur.

For example, a biotin-labeled antigen-binding molecule comprising FcγR-binding domain is immobilized to the donor beads and glutathione S-transferase (GST)-tagged Fcγ receptor is immobilized to the acceptor beads. In the absence of an antigen-binding molecule comprising a competitive altered FcγR-binding domain, Fcγ receptor interacts with an antigen-binding molecule comprising a wild-type FcγR-binding domain, inducing a signal of 520 to 620 nm as a result. The antigen-binding molecule having a non-tagged altered FcγR-binding domain competes with the antigen-binding molecule comprising a native FcγR-binding domain for the interaction with Fcγ receptor. The relative binding affinity can be determined by quantifying the reduction of fluorescence as a result of competition. Methods for biotinylating the antigen-binding molecules such as antibodies using Sulfo-NHS-biotin or the like are known. Appropriate methods for adding the GST tag to an Fcγ receptor include methods that involve fusing polypeptides encoding Fcγ and GST in-frame, expressing the fused gene using cells introduced with a vector to which the gene is operably linked, and then purifying using a glutathione column. The induced signal can be preferably analyzed, for example, by fitting to a one-site competition model based on nonlinear regression analysis using software such as GRAPHPAD PRISM (GraphPad; San Diego).

One of the substances for observing their interaction is immobilized as a ligand onto the gold thin layer of a sensor chip. When light is shed on the rear surface of the sensor chip so that total reflection occurs at the interface between the gold thin layer and glass, the intensity of reflected light is partially reduced at a certain site (SPR signal). The other substance for observing their interaction is injected as an analyte onto the surface of the sensor chip. The mass of immobilized ligand molecule increases when the analyte binds to the ligand. This alters the refraction index of solvent on the surface of the sensor chip. The change in refraction index causes a positional shift of SPR signal (conversely, the dissociation shifts the signal back to the original position). In the Biacore system, the amount of shift described above (i.e., the change of mass on the sensor chip surface) is plotted on the vertical axis, and thus the change of mass over time is shown as measured data (sensorgram). Kinetic parameters (association rate constant (ka) and dissociation rate constant (kd)) are determined from the curve of sensorgram, and affinity (KD) is determined from the ratio between these two constants. Inhibition assay is also preferably used in the BIACORE methods. Examples of such inhibition assay are described in Proc. Natl. Acad. Sci. USA (2006) 103(11), 4005-4010. Binding activities of the FcγR-binding domain included in the antigen-binding molecule of the present invention towards any of the human Fcγ receptors, FcγRI, FcγRIIa, FcγRIIb, FcγRIIIa, and/or FcγRIIIb, can be determined from the amount of binding and KD value for each of the human Fcγ receptors calculated using the Biacore system according to the examples described above. Here, the amount of binding of the various FcγRs to the polypeptides is also represented by values obtained by determining the difference in the RU values of sensorgrams that changed before and after interaction of various FcγRs as the analyte with each polypeptide, and dividing them by differences in the RU values of sensorgrams that changed before and after capturing polypeptides to the sensor chips.

An acidic pH range condition or neutral pH range condition may be suitably used for the pH conditions to measure the Fcγ receptor-binding activity of the FcγR-binding domain included in the antigen-binding molecule of the present invention or an antigen-binding molecule containing the domain. A neutral pH range as a condition to measure the Fcγ receptor-binding activity of the FcγR-binding domain of the present invention or an antigen-binding molecule containing the domain generally refers to pH 6.7 to pH 10.0. Preferably, it is a range indicated with arbitrary pH values between pH 7.0 and pH 8.0; and preferably, it is selected from pH 7.0, pH 7.1, pH 7.2, pH 7.3, pH 7.4, pH 7.5, pH 7.6, pH 7.7, pH 7.8, pH 7.9, and pH 8.0; and particularly preferably, it is pH 7.4, which is close to the pH of plasma (blood) in vivo. In the present invention, an acidic pH range as a condition for the FcγR-binding domain of the present invention or an antigen-binding molecule containing the domain to have Fcγ receptor-binding activity generally refers to pH 4.0 to pH 6.5. Preferably, it refers to pH 5.5 to pH 6.5, and particularly preferably, it refers to pH 5.8 to pH 6.0, which are close to the pH in the early endosome in vivo. With regard to the temperature used as a measurement condition, the binding affinity between the FcγR-binding domain or an antigen-binding molecule containing the domain and a human Fcγ receptor can be evaluated at any temperature between 10° C. and 50° C. Preferably, a temperature between 15° C. and 40° C. is used to determine the binding affinity between the FcγR-binding domain or an antigen-binding molecule containing the domain and an Fcγ receptor. More preferably, any temperature between 20° C. and 35° C. such as any one of 20° C., 21° C., 22° C., 23° C., 24° C., 25° C., 26° C., 27° C., 28° C., 29° C., 30° C., 31° C., 32° C., 33° C., 34° C., and 35° C. can be used in a similar manner to determine the binding affinity between the FcγR-binding domain or an antigen-binding molecule containing the domain and an Fcγ receptor. A temperature of 25° C. is a non-limiting example in an embodiment of the present invention.

FcγR-Binding Domain

An antigen-binding molecule of the present invention comprises an antigen-binding domain whose antigen-binding activity varies depending on ion concentration conditions, an FcRn-binding domain having FcRn-binding activity under an acidic pH range condition, and an Fcγ receptor-binding domain having selective binding activity to an Fcγ receptor (hereinafter also referred to as a selective FcγR-binding domain). Preferred examples of the FcγR-binding domain include Fc regions of IgG-type immunoglobulins, FcγR-binding domains of IgG-type immunoglobulins, anti-FcγR antibodies, and anti-FcγR scaffold molecules. A domain originally having FcγR-binding activity may be suitably used as it is for the domain. When the domain has weak or no FcγR-binding activity, FcγR-binding activity can be conferred by altering amino acids forming the FcγR-binding domain in the antigen-binding molecule. Alternatively, FcγR-binding activity can be increased by altering amino acids in the domain originally having FcγR-binding activity. The amino acid alterations of the FcγR-binding domain that results in such desired binding activity may be discovered by comparing the FcγR-binding activity before and after the amino acid alteration. A non-limiting embodiment of such FcγR-binding domains is, for example, the FcγR-binding domain included in the Fc region of human IgG1 (SEQ ID NO: 14), IgG2 (SEQ ID NO: 15), IgG3 (SEQ ID NO: 16), or IgG4 (SEQ ID NO: 17). For example, when the Fc region of an IgG antibody is used as the FcRn-binding domain having FcRn-binding activity under an acidic pH range condition, the FcγR-binding domain included in the Fc region may be used as the FcγR-binding domain.

FcγR-Binding Domain Having Selective Binding Activity to an Fcγ Receptor

Whether or not an FcγR-binding domain of the present invention has selective binding activity can be confirmed by comparing binding activities to the respective Fcγ receptors, determined by the method described in the above-mentioned section on binding activity to Fcγ receptors. An FcγR-binding domain with higher binding activity to inhibitory Fcγ receptors than to activating Fcγ receptors may be used as the selective FcγR-binding domain included in the antigen-binding molecule provided by the present invention. In a non-limiting embodiment, an FcγR-binding domain with higher binding activity to FcγRIIb (including FcγRIIb-1 and FcγRIIb-2) than to an activating Fcγ receptor selected from the group consisting of FcγRI (CD64) including FcγRIa, FcγRIb, FcγRIc, FcγRIII (CD16) including isoforms FcγRIIIa (including allotypes V158 and F158) and FcγRIIIb (including allotypes FcγRIIIb-NA1 and FcγRIIIb-NA2), and FcγRII (CD32) including isoforms FcγRIIa and FcγRIIc (including allotypes H131 and R131) may be used as a selective FcγR-binding domain included in an antigen-binding molecule provided by the present invention. Furthermore, in a non-limiting embodiment of the present invention, an FcγR-binding domain with higher binding activity to FcγRIIb-1 and/or FcγRIIb-2 than to FcγRIa, FcγRIb, and FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, FcγRIIa including allotype R131, and/or FcγRIIc may be used as a selective FcγR-binding domain included in an antigen-binding molecule provided by the present invention. Whether an FcγR-binding domain to be tested has selective binding activity to Fcγ receptors can be determined by comparing the value (ratio) obtained by dividing the KD values of the FcγR-binding domain for FcγRIa, FcγRIb, FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, FcγRIIa including allotype R131, and/or FcγRIIc by the KD values for FcγRIIb-1 and/or FcγRIIb-2, wherein the KD values are determined by the method described in the above-mentioned section on binding activity to Fcγ receptors, or more specifically, by comparing the FcγR selectivity indices shown in Equation 1.

$$\text{FcγR selectivity index} = KD \text{ value for activating FcγR}/KD \text{ value for inhibitory FcγR} \quad \text{[Equation 1]}$$

In Equation 1 mentioned above, "activating FcγR" refers to FcγRIa, FcγRIb, FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, FcγRIIa including allotype R131, and/or FcγRIIc, and inhibitory FcγR refers to FcγRIIb-1 and/or FcγRIIb-2. Although the activating FcγR and inhibitory FcγR used for the KD value measurements may be selected from any combination, in a non-limiting embodiment, a value (ratio) obtained by dividing the KD value for FcγRIIa including allotype H131 by the KD value for FcγRIIb-1 and/or FcγRIIb-2 may be used.

For example, the FcγR selectivity indices have values of, 1.2 or greater, 1.3 or greater, 1.4 or greater, 1.5 or greater, 1.6 or greater, 1.7 or greater, 1.8 or greater, 1.9 or greater, 2 or greater, 3 or greater, 5 or greater, 6 or greater, 7 or greater, 8 or greater, 9 or greater, 10 or greater, 15 or greater, 20 or greater, 25 or greater, 30 or greater, 35 or greater, 40 or greater, 45 or greater, 50 or greater, 55 or greater, 60 or greater, 65 or greater, 70 or greater, 75 or greater, 80 or greater, 85 or greater, 90 or greater, 95 or greater, 100 or greater, 110 or greater, 120 or greater, 130 or greater, 140 or greater, 150 or greater, 160 or greater, 170 or greater, 180 or greater, 190 or greater, 200 or greater, 210 or greater, 220 or greater, 230 or greater, 240 or greater, 250 or greater, 260 or greater, 270 or greater, 280 or greater, 290 or greater, 300 or greater, 310 or greater, 320 or greater, 330 or greater, 340 or greater, 350 or greater, 360 or greater, 370 or greater, 380 or greater, 390 or greater, 400 or greater, 410 or greater, 420 or greater, 430 or greater, 440 or greater, 450 or greater, 460 or greater, 470 or greater, 480 or greater, 490 or greater, 500 or greater, 520 or greater, 540 or greater, 560 or greater, 580 or greater, 600 or greater, 620 or greater, 640 or greater, 660 or greater, 680 or greater, 700 or greater, 720 or greater, 740 or greater, 760 or greater, 780 or greater, 800 or greater, 820 or greater, 840 or greater, 860 or greater, 880 or greater, 900 or greater, 920 or greater, 940 or greater, 960 or greater, 980 or greater, 1000 or greater, 1500 or greater, 2000 or greater, 2500 or greater, 3000 or greater, 3500 or greater, 4000 or greater, 4500 or greater, 5000 or greater, 5500 or greater, 6000 or greater, 6500 or greater, 7000 or greater, 7500 or greater, 8000 or greater, 8500 or greater, 9000 or greater, 9500 or greater, 10000 or greater, or 100000 or greater.

A non-limiting embodiment of the selective FcγR-binding domain in an antigen-binding molecule of the present invention includes, for example, Fc regions produced by modifying the FcγR-binding domain included in an Fc region presented as human IgG1 (SEQ ID NO: 14), IgG2 (SEQ ID NO: 15), IgG3 (SEQ ID NO: 16), or IgG4 (SEQ ID NO: 17). An example of a method for producing the modified Fc regions includes the method described in the above-mentioned section on amino acid alterations. Examples of such altered Fc regions include an Fc region in which amino acid at position 238 (EU numbering) is Asp or an Fc region in which amino acid at position 328 (EU numbering) is Glu in a human IgG (IgG1, IgG2, IgG3, or IgG4). An Fc region in which amino acid at position 238 (EU numbering) is Asp or an Fc region in which amino acid at position 328 (EU numbering) is Glu in a human IgG (IgG1, IgG2, IgG3, or IgG4), and antigen-binding molecules containing such an Fc region show higher binding activity to FcγRIIb-1 and/or FcγRIIb-2 than to FcγRIa, FcγRIb, FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, FcγRIIa including allotype R131, and/or FcγRIIc.

Fc regions containing a selective FcγR-binding domain which are included in the antigen-binding molecules of the present invention and antigen-binding molecules containing such an Fc region may also be Fc regions and antigen-binding molecules containing such an Fc region which maintains or shows reduced binding activity to activating FcγR (FcγRIa, FcγRIb, FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, FcγRIIa including allotype R131, and/or FcγRIIc) when compared to an Fc region presented as human IgG1 (SEQ ID NO: 14), IgG2 (SEQ ID NO: 15), IgG3 (SEQ ID NO: 16), or IgG4 (SEQ ID NO: 17) (hereinafter referred to as a wild-type Fc region) and an antigen-binding molecule containing such a wild-type Fc region.

Compared to a wild-type Fc region and an antigen-binding molecule containing a wild-type Fc region, the degree of the aforementioned reduction in binding activity to activating FcγR of an Fc region containing a selective FcγR-binding domain included in an antigen-binding molecule of the present invention, and an antigen-binding molecule containing such an Fc region is, for example, 99% or less, 98% or less, 97% or less, 96% or less, 95% or less, 94% or less, 93% or less, 92% or less, 91% or less, 90% or less, 88% or less, 86% or less, 84% or less, 82% or less, 80% or less, 78% or less, 76% or less, 74% or less, 72% or less, 70% or less, 68% or less, 66% or less, 64% or less, 62% or less, 60% or less, 58% or less, 56% or less, 54% or less, 52% or less, 50% or less, 45% or less, 40% or less, 35% or less, 30% or less, 25% or less, 20% or less, 15% or less, 10% or less, 5% or less, 4% or less, 3% or less, 2% or less, 1% or less, 0.5% or less, 0.4% or less, 0.3% or less, 0.2% or less, 0.1% or less, 0.05% or less, 0.01% or less, or 0.005% or less.

The Fc regions containing a selective FcγR-binding domain and antigen-binding molecules containing such an Fc region, which are included in the antigen-binding molecules of the present invention, may also be Fc regions and antigen-binding molecules containing such an Fc region which shows enhanced binding activity to inhibitory FcγR (FcγRIIb-1 and/or FcγRIIb-2) when compared to an Fc region presented as human IgG1 (SEQ ID NO: 14), IgG2 (SEQ ID NO: 15), IgG3 (SEQ ID NO: 16), or IgG4 (SEQ ID NO: 17) (hereinafter referred to as a wild-type Fc region) and an antigen-binding molecule containing such a wild-type Fc region.

Compared to a wild-type Fc region and an antigen-binding molecule containing a wild-type Fc region, the degree of the aforementioned enhancement in binding activity to inhibitory FcγR of an Fc region containing a selective FcγR-binding domain included in an antigen-binding molecule of the present invention and an antigen-binding molecule containing such an Fc region is, for example, 101% or greater, 102% or greater, 103% or greater, 104% or greater, 105% or greater, 106% or greater, 107% or greater, 108% or greater, 109% or greater, 110% or greater, 112% or greater, 114% or greater, 116% or greater, 118% or greater, 120% or greater, 122% or greater, 124% or greater, 126% or greater, 128% or greater, 130% or greater, 132% or greater, 134% or greater, 136% or greater, 138% or greater, 140% or greater, 142% or greater, 144% or greater, 146% or greater, 148% or greater, 150% or greater, 155% or greater, 160% or greater, 165% or greater, 170% or greater, 175% or greater, 180% or greater, 185% or greater, 190% or greater, 195% or greater, 2-fold or greater, 3-fold or greater, 4-fold or greater, 5-fold or greater, 6-fold or greater, 7-fold or greater, 8-fold or greater, 9-fold or greater, 10-fold or greater, 20-fold or greater, 30-fold or greater, 40-fold or greater, 50-fold or greater, 60-fold or greater, 70-fold or greater, 80-fold or greater, 90-fold or greater, 100-fold or greater, 200-fold or greater, 300-fold or greater, 400-fold or greater, 500-fold or greater, 600-fold or greater, 700-fold or greater, 800-fold or greater, 900-fold or greater, 1000-fold or greater, 10000-fold or greater, or 100000-fold or greater.

Furthermore, the Fc region containing a selective FcγR-binding domain included in an antigen-binding molecule of the present invention and the antigen-binding molecule containing such an Fc region may be an Fc region and an antigen-binding molecule containing such an Fc region which maintains or shows reduced binding activity to activating FcγR (FcγRIa, FcγRIb, FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, FcγRIIa including allotype R131, and/or FcγRIIc) when compared to an Fc region presented as human IgG1 (SEQ ID NO: 14), IgG2 (SEQ ID NO: 15), IgG3 (SEQ ID NO: 16), or IgG4 (SEQ ID NO: 17) (hereinafter referred to as a wild-type Fc region) and an antigen-binding molecule containing such a wild-type Fc region; and shows enhanced binding activity to inhibitory FcγR (FcγRIIb-1 and/or FcγRIIb-2) when compared to an Fc region presented as human IgG1 (SEQ ID NO: 14), IgG2 (SEQ ID NO: 15), IgG3 (SEQ ID NO: 16), or IgG4 (SEQ ID NO: 17) (hereinafter referred to as a wild-type Fc region) and an antigen-binding molecule containing such a wild-type Fc region.

Furthermore, the Fc region containing a selective FcγR-binding domain included in an antigen-binding molecule of the present invention and the antigen-binding molecule containing such an Fc region may be an Fc region and an antigen-binding molecule containing such an Fc region with higher degree of enhancement of binding activity to an inhibitory Fcγ receptor (FcγRIIb-1 and/or FcγRIIb-2) than to an activating Fcγ receptor (FcγRIa, FcγRIb, FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, FcγRIIa including allotype R131), when compared to an Fc region presented as human IgG1 (SEQ ID NO: 14), IgG2 (SEQ ID NO: 15), IgG3 (SEQ ID NO: 16), or IgG4 (SEQ ID NO: 17) (hereinafter referred to as a wild-type Fc region) and an antigen-binding molecule containing such a wild-type Fc region.

In the present invention, at least another alteration to the Fc region may be added to the Fc region in which amino acid at position 238 (EU numbering) is Asp and the Fc region in which amino acid at position 328 (EU numbering) is Glu, by the embodiments and such described in the aforementioned section on amino acid alterations. In addition to these alterations, additional alterations may also be added. The additional alterations can be selected from any of substitutions, deletions, and modifications of an amino acid, and combinations thereof. For example, alterations that enhance binding activity to FcγRIIb while maintaining or reducing binding activity to FcγRIIa (H type) and FcγRIIa (R type) may be added. Addition of such alterations improves binding selectivity to FcγRIIb over FcγRIIa.

Among these, alterations that improve binding selectivity to FcγRIIb over FcγRIIa (R type) is favorable, and alterations that improve binding selectivity to FcγRIIb over FcγRIIa (H type) is more favorable. Examples of preferred amino acid substitutions for such alterations include: an alteration by substituting Gly at position 237 (EU numbering) with Trp; an alteration by substituting Gly at position 237 (EU numbering) with Phe; an alteration by substituting Pro at position 238 (EU numbering) with Phe; an alteration by substituting Asn at position 325 (EU numbering) with Met; an alteration by substituting Ser at position 267 (EU numbering) with Ile; an alteration by substituting Leu at position 328 (EU numbering) with Asp; an alteration by substituting Ser at position 267 (EU numbering) with Val; an alteration by substituting Leu at position 328 (EU numbering) with Trp; an alteration by substituting Ser at position 267 (EU numbering) with Gln; an alteration by substituting Ser at position 267 (EU numbering) with Met; an alteration by substituting Gly at position 236 (EU numbering) with Asp; an alteration by substituting Ala at position 327 (EU numbering) with Asn; an alteration by substituting Asn at position 325 (EU numbering) with Ser; an alteration by substituting Leu at position 235 (EU numbering) with Tyr; an alteration by substituting Val at position 266 (EU numbering) with Met; an alteration by substituting Leu at position 328 (EU numbering) with Tyr; an alteration by substituting Leu at position 235 (EU numbering) with Trp; an alteration by substituting Leu at position 235 (EU numbering) with Phe; an alteration by substituting Ser at position 239 (EU numbering) with Gly; an alteration by substituting Ala at position 327 (EU numbering) with Glu; an alteration by substituting Ala at position 327 (EU numbering) with Gly; an alteration by substituting Pro at position 238 (EU numbering) with Leu; an alteration by substituting Ser at position 239 (EU numbering) with Leu; an alteration by substituting Leu at position 328 (EU numbering) with Thr; an alteration by substituting Leu at position 328 (EU numbering) with Ser; an alteration by substituting Leu at position 328 (EU numbering) with Met; an alteration by substituting Pro at position 331 (EU numbering) with Trp; an alteration by substituting Pro at position 331 (EU numbering) with Tyr; an alteration by substituting Pro at position 331 (EU numbering) with Phe; an alteration by substituting Ala at position 327 (EU numbering) with Asp; an alteration by substituting Leu at position 328 (EU numbering) with Phe; an alteration by substituting Pro at position 271 (EU numbering) with Leu; an alteration by substituting Ser at position 267 (EU numbering) with Glu; an alteration by substituting Leu at position 328 (EU numbering) with Ala; an alteration by substituting Leu at position 328 (EU numbering) with Ile; an alteration by substituting Leu at position 328 (EU numbering) with Gln; an alteration by substituting Leu at position 328 (EU numbering) with Val; an alteration by substituting Lys at position 326 (EU numbering) with Trp; an alteration by substituting Lys at position 334 (EU numbering) with Arg; an alteration by substituting His at position 268 (EU numbering) with Gly; an alteration by substituting His at position 268 (EU numbering) with Asn; an alteration by substituting Ser at position 324 (EU numbering) with Val; an alteration by substituting Val at position 266 (EU numbering) with Leu; an alteration by substituting Pro at position 271 (EU numbering) with Gly; an alteration by substituting Ile at position 332 (EU numbering) with Phe; an alteration by substituting Ser at position 324 (EU numbering) with Ile; an alteration by substituting Glu at position 333 (EU numbering) with Pro; an alteration by substituting Tyr at position 300 (EU numbering) with Asp; an alteration by substituting Ser at position 337 (EU numbering) with Asp; an alteration by substituting Tyr at position 300 (EU numbering) with Gln; an alteration by substituting Thr at position 335 (EU numbering) with Asp; an alteration by substituting Ser at position 239 (EU numbering) with Asn; an alteration by substituting Lys at position 326 (EU numbering) with Leu; an alteration by substituting Lys at position 326 (EU numbering) with Ile; an alteration by substituting Ser at position 239 (EU numbering) with Glu; an alteration by substituting Lys at position 326 (EU numbering) with Phe; an alteration by substituting Lys at position 326 (EU numbering) with Val; an alteration by substituting Lys at position 326 (EU numbering) with Tyr; an alteration by substituting Ser at position 267 (EU numbering) with Asp; an alteration by substituting Lys at position 326 (EU numbering) with Pro; an alteration by substituting Lys at position 326 (EU numbering) with His; an alteration by substituting Lys at position 334 (EU numbering) with Ala; an alteration by substituting Lys at position 334 (EU numbering) with Trp; an alteration by substituting His at position 268 (EU numbering) with Gln; an alteration by substituting Lys at position 326 (EU numbering) with Gln; an alteration by substituting Lys at position 326 (EU numbering) with Glu; an alteration by substituting Lys at position 326 (EU numbering) with Met; an alteration by substituting Val at position 266 (EU numbering) with Ile; an alteration by substituting Lys at position 334 (EU numbering) with Glu; an alteration by substituting Tyr at position 300 (EU numbering) with Glu; an alteration by substituting Lys at position 334 (EU numbering) with Met; an alteration by substituting Lys at position 334 (EU numbering) with Val; an alteration by substituting Lys at position 334 (EU numbering) with Thr; an alteration by substituting Lys at position 334 (EU numbering) with Ser; an alteration by substituting Lys at position 334 (EU numbering) with His; an alteration by substituting Lys at position 334 (EU numbering) with Phe; an alteration by substituting Lys at position 334 (EU numbering) with Gln; an alteration by substituting Lys at position 334 (EU numbering) with Pro; an alteration by substituting Lys at position 334 (EU numbering) with Tyr; an alteration by substituting Lys at position 334 (EU numbering) with Ile; an alteration by substituting Gln at position 295 (EU numbering) with Leu; an alteration by substituting Lys at position 334 (EU numbering) with Leu; an alteration by substituting Lys at position 334 (EU numbering) with Asn; an alteration by substituting His at position 268 (EU numbering) with Ala; an alteration by substituting Ser at position 239 (EU numbering) with Asp; an alteration by substituting Ser at position 267 (EU numbering) with Ala; an alteration by substituting Leu at position 234 (EU numbering) with Trp; an alteration by substituting Leu at position 234 (EU numbering) with Tyr; an alteration by substituting Gly at position 237 (EU numbering) with Ala; an alteration by substituting Gly at position 237 (EU numbering) with Asp; an alteration by substituting Gly at position 237 (EU numbering) with Glu; an alteration by substituting Gly at position 237 (EU numbering) with Leu; an alteration by substituting Gly at position 237 (EU numbering) with Met; an alteration by substituting Gly at position 237 (EU numbering) with Tyr; an alteration by substituting Ala at position 330 (EU numbering) with Lys; an alteration by substituting Ala at position 330 (EU numbering) with Arg; an alteration by substituting Glu at position 233 (EU numbering) with Asp; an alteration by substituting His at position 268 (EU numbering) with Asp; an alteration by substituting His at position 268 (EU numbering) with Glu; an alteration by substituting Lys at position 326 (EU numbering) with Asp; an alteration by substituting Lys at position 326 (EU numbering) with Ser; an alteration by substituting Lys at position 326 (EU numbering) with Thr; an alteration by substituting Val at position 323 (EU numbering) with Ile; an alteration by substituting Val at position 323 (EU numbering) with Leu; an alteration by substituting Val at position 323 (EU numbering) with Met; an alteration by substituting Tyr at position 296 (EU numbering) with Asp; an alteration by substituting Lys at position 326 (EU numbering) with Ala; an alteration by substituting Lys at position 326 (EU numbering) with Asn; and an alteration by substituting Ala at position 330 (EU numbering) with Met.

Favorable amino acid substitutions among these alterations are, for example, an alteration by substituting Gly at position 237 (EU numbering) with Trp; an alteration by substituting Gly at position 237 (EU numbering) with Phe; an alteration by substituting Ser at position 267 (EU numbering) with Val; an alteration by substituting Ser at position 267 (EU numbering) with Gln; an alteration by substituting His at position 268 (EU numbering) with Asn; an alteration by substituting Pro at position 271 (EU numbering) with Gly; an alteration by substituting Lys at position 326 (EU numbering) with Leu; an alteration by substituting Lys at position 326 (EU numbering) with Gln; an alteration by substituting Lys at position 326 (EU numbering) with Glu; an alteration by substituting Lys at position 326 (EU numbering) with Met; an alteration by substituting Ser at position 239 (EU numbering) with Asp; an alteration by substituting Ser at position 267 (EU numbering) with Ala; an alteration by substituting Leu at position 234 (EU numbering) with Trp; an alteration by substituting Leu at position 234 (EU numbering) with Tyr; an alteration by substituting Gly at position 237 (EU numbering) with Ala; an alteration by substituting Gly at position 237 (EU numbering) with Asp; an alteration by substituting Gly at position 237 (EU numbering) with Glu; an alteration by substituting Gly at position 237 (EU numbering) with Leu; an alteration by substituting Gly at position 237 (EU numbering) with Met; an alteration by substituting Gly at position 237 (EU numbering) with Tyr; an alteration by substituting Ala at position 330 (EU numbering) with Lys; an alteration by substituting Ala at position 330 (EU numbering) with Arg; an alteration by substituting Glu at position 233 (EU numbering) with Asp; an alteration by substituting His at position 268 (EU numbering) with Asp; an alteration by substituting His at position 268 (EU numbering) with Glu; an alteration by substituting Lys at position 326 (EU numbering) with Asp; an alteration by substituting Lys at position 326 (EU numbering) with Ser; an alteration by substituting Lys at position 326 (EU numbering) with Thr; an alteration by substituting Val at position 323 (EU numbering) with Ile; an alteration by substituting Val at position 323 (EU numbering) with Leu; an alteration by substituting Val at position 323 (EU numbering) with Met; an alteration by substituting Tyr at position 296 (EU numbering) with Asp; an alteration by substituting Lys at position 326 (EU numbering) with Ala; an alteration by substituting Lys at position 326 (EU numbering) with Asn; and an alteration by substituting Ala at position 330 (EU numbering) with Met.

The above-mentioned alteration may be at one position, or alterations at two or more positions may be combined. Favorable examples of such alterations are those described in Tables 13 to 14, Tables 16 to 23, and Tables 25 to 27.

Fc region produced by altering the FcγR-binding domain included in the Fc region presented as human IgG1 (SEQ ID NO: 14), IgG2 (SEQ ID NO: 15), IgG3 (SEQ ID NO: 16), or IgG4 (SEQ ID NO: 17) can be given as an example of another non-limiting embodiment of the selective FcγR-binding domain included in the antigen-binding molecules of the present invention. A method for producing the modified Fc regions is, for example, the method described in the above-mentioned section on amino acid alterations. Examples of such altered Fc regions include an Fc region in which amino acid at position 238 (EU numbering) is Asp and amino acid at position at 271 (EU numbering) is Gly in a human IgG (IgG1, IgG2, IgG3, or IgG4). An Fc region in which amino acid at position 238 (EU numbering) is Asp and amino acid at position at 271 (EU numbering) is Gly in a human IgG (IgG1, IgG2, IgG3, or IgG4), and antigen-binding molecules containing such an Fc region show higher binding activity to FcγRIIb-1 and/or FcγRIIb-2 than to FcγRIa, FcγRIb, FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, FcγRIIa including allotype R131, and/or FcγRIIc.

In the present invention, at least another alteration to the Fc region may be added to the Fc region in which amino acid at position 238 (EU numbering) is Asp and the amino acid at position 271 (EU numbering) is Gly, by the embodiments and such described in the aforementioned section on amino acid alterations. In addition to these alterations, additional alterations may also be added. The additional alterations can be selected from any of substitutions, deletions, and modifications of an amino acid, and combinations thereof. For example, alterations that maintain or reduce binding activity to activating Fcγ receptors (FcγRIa, FcγRIb, FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, FcγRIIa including allotype R131) can be added. Alterations that enhance binding activity to inhibitory Fcγ receptors (FcγRIIb-1 and/or FcγRIIb-2) while maintaining or reducing binding activity to FcγRIIa (H type) and FcγRIIa (R type) may be added. Furthermore, alterations where the degree of enhancement of binding activity to inhibitory Fcγ receptors (FcγRIIb-1 and/or FcγRIIb-2) is higher than the degree of enhancement of binding activity to activating Fcγ receptors (FcγRIa, FcγRIb, FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, FcγRIIa including allotype R131) may also be added. Addition of such alterations improves binding selectivity to FcγRIIb over FcγRIIa.

An example of a non-limiting embodiment of the altered Fc region comprising a selective FcγR-binding domain includes an altered Fc region in which at least one or more amino acid selected from the group consisting of those at positions 233, 234, 237, 264, 265, 266, 267, 268, 269, 272, 274, 296, 326, 327, 330, 331, 332, 333, 355, 356, 358, 396, 409, and 419 (EU numbering) are substituted in the Fc region in which amino acid at position 238 (EU numbering) is Asp and amino acid at position 271 (EU numbering) is Gly in a human IgG (IgG1, IgG2, IgG3, or IgG4).

In addition, an example of a non-limiting embodiment of the altered Fc region comprising a selective FcγR-binding domain is an altered Fc region comprising any one or more of Asp at amino acid position 233,
Tyr at amino acid position 234,
Asp at amino acid position 237, Ile at amino acid position 264,
Glu at amino acid position 265,
any one of Phe, Met, and Leu at amino acid position 266,
any one of Ala, Glu, Gly, and Gln at amino acid position 267,
any one of Asp, Glu, and Gln at amino acid position 268,
Asp at amino acid position 269,
any one of Asp, Phe, Ile, Met, Asn, Pro, and Gln at amino acid position 272,
Gln at position 274,
Asp or Phe at amino acid position 296,
Ala or Asp at amino acid position 326,
Gly at amino acid position 327,
Lys or Arg at amino acid position 330,
Ser at amino acid position 331,
Thr at amino acid position 332,
any one of Thr, Lys, and Arg at amino acid position 333,
Gln at amino acid position 355,
Glu at amino acid position 356,
Met at amino acid position 358,
any one of Asp, Glu, Phe, Ile, Lys, Leu, Met, Gln, Arg, and Tyr at amino acid position 396,
Arg at amino acid position 409,
Glu at amino acid position 419,
shown by EU numbering, in the Fc region in which amino acid at position 238 is Asp and amino acid at position 271 (EU numbering) is Gly in a human IgG (IgG1, IgG2, IgG3, or IgG4).

Examples of a non-limiting embodiment of Fc region which further comprises at least another alteration to the Fc region and further comprises additional alterations mentioned above include Fc regions shown in Tables 5-1 to 5-7.

TABLE 5-1

| ALTERED Fc REGION | ALTERED AMINO ACID (EU NUMBERING) |
|---|---|
| BP208 | E233D/G237D/P238D/H268D/P271G/A330R |
| BP209 | G237D/P238D/H268D/P271G/K326A/A330R |
| BP210 | G237D/P238D/H268D/P271G/A330R |
| BP211 | E233D/P238D/H268D/P271G/K326A/A330R |
| BP212 | E233D/P238D/H268D/P271G/Y296D/A330R |
| BP213 | E233D/P238D/H268D/P271G/A330R |
| BP214 | E233D/L234Y/G237D/P238D/Y296D/K326D/A330K |
| BP215 | G237D/P238D/H268D/P271G/Y296D/A330K |
| BP216 | G237D/P238D/S267Q/H268D/P271G/A330K |
| BP217 | G237D/P238D/S267Q/H268D/P271G/Y296D/A330K |
| BP218 | G237D/P238D/H268D/P271G/K326D/A330K |
| BP219 | L234Y/G237D/P238D/H268D/P271G/A330K |
| BP220 | E233D/G237D/P238D/H268D/P271G/Y296D/A330K |
| BP221 | L234Y/G237D/P238D/Y296D/K326A/A330R |
| BP222 | L234Y/G237D/P238D/P271G/K326A/A330R |
| BP223 | L234Y/G237D/P238D/H268D/P271G/K326A/A330R |
| BP224 | L234Y/G237D/P238D/S267Q/H268D/P271G/K326A/A330R |
| BP225 | L234Y/G237D/P238D/K326D/A330R |
| BP226 | L234Y/G237D/P238D/P271G/K326D/A330R |
| BP227 | L234Y/G237D/P238D/H268D/P271G/K326D/A330R |
| BP228 | L234Y/G237D/P238D/S267Q/H268D/P271G/K326D/A330R |
| BP229 | E233D/L234Y/G237D/P238D/P271G/K326A/A330R |
| BP230 | E233D/G237D/P238D/H268D/P271G/Y296D/A330R |
| BP231 | G237D/P238D/H268D/P271G/Y296D/A330R |
| BP232 | L234Y/G237D/P238D/P271G/K326A/A330K |
| BP233 | L234Y/G237D/P238D/P271G/A330K |
| BP234 | E233D/L234Y/G237D/P238D/S267Q/H268D/P271G/Y296D/K326D/A330K |
| BP235 | E233D/L234Y/G237D/P238D/H268D/P271G/Y296D/K326D/A330R |
| BP236 | E233D/L234Y/G237D/P238D/S267Q/H268D/P271G/Y296D/K326D/A330R |
| BP237 | E233D/L234Y/G237D/P238D/S267Q/H268D/P271G/Y296D/K326A/A330K |

(Table 5-2 is a continuation table of Table 5-1.)

TABLE 5-2

| ALTERED Fc REGION | ALTERED AMINO ACID (EU NUMBERING) |
|---|---|
| BP238 | E233D/L234Y/G237D/P238D/H268D/P271G/Y296D/K326A/A330R |
| BP239 | E233D/L234Y/G237D/P238D/S267Q/H268D/P271G/Y296D/K326A/A330R |
| BP240 | E233D/G237D/P238D/S267Q/H268D/P271G/A330R |
| BP241 | E233D/G237D/P238D/H268D/P271G/K326D/A330R |
| BP242 | E233D/G237D/P238D/H268D/P271G/K326A/A330R |
| BP243 | E233D/L234Y/G237D/P238D/H268D/P271G/A330R |
| BP244 | E233D/G237D/P238D/S267Q/H268D/P271G/Y296D/A330R |
| BP245 | E233D/G237D/P238D/S267Q/H268D/P271G/Y296D/K326D/A330R |
| BP246 | E233D/G237D/P238D/S267Q/H268D/P271G/Y296D/K326A/A330R |
| BP247 | E233D/G237D/P238D/H268D/P271G/Y296D/K326D/A330R |
| BP248 | E233D/G237D/P238D/H268D/P271G/Y296D/K326A/A330R |
| BP249 | E233D/L234Y/G237D/P238D/H268D/P271G/Y296D/A330R |
| BP262 | G237D/P238D/H268E/P271G |
| BP264 | E233D/G237D/P238D/H268E/P271G/Y296D/A330R |
| BP265 | G237D/P238D/H268E/P271G/Y296D/A330R |
| BP266 | E233D/G237D/P238D/H268E/P271G/A330R |
| BP267 | E233D/G237D/P238D/H268E/P271G |
| BP268 | E233D/G237D/P238D/H268E/P271G/Y296D |
| BP269 | G237D/P238D/H268E/P271G/Y296D |
| BP300 | E233D/G237D/P238D/V264I/H268E/P271G |
| BP313 | E233D/G237D/P238D/D265E/H268E/P271G |
| BP333 | E233D/G237D/P238D/V266F/H268E/P271G |
| BP338 | E233D/G237D/P238D/V266L/H268E/P271G |
| BP339 | E233D/G237D/P238D/V266M/H268E/P271G |
| BP348 | E233D/G237D/P238D/S267A/H268E/P271G |
| BP350 | E233D/G237D/P238D/S267E/H268E/P271G |
| BP352 | E233D/G237D/P238D/S267G/H268E/P271G |
| BP367 | E233D/G237D/P238D/H268E/E269D/P271G |
| BP384 | E233D/G237D/P238D/H268D/P271G/Y296D/A330R/K334R |
| BP390 | E233D/G237D/P238D/H268D/P271G/Y296D/A330R/I332S |
| BP391 | E233D/G237D/P238D/H268D/P271G/Y296D/A330R/I332T |

(Table 5-3 is a continuation table of Table 5-2.)

TABLE 5-3

| ALTERED Fc REGION | ALTERED AMINO ACID (EU NUMBERING) |
|---|---|
| BP392 | E233D/G237D/P238D/H268D/P271G/Y296D/A330R/I332K |
| BP393 | E233D/G237D/P238D/H268D/P271G/Y296D/A330R/I332R |
| BP423 | E233D/G237D/P238D/S267A/H268E/P271G/A330R |
| BP425 | E233D/G237D/P238D/V266L/S267A/H268E/P271G/A330R |
| BP426 | E233D/G237D/P238D/S267A/H268E/E269D/P271G/A330R |
| BP427 | E233D/G237D/P238D/S267A/H268E/E269Y/P271G/A330R |
| BP428 | E233D/G237D/P238D/S267G/H268E/P271G/A330R |
| BP429 | E233D/G237D/P238D/V264I/S267G/H268E/P271G/A330R |
| BP430 | E233D/G237D/P238D/V266L/S267G/H268E/P271G/A330R |
| BP431 | E233D/G237D/P238D/S267G/H268E/E269D/P271G/A330R |
| BP432 | E233D/G237D/P238D/S267G/H268E/E269Y/P271G/A330R |
| BP433 | E233D/G237D/P238D/H268D/P271G/Y296D/A330K/I332T |
| BP434 | E233D/G237D/P238D/H268D/P271G/Y296D/K326D/A330R/I332T |
| BP435 | E233D/G237D/P238D/H268D/P271G/Y296D/K326A/A330R/I332T |
| BP436 | E233D/G237D/P238D/S267A/H268E/P271G/Y296D/A330R/I332T |
| BP437 | G237D/P238D/S267A/H268E/P271G/Y296D/A330R/I332T |
| BP438 | E233D/G237D/P238D/S267A/H268E/P271G/A330R/I332T |
| BP439 | E233D/G237D/P238D/V264I/V266L/S267A/H268E/P271G/A330R |
| BP440 | E233D/G237D/P238D/V264I/H268E/P271G/A330R |
| BP441 | E233D/G237D/P238D/V266L/H268E/P271G/A330R |
| BP442 | E233D/G237D/P238D/H268E/E269D/P271G/A330R |
| BP443 | E233D/G237D/P238D/V266L/H268E/E269D/P271G/A330R |
| BP444 | E233D/G237D/P238D/H268E/E269N/P271G/A330R |
| BP445 | E233D/G237D/P238D/V264I/S267A/H268E/P271G/A330R |
| BP446 | E233D/G237D/P238D/S267A/H268E/E269N/P271G/A330R |
| BP447 | E233D/G237D/P238D/S267A/H268E/P271G/A330R/P396A |
| BP448 | E233D/G237D/P238D/S267A/H268E/P271G/A330R/P396D |
| BP449 | E233D/G237D/P238D/S267A/H268E/P271G/A330R/P396E |
| BP450 | E233D/G237D/P238D/S267A/H268E/P271G/A330R/P396F |
| BP451 | E233D/G237D/P238D/S267A/H268E/P271G/A330R/P396G |
| BP452 | E233D/G237D/P238D/S267A/H268E/P271G/A330R/P396H |

(Table 5-4 is a continuation table of Table 5-3.)

TABLE 5-4

| ALTERED Fc REGION | ALTERED AMINO ACID (EU NUMBERING) |
|---|---|
| BP453 | E233D/G237D/P238D/S267A/H268E/P271G/A330R/P396I |
| BP454 | E233D/G237D/P238D/S267A/H268E/P271G/A330R/P396K |
| BP455 | E233D/G237D/P238D/S267A/H268E/P271G/A330R/P396L |
| BP456 | E233D/G237D/P238D/S267A/H268E/P271G/A330R/P396M |
| BP457 | E233D/G237D/P238D/S267A/H268E/P271G/A330R/P396N |
| BP458 | E233D/G237D/P238D/S267A/H268E/P271G/A330R/P396Q |
| BP459 | E233D/G237D/P238D/S267A/H268E/P271G/A330R/P396R |
| BP460 | E233D/G237D/P238D/S267A/H268E/P271G/A330R/P396S |
| BP461 | E233D/G237D/P238D/S267A/H268E/P271G/A330R/P396T |
| BP462 | E233D/G237D/P238D/S267A/H268E/P271G/A330R/P396V |
| BP463 | E233D/G237D/P238D/S267A/H268E/P271G/A330R/P396W |
| BP464 | E233D/G237D/P238D/S267A/H268E/P271G/A330R/P396Y |
| BP465 | E233D/G237D/P238D/H268D/P271G/Y296D/A330R/E333K |
| BP466 | E233D/G237D/P238D/H268D/P271G/Y296D/A330R/E333R |
| BP467 | E233D/G237D/P238D/H268D/P271G/Y296D/A330R/E334S |
| BP468 | E233D/G237D/P238D/H268D/P271G/Y296D/A330R/E334T |
| BP469 | E233D/G237D/P238D/H268D/P271G/Y296D/A330R/E333S |
| BP470 | E233D/G237D/P238D/H268D/P271G/Y296D/A330R/E333T |
| BP471 | E233D/G237D/P238D/H268D/P271G/Y296D/A330R/P331S |
| BP472 | E233D/G237D/P238D/H268D/P271G/Y296D/A330S |
| BP473 | E233D/G237D/P238D/H268D/P271G/Y296D/A327G/A330R |
| BP474 | E233D/G237D/P238D/H268D/P271G/Y296D/A330R/P331S |
| BP475 | E233D/G237D/P238D/H268D/P271G/Y296D/A327G/A330S |
| BP476 | E233D/G237D/P238D/H268D/P271G/Y296D/A327G/A330S/P331S |
| BP477 | E233D/G237D/P238D/H268D/P271G/Y296D/A327G/A330R/P331S |
| BP478 | E233D/G237D/P238D/H268D/P271G/Y296D/A330R + S131C/K133R/G137E/G138S/Q196K/I199T/N203D/K214R/P217S + 219-221 DELETION + K222Y/T223G/H224P/T225P |
| BP479 | E233D/G237D/P238D/V264I/V266L/S267A/H268E/P271G |
| BP480 | E233D/G237D/P238D/V266L/H268E/E269D/P271G |
| BP481 | E233D/G237D/P238D/V264I/S267A/II268E/P271G |

(Table 5-5 is a continuation table of Table 5-4.)

TABLE 5-5

| ALTERED Fc REGION | ALTERED AMINO ACID (EU NUMBERING) |
|---|---|
| BP482 | E233D/G237D/P238D/S267A/H268E/E269N/P271G |
| BP483 | E233D/G237D/P238D/V266L/S267A/H268E/P271G |
| BP484 | E233D/G237D/P238D/S267A/H268E/E269D/P271G |
| BP485 | E233D/G237D/P238D/S267A/H268E/E269Y/P271G |
| BP487 | E233D/G237D/P238D/V264I/S267A/H268E/P271G/A330R/P396M |
| BP488 | E233D/G237D/P238D/V264I/S267A/H268E/P271G/Y296D/A330R |
| BP489 | E233D/G237D/P238D/V264I/S267A/H268E/P271G/Y296D/A330R/P396M |
| BP490 | G237D/P238D/V264I/S267A/H268E/P271G/A330R |
| BP491 | G237D/P238D/V264I/S267A/H268E/P271G/Y296D/A330R |
| BP492 | P238D/V264I/S267A/H268E/P271G |
| BP493 | P238D/V264I/S267A/H268E/P271G/Y296D |
| BP494 | G237D/P238D/S267A/H268E/P271G/Y296D/A330R |
| BP495 | G237D/P238D/S267G/H268E/P271G/Y296D/A330R |
| BP496 | E233D/G237D/P238D/V264I/S267A/H268E/P271G/Y296D |
| BP497 | E233D/G237D/P238D/V264I/S267A/H268E/P271G/A327G/A330R |
| BP498 | E233D/G237D/P238D/V264I/S267A/H268E/P271G/A330R/P396L |
| BP499 | E233D/G237D/P238D/V264I/S267A/H268E/P271G/Y296D/A330R/P396L |
| BP500 | G237D/P238D/V264I/S267A/H268E/P271G/Y296D |
| BP501 | G237D/P238D/V264I/S267A/H268E/P271G |
| BP502 | E233D/G237D/P238D/V264I/S267A/H268E/P271G/Y296D/A327G/A330R |
| BP503 | E233D/G237D/P238D/V264I/S267A/H268E/P271G/Y296D/A327G/A330R/P396M |
| BP504 | E233D/G237D/P238D/V264I/S267A/H268E/P271G/E272P |
| BP505 | E233D/G237D/P238D/V264I/S267A/H268E/P271G/E272D |
| BP506 | E233D/G237D/P238D/V264I/S267A/H268E/P271G/E272P/Y296D/A330R |
| BP507 | E233D/G237D/P238D/V264I/S267A/H268E/P271G/E272P/A330R |
| BP508 | E233D/G237D/P238D/V264I/S267A/H268E/P271G/E272P/Y296D |
| BP509 | E233D/G237D/P238D/V264I/S267A/H268E/P271G/E272D/Y296D |
| BP510 | G237D/P238D/V264I/S267A/H268E/P271G/E272P/A330R |
| BP511 | G237D/P238D/V264I/S267A/H268E/P271G/E272P/Y296D/A330R |
| BP513 | E233D/G237D/P238D/H268E/E272D/P271G |

(Table 5-6 is a continuation table of Table 5-5.)

TABLE 5-6

| ALTERED Fc REGION | ALTERED AMINO ACIDS (EU NUMBERING) |
|---|---|
| BP514 | E233D/G237D/P238D/H268E/E272F/P271G |
| BP517 | E233D/G237D/P238D/H268E/E272I/P271G |
| BP520 | E233D/G237D/P238D/H268E/E272M/P271G |
| BP521 | E233D/G237D/P238D/H268E/E272N/P271G |
| BP523 | E233D/G237D/P238D/H268E/E272Q/P271G |
| BP531 | E233D/G237D/P238D/V264I/S267G/H268E/P271G/Y296D/A330R/P396M |
| BP532 | E233D/G237D/P238D/V264I/H268E/P271G/Y296D/A330R/P396M |
| BP533 | E233D/G237D/P238D/V264I/S267G/H268E/P271G/Y296D/A330R/P396L |
| BP534 | E233D/G237D/P238D/V264I/H268E/P271G/Y296D/A330R/P396L |
| BP535 | E233D/G237D/P238D/V264I/S267G/H268E/P271G/Y296D/A327G/A330R/P396M |
| BP536 | E233D/G237D/P238D/V264I/H268E/P271G/Y296D/A327G/A330R/P396M |
| BP537 | G237D/P238D/V264I/S267G/H268E/P271G/A330R |
| BP538 | G237D/P238D/V264I/H268E/P271G/A330R |
| BP539 | G237D/P238D/V264I/S267G/H268E/P271G/E272P/Y296D/A330R |
| BP540 | G237D/P238D/V264I/H268E/P271G/E272P/Y296D/A330R |
| BP549 | G237D/P238D/S267G/H268E/P271G/A330R |
| BP550 | G237D/P238D/V264I/S267G/H268E/P271G/E272D/Y296D/A330R |
| BP551 | G237D/P238D/V264I/H268E/P271G/E272D/Y296D/A330R |
| BP552 | E233D/G237D/P238D/V264I/S267A/H268E/P271G/E272D/Y296D/A330R |
| BP553 | E233D/G237D/P238D/V264I/S267A/H268E/P271G/E272D/A330R |
| BP554 | G237D/P238D/V264I/S267A/H268E/P271G/E272D/A330R |
| BP555 | G237D/P238D/V264I/S267A/H268E/P271G/E272D/Y296D/A330R |
| BP556 | G237D/P238D/V264I/S267G/H268E/P271G/Y296D/A330R |
| BP557 | G237D/P238D/S267G/H268D/P271G/Y296D/A330R |
| BP558 | G237D/P238D/V264I/S267G/H268E/P271G/E272D/A330R |
| BP559 | P238D/V264I/S267A/H268E/P271G/E272D/Y296D |
| BP560 | P238D/S267G/H268E/P271G/Y296D/A330R |
| BP561 | E233D/G237D/P238D/H268D/P271G/E272D/Y296D/A330R |
| BP562 | G237D/P238D/H268D/P271G/E272D/Y296D/A330R |
| BP563 | E233D/G237D/P238D/H268E/P271G/E272D/Y296D/A330R |

(Table 5-7 is a continuation table of Table 5-6.)

TABLE 5-7

| ALTERED Fc REGION | ALTERED AMINO ACIDS (EU NUMBERING) |
|---|---|
| BP564 | G237D/P238D/H268E/P271G/E272D/Y296D/A330R |
| BP565 | E233D/G237D/P238D/S267A/H268E/P271G/Y296D/A330R |
| BP567 | E233D/P238D/V264I/S267A/H268E/P271G/Y296D |
| BP568 | E233D/P238D/V264I/S267A/H268E/P271G |

Antigen-Binding Molecule

In the present invention, "an antigen-binding molecule" is used in the broadest sense to refer to a molecule comprising an antigen-binding domain whose antigen-binding activity varies depending on ion concentration conditions, an FcRn-binding domain having FcRn-binding activity under an acidic pH range condition, and an Fcγ receptor-binding domain having selective binding activity to an Fcγ receptor (a selective FcγR-binding domain). Specifically, the antigen-binding molecules include various types of molecules as long as they exhibit antigen-binding activity. Antibodies are examples of molecules in which an antigen-binding domain whose antigen-binding activity varies depending on ion concentration conditions, an FcRn-binding domain having FcRn-binding activity under an acidic pH range condition, and an Fcγ receptor-binding domain having selective binding activity to an Fcγ receptor (a selective FcγR-binding domain) are linked together. Antibodies may include single monoclonal antibodies (including agonistic antibodies and antagonistic antibodies), human antibodies, humanized antibodies, chimeric antibodies, and such. Alternatively, when used as antibody fragments, they preferably include antigen-binding domains and antigen-binding fragments (for example, Fab, F(ab')2, scFv, and Fv). Scaffold molecules where three dimensional structures, such as already-known stable α/β barrel protein structure, are used as a scaffold (base) and only some portions of the structures are made into libraries to construct antigen-binding domains are also included in antigen-binding molecules of the present invention.

An antigen-binding molecule of the present invention may contain at least some portions of an Fc region that mediates the binding to FcRn and binding to Fcγ receptor and/or complement receptor. In a non-limiting embodiment, the antigen-binding molecule includes, for example, antibodies and Fc fusion proteins. A fusion protein refers to a chimeric polypeptide comprising a polypeptide having a first amino acid sequence that is linked to a polypeptide having a second amino acid sequence that would not naturally link in nature. For example, a fusion protein may comprise the amino acid sequence of at least a portion of an Fc region (for example, a portion of an Fc region responsible for the binding to FcRn, a portion of an Fc region responsible for the binding to Fcγ receptor, or a portion of an Fc region responsible for the binding to complement) and a non-immunoglobulin polypeptide containing, for example, the amino acid sequence of the ligand-binding domain of a receptor or a receptor-binding domain of a ligand. The amino acid sequences may be present in separate proteins that are transported together to a fusion protein, or generally may be present in a single protein; however, they are included in a new rearrangement in a fusion polypeptide. Fusion proteins can be produced, for example, by chemical synthesis, or by genetic recombination techniques to express a polynucleotide encoding peptide regions in a desired arrangement.

Respective domains of the present invention such as the antigen-binding domain, the FcRn-binding domain having FcRn-binding activity under an acidic pH range condition, and the Fcγ receptor-binding domain having selective binding activity to an Fcγ receptor (selective FcγR-binding domain), can be linked together via linkers or directly via polypeptide bonds. The linkers comprise arbitrary peptide linkers that can be introduced by genetic engineering, synthetic linkers, and linkers disclosed in, for example, Protein Engineering (1996) 9(3), 299-305. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids.

For example, such peptide linkers preferably include:

```
    Ser

Gly•Ser

Gly•Gly•Ser

Ser•Gly•Gly
                                    (SEQ ID NO: 28)
    Gly•Gly•Gly•Ser
                                    (SEQ ID NO: 29)
    Ser•Gly•Gly•Gly
                                    (SEQ ID NO: 30)
    Gly•Gly•Gly•Gly•Ser
                                    (SEQ ID NO: 31)
    Ser•Gly•Gly•Gly•Gly
                                    (SEQ ID NO: 32)
    Gly•Gly•Gly•Gly•Gly•Ser
                                    (SEQ ID NO: 33)
    Ser•Gly•Gly•Gly•Gly•Gly
                                    (SEQ ID NO: 34)
    Gly•Gly•Gly•Gly•Gly•Gly•Ser
                                    (SEQ ID NO: 35)
    Ser•Gly•Gly•Gly•Gly•Gly•Gly (Gly•Gly•Gly•Gly•Ser (SEQ ID NO: 30))n (Ser•Gly•Gly•Gly•Gly (SEQ ID NO: 31))n
``` where n is an integer of 1 or larger. The length or sequences of peptide linkers can be selected accordingly by those skilled in the art depending on the purpose.

Synthetic linkers (chemical crosslinking agents) is routinely used to crosslink peptides, and for example:

N-hydroxy succinimide (NHS),
disuccinimidyl suberate (DSS), bis(sulfosuccinimidyl) suberate (B S3),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl] sulfone (BSOCOES),
and bis[2-(sulfosuccinimidoxycarbonyloxy)ethyl] sulfone (sulfo-BSOCOES). These crosslinking agents are commercially available.

When multiple linkers for linking the respective domains are used, they may all be of the same type, or may be of different types.

In addition to the linkers exemplified above, linkers with peptide tags such as His tag, HA tag, myc tag, and FLAG tag may also be suitably used. Furthermore, hydrogen bonding, disulfide bonding, covalent bonding, ionic interaction, and properties of binding with each other as a result of combination thereof may be suitably used. For example, the affinity between CH1 and CL of antibody may be used, and Fc regions originating from the above-described bispecific antibodies may also be used for hetero Fc region association. Moreover, disulfide bonds formed between domains may also be suitably used.

In order to link the respective domains via peptide linkage, polynucleotides encoding the domains are linked in frame. Known methods for linking polynucleotides in frame include techniques such as ligation of restriction fragments, fusion PCR, and overlapping PCR. Such methods can be appropriately used alone or in combination to produce the antigen-binding molecules of the present invention. In the present invention, the terms "linked" and "fused", or "linkage" and "fusion" are used interchangeably. These terms mean that two or more elements or components such as polypeptides are linked together to form a single structure by any means including the above-described chemical linking means and recombination techniques. When two or more domains, elements, or components are polypeptides, linking in frame means linking two or more units of reading frames to form a longer continuous reading frame while maintaining the correct reading frames of the polypeptides. When two molecules of Fab are used as an antigen-binding domain, an antibody, which is an antigen-binding molecule of the present invention where the antigen-binding domain is linked in frame via peptide bonds without a linker to an FcRn-binding domain having FcRn-binding activity under an acidic pH range condition and the Fcγ receptor-binding domain having selective binding activity to an Fcγ receptor (selective FcγR-binding domain), may be used as a preferred antigen-binding molecule of the present application. Examples of non-limiting multiple embodiments of the antigen-binding molecule of the present invention including the antibody structure are shown below:

(1) an antibody which comprises F(ab')2 comprising two variable regions and having antigen-binding activity that varies depending on ion concentration conditions and an Fc region having FcRn-binding activity under an acidic pH range condition and selective binding activity to an Fcγ receptor;

(2) an antibody which comprises F(ab')2 wherein one of the variable regions forming F(ab')2 has antigen-binding activity that varies depending on ion concentration conditions and the other variable region has selective binding activity to an Fcγ receptor, and an Fc region having FcRn-binding activity under an acidic pH range condition; and (3) an antibody which comprises F(ab')2 wherein one of the variable regions forming F(ab')2 has antigen-binding activity that varies depending on ion concentration conditions and the other variable region has FcRn-binding activity under an acidic pH range condition, and an Fc region having selective binding activity to an Fcγ receptor.

When an antibody comprises the above-mentioned structure of (3), a variable region having FcRn-binding activity that varies depending on pH conditions can be used preferably as the variable region having FcRn-binding activity under an acidic pH range condition. Without being bound by a particular theory, if a variable region whose FcRn-binding activity varies depending on pH conditions is used and if the variable region does not have FcRn-binding activity under a neutral pH range condition, the antibody is released from FcRn at the cell surface when the antibody bound to FcRn in the acidic endosome is transported to the cell surface and can be easily recycled into the plasma.

Bispecific Antibodies and Methods for Producing Them

Methods for producing bispecific antibodies may be applied as an embodiment of the method for preparing antibodies comprising the structures of (2) and (3) mentioned above. Bispecific antibodies are antibodies comprising two types of variable regions that bind specifically to different epitopes. IgG-type bispecific antibodies can be secreted from a hybrid hybridoma (quadroma) produced by fusing two types of hybridomas that produce IgG antibodies (Milstein et al., Nature (1983) 305, 537-540).

When a bispecific antibody is produced by using recombination techniques such as those described in the above-mentioned section on antibodies, one may adopt a method that introduces genes encoding heavy chains containing the two types of variable regions of interest into cells to co-express them. However, even when only the heavy-chain combination is considered, such a co-expression method will produce a mixture of (i) a combination of a pair of heavy chains in which one of the heavy chains contains a variable region that binds to a first epitope and the other heavy chain contains a variable region that binds to a second epitope, (ii) a combination of a pair of heavy chains which include only heavy chains containing a variable region that binds to the first epitope, and (iii) a combination of a pair of heavy chains which include only heavy chains containing a variable region that binds to the second epitope, which are present at a molecular ratio of 2:1:1. It is difficult to purify antigen-binding molecules containing the desired combination of heavy chains from the mixture of three types of heavy chain combinations.

When producing bispecific antibodies using recombination techniques such as described above, bispecific antibodies comprising the hetero combination of heavy chains can be preferentially secreted by altering the CH3 domain that constitutes a heavy chain using appropriate amino acid substitutions. Specifically, it is a method of enhancing heterogeneous heavy chain formation and inhibiting homogeneous heavy chain formation by substituting amino acid side chain in one heavy chain CH3 domain with a bulker side chain (knob (meaning "projection")) while substituting amino acid side chain in the other heavy chain CH3 domain with a smaller side chain (hole (meaning "void")) so that the "knob" is placed in the "hole" (WO 1996/027011, Ridgway et al. (Protein Engineering (1996) 9, 617-621), Merchant et al. (Nat. Biotech. (1998) 16, 677-681)).

Furthermore, known techniques for producing bispecific antibodies include those in which a means for regulating polypeptide association or association to form heteromeric multimers constituted by polypeptides is applied to the association of heavy chains. Specifically, to produce bispecific antibodies, one can use methods for regulating heavy chain association by altering amino acid residues forming interface between heavy chains so as to form two heavy chains with different sequences, while inhibiting the association of heavy chains having an identical sequence (WO 2006/106905). Such methods can be used to produce bispecific antibodies.

In a non-limiting embodiment of the present invention, two polypeptides constituting an Fc region derived from a bispecific antibody described above can be suitably used as the Fc region contained in an antigen-binding molecule. More specifically, two polypeptides constituting an Fc region may be suitably used, in which, of the amino acid sequence of one of the polypeptides, the amino acid at position 349 as indicated by EU numbering is Cys and the amino acid at position 366 is Trp, and of the amino acid sequence of the other of the polypeptides, the amino acid at position 356 as indicated by EU numbering is Cys, the amino acid at position 366 is Ser, the amino acid at position 368 is Ala, and the amino acid at position 407 is Val.

In another non-limiting embodiment of the present invention, two polypeptides constituting an Fc region, in which, of the amino acid sequence of one of the polypeptides, the amino acid at position 409 according to EU numbering is Asp, and of the amino acid sequence of the other of the polypeptides, the amino acid at position 399 according to EU numbering is Lys, may be suitably used as the Fc region. In the above embodiment, the amino acid at position 409 may be Glu instead of Asp, and the amino acid at position 399 may be Arg instead of Lys. Moreover, in addition to the amino acid Lys at position 399, Asp may suitably be added as amino acid at position 360 or Asp may suitably be added as amino acid at position 392.

In still another non-limiting embodiment of the present invention, two polypeptides constituting an Fc region, in which, of the amino acid sequence of one of the polypeptides, the amino acid at position 370 according to EU numbering is Glu, and of the amino acid sequence of the other of the polypeptides, the amino acid at position 357 according to EU numbering is Lys, may be suitably used as the Fc region.

In yet another non-limiting embodiment of the present invention, two polypeptides constituting an Fc region, in which, of the amino acid sequence of one of the polypeptides, the amino acid at position 439 according to EU numbering is Glu, and of the amino acid sequence of the other of the polypeptides, the amino acid at position 356 according to EU numbering is Lys, may be suitably used as the Fc region.

In still yet another non-limiting embodiment of the present invention, any of the embodiments indicated below, in which the above have been combined, may be suitably used as the Fc region:

(i) two polypeptides constituting an Fc region, in which, of the amino acid sequence of one of the polypeptides, the amino acid at position 409 according to EU numbering is Asp and the amino acid at position 370 is Glu, and of the amino acid sequence of the other of the polypeptides, the amino acid at position 399 according to EU numbering is Lys and the amino acid at position 357 is Lys (in this embodiment, the amino acid at position 370 according to EU numbering may be Asp instead of Glu, and the amino acid Asp at position 392 according to EU numbering may be used instead of the amino acid Glu at position 370 according to EU numbering);

(ii) two polypeptides constituting an Fc region, in which, of the amino acid sequence of one of the polypeptides, the amino acid at position 409 according to EU numbering is Asp and the amino acid at position 439 is Glu, and of the amino acid sequence of the other of the polypeptides, the amino acid at position 399 according to EU numbering is Lys and the amino acid at position 356 is Lys (in this embodiment, the amino acid Asp at position 360 according to EU numbering, the amino acid Asp at position 392 according to EU numbering, or the amino acid Asp at position 439 according to EU numbering may be used instead of the amino acid Glu at position 439 according to EU numbering);

(iii) two polypeptides constituting an Fc region, in which, of the amino acid sequence of one of the polypeptides, the amino acid at position 370 according to EU numbering is Glu and the amino acid at position 439 is Glu, and of the amino acid sequence of the other of the polypeptides, the amino acid at position 357 according to EU numbering is Lys and the amino acid at position 356 is Lys; and two polypeptides constituting an Fc region, in which, of the amino acid sequence of one of the polypeptides, the amino acid at position 409 according to EU numbering is Asp, the amino acid at position 370 is Glu, and the amino acid at position 439 is Glu, and of the amino acid sequence of the other of the polypeptides, the amino acid at position 399 according to EU numbering is Lys, the amino acid at position 357 is Lys, and the amino acid at position 356 is Lys (in this embodiment, the amino acid at position 370 according to EU numbering may not be substituted to Glu, and furthermore, when the amino acid at position 370 is not substituted to Glu, the amino acid at position 439 may be Asp instead of Glu, or the amino acid Asp at position 392 may be used instead of the amino acid Glu at position 439).

Further, in another non-limiting embodiment of the present invention, two polypeptides constituting an Fc region, in which, of the amino acid sequence of one of the polypeptides, the amino acid at position 356 according to EU numbering is Lys, and of the amino acid sequence of the other of the polypeptides, the amino acid at position 435 according to EU numbering is Arg and the amino acid at position 439 is Glu, may also be suitably used.

In still another non-limiting embodiment of the present invention, two polypeptides constituting an Fc region, in which, of the amino acid sequence of one of the polypeptides, the amino acid at position 356 according to EU numbering is Lys and the amino acid at position 357 is Lys, and of the amino acid sequence of the other of the polypeptides, the amino acid at position 370 according to EU numbering is Glu, the amino acid at position 435 is Arg, and the amino acid at position 439 is Glu, may also be suitably used.

Furthermore, in addition to the above-mentioned technique of associating heterologous heavy chains, the CrossMab technology which is known as a technology for associating heterologous light chains, in which a light chain forming a variable region that binds to a first epitope and a light chain forming a variable region that binds to a second epitope are respectively associated with a heavy chain forming a variable region that binds to the first epitope and a heavy chain forming a variable region that binds to the second epitope (Scaefer et al. (Proc. Natl. Acad. Sci. U.S.A. (2011) 108, 11187-11192)), may also be used to produce the antigen-binding molecules provided by the present invention.

Improvement of Pharmacokinetics

In the present invention, the "ability to eliminate antigens in plasma" refers to the ability to eliminate from the plasma antigens that are present in the plasma when the antigen-binding molecules are administered in vivo or when the antigen-binding molecules are secreted in vivo. Accordingly, in the present invention, "ability of antigen-binding molecules to eliminate antigens in plasma is increased" means that when the antigen-binding molecules are administered, the rate of antigen elimination from plasma is accelerated as compared to when an antigen-binding molecule comprising an antigen-binding domain whose antigen-binding activity does not vary depending on ion concentrations, an antigen-binding molecule comprising an FcRn-binding domain without FcRn-binding activity under an acidic pH range condition, or an antigen-binding molecule comprising an Fcγ receptor-binding domain without selective binding activity to an Fcγ receptor is administered. Whether or not the ability of an antigen-binding molecule to eliminate antigens in the plasma increased can be determined, for example, by administering soluble antigens and the antigen-binding molecule in vivo, and then measuring the plasma concentration of the soluble antigen after administration. When the concentration of the soluble antigens in the plasma is decreased after administration of the soluble antigens and the antigen-binding molecules comprising an antigen-binding domain whose antigen-binding activity varies depending on ion concentration conditions, the FcRn-binding domain having FcRn-binding activity under an acidic pH range condition, and an Fcγ receptor-binding domain having selective binding activity to an Fcγ receptor (a selective FcγR-binding domain), the ability of the antigen-binding molecules to eliminate antigens in the plasma is judged to be increased. The soluble antigen may be an antigen that is bound to an antigen-binding molecule or an antigen that is not bound to an antigen-binding molecule in the plasma, and its concentration can be determined as a "plasma concentration of the antigen bound to the antigen-binding molecule" or as a "plasma concentration of the antigen not bound to the antigen-binding molecule", respectively (the latter is synonymous with "free antigen concentration in plasma"). The "total antigen concentration in plasma" means the sum of concentrations of the antigen-binding molecule-bound antigen and the antigen not bound by an antigen-binding molecule, or the "free antigen concentration in plasma" which is the concentration of the antigen not bound by an antigen-binding molecule. Thus, the soluble antigen concentration can be determined as the "total antigen concentration in plasma". Various methods for measuring the "total antigen concentration in plasma" or the "free antigen concentration in plasma" are well known in the art as described hereinafter.

In the present invention, "enhancement of pharmacokinetics", "improvement of pharmacokinetics", and "superior pharmacokinetics" can be restated as "enhancement of plasma (blood) retention", "improvement of plasma (blood) retention", "superior plasma (blood) retention", and "prolonged plasma (blood) retention". These terms are synonymous.

In the present invention, "improvement of pharmacokinetics" means not only prolongation of the period until elimination from the plasma (for example, until the antigen-binding molecule is degraded intracellularly or the like and cannot return to the plasma) after administration of the antigen-binding molecule to humans, or non-human animals such as mice, rats, monkeys, rabbits, and dogs, but also prolongation of the plasma retention of the antigen-binding molecule in a form that allows antigen binding (for example, in an antigen-free form of the antigen-binding molecule) during the period of administration to elimination due to degradation. Human IgG having native Fc region can bind to FcRn from non-human animals. For example, mouse can be preferably used to be administered in order to confirm the property of the antigen-binding molecule of the invention since human IgG having native Fc region can bind to mouse FcRn stronger than to human FcRn (Int Immunol. (2001) 13(12): 1551-1559). As another example, mouse in which its native FcRn genes are disrupted and a transgene for human FcRn gene is harbored to be expressed (Methods Mol Biol. 2010; 602: 93-104) can also be preferably used to be administered in order to confirm the property of the antigen-binding molecule of the invention described hereinafter. Specifically, "improvement of pharmacokinetics" also includes prolongation of the period until elimination due to degradation of the antigen-binding molecule not bound to antigens (the antigen-free form of antigen-binding molecule). The antigen-binding molecule in plasma cannot bind to a new antigen if the antigen-binding molecule has already bound to an antigen. Thus, the longer the period that the antigen-binding molecule is not bound to an antigen, the longer the period that it can bind to a new antigen (the higher the chance of binding to another antigen). This enables reduction of the time period that an antigen is free of the antigen-binding molecule in vivo and prolongation of the period that an antigen is bound to the antigen-binding molecule. The plasma concentration of the antigen-free form of antigen-binding molecule can be increased and the period that the antigen is bound to the antigen-binding molecule can be prolonged by accelerating the antigen elimination from the plasma by administration of the antigen-binding molecule. Specifically, "improvement of the pharmacokinetics of antigen-binding molecule" in the present invention includes the improvement of a pharmacokinetic parameter of the antigen-free form of the antigen-binding molecule (any of prolongation of the half-life in plasma, prolongation of mean retention time in plasma, and impairment of plasma clearance), prolongation of the period that the antigen is bound to the antigen-binding molecule after administration of the antigen-binding molecule, and acceleration of antigen-binding molecule-mediated antigen elimination from the plasma. The improvement of pharmacokinetics of antigen-binding molecule can be assessed by determining any one of the parameters, half-life in plasma, mean plasma retention time, and plasma clearance for the antigen-binding molecule or the antigen-free form thereof ("Pharmacokinetics: Enshu-niyoru Rikai (Understanding through practice)" Nanzando). For example, the plasma concentration of the antigen-binding molecule or antigen-free form thereof is determined after administration of the antigen-binding molecule to mice, rats, monkeys, rabbits, dogs, or humans. Then, each parameter is determined. When the plasma half-life or mean plasma retention time is prolonged, the pharmacokinetics of the antigen-binding molecule can be judged to be improved. The parameters can be determined by methods known to those skilled in the art. The parameters can be appropriately assessed, for example, by noncompartmental analysis using the pharmacokinetics analysis software WinNonlin (Pharsight) according to the appended instruction manual. The plasma concentration of antigen-free antigen-binding molecule can be determined by methods known to those skilled in the art, for example, using the assay method described in Clin Pharmacol. 2008 April; 48 (4): 406-417.

In the present invention, "improvement of pharmacokinetics" also includes prolongation of the period that an antigen is bound to an antigen-binding molecule after administration of the antigen-binding molecule. Whether the period that an antigen is bound to the antigen-binding molecule after administration of the antigen-binding molecule is prolonged can be assessed by determining the plasma concentration of free antigen. The prolongation can be judged based on the determined plasma concentration of free antigen or the time period required for an increase in the ratio of free antigen concentration to the total antigen concentration.

The plasma concentration of free antigen not bound to the antigen-binding molecule or the ratio of free antigen concentration to the total concentration can be determined by methods known to those skilled in the art, for example, by the method used in Pharm Res. 2006 January; 23 (1): 95-103. Alternatively, when an antigen exhibits a particular function in vivo, whether the antigen is bound to an antigen-binding molecule that neutralizes the antigen function (antagonistic molecule) can be assessed by testing whether the antigen function is neutralized. Whether the antigen function is neutralized can be assessed by assaying an in vivo marker that reflects the antigen function. Whether the antigen is bound to an antigen-binding molecule that activates the antigen function (agonistic molecule) can be assessed by assaying an in vivo marker that reflects the antigen function.

Determination of the plasma concentration of free antigen and ratio of the amount of free antigen in plasma to the amount of total antigen in plasma, in vivo marker assay, and such measurements are not particularly limited; however, the assays are preferably carried out after a certain period of time has passed after administration of the antigen-binding molecule. In the present invention, the period after administration of the antigen-binding molecule is not particularly limited; those skilled in the art can determine the appropriate period depending on the properties and the like of the administered antigen-binding molecule. Such periods include, for example, one day after administration of the antigen-binding molecule, three days after administration of the antigen-binding molecule, seven days after administration of the antigen-binding molecule, 14 days after administration of the antigen-binding molecule, and 28 days after administration of the antigen-binding molecule. In the present invention, the concept "plasma antigen concentration" comprises both "total antigen concentration in plasma" which is the sum of antigen-binding molecule bound antigen and non-bound antigen concentration or "free antigen concentration in plasma" which is antigen-binding molecule non-bound antigen concentration.

The total antigen concentration in the plasma can be lowered by administration, as antigen-binding molecule, of the antigen-binding molecule of the present invention by 2-fold, 5-fold, 10-fold, 20-fold, 50-fold, 100-fold, 200-fold, 500-fold, 1,000-fold, or even higher as compared to administration of an antigen-binding molecule containing an antigen-binding domain whose antigen-binding activity is ion concentration-independent or an antigen-binding molecule containing an Fc region with an impaired FcγR-binding activity, or compared to when the antigen-binding domain molecule of the present invention is not administered.

Molar antigen/antigen-binding molecule ratio can be calculated as shown below:

value A: Molar antigen concentration at each time point value B: Molar antigen-binding molecule concentration at each time point value C: Molar antigen concentration per molar antigen-binding molecule concentration (molar antigen/antigen-binding molecule ratio) at each time point $$C=A/B.$$

Smaller value C indicates higher efficiency of antigen elimination per antigen-binding molecule whereas higher value C indicates lower efficiency of antigen elimination per antigen-binding molecule.

Molar antigen/antigen-binding molecule ratio can be calculated as described above.

A 2-fold, 5-fold, 10-fold, 20-fold, 50-fold, 100-fold, 200-fold, 500-fold, 1,000-fold or even greater reduction of molar antigen/antigen-binding molecule ratio can be achieved by administration of an antigen-binding molecule of the present invention as compared to when an antigen-binding molecule comprising an antigen-binding domain whose antigen-binding activity does not vary depending on ion concentrations, an antigen-binding molecule comprising an FcRn-binding domain without FcRn-binding activity under an acidic pH range condition, or an antigen-binding molecule comprising an Fcγ receptor-binding domain without selective binding activity to an Fcγ receptor is administered as the antigen-binding molecule.

In the present invention, an antigen-binding molecule comprising an antigen-binding domain whose antigen-binding activity does not vary depending on ion concentrations, an antigen-binding molecule comprising an FcRn-binding domain without FcRn-binding activity under an acidic pH range condition, or an antigen-binding molecule comprising an Fcγ receptor-binding domain without selective binding activity to an Fcγ receptor is used as a reference antigen-binding molecule to be compared with the antigen-binding molecules of the present invention.

When evaluating the effect of an FcRn-binding domain having FcRn-binding activity under an acidic pH range condition, reduction of total antigen concentration in plasma or molar antigen/antibody ratio can be assessed by either antigen and antibody co-injection model or steady-state antigen infusion model using human FcRn transgenic mouse line 32 or line 276 (Jackson Laboratories, Methods Mol. Biol. (2010) 602, 93-104), when the antigen-binding molecule does not cross-react with the mouse counterpart antigen. When an antigen-binding molecule cross-react with mouse counterpart, they can be assessed by simply injecting antigen-binding molecule to human FcRn transgenic mouse line 32 or line 276 (Jackson Laboratories). In co-injection model, mixture of antigen-binding molecule and antigen is administered to the mouse. In steady-state antigen infusion model, infusion pump containing antigen solution is implanted to the mouse to achieve constant plasma antigen concentration, and then antigen-binding molecule is injected to the mouse. Test antigen-binding molecule is administered at same dosage. Total antigen concentration in plasma, free antigen concentration in plasma and plasma antigen-binding molecule concentration is measured at appropriate time point using method known to those skilled in the art.

For assessing the effects of an Fcγ receptor-binding domain having selective binding activity to Fcγ receptors, when an antigen-binding molecule does not cross-react with a mouse counterpart antigen, total antigen concentration in plasma or decrease in antigen/antibody mole ratio can be assessed by either the antigen-antibody simultaneous injection model or the steady-state antigen injection model using the conventionally used C57BL/6J mice (Charles River Japan). When an antigen-binding molecule cross-reacts with the mouse counterpart, the antigen-binding molecule can simply be injected to conventionally used C57BL/6J mice (Charles River Japan) to carry out the assessment.

In the co-injection model, a mixture of the antigen-binding molecule and antigen is administered to mice. In the steady-state antigen infusion model, an infusion pump filled with an antigen solution is embedded into mice to achieve a constant plasma antigen concentration, and then the antigen-binding molecule is injected into the mice. Test antigen-binding molecules are administered at the same dose. The total antigen concentration in plasma, free antigen concentration in plasma, and antigen-binding molecule concentration in plasma are measured at appropriate time points using methods known to those skilled in the art.

Total or free antigen concentration in plasma and molar antigen/antigen-binding molecule ratio can be measured at 2, 4, 7, 14, 28, 56, or 84 days after administration to evaluate the long-term effect of the present invention. In other words, a long term plasma antigen concentration is determined by measuring total or free antigen concentration in plasma and molar antigen/antigen-binding molecule ratio at 2, 4, 7, 14, 28, 56, or 84 days after administration of an antigen-binding molecule in order to evaluate the property of the antigen-binding molecule of the present invention. Whether the reduction of plasma antigen concentration or molar antigen/antigen-binding molecule ratio is achieved by antigen-binding molecule described in the present invention can be determined by the evaluation of the reduction at any one or more of the time points described above.

Total or free antigen concentration in plasma and molar antigen/antigen-binding molecule ratio can be measured at 15 minutes, 1, 2, 4, 8, 12, or 24 hours after administration to evaluate the short-term effect of the present invention. In other words, a short term plasma antigen concentration is determined by measuring total or free antigen concentration in plasma and molar antigen/antigen-binding molecule ratio at 15 minutes, 1, 2, 4, 8, 12, or 24 hours after administration of an antigen-binding molecule in order to evaluate the property of the antigen-binding molecule of the present invention.

Route of administration of an antigen-binding molecule of the present invention can be selected from intradermal, intravenous, intravitreal, subcutaneous, intraperitoneal, parenteral and intramuscular injection.

In the present invention, improvement of pharmacokinetics of antigen-binding molecule in human is preferred. When the plasma retention in human is difficult to determine, it may be predicted based on the plasma retention in mice (for example, normal mice, human antigen-expressing transgenic mice, human FcRn-expressing transgenic mice) or monkeys (for example, cynomolgus monkeys).

"The improvement of the pharmacokinetics and prolonged plasma retention of an antigen-binding molecule" in the present invention means improvement of any pharmacokinetic parameter (any of prolongation of the half-life in plasma, prolongation of mean retention time in plasma, reduction of plasma clearance, and bioavailability) after in vivo administration of the antigen-binding molecule, or an increase in the concentration of the antigen-binding molecule in the plasma in an appropriate time after administration. It may be determined by measuring any parameter such as half-life in plasma, mean retention time in plasma, plasma clearance, and bioavailability of the antigen-binding molecule (Pharmacokinetics: Enshu-niyoru Rikai (Understanding through practice), (Nanzando)). For example, when an antigen-binding molecule is administered to mice (normal mice and human FcRn transgenic mice), rats, monkeys, rabbits, dogs, humans, and so on, and the concentration of the antigen-binding molecule in the plasma is determined and each of the parameters is calculated, the pharmacokinetics of the antigen-binding molecule can be judged to be improved when the plasma half-life or mean retention time in the plasma is prolonged. These parameters can be determined by methods known to those skilled in the art. For example, the parameters can be appropriately assessed by non-compartmental analysis using pharmacokinetics analysis software WinNonlin (Pharsight) according to the attached instruction manual.

Four types of FcγRs, FcγRI, FcγRIIb, FcγRIII, and FcγRIV, have been identified in mice. In humans as well, as corresponding FcγRs, FcγRI, FcγRIIa, FcγRIIb, FcγRIIIa, FcγRIIIa, and FcγRIIIb have been identified. FcγRIIb which is considered to be the only inhibitory type among these FcγRs is conserved in both humans and mice. The other FcγRs, except for FcγRIIIb, transmit activation signals via the immunoreceptor tyrosine-based activating motif (ITAM), whereas FcγRIIb transmits inhibitory signals via the immunoreceptor tyrosine-based inhibitory motif (ITIM) present inside the cells (Nat. Rev. Immunol. (2008) 8, 34-47).

FcγRIIb1 and FcγRIIb2 have been reported as splicing variants of FcγRIIb. In both humans and mice, FcγRIIb 1 has a longer intracellular domain than FcγRIIb2. FcγRIIb1 has been confirmed to be expressed in B cells, and FcγRIIb2 has been confirmed to be expressed in macrophages, mast cells, dendritic cells, basophils, neutrophils, and eosinophils (J. Clin. Immunol. (2005) 25 (1), 1-18).

So far, in humans, dysfunction and decreased expression of FcγRIIb have been reported to be correlated with onset of autoimmune diseases. For example, it has been reported that in some SLE patients, binding of transcriptional activators is attenuated due to polymorphism in an expression promoter region of FcγRIIb, which results in the decreased FcγRIIb expression (Hum. Genet. (2005) 117, 220-227; J. Immunol. (2004) 172, 7192-7199; and J. Immunol. (2004) 172, 7186-7191). Furthermore, among SLE patients, two types of allotypes have been reported, where the amino acid at position 233 is Ile or Thr in FcγRIIb. This position exists in the transmembrane region of FcγRIIb, and it is reported that FcγRIIb is less likely to exist in the lipid raft when the amino acid at position 233 is Thr compared to when this amino acid is Ile, and as a result, signal transduction function of FcγRIIb decreases (Nat. Med. (2005) 11, 1056-1058; Hum. Mol. Genet., (2005) 14, 2881-2892). In mice as well, knockout mice produced by disrupting the FcγRIIb gene in C57BL/6 mice has been reported to present SLE-like symptoms such as autoantibody production and glomerulonephritis (Immunity 13 (2000) 277-285; J. Exp. Med. (2002) 195, 1167-1174). Furthermore, so far, reduced expression level of FcγRIIb and such have been reported in mice considered to be models with natural onset of SLE (Immunogenetics (2000) 51, 429-435; Int. Immunol. (1999) 11, 1685-1691; Curr. Biol. (2000) 10, 227-230; J. Immunol. (2002) 169, 4340-4346). From these reports, FcγRIIb is considered to regulate humoral immunity in mice as in humans.

When an antibody carrying an Fc of the present invention eliminates antigens via FcγRIIb, the endocytosis function of FcγRIIb is considered to be making the most important contribution among the functions of FcγRIIb. As described above, FcγRIIb1 and FcγRIIb2 exist as splicing variants of FcγRIIb, but it is reported that the latter is mainly involved in the endocytosis of an immune complex of an antibody and antigen (J. Immunol. (1994), 152 574-585; Science (1992) 256, 1808-1812; Cell (1989) 58, 317-327). So far, mouse FcγRIIb2 has been reported to be incorporated into a clathrin-coated pit and endocytosed (Cell (1989) 58, 317-327). Furthermore, it has been reported that a dileucine motif is necessary for FcγRIIb2-mediated endocytosis, and the dileucine motif is conserved in both humans and mice (EMBO J. (1994) 13 (13), 2963-2969). From these, FcγRIIb2 may have an endocytotic ability in humans as in mice.

On the other hand, unlike FcγRIIb2, it has been reported that FcγRIIb1 does not cause endocytosis. FcγRIIb1 has an inserted sequence in its intracellular domain that is not found in FcγRIIb2. It is considered that this sequence inhibits the uptake of FcγRIIb1 into a clathrin-coated pit, and as a result endocytosis is inhibited (J. Cell. Biol. (1992) 116, 875-888; J. Cell. Biol. (1989) 109, 3291-3302). In humans as well, FcγRIIb1 has an insertion sequence at a site similar to that of FcγRIIb2 as in mice; therefore, difference in the endocytotic ability between FcγRIIb1 and FcγRIIb2 is presumed to be caused by a similar mechanism. Furthermore, in both humans and mice, approximately 40% of immune complexes on the cell surface is reported to be taken up into the cell in 20 minutes (Mol. Immunol. (2011) 49, 329-337; Science (1992) 256, 1808-1812). Therefore, in humans as well, FcγRIIb2 is presumed to uptake immune complexes into cells at rates similar to those in mice.

Since FcγRIIb is the only one that has ITIM inside the cell in both humans and mice among the FcγR family and the distribution of expressing cells are the same, it is presumed that its function in immune control is similar. Furthermore, considering the fact that immune complexes are taken up into cells at similar rates in humans and mice, antigen elimination effects of antibodies mediated by FcγRIIb in humans may be predictable using mice. Antigen-binding molecules mF44 and mF46 have properties of binding to soluble antigens in a pH-dependent manner, and have enhanced affinity to mouse FcγRIIb and FcγRIII compared to mIgG1 which is an antigen-binding molecule having the property of binding to a soluble antigen in a pH-dependent manner. Indeed, it is shown in Example 5 that antigen clearance increased when mF44 or mF46 was administered to normal mice compared to when mIgG1 was administered.

Furthermore, in the later-described Example 6, a similar experiment was carried out using Fc receptor γ chain-deficient mice. It has been reported that FcγRs other than FcγRIIb are expressed only in the co-presence of a gamma chain in mice. Thus, only FcγRIIb is expressed in the Fc receptor γ chain-deficient mice. Administration of mF44 or mF46, which are antigen-binding molecules having the property of binding to soluble antigens in a pH-dependent manner, to Fc receptor γ chain-deficient mice enables assessment of antigen elimination-acceleration effects when FcγRIIb-binding is selectively enhanced. From the results of Example 6, when mF44 or mF46 (which are antigen-binding molecules having the property of binding to soluble antigens in a pH-dependent manner) was administered to Fc receptor γ chain-deficient mice, antigen clearance was shown to increase compared to when mIgG1 (which is an antigen-binding molecule having the property of binding to soluble antigens in a pH-dependent manner) was administered to the mice. Furthermore, the results of Example 6 shows that when administered to Fc receptor γ chain-deficient mice, mF44 or mF46 cause similar degrees of antigen elimination as when administered to normal mice.

In Example 6, a similar experiment was performed using FcγRIII-deficient mice. Since mIgG1, mF44, and mF46 bind only to FcγRIIb and FcγRIII among the mFcγRs, administration of the antibodies to FcγRIII-deficient mice enables assessment of antigen elimination-accelerating effects when FcγRIIb-binding is selectively enhanced. The results of Example 6 indicate that when mF44 or mF46 was administered to FcγRIII-deficient mice, antigen clearance was increased compared to when mIgG1 was administered to the mice antigen clearance. Furthermore, the results of Example 6 showed that when administered to FcγRIII-deficient mice, mF44 and mF46 cause similar degrees of antigen elimination as when administered to Fc receptor γ chain-deficient mice and when administered to normal mice.

These results revealed that antigen elimination can be accelerated by enhancing selective binding to FcγRIIb alone without enhancing binding to active FcγRs.

In addition to the reported documents discussed so far, based on the above-mentioned assessment results using mice, it is considered that uptake of immune complexes into cells via FcγRIIb takes place in vivo in humans as in mice, and as a result, antibodies that have Fc with selectively enhanced binding to human FcγRIIb can accelerate elimination of its antigens. Furthermore, as discussed above, since uptake of immune complexes into cells via FcγRIIb is considered to take place at similar rates in mice and humans, effects of accelerating antigen elimination comparable to those of antibodies having Fc with enhanced affinity to mouse FcγRIIb may be achieved in vivo in humans by using Fc in which affinity to human FcγRIIb is enhanced to a similar extent.

As described in WO 2009/125825, Fv4-IgG1 is an antibody that results from conferring to a humanized anti-IL-6 receptor antibody H54/L28-IgG1 the activity to bind to the antigen in a pH-dependent manner, i.e., altering the variable region to confer the property to bind to an antigen at pH 7.4 and dissociate from the antigen at pH 5.8. WO 2009/125825 showed that the elimination of soluble human IL-6 receptor is greatly accelerated in mice co-administered with Fv4 IgG1 and soluble human IL-6 receptor as the antigen as compared to mice co-administered with H54/L28-IgG1 and the antigen. Herein, heavy-chain H54-IgG1 and light-chain L28-CK included in H54/L28-IgG1 are shown in SEQ ID NO: 36 and SEQ ID NO: 37, respectively; and heavy chain VH3-IgG1 and light-chain VL3-CK included in Fv4-IgG1 are shown in SEQ ID NO: 38 and SEQ ID NO: 39, respectively.

Soluble human IL-6 receptor bound to an antibody H54/L28-IgG1, which binds to soluble human IL-6 receptor, is recycled to the plasma along with the antibody via FcRn. Meanwhile, antibody Fv4-IgG1 which binds to soluble human IL-6 receptor in a pH-dependent manner dissociates from the soluble human IL-6 receptor that has been bound to the antibody under an acidic condition in the endosome. Since the dissociated soluble human IL-6 receptor is degraded in the lysosome, elimination of the soluble human IL-6 receptor can be greatly accelerated, and the antibody Fv4-IgG1 which binds to the soluble human IL-6 receptor in a pH-dependent manner is recycled to the plasma after binding to FcRn in the endosome. Since the recycled antibody can bind to a soluble human IL-6 receptor again, binding to the antigen (soluble human IL-6 receptor) and recycling to the plasma via FcRn are repeated. As a result, a single antibody molecule can repeatedly bind to the soluble human IL-6 receptor multiple times (FIG. 1).

On the other hand, as disclosed in the present invention, it was found that plasma concentration of the soluble antigen can be reduced greatly by administration of an antigen-binding molecule with enhanced FcγR-binding activity of the Fcγ receptor-binding domain included in the antigen-binding molecule which comprises an antigen-binding domain in which antigen-binding activity changes depending on the ion concentration condition such as pH, an FcRn-binding domain having FcRn-binding activity under an acidic pH range condition, and an Fcγ receptor-binding domain.

While not being restricted to a particular theory, the unexpected decrease in soluble antigen concentration in plasma observed by administration of an antigen-binding molecule with enhanced binding to FcγRs, which comprises an antigen-binding domain in which antigen-binding activity changes depending on the ion-concentration condition such as pH and an FcRn-binding domain having FcRn-binding activity under an acidic pH range condition can be explained as follows.

As described above, an antigen-binding molecule such as Fv4-IgG1 comprising an antigen-binding domain in which antigen-binding activity changes depending on the ion-concentration condition may be able to bind repeatedly to the antigen multiple times, but the effect of dissociating the soluble antigen in the endosome to accelerate the antigen elimination from plasma may be dependent on the rate of uptake of the complex of the antigen and antigen-binding molecule into the endosome. The antigen-binding molecules with enhanced binding activities to various FcγRs, which comprise an antigen-binding domain in which antigen-binding activity changes depending on the ion-concentration condition, are actively taken up into cells by binding to various FcγRs expressed on the cell membrane, and can circulate in the plasma again by recycling via binding between FcRn and the FcRn-binding domain in the molecule having binding activity to FcRn under an acidic pH range condition. More specifically, since the aforementioned antigen-binding molecules that formed complexes with soluble antigens in plasma are taken up actively into cells via FcγRs expressed on the cell membrane, the effect of accelerating elimination of soluble antigens in plasma may be more pronounced than that of antigen-binding molecules whose binding activities to various FcγRs are not enhanced.

FcγR-binding activities of antibodies that bind to membrane antigens have an important role in cytotoxic activity of the antibodies. Therefore, when cytotoxic activity is necessary for an antibody to be used as a pharmaceutical, a human IgG1 isotype which has high FcγR-binding activity is used, and the technique of enhancing the FcγR-binding activities of the antibody to enhance the cytotoxic activity of the antibody is widely utilized. On the other hand, the role of FcγR-binding activities of antibodies that bind to soluble antigens and are used as pharmaceuticals had not been known, and differences in physiological effects on organisms administered with human IgG1 with high FcγR-binding activities and human IgG2 and human IgG4 with low FcγR-binding activities, due to their differences in FcγR-binding activities, had not been fully examined so far. As described later in the Examples, it was actually confirmed that in the plasma of individuals administered with antibodies whose FcγR-binding activities have been lost, changes in soluble-antigen concentration were not affected. On the other hand, in the present invention, the concentration of soluble antigens in the plasma was found to be greatly reduced in individuals administered with antigen-binding molecules with enhanced FcγR-binding activities and comprising an antigen-binding domain whose binding activity to soluble antigens changes depending on the ion concentration condition. More specifically, by combining an FcRn-binding domain having an FcRn-binding activity under an acidic pH range condition and an antigen-binding domain whose binding to soluble antigens changes depending on the ion concentration condition, which are domains included in antigen-binding molecules targeting soluble antigens, an advantage of enhancing binding to FcγR was found for the first time. Ex Vivo Method of Eliminating the Antigens from Plasma An example of a non-limiting embodiment of the use of an antigen-binding molecule for the method of eliminating the antigens from plasma, which is provided by the present invention, includes use of the antigen-binding molecule for a so-called ex vivo method of eliminating the antigens from plasma, which comprises contacting the antigen-binding molecule of the present invention with plasma isolated from subjects to allow forming immune complexes, and allowing the immune complexes to contact cells expressing Fcγ receptors and FcRn. The speed of antigen elimination from the plasma can also be promoted by substituting/combining a method for administering antigen-binding molecules in vivo with a so-called ex vivo method, in which the plasma containing antigen-binding molecules and antigens that bind to the antigen-binding molecules is temporarily taken out of the body and then contacted with cells expressing FcRn and Fcγ receptors for a certain period of time, and the plasma containing extracellularly recycled (or re-secreted or re-circulated) antigen-binding molecules that are not bound to antigen is returned to the body.

Furthermore, an example of a non-limiting embodiment of the use of an antigen-binding molecule in the method provided by the present invention for eliminating antigens from plasma includes use of the antigen-binding molecule in a so-called ex vivo method for eliminating antigens from the plasma, which includes contacting an immune complex present in the plasma isolated from a subject to whom the antigen-binding molecules of the present invention are administered with cells expressing FcRn and Fcγ receptors.

Whether or not the antigen is eliminated from plasma can be confirmed, for example, by assessing whether or not the rate of antigen elimination in plasma is accelerated as compared to when an antigen-binding molecule comprising an antigen-binding domain whose antigen-binding activity does not vary depending on ion concentrations, an antigen-binding molecule comprising an FcRn-binding domain without FcRn-binding activity under an acidic pH range condition, or an antigen-binding molecule comprising an Fcγ receptor-binding domain without selective binding activity to an Fcγ receptor is used as a control instead of an antigen-binding molecule of the present invention.
Methods for Producing Antigen-Binding Molecules The present invention provides a method for producing an antigen-binding molecule having the function of eliminating antigens in plasma, wherein the method comprises the steps of (a) to (e) below:

(a) obtaining an antigen-binding domain whose antigen-binding activity varies depending on ion concentration conditions;

(b) obtaining a gene encoding the antigen-binding domain selected in step (a);

(c) operably linking the gene obtained in step (b) with a gene encoding an FcRn-binding domain having FcRn-binding activity under an acidic pH range condition and an Fcγ receptor-binding domain having selective binding activity to an Fcγ receptor;

(d) culturing host cells containing the gene operably linked in step (c); and (e) isolating an antigen-binding molecule from the culture solution obtained in step (d).

In a non-limiting embodiment of the present invention, after isolating a polynucleotide encoding an antigen-binding domain whose binding activity changes depending on the condition selected as described above, the polynucleotide is inserted into an appropriate expression vector. For example, when the antigen-binding domain is an antibody variable region, once a cDNA encoding the variable region is obtained, the cDNA is digested with restriction enzymes that recognize the restriction sites inserted at the two ends of the cDNA. Preferably, the restriction enzymes recognize and digest a nucleotide sequence that appears at a low frequency in the nucleotide sequence composing the gene of the antigen-binding molecule. Furthermore, restriction enzymes that provide cohesive ends are preferably inserted to insert a single copy of a digested fragment into the vector in the correct orientation. The cDNA encoding a variable region of an antigen-binding molecule digested as described above is inserted into an appropriate expression vector to obtain an expression vector for the antigen-binding molecule of the present invention.

The polynucleotide encoding an antigen-binding domain obtained as described above is operably linked to the gene encoding an FcRn-binding domain having FcRn-binding activity under an acidic pH range condition and an Fcγ receptor-binding domain having selective binding activity to an Fcγ receptor, which are described in the sections "FcRn-binding domain having FcRn-binding activity under an acidic pH range condition" and "Fcγ receptor-binding domain having selective binding activity to an Fcγ receptor", respectively. When linking, the genes can be directly linked in-frame, or the polynucleotides encoding each domain may be linked in-frame via linkers. In addition to each of the above-mentioned domains, it may be operably linked with a gene encoding the FcγR-binding domain described in the above-mentioned section "FcγR-binding domain".

When an antibody is used as the antigen-binding molecule of the present invention, a polynucleotide encoding an antibody Fc region may be used appropriately as the above-mentioned "FcRn-binding domain having FcRn-binding activity under an acidic pH range condition and Fcγ receptor-binding domain having selective binding activity to an Fcγ receptor". Fc regions whose "FcRn-binding activity under an acidic pH range condition" and "selective binding activity to an Fcγ receptor" are appropriately modified through modification of the polynucleotides may also be used. Examples of non-limiting embodiments of such modifications are shown in the above-mentioned sections "FcRn-binding domain having FcRn-binding activity under an acidic pH range condition" and "Fcγ receptor-binding domain having selective binding activity to an Fcγ receptor", respectively.

To produce an antigen-binding molecule of interest, a polynucleotide encoding the antigen-binding molecule is inserted in a manner operably linked to a regulatory sequence into an expression vector. Regulatory sequences include, for example, enhancers and promoters. Furthermore, an appropriate signal sequence may be linked to the amino terminus so that the expressed antigen-binding molecule is secreted to the outside of the cells. As signal sequence, for example, a peptide having the amino acid sequence MGWSCIILFLVATATGVHS (SEQ ID NO: 4) is used; however, it is also possible to link other appropriate signal sequences. The expressed polypeptide is cleaved at the carboxyl terminus of the above-described sequence, and the cleaved polypeptide is secreted as a mature polypeptide to the outside of cells. Then, appropriate host cells are transformed with this expression vector so that recombinant cells expressing the polynucleotide encoding the antigen-binding molecule of interest can be obtained. The antigen-binding molecules of the present invention can be produced from the recombinant cells by following the methods described above in the section on antibodies.

For a nucleic acid, "operably linked" means that the nucleic acid has a functional relationship with another nucleic acid sequence. For example, a DNA encoding a presequence or a secretory leader is operably linked to a DNA encoding a certain polypeptide if it is to be expressed as a precursor protein involved in the secretion of the polypeptide. A promoter or enhancer is operably linked to a coding sequence if it affects the transcription of the coding sequence. A ribosome binding site is operably linked to a coding sequence if it is in a position that facilitates translation. Generally, "operably linked" means that the linked DNA sequences are contiguous, and in the case of a secretory leader, it means that the linked DNA sequences are contiguous and in a reading frame. However, enhancers do not have to be contiguous. Linking is accomplished by ligation at suitable restriction sites. If such sites do not exist, synthetic oligonucleotide adaptors or linkers are used in accordance with conventional practice. Furthermore, linked nucleic acids may be produced by the above-mentioned overlap extension PCR technique.

In a non-limiting embodiment of the present invention, after isolating a polynucleotide encoding the above-described antigen-binding molecule whose antigen-binding activity varies depending on a selected condition, a variant of the polynucleotide is inserted into an appropriate expression vector. Such variants preferably include those prepared via humanization based on the polynucleotide sequence encoding an antigen-binding molecule of the present invention obtained by screening as a randomized variable region library a synthetic library or an immune library constructed originating from nonhuman animals. The same methods as described above for producing above-described humanized antibodies can be used as a method for producing humanized antigen-binding molecule variants.

In another embodiment, such variants preferably include those obtained by introducing an alteration that increases the antigen affinity (affinity maturation) of an antigen-binding molecule of the present invention into an isolated polynucleotide sequence for the molecule obtained by screening using a synthetic library or a naive library as a randomized variable region library. Such variants can be obtained by various known procedures for affinity maturation, including CDR mutagenesis (Yang et al. (J. Mol. Biol. (1995) 254, 392-403)), chain shuffling (Marks et al. (Bio/Technology (1992) 10, 779-783)), use of E. coli mutant strains (Low et al. (J. Mol. Biol. (1996) 250, 359-368)), DNA shuffling (Patten et al. (Curr. Opin. Biotechnol. (1997) 8, 724-733)), phage display (Thompson et al. (J. Mol. Biol. (1996) 256, 77-88)), and sexual PCR (Clameri et al. (Nature (1998) 391, 288-291)).

In an embodiment of variants of the present invention, polynucleotides encoding antigen-binding molecules which have a heavy chain where a polynucleotide encoding an Fc region modified to have an amino acid mutation as described above is linked in frame to a polynucleotide encoding the above-described antigen-binding domain whose binding activity varies depending on a selected condition.

The present invention provides methods for producing antigen-binding molecules, comprising collecting the antigen-binding molecules from culture media of cells introduced with vectors in which a polynucleotide encoding an Fc region is operably linked in frame to a polynucleotide encoding an antigen-binding domain whose binding activity varies depending on ion concentration condition. Furthermore, the present invention also provides methods for producing antigen-binding molecules, comprising collecting the antigen-binding molecules from culture media of cells introduced with vectors constructed by operably linking a polynucleotide encoding an antigen-binding domain whose binding activity varies depending on ion concentration condition to a polynucleotide encoding an Fc region which is in advance operably linked to a vector.

In the "Methods for producing antigen-binding molecules" of the present invention, known methods may be employed as methods for assessing antigen elimination from plasma by the antigen-binding molecules. An antigen-binding molecule of the present invention is administered to each group of non-human animals such as mice at an appropriate age in month. As described later in the section "Pharmaceutical composition", antigen-binding molecule may be systemically or locally administered by intravenous injection, intramuscular injection, intraperitoneal injection, subcutaneous injection, intracranial injection, or such, as compositions in the dosage form for injections, transnasal administration, transpulmonary administration, or transdermal administration.

Spectroscopic methods such as nuclear magnetic resonance (NMR) or mass spectrometry (MS) analyses including SELDI(-TOF), MALDI(-TOF), 1D gel-based analysis, 2D gel-based analysis, liquid chromatography (for example, high-pressure liquid chromatography (HPLC) or low-pressure liquid chromatography (LPLC)), thin layer chromatography, and LC-MS-based techniques may be used to measure the concentrations. Examples of appropriate LCMS techniques include ICAT (registered trademark) (Applied Biosystems) and iTRAQ (registered trademark) (Applied Biosystems). A method for detecting antigen fragments that have been produced by further digestion of a targeted antigen by an appropriate enzyme may also be employed when appropriate. Furthermore, the antigen concentration may be measured by a direct or indirect detection method. More specifically, the antigen may be detected directly or indirectly via interaction with a ligand or ligands such as enzymes, binding, receptors or transport proteins, antibodies, peptides, aptamers or oligonucleotides, or any synthetic chemical receptors or compounds that can bind specifically to the antigen. The ligand can be modified with a detectable label such as a luminescent label, fluorescent label, or radioactive label, and/or an affinity tag. An immunological method may be given as such an example.

A preferred measurement method may be, for example, an immunological method that uses an antibody that binds to an epitope present in the antigen. Examples of such an immunological method include enzyme immunoassay (ELISA, EIA), fluoroimmunoassay (FIA), radioimmunoassay (RIA), luminescence immunoassay (LIA), enzyme antibody technique, fluorescent antibody technique, immunochromatography method, immunoturbidimetry, latex turbidimetry, and latex agglutination measurement method. Furthermore, measurements in these immunological methods may be carried out manually by hand or using a device such as an analyzer. Immunological method in the present invention may be carried out according to a known method such as the sandwich method. For example, a first antibody immobilized onto a carrier is allowed to react simultaneously or sequentially with a biological sample and a second antibody modified by a labeling substance. The above-mentioned reaction leads to formation of a complex comprising the first antibody immobilized onto a carrier, the antigen, and a second antibody modified by a labeling substance, and quantification of the labeling substance linked to the second antibody included in this complex enables measurement of the amount (concentration) of the antigen included in the biological sample.

For example, in the case of enzyme immunoassay, a microplate onto which a first antibody is immobilized, serially diluted biological samples, a secondary antibody modified by an enzyme such as HRP, washing buffer, and a solution containing a substrate to which an enzyme such as HRP reacts are preferably used. In a non-limiting embodiment of the measurement, a substrate is allowed to react under an optimal condition with the enzyme which modifies the secondary antibody, and the amount of the enzyme reaction product can be determined by an optical method. In the case of fluoroimmunoassay, an optical waveguide onto which a first antibody is immobilized, serially diluted biological samples, a secondary antibody modified by a fluorescent substance, and washing buffer are preferably used. In a non-limiting embodiment of the measurement, the intensity of the fluorescence emitted by the fluorescent substance through irradiation of excitation light onto the fluorescent substance modifying the secondary antibody may be measured.

Furthermore, in the case of radioimmunoassay, the amount of radiation emitted by the radioactive substance is measured. In the case of luminescence immunoassay, the amount of luminescence emitted by the luminescent reaction system is measured. Furthermore, in the case of immunoturbidimetry, latex turbidimetry, latex agglutination measurement method, and such, transmitted light or scattered light is measured by the end-point method or the rate method. When immunochromatography measurements are made by visual observation, the color of the labeled substance that appears on the test line is determined by visual observation. Instead of such measurement by visual observation, an instrument such as an analyzer may be used when appropriate.

Pharmaceutical Composition

The present invention relates to pharmaceutical compositions comprising antigen-binding molecules of the present invention, antigen-binding molecules produced by alteration methods of the present invention, or antigen-binding molecules produced by production methods of the present invention. Antigen-binding molecules of the present invention or antigen-binding molecules produced by production methods of the present invention are useful as pharmaceutical compositions since they, when administered, have the strong effect to reduce the plasma antigen concentration as compared to typical antigen-binding molecules, and exhibit the improved in vivo immune response, pharmacokinetics, and others in animals administered with the molecules. The pharmaceutical compositions of the present invention may comprise pharmaceutically acceptable carriers.

In the present invention, pharmaceutical compositions generally refer to agents for treating or preventing, or testing/diagnosing diseases.

The pharmaceutical compositions of the present invention can be formulated by methods known to those skilled in the art. For example, they can be used parenterally, in the form of injections of sterile solutions or suspensions including water or other pharmaceutically acceptable liquid. For example, such compositions can be formulated by mixing in the form of unit dose required in the generally approved medicine manufacturing practice, by appropriately combining with pharmacologically acceptable carriers or media, specifically with sterile water, physiological saline, vegetable oil, emulsifier, suspension, surfactant, stabilizer, flavoring agent, excipient, vehicle, preservative, binder, or such. In such formulations, the amount of active ingredient is adjusted to obtain an appropriate amount in a pre-determined range.

Sterile compositions for injection can be formulated using vehicles such as distilled water for injection, according to standard formulation practice. Aqueous solutions for injection include, for example, physiological saline and isotonic solutions containing dextrose or other adjuvants (for example, D-sorbitol, D-mannose, D-mannitol, and sodium chloride). It is also possible to use in combination appropriate solubilizers, for example, alcohols (ethanol and such), polyalcohols (propylene glycol, polyethylene glycol, and such), non-ionic surfactants (polysorbate 80™, HCO-50, and such).

Oils include sesame oil and soybean oils. Benzyl benzoate and/or benzyl alcohol can be used in combination as solubilizers. It is also possible to combine buffers (for example, phosphate buffer and sodium acetate buffer), soothing agents (for example, procaine hydrochloride), stabilizers (for example, benzyl alcohol and phenol), and/or antioxidants. Appropriate ampules are filled with the prepared injections.

The pharmaceutical compositions of the present invention are preferably administered parenterally. For example, the compositions in the dosage form for injections, transnasal administration, transpulmonary administration, or transdermal administration are administered. For example, they can be administered systemically or locally by intravenous injection, intramuscular injection, intraperitoneal injection, subcutaneous injection, or such.

Administration methods can be appropriately selected in consideration of the patient's age and symptoms. The dose of a pharmaceutical composition containing an antigen-binding molecule can be, for example, from 0.0001 mg to 1000 mg/kg for each administration. Alternatively, the dose can be, for example, from 0.001 to 100000 mg per patient. However, the present invention is not limited by the numeric values described above. The doses and administration methods vary depending on the patient's weight, age, symptoms, and such. Those skilled in the art can set appropriate doses and administration methods in consideration of the factors described above.

Furthermore, the present invention provides kits for use in the methods of the present invention, which comprise at least an antigen-binding molecule of the present invention. In addition to the above, pharmaceutically acceptable carriers, media, instruction manuals describing the using method, and such may be packaged into the kits.

Furthermore, the present invention relates to pharmaceutical agents for eliminating, from the plasma, complexes containing two or more antigenic binding units and two or more antigen-binding molecules present in the plasma, which contain as an active ingredient the antigen-binding molecules of the present invention or the antigen-binding molecules produced by the production methods of the present invention.

The present invention relates to methods for treating a disease, which includes administering to subjects (patients, human subjects, etc.) the antigen-binding molecules of the present invention or the antigen-binding molecules produced by the production methods of the present invention. A non-limiting example of the disease includes cancer and inflammatory diseases.

The present invention also relates to use of the antigen-binding molecules of the present invention or the antigen-binding molecules produced by the production methods of the present invention in the manufacture of a pharmaceutical agent for eliminating from the plasma complexes containing two or more antigenic binding units and two or more antigen-binding molecules present in the plasma.

The present invention further relates to use of the antigen-binding molecules of the present invention or the antigen-binding molecules produced by the production methods of the present invention for eliminating, from the plasma, complexes containing two or more antigenic binding units and two or more antigen-binding molecules present in the plasma.

In addition, the present invention relates to antigen-binding molecules of the present invention and antigen-binding molecules produced by the production methods of present invention for use in the methods of the present invention.

Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

All prior art documents cited in the specification are incorporated herein by reference.

Herein below, the present invention will be specifically described with reference to the Examples, but it is not to be construed as being limited thereto.

EXAMPLES

[Example 1] Preparation of Antigen-Binding Molecules Whose Mouse FcγR-Binding Activity Under a Neutral pH Range Condition is Higher Than the Binding Activity of Native Human IgG Fc Region (1-1) pH-Dependent Human IL-6 Receptor-Binding Antibodies H54/L28-IgG1 which comprises H54-IgG1 (SEQ ID NO: 36) and L28-CK (SEQ ID NO: 37) described in WO2009/125825 is a humanized anti-IL-6 receptor antibody. Meanwhile, Fv4-IgG1 which comprises VH3-IgG1 (SEQ ID NO: 38) and VL3-CK (SEQ ID NO: 39) is a humanized anti-IL-6 receptor antibody resulting from conferring, to H54/L28-IgG1, the property of binding to soluble human IL-6 receptor in a pH-dependent manner (which binds at pH 7.4 and dissociates at pH 5.8). The in vivo mouse test described in WO2009/125825 demonstrated that, in the group administered with a mixture of Fv4-IgG1 and soluble human IL-6 receptor as the antigen, the elimination of soluble human IL-6 receptor from plasma was significantly accelerated as compared to the group administered with a mixture of H54/L28-IgG1 and soluble human IL-6 receptor as the antigen.

The soluble human IL-6 receptor bound to H54/L28-IgG1, which is an antibody that binds to a soluble human IL-6 receptor, is, together with the antibody, recycled to plasma by FcRn. Meanwhile, Fv4-IgG1, which is an antibody that binds to a soluble human IL-6 receptor in a pH dependent manner, dissociates soluble human IL-6 receptor under the acidic condition in the endosome. The dissociated soluble human IL-6 receptor is degraded in the lysosomes, thus this enables considerable acceleration of the elimination of soluble human IL-6 receptor. Furthermore, after binding to FcRn in the endosome, Fv4-IgG1, which is an antibody that binds to a soluble human IL-6 receptor in a pH dependent manner, is recycled to the plasma. Since the recycled antibody can bind to soluble human IL-6 receptor again, the antibody repeatedly binds to the antigen (soluble human IL-6 receptor) and is recycled by FcRn to the plasma. It is thought that, as a result, a single antibody molecule can bind repeatedly several times to soluble human IL-6 receptor (FIG. 1).

(1-2) Preparation of an Anti-Human IL-6 Receptor Antibody with Enhanced Mouse FcγR Binding and Anti-Human IL-6 Receptor Antibody Without Mouse FcγR Binding VH3-IgG1-F1022 (SEQ ID NO: 40), an antigen-binding molecule with enhanced mouse FcγR binding, was prepared by substituting Asp for Lys at position 326 (EU numbering) and Tyr for Leu at position 328 (EU numbering) in VH3-IgG1. Fv4-IgG1-F1022 containing VH3-IgG1-F1022 as the heavy chain and VL3-CK as the light chain was produced using the method described in Reference Example 1.

Meanwhile, VH3-IgG1-F760 (SEQ ID NO: 41), an antigen-binding molecule without mouse FcγR binding, was prepared by substituting Arg for Leu at position 235 and Lys for Ser at position 239 (EU numbering) in VH3-IgG1. Fv4-IgG1-F760 containing VH3-IgG1-F760 as the heavy chain and VL3-CK as the light chain was produced using the method described in Reference Example 1.

(1-3) Assessment of Mouse FcγR-Binding Activity

VH3/L(WT)-IgG1, VH3/L(WT)-IgG1-F1022, and VH3/L(WT)-IgG1-F760, which contain VH3-IgG1, VH3-IgG1-F1022, and VH3-IgG1-F760 as the heavy chain, and L(WT)-CK (SEQ ID NO: 42) as the light chain, were produced using the method described in Reference Example 1. These antibodies were kinetically analyzed for their mouse FcγR binding as described below.

(1-4) Kinetic Analysis of Mouse FcγR Binding

The binding of antibodies to mouse FcγRI, FcγRIIb, FcγRIII, and FcγRIV (hereinafter, referred to as mouse FcγRs) (R & D systems, SinoBiological, or prepared by the method described in Reference Example 2) was kinetically analyzed using Biacore T100 and T200 (GE Healthcare). An appropriate amount of protein L (ACTIGEN or BioVision) was immobilized onto a Sensor chip CM4 (GE Healthcare) by an amino coupling method, and antibodies of interest were captured thereto. Then, diluted solutions of mouse FcγRs and a running buffer as a blank were injected, and the mouse FcγRs were allowed to interact with antibodies captured onto the sensor chip. The running buffer used was 20 mmol/l ACES, 150 mmol/l NaCl, 0.05% (w/v) Tween20, pH 7.4. This buffer was also used to dilute the mouse FcγRs. The sensor chip was regenerated using 10 mmol/l glycine-HCl, pH 1.5. All measurements were carried out at 25° C. The binding rate constant ka (1/Ms) and dissociation rate constant kd (1/s), which are kinetic parameters, were calculated from the sensorgrams obtained by the measurement. KD (M) of each antibody for human FcγR was calculated based on the values. Each parameter was calculated using Biacore T100 or T200 Evaluation Software (GE Healthcare).

The result shown in Table 6 was obtained by the measurement. VH3/L (WT)-IgG1-F1022 was demonstrated to have increased binding activity to mFcγRI, mFcγRII, and mFcγRIII as compared to VH3/L (WT)-IgG1. Regarding VH3/L (WT)-IgG1-F760, the binding to the various mouse FcγRs was undetectable, demonstrating that VH3/L (WT)-IgG1-F760 lacks the binding activity to the various mouse FcγRs. In the table, VH3/L (WT)-IgG1, VH3/L (WT)-IgG1-F1022, and VH3/L (WT)-IgG1-F760 are shown as IgG1, F1022, and F760, respectively.

TABLE 6

| VARIANT | KD (M) | | | |
|---|---|---|---|---|
| NAME | mFc γ RI | mFc γ RII | mFc γ RIIII | mFc γ RIV |
| IgG1 | 5.3E−08 | 9.8E−07 | 2.4E−06 | 8.6E−08 |
| F1022 | 7.6E−09 | 1.0E−08 | 5.5E−09 | 1.4E−07 |
| F760 | NOT DETECTED | NOT DETECTED | NOT DETECTED | NOT DETECTED |

(1-5) Preparation of Antibodies with Low Fucose Content

Known methods for increasing the FcγR-binding activity of antibodies include methods for making sugar chains linked to an antibody be sugar chains with low fucose content (J. Biol. Chem. (2003) 278, 3466-3473) in addition to methods for introducing an amino acid alteration into the Fc region of an antibody. An Fv4-IgG1 with low fucose content (hereinafter, abbreviated as Fv4-IgG1-Fuc) was produced by expressing Fv4-IgG1 using fucose transporter gene-deficient CHO cells (WO 2006/067913) as host cells according to the method described in Reference Example 1. It has been reported that, of the mFcγRs (mouse Fcγ receptors), antibodies with low fucose content have selectively increased FcγRIV-binding activity (Science, 2005, 310 (5753) 1510-1512).

[Example 2] Effect of Eliminating Antigens from Plasma by Antigen-Binding Molecules Whose FcγR-Binding Activity is Higher Than the Binding Activity of Native Human IgG Fc Region (2-1) Effect of H54/L28-IgG1 and Fv4-IgG1 to Eliminate Antigens from Plasma H54/L28-IgG1, which is an anti-human IL-6 receptor antibody, and Fv4-IgG1 having the property of binding to human IL-6 receptor in a pH-dependent manner were produced by the method described in Reference Example 1. In vivo infusion tests were carried out using the produced H54/L28-IgG1 and Fv4-IgG1 by the method described below.

(2-1-1) In Vivo Infusion Tests Using Human FcRn Transgenic Mice

An animal model in which the soluble human IL-6 receptor concentration is maintained constant in plasma was created by implanting an infusion pump (MINI-OSMOTIC PUMP MODEL2004, alzet) containing soluble human IL-6 receptor under the skin on the back of human FcRn transgenic mice (B6.mFcRn−/−.hFcRn Tg line 32+/+mouse, Jackson Laboratories, Methods Mol Biol. (2010) 602, 93-104). The in vivo dynamics after administration of an anti-human IL-6 receptor antibody was assessed in the animal model. To suppress the production of neutralizing antibodies against soluble human IL-6 receptor, an anti-mouse CD4 monoclonal antibody (prepared by a known method) was administered once at 20 mg/kg into the caudal vein. Then, an infusion pump containing 92.8 μg/ml soluble human IL-6 receptor was subcutaneously implanted on the back of the mice. Three days after implantation of the infusion pump, an anti-human IL-6 receptor antibody was administered once at 1 mg/kg into the caudal vein. The blood was collected from the mice 15 minutes, seven hours, one day, two days, four days, and seven days after administration of the anti-human IL-6 receptor antibody. Immediately, the collected blood was centrifuged at 15,000 rpm and 4° C. for 15 minutes to prepare plasma. The isolated plasma was stored in a freezer set at −20° C. or below until use.

(2-1-2) Determination of the hsIL-6R Soluble Human IL-6 Receptor Concentration in Plasma by an Electrochemilumi-nescent Method The hsIL-6R soluble human IL-6 receptor concentrations in mouse plasma were determined by an electrochemilumi-nescent method. hsIL-6R soluble human IL-6 receptor standard curve samples prepared at 2000, 1000, 500, 250, 125, 62.5, and 31.25 pg/ml and assay samples of mouse plasma diluted 50 times or more were mixed with Monoclonal Anti-human IL-6R Antibody (R&D), Biotinylated Anti-human IL-6 R Antibody (R&D), Tocilizumab, which had been ruthenated with SULFO-TAG NHS Ester (Meso Scale Discovery). The mixtures were incubated at 37° C. over-night. Tocilizumab was prepared at a final concentration of 333 μg/ml. Then, the reaction mixtures were aliquoted in an MA400 PR Streptavidin Plate (Meso Scale Discovery). The solution reacted at room temperature for one hour was washed out, and then Read Buffer T (×4) (Meso Scale Discovery) was aliquoted. Immediately thereafter, the measurement was carried out using SECTOR PR 400 Reader (Meso Scale Discovery). The concentration of hsIL-6R soluble human IL-6 receptor was determined based on the response of the standard curve using analysis software SOFTmax PRO (Molecular Devices).

Figure 2:
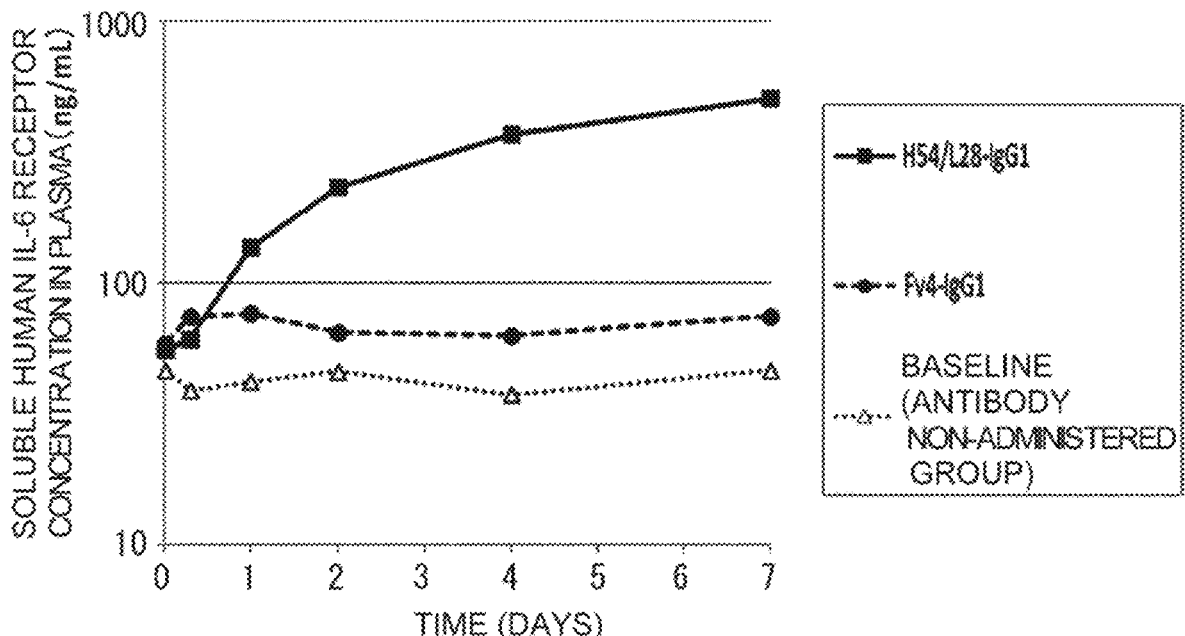
FIG. 2 shows a time course of human IL-6 receptor concentration in the plasma of human FcRn transgenic mice administered with Fv4-IgG1, which binds to human IL-6 receptor in a pH-dependent manner, or H54/L28-IgG1.

A time course of the monitored human IL-6 receptor concentration is shown in FIG. 2. As compared to H54/L28-IgG1, Fv4-IgG1 that binds to human IL-6 receptor in a pH-dependent manner could reduce the human IL-6 receptor concentration, but could not reduce it below the baseline without antibody administration. That is, the administered antibody which binds to an antigen in a pH-dependent manner could not reduce the antigen concentration in plasma below the level prior to antibody administration.

(2-2) The Effect of Eliminating an Antigen from Plasma by an Antibody with Increased or Reduced FcγR-Binding Activity Whether the time course of human IL-6 receptor concentration is influenced by increasing or reducing the FcγR-binding activity of Fv4-IgG1, which is a pH-dependent human IL-6 receptor-binding antibody, was assessed by the method described below. Using Fv4-IgG1, Fv4-IgG1-F760, Fv4-IgG1-F1022, and Fv4-IgG1-Fuc prepared as described in Example 1, in vivo infusion tests were performed by the method described below.

(2-2-1) In Vivo Infusion Tests Using Human FcRn Transgenic Mice

A animal model in which the soluble human IL-6 receptor concentration is maintained constant in plasma was created by implanting an infusion pump (MINI-OSMOTIC PUMP MODEL2004, alzet) containing soluble human IL-6 receptor under the skin on the back of human FcRn transgenic mice (B6.mFcRn−/−.hFcRn Tg line 32+/+ mouse, Jackson Laboratories, Methods Mol Biol. (2010) 602, 93-104). In the animal model, an anti-human IL-6 receptor antibody was administered simultaneously with Sanglopor (CSL Behring) which is a human immunoglobulin preparation, to assess the in vivo dynamics of the soluble human IL-6 receptor after antibody administration. To suppress the production of neutralizing antibodies against soluble human IL-6 receptor, an anti-mouse CD4 monoclonal antibody (prepared by a known method) was administered once at 20 mg/kg into the caudal vein. Then, an infusion pump containing 92.8 μg/ml soluble human IL-6 receptor was subcutaneously implanted on the back of the mice. Three days after implantation of the infusion pump, an anti-human IL-6 receptor antibody and Sanglopor were administered once at 1 mg/kg and 1000 mg/kg, respectively, into the caudal vein. The blood was collected from the mice 15 minutes, seven hours, one day, two days, four days, seven days, 14 days, and 21 days after administration of the anti-human IL-6 receptor antibody. The blood was collected from the mice 15 minutes, seven hours, one day, two days, three days, seven days, 14 days, and 21 days after administration of the anti-human IL-6 receptor antibody. Immediately, the collected blood was centrifuged at 15,000 rpm and 4° C. for 15 minutes to prepare the plasma. The isolated plasma was stored in a freezer set at −20° C. or below until use.

(2-2-2) Determination of the Soluble Human IL-6 Receptor (hsIL-6R) Concentration in Plasma by an Electrochemiluminescent Method The hsIL-6R soluble human IL-6 receptor concentrations in mouse plasma were determined by the same electrochemiluminescent method as described in (2-1-2).

Figure 3:
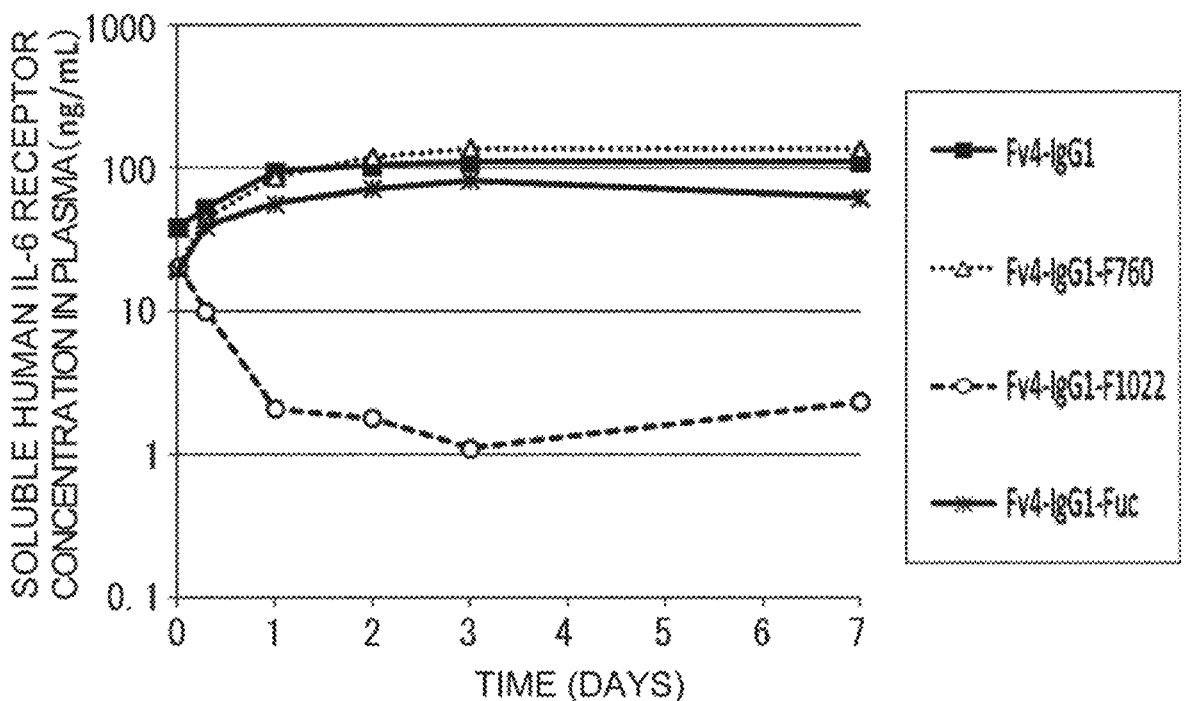
FIG. 3 shows a time course of human IL-6 receptor concentration in the plasma of human FcRn transgenic mice administered with Fv4-IgG1 which binds to human IL-6 receptor in a pH-dependent manner, Fv4-IgG1-F760 which is an Fv4-IgG1 variant that lacks mouse FcγR binding, Fv4-IgG1-F1022 which is an Fv4-IgG1 variant with enhanced mouse FcγR binding, or Fv4-IgG1-Fuc which is an Fv4-IgG1 antibody with low fucose content.

The result is shown in FIG. 3. The time course of human IL-6 receptor concentration in plasma of mice administered with Fv4-IgG1-F760, from which the mouse FcγR binding of Fv4-IgG1 is deleted, was demonstrated to be comparable to that in mice administered with Fv4-IgG1. The cytotoxic activity to a membrane antigen depends on the FcγR binding, and thus the cytotoxic activity is lost when eliminating the FcγR binding. On the other hand, even when administering an antibody, from which mouse FcγR binding is deleted, against human IL-6 receptor which is a soluble antigen, there was no effect on the time course of human IL-6 receptor concentration in the plasma of the administered mice. Thus, it would be thought that the FcγR binding of an antibody against the soluble antigen has no contribution to the time course of antigen concentration in the plasma of mice administered with the antibody.

Surprisingly, however, the human IL-6 receptor concentration in the plasma of mice administered with Fv4-IgG1-F1022 with enhanced mouse FcγR binding was considerably reduced as compared to the human IL-6 receptor concentration in the plasma of mice administered with Fv4-IgG1. As to the degree of reduction, the concentration was confirmed to be decreased below the baseline human IL-6 receptor concentration without antibody administration. In particular, the human IL-6 receptor concentration in the plasma of mice administered with Fv4-IgG1-F1022 was reduced down to about 1/100 three days after administration as compared to the case of Fv4-IgG1 administration. This finding demonstrates that, by administering to mice an antibody that binds to human IL-6 receptor in a pH-dependent manner and whose FcγR binding has been enhanced, the human IL-6 receptor concentration in the plasma of the mice can be significantly reduced, and as to the degree of reduction, the antigen concentration in plasma can be reduced below the level before antibody administration.

Furthermore, it was also demonstrated that, as compared to mice administered with Fv4-IgG1, the human IL-6 receptor concentration in plasma was reduced in mice administered with Fv4-IgG1-Fuc which has sugar chains with low fucose content and with increased mouse FcγR IV-binding activity. In particular, the human IL-6 receptor concentration in the plasma of mice administered with Fv4-IgG1-Fuc was reduced down to about 1/2 seven days after administration as compared to the case of Fv4-IgG1 administration. The above finding demonstrates that, by administering to mice a pH-dependent antigen-binding molecule that binds to human IL-6 receptor in a pH-dependent manner and whose FcγR binding has been enhanced, the soluble antigen concentration in the plasma of the mice can be reduced. In this case, methods for enhancing the FcγR binding are not particularly limited to introduction of amino acid alterations. It was demonstrated that such enhancement can be achieved, for example, by using a human IgG Fc region to which a sugar chain with low fucose content is linked at position 297 (EU numbering); however, the effect of Fv4-IgG1-Fuc to reduce antigen concentration was smaller than Fv4-F1022. Based on this result, it would be thought that, of several FcγRs (FcγRI, II, III, and IV for mouse), mFcγIV, to which the binding of Fv4-IgG1-Fuc is enhanced, does not have a large contribution to the reduction of antigen concentration as an FcγR.

Thus, it was revealed that, by administering to an individual an antibody that binds to a soluble antigen in a pH-dependent manner and whose FcγR binding has been enhanced, the soluble antigen concentration in the plasma of the individual can be markedly reduced.

Without being bound by a particular theory, the unexpected reduction of soluble antigen concentration in plasma, which was observed when administering an antigen-binding molecule that comprises an antigen-binding domain whose FcγR binding has been enhanced and whose antigen-binding activity is altered depending on the ion concentration condition such as pH and an FcRn-binding domain that has FcRn-binding activity under an acidic pH range condition, can be explained as follows.

IgG antibodies that are non-specifically incorporated into cells return to the cell surface by binding to FcRn under the acidic condition in the endosome, and then dissociate from FcRn under the neutral condition in plasma. In such a case, when an antibody that neutralizes the function of a soluble antigen by binding to the antigen is administered to mice in which the concentration of the soluble antigen is maintained constant in plasma, the soluble antigen in plasma forms a complex with the antibody administered. The soluble antigen incorporated into cells while remaining as the complex is thought to be recycled, in a state bound to the antibody, to the plasma together with the antibody, because the Fc region of the antibody binds to FcRn under the acidic condition in the endosome.

Meanwhile, when the antibody against the soluble antigen is an antibody that binds to the antigen in a pH-dependent manner (i.e., an antibody that dissociates the soluble antigen under the acidic condition in the endosome), the soluble antigen that is non-specifically incorporated into cells while remaining as a complex with the antibody, is dissociated from the antibody in the endosome and degraded in the lysosome in the cell; thus, the soluble antigen is not recycled to the plasma. That is, it is thought that Fv4-IgG1 incorporated as a complex with the soluble antigen into cells can dissociate the soluble antigen in the endosome and thus accelerate the elimination of the soluble antigen.

As described above, antigen-binding molecules such as Fv4-IgG1, which contain an antigen-binding domain whose antigen-binding activity is altered depending on the ion concentration, are thought to be capable of binding to antigens repeatedly several times. The effect to accelerate the elimination of soluble antigens from the plasma by dissociating them in the endosome is thought to depend on the rate of incorporation of the antigen/antigen-binding molecule complex into the endosome. An antigen-binding molecule that contains an antigen-binding domain whose binding activity to various FcγRs has been increased and whose antigen-binding activity is altered depending on the condition of ion concentration, is actively incorporated into cells by binding to various FcγRs expressed on the cell membrane, and can be shuttled back to plasma by recycling via the binding between FcRn and the FcRn-binding domain comprised in the molecule, which has FcRn-binding activity under an acidic pH range condition. That is, it is thought that, since the above antigen-binding molecule which forms a complex with a soluble antigen in plasma is actively incorporated into cells via FcγR expressed on the cell membrane, its effect to accelerate the elimination of the soluble antigen from plasma is more markedly shown than antigen-binding molecules whose binding activity to various FcγRs has not been increased.

The FcγR-binding activity of an antibody that binds to a membrane antigen plays an important role in the cytotoxic activity of the antibody. Thus, when it is necessary for an antibody used as a pharmaceutical agent to have cytotoxic activity, a human IgG1 isotype with strong FcγR-binding activity is used. In addition, techniques to enhance the cytotoxic activity of such antibodies by increasing the FcγR-binding activity of the antibodies are used commonly in the art.

Meanwhile, the role of the FcγR-binding activity of antibodies that bind to soluble antigens and which are used as pharmaceutical agents has not been known in the art. There has been no sufficient assessment on what difference in the effect on the living organism administered with the antibodies is caused by the difference in the FcγR-binding activity between human IgG1 with high FcγR-binding activity and human IgG2 and human IgG4 with low FcγR-binding activity. Actually, it was demonstrated in the present Example that there was no influence on the time course of soluble antigen concentration in the plasma of the individuals administered with an antibody that lacks FcγR-binding activity. Meanwhile, in the present invention, it was revealed that the soluble antigen concentration was significantly reduced in the plasma of the individuals administered with an antigen-binding molecule whose FcγR-binding activity has been increased and which contains an antigen-binding domain whose soluble antigen-binding activity is altered depending on the ion concentration condition. Specifically, it can be said that the present inventors revealed for the first time the benefit of the enhancement of FcγR binding by combining an FcRn-binding domain that has FcRn-binding activity under an acidic pH range condition with an antigen-binding domain whose soluble antigen binding is altered depending on the ion concentration condition, comprised in an antigen-binding molecule targeted to a soluble antigen.

[Example 3] Effect of Eliminating Antigens from Plasma by Antigen-Binding Molecules Whose FcγR-Binding Activity is Greater Than that of Native Human IgG Fc Region and Whose Human FcRn-Binding Activity has been Increased Under an Acidic pH Range Condition (3-1) Preparation of Antigen-Binding Molecules Whose FcγR-Binding Activity Is Greater Than the Binding Activity of Native Human IgG Fc Region and Whose Human FcRn-Binding Activity Has Been Increased Under an Acidic pH Range Condition A reported method for improving the retention of IgG antibody in plasma is to improve the FcRn binding under an acidic pH range condition. It is thought that, when the FcRn binding under an acidic pH range condition is improved by introducing an amino acid substitution into the Fc region of an IgG antibody, this increases the recycling efficiency from the endosome to plasma, resulting in an improvement of the plasma retention of the IgG antibody.

There are many reports on amino acid alterations to improve the plasma retention by improving the human FcRn-binding activity under an acidic pH range condition. Such alterations include, for example:

the method for substituting Leu for Met at position 428 and Ser for Asn at position 434 (EU numbering) in an IgG antibody (Nat. Biotechnol, (2010) 28, 157-159); the method for substituting Ala for Asn at position 434 (Drug. Metab. Dispos. (2010) 38 (4), 600-605); the method for substituting Tyr for Met at position 252, Thr for Ser at position 254, and Glu for Thr at position 256 (J. Biol. Chem. (2006) 281, 23514-23524); the method for substituting Gln for Thr at position 250 and Leu for Met at position 428 (J. Immunol. (2006) 176 (1) 346-356); the method for substituting His for Asn at position 434 (Clin. Pharm. & Ther. (2011) 89 (2) 283-290.); and WO2010/106180; WO2010/045193; WO2009/058492; WO2008/022152; WO2006/050166, WO2006/053301, WO2006/031370; WO2005/123780; WO2005/047327; WO2005/037867; WO2004/035752; and WO2002/060919.

VH3-IgG1-F1093 (SEQ ID NO: 43) with a substitution of Leu for Met at position 428 and Ser for Asn at position 434 (EU numbering) in VH3-IgG1-F1022 was prepared to improve the pharmacodynamics of Fv4-IgG1-F1022 that was demonstrated to produce, when administered, the effect of significantly reducing the soluble antigen concentration in plasma, as described in Example 2. Fv4-IgG1-F1093 comprising VH3-IgG1-F1093 as the heavy chain and VL3-CK as the light chain was constructed using the method described in Reference Example 1.

Figure 4:
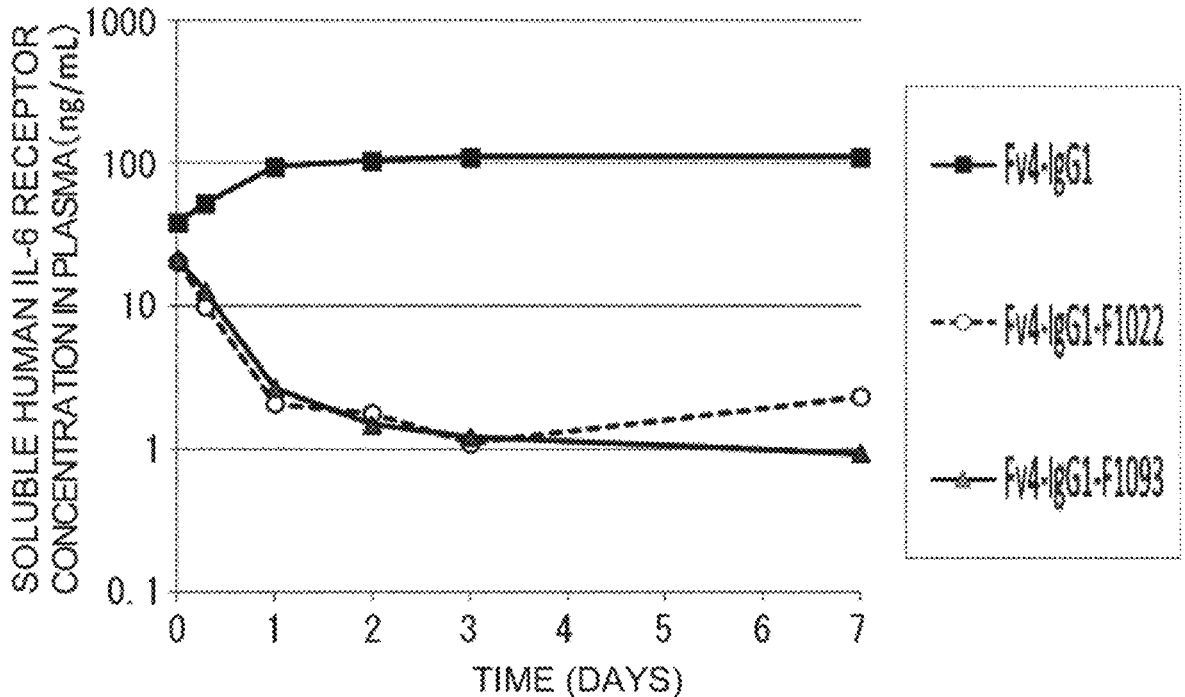
FIG. 4 shows a time course of human IL-6 receptor concentration in the plasma of human FcRn transgenic mice administered with Fv4-IgG1 or antigen-binding molecules comprising as the heavy chain, Fv4-IgG1-F1022 or Fv4-IgG1-F1093 which is a Fv4-IgG1-F1022 variant with improved FcRn binding in an acidic pH range.

(3-2) Effect of Eliminating Antigens from Plasma by Antigen-Binding Molecules Whose FcγR-Binding Activity is Greater Than that of Native Human IgG Fc Region and Whose Human FcRn-Binding Activity has been Increased under an Acidic pH Range Condition An in vivo infusion test was carried out for Fv4-IgG1-F1093 by the same method as described in Example (2-1-1) using human FcRn transgenic mice in which the soluble human IL-6 receptor concentration is maintained constant in plasma. Soluble human IL-6 receptor concentrations in the plasma of the mice were determined by the method described in Example (2-1-2). The result is shown in FIG. 4.

(3-2-1) Determination of the Anti-Human IL-6 Receptor Antibody Concentration in Plasma by the ELISA Method Anti-human IL-6 receptor antibody concentrations in mouse plasma were determined by the ELISA method. First, an anti-Human IgG (γ-chain specific) F(ab')2 Fragment of Antibody (SIGMA) was aliquoted in a Nunc-Immuno Plate, MaxiSoup (Nalge nunc International). The plate was allowed to stand at 4° C. overnight to prepare a plate immobilized with the anti-human IgG. Standard curve samples containing an anti-human IL-6 receptor antibody (concentration in plasma: 0.8, 0.4, 0.2, 0.1, 0.05, 0.025, and 0.0125 μg/ml) and assay samples of mouse plasma diluted 100 times or more were prepared. 100 μl each of the standard curve and assay samples were combined with 200 μl of 20 ng/ml soluble human IL-6 receptor. The resulting mixtures were allowed to stand at room temperature for one hour, and aliquoted to each well of the plate immobilized with the anti-human IgG. The plate was allowed to stand at room temperature for another one hour. Then, Biotinylated Anti-human IL-6 R Antibody (R&D) was reacted thereto at room temperature for one hour. Next, Streptavidin-PolyHRP80 (Stereospecific Detection Technologies) was reacted thereto at room temperature for one hour. The chromogenic reaction of the reaction solution was performed using as a substrate TMB One Component HRP Microwell Substrate (BioFX Laboratories). After terminating the reaction with 1 N sulfuric acid (Showa Chemical), the absorbance at 450 nm of the reaction solution of each well was measured with a microplate reader. Antibody concentrations in mouse plasma were determined based on the absorbance of the standard curve using the analysis software SOFTmax PRO (Molecular Devices).

Figure 5:
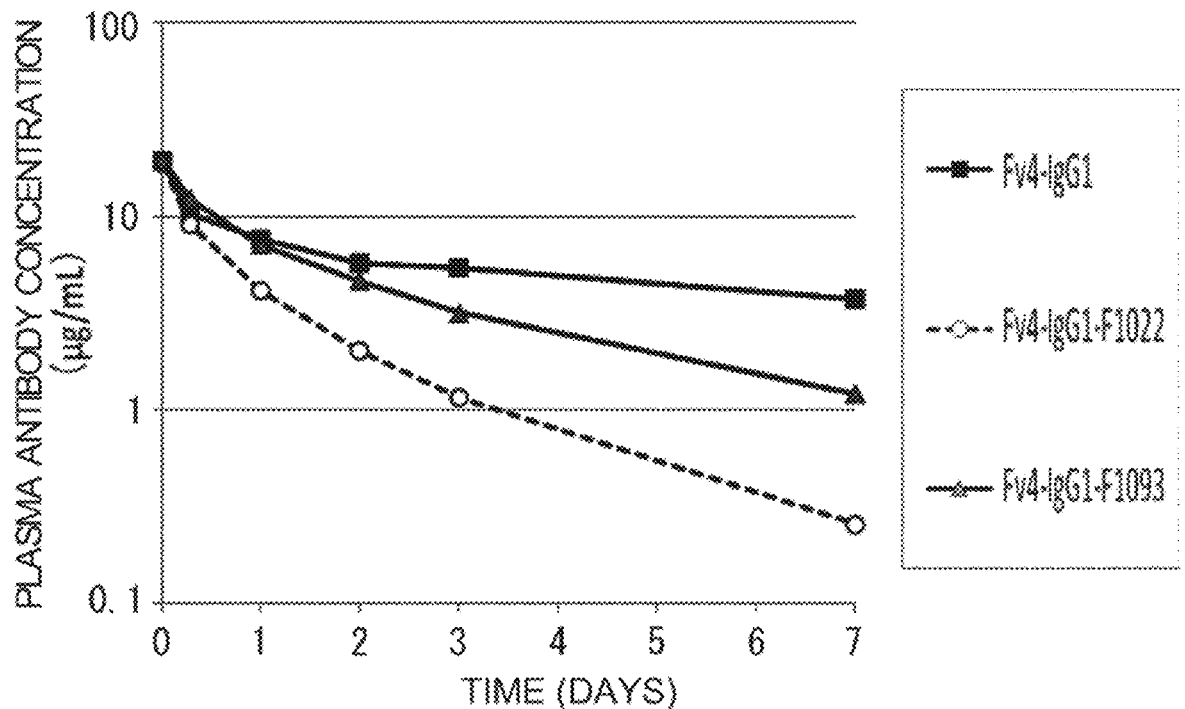
FIG. 5 shows a concentration time course of the administered antigen-binding molecules in the plasma of human FcRn transgenic mice administered with Fv4-IgG1 or antigen-binding molecules comprising as the heavy chain, Fv4-IgG1-F1022 or Fv4-IgG1-F1093 which is a Fv4-IgG1-F1022 variant with improved FcRn binding in an acidic pH range.

The result is shown in FIG. 5.

(3-3) Improvement of Pharmacodynamics by Increasing the Human FcRn-Binding Activity under an Acidic pH Range Condition As shown in FIG. 5, in the group administered with Fv4-IgG1-F1022 resulting from the enhancement of the FcγR-binding activity of Fv4-IgG1 under a neutral pH range condition, the plasma retention of the administered antibody was demonstrated to be reduced as compared to the group administered with Fv4-IgG1. Meanwhile, in the group administered with Fv4-IgG1-F1093 resulting from the enhancement of the human FcRn-binding activity of Fv4-IgG1-F1022 under an acidic pH range condition, the plasma retention of the administered antibody was demonstrated to be significantly improved as compared to the group administered with Fv4-IgG1-F1022.

Furthermore, as shown in FIG. 4, the time course of the soluble human IL-6 receptor concentration in the plasma of the Fv4-IgG1-F1022-administered group was equivalent to that of the Fv4-IgG1-F1093-administered group, up to three days after antibody administration. On day three after administration, as compared to the Fv4-IgG1-administered group, the soluble human IL-6 receptor concentration in plasma was reduced as much as about 100 times in both of the Fv4-IgG1-F1022 and Fv4-IgG1-F1093-administered groups. However, on day seven after antibody administration, the soluble human IL-6 receptor concentration in plasma was observed to be elevated in the Fv4-IgG1-F1022-administered group as compared to on day three after administration. On the other hand, in the Fv4-IgG1-F1093-administered group, an increase in the plasma concentration of soluble human IL-6 receptor was not observed, showing that the effect to reduce the soluble human IL-6 receptor concentration was sustained in this administration group.

Specifically, Fv4-IgG1-F1093, when administered, reduced the soluble human IL-6 receptor concentration in the plasma of the administered individual down to about $\frac{1}{100}$ as compared to Fv4-IgG1, and in addition, it sustained this condition for a long period. Thus, Fv4-IgG1-F1093 was demonstrated to be a highly excellent antigen-binding molecule. Without being bound by a particular theory, the phenomenon observed herein can be explained as follows. Fv4-IgG1-F1022 in which the FcγR-binding activity of Fv4-IgG1 has been increased under a neutral pH range condition is thought to be incorporated in a large amount mainly into cells expressing FcγR on the cell membrane. The incorporated antibody is transferred into the endosome, and by binding to FcRn in the endosome, the antibody is recycled to the plasma. When the FcRn-binding activity of the antibody is not high enough under the condition at acidic pH in the endosome, the antibody incorporated into the endosome is thought to be incapable of sufficient recycling. Specifically, a possible reason for the reduced plasma retention of Fv4-IgG1-F1022 relative to Fv4-IgG1 would be that the FcRn-binding activity under an acidic pH range condition is insufficient for sufficient recycling of the endosome-incorporated antibody to the plasma by FcRn binding, and the antibody that was not recycled was degraded in the lysosome.

On the other hand, as with Fv4-IgG1-F1022, Fv4-IgG1-F1093 resulting from the enhancement of the human FcRn-binding activity of Fv4-IgG1-F1022 under an acidic pH range condition is thought to be incorporated in a large amount mainly into cells expressing FcγR on the cell membrane. An antibody incorporated and transferred into the endosome is recycled to the plasma by binding to FcRn in the endosome. Since its human FcRn-binding activity under an acidic pH range condition is enhanced, Fv4-IgG1-F1093 is thought to have sufficient FcRn-binding activity in the endosome. Thus, after incorporation into cells, most of Fv4-IgG1-F1093 is recycled to the plasma. Thus, it would be thought that the plasma retention of Fv4-IgG1-F1093 was improved in administered individuals as compared to Fv4-IgG1-F1022.

On the other hand, it has been known that the plasma retention of ordinary antibodies is improved when their FcRn-binding activity is improved under an acidic pH range condition. However, it is thought that, when the antibody retention in plasma is improved, the plasma retention of antibody-bound antigens is also improved, and this results in an increase of the antigen concentration in plasma. In actual, as described in WO2010/088444, Antibody 18E introduced with the alteration YTE into Antibody 18, which is a human IgG1 antibody against IL-6, to increase the FcRn-binding activity under an acidic pH range condition, showed improved antibody retention in the plasma of cynomolgus monkeys, and at the same time, the concentration of the IL-6 antigen was also elevated in the plasma.

Surprisingly, however, when administering Fv4-IgG1-F1093 introduced with an alteration similar to YTE for increasing the FcRn-binding activity under an acidic pH range condition into Fv4-F1022 that binds to the antigen in a pH-dependent manner and has increased FcγR-binding activity, the plasma retention of the antibody was significantly improved in the administered individuals without increasing the concentration of soluble human IL-6 receptor which is the antigen. Rather, on day seven after antibody administration, the soluble human IL-6 receptor concentration remained low in the individuals administered with Fv4-IgG1-F1093 as compared to those administered with Fv4-F1022.

Without being bound by a particular theory, the phenomenon observed herein can be explained as follows. When administered to a living organism, an antibody without pH-dependent antigen binding is non-specifically incorporated into cells. Antigens that remain to be bound to the antibody are recycled to the plasma in the same extent as the antibody. Meanwhile, for an antibody with increased FcRn-binding activity under an acidic pH range condition, the extent of recycling to the plasma in a living organism administered with the antibody is higher than that of an antibody without increased FcRn-binding activity, and this results in an increased extent of recycling of antigens bound to the antigen to the plasma in the living organism. Thus, due to the improved plasma retention of the antibody administered in the living organism, the plasma concentration of the antigen to which the antibody binds is thought to be also increased in the living organism.

Meanwhile, when administered to a living organism, an antibody that binds to an antigen in a pH-dependent manner and which has increased FcγR-binding activity is mainly incorporated into cells expressing FcγR on the cell membrane, and this reduces the plasma retention. Furthermore, after being incorporated into the cells while bound to the antibody, the antigen is dissociated from the antibody in the endosome and then degraded in the lysosome, resulting in a decrease of the antigen concentration in plasma in the living organism. When the FcRn-binding activity is increased under an acidic pH range condition, the antibody retention in plasma, even if worsened due to increased FcγR-binding activity, is improved by an increase in the rate of recycling by FcRn. In this case, since the antigen bound to the antibody that binds to the antigen in a pH-dependent manner is dissociated from the antibody in the endosome and directly degraded in the lysosome, it is not thought that the antigen concentration is increased in the plasma. Furthermore, the improved plasma retention of the antibody administered to the living organism is thought to allow the antigen elimination effect of the antibody to be sustained, and the antigen concentration to be maintained low for a longer period.

The above findings demonstrate that the plasma retention of an administered antibody is improved in a living organism administered with the antibody in which the human FcRn-binding activity under an acidic pH range condition is enhanced in an antigen-binding molecule whose FcγR-binding activity is higher than that of native human IgG Fc region. Furthermore, it was revealed that, in this case, the antibody retention in plasma is improved without deteriorating the antigen-elimination effect.

[Example 4] Further Assessment of the Effect of Eliminating Antigens from Plasma Antigen-Binding Molecules Whose FcγR-Binding Activity is Greater Than that of Native Human IgG Fc Region and Whose Human FcRn-Binding Activity Has Been Increased Under an Acidic pH Range Condition (4-1) The Antigen Elimination Effect of an Antibody Whose FcγR-Binding Activity is Enhanced As described in Example 2, the antigen concentration in plasma was significantly reduced in the group administered with Fv4-IgG1-F1022 with enhanced mouse FcγR binding. Meanwhile, as shown in Example 3, the reduced plasma retention observed in the Fv4-IgG1-F1022-administered group was markedly improved by increasing the human FcRn-binding activity of Fv4-IgG1-F1022 under an acidic pH range condition. Next, the effect of eliminating soluble antigens from plasma by enhancing mouse FcγR binding and the effect of improving the plasma retention of an antibody by enhancing the human FcRn binding activity under an acidic pH range condition were further assessed as described below.

(4-2) Preparation of an Anti-Human IL-6 Receptor Antibody with Enhanced Mouse FcγR Binding VH3-IgG1-F1087 (SEQ ID NO: 44) resulting from substituting Asp for Lys at position 326 (EU numbering) in VH3-IgG1, and VH3-IgG1-F1182 (SEQ ID NO: 45) resulting from substituting Asp for Ser at position 239 and Glu for Ile at position 332 (EU numbering) in VH3-IgG1, were prepared as antigen-binding molecules with enhanced mouse FcγR binding. Fv4-IgG1-F1087 that contains VH3-IgG1-F1087 as the heavy chain and VL3-CK as the light chain, and Fv4-IgG1-F1182 that contains VH3-IgG1-F1182 as the heavy chain and VL3-CK as the light chain, were produced using the method described in Reference Example 1.

(4-3) Assessment of Mouse FcγR-Binding Activity

VH3/L (WT)-IgG1-F1087 and VH3/L (WT)-IgG1-F1182 which contain VH3-IgG1-F1087 and VH3-IgG1-F1182 as the heavy chain, respectively, and L (WT)-CK (SEQ ID NO: 42) as the light chain, were prepared by the method described in Reference Example 1. These antibodies, and VH3/L (WT)-IgG1-F1022 and VH3/L (WT)-IgG1 were assessed for their mouse FcγR-binding activity by the method described in Reference Example 2. The result is shown in Table 7. In addition, the ratio of the increase in the mouse FcγR-binding activity of each variant relative to the IgG1 before alteration is shown in Table 8. In the table, VH3/L (WT)-IgG1, VH3/L (WT)-IgG1-F1022, VH3/L (WT)-IgG1-F1087, and VH3/L (WT)-IgG1-F1182 are shown as IgG1, F1022, F1087, and F1182, respectively.

TABLE 7

| VARIANT | KD (M) | | | |
| NAME | mFc γ RI | mFc γ RIIb | mFc γ RIII | mFc γ RIV |
| --- | --- | --- | --- | --- |
| IgG1 | 5.3E−08 | 9.8E−07 | 2.4E−06 | 8.6E−08 |
| F1022 | 7.6E−09 | 1.0E−08 | 5.5E−09 | 1.4E−07 |
| F1087 | 2.9E−08 | 5.6E−08 | 5.2E−08 | 3.3E−07 |
| F1182 | 2.4E−09 | 1.1E−07 | 4.8E−07 | 5.3E−10 |

TABLE 8

| VARIANT | RATIO OF BINDING TO IgG1 | | | |
| NAME | mFc γ RI | mFc γ RIIb | mFc γ RIII | mFc γ RIV |
| --- | --- | --- | --- | --- |
| IgG1 | 1.0 | 1.0 | 1.0 | 1.0 |
| F1022 | 7.0 | 93.6 | 440.5 | 0.6 |
| F1087 | 1.8 | 17.5 | 46.2 | 0.3 |
| F1182 | 22.1 | 9.1 | 5.0 | 162.3 |

As shown in Table 8, it was demonstrated that F1087 and F1022 had increased binding activity to mouse FcγRI, mouse FcγRIIb, and mouse FcγRIII as compared to IgG1, whereas their mouse FcγRIV-binding activity was not increased. Regarding the binding activity of F1087 to mouse FcγRI, mouse FcγRIIb, mouse FcγRIII, and mouse FcγRIV, the extent of its increase was revealed to be smaller than that of F1022. Meanwhile, it was shown that the binding activity of F1182 to mouse FcγRI and mouse FcγRIV was considerably increased, whereas the extent of increase in its binding activity to FcγRIIb and FcγRIII was smaller than those of F1022 and F1087. As mentioned above, these three types of variants showed enhanced binding to some mouse FcγRs; however, it was shown that the FcγR to which the binding activity is selectively increased and the extent of the increase vary depending on the variant.

(4-4) The Effect of Eliminating Antigens from the Plasma of Fv4-IgG1-F1087 and Fv4-IgG1-F1182

Figure 6:
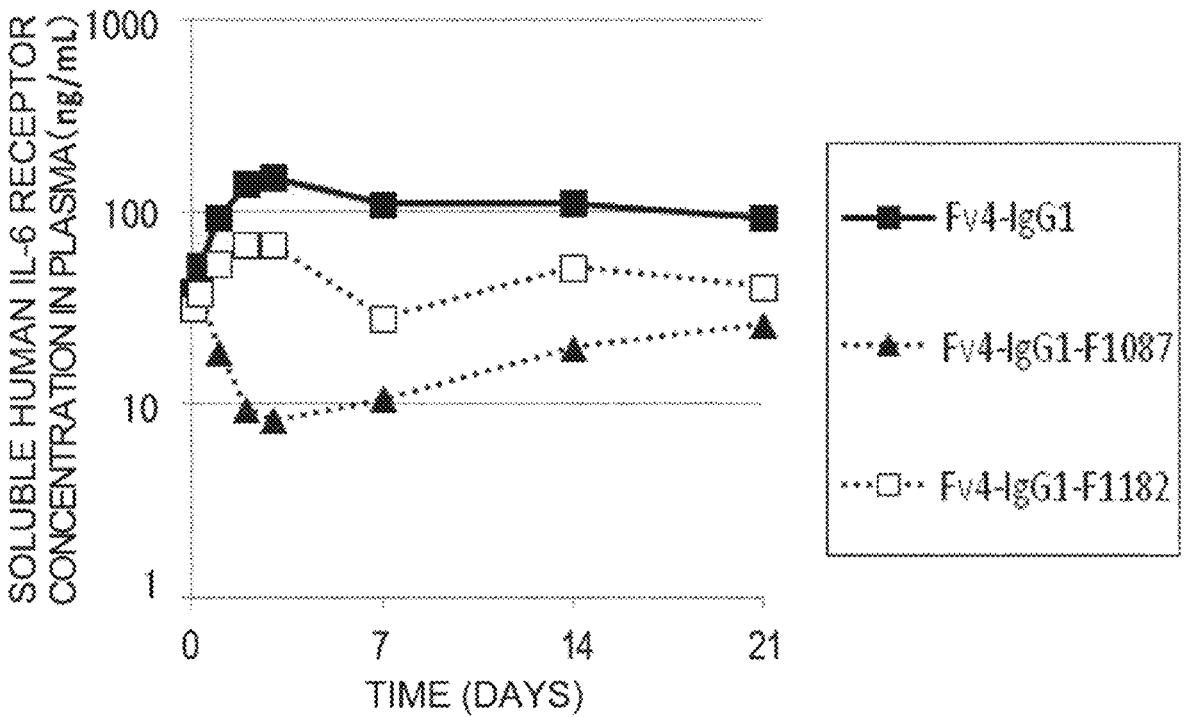
FIG. 6 shows a time course of human IL-6 receptor concentration in the plasma of human FcRn transgenic mice administered with Fv4-IgG1, Fv4-IgG1-F1087 which is an Fv4-IgG1 variant with enhanced mouse FcγR binding (in particular, enhanced mouse FcγRIIb binding and mouse FcγRIII binding), and Fv4-IgG1-F1182 which is an Fv4-IgG1 variant with enhanced mouse FcγR binding (in particular, enhanced mouse FcγRI binding and mouse FcγRIV binding).

By the same method as described in Example 2, in vivo infusion tests using human FcRn transgenic mice were carried out to determine the soluble IL-6 receptor concentrations in the plasma of the mice. The result is shown in FIG. 6.

In both of the groups administered with Fv4-IgG1-F1087 and Fv4-IgG1-F1182 in vivo, which have increased mouse FcγR-binding activity as compared to Fv4-IgG1, the in vivo plasma concentration of soluble human IL-6 receptor could be reduced as compared to the group administered with Fv4-IgG1. The effect to reduce the plasma concentration of soluble human IL-6 receptor was high especially in the group administered with Fv4-IgG1-F1087 which has enhanced binding to mouse FcγRII and mouse FcγRIII. Meanwhile, the effect of F1182 administration to reduce the plasma concentration of soluble human IL-6 receptor was small in the group administered with F1182 in vivo which has considerably increased binding activity to mouse FcγRI and mouse FcγRIV (as well as several-fold enhanced binding to mouse FcγRII and mouse FcγRIII). It was thought from these results that the mouse FcγRs that more significantly contribute by an effect that efficiently decreases the antigen concentration in the plasma of mice administered with a pH-dependent antigen-binding antibody, are mouse FcγRII and/or mouse FcγRIII. Specifically, it is thought that the plasma antigen concentration can be more efficiently reduced in vivo by administering into a living organism a pH-dependent antigen-binding antibody with enhanced binding to mouse FcγRII and/or mouse FcγRIII.

(4-5) Preparation of Antigen-Binding Molecules Whose FcγR-Binding Activity is Greater Than the Binding Activity of Native Human IgG Fc Region and Which Have Increased Human FcRn-Binding Activity Under an Acidic pH Range Condition As described in Example 3, when compared to human FcRn transgenic mice administered with Fv4-IgG1-F1022, the plasma retention of an antibody is markedly improved in human FcRn transgenic mice administered with Fv4-IgG1-F1093 resulting from increasing the human FcRn-binding activity under an acidic pH range condition of Fv4-IgG1-F1022 in which the mouse FcγR-binding activity has been increased. Whether this effect is also observed in human FcRn transgenic mice administered with Fv4-IgG1-F1087 and Fv4-IgG1-F1182, and whether the same effect is observed in mice administered with variants whose human FcRn-binding activity has been increased under an acidic pH range condition by addition of an alteration distinct from the alteration assessed in Example 3 were assessed as follows.

VH3-IgG1-F1180 (SEQ ID NO: 46) and VH3-IgG1-F1181 (SEQ ID NO: 47) were prepared by substituting Leu for Met at position 428 and Ser for Asn at position 434 (EU numbering) in the heavy chains VH3-IgG1-F1087 and VH3-IgG1-F1182, in order to increase their human FcRn-binding activity of Fv4-IgG1-F1087 and Fv4-IgG1-F1182 under an acidic pH range condition. Furthermore, VH3-IgG1-F1412 (SEQ ID NO: 48) was prepared by substituting Ala for Asn at position 434 (EU numbering) in the heavy chain VH3-IgG1-F1087, in order to increase the human FcRn-binding activity of Fv4-IgG1-F1087 under an acidic pH range condition. Fv4-IgG1-F1180, Fv4-IgG1-F1181, and Fv4-IgG1-F1412, which contain the above heavy chains and VL3-CK as the light chain, were prepared using the method described in Reference Example 1.

Figure 7:
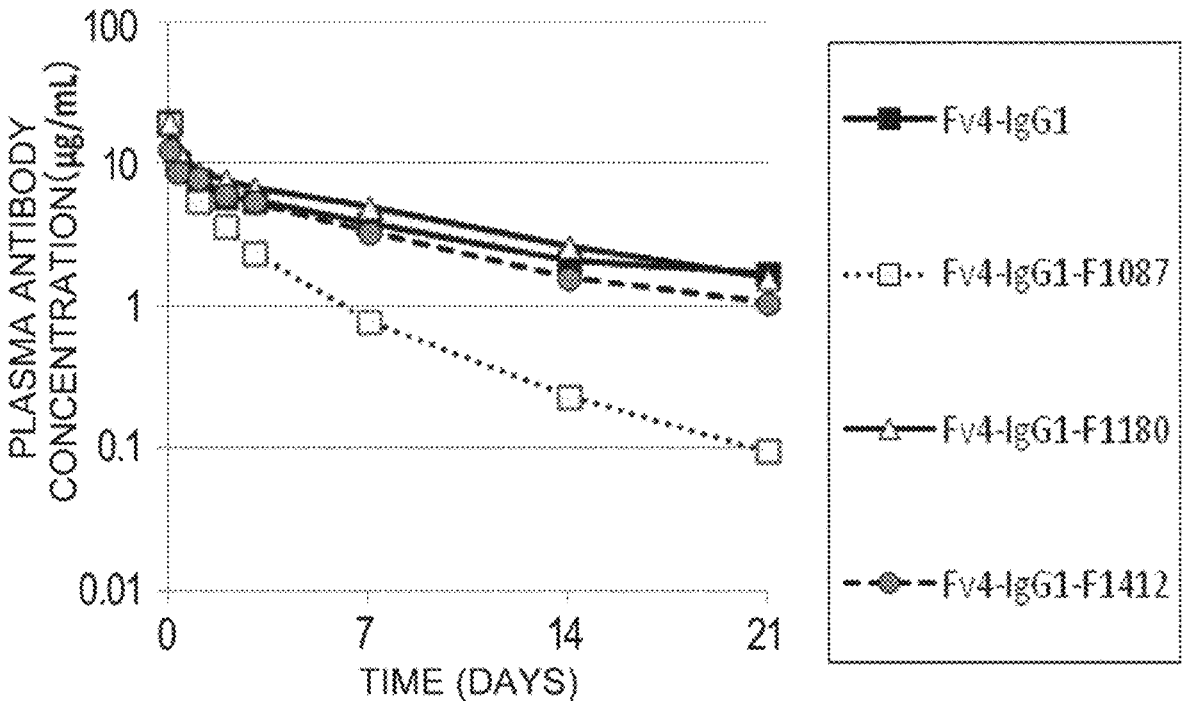
FIG. 7 shows a concentration time course of the administered antigen-binding molecules in the plasma of human FcRn transgenic mice administered with Fv4-IgG1, Fv4-IgG1-F1087, and Fv4-IgG1-F1180 and Fv4-IgG1-F1412 which are Fv4-IgG1-F1087 variants with improved FcRn binding in an acidic pH range.
Figure 8:
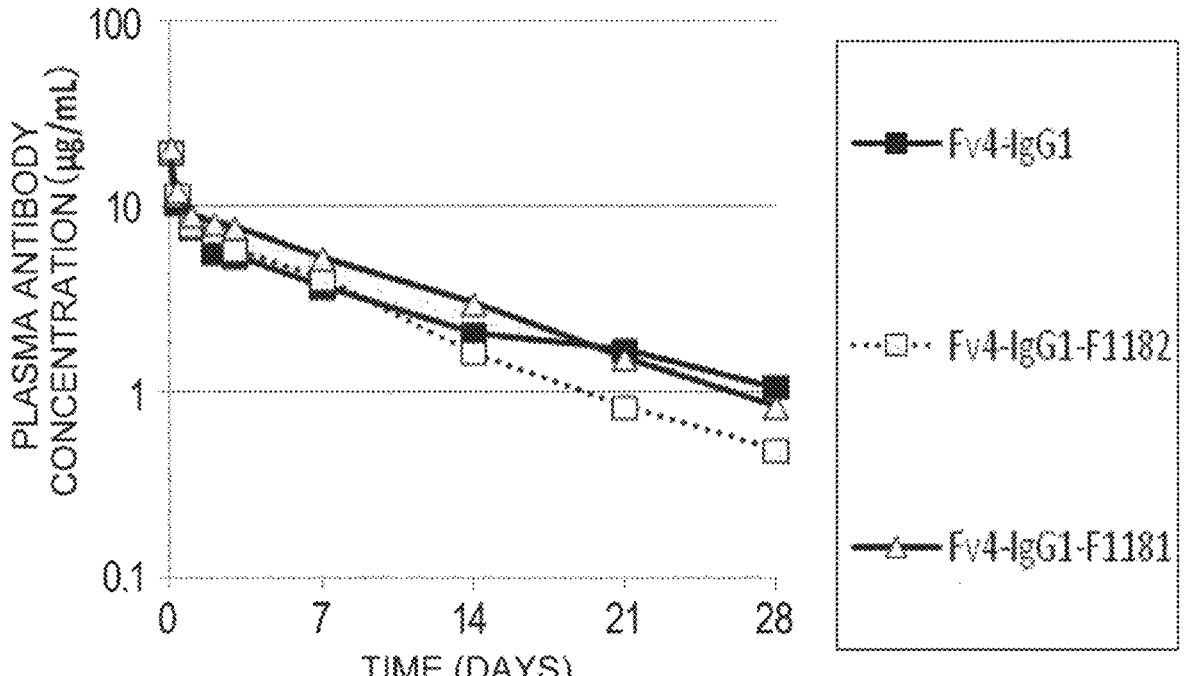
FIG. 8 shows a concentration time course of the administered antigen-binding molecules in the plasma of human FcRn transgenic mice administered with Fv4-IgG1, Fv4-IgG1-F1182, and Fv4-IgG1-F1181 which is an Fv4-IgG1-F1182 variant with improved FcRn binding in an acidic pH range.
Figure 9:
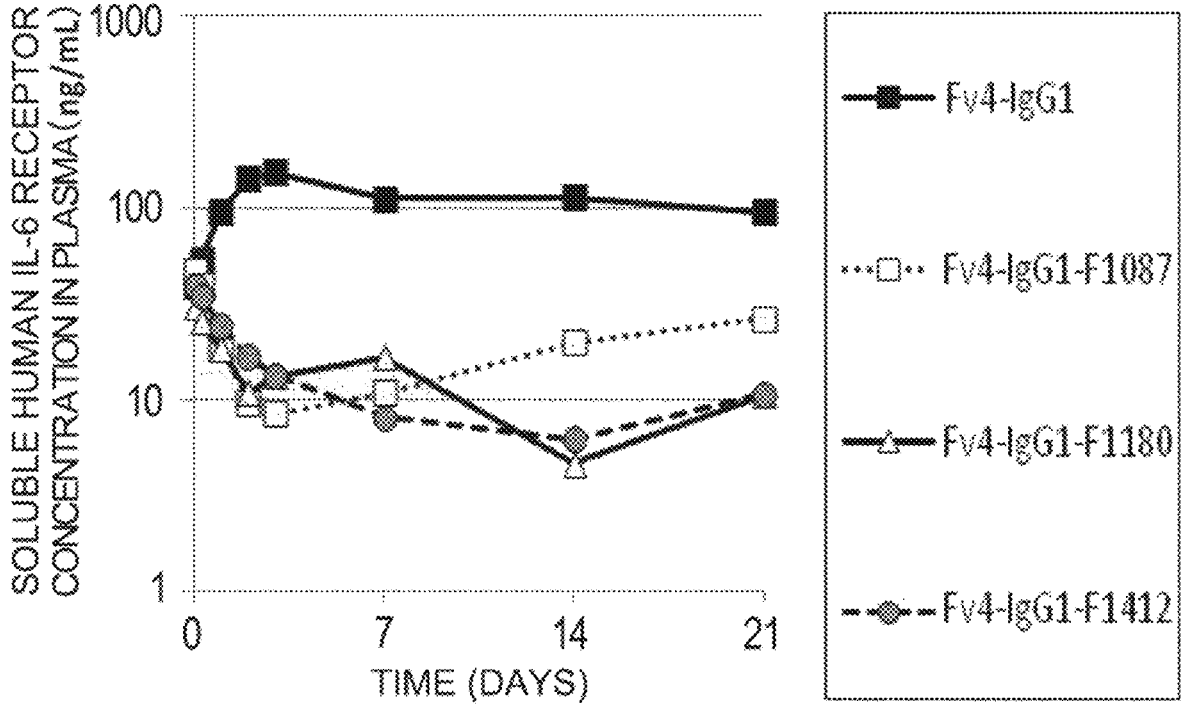
FIG. 9 shows a time course of human IL-6 receptor concentration in the plasma of human FcRn transgenic mice administered with Fv4-IgG1, Fv4-IgG1-F1087, and Fv4-IgG1-F1180 and Fv4-IgG1-F1412 which are Fv4-IgG1-F1087 variants with improved FcRn binding in an acidic pH range.
Figure 10:
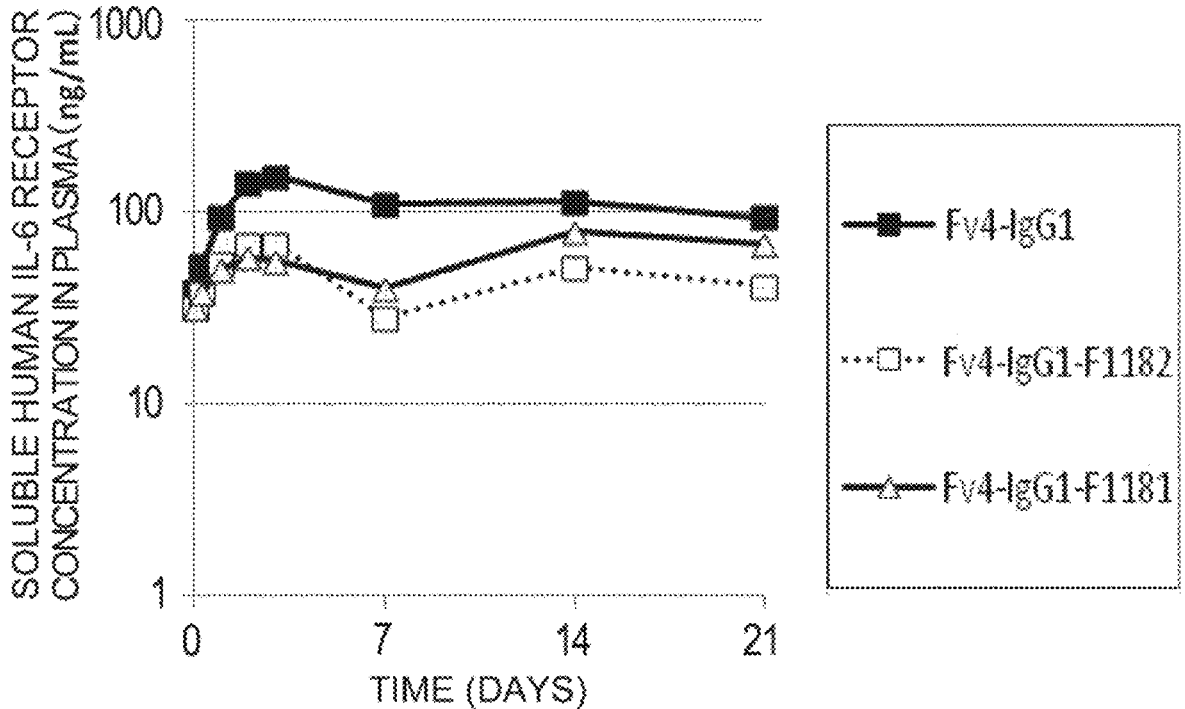
FIG. 10 shows a time course of human IL-6 receptor concentration in the plasma of human FcRn transgenic mice administered with Fv4-IgG1, Fv4-IgG1-F1182, and Fv4-IgG1-F1181 which is an Fv4-IgG1-F1182 variant with improved FcRn binding in an acidic pH range.

(4-6) Improvement of Pharmacodynamics of Antibodies by Increasing Human FcRn-Binding Activity under an Acidic pH Range Condition In vivo infusion tests were carried out by administering Fv4-IgG1-F1180, Fv4-IgG1-F1181, and Fv4-IgG1-F1412 to human FcRn transgenic mice according to the same method as described in Example 2 to determine the soluble IL-6 receptor concentrations in the plasma of the mice. The results on the soluble IL-6 receptor concentrations in the plasma of the mouse groups administered with Fv4-IgG1-F1087, Fv4-IgG1-F1180, Fv4-IgG1-F1412, and Fv4-IgG1 are shown in FIG. 9. The results on the soluble IL-6 receptor concentrations in the plasma of the mouse groups administered with Fv4-IgG1-F1182, Fv4-IgG1-F1181, and Fv4-IgG1 are shown in FIG. 10. Meanwhile, the plasma antibody concentrations in the mouse groups were measured by the method described in Example 3. The results on the plasma antibody concentrations of Fv4-IgG1-F1087, Fv4-IgG1-F1180, Fv4-IgG1-F1412, and Fv4-IgG1 in the mouse groups are shown in FIG. 7; and the results on the plasma antibody concentrations of Fv4-IgG1-F1182, Fv4-IgG1-F1181, and Fv4-IgG1 are shown in FIG. 8.

It was confirmed that, as compared to the group of mice administered with Fv4-IgG1-F1182, the plasma retention of antibodies was improved in the group of mice administered with Fv4-IgG1-F1181 resulting from increasing the human FcRn-binding activity of Fv4-IgG1-F1182 in an acidic pH range. Meanwhile, the soluble IL-6 receptor concentration in the plasma of the mouse groups administered with Fv4-IgG1-F1181 was comparable to that in the group of mice administered with Fv4-IgG1-F1182. When compared to the mouse groups administered with Fv4-IgG1, the soluble IL-6 receptor concentration in the plasma was decreased in both groups.

On the other hand, as compared to the group of mice administered with Fv4-IgG1-F1087, the plasma retention of antibodies was improved in both groups of mice administered with Fv4-IgG1-F1180 and Fv4-IgG1-F1412 resulting from increasing the human FcRn-binding activity of Fv4-IgG1-F1087 in an acidic pH range, and surprisingly, the plasma retention was improved up to a level comparable to that of the mouse groups administered with Fv4-IgG1. Furthermore, the sustainability of the effect of reducing the soluble IL-6 receptor concentration in plasma was improved by the improvement of the plasma antibody retention in the groups of administered mice. Specifically, in the groups of administered mice, the soluble IL-6 receptor concentrations in plasma 14 days and 21 days after administration of Fv4-IgG1-F1180 and Fv4-IgG1-F1412 were significantly reduced as compared to the concentrations 14 days and 21 days after administration of Fv4-IgG1-F1087.

In view of the above, as for the groups of mice administered with the four examples of antibodies, Fv4-IgG1-F1093, Fv4-IgG1-F1181, Fv4-IgG1-F1180, and Fv4-IgG1-F1412, it was demonstrated that the plasma retention can be improved in a living organism administered with an antibody in which the human FcRn-binding activity under an acidic pH range condition has been enhanced in an antigen-binding molecule whose FcγR-binding activity is higher than the binding activity of native human IgG Fc region. It was also demonstrated that, in the living organism administered with the antigen-binding molecule, the plasma retention is improved without deteriorating the effect of eliminating antigens from the living organism, and rather, the antigen elimination effect can be sustained.

It is demonstrated that alteration for enhancing human FcRn-binding activity under an acidic pH range condition could be accomplished by the method that substitutes Ala for Asn at position 434 (EU numbering), in addition to the method that substitutes Leu for Met at position 428 (EU numbering) and Ser for Asn at position 434 (EU numbering). Therefore, alterations used for enhancing human FcRn-binding activity under an acidic pH range condition are not particularly limited, and the method that substitutes Leu for Met at position 428 (EU numbering) and Ser for Asn at position 434 (EU numbering) in an IgG antibody (Nat. Biotechnol. (2010) 28, 157-159), the method that substitutes Ala for Asn at position 434 (EU numbering) in an IgG antibody (Drug Metab. Dispos. (2010) 38 (4), 600-605), the method that substitutes Tyr for Met at position 252 (EU numbering), Thr for Ser at position 254 (EU numbering), and Glu for Thr at position 256 (EU numbering) in an IgG antibody (J. Biol. Chem. (2006) 281, 23514-23524), the method that substitutes Gln for Thr at position 250 (EU numbering) and Leu for Met at position 428 (EU numbering) in an IgG antibody (J. Immunol. (2006) 176 (1), 346-356), the method that substitutes His for Asn at position 434 (EU numbering) in an IgG antibody (Clin. Pharmcol. Ther. (2011) 89 (2), 283-290), as well as alterations described in WO 2010/106180, WO 2010/045193, WO 2009/058492, WO 2008/022152, WO 2006/050166, WO 2006/053301, WO 2006/031370, WO 2005/123780, WO 2005/047327, WO 2005/037867, WO 2004/035752, WO 2002/060919 and such can be used.

(4-7) Preparation of Antigen-Binding Molecules with Increased Human FcRn-Binding Activity Under an Acidic pH Range Condition and Suppressed Binding to a Rheumatoid Factor In recent years, an antibody molecule resulting from substituting His for Asn at position 434 (EU numbering) in a humanized anti-CD4 antibody to improve the plasma retention by increasing its human FcRn-binding activity under an acidic pH range condition, has been reported to bind to the rheumatoid factor (RF) (Clin. Pharmacol. Ther. (2011) 89 (2), 283-290). This antibody has a human IgG1 Fc region and a substitution of His for Asn at position 434 (EU numbering) in the FcRn-binding site. The rheumatoid factor has been demonstrated to recognize and bind to the substituted portion.

As shown in (4-6), various alterations have been reported as alterations for enhancing human FcRn-binding activity under an acidic pH range condition, and introducing these alterations to the FcRn-binding site in an Fc region may enhance its affinity to a rheumatoid factor that recognizes this site.

However, antigen-binding molecules that have increased human FcRn-binding activity under an acidic pH range condition but do not have the binding to the rheumatoid factor can be produced by introducing into the site of the Fc region an alteration that reduces the rheumatoid factor-binding activity alone without reducing the FcRn-binding activity under an acidic pH range condition.

Such alterations used for reducing the rheumatoid factor-binding activity include alterations at positions 248-257, 305-314, 342-352, 380-386, 388, 414-421, 423, 425-437, 439, and 441-444 (EU numbering), preferably those at positions 387, 422, 424, 426, 433, 436, 438, and 440 (EU numbering), and particularly preferably, an alteration that substitutes Glu or Ser for Val at position 422, an alteration that substitutes Arg for Ser at position 424, an alteration that substitutes Asp for His at position 433, an alteration that substitutes Thr for Tyr at position 436, an alteration that substitutes Arg or Lys for Gln at position 438, and an alteration that substitutes Glu or Asp for Ser at position 440 (EU numbering). These alterations may be used alone or in combination.

Alternatively, it is possible to introduce N-type glycosylation sequences to reduce the rheumatoid factor-binding activity. Specifically, known N-type glycosylation sequences include Asn-Xxx-Ser/Thr (Xxx represents an arbitrary amino acid other than Pro). This sequence can be introduced into the Fc region to add an N-type sugar chain, and the binding to RF can be inhibited by the steric hindrance of the N-type sugar chain. Alterations used for adding an N-type sugar chain preferably include an alteration that substitutes Asn for Lys at position 248, an alteration that substitutes Asn for Ser at position 424, an alteration that substitutes Asn for Tyr at position 436 and Thr for Gln at position 438, and an alteration that substitutes of Asn for Qln at position 438, according to EU numbering, particularly preferably an alteration that substitutes Asn for Ser at position 424 (EU numbering).

[Example 5] Effects of Eliminating Antigens from Plasma for Antigen-Binding Molecules Whose FcγR-Binding Activity is Higher Than that of an Fc Region of Native Mouse IgG (5-1) Antigen Elimination Effect of Mouse Antibodies with Enhanced FcγR-Binding Activity As described in Examples 1 to 4, it was demonstrated that the elimination of soluble human IL-6 receptor from mouse plasma is accelerated in the groups of human FcRn transgenic mice administered with antigen-binding molecules resulting from increasing the mouse FcγR-binding activity of antigen-binding molecules that have a human antibody Fc region and the property of binding to human IL-6 receptor in a pH-dependent manner. Whether this effect is also achieved in normal mice having mouse FcRn that was administered with antigen-binding molecules that have a mouse antibody Fc region and the property of binding to human IL-6 receptor in a pH-dependent manner, was assessed in normal mice having mouse FcRn as follows.

(5-2) Preparation of Mouse Antibodies with Increased FcγR-Binding Activity

For a mouse IgG1 antibody having the property of binding to human IL-6 receptor in a pH-dependent manner, the heavy chain VH3-mIgG1 (SEQ ID NO: 49) and the light chain VL3-mk1 (SEQ ID NO: 50) were constructed using the method described in Reference Example 1. Meanwhile, to increase the mouse FcγR-binding activity of VH3-mIgG1, VH3-mIgG1-mF44 (SEQ ID NO: 51) was produced by substituting Asp for Ala at position 327 (EU numbering). Likewise, VH3-mIgG1-mF46 (SEQ ID NO: 52) was produced by substituting Asp for Ser at position 239 and Asp for Ala at position 327, according to EU numbering, in VH3-mIgG1. Fv4-mIgG1, Fv4-mIgG1-mF44, and Fv4-mIgG1-mF46, which contain VH3mIgG1, VH3-mIgG1-mF44, and VH3-mIgG1-mF46, respectively, as the heavy chain, and VL3-mk1 as the light chain, were prepared using the method described in Reference Example 1.

(5-3) Assessment of Mouse FcγR-Binding Activity

VH3/L (WT)mIgG1, VH3/L (WT)mIgG1-mF44, and VH3/L (WT)mIgG1-mF46, which contain VH3mIgG1, VH3-mIgG1-mF44, and VH3-mIgG1-mF46, respectively, as the heavy chain, and L (WT)-CK (SEQ ID NO: 42) as the light chain, were prepared by the method described in Reference Example 1. These antibodies were assessed for their mouse FcγR-binding activity by the method described in Reference Example 2. The result is shown in Table 9. In addition, the ratio of the increase in the mouse FcγR-binding activity of each variant relative to the mIgG1 before alteration is shown in Table 10. In the table, VH3/L (WT)mIgG1, VH3/L (WT)mIgG1-mF44, and VH3/L (WT)-mIgG1-mF46 are shown as mIgG1, mF44, and mF46, respectively.

TABLE 9

| VARIANT | KD (M) | | | |
| NAME | mFc γ RI | mFc γ RIIb | mFc γ RIII | mFc γ RIV |
| mIgG1 | NOT DETECTED | 1.1E−07 | 2.1E−07 | NOT DETECTED |
| mF44 | NOT DETECTED | 8.9E−09 | 6.7E−09 | NOT DETECTED |
| mF46 | NOT DETECTED | 1.2E−09 | 3.6E−09 | NOT DETECTED |

TABLE 10

| VARIANT | BINDING RATIO TO mIgG1 | | | |
| NAME | mFc γ RI | mFc γ RIIb | mFc γ RIII | mFc γ RIV |
| mIgG1 | NOT DETECTED | 1.0 | 1.0 | NOT DETECTED |

TABLE 10-continued

| VARIANT | BINDING RATIO TO mIgG1 | | | |
| --- | --- | --- | --- | --- |
| NAME | mFc γ RI | mFc γ RIIb | mFc γ RIII | mFc γ RIV |
| mF44 | NOT DETECTED | 11.9 | 31.0 | NOT DETECTED |
| mF46 | NOT DETECTED | 91.4 | 57.5 | NOT DETECTED |

The assessment result of Example 4 showing that VH3/L (WT)-mIgG1 having the Fc region of native mouse IgG1 antibody only binds to mouse FcγRIIb and mouse FcγRIII but not to mouse FcγRI and mouse FcγRIV, suggests that mouse FcγRs important for the reduction of antigen concentration are mouse FcγRII and/or mouse FcγRIII. VH3/L (WT)-mIgG-mF44 and VH3/L (WT)-mIgG1-mF46 introduced with an alteration that is thought to increase the FcγR-binding activity of VH3/L (WT)-mIgG1 was demonstrated to have increased binding activity to both of mouse FcγRIIb and mouse FcγRIII.

(5-4) Assessment of the Effect to Reduce the Soluble IL-6 Receptor Concentration in the Plasma of Normal Mice The effect to eliminate soluble IL-6 receptor from the plasma of normal mice administered with the anti-human IL-6 receptor antibody Fv4-mIgG1, Fv4-mIgG1-mF44, or Fv4-mIgG1mF46 was assessed as follows.

An animal model where the soluble human IL-6 receptor concentration is maintained in a steady state in plasma was created by implanting an infusion pump (MINI-OSMOTIC PUMP MODEL2004, alzet) containing soluble human IL-6 receptor under the skin on the back of normal mice (C57BL/6J mouse, Charles River Japan). The in vivo dynamics of soluble human IL-6 receptor after administration of the anti-human IL-6 receptor antibody was assessed in the animal model. To suppress the production of antibodies against soluble human IL-6 receptor, an anti-mouse CD4 monoclonal antibody was administered once at 20 mg/kg into the caudal vein. Then, an infusion pump containing 92.8 μg/ml soluble human IL-6 receptor was subcutaneously implanted on the back of the mice. Three days after implantation of the infusion pump, the anti-human IL-6 receptor antibody was administered once at 1 mg/kg into the caudal vein. The blood was collected from the mice 15 minutes, seven hours, one day, two days, four days, seven days, 14 days (or 15 days), and 21 days (or 22 days) after administration of the anti-human IL-6 receptor antibody. Immediately thereafter, the collected blood was centrifuged at 15,000 rpm and 4° C. for 15 minutes to prepare the plasma. The isolated plasma was stored in a freezer set at −20° C. or below until use.

Figure 11:
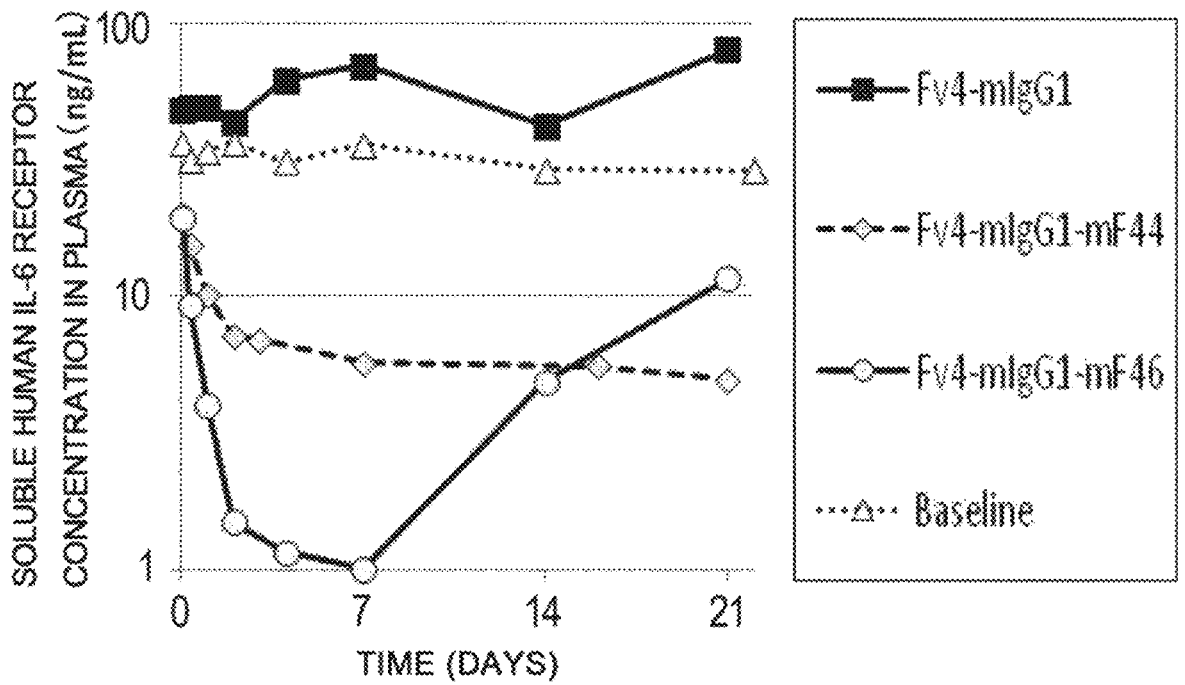
FIG. 11 shows a time course of human IL-6 receptor concentration in the plasma of normal mice administered with Fv4-mIgG1, Fv4-mIgG1-mF44 which is an Fv4-mIgG1 variant with enhanced mouse FcγRIIb binding and mouse FcγRIII binding, and Fv4-mIgG1-mF46 which is an Fv4-mIgG1 variant with further enhanced mouse FcγRIIb binding and mouse FcγRIII binding.

The soluble human IL-6 receptor concentrations in plasma were determined by the method described in (2-1-2). The result is shown in FIG. 11.

Surprisingly, it was demonstrated that, in mice administered with mF44 and mF46 introduced with an alteration to increase the binding activity of mIgG1 (native mouse IgG1) to mouse FcγRIIb and mouse FcγRIII, the plasma IL-6 receptor concentration was markedly reduced as compared to mice administered with mIgG1. In particular, even on day 21 after administration of mF44, the plasma IL-6 receptor concentration in the mF44-administered group was reduced by about 6 times as compared to the plasma IL-6 receptor concentration in the group without antibody administration, and about 10 times as compared to the mIgG1-administered group. On the other hand, on day seven after administration of mF46, the plasma IL-6 receptor concentration in the mF46-administered group was markedly reduced by about 30 times as compared to the plasma IL-6 receptor concentration in the group without antibody administration, and about 50 times as compared to the mIgG1-administered group.

The above findings demonstrate that the elimination of soluble IL-6 receptor from plasma was also accelerated in mice administered with antibodies in which the mouse FcγR-binding activity of an antigen-binding molecule having the Fc regions of mouse IgG1 antibody is increased, as with antibodies in which the mouse FcγR-binding activity of an antigen-binding molecule having the Fc region of human IgG1 antibody is increased. Without being bound by a particular theory, the phenomenon observed as described above can be explained as follows.

When administered to mice, antibodies that bind to a soluble antigen in a pH-dependent manner and have increased FcγR-binding activity are actively incorporated mainly into cells expressing FcγR on the cell membrane. The incorporated antibodies dissociate the soluble antigen under an acidic pH condition in the endosome, and then recycled to plasma via FcRn. Thus, a factor that achieves the effect of eliminating the plasma soluble antigen of such an antibody is the FcγR-binding activity level of the antibody. Specifically, as the FcγR-binding activity is greater, the incorporation into FcγR-expressing cells occurs more actively, and this makes the elimination of soluble antigens from plasma more rapid. Furthermore, as long as the FcγR-binding activity has been increased, the effect can be assessed in the same manner regardless of whether the Fc region contained in an antibody originates from human or mouse IgG1. Specifically, the assessment can be achieved for an Fc region of any animal species, such as any of human IgG1, human IgG2, human IgG3, human IgG4, mouse IgG1, mouse IgG2a, mouse IgG2b, mouse IgG3, rat IgG, monkey IgG, and rabbit IgG, as long as the binding activity to the FcγR of the animal species to be administered has been increased.

[Example 6] The Antigen Elimination Effect by Antibodies with the Binding Activity Increased in an FcγRIIb-Selective Manner (6-1) The Antigen Elimination Effect of Antibodies in which the FcγRIIb-Binding Activity has been Selectively Increased FcγRIII-deficient mice (B6.129P2-FcgrR3tm1Sjv/J mouse, Jackson Laboratories) express mouse FcγRI, mouse FcγRIIb, and mouse FcγRIV, but not mouse FcγRIII. Meanwhile, Fc receptor γ chain-deficient mice (Fcer1g mouse, Taconic, Cell (1994) 76, 519-529) express mouse FcγRIIb alone, but not mouse FcγRI, mouse FcγRIII, and mouse FcγRIV.

As described in Example 5, it was demonstrated that mF44 and mF46 with increased FcγR-binding activity of native mouse IgG1 show selectively enhanced binding to mouse FcγRIIb and mouse FcγRIII. It was conceived that, using the selectively increased binding activity of the antibodies, the condition under which an antibody with selectively enhanced mouse FcγRIIb binding is administered can be mimicked by administering mF44 and mF46 to mouse FcγRIII-deficient mice or Fc receptor γ chain-deficient mice which do not express mouse FcγRIII.

Figure 12:
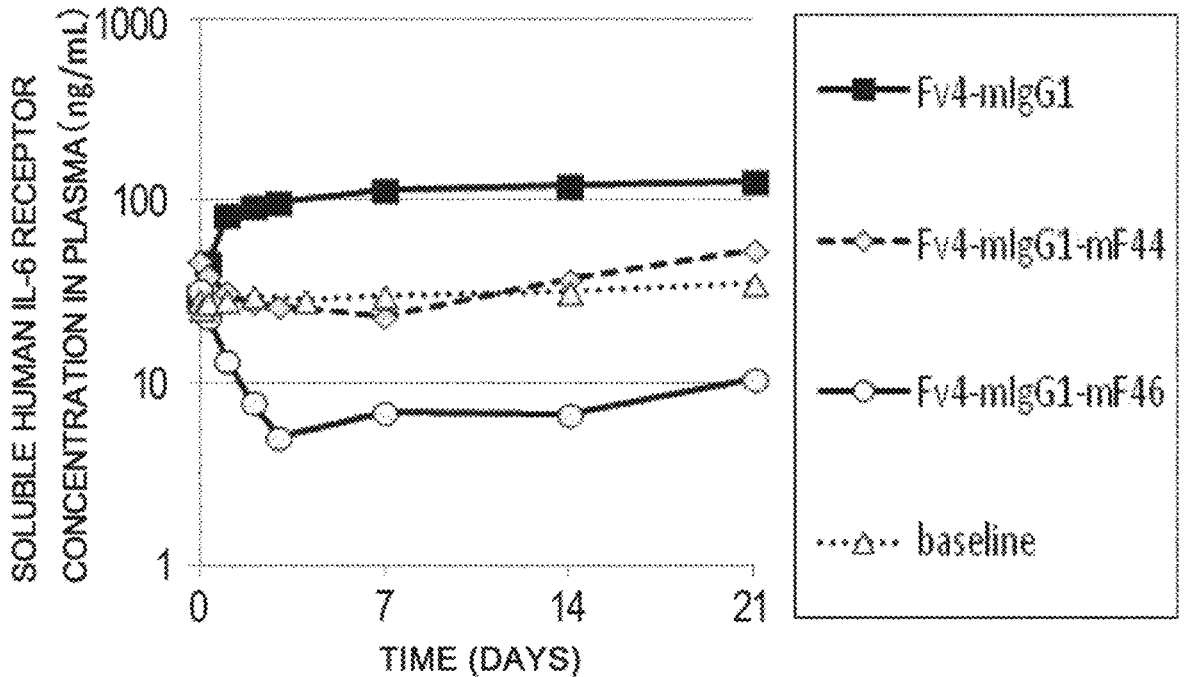
FIG. 12 shows a time course of human IL-6 receptor concentration in the plasma of FcγRIII-deficient mice administered with Fv4-mIgG1, Fv4-mIgG1-mF44 which is an Fv4-mIgG1 variant with enhanced mouse FcγRIIb binding and mouse FcγRIII binding, and Fv4-mIgG1-mF46 which is an Fv4-mIgG1 variant with further enhanced mouse FcγRIIb binding and mouse FcγRIII binding.

(6-2) Assessment of the Antigen Elimination Effect by Selective Enhancement of Binding to Mouse FcγRIIb Using FcγRIII-Deficient Mice The effect to eliminate soluble IL-6 receptor from plasma in FcγRIII-deficient mice administered with the anti-human IL-6 receptor antibody Fv4-mIgG1, Fv4-mIgG1-mF44, or Fv4-mIgG1-mF46 was assessed by the same method described in Example 5. The soluble human IL-6 receptor concentrations in the plasma of the mice were determined by the method described in Example (2-1-2). The result is shown in FIG. 12.

Surprisingly, it was demonstrated that, the plasma IL-6 receptor concentrations in FcγRIII-deficient mice administered with mF44 and mF46, which mimic the condition under which the mouse FcγRIIb-binding activity of mIgG1 (native mouse IgG1) is selectively increased, were markedly reduced as compared to the plasma IL-6 receptor concentration in mice administered with mIgG1. In particular, the plasma IL-6 receptor concentration of the mF44-administered group was reduced by about three times as compared to that of the mIgG1-administered group and the accumulation of antibody concentration due to antibody administration was suppressed. Meanwhile, on day three after administration, the plasma IL-6 receptor concentration of the mF46-administered group was markedly reduced by about six times as compared to the plasma IL-6 receptor concentration of the group without antibody administration, and about 25 times as compared to the plasma IL-6 receptor concentration of the mIgG1-administered group. This result shows that, as the mouse FcγRIIb-binding activity of an anti-human IL-6 receptor antibody that binds to the antigen in a pH-dependent manner is greater, the IL-6 receptor concentration can be reduced more in the plasma of mice administered with the antibody.

Figure 13:
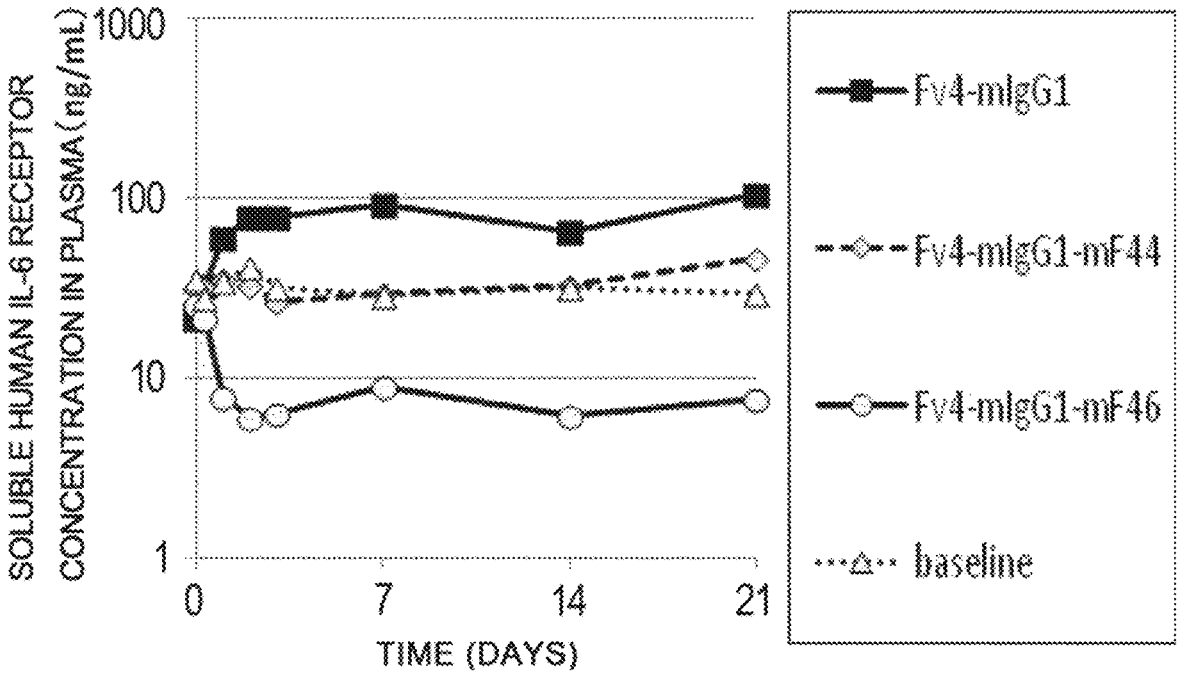
FIG. 13 shows a time course of human IL-6 receptor concentration in the plasma of Fc receptor γ chain-deficient mice administered with Fv4-mIgG1, Fv4-mIgG1-mF44 which is an Fv4-mIgG1 variant with enhanced mouse FcγRIIb binding and mouse FcγRIII binding, and Fv4-mIgG1-mF46 which is an Fv4-mIgG1 variant with further enhanced mouse FcγRIIb binding and mouse FcγRIII binding.

(6-3) Assessment of the Antigen Elimination Effect by Selective Enhancement of Mouse FcγRIIb Binding Using Fc Receptor γ Chain-Deficient Mice The effect to eliminate soluble IL-6 receptor from the plasma of Fc receptor γ chain-deficient mice administered with the anti-human IL-6 receptor antibody Fv4-mIgG1, Fv4-mIgG1-mF44, or Fv4-mIgG1mF46, was assessed by the same method as described in Example 5. The soluble human IL-6 receptor concentrations in the plasma of the mice were determined by the method described in Example (2-1-2). The result is shown in FIG. 13.

As with the case where mF44 and mF46 were administered to FcγRIII-deficient mice, the plasma IL-6 receptor concentration in Fc receptor γ chain-deficient mice administered with mF44 and mF46, which mimic the condition resulting from the selective increase in the mouse FcγRIIb-binding activity of mIgG1 (native mouse IgG1), was demonstrated to be markedly reduced as compared to the plasma IL-6 receptor concentration in Fc receptor γ chain-deficient mice administered with mIgG1. In particular, the plasma IL-6 receptor concentration in the mF44-administered group was reduced to about three times that in the mIgG1-administered group, and the accumulation of antigen concentration due to antibody administration was suppressed. Meanwhile, on day three after administration, the plasma IL-6 receptor concentration in the mF46-administered group was markedly reduced by about five times as compared to that in the group without antibody administration, and about 15 times as compared to that in the mIgG1-administered group.

The results described in Examples (6-2) and (6-3) show that the soluble antigen concentration in the plasma is markedly reduced in the group administered with an antibody that binds to a soluble antigen in a pH-dependent manner and has selectively increased mouse FcγRIIb-binding activity.

[Example 7] The Antigen Elimination Effect of Antibodies with Selective Enhancement of the Binding to FcγRIII (7-1) The Antigen Elimination Effect of Antibodies with Selectively Enhanced FcγRIII Binding FcγRIIb-deficient mice (Fcgr2b (FcγRII) mouse, Taconic) (Nature (1996) 379 (6563), 346-349) express mouse FcγRI, mouse FcγRIII, and mouse FcγRIV, but not mouse FcγRIIb. As described in Example 5, it was demonstrated that mF44 and mF46 resulting from increasing the FcγR-binding activity of native mouse IgG1 show selectively enhanced binding to mouse FcγRIIb and mouse FcγRIII. It was conceived that, based on the use of the selectively increased binding activity of the antibodies, the condition of administration of an antibody with selectively enhanced binding to mouse FcγRIII can be mimicked by administering mF44 or mF46 to mouse FcγRIIb-deficient mice which do not express mouse FcγRIIb.

As described in Example 6, the soluble antigen concentration was reduced in the plasma of FcγRIII-deficient mice, which mimic the condition of administration of an antibody with selectively increased mouse FcγRIIb-binding activity. Meanwhile, whether the soluble antigen concentration is reduced in the plasma of FcγRIIb-deficient mice, which mimic the condition of administration of an antibody with selectively increased mouse FcγRIII-binding activity, was assessed by the test described below.

Figure 14:
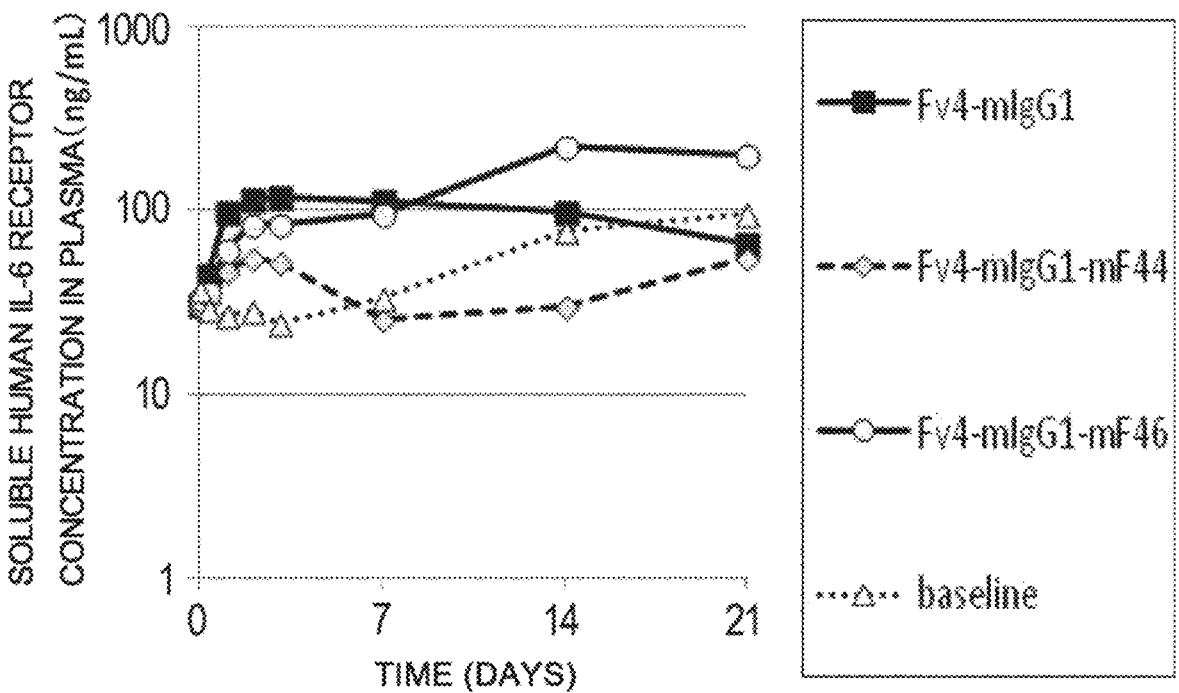
FIG. 14 shows a time course of human IL-6 receptor concentration in the plasma of FcγRIIb-deficient mice administered with Fv4-mIgG1, Fv4-mIgG1-mF44 which is an Fv4-mIgG1 variant with enhanced mouse FcγRIIb binding and mouse FcγRIII binding, and Fv4-mIgG1-mF46 which is an Fv4-mIgG1 variant with further enhanced mouse FcγRIIb binding and mouse FcγRIII binding.

(7-2) Assessment of the Antigen Elimination Effect by Selective Enhancement of Mouse FcγRIII Binding Using FcγRIIb-Deficient Mice The effect to eliminate soluble IL-6 receptor from the plasma of FcγRIIb-deficient mice administered with the anti-human IL-6 receptor antibody Fv4-mIgG1, Fv4-mIgG1-mF44, or Fv4-mIgG1mF46, was assessed by the same method as described in Example 5. The soluble human IL-6 receptor concentrations in plasma were determined by the method described in Example (2-1-2). The result is shown in FIG. 14.

Surprisingly, in the groups administered with mF44 and mF46, which mimic selective increase of the mouse FcγRIII-binding activity of mIgG1 (native mouse IgG1), the plasma IL-6 receptor concentration was reduced, but the remarkable reduction was not confirmed compared to that shown in Example 6.

Without being bound by a particular theory, based on the results described in Examples 5, 6, and 7, the following discussion is possible. The elimination of soluble IL-6 receptor from plasma was found to be markedly accelerated in normal mice expressing both mouse FcγRIIb and mouse FcγRIII that were administered with mF44 and mF46 with selectively increased binding activity of mIgG1 (native mouse IgG1) to mouse FcγRIIb and mouse FcγRIII. Furthermore, it was revealed that, when mF44 and mF46 were administered to mice that express mouse FcγRIIb but not mouse FcγRIII (i.e., FcγRIII-deficient mice and Fc receptor γ chain-deficient mice), the elimination of soluble IL-6 receptor from plasma was also accelerated markedly in the mice. Meanwhile, when mF44 and mF46 were administered to mice that express mouse FcγRIII but not mouse FcγRIIb (i.e., FcγRII-deficient mice), the elimination of soluble IL-6 receptor from plasma was not remarkably accelerated in the mice.

From the above findings, it is thought that, the antibodies mF44 and mF46 in which the binding activity of mIgG1 (native mouse IgG1) to mouse FcγRIIb and mouse FcγRIII is increased, are incorporated into FcγR-expressing cells mainly by mouse FcγRIIb, and thus the soluble antigen in the plasma that binds to the antibodies is eliminated. Meanwhile, the FcγRIII-mediated incorporation of antibody/antigen complexes into FcγR-expressing cells is thought not to significantly contribute to the elimination of the soluble antigen from plasma.

Furthermore, as shown in Example 4, the plasma concentration of soluble IL-6 receptor was markedly reduced in mice administered with Fv4-IgG1-F1087 having increased binding activity to mouse FcγRIIb and mouse FcγRIII, in particular. Meanwhile, the effect to eliminate soluble IL-6 receptor from the plasma of mice administered with Fv4-IgG1-F1182 with increased binding activity to mouse FcγRI and mouse FcγRIV, in particular, was smaller than that of Fv4-IgG1-F1087.

Furthermore, as shown in Example 2, in mice administered with Fv4-IgG1-Fuc whose mouse FcγRIV-binding activity has been considerably increased by having sugar chains with low fucose content (Science (2005) 310 (5753), 1510-1512), the plasma concentration of soluble IL-6 receptor was reduced as compared to that in mice administered with Fv4-IgG1; however, the reduction effect was as small as about twice. Thus, mouse FcγRIV-mediated incorporation of antibodies into FcγR-expressing cells is thought not to significantly contribute to the elimination of soluble antigens from plasma.

In view of the above, it was demonstrate that, of several mouse FcγRs, mouse FcγRIIb plays a major role in antibody incorporation into FcγR-expressing cells in mice. Thus, it would be thought that mutations to be introduced into the mouse FcγR-binding domain particularly preferably include, but are not limited to, mutations that enhance the binding to mouse FcγRIIb.

The above findings demonstrate that, in mice, the FcγRIIb-binding activity of the antibodies to be administered is more preferably increased to accelerate the elimination of soluble antigens from the plasma of a living organism by administering to it antigen-binding molecules that bind to soluble antigens in a pH-dependent manner and have increased FcγR binding activity. Specifically, when administered to a living organism, antigen-binding molecules that bind to soluble antigens in a pH-dependent manner and have increased FcγRIIb-binding activity can accelerate the elimination of the soluble antigens from plasma and effectively reduce the plasma concentration of soluble antigens, and thus, the antigen-binding molecules were revealed to show a very effective action.

[Example 8] Assessment of the Platelet Aggregatory Ability of Antibodies Containing an Fc Region Introduced with an Existing Alteration that Enhances the FcγRIIb Binding (8-1) Preparation of Antibodies Containing an Fc Region Introduced with an Existing Alteration that Enhances the FcγRIIb Binding As described in Example 7, antigens can be efficiently eliminated from the plasma of the living organism by administering antibodies with selectively increased FcγRIIb-binding activity to the living organism. Furthermore, the administration of antibodies containing an Fc region with selectively increased FcγRIIb-binding activity is thought to be preferred from the viewpoint of safety and side effects in the living organism administered with such antibodies.

However, the mouse FcγRIIb binding and mouse FcγRIII binding are both enhanced in mF44 and mF46, and thus the binding enhancement is not selective for mouse FcγRIIb. Since the homology between mouse FcγRIIb and mouse FcγRIII is high, it would be difficult to find an alteration that enhances the mouse FcγRIIb-selective binding while distinguishing the two. Moreover, there is no previous report on Fc regions with selectively enhanced mouse FcγRIIb binding. Also, the homology between human FcγRIIb and human FcγRIIa (the two allotypes, 131Arg and 131His) is also known to be high. Moreover, there is no report on Fc regions that contain an alteration that enhances the human FcγRIIb-selective binding while distinguishing the two (Seung et al., (Mol. Immunol. (2008) 45, 3926-3933); Greenwood et al., (Eur. J. Immunol. (1993) 23 (5), 1098-1104)). Furthermore, it has been reported that antibodies with enhanced FcγRIIa-binding has increased platelet aggregation activity and may increase the risk for developing thrombosis when administered to organisms (Meyer et al. (J. Thromb. Haemost. (2009), 7 (1), 171-181) and Robles-Carrillo et al. (J. Immunol. (2010), 185 (3), 1577-1583)). Thus, whether antibodies with enhanced FcγRIIa binding have an increased platelet aggregatory activity was assessed as follows.

(8-2) Assessment of the Human FcγR-Binding Activity of Antibodies Containing an Fc Region Introduced with an Existing Alteration that Enhances the FcγRIIb Binding Antibodies containing an Fc region introduced with an existing alteration that enhances the human FcγRIIb binding were analyzed for their affinity for human FcγRIa, R-type and H-type FcγRIIa, FcγRIIb, and FcγRIIIa by the following procedure. An H chain was constructed to have, as the antibody H chain variable region, the antibody variable region IL6R-H (SEQ ID NO: 53) against human interleukin 6 receptor which is disclosed in WO2009/125825, and as the antibody H chain constant region, IL6R-G1d (SEQ ID NO: 54) that has G1d resulting from removing the C-terminal Gly and Lys from human IgG1. Then, IL6R-G1d-v3 (SEQ ID NO: 55) was constructed by altering the Fc region of IL6R-G1d by the substitution of Glu for Ser at position 267 (EU numbering) and Phe for Leu at position 328 (EU numbering), as described in Seung et al., (Mol. Immunol. (2008) 45, 3926-3933). IL6R-L (SEQ ID NO: 56) which is the L chain of anti-human interleukin 6 receptor antibody was used as a common antibody L chain, and expressed in combination with respective H chains according to the method described in Reference Example 1, and the resulting antibodies were purified. Hereinafter, antibodies containing IL6R-G1d and IL6R-G1d-v3 as the heavy chain are referred to as IgG1 and IgG1-v3, respectively.

Then, the interaction between FcγR and the above antibodies was kinetically analyzed using Biacore T100 (GE Healthcare). The assay for the interaction was carried out at 25° C. using HBS-EP+ (GE Healthcare) as a running buffer. The chip used was a Series S Sencor Chip CM5 (GE Healthcare) immobilized with Protein A by an amino coupling method. Each FcγR diluted with the running buffer was allowed to interact with the antibodies of interest captured onto the chip to measure the binding of the antibodies to each FcγR. After measurement, 10 mM glycine-HCl (pH 1.5) was reacted to the chip to wash off the captured antibodies to repeatedly use the regenerated chip. A sensorgram obtained as a result of the measurement was analyzed using 1:1 Langmuir binding model with Biacore Evaluation Software, and binding rate constant ka (L/mol/s) and dissociation rate constant kd (1/s) were calculated, and the dissociation constant KD (mol/l) was calculated from these values. The KD values of IgG1 and IgG1-v3 to each FcγR (the KD values of each antibody to each FcγR) are shown in Table 11, while the relative KD values of IgG1-v3, which are obtained by dividing KD of IgG1 to each FcγR by KD of IgG1-v3 to each FcγR, are shown in Table 12.

TABLE 11

| | KD (M) | | | | |
| ANTIBODY | Fc γ RIa | Fc γ RIIaR | Fc γ RIIaH | Fc γ RIIb | Fc γ RIIIa |
|---|---|---|---|---|---|
| IgG1 | 3.4E−10 | 1.2E−06 | 7.7E−07 | 5.3E−06 | 3.1E−06 |
| IgG1-v3 | 1.9E−10 | 2.3E−09 | 1.5E−06 | 1.3E−08 | 8.8E−06 |

TABLE 12

| | Fc γ RIa | Fc γ RIIaR | Fc γ RIIaH | Fc γ RIIb | Fc γ RIIIa |
|---|---|---|---|---|---|
| KD VALUE RATIO | 1.8 | 522 | 0.51 | 408 | 0.35 |

These results confirmed that compared to the antibody containing the IgG1 Fc region, the antibody containing an altered Fc region in which Ser at position 267 has been substituted with Glu and Leu at position 328 has been substituted with Phe, as indicated by EU numbering, in the IgG1 Fc region (Mol. Immunol. (2008) 45, 3926-3933), has 408-times increased affinity to FcγRIIb, and while affinity to FcγRIIa H type was decreased to 0.51 times, affinity to FcγRIIa R type was increased 522 times.

(8-3) Assessment of the Ability to Aggregate Platelets

Next, whether the increased/reduced FcγRIIa affinity of the antibody containing the Fc region with the substitution of Glu for Ser at position 267 and Phe for Leu at position 328 (EU numbering) in the Fc region of IgG1 changes the platelet aggregatory ability, was assessed using platelets derived from donors with H-type or R-type FcγRIIa. The antibody comprising as the light chain omalizumab_VL-CK (SEQ ID NO: 58) and omalizumab_VH-G1d (SEQ ID NO: 57) that contains the heavy chain variable region of hIgG1 antibody (human IgG1 constant region) that binds to IgE and the G1d heavy chain constant region, was constructed using the method described in Reference Example 1. Furthermore, omalizumab_VH-G1d-v3 (SEQ ID NO: 59) was constructed by substituting Glu for Ser at position 267 and Phe for Leu at position 328 (EU numbering) in omalizumab_VH-G1d. Omalizumab-G1d-v3, which contains omalizumab_VH-G1d-v3 as the heavy chain and omalizumab_VL-CK as the light chain, was prepared using the method described in Reference Example 1. This antibody was assessed for the platelet aggregatory ability.

Platelet aggregation was assayed using the platelet aggregometer HEMA TRACER 712 (LMS Co.). First, about 50 ml of whole blood was collected at a fixed amount into 4.5-ml evacuated blood collection tubes containing 0.5 ml of 3.8% sodium citrate, and this was centrifuged at 200 g for 15 minutes. The resultant supernatant was collected and used as platelet-rich plasma (PRP). After PRP was washed with buffer A (137 mM NaCl, 2.7 mM KCl, 12 mM NaHCO₃, 0.42 mM NaH₂PO₄, 2 mM MgCl₂, 5 mM HEPES, 5.55 mM dextrose, 1.5 U/ml apyrase, 0.35% BSA), the buffer was replaced with buffer B (137 mM NaCl, 2.7 mM KCl, 12 mM NaHCO₃, 0.42 mM NaH₂PO₄, 2 mM MgCl₂, 5 mM HEPES, 5.55 mM dextrose, 2 mM CaCl₂, 0.35% BSA). This yielded washed platelets at a density of about 300,000/μl. 156 μl of the washed platelets was aliquoted into assay cuvettes containing a stir bar in the platelet aggregometer. The platelets were stirred at 1000 rpm with the stir bar in the cuvettes maintained at 37.0° C. in the platelet aggregometer. 44 μl of the immune complex of omalizumab-G1d-v3 and IgE at a molar ratio of 1:1, prepared at final concentrations of 600 μg/ml and 686 μg/ml, respectively, was added to the cuvettes. The platelets were reacted with the immune complex for five minutes. Then, at a concentration that does not allow secondary platelet aggregation, adenosine diphosphate (ADP, SIGMA) was added to the reaction mixture to test whether the aggregation is enhanced.

Figure 15:
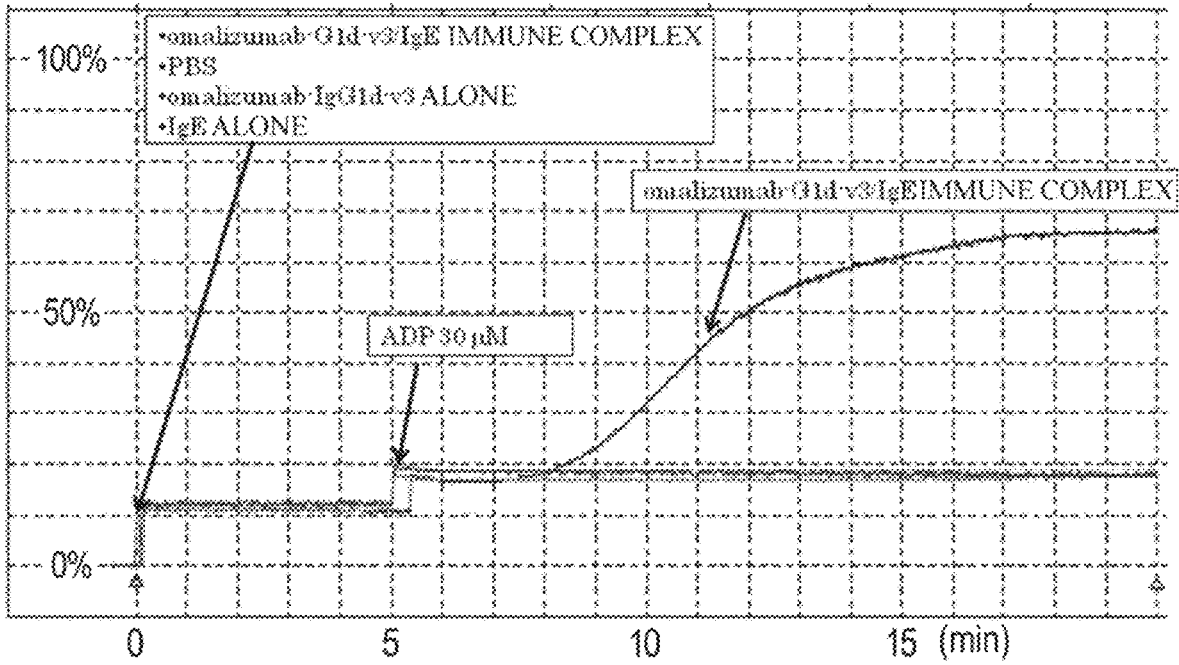
FIG. 15 shows a result of evaluating the platelet aggregation ability of the omalizumab-G1d-v3/IgE immune complex by platelet aggregation assay using platelets derived from donors with FcγRIIa allotype (R/H).
Figure 16:
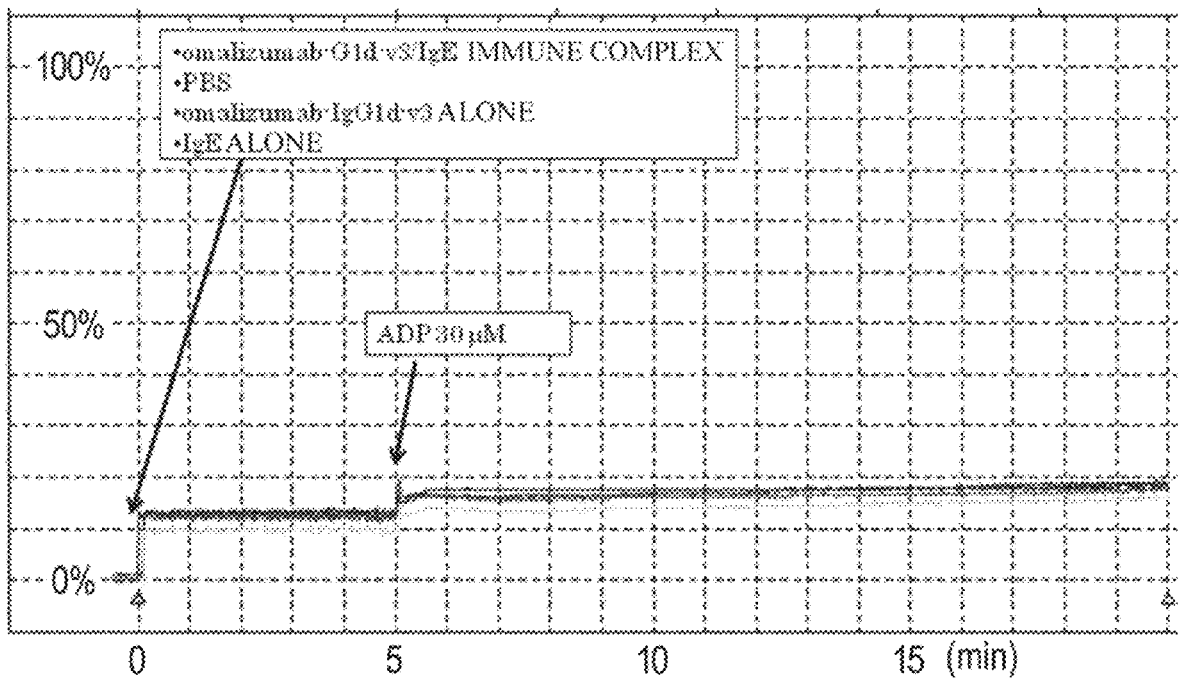
FIG. 16 shows a result of evaluating the platelet aggregation ability of the omalizumab-G1d-v3/IgE immune complex by platelet aggregation assay using platelets derived from donors with FcγRIIa allotype (H/H).

The result of platelet aggregation for each donor with an FcγRIIa polymorphic form (H/H or R/H) obtained from the above assay is shown in FIGS. 15 and 16. From the result in FIG. 15, it is shown that platelet aggregation is enhanced when the immune complex is added to the platelets of a donor with the FcγRIIa polymorphic form (R/H). Meanwhile, as shown in FIG. 16, platelet aggregation was not enhanced when the immune complex is added to the platelets of a donor with the FcγRIIa polymorphic form (H/H).

Next, platelet activation was assessed using activation markers. Platelet activation can be measured based on the increased expression of an activation marker such as CD62p (p-selectin) or active integrin on the platelet membrane surface. 2.3 μl of the immune complex was added to 7.7 μl of the washed platelets prepared by the method described above. After five minutes of reaction at room temperature, activation was induced by adding ADP at a final concentration of 30 μM, and whether the immune complex enhances the ADP-dependent activation was assessed. A sample added with phosphate buffer (pH 7.4) (Gibco), instead of the immune complex, was used as a negative control. Staining was performed by adding, to each post-reaction sample, PE-labeled anti-CD62 antibody (BECTON DICKINSON), PerCP-labeled anti-CD61 antibody, and FITC-labeled PAC-1 antibody (BD bioscience). Fluorescence intensity for each stain was measured using a flow cytometer (FACS CantoII, BD bioscience).

Figure 17:
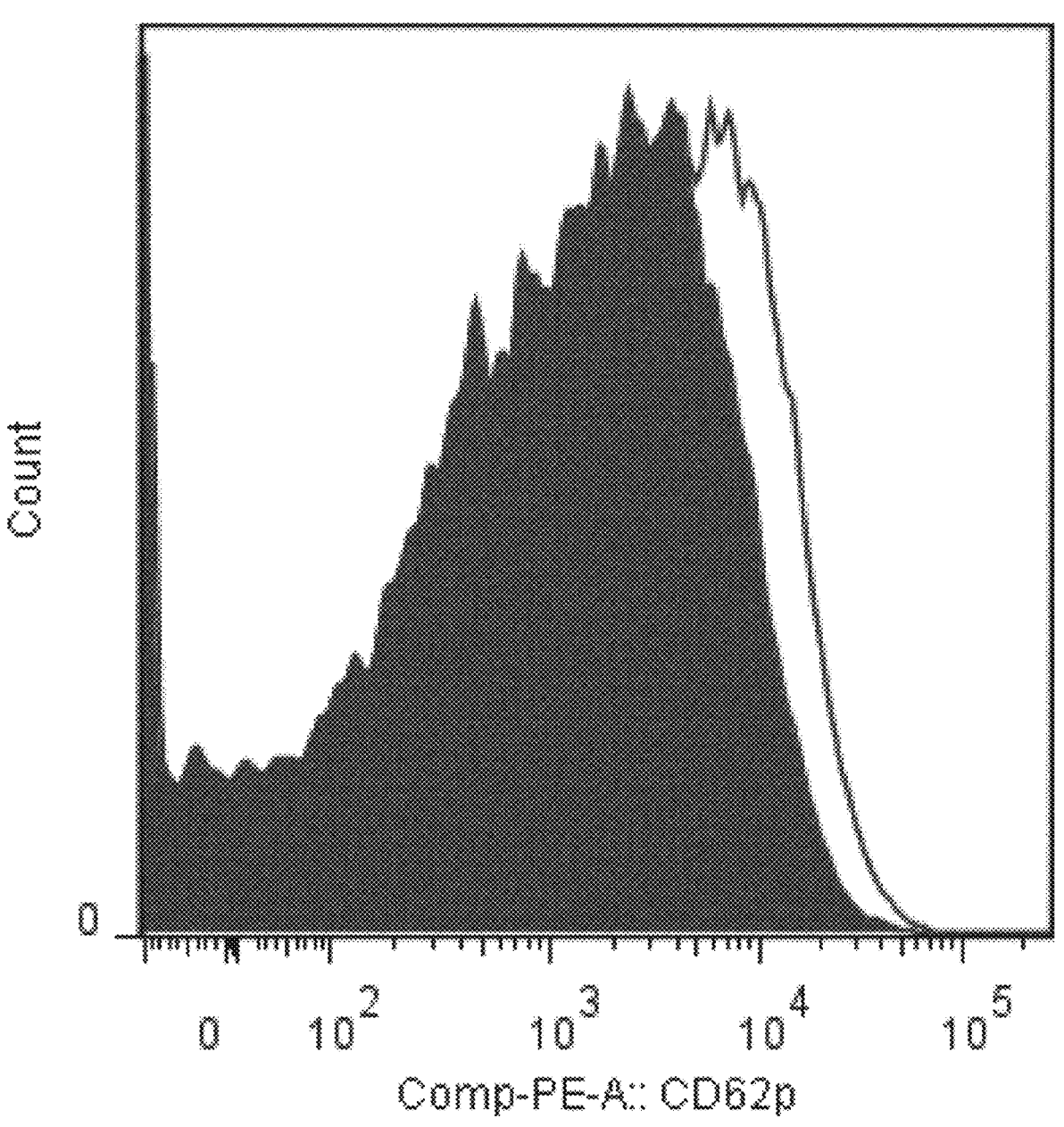
FIG. 17 shows a result of assessing CD62p expression on the membrane surface of washed platelets. The black-filled area in the graph indicates a result of ADP stimulation after reaction with PBS. The area that is not filled in the graph indicates a result of ADP stimulation after reaction with the immune complex.
Figure 18:
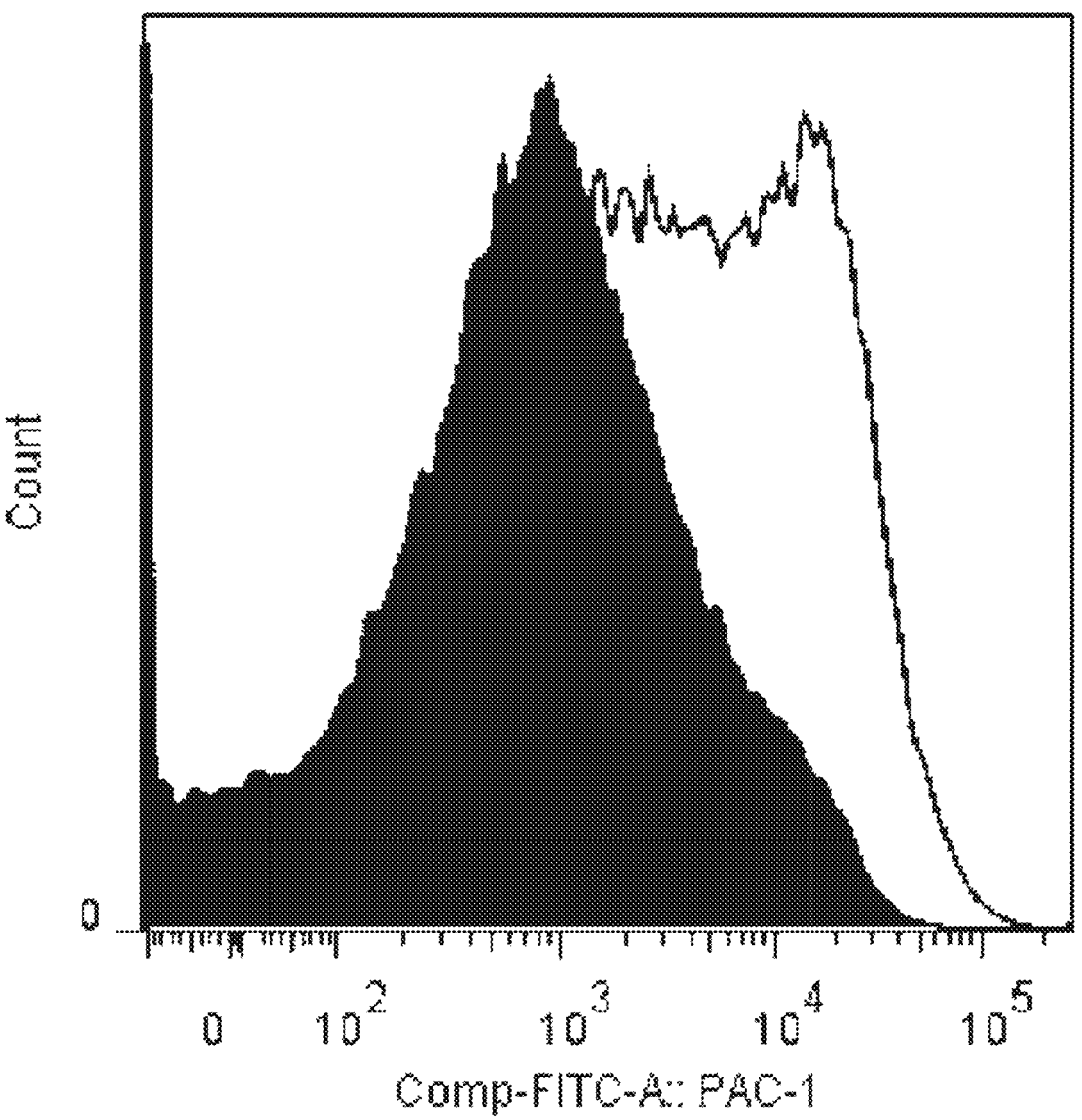
FIG. 18 shows a result of assessing the expression of active integrin on the membrane surface of washed platelets. The black-filled area in the graph indicates a result of ADP stimulation after reaction with PBS. The area that is not filled in the graph indicates a result of ADP stimulation after reaction with the immune complex.

The result on CD62p expression, obtained by the above assay method, is shown in FIG. 17. The result on the activated integrin expression is shown in FIG. 18. The washed platelets used were obtained from a healthy person with the FcγRIIa polymorphic form R/H. Both CD62p and active integrin expressed on platelet membrane surface, which is induced by ADP stimulation, was enhanced in the presence of the immune complex.

The above results demonstrate that the antibody having the Fc region introduced with an existing alteration that enhances the human FcγRIIb binding, which is the substitution of Glu for Ser at position 267 and Phe for Leu at position 328 (EU numbering) in the Fc region of IgG1, promotes the aggregation of platelets whose FcγRIIa allotype is that in which the amino acid at position 131 is R, as compared to platelets whose FcγRIIa allotype is that in which the amino acid at position 131 is H. That is, it was suggested that the risk of developing thrombosis due to platelet aggregation can be increased when an antibody containing an Fc region introduced with an existing alteration that enhances the binding to existing human FcγRIIb is administered to humans having R-type FcγRIIa. It was shown that the antigen-binding molecules containing an Fc region of the present invention that enhances the FcγRIIb binding more selectively not only improves the antigen retention in plasma, but also possibly solves the above problems. Thus, the usefulness of the antigen-binding molecules of the present invention is obvious.

[Example 9] Comprehensive Analysis of FcγRIIb Binding of Variants Introduced with an Alteration at the Hinge Portion in Addition to the P238D Alteration In an Fc produced by substituting Pro at position 238 (EU numbering) with Asp in a naturally-occurring human IgG1, an anticipated combinatorial effect could not be obtained even by combining it with another alteration predicted to further increase FcγRIIb binding from the analysis of naturally-occurring antibodies. Therefore, in order to find variants that further enhance FcγRIIb binding, alterations were comprehensively introduced into the altered Fc produced by substituting Pro at position 238 (EU numbering) with Asp. IL6R-F11 (SEQ ID NO: 60) was produced by introducing an alteration of substituting Met at position 252 (EU numbering) with Tyr and an alteration of substituting Asn at position 434 (EU numbering) with Tyr in IL6R-G1d (SEQ ID NO: 54) which was used as the antibody H chain. Furthermore, IL6R-F652 (SEQ ID NO: 61) was prepared by introducing an alteration of substituting Pro at position 238 (EU numbering) with Asp into IL6R-F11. Expression plasmids containing an antibody H chain sequence were prepared for each of the antibody H chain sequences produced by substituting the region near the residue at position 238 (EU numbering) (positions 234 to 237, and 239 (EU numbering)) in L6R-F652 each with 18 amino acids excluding the original amino acids and Cysteine. IL6R-L (SEQ ID NO: 56) was utilized as an antibody L chain. These variants were expressed and purified by the method of Reference Example 1. These Fc variants are called PD variants. Interactions of each PD variant with FcγRIIa type R and FcγRIIb were comprehensively evaluated by the method of Reference Example 2.

Figure 19:
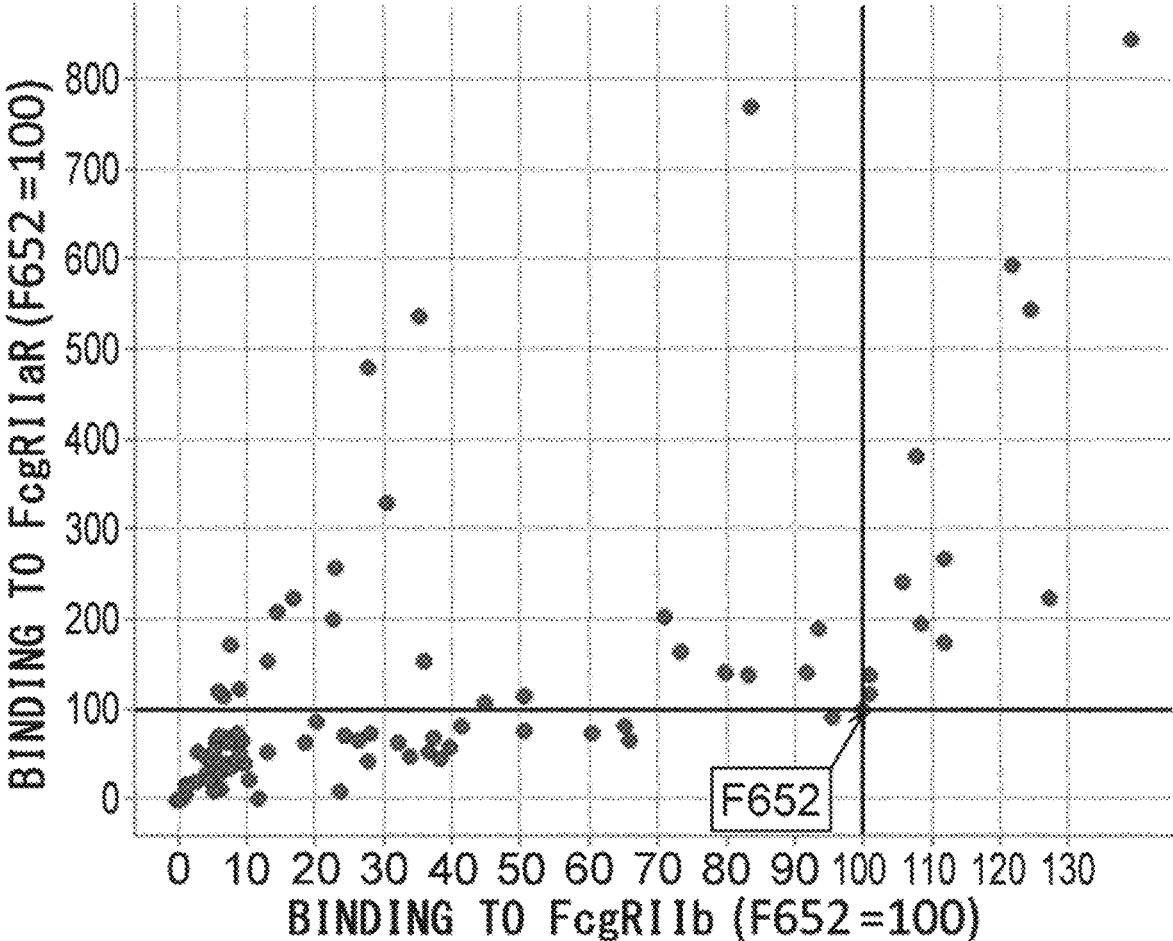
FIG. 19 shows a graph in which the horizontal axis shows the relative value of FcγRIIb-binding activity of each PD variant, and the vertical axis shows the relative value of FcγRIIa type R-binding activity of each PD variant. The value for the amount of binding of each PD variant to each FcγR was divided by the value for the amount of binding of IL6R-F652/IL6R-L, which is a control antibody prior to introduction of the alteration (IL6R-F652, defined by SEQ ID NO: 61, is an antibody heavy chain comprising an altered Fc with substitution of Pro at position 238 (EU numbering) with Asp), to each FcγR; and then the obtained value was multiplied by 100, and used as the relative binding activity value for each PD variant to each FcγR. The F652 plot in the figure shows the value for IL6R-F652/IL6R-L.

A figure that shows the results of analyzing the interaction with the respective FcγRs was produced according to the following method. The value obtained by dividing the value for the amount of binding of each PD variant to each FcγR by the value for the amount of FcγR binding of the pre-altered antibody which is used as the control (IL6R-F652/IL6R-L, which has an alteration of substituting Pro at position 238 (EU numbering) with Asp and then multiplying the result by 100, was shown as the relative binding activity value of each PD variant to each FcγR. The horizontal axis shows relative values of the FcγRIIb-binding activity of each PD variant, and the vertical axis shows relative values of the FcγRIIa type R-binding activity values of each PD variant (FIG. 19).

As a result, it was found that the FcγRIIb binding of eleven types of alterations were enhanced compared with the antibody before introducing alterations, and they have the effects of maintaining or enhancing FcγRIIa type R-binding. The activities of these eleven variants to bind FcγRIIb and FcγRIIa R are summarized in Table 13. In the table, the sequence ID numbers refer to those of the H chains of the variants, and alteration refers to the alteration introduced into IL6R-F11 (SEQ ID NO: 60).

TABLE 13

| VARIANT NAME | ALTERATION | RELATIVE BINDING ACTIVITY TO FcγRIIb | RELATIVE BINDING ACTIVITY TO FcγRIIaR |
|---|---|---|---|
| IL6R-F652/IL6R-L | P238D | 100 | 100 |
| IL6R-PD042/IL6R-L | P238D/L234W | 106 | 240 |
| IL6R-PD043/IL6R-L | P238D/L234Y | 112 | 175 |
| IL6R-PD079/IL6R-L | P238D/G237A | 101 | 138 |
| IL6R-PD080/IL6R-L | P238D/G237D | 127 | 222 |
| IL6R-PD081/IL6R-L | P238D/G237E | 101 | 117 |
| IL6R-PD082/IL6R-L | P238D/G237F | 108 | 380 |
| IL6R-PD086/IL6R-L | P238D/G237L | 112 | 268 |
| IL6R-PD087/IL6R-L | P238D/G237M | 109 | 196 |
| IL6R-PD094/IL6R-L | P238D/G237W | 122 | 593 |

TABLE 13-continued

| VARIANT NAME | ALTERATION | RELATIVE BINDING ACTIVITY TO FcγRIIb | RELATIVE BINDING ACTIVITY TO FcγRIIaR |
|---|---|---|---|
| IL6R-PD095/IL6R-L | P238D/G237Y | 124 | 543 |
| IL6R-PD097/IL6R-L | P238D/S239D | 139 | 844 |

Figure 20:
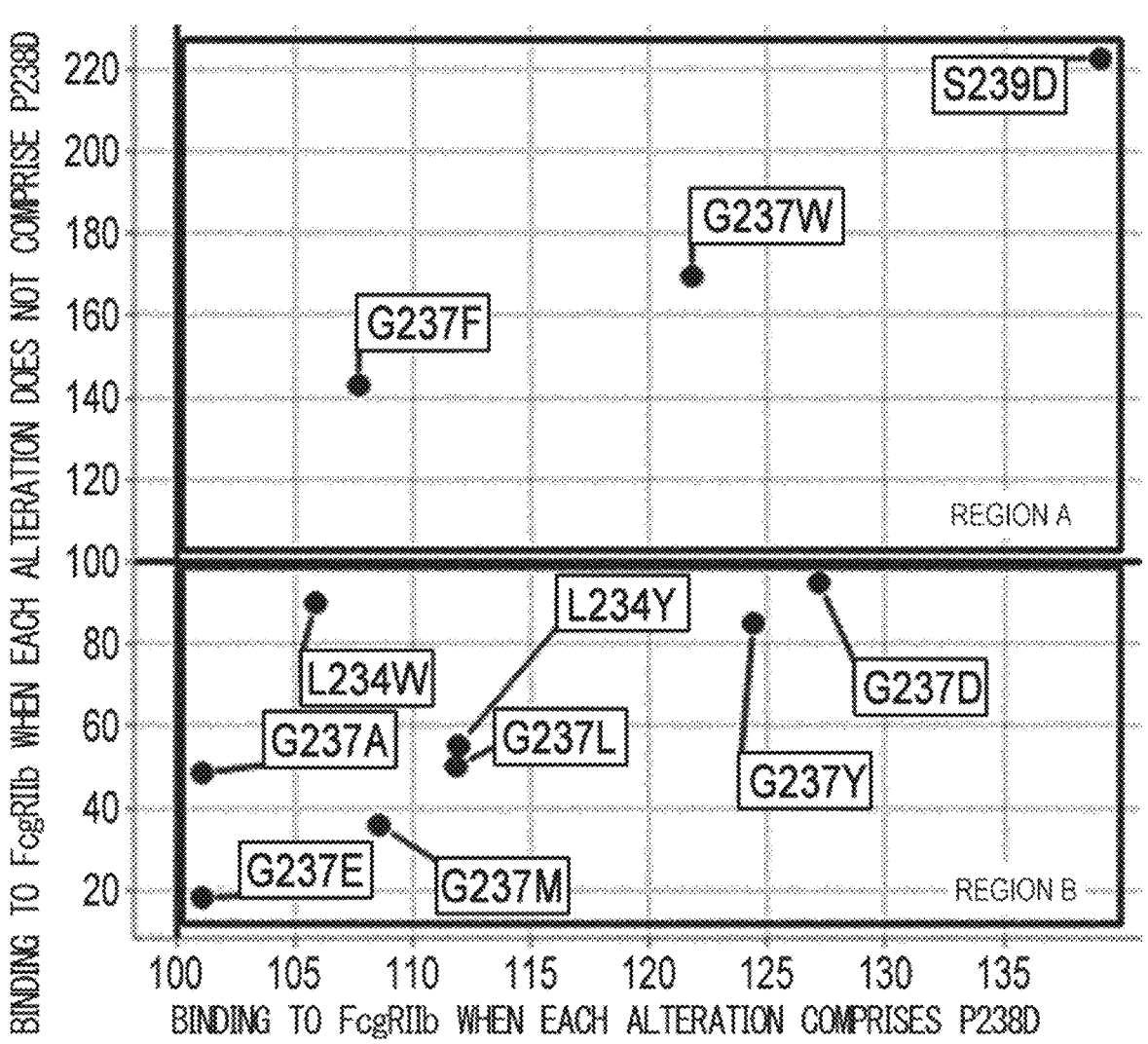
FIG. 20 shows a graph in which the vertical axis shows the relative value of FcγRIIb-binding activity of variants produced by introducing each alteration into GpH7-B3 (SEQ ID NO: 63)/GpL16-k0 which does not have the P238D alteration, and the horizontal axis shows the relative value of FcγRIIb-binding activity of variants produced by introducing each alteration into IL6R-F652 (SEQ ID NO: 61)/IL6R-L which has the P238D alteration. The value for the amount of FcγRIIb binding of each variant was divided by the value for the amount of FcγRIIb binding of the pre-altered antibody; and then the obtained value was multiplied by 100, and used as the value of relative binding activity. Here, region A contains alterations that exhibit the effect of enhancing FcγRIIb binding in both cases where an alteration is introduced into GpH7-B3/GpL16-k0 which does not have P238D and where an alteration is introduced into IL6R-F652/IL6R-L which has P238D. Region B contains alterations that exhibit the effect of enhancing FcγRIIb binding when introduced into GpH7-B3/GpL16-k0 which does not have P238D, but do not exhibit the effect of enhancing FcγRIIb binding when introduced into IL6R-F652/IL6R-L which has P238D.

FIG. 20 shows relative values for the FcγRIIb-binding activity obtained by additionally introducing the above eleven alterations into a variant carrying the P238D alteration, and relative values for the FcγRIIb-binding activity of a variant obtained by introducing the alterations into an Fc that does not contain the P238D. These eleven alterations enhanced the amount of FcγRIIb binding compared with before introduction when they were further introduced into the P238D variant. On the contrary, the effect of lowering FcγRIIb binding was observed for eight of those alterations except G237F, G237W, and S239D, when they were introduced into the variant that does not contain P238D (data not shown).

These results showed that, based on the effects of introducing alterations into a naturally-occurring IgG1, it is difficult to predict the effects of combining and introducing the same alterations into the variant containing the P238D alteration. In other words, it would not have been possible to discover these eight alterations identified this time without this investigation that introduces the same alterations are combined and introduced into the variant containing the P238D alteration.

The results of measuring KD values of the variants indicated in Table 13 for FcγRIa, FcγRIIaR, FcγRIIaH, FcγRIIb, and FcγRIIIaV by the method of Reference Example 2 are summarized in Table 14. In the table, alteration refers to the alteration introduced into IL6R-F11 (SEQ ID NO: 60). The template used for producing IL6R-F11, IL6R-G1d/IL6R-L, is indicated with an asterisk (*). Furthermore, KD (IIaR)/KD (IIb) and KD (IIaH)/KD (IIb) in the table respectively show the value obtained by dividing the KD value of each variant for FcγRIIaR by the KD value of each variant for FcγRIIb, and the value obtained by dividing the KD value of each variant for FcγRIIaH by the KD value of each variant for FcγRIIb. KD (IIb) of the parent polypeptide/KD (IIb) of the variant refers to a value obtained by dividing the KD value of the parent polypeptide for FcγRIIb by the KD value of each variant for FcγRIIb. In addition, Table 14 shows KD values for the stronger of the FcγRIIaR- and FcγRIIaH-binding activities of each variant/KD values for the stronger of the FcγRIIaR- and FcγRIIaH-binding activities of the parent polypeptide. Here, parent polypeptide refers to a variant which has IL6R-F11 (SEQ ID NO: 60) as the H chain. It was determined that, due to weak binding of FcγR to IgG, it was impossible to accurately analyze some of the binding by kinetic analysis, and thus the values in the last 11 rows of the fourth column (FcγRIIaH) and the last 12 rows of the sixth column (FcγRIIIaV) in Table 14 were calculated by using Equation 2 of Reference Example 2.

$$KD = C \cdot R_{max}/(R_{eq} - RI) - C \qquad \text{[Equation 2]}$$

Table 14 shows that all variants improved their affinity for FcγRIIb in comparison with IL6R-F11, and the range of improvement was 1.9 fold to 5.0 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, these values show the degree of binding selectivity of each variant for FcγRIIb, and a larger value indicates a higher binding selectivity for FcγRIIb. For the parent polypeptide IL6R-F11/Th6R-L, the ratio of KD value for FcγRIIaR/KD value for FcγRIIb and the ratio of KD value for FcγRIIaH/KD value for FcγRIIb are both 0.7, and accordingly all variants in Table 14 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or reduced binding compared with the binding by the stronger of the FcγRIIaR- and FcγRIIaH-binding activities of the parent polypeptide. Since this value was 0.7 to 5.0 for the variants obtained this time, one may say that binding by the stronger of the FcγRIIaR- and FcγRIIaH-binding activities of the variants obtained this time was nearly the same or decreased in comparison with the parent polypeptide. These results showed that compared with the parent polypeptide, the variants obtained this time have maintained or decreased binding activities to FcγRIIa type R and type H and enhanced binding activity to FcγRIIb, and thus have improved selectivity for FcγRIIb. Furthermore, compared with IL6R-F11, all variants had lower affinity to FcγRIa and FcγRIIIaV.

to introduction of P238D. Therefore, to pursue the reason for this phenomena, the three-dimensional structure of the complex formed between an IgG1 Fc containing the P238D mutation (hereinafter, referred to as Fc (P238D)) and the extracellular region of FcγRIIb was elucidated by X-ray crystal structure analysis, and this was compared to the three-dimensional structure of the complex formed between the Fc of a naturally-occurring IgG1 (hereinafter, referred to as Fc (WT)) and the extracellular region of FcγRIIb, and the binding modes were compared. Multiple reports have been made on the three-dimensional structure of a complex formed between an Fc and an FcγR extracellular region; and the three-dimensional structures of the Fc (WT)/FcγRIIIb extracellular region complex (Nature (2000) 400, 267-273; J. Biol. Chem. (2011) 276, 16469-16477), the Fc (WT)/FcγRIIIa extracellular region complex (Proc. Natl. Acad. Sci. USA (2011) 108, 12669-126674), and the Fc (WT)/FcγRIIa extracellular region complex (J. Immunol. (2011) 187, 3208-3217) have been analyzed. While the three-dimensional structure of the Fc (WT)/FcγRIIb extracellular region complex has not been analyzed, FcγRIIa, whose three-dimensional structure in complex with Fc (WT) has already known, and FcγRIIb match 93% in amino acid sequence of their extracellular region and have very high homology. Thus, the three-dimensional structure of the Fc (WT)/FcγRIIb extracellular region complex was predicted by modeling using the crystal structure of the Fc (WT)/FcγRIIa extracellular region complex.

TABLE 14

| ALTERATION | KD (mol/L) | | | | | KD (IIaR)/ KD (IIb) | KD (IIaH)/ KD (IIb) | KD (IIb) OF PARENT POLYPEPTIDE/ KD (IIb) OF ALTERED POLYPEPTIDE | KD VALUE FOR THE STRONGER OF THE BINDING ACTIVITIES OF A VARIANT TO FcγRIIaR AND FcγRIIaH/ KD VALUE FOR THE STRONGER OF THE BINDING ACTIVITIES OF THE PARENT POLYPEPTIDE TO FcγRIIaR AND FcγRIIaH |
|---|---|---|---|---|---|---|---|---|---|
| | FcγRIa | FcγRIIaR | FcγRIIaH | FcγRIIb | FcγRIIIaV | | | | |
| * | 3.2E−10 | 1.0E−06 | 6.7E−07 | 2.6E−06 | 3.5E−07 | 0.4 | 0.3 | 2.6 | 0.1 |
| | 9.0E−10 | 5.0E−06 | 5.0E−06 | 6.8E−06 | 1.5E−06 | 0.7 | 0.7 | 1.0 | 1.0 |
| L234W/P238D | 6.3E−08 | 1.6E−05 | 1.9E−05 | 2.0E−06 | 3.7E−05 | 8.1 | 9.5 | 3.4 | 3.2 |
| L234Y/P238D | 7.5E−08 | 2.6E−05 | 2.3E−05 | 1.6E−06 | 4.5E−05 | 15.9 | 14.4 | 4.2 | 4.6 |
| G237A/P238D | 1.4E−07 | 3.2E−05 | 2.1E−05 | 3.0E−06 | 3.7E−05 | 10.5 | 7.0 | 2.3 | 4.2 |
| G237D/P238D | 1.4E−07 | 2.1E−05 | 2.5E−05 | 2.0E−06 | 4.3E−05 | 10.7 | 12.8 | 3.5 | 4.2 |
| G237E/P238D | 3.4E−07 | 3.8E−05 | 2.5E−05 | 3.6E−06 | 4.1E−05 | 10.6 | 7.0 | 1.9 | 5.0 |
| G237F/P238D | 5.2E−08 | 1.4E−05 | 1.6E−05 | 3.4E−06 | 4.3E−05 | 4.1 | 4.7 | 2.0 | 2.8 |
| G237L/P238D | 1.2E−07 | 1.8E−05 | 1.8E−05 | 2.6E−06 | 4.1E−05 | 6.9 | 7.1 | 2.7 | 3.5 |
| G237M/P238D | 5.2E−08 | 2.2E−05 | 2.0E−05 | 2.9E−06 | 3.7E−05 | 7.7 | 7.0 | 2.4 | 4.0 |
| G237W/P238D | 3.6E−08 | 7.2E−06 | 1.2E−05 | 2.3E−06 | 3.8E−05 | 3.1 | 5.2 | 2.9 | 1.4 |
| G237Y/P238D | 9.3E−08 | 7.9E−06 | 1.5E−05 | 2.3E−06 | 4.2E−05 | 3.4 | 6.4 | 2.9 | 1.6 |
| P238D/S239D | 4.9E−09 | 3.5E−06 | 1.9E−05 | 1.4E−06 | 1.7E−05 | 2.6 | 14.0 | 5.0 | 0.7 |

Figure 21:
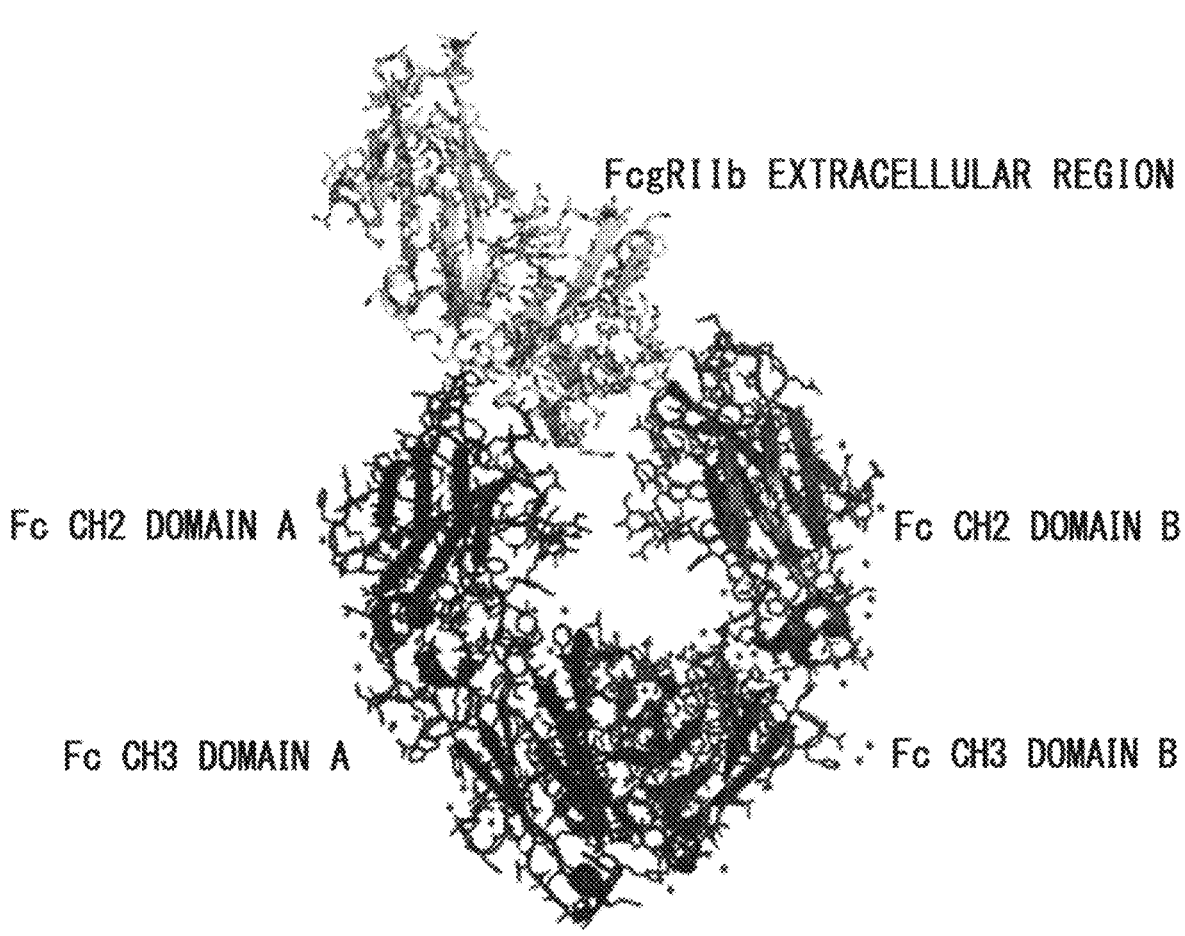
FIG. 21 shows a crystal structure of the Fc(P238D)/FcγRIIb extracellular region complex.
Figure 22:
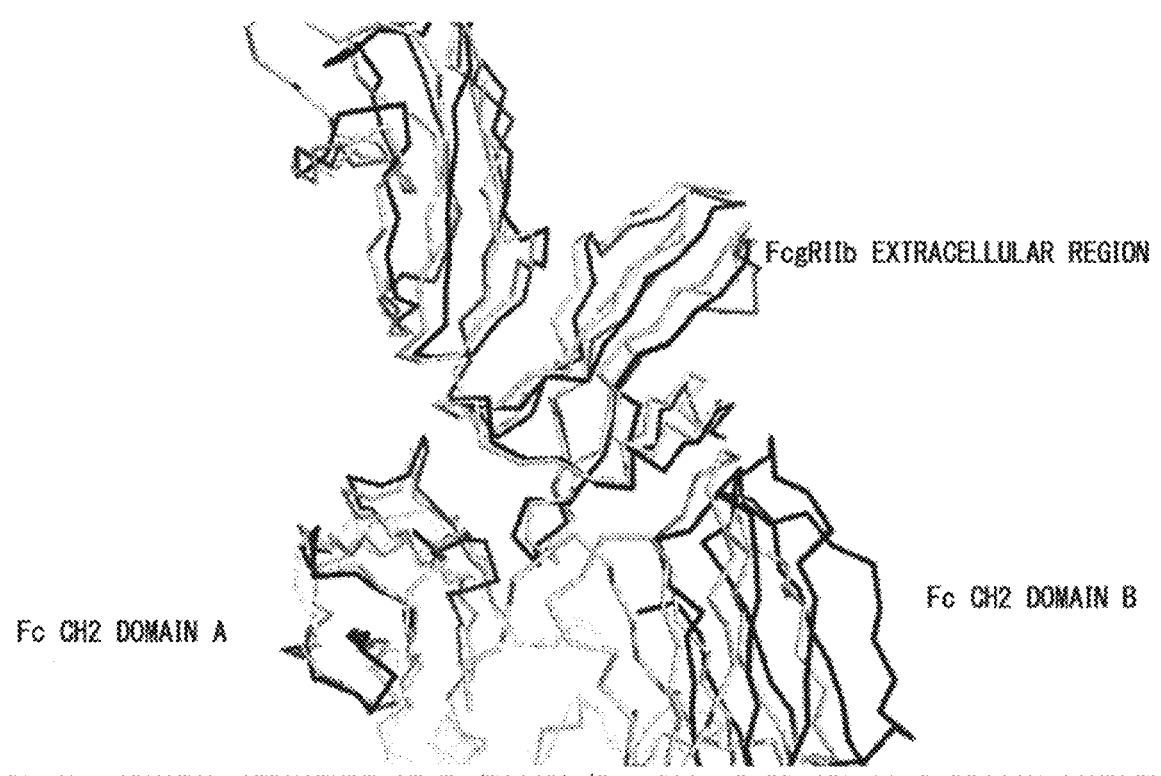
FIG. 22 shows an image of superimposing the crystal structure of the Fc(P238D)/FcγRIIb extracellular region complex and the model structure of the Fc(WT)/FcγRIIb extracellular region complex, with respect to the FcγRIIb extracellular region and the Fc CH2 domain A by the least squares fitting based on the Cα atom pair distances.

[Example 10] X-Ray Crystal Structure Analysis of a Complex Formed Between an Fc Containing P238D and an Extracellular Region of FcγRIIb As indicated earlier in Example 9, even though an alteration that is predicted from the analysis of naturally-occurring IgG1 antibodies to improve FcγRIIb-binding activity or selectivity for FcγRIIb is introduced into an Fc containing P238D, the FcγRIIb-binding activity was found to decrease, and the reason for this may be that the structure at the interacting interface between Fc and FcγRIIb is changed due The three-dimensional structure of the Fc (P238D)/FcγRIIb extracellular region complex was determined by X-ray crystal structure analysis at 2.6 Å resolution. The structure obtained as a result of this analysis is shown in FIG. 21. The FcγRIIb extracellular region is bound between two Fc CH2 domains, and this was similar to the three-dimensional structures of complexes formed between Fc (WT) and the respective extracellular region of FcγRIIIa, FcγRIIIb, or FcγRIIa analyzed so far. Next, for detailed comparison, the crystal structure of the Fc (P238D)/FcγRIIb extracellular region complex and the model structure of the Fc (WT)/FcγRIIb extracellular region complex were super-imposed by the least squares fitting based on the Cα atom pair distances with respect to the FcγRIIb extracellular region and the Fc CH2 domain A (FIG. 22). In that case, the degree of overlap between Fc CH2 domains B was not satisfactory, and conformational differences were found in this portion. Furthermore, using the crystal structure of the Fc (P238D)/FcγRIIb extracellular region complex and the model structure of the Fc (WT)/FcγRIIb extracellular region complex, pairs of atoms that have a distance of 3.7 Å or less between the extracted FcγRIIb extracellular region and Fc CH2 domain B were compared for comparison of the interatomic interaction between FcγRIIb and Fc (WT) CH2 domain B with the interatomic interaction between FcγRIIb and Fc (P238D) CH2 domain B. As shown in Table 15, the interatomic interactions between Fc CH2 domain B and FcγRIIb in Fc (P238D) and Fc (WT) did not match.

located inside Fc (WT), forming a hydrophobic core with residues around position 238. However, if Pro at position 238 (EU numbering) is altered to highly hydrophilic and charged Asp, the presence of the altered Asp residue in a hydrophobic core is energetically disadvantageous in terms of desolvation. Therefore, in Fc (P238D), to cancel this energetically disadvantageous situation, the amino acid residue at position 238 (EU numbering) changes its orientation to face the solvent region, and this may have caused this change in the loop structure near the amino acid residue at position 238. Furthermore, since this loop is not far from the hinge region crosslinked by S—S bonds, its structural change will not be limited to a local change, and will affect the relative positioning between the FcCH2 domain A and domain B. As a result, the interatomic interactions between FcγRIIb and Fc CH2 domain B were assumed to have been changed. Therefore, predicted effects could not be observed

TABLE 15

| FcγRIIb ATOM | | | Fc (P648D) CH2 DOMAIN B INTERACTION PARTNER (DISTANCE BETWEEN ATOMS, Å) | | | | Fc (WT) CH2 DOMAIN B INTERACTION PARTNER (DISTANCE BETWEEN ATOMS, Å) | | | |
|---|---|---|---|---|---|---|---|---|---|---|
| Val | 116 | CG2 | | | | | Asp | 265 | OD2 | (3.47) |
| | | | | | | | Gly | 237 | O | (3.65) |
| Ser | 126 | OG | Ser | 298 | N | (3.31) | | | | |
| | | | Ser | 298 | CB | (3.32) | | | | |
| | | | Tyr | 296 | O | (3.05) | | | | |
| Lys | 128 | CA | Ser | 298 | OG | (3.50) | | | | |
| Phe | 129 | CB | Ser | 298 | O | (3.36) | | | | |
| Phe | 129 | CD2 | | | | | Asn | 297 | CB | (3.50) |
| | | | | | | | Asn | 297 | CG | (3.43) |
| Lys | 128 | C | Ser | 298 | OG | (3.47) | | | | |
| Phe | 129 | N | Ser | 298 | OG | (3.30) | | | | |
| Phe | 129 | O | Ser | 267 | OG | (3.54) | | | | |
| Arg | 131 | CB | | | | | Val | 266 | O | (3.02) |
| Arg | 131 | CG | | | | | Val | 266 | O | (3.22) |
| Arg | 131 | CD | | | | | Val | 266 | CG1 | (3.45) |
| | | | | | | | Val | 266 | C | (3.55) |
| | | | | | | | Val | 266 | O | (3.10) |
| Arg | 131 | NE | Ala | 327 | O | (3.60) | Val | 266 | C | (3.66) |
| | | | | | | | Val | 266 | O | (3.01) |
| | | | | | | | Val | 266 | N | (3.49) |
| Arg | 131 | CZ | Asp | 270 | CG | (3.64) | Val | 266 | N | (3.13) |
| | | | Asp | 270 | OD2 | (3.22) | | | | |
| | | | Asp | 270 | OD1 | (3.27) | | | | |
| | | | Ala | 327 | CB | (3.63) | | | | |
| Arg | 131 | NH1 | Asp | 270 | CG | (3.19) | Val | 266 | CG1 | (3.47) |
| | | | Asp | 270 | OD2 | (2.83) | Val | 266 | N | (3.43) |
| | | | Asp | 270 | OD1 | (2.99) | Thr | 299 | OG1 | (3.66) |
| | | | Ser | 267 | CB | (3.56) | Ser | 298 | O | (3.11) |
| Arg | 131 | NH2 | Asp | 270 | CG | (3.20) | Asp | 265 | CA | (3.16) |
| | | | Asp | 270 | OD2 | (2.80) | Val | 266 | N | (3.37) |
| | | | Asp | 270 | OD1 | (2.87) | | | | |
| | | | Ala | 327 | CB | (3.66) | | | | |
| Tyr | 157 | CE1 | | | | | Leu | 234 | CG | (3.64) |
| | | | | | | | Leu | 234 | CD1 | (3.61) |
| Tyr | 157 | OH | | | | | Gly | 236 | O | (3.62) |
| | | | | | | | Leu | 234 | CA | (3.48) |
| | | | | | | | Leu | 234 | CG | (3.45) |

Figure 23:
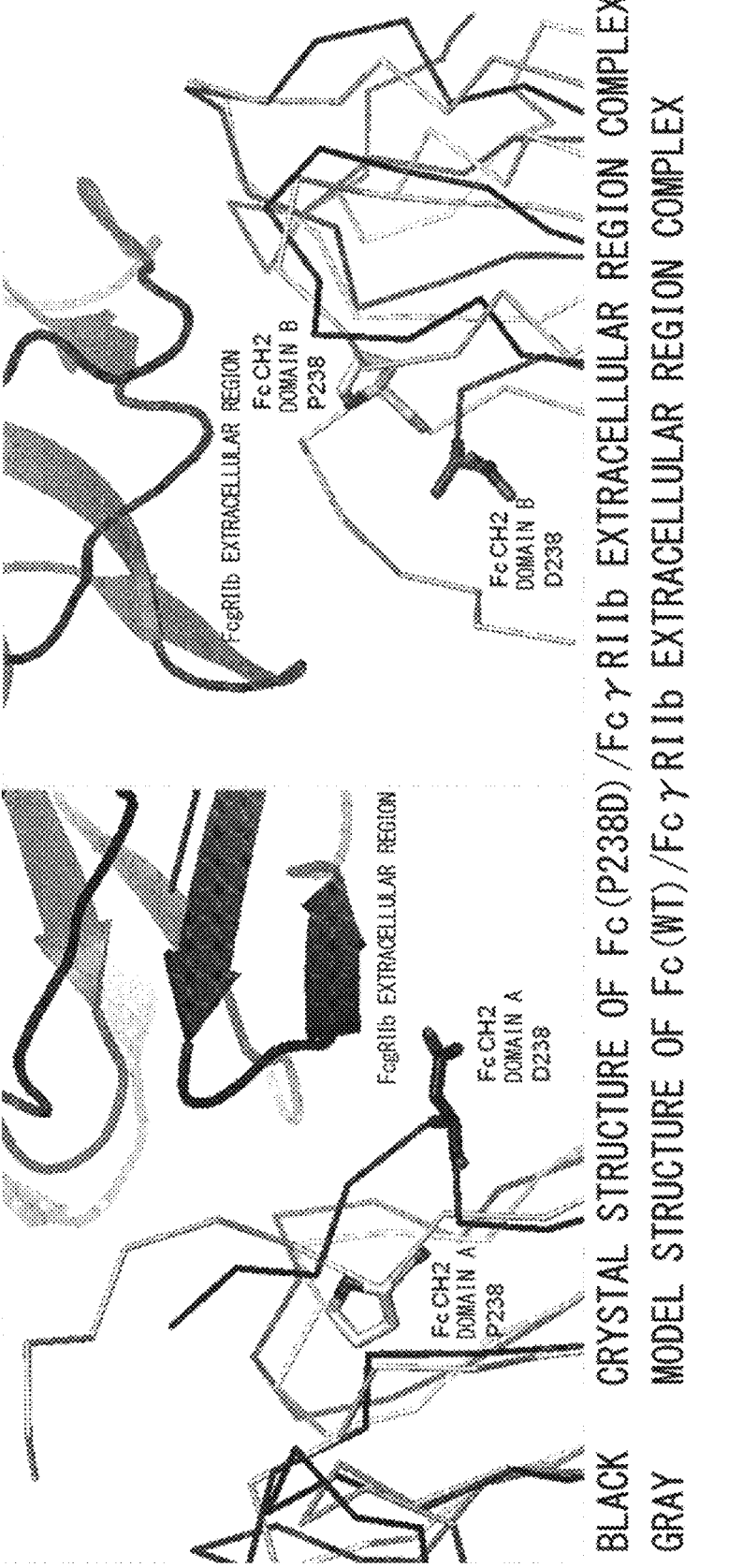
FIG. 23 shows comparison of the detailed structure around P238D after superimposing the crystal structure of the Fc(P238D)/FcγRIIb extracellular region complex and the model structure of the Fc(WT)/FcγRIIb extracellular region complex with respect to the only Fc CH2 domain A or the only Fc CH2 domain B by the least squares fitting based on the Cα atom pair distances.

Furthermore, the detailed structures around P238D were compared by superposing the X-ray crystal structure of Fc (P238D)/FcγRIIb extracellular region complex on the model structure of the Fc (WT)/FcγRIIb extracellular region complex using the least squares method based on the Cα atomic distance between Fc CH2 domains A and B alone. As the position of the amino acid residue at position 238 (EU numbering), i.e., a mutagenesis position of Fc (P238D), is altered from Fc (WT), the loop structure around the amino acid residue at position 238 following the hinge region is found to be different between Fc (P238D) and Fc (WT) (FIG. 23). Pro at position 238 (EU numbering) is originally when alterations that improve selectivity and binding activity towards FcγRIIb in a naturally-occurring IgG were combined with an Fc containing the P238D alteration.

Figure 24:
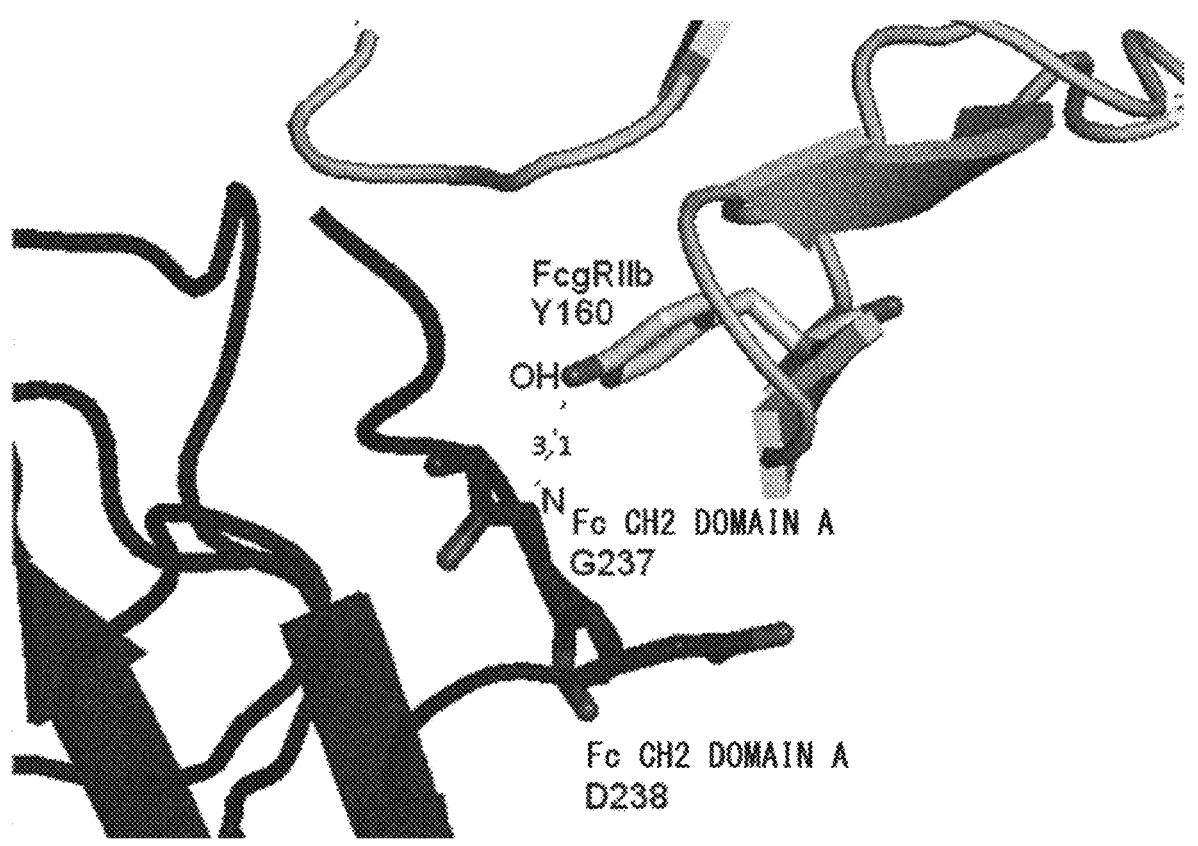
FIG. 24 shows that a hydrogen bond can be found between the main chain of Gly at position 237 (indicated by EU numbering) in Fc CH2 domain A, and Tyr at position 160 in FcγRIIb in the crystal structure of the Fc(P238D)/FcγRIIb extracellular region complex.
Figure 25:
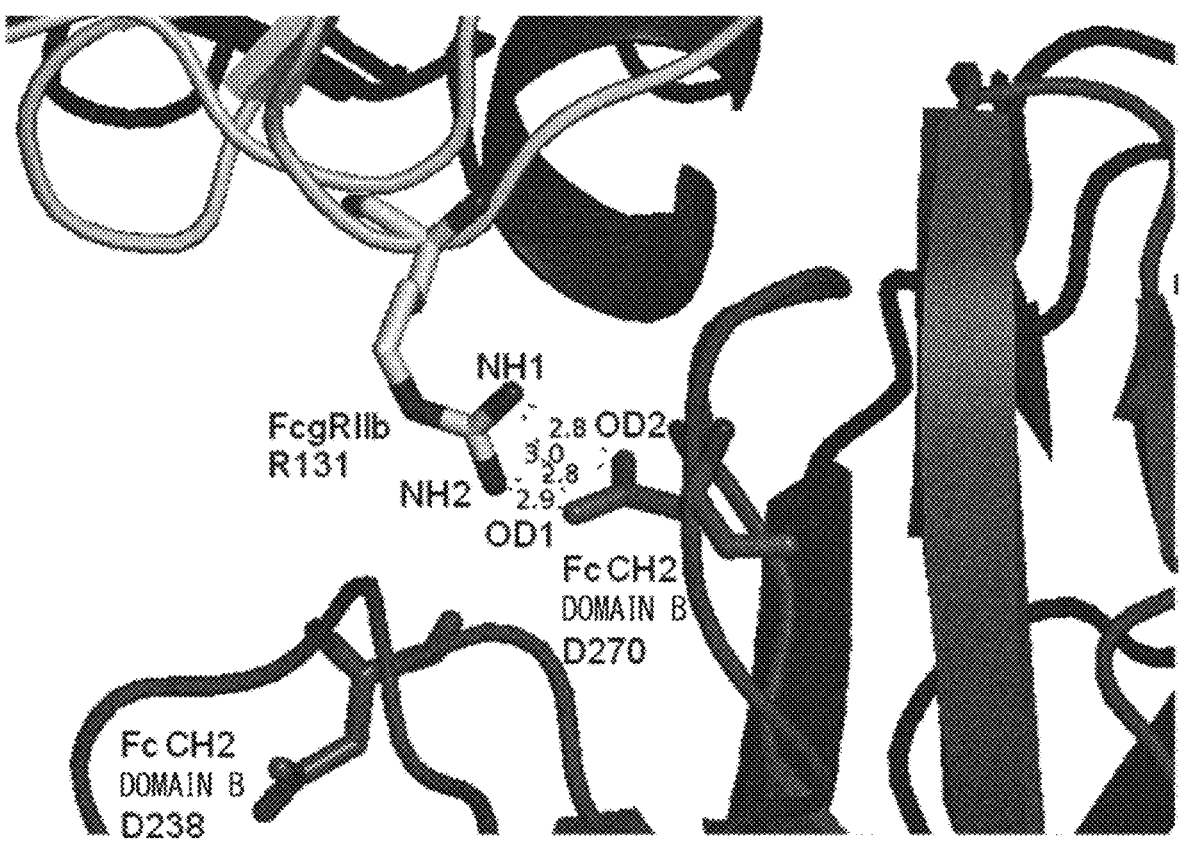
FIG. 25 shows that an electrostatic interaction can be found between Asp at position 270 (indicated by EU numbering) in Fc CH2 domain B, and Arg at position 131 in FcγRIIb in the crystal structure of the Fc(P238D)/FcγRIIb extracellular region complex.

Furthermore, as a result of structural changes due to introduction of P238D in Fc CH2 domain A, a hydrogen bond has been found between the main chain of Gly at position 237 (EU numbering), which is adjacent to P238D which is mutated, and Tyr at position 160 in FcγRIIb (FIG. 24). The residue in FcγRIIa that corresponds to this Tyr 160 is Phe; and when the binding is to FcγRIIa, this hydrogen bond is not formed. Considering that the amino acid at position 160 is one of the few differences between FcγRIIa and FcγRIIb in the interface of interaction with Fc, the presence of this hydrogen bond which is specific to FcγRIIb is presumed to have led to improvement of FcγRIIb-binding activity and decrease of FcγRIIa-binding activity in Fc (P238D), and improvement of its selectivity. Furthermore, in Fc CH2 domain B, an electrostatic interaction is observed between Asp at position 270 (EU numbering) and Arg at position 131 in FcγRIIb (FIG. 25). In FcγRIIa type H, which is one of the allotypes of FcγRIIa, the residue corresponding to Arg at position 131 of FcγRIIb is His, and therefore cannot form this electrostatic interaction. This can explain why the Fc (P238D)-binding activity is lowered in FcγRIIa type H compared with FcγRIIa type R. Observations based on such results of X-ray crystal structure analysis showed that the change of the loop structure near P238D due to P238D introduction and the accompanying change in the relative domain positioning causes formation of new interactions which is not found in the binding of the naturally-occurring IgG and FcγR, and this could lead to a selective binding profile of P238D variants for FcγRIIb.

[Expression and Purification of Fc (P238D)]

An Fc containing the P238D alteration was prepared as follows. First, Cys at position 220 (EU numbering) of hIL6R-IgG1-v1 (SEQ ID NO: 62) was substituted with Ser. Then, genetic sequence of Fc (P238D) from Glu at position 236 (EU numbering) to its C terminal was cloned by PCR. Using this cloned genetic sequence, production of expression vectors, and expression and purification of Fc (P238D) were carried out according to the method of Reference Example 1. Cys at position 220 (EU numbering) forms a disulfide bond with Cys of the L chain in general IgG1. The L chain is not co-expressed when Fc alone is prepared, and therefore, the Cys residue was substituted with Ser to avoid formation of unnecessary disulfide bonds.

[Expression and Purification of the FcγRIIb Extracellular Region]

The FcγRIIb extracellular region was prepared according to the method of Reference Example 2.

[Purification of the Fc (P238D)/FcγRIIb Extracellular Region Complex]

To 2 mg of the FcγRIIb extracellular region sample obtained for use in crystallization, 0.29 mg of Endo F1 (Protein Science (1996) 5: 2617-2622) expressed and purified from *Escherichia coli* as a glutathione S-transferase fusion protein was added. This was allowed to remain at room temperature for three days in 0.1 M Bis-Tris buffer at pH 6.5, and the N-linked sugar chains were cleaved, except for N-acetylglucosamine directly bound to Asn of the FcγRIIb extracellular region. Next, the FcγRIIb extracellular region sample subjected to sugar chain cleavage treatment, which was concentrated by ultrafiltration with 5000 MWCO, was purified by gel filtration chromatography (Superdex200 10/300) using a column equilibrated in 20 mM HEPS at pH 7.5 containing 0.05 M NaCl. Furthermore, to the obtained carbohydrate-cleaved FcγRIIb extracellular region fraction, Fc (P238D) was added so that the molar ratio of the FcγRIIb extracellular region would be present in slight excess. The mixture concentrated by ultrafiltration with 10,000 MWCO was purified by gel filtration chromatography (Superdex200 10/300) using a column equilibrated in 20 mM HEPS at pH 7.5 containing 0.05 M NaCl. Thus, a sample of the Fc (P238D)/FcγRIIb extracellular region complex was obtained.

[Crystallization of the Fc (P238D)/FcγRIIb Extracellular Region Complex]

Using the sample of the Fc (P238D)/FcγRIIb extracellular region complex which was concentrated to approximately 10 mg/mL by ultrafiltration with 10,000 MWCO, crystallization of the complex was carried out by the sitting drop vapor diffusion method. Hydra II Plus One (MATRIX) was used for crystallization; and for a reservoir solution containing 100 mM Bis-Tris pH 6.5, 17% PEG3350, 0.2 M ammonium acetate, and 2.7% (w/v) D-Galactose, a crystallization drop was produced by mixing at a ratio of reservoir solution: crystallization sample=0.2 μl:0.2 μl. The crystallization drop after sealing was allowed to remain at 20° C., and thus thin plate-like crystals were obtained.

[Measurement of X-Ray Diffraction Data from an Fc (P238D)/FcγRIIb Extracellular Region Complex Crystal]

One of the obtained single crystals of the Fc (P238D)/FcγRIIb extracellular region complex was soaked into a solution of 100 mM Bis-Tris pH 6.5, 20% PEG3350, ammonium acetate, 2.7% (w/v) D-Galactose, 22.5% (v/v) ethylene glycol. The single crystal was fished out of the solution using a pin with attached tiny nylon loop, and frozen in liquid nitrogen. Then, the X-ray diffraction data of the crystal was measured at synchrotron radiation facility Photon Factory BL-1A in High Energy Accelerator Research Organization. During the measurement, the crystal was constantly placed in a nitrogen stream at −178° C. to maintain in a frozen state, and a total of 225 X ray diffraction images were collected using Quantum 270 CCD detector (ADSC) attached to a beam line with rotating the crystal 0.8° at a time. Determination of cell parameters, indexing of diffraction spots, and diffraction data processing from the obtained diffraction images were performed using the Xia2 program (CCP4 Software Suite), XDS Package (Walfgang Kabsch) and Scala (CCP4 Software Suite); and finally, diffraction intensity data of the crystal up to 2.46 Å resolution was obtained. The crystal belongs to the space group P21, and has the following cell parameters; a=48.85 Å, b=76.01 Å, c=115.09 Å, α=90°, β=100.70°, γ=90°.

[X Ray Crystal Structure Analysis of the Fc (P238D)/FcγRIIb Extracellular Region Complex]

Crystal structure of the Fc (P238D)/FcγRIIb extracellular region complex was determined by the molecular replacement method using the program Phaser (CCP4 Software Suite). From the size of the obtained crystal lattice and the molecular weight of the Fc (P238D)/FcγRIIb extracellular region complex, the number of complexes in the asymmetric unit was predicted to be one. From the structural coordinates of PDB code: 3SGJ which is the crystal structure of the Fc (WT)/FcγRIIIa extracellular region complex, the amino acid residue portions of the A chain positions 239-340 and the B chain positions 239-340 were taken out as separate coordinates, and they were set respectively as models for searching the Fc CH2 domains. The amino acid residue portions of the A chain positions 341-444 and the B chain positions 341-443 were taken out as a single set of coordinates from the same structural coordinates of PDB code: 3SGJ; and this was set as a model for searching the Fc CH3 domains. Finally, from the structural coordinates of PDB code: 2FCB which is a crystal structure of the FcγRIIb extracellular region, the amino acid residue portions of the A chain positions 6-178 was taken out and set as a model for searching the FcγRIIb extracellular region. The orientation and position of each search model in the crystal lattice were determined in the order of Fc CH3 domain, FcγRIIb extracellular region, and Fc CH2 domain, based on the rotation function and translation function to obtain the initial model for the crystal structure of the Fc (P238D)/FcγRIIb extracellular region complex. When rigid body refinement which moves the two Fc CH2 domains, the two Fc CH3 domains, and the FcγRIIb extracellular region was performed on the obtained initial model, the crystallographic reliability factor, R value became 40.4%, and the Free R value became 41.9% to diffraction intensity data from 25 Å to 3.0 Å at this point. Furthermore, structural refinement using the program Refmac5 (CCP4 Software Suite), and revision of the model to observe the electron density maps whose coefficient have 2Fo-Fc or Fo-Fc, which are calculated based on the experimentally determined structural factor Fo, the calculated structural factor Fc and the calculated phase using the model, was carried out by the Coot program (Paul Emsley). Model refinement was carried out by repeating these steps. Finally, as a result of incorporation of water molecules into the model based on the electron density maps which use 2Fo-Fc or Fo-Fc as the coefficient, and the following refinement, the crystallographic reliability factor, R values and the Free R value of the model containing 4846 non-hydrogen atoms became 23.7% and 27.6% to 24291 diffraction intensity data from 25 Å to 2.6 Å resolution, respectively.

[Production of a Model Structure of the Fc (WT)/FcγRIIb Extracellular Region Complex]

Based on the structural coordinates of PDB code: 3RY6 which is a crystal structure of the Fc (WT)/FcγRIIa extracellular region complex, the Build Mutants function of the Discovery Studio 3.1 program (Accelrys) was used to introduce mutations to match the amino acid sequence of FcγRIIb into FcγRIIa in this structural coordinates. In that case, the Optimization Level was set to High, Cut Radius was set to 4.5, five models were generated, and the one with the best energy score from among them was set as the model structure for the Fc (WT)/FcγRIIb extracellular region complex.

[Example 11] Analysis of FcγR Binding of Fc Variants Whose Alteration Sites were Determined Based on Crystal Structures Based on the results of X-ray crystal structure analysis on the complex formed between Fc (P238D) and the FcγRIIb extracellular region obtained in Example 10, variants were constructed by comprehensively introducing alterations into sites on the altered Fc having substitution of Pro at position 238 (EU numbering) with Asp that were predicted to affect interaction with FcγRIIb (residues of positions 233, 240, 241, 263, 265, 266, 267, 268, 271, 273, 295, 296, 298, 300, 323, 325, 326, 327, 328, 330, 332, and 334 (EU numbering)), and whether combinations of alterations that further enhance FcγRIIb binding in addition to the P238D alteration can be obtained, was examined.

IL6R-B3 (SEQ ID NO: 63) was produced by introducing into IL6R-G1d (SEQ ID NO: 54), the alteration produced by substituting Lys at position 439 (EU numbering) with Glu. Next, IL6R-BF648 was produced by introducing into IL6R-B3, the alteration produced by substituting Pro at position 238 (EU numbering) with Asp. IL6R-L (SEQ ID NO: 56) was utilized as the common antibody L chain. These antibody variants expressed were purified according to the method of Reference Example 1. The binding of these antibody variants to each of the FcγRs (FcγRIa, FcγRIIa type H, FcγRIIa type R, FcγRIIb, and FcγRIIIa type V) was comprehensively evaluated by the method of Reference Example 2.

A figure was produced according to the following method to show the results of analyzing the interactions with the respective FcγRs. The value for the amount of binding of each variant to each FcγR was divided by the value for the amount of binding of the pre-altered control antibody (IL6R-BF648/IL6R-L, alteration by substituting Pro at position 238 (EU numbering) with Asp) to each FcγR, and the obtained was then multiplied by 100 and shown as the relative binding activity value of each variant to each FcγR. The horizontal axis shows the relative binding activity value of each variant to FcγRIIb, and the vertical axis shows the relative binding activity value of each variant to FcγRIIa type R (FIG. 26).

Figure 26:
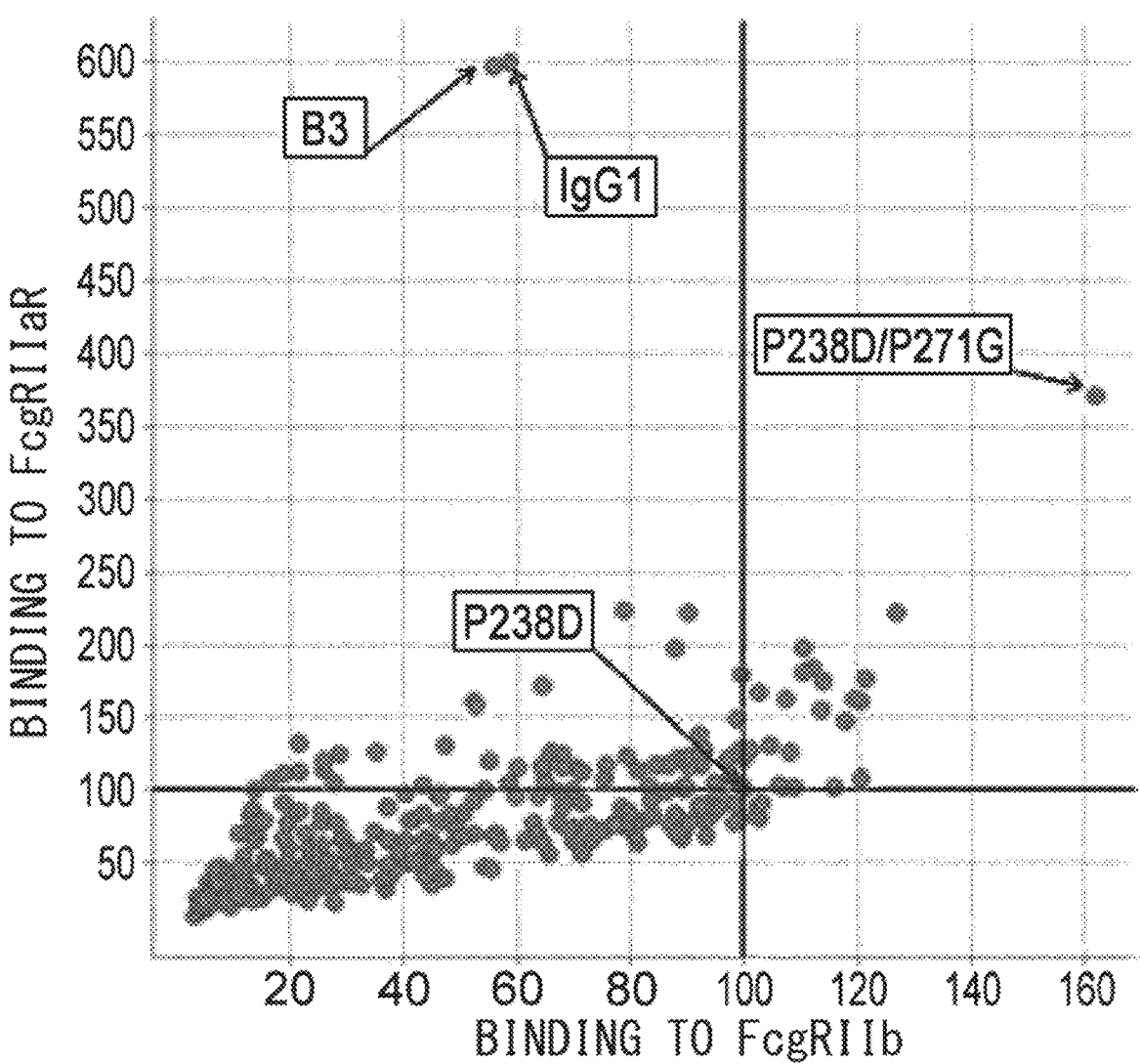
FIG. 26 shows a graph in which the horizontal axis shows the relative value of FcγRIIb-binding activity of each 2B variant, and the vertical axis shows the relative value of FcγRIIa type R-binding activity of each 2B variant. The value for the amount of binding of each 2B variant to each FcγR was divided by the value for the amount of binding of a control antibody prior to alteration (altered Fc with substitution of Pro at position 238 (indicated by EU numbering) with Asp) to each FcγR; and then the obtained value was multiplied by 100, and used as the value of relative binding activity of each 2B variant towards each FcγR.

As shown in FIG. 26, the results show that of all the alterations, 24 types of alterations were found to maintain or enhance FcγRIIb binding in comparison with the pre-altered antibody. The binding of these variants to each of the FcγRs are shown in Table 16. In the table, alteration refers to the alteration introduced into IL6R-B3 (SEQ ID NO: 63). The template used for producing IL6R-B3, IL6R-G1d/IL6R-L, is indicated with an asterisk (*).

TABLE 16

| VARIANT NAME | ALTERATION | RELATIVE BINDING | | | | |
| | | FcγRIa | FcγRIIaR | FcγRIIaH | FcγRIIb | FcγRIIIa |
| --- | --- | --- | --- | --- | --- | --- |
| IL6R-G1d/IL6R-L | * | 140 | 650 | 1670 | 62 | 3348 |
| IL6R-B3/IL6R-L | | 145 | 625 | 1601 | 58 | 3264 |
| IL6R-BF648/IL6R-L | P238D | 100 | 100 | 100 | 100 | 100 |
| IL6R-2B002/IL6R-L | P238D/E233D | 118 | 103 | 147 | 116 | 147 |
| IL6R-BP100/IL6R-L | P238D/S267A | 121 | 197 | 128 | 110 | 138 |
| IL6R-BP102/IL6R-L | P238D/S267Q | 104 | 165 | 66 | 106 | 86 |
| IL6R-BP103/IL6R-L | P238D/S267V | 56 | 163 | 69 | 107 | 77 |

TABLE 16-continued

| | | RELATIVE BINDING | | | | |
|---|---|---|---|---|---|---|
| VARIANT NAME | ALTERATION | FcγRIa | FcγRIIaR | FcγRIIaH | FcγRIIb | FcγRIIIa |
| IL6R-BP106/IL6R-L | P238D/H268D | 127 | 150 | 110 | 116 | 127 |
| IL6R-BP107/IL6R-L | P238D/H268E | 123 | 147 | 114 | 118 | 129 |
| IL6R-BP110/IL6R-L | P238D/H268N | 105 | 128 | 127 | 101 | 127 |
| IL6R-BP112/IL6R-L | P238D/P271G | 119 | 340 | 113 | 157 | 102 |
| IL6R-2B128/IL6R-L | P238D/Y296D | 95 | 87 | 37 | 103 | 96 |
| IL6R-2B169/IL6R-L | P238D/V323I | 73 | 92 | 83 | 104 | 94 |
| IL6R-2B171/IL6R-L | P238D/V323L | 116 | 117 | 115 | 113 | 122 |
| IL6R-2B172/IL6R-L | P238D/V323M | 140 | 244 | 179 | 132 | 144 |
| IL6R-BP136/IL6R-L | P238D/K326A | 117 | 159 | 103 | 119 | 102 |
| IL6R-BP117/IL6R-L | P238D/K326D | 124 | 166 | 96 | 118 | 105 |
| IL6R-BP120/IL6R-L | P238D/K326E | 125 | 175 | 92 | 114 | 103 |
| IL6R-BP126/IL6R-L | P238D/K326L | 113 | 167 | 132 | 103 | 146 |
| IL6R-BP119/IL6R-L | P238D/K326M | 117 | 181 | 133 | 110 | 145 |
| IL6R-BP142/IL6R-L | P238D/K326N | 98 | 103 | 97 | 106 | 102 |
| IL6R-BP121/IL6R-L | P238D/K326Q | 118 | 155 | 135 | 113 | 157 |
| IL6R-BP118/IL6R-L | P238D/K326S | 101 | 132 | 128 | 104 | 144 |
| IL6R-BP116/IL6R-L | P238D/K326T | 110 | 126 | 110 | 108 | 114 |
| IL6R-BP911/IL6R-L | P238D/A330K | 52 | 101 | 108 | 119 | 120 |
| IL6R-BP078/IL6R-L | P238D/A330M | 106 | 101 | 89 | 105 | 91 |
| IL6R-BP912/IL6R-L | P238D/A330R | 60 | 81 | 93 | 103 | 97 |

The results of measuring KD values of the variants shown in Table 16 for FcγRIa, FcγRIIaR, FcγRIIaH, FcγRIIb, and FcγRIIIa V types by the method of Reference Example 2 are summarized in Table 17. In the table, alteration refers to the alteration introduced into IL6R-B3 (SEQ ID NO: 63). The template used for producing IL6R-B3, IL6R-G1d/IL6R-L, is indicated with an asterisk (*). Furthermore, KD (IIaR)/KD (IIb) and KD (IIaH)/KD (IIb) in the table respectively represent the value obtained by dividing the KD value of each variant for FcγRIIaR by the KD value of each variant for FcγRIIb, and the value obtained by dividing the KD value of each variant for FcγRIIaH by the KD value of each variant for FcγRIIb. KD (IIb) of the parent polypeptide/KD (IIb) of the altered polypeptide refers to the value obtained by dividing the KD value of the parent polypeptide for FcγRIIb by the KD value of each variant for FcγRIIb. In addition, the KD value for the stronger of the FcγRIIaR- and FcγRIIaH-binding activities of each variant/KD value for the stronger of the FcγRIIaR- and FcγRIIaH-binding activities of the parent polypeptide are shown in Table 17. Here, parent polypeptide refers to the variant which has IL6R-B3 (SEQ ID NO: 63) as the H chain. It was determined that, due to weak binding of FcγR to IgG, it was impossible to accurately analyze some of the binding by kinetic analysis, and thus the values in the fourth row of the fourth column (FcγRIIaR), the last twenty-five rows of the fifth column (FcγRIIaH), and the last twenty-five rows of the seventh column (FcγRIIIaV) in Table 17 were calculated by using Equation 2 of Reference Example 2.

$$KD = C \cdot R_{max}/(R_{eq} - RI) - C \qquad \text{[Equation 2]}$$

TABLE 17

| VARIANT NAME | ALTERATION | KD (mol/L) | | | | | KD (IIaR)/KD (IIb) | KD (IIaH)/KD (IIb) | KD (IIb) OF THE PARENT POLYPEPTIDE/KD (IIb) OF THE ALTERED POLYPEPTIDE | KD VALUE FOR THE STRONGER OF THE FcγRIIaR- AND FcγRIIaH-BINDING ACTIVITIES OF THE VARIANT/KD VALUE FOR THE STRONGER OF THE FcγRIIaR- AND FcγRIIaH-BINDING ACTIVITIES OF THE PARENT POLYPEPTIDE |
|---|---|---|---|---|---|---|---|---|---|---|
| | | FcγRIa | FcγRIIaR | FcγRIIaH | FcγRIIb | FcγRIIaV | | | | |
| IL6R-G1D/IL6R-L | * | 3.2E-10 | 1.0E-06 | 6.7E-07 | 2.6E-06 | 3.5E-07 | 0.4 | 0.3 | 1.2 | 0.9 |
| IL6R-B3/IL6R-L | | 4.2E-10 | 1.1E-06 | 7.7E-07 | 3.1E-06 | 3.3E-07 | 0.3 | 0.2 | 1.0 | 1.0 |
| IL6R-BF648/IL6R-L | P238D | 1.1E-08 | 1.5E-05 | 4.0E-05 | 1.2E-06 | 1.1E-05 | 13.0 | 33.9 | 2.6 | 19.9 |
| IL6R-2B002/IL6R-L | P238D/E233D | 6.4E-09 | 1.9E-05 | 8.6E-05 | 9.3E-07 | 5.3E-05 | 20.4 | 92.3 | 3.3 | 24.7 |
| IL6R-BP100/IL6R-L | P238D/S267A | 1.1E-09 | 7.8E-06 | 4.6E-05 | 1.1E-06 | 5.9E-05 | 7.3 | 42.6 | 2.9 | 10.2 |
| IL6R-BP102/IL6R-L | P238D/S267Q | 8.2E-09 | 8.4E-06 | 6.1E-05 | 9.0E-07 | 8.2E-05 | 9.4 | 67.6 | 3.4 | 11.0 |
| IL6R-BP103/IL6R-L | P238D/S267V | 3.5E-08 | 1.1E-05 | 8.8E-05 | 1.2E-06 | 1.1E-04 | 9.0 | 71.5 | 2.5 | 14.4 |
| IL6R-BP106/IL6R-L | P238D/H268D | 4.0E-09 | 1.1E-05 | 3.6E-05 | 9.3E-07 | 5.5E-05 | 11.6 | 38.7 | 3.3 | 14.0 |
| IL6R-BP107/IL6R-L | P238D/H268E | 1.5E-08 | 1.2E-05 | 3.2E-05 | 9.3E-07 | 6.3E-05 | 12.7 | 56.1 | 3.3 | 15.3 |
| IL6R-BP110/IL6R-L | P238D/H268N | 7.3E-09 | 1.7E-05 | 4.7E-05 | 1.5E-06 | 6.4E-05 | 11.7 | 31.5 | 2.1 | 22.6 |
| IL6R-BP112/IL6R-L | P238D/P271G | 6.5E-09 | 3.5E-06 | 3.5E-05 | 3.2E-07 | 6.9E-05 | 11.0 | 109.4 | 9.7 | 4.6 |
| IL6R-2B128/IL6R-L | P238D/Y296D | 1.3E-08 | 2.6E-05 | 3.4E-05 | 1.4E-06 | 7.2E-05 | 17.7 | 23.6 | 2.1 | 33.1 |
| IL6R-2B169/IL6R-L | P238D/V323I | 2.5E-08 | 1.9E-05 | 4.8E-05 | 1.2E-06 | 7.5E-05 | 15.8 | 40.7 | 2.6 | 24.3 |
| IL6R-2B171/IL6R-L | P238D/V323L | 9.1E-09 | 1.6E-05 | 34E-05 | 1.1E-06 | 5.7E-65 | 15.0 | 31.8 | 2.9 | 20.8 |
| IL6R-2B172/IL6R-L | P238D/V323M | 3.0E-09 | 6.1E-06 | 2.1E-05 | 8.0E-07 | 4.8E-05 | 8.0 | 27.3 | 4.0 | 8.0 |
| IL6R-BP136/IL6R-L | P238D/K326A | 6.6E-09 | 9.1E-06 | 3.8E-05 | 8.0E-07 | 6.9E-05 | 11.4 | 47.6 | 3.9 | 11.8 |
| IL6R-BP117/IL6R-L | P238D/K326D | 4.1E-09 | 9.2E-06 | 4.1E-05 | 8.0E-07 | 6.7E-05 | 11.6 | 51.4 | 3.9 | 12.0 |
| IL6R-BP120/IL6R-L | P238D/K326E | 6.8E-09 | 5.6E-06 | 6.5E-05 | 1.0E-06 | 7.9E-05 | 9.3 | 63.1 | 3.0 | 12.5 |
| IL6R-BF126/IL6R-L | P238D/R326L | 7.4E-09 | 1.1E-05 | 4.5E-05 | 1.4E-06 | 5.6E-05 | 7.8 | 31.7 | 2.2 | 14.4 |
| IL6R-BP119/IL6R-L | P328D/K326M | 7.0E-09 | 9.9E-08 | 4.5E-05 | 1.1E-06 | 5.6E-05 | 8.7 | 39.5 | 2.7 | 12.8 |
| IL6R-BP142/IL6R-L | P238D/K326N | 5.3E-09 | 1.8E-05 | 9.3E-05 | 1.2E-06 | 1.1E-04 | 15.5 | 79.5 | 2.6 | 23.5 |
| IL6R-BP121/IL6R-L | P238D/K326Q | 1.1E-08 | 1.3E-05 | 4.4E-05 | 1.1E-06 | 5.2E-05 | 11.7 | 40.4 | 2.8 | 16.6 |
| IL6R-BP118/IL6R-L | P238D/K326S | 1.2E-08 | 1.5E-05 | 4.6E-05 | 1.2E-06 | 5.6E-05 | 13.2 | 40.0 | 2.7 | 19.7 |
| IL6R-BP116/IL6R-L | P238D/K326T | 2.6E-09 | 1.5E-05 | 5.4E-05 | 1.1E-06 | 7.2E-05 | 13.3 | 48.2 | 2.8 | 19.4 |
| IL6R-BP911/IL6R-L | P238D/A330K | 4.9E-08 | 1.6E-05 | 3.7E-05 | 8.9E-07 | 5.8E-05 | 18.5 | 41.7 | 3.5 | 21.3 |
| IL6R-BP078/IL6R-L | P238D/A330M | 8.2E-09 | 1.5E-05 | 4.5E-05 | 1.1E-06 | 7.8E-05 | 13.4 | 41.3 | 2.8 | 19.0 |
| IL6R-BP912/IL6R-L | P238D/A330R | 3.8E-08 | 2.6E-05 | 3.8E-05 | 1.5E-06 | 7.8E-05 | 17.8 | 25.9 | 2.1 | 34.0 |

Table 17 shows that in comparison with IL6R-B3, all variants showed improvement of affinity for FcγRIIb, and the range of improvement was 2.1 fold to 9.7 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, these values show the degree of binding selectivity of each variant for FcγRIIb, and a greater value indicates a higher binding selectivity for FcγRIIb. Since the ratio of KD value for FcγRIIaR/KD value for FcγRIIb, and the ratio of KD value for FcγRIIaH/KD value for FcγRIIb in the parent polypeptide IL6R-B3/IL6R-L were 0.3 and 0.2, respectively, all variants in Table 17 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or decreased binding compared with the binding by the stronger of the FcγRIIaR- and FcγRIIaH-binding activities of the parent polypeptide. Since this value was 4.6 to 34.0 for the variants obtained this time, one may say that in comparison with the parent polypeptide, the variants obtained this time had reduced binding by the stronger of the FcγRIIaR- and FcγRIIaH-binding activities. These results showed that compared with the parent polypeptide, the variants obtained this time have maintained or decreased FcγRIIa type R- and type H-binding activities, enhanced FcγRIIb-binding activity, and improved selectivity for FcγRIIb. Furthermore, compared with IL6R-B3, all variants had lower affinity to FcγRIa and FcγRIIIaV.

Figure 27:
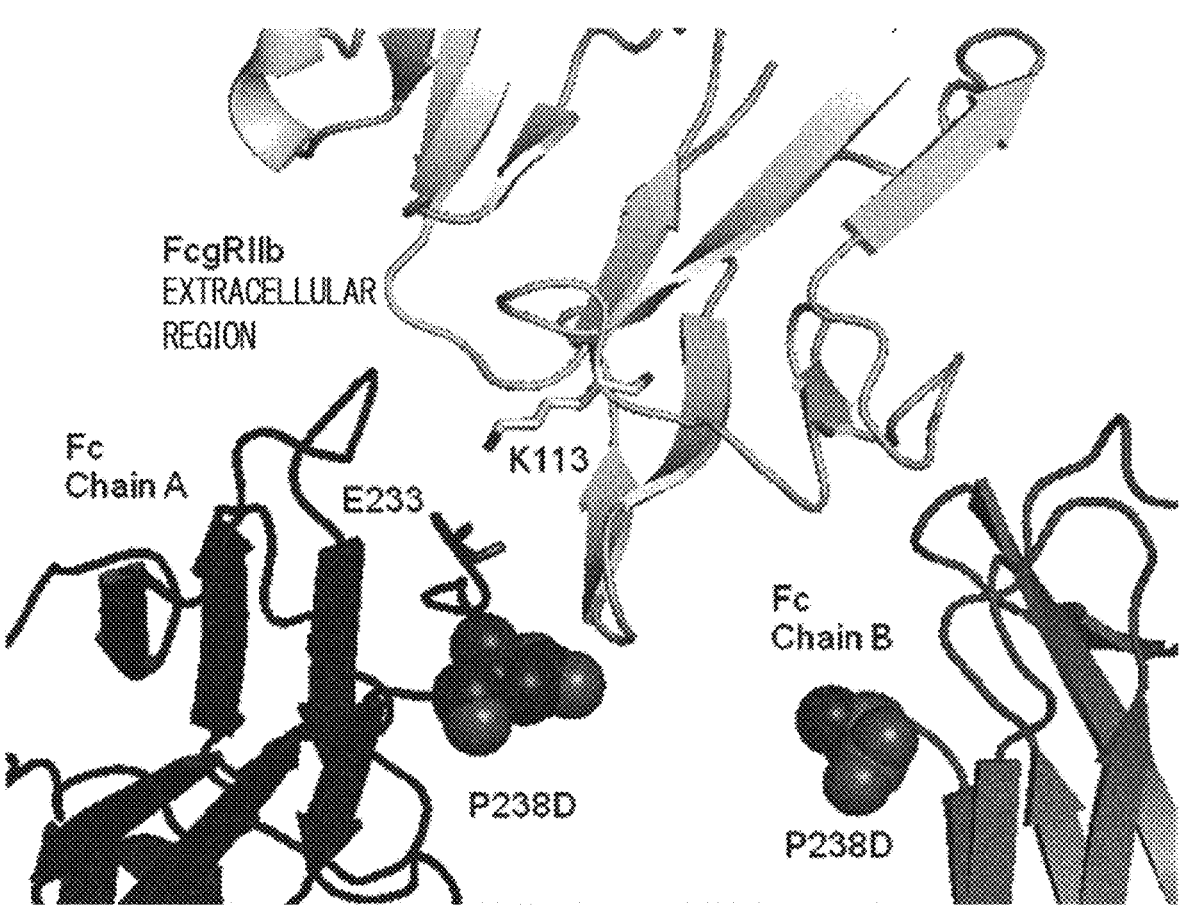
FIG. 27 shows Glu at position 233 (indicated by EU numbering) in Fc Chain A and the surrounding residues in the extracellular region of FcγRIIb in the crystal structure of the Fc(P238D)/FcγRIIb extracellular region complex.

With regard to the promising variants among the obtained combination variants, the factors leading to their effects were investigated using the crystal structure. FIG. 27 shows the crystal structure of the Fc (P238D)/FcγRIIb extracellular region complex. In this figure, the H chain positioned on the left side is Fc Chain A, and the H chain positioned on the right side is Fc Chain B. Here, one can see that the site at position 233 (EU numbering) in Fc Chain A is located near Lys at position 113 of FcγRIIb. However, in this crystal structure, the E233 side chain is in a condition of considerably high mobility, and its electron density is not well observed. Therefore, the alteration produced by substituting Glu at position 233 (EU numbering) with Asp leads to decrease in the degree of freedom of the side chain since the side chain becomes one carbon shorter. As a result, the entropy loss when forming an interaction with Lys at position 113 of FcγRIIb may be decreased, and consequently this is speculated to contribute to improvement of binding free energy.

Figure 28:
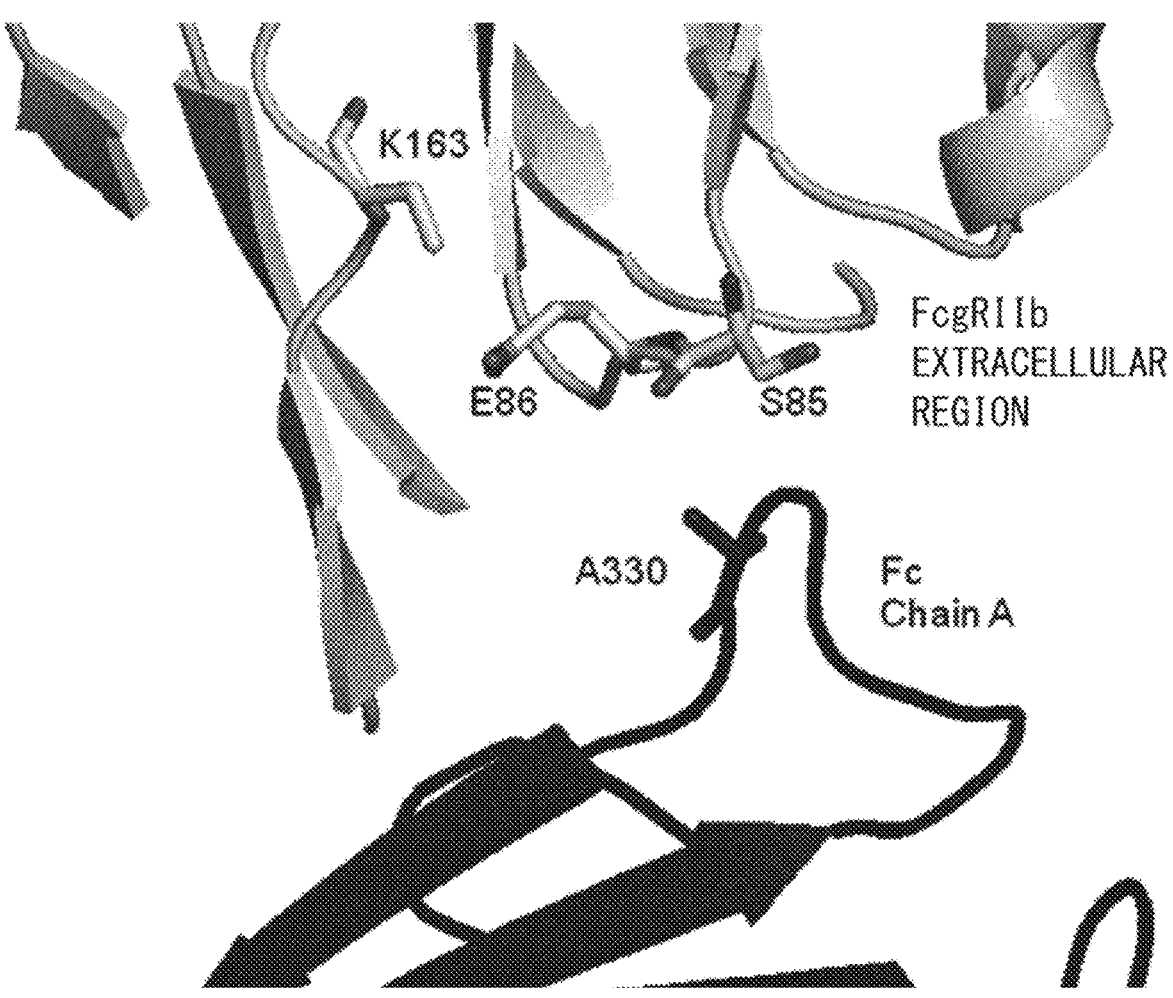
FIG. 28 shows Ala at position 330 (indicated by EU numbering) in Fc Chain A and the surrounding residues in the extracellular region of FcγRIIb in the crystal structure of the Fc(P238D)/FcγRIIb extracellular region complex.

Similarly, FIG. 28 shows the surrounding near the site at position 330 (EU numbering) in the structure of the Fc (P238D)/FcγRIIb extracellular region complex. This figure shows that the surrounding around the site at position 330 (EU numbering) of Fc Chain A of Fc (P238D) is a hydrophilic environment composed of Ser at position 85, Glu at position 86, Lys at position 163, and such of FcγRIIb. Therefore, the alteration produced by substituting Ala at position 330 (EU numbering) with Lys or Arg is speculated to contribute to strengthening the interaction with Ser at position 85 or Glu at position 86 in FcγRIIb.

Figure 29:
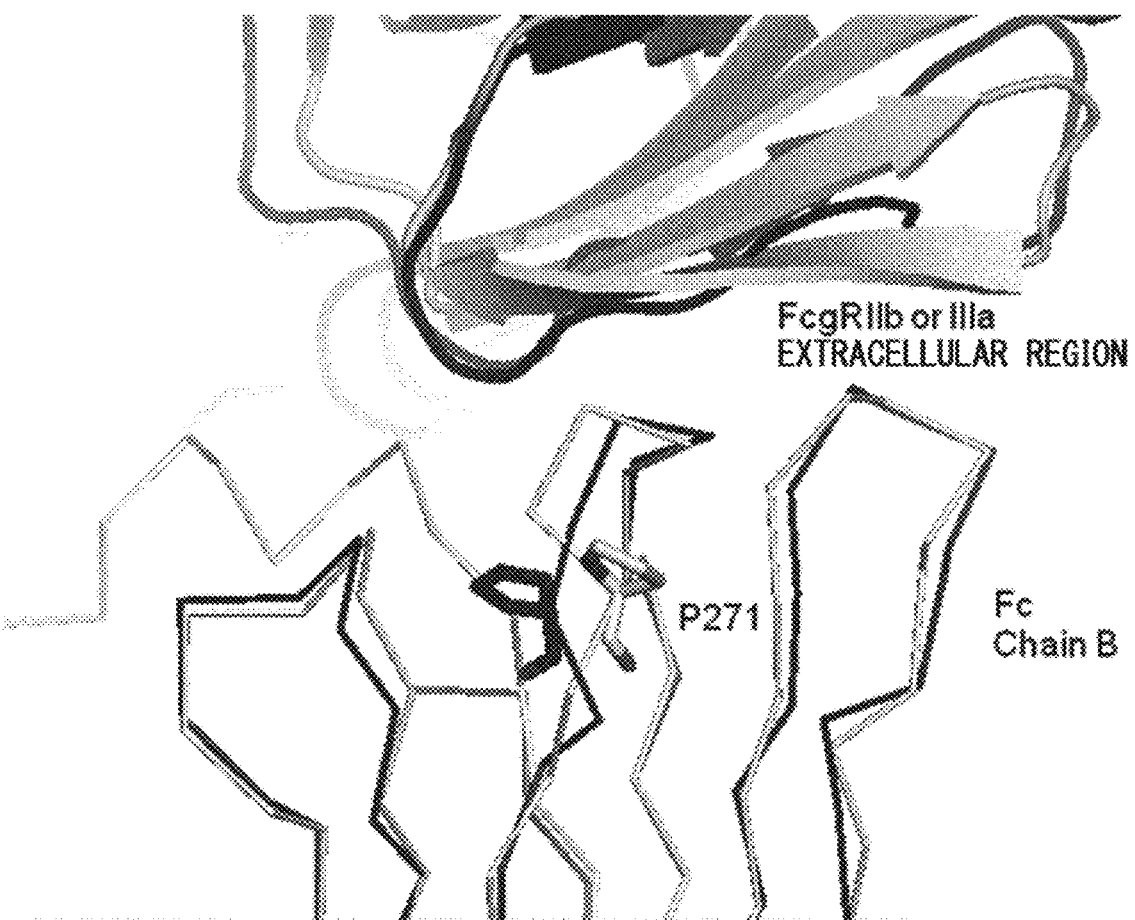
FIG. 29 shows the structures of Pro at position 271 (EU numbering) of Fc Chain B after superimposing the crystal structures of the Fc(P238D)/FcγRIIb extracellular region complex and the Fc(WT)/FcγRIIIa extracellular region complex by the least squares fitting based on the Cα atom pair distances with respect to Fc Chain B.

FIG. 29 depicts the structures of Pro at position 271 (EU numbering) of Fc Chain B after superimposing the crystal structures of the Fc (P238D)/FcγRIIb extracellular region complex and the Fc (WT)/FcγRIIIa extracellular region complex by the least squares fitting based on the Cα atom pair distances with respect to Fc Chain B. These two structures match well, but have different three-dimensional structures of Pro at position 271 (EU numbering). When the weak electron density around this area in the crystal structure of the Fc (P238D)/FcγRIIb extracellular region complex is also taken into consideration, it is suggested that there is possibility that Pro at position 271 (EU numbering) in Fc (P238D)/FcγRIIb causes a large strain on the structure, thus disturbing the loop structure to attain an optimal structure. Therefore, the alteration produced by substituting Pro at position 271 (EU numbering) with Gly gives flexibility to this loop structure, and is speculated to contribute to enhancement of binding by reducing the energetic barrier when allowing an optimum structure to form during interaction with FcγRIIb.

[Example 12] Examination of the Combinatorial Effect of Alterations that Enhance FcγRIIb Binding when Combined with P238D Of the alterations obtained in Examples 9 and 11, those that enhanced FcγRIIb binding or maintained FcγRIIb binding and showed effects of suppressing binding to other FcγRs were combined with each other, and its effect was examined.

Particularly good alterations selected from Tables 13 and 17 were introduced into the antibody H chain IL6R-BF648 in a similar manner to the method of Example 11. IL6R-L was utilized as the antibody L chain, the expressed antibodies were purified according to the method of Reference Example 1. The binding to each of the FcγRs (FcγRIa, FcγRIIa H type, FcγRIIa R type, FcγRIIb, and FcγRIIIa V type) was comprehensively evaluated by the method of Reference Example 2.

According to the following method, relative binding activities were calculated for the results of analyzing interactions with the respective FcγRs. The value for the amount of binding of each variant to each FcγR was divided by the value for the amount of binding of the pre-altered control antibody (IL6R-BF648/IL6R-L with substitution of Pro at position 238 (EU numbering) with Asp to each FcγR, and multiplied by 100; and then the value was shown as the relative binding activity value of each variant to each FcγR (Table 18). In the table, alteration refers to the alteration introduced into IL6R-B3 (SEQ ID NO: 63). The template used for producing IL6R-B3, IL6R-G1d/IL6R-L, is indicated with an asterisk (*).

TABLE 18-1

| VARIANT | | RELATIVE BINDING ACTIVITY | | | | |
|---------|---|---|---|---|---|---|
| NAME | ALTERATION | FcgRIa | FcgRIIaR | FcgRIIaH | FcgRIIb | FcgRIIIaV |
| IL6R-G1d/IL6R-L | * | 140 | 650 | 1670 | 62 | 3348 |
| IL6R-B3/IL5R-L | | 145 | 625 | 1601 | 58 | 3264 |
| IL6R-BF648/IL6R-L | P238D | 100 | 100 | 100 | 100 | 100 |
| IL6R-2B253/IL6R-L | E233D/P238D/V323M | 155 | 288 | 207 | 156 | 126 |
| IL6R-2B261/IL6R-L | E233D/P238D/Y296D | 100 | 94 | 91 | 115 | 87 |
| IL6R-BP082/IL6R-L | E233D/P238D/A330K | 74 | 126 | 106 | 136 | 87 |
| IL6R-BP083/IL6R-L | P238D/Y296D/A330K | 50 | 87 | 91 | 122 | 107 |
| IL6R-BP084/IL6R-L | P238D/V323M/A330K | 109 | 203 | 162 | 141 | 106 |
| IL6R-BP085/IL6R-L | G237D/P238D/A330K | 19 | 279 | 158 | 152 | 104 |
| IL6R-BP086/IL6R-L | P238D/K326A/A330K | 72 | 155 | 116 | 137 | 123 |
| IL6R-BP087/IL6R-L | L234Y/P238D/A330K | 33 | 163 | 179 | 137 | 158 |
| IL6R-BP088/IL6R-L | G237D/P238D/K326A/A330K | 25 | 377 | 166 | 161 | 122 |
| IL6R-BP089/IL6R-L | L234Y/P238D/K326A/A330K | 43 | 222 | 186 | 147 | 136 |
| IL6R-BP129/IL6R-L | E233D/P238D/Y296D/A330K | 68 | 111 | 98 | 138 | 95 |
| IL6R-BP130/IL6R-L | E233D/P238D/V323M/A330K | 104 | 272 | 224 | 160 | 115 |
| IL6R-BP131/IL6R-L | E233D/G237D/P238D/A330K | 33 | 364 | 253 | 160 | 118 |
| IL6R-BP132/IL6R-L | E233D/P238D/K326A/A330K | 91 | 191 | 130 | 150 | 120 |
| IL6R-BP133/IL6R-L | E233D/L234Y/P238D/A330K | 41 | 174 | 151 | 137 | 114 |
| IL6R-BP143/IL6R-L | L234Y/P238D/K326A | 86 | 238 | 143 | 133 | 114 |
| IL6R-BP144/IL6R-L | G237D/P238D/K326A | 64 | 204 | 108 | 121 | 128 |
| IL6R-BP145/IL6R-L | L234Y/G237D/P238D | 41 | 350 | 224 | 152 | 153 |
| IL6R-BP146/IL6R-L | L234Y/G237D/P238D/K326A | 50 | 445 | 203 | 156 | 180 |
| IL6R-BP147/IL6R-L | L234Y/G237D/P238D/K326A/A330K | 24 | 650 | 582 | 177 | 209 |
| IL6R-BP148/IL6R-L | E233D/L234Y/G237D/P238D/K326A/A330K | 33 | 603 | 462 | 176 | 227 |
| IL6R-BP149/IL6R-L | E233D/L234Y/G237D/P238D/Y296D/K326A/A330K | 29 | 539 | 401 | 173 | 186 |
| IL6R-BP150/IL6R-L | L234Y/G237D/P238D/K326A/A330R | 30 | 757 | 770 | 183 | 204 |
| IL6R-BP151/IL6R-L | E233D/L234Y/G237D/P238D/K326A/A330R | 39 | 705 | 621 | 180 | 221 |
| IL6R-BP152/IL6R-L | E233D/L234Y/G237D/P238D/Y296D/K326A/A330R | 34 | 638 | 548 | 178 | 146 |
| IL6R-BP176/IL6R-L | E233D/P238D/K326D/A330K | 102 | 201 | 128 | 147 | 131 |
| IL6R-BP177/IL6R-L | E233D/L234Y/G237D/P238D/P271G/K326D/A330K | 57 | 691 | 409 | 177 | 186 |
| IL6R-BP178/IL6R-L | E233D/G237D/P238D/P271G/A330K | 51 | 653 | 259 | 179 | 110 |
| IL6R-BP179/IL6R-L | G237D/P238D/P271G/K326A/A330K | 39 | 570 | 226 | 177 | 125 |
| IL6R-BP180/IL6R-L | G237D/P238D/P271G/A330K | 29 | 602 | 203 | 179 | 100 |

Table 18-2 is a continuation table of Table 18-1.

TABLE 18-2

| IL6R-BP181/IL6R-L | E233D/P238D/P271G/K326A/A330K | 108 | 362 | 150 | 170 | 122 |
|---|---|---|---|---|---|---|
| IL6R-BP182/IL6R-L | E233D/P238D/P271G/Y296D/A330K | 95 | 413 | 139 | 173 | 120 |
| IL6R-BP183/IL6R-L | E233D/L234Y/P238D/P271G/K326A/A330K | 83 | 423 | 191 | 164 | 113 |
| IL6R-BP184/IL6R-L | E233D/P238D/P271G/A330K | 96 | 436 | 131 | 171 | 106 |
| IL6R-BP185/IL6R-L | E233D/L234Y/G237D/P238D/P271G/K326A/A330K | 47 | 670 | 446 | 179 | 191 |
| IL6R-BP186/IL6R-L | E233D/L234Y/G237D/P238D/P271G/Y296D/K326A/A330K | 43 | 614 | 368 | 175 | 143 |
| IL6R-BP187/IL6R-L | L234Y/P238D/P271G/K326A/A330K | 68 | 387 | 205 | 157 | 124 |
| IL6R-BP188/IL6R-L | E233D/G237D/P238D/H268D/P271G/A330K | 74 | 636 | 234 | 179 | 121 |
| IL6R-BP189/IL6R-L | G237D/P238D/H268D/P271G/K326A/A330K | 56 | 557 | 183 | 177 | 141 |
| IL6R-BP190/IL6R-L | G237D/P238D/H268D/P271G/A330K | 50 | 615 | 224 | 181 | 155 |
| IL6R-BP191/IL6R-L | E233D/P238D/H268D/P271G/K326A/A330K | 125 | 382 | 145 | 170 | 142 |
| IL6R-BP192/IL6R-L | E233D/P238D/H268D/P271G/Y296D/A330K | 109 | 406 | 122 | 172 | 118 |
| IL6R-BP193/IL6R-L | E233D/P238D/H268D/P271G/A330K | 113 | 449 | 154 | 173 | 135 |
| IL6R-BP194/IL6R-L | E233D/L234Y/G237D/P238D/H268D/P271G/K326A/A330K | 69 | 672 | 395 | 178 | 249 |
| IL6R-BP195/IL6R-L | E233D/L234Y/G237D/P238D/H268D/P271G/Y296D/K326A/A330K | 68 | 661 | 344 | 181 | 221 |
| IL6R-BP196/IL6R-L | L234Y/P238D/H268D/P271G/K326A/A330K | 89 | 402 | 195 | 157 | 137 |
| IL6R-BP197/IL6R-L | E233D/L234Y/G237D/P238D/H268D/P271G/Y296D/K326A/A330K | 71 | 642 | 294 | 179 | 206 |
| IL6R-BP198/IL6R-L | E233D/L234Y/P238D/H268D/P271G/K326A/A330K | 104 | 449 | 188 | 164 | 157 |
| IL6R-BP199/IL6R-L | E233D/P238D/K326A/A330R | 112 | 172 | 116 | 144 | 103 |
| IL6R-BP200/IL6R-L | E233D/L234Y/G237D/P238D/P271G/K326A/A330R | 60 | 754 | 517 | 188 | 164 |
| IL6R-BP201/IL6R-L | E233D/G237D/P238D/P271G/A330R | 57 | 696 | 359 | 186 | 121 |
| IL6R-BP202/IL6R-L | G237D/P238D/P271G/K326A/A330R | 43 | 615 | 285 | 185 | 108 |
| IL6R-BP203/IL6R-L | G237D/P238D/P271G/A330R | 35 | 637 | 255 | 185 | 88 |
| IL6R-BP204/IL6R-L | E233D/P238D/P271G/K326A/A330R | 110 | 301 | 137 | 165 | 121 |
| IL6R-BP205/IL6R-L | E233D/P238D/P271G/Y296D/A330R | 97 | 335 | 108 | 167 | 93 |
| IL6R-BP206/IL6R-L | E233D/P238D/P271G/A330R | 101 | 362 | 123 | 168 | 92 |
| IL6R-BP207/IL6R-L | E233D/P238D/A330R | 74 | 103 | 103 | 124 | 97 |
| IL6R-BP208/IL6R-L | E233D/G237D/P238D/H268D/P271G/A330R | 81 | 690 | 310 | 188 | 118 |
| IL6R-BP209/IL6R-L | G237D/P238D/H268D/P271G/K326A/A330R | 68 | 625 | 267 | 186 | 153 |
| IL6R-BP210/IL6R-L | G237D/P238D/H268D/P271G/A330R | 57 | 661 | 279 | 187 | 135 |
| IL6R-BP211/IL6R-L | E233D/P238D/H268D/P271G/K326A/A330R | 128 | 312 | 111 | 165 | 87 |
| IL6R-BP212/IL6R-L | E233D/P238D/H268D/P271G/Y296D/A330R | 117 | 363 | 135 | 173 | 122 |
| IL6R-BP213/IL6R-L | E233D/P238D/H268D/P271G/A330R | 118 | 382 | 123 | 169 | 100 |
| IL6R-BP214/IL6R-L | E233D/L234Y/G237D/P238D/Y296D/K326D/A330K | 36 | 498 | 285 | 174 | 165 |

The results of measuring KD values of the variants shown in Table 18 for FcγRIa, FcγRIIaR, FcγRIIaH, FcγRIIb, and FcγRIIIaV types by the method of Reference Example 2 are summarized in Tables 19-1 and 19-2. In the table, alteration refers to the alteration introduced into IL6R-B3 (SEQ ID NO: 63). The template used for producing IL6R-B3, IL6R-G1d/IL6R-L, is indicated with an asterisk (*). Furthermore, KD (IIaR)/KD (IIb) and KD (IIaH)/KD (IIb) in the table respectively represent the value obtained by dividing the KD value of the variant for FcγRIIaR by the KD value of the variant for FcγRIIb, and the value obtained by dividing the KD value of the variant for FcγRIIaH by the KD value of each variant for FcγRIIb. KD (IIb) of the parent polypeptide/ KD (IIb) of the altered polypeptide refers to the value obtained by dividing the KD value of the parent polypeptide for FcγRIIb by the KD value of each variant for FcγRIIb. In addition, the KD value for the stronger of the FcγRIIaR- and FcγRIIaH-binding activities of each variant/KD value for the stronger of the FcγRIIaR- and FcγRIIaH-binding activities of the parent polypeptide are shown in Tables 19-1 and 19-2. Here, parent polypeptide refers to the variant which has IL6R-B3 (SEQ ID NO: 63) as the H chain. It was determined that, due to weak binding of FcγR to IgG, it was impossible to accurately analyze some of the binding by kinetic analysis, and thus the values in the last thirty-three rows of the fifth column (FcγRIIaH) and the last thirty-three rows of the seventh column (FcγRIIIaV) in Table 19-1 and the values in all rows of the fifth column (FcγRIIaH) and all rows of the seventh column (FcγRIIIaV) in Table 19-2 were calculated by using Equation 2 of Reference Example 2.

$$KD = C \cdot R_{max} / (R_{eq} - RI) - C \qquad \text{[Equation 2]}$$

Tables 19-1 and 19-2 show that in comparison with IL6R-B3, all variants showed improvement of affinity for FcγRIIb, and the range of improvement was 3.0 fold to 99.0 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, those values show the degree of binding selectivity of each variant for FcγRIIb, and a greater value indicates a higher binding selectivity for FcγRIIb. Since the ratio of KD value for FcγRIIaR/KD value for FcγRIIb, and the ratio of KD value for FcγRIIaH/KD value for FcγRIIb of the parent polypeptide IL6R-B3/IL6R-L were 0.3 and 0.2, respectively, all variants in Tables 19-1 and 19-2 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or decreased binding compared with the binding by the stronger of the FcγRIIaR- and FcγRIIaH-binding activities of the parent polypeptide. Since this value was 0.7 to 29.9 for the variants obtained this time, one may say that binding by the stronger of the FcγRIIaR- and FcγRIIaH-binding activities of the variants obtained this time was nearly equivalent or decreased compared with that of the parent polypeptide. These results showed that compared with the parent polypeptide, the variants obtained this time have maintained or decreased FcγRIIa type R- and type H-binding activities, enhanced FcγRIIb-binding activity, and improved selectivity for FcγRIIb. Furthermore, compared with IL6R-B3, all variants had lower affinity for FcγRIa and FcγRIIIaV.

TABLE 19-1

| VARIANT NAME | ALTERATION | KD (mol/L) | | | | | KD (IIaR)/ KD (IIb) | KD (IIaH)/ KD (IIb) | KD (IIb) OF THE PARENT POLYPEPTIDE/ KD (IIb) OF THE ALTERED POLYPEPTIDE | KD VALUE FOR THE STRONGER OF THE FcγRIIaR- AND FcγRIIaH BINDING ACTIVITIES OF THE VARIANT/ KD VALUE FOR THE STRONGER OF THE FcγRIIaR- AND FcγRIIaH-BINDING ACTIVITIES OF THE PARENT POLYPEPTIDE |
|---|---|---|---|---|---|---|---|---|---|---|
| | | FcγRIa | FcγRIIaR | FcγRIIaH | FcγRIIb | FcγRIIaV | | | | |
| IL6R-G1d/ IL6R-L | * | 3.2E−10 | 1.0E−06 | 6.7E−07 | 2.6E−06 | 3.5E−07 | 0.4 | 0.3 | 1.2 | 0.9 |
| IL6R-B3/ IL6R-L | | 4.2E−10 | 1.1E−06 | 7.7E−07 | 3.1E−06 | 3.3E−07 | 0.3 | 0.2 | 1.0 | 1.0 |
| IL6R-BF648/ IL6R-L | P238D | 1.1E−08 | 1.5E−05 | 4.0E−05 | 1.2E−06 | 7.1E−05 | 13.0 | 33.9 | 2.6 | 19.9 |
| IL6R-2B253/ IL6R-L | E233D/P238D/ V323M | 1.4E−09 | 5.0E−06 | 1.3E−05 | 4.3E−07 | 5.0E−05 | 11.5 | 30.1 | 7.2 | 6.5 |
| IL6R-2B261/ IL6R-L | E233D/P238D/ Y296D | 9.0E−09 | 2.2E−05 | 3.3E−05 | 1.0E−06 | 7.3E−05 | 21.8 | 32.4 | 3.0 | 28.8 |
| IL6R-BP082/ IL6R-L | E233D/P238D/ A330K | 1.8E−08 | 1.2E−05 | 3.7E−05 | 5.4E−07 | 8.1E−05 | 22.8 | 69.0 | 5.8 | 15.8 |
| IL6R-BP083/ IL6R-L | P238D/Y296D/ A330K | 3.8E−08 | 2.3E−05 | 4.4E−05 | 7.9E−07 | 6.5E−05 | 29.0 | 55.5 | 3.9 | 29.9 |
| IL6R-BP084/ IL6R-L | P238D/V323M/ A330K | 7.0E−09 | 7.2E−06 | 2.4E−05 | 5.0E−07 | 6.7E−05 | 14.3 | 47.6 | 6.1 | 9.4 |
| IL6R-BP085/ IL6R-L | G237D/P238D/ A330K | 2.9E−07 | 4.2E−06 | 2.4E−05 | 3.2E−07 | 6.8E−05 | 13.1 | 74.5 | 9.5 | 5.5 |
| IL6R-BP086/ IL6R-L | P238D/K326A/ A330K | 2.7E−08 | 9.7E−06 | 3.4E−05 | 5.7E−07 | 5.7E−05 | 17.1 | 59.9 | 5.4 | 12.6 |
| IL6R-BP087/ IL6R-L | L234Y/P238D/ A330K | 3.8E−06 | 9.7E−06 | 2.1E−05 | 6.1E−07 | 4.4E−05 | 16.0 | 34.7 | 5.1 | 12.6 |
| IL6R-BP088/ IL6R-L | G237D/P238D/ K326A/A330K | 3.9E−07 | 2.9E−06 | 2.3E−05 | 2.2E−07 | 5.7E−05 | 13.3 | 106.5 | 14.3 | 3.7 |
| IL6R-BP089/ IL6R-L | L234Y/P238D/ V323M/A330K | 6.3E−08 | 6.4E−06 | 2.0E−05 | 3.9E−07 | 5.1E−05 | 16.6 | 51.9 | 8.0 | 8.3 |
| IL6R-BP129/ IL6R-L | E233D/P238D/ Y296D/A330K | 2.5E−08 | 1.5E−05 | 4.0E−05 | 5.2E−07 | 7.5E−05 | 29.3 | 77.5 | 6.0 | 19.6 |
| IL6R-BP130/ IL6R-L | E233D/2238D/ V323M/A330K | 1.8E−09 | 5.3E−06 | 2.6E−05 | 3.0E−07 | 7.1E−05 | 17.5 | 85.5 | 10.2 | 6.9 |
| IL6R-BP131/ IL6R-L | E233D/G237D/ P236D/A330K | 1.2E−07 | 3.1E−06 | 1.4E−05 | 2.5E−07 | 5.9E−05 | 12.5 | 56.9 | 12.6 | 4.0 |
| IL6R-BP132/ IL6R-L | E233D/P238D/ K326A/A330K | 1.5E−08 | 8.0E−05 | 3.0E−05 | 3.7E−07 | 5.8E−05 | 21.5 | 81.1 | 8.4 | 10.3 |
| IL6R-BP133/ IL6R-L | E233D/L234Y/ P238D/A330K | 1.3E−07 | 8.6E−06 | 2.6E−05 | 5.6E−07 | 6.9E−05 | 15.5 | 46.8 | 5.6 | 11.2 |
| IL6R-BP143/ IL6R-L | L234Y/P238D/ K326A | 1.8E−08 | 5.7E−06 | 2.7E−05 | 5.7E−07 | 6.2E−05 | 10.0 | 47.1 | 5.4 | 7.5 |
| IL6R-BP144/ IL6R-L | G237D/P238D/ K326A | 3.7E−08 | 6.9E−06 | 3.6E−05 | 7.9E−07 | 5.5E−05 | 8.7 | 45.8 | 3.9 | 8.9 |
| IL6R-BP145/ IL6R-L | L234Y/G237D/ P238D | 1.2E−07 | 3.4E−06 | 1.7E−05 | 3.4E−07 | 4.5E−05 | 9.9 | 49.9 | 9.1 | 4.4 |
| IL6R-BP146/ IL6R-L | L234Y/G237D/ P238D/K326A | 7.4E−08 | 2.1E−06 | 1.8E−05 | 2.3E−07 | 3.8E−05 | 9.3 | 80.0 | 13.7 | 2.7 |
| IL6R-BP147/ IL6R-L | L234Y/G237D/ P238D/K326A A330K | 1.4E−07 | 8.9E−07 | 5.1E−06 | 6.6E−08 | 3.3E−05 | 13.6 | 77.7 | 47.1 | 1.2 |
| IL6R-BP148/ IL6R-L | E233D/L234Y/ G237D/P238D/ K326A/A330K | 8.9E−08 | 1.1E−06 | 7.0E−06 | 7.5E−08 | 3.0E−05 | 14.5 | 93.8 | 41.4 | 1.4 |
| IL6R-BP149/ IL6R-L | E233D/L234Y/ G237D/P238D/ Y296D/K326A/ A330K | 1.2E−07 | 1.4E−05 | 8.4E−06 | 9.3E−08 | 3.7E−05 | 15.0 | 89.9 | 33.1 | 1.8 |
| IL6R-BP150/ IL6R-L | L234Y/G237D/ P238D/K326A A330R | 3.0E−07 | 5.5E−07 | 3.4E−06 | 3.1E−08 | 3.4E−05 | 17.7 | 109.0 | 99.0 | 0.7 |
| IL6R-BP151/ IL6R-L | E233D/L234Y/ G237D/P238D/ K326A/A330R | 8.4E−08 | 6.7E−07 | 4.7E−06 | 4.0E−08 | 3.1E−05 | 16.9 | 117.8 | 77.4 | 0.9 |

TABLE 19-1-continued

| VARIANT NAME | ALTERATION | KD (mol/L) | | | | | KD (IIaR)/ KD (IIb) | KD (IIaH)/ KD (IIb) | KD (IIb) OF THE PARENT POLYPEPTIDE/ KD (IIb) OF THE ALTERED POLYPEPTIDE | KD VALUE FOR THE STRONGER OF THE FcγRIIaR- AND FcγRIIaH BINDING ACTIVITIES OF THE VARIANT/ KD VALUE FOR THE STRONGER OF THE FcγRIIaR- AND FcγRIIaH-BINDING ACTIVITIES OF THE PARENT POLYPEPTIDE |
|---|---|---|---|---|---|---|---|---|---|---|
| | | FcγRIa | FcγRIIaR | FcγRIIaH | FcγRIIb | FcγRIIaV | | | | |
| IL6R-BP152/ IL6R-L | E233D/L234Y/ G237D/P238D/ Y296D/K326A/ A330R | 7.3E−08 | 8.1E−07 | 5.6E−06 | 4.1E−08 | 4.8E−05 | 19.5 | 135.9 | 75.0 | 1.0 |
| IL6R-BP176/ IL6R-L | E233D/P238D/ K326A/A330K | 7.3E−09 | 6.9E−06 | 3.0E−05 | 3.6E−07 | 5.4E−08 | 19.1 | 83.1 | 8.5 | 8.9 |
| IL6R-BP177/ IL6R-L | E233D/L234Y/ G237D/P238D/ P271G/K326A/ A330K | 3.3E−08 | 7.1E−07 | 8.2E−06 | 5.2E−08 | 3.7E−05 | 13.8 | 159.2 | 60.0 | 0.9 |
| IL6R-BP178/ IL6R-L | E233D/G237D/ P238D/P271G/ A330K | 4.3E−08 | 9.3E−07 | 1.4E−05 | 5.1E−08 | 6.4E−05 | 18.1 | 272.4 | 60.1 | 1.2 |
| IL6R-BP179/ IL6R-L | G237D/P238D/ P271G/K326A/ A330K | 6.4E−08 | 1.4E−06 | 1.8E−05 | 8.4E−08 | 5.8E−05 | 16.7 | 190.9 | 36.9 | 1.8 |
| IL6R-BP180/ IL6R-L | G237D/P238D/ P271G/A330K/ | 9.8E−08 | 1.2E−06 | 1.8E−05 | 6.2E−08 | 7.0E−05 | 18.6 | 290.8 | 49.9 | 1.5 |
| IL6R-BP181/ IL6R-L | E233D/P238D/ P271G/K326A/ A330K | 7.5E−09 | 3.2E−06 | 2.8E−05 | 1.6E−07 | 5.7E−05 | 20.3 | 162.5 | 19.3 | 4.2 |
| IL6R-BP182/ IL6R-L | E233D/P238D/ P271G/Y296D/ A330K | 1.0E−08 | 2.6E−06 | 2.8E−05 | 1.1E−07 | 5.6E−05 | 23.5 | 256.9 | 28.3 | 3.3 |

Table 19-2 is a continuation table of Table 19-1.

TABLE 19-2

| IL6R-BP183/ IL6R-L | E233D/L234Y/P238D/ P271G/K326A/A330K | 1.7E−08 | 2.5E−06 | 1.5E−05 | 2.4E−07 | 5.6E−05 | 10.7 | 62.5 | 12.9 | 3.3 |
|---|---|---|---|---|---|---|---|---|---|---|
| IL6R-BP184/ IL6R-L | E233D/P238D/P271G/ A330K | 1.1E−08 | 2.3E−06 | 3.0E−05 | 1.3E−07 | 6.8E−08 | 18.2 | 238.1 | 24.5 | 3.0 |
| IL6R-BP185/ IL6R-L | E233D/L234Y/G237D/ P238D/P271G/K326A/ A330K | 6.3E−08 | 8.8E−07 | 7.3E−06 | 6.9E−08 | 3.6E−05 | 12.6 | 105.2 | 44.5 | 1.1 |
| IL6R-BP186/ IL6R-L | E233D/L234Y/G237D/ P238D/P271G/Y296D/ K326A/A330K | 4.5E−08 | 9.5E−07 | 9.3E−06 | 6.1E−08 | 4.9E−05 | 15.6 | 152.5 | 50.7 | 1.3 |
| IL6R-BP187/ IL6R-L | L234Y/P238D/P271G/ K326A/A330K | 2.5E−08 | 2.8E−06 | 1.8E−05 | 2.9E−07 | 5.6E−05 | 9.7 | 62.3 | 10.7 | 3.5 |
| IL6R-BP188/ IL6R-L | E233D/G237D/P238D/ H268D/P271G/A330K | 2.1E−08 | 1.0E−06 | 1.6E−05 | 4.5E−08 | 5.8E−05 | 21.9 | 350.1 | 57.5 | 1.3 |
| IL6R-BP189/ IL6R-L | G237D//P238D/H268D/ P271G/K326A/A330K | 4.2E−08 | 1.4E−06 | 2.1E−05 | 7.4E−08 | 4.9E−05 | 18.5 | 283.8 | 41.8 | 1.8 |
| IL6R-BP190/ IL6R-L | G237D//P238D/H268D/ P271G/A330K | 6.3E−08 | 1.1E−06 | 1.7E−05 | 5.8E−08 | 4.5E−05 | 19.3 | 292.6 | 53.2 | 1.5 |
| IL6R-BP191/ IL6R-L | E233D/P238D/H268D/ P271G/K326A/A330K | 4.0E−09 | 3.0E−06 | 2.7E−05 | 1.5E−07 | 4.9E−05 | 20.3 | 184.9 | 21.1 | 3.8 |
| IL6R-BP192/ IL6R-L | E233D/P238D/H268D/ P271G/Y296D/A330K | 6.5E−09 | 2.5E−06 | 3.2E−05 | 1.1E−07 | 5.9E−05 | 23.1 | 283.2 | 27.3 | 3.4 |
| IL6R-BP193/ IL6R-L | E233D/P238D/H268D/ P271G/A330K | 6.3E−09 | 2.3E−06 | 2.5E−05 | 1.2E−07 | 5.2E−05 | 18.3 | 205.5 | 25.5 | 2.9 |
| IL6R-BP194/ IL6R-L | E233D/L234Y/G237D/ P238D/H268D/P271G/ K326A/A330K | 2.4E−08 | 8.2E−07 | 8.5E−06 | 5.2E−08 | 2.7E−05 | 15.8 | 163.5 | 59.4 | 1.1 |

TABLE 19-2-continued

| | Alteration | | | | | | | | |
|---|---|---|---|---|---|---|---|---|---|
| IL6R-BP195/ IL6R-L | E233D/L234Y/G237D/ P238D/H268D/P271G/ Y296D/K326A/A330K | 2.3E−08 | 9.1E−07 | 1.0E−05 | 5.0E−08 | 3.1E−05 | 18.2 | 200.8 | 62.0 | 1.2 |
| IL6R-BP196/ IL6R-L | L234Y/P238D/H268D/ P271G/K326A/A330K | 1.4E−08 | 3.0E−06 | 1.9E−05 | 2.2E−07 | 5.1E−05 | 13.4 | 85.2 | 13.9 | 3.9 |
| IL6R-BP197/ IL6R-L | E233D/L234Y/G237D/ P238D/P271G/H268D/ P271G/Y296D/A330K | 1.9E−08 | 9.8E−07 | 1.2E−05 | 5.8E−08 | 3.3E−05 | 17.1 | 208.7 | 53.7 | 1.3 |
| IL6R-BP198/ IL6R-L | E233D/L234Y/P238D/ H268D/P271G/K326A/ A330K | 1.1E−08 | 2.2E−06 | 2.0E−05 | 2.0E−07 | 4.4E−05 | 11.0 | 101.5 | 15.7 | 2.8 |
| IL6R-BP199/ IL6R-L | E233D/P238D/K326A/ A330R | 6.4E−09 | 8.5E−06 | 2.8E−05 | 4.9E−07 | 6.1E−05 | 17.5 | 53.0 | 6.3 | 11.1 |
| IL6R-BP200/ IL6R-L | E233D/L234Y/G237D/ P238D/P271G/K326A/ A330R | 3.3E−08 | 6.3E−07 | 4.3E−06 | 3.4E−08 | 3.8E−05 | 18.6 | 123.9 | 91.2 | 0.8 |
| IL6R-BP201/ IL6R-L | E233D/G237D/P238D/ P271G/A330R | 5.1E−08 | 8.4E−07 | 6.9E−06 | 4.0E−08 | 5.2E−05 | 21.0 | 172.1 | 77.1 | 1.1 |
| IL6R-BP202/ IL6R-L | G237D/P238D/P271G/ K326A/A330R | 9.5E−08 | 1.2E−06 | 9.2E−06 | 6.4E−08 | 5.9E−05 | 19.2 | 144.0 | 48.4 | 1.5 |
| IL6R-BP203/ IL6R-L | G237D/P238D/P271G/ A330R | 1.8E−07 | 9.9E−07 | 1.1E−05 | 4.9E−08 | 7.2E−05 | 20.5 | 226.8 | 63.7 | 1.3 |
| IL6R-BP204/ IL6R-L | E233D/P238D/P271G/ K326A/A330R | 7.6E−09 | 4.5E−06 | 2.1E−06 | 2.5E−07 | 5.2E−05 | 17.5 | 82.7 | 12.2 | 5.8 |
| IL6R-BP205/ IL6R-L | E233D/P238D/P271G/ Y296D/A330R | 7.7E−09 | 3.5E−06 | 2.8E−05 | 1.6E−07 | 6.8E−05 | 21.6 | 176.1 | 19.4 | 4.5 |
| IL6R-BP206/ IL6R-L | E233D/P238D/P271G/ A330R | 8.2E−09 | 3.1E−06 | 2.4E−05 | 2.0E−07 | 6.9E−05 | 16.1 | 123.1 | 15.8 | 4.1 |
| IL6R-BP207/ IL6R-L | E233D/P238D/A330R | 2.2E−08 | 1.9E−05 | 2.9E−05 | 8.4E−07 | 6.5E−05 | 23.0 | 34.5 | 3.7 | 25.1 |
| IL6R-BP208/ IL6R-L | E233D/G237D/P238D/ H268D/P271G/A330R | 1.9E−08 | 8.5E−07 | 8.3E−06 | 3.2E−08 | 5.3E−05 | 26.3 | 256.2 | 95.4 | 1.1 |
| IL6R-BP209/ IL6R-L | G237D/P238D/H268D/ P271G/K326A/A330R | 3.9E−08 | 1.2E−06 | 1.0E−06 | 5.1E−08 | 4.1E−05 | 22.7 | 195.3 | 60.4 | 1.5 |
| IL6R-BP210/ IL6R-L | G237D/P238D/H268D/ P271G/A330R | 6.5E−08 | 1.0E−06 | 9.5E−06 | 3.9E−08 | 4.5E−05 | 25.4 | 241.1 | 78.4 | 1.3 |
| IL6R-BP211/ IL6R-L | E233D/P238D/H268D/ P271G/K326A/A330R | 4.2E−09 | 4.1E−06 | 2.7E−05 | 2.2E−07 | 7.3E−05 | 18.5 | 120.5 | 13.8 | 5.4 |
| IL6R-BP212/ IL6R-L | E233D/P238D/H268D/ P271G/Y296D/A330R | 5.2E−09 | 3.5E−06 | 2.2E−05 | 1.7E−07 | 5.2E−05 | 21.1 | 133.3 | 18.7 | 4.5 |
| IL6R-BP213/ IL6R-L | E233D/P238D/H268D/ P271G/A330R | 4.1E−09 | 3.1E−06 | 2.4E−05 | 1.8E−07 | 6.5E−05 | 17.7 | 186.4 | 17.5 | 4.0 |
| IL6R-BP214/ IL6R-L | E233D/L234Y/G237D/ P238D/Y296D/K326A/ A330K | 5.9E−08 | 1.7E−06 | 9.2E−06 | 1.2E−07 | 3.8E−05 | 14.5 | 78.0 | 26.2 | 2.2 |

[Example 13] Preparation of Variants with Enhanced FcγRIIb Binding

As shown in Example 8, when enhancing the FcγRIIb binding, it is preferable that the FcγRIIb binding is enhanced while maximally suppressing the binding to other activating FcγRs. Thus, the present inventors additionally produced variants with enhanced FcγRIIb binding or improved selectivity to FcγRIIb by combining alterations that enhance the FcγRIIb binding or improving the selectivity to FcγRIIb. Specifically, the alterations described in Examples 9, 11, and 12 which were found to be effective when combined with alteration P238D, were combined with one another, on the basis of the P238D alteration which showed the excellent effect to enhance the FcγRIIb binding and to improve the selectivity to FcγRIIb.

Variants were produced by combining the Fc regions of IL6R-G1d (SEQ ID NO: 54) and IL6R-B3 (SEQ ID NO: 63) with alterations E233D, L234Y, G237D, S267Q, H268D, P271G, Y296D, K326D, K326A, A330R, and A330K described in Examples 9, 11, and 12 which were found to be effective when combined with alteration P238D. Using IL6R-L (SEQ ID NO: 56) as the antibody L chain, antibodies comprising the above-described variants in the heavy chain were expressed and purified according to the method described in Reference Example 1. The resulting variants were respectively assessed for the binding to each FcγR (FcγRIa, FcγRIIaH, FcγRIIaR, FcγRIIb, or FcγRIIIaV) by the method described in Reference Example 2.

The KD of each variant to each FcγR is shown in Table 20. "Alteration" refers to an alteration introduced into IL6R-B3 (SEQ ID NO: 63). IL6R-B3/IL6R-L which is used as the template to produce each variant is indicated by asterisk (*). "KD (IIaR)/KD (IIb)" in the table shows the value obtained by dividing the KD of each variant for FcγRIIaR by the KD of each variant for FcγRIIb. The greater the value, the higher the selectivity to FcγRIIb. "KD (IIb) of parent polypeptide/ KD (IIb) of altered polypeptide" shows the value obtained by dividing the KD value of IL6R-B3/IL6R-L for FcγRIIb by the KD value of each variant for FcγRIIb. Meanwhile, "KD (IIaR) of parent polypeptide/KD (IIaR) of altered polypeptide" shows the value obtained by dividing the KD value of IL6R-B3/IL6R-L for FcγRIIaR by the KD value of each variant for FcγRIIaR. In Table 20, the binding of FcγR to IgG in some cases was concluded to be too weak to analyze correctly by kinetic analysis, and thus the values in the last thirty-six rows of the fifth column (KD against FcγRIIaH) and the last thirty-six rows of the seventh column (KD against FcγRIIIaV) were calculated using:

$$KD = C \cdot R_{max}/(R_{eq} - RI) - C \qquad \text{[Equation 2]}$$

described in Reference Example 2.

TABLE 20

| VARIANT NAME | ALTERATION | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD (IIaR)/ KD (IIb) | KD (IIb) OF PARENT POLYPEPTIDE/ KD (IIb) OF ALTERED POLYPEPTIDE | KD (IIaR) OF PARENT POLYPEPTIDE/ KD (IIaR) OF ALTERED POLYPEPTIDE |
|---|---|---|---|---|---|---|---|---|---|
| IL6R-G1d/ IL6R-L | | 3.20E−10 | 1.00E−06 | 6.70E−07 | 2.60E−06 | 3.50E−07 | 0.4 | 1.2 | 1.1 |
| IL6R-B3/ IL6R-L | * | 4.20E−10 | 1.10E−06 | 7.70E−07 | 3.10E−06 | 3.30E−07 | 0.3 | 1 | 1 |
| IL6R-BF648/ IL6R-L | P238D | 1.10E−08 | 1.50E−05 | 4.00E−05 | 1.20E−06 | 7.10E−05 | 12.5 | 2.6 | 0.1 |
| IL6R-BP215/ IL6R-L | G237D/P238D/ H268D/P271G/ Y296D/A330K | 4.30E−08 | 1.30E−06 | 1.40E−05 | 4.10E−08 | 6.70E−05 | 31.7 | 75.6 | 0.8 |
| IL6R-BP216/ IL6R-L | G237D/P238D/ S267Q/H268D/ P271G/A330K | 6.20E−07 | 2.90E−06 | 2.60E−05 | 1.40E−07 | 5.30E−05 | 20.7 | 22.1 | 0.4 |
| IL6R-BP217/ IL6R-L | G237D/P238D/ S267Q/H268D/ P271G/Y296D/ A330K | 2.80E−06 | 3.60E−06 | 2.80E−05 | 1.50E−07 | 6.00E−05 | 24 | 20.7 | 0.3 |
| IL6R-BP218/ IL6R-L | G237D/P238D/ H268D/P271G/ K326/A330K | 3.70E−08 | 1.50E−06 | 1.20E−05 | 7.60E−08 | 3.80E−05 | 19.7 | 40.8 | 0.7 |
| IL6R-BP219/ IL6R-L | L234Y/G237D/ P238D/H268D/ P271G/A330K | 4.60E−08 | 6.10E−07 | 2.50E−06 | 3.40E−08 | 2.90E−05 | 17.9 | 91.2 | 1.8 |
| IL6R-BP220/ IL6R-L | E233D/G237D/ P238D/H268D/ P271G/Y296D/ A330K | 2.00E−08 | 1.10E−06 | 1.20E−05 | 3.60E−08 | 5.80E−05 | 30.6 | 86.1 | 1 |
| IL6R-BP221/ IL6R-L | L234Y/G237D/ P238D/Y296D/ K326A/A330R | 1.30E−07 | 7.10E−07 | 2.50E−06 | 2.80E−08 | 4.60E−05 | 25.4 | 110.7 | 1.5 |
| IL6R-BP222/ IL6R-L | L234Y/G237D /P238D/P271G/ K326A/A330R | 5.10E−08 | 7.10E−07 | 2.60E−06 | 3.40E−08 | 4.70E−05 | 20.9 | 91.2 | 1.5 |
| IL6R-BP223/ IL6R-L | L234Y/G237D/ P238D/H268D/ P271G/K326A/ A330R | 2.70E−08 | 6.00E−07 | 2.80E−06 | 2.50E−08 | 3.20E−05 | 24 | 12.4 | 1.8 |
| IL6R-BP224/ IL6R-L | L234Y/G237D/ P238D/S267Q/ H268D/P271G/ K326A/A330R | 6.20E−09 | 4.50E−07 | 9.50E−06 | 3.50E−08 | 4.10E−05 | 12.9 | 88.6 | 2.4 |
| IL6R-BP225/ IL6R-L | I234Y/G237D/ P238D/K326D/ A330R | 9.50E−08 | 6.90E−07 | 2.80E−06 | 3.50E−08 | 3.20E−05 | 19.7 | 88.6 | 1.6 |
| IL6R-BP226/ IL6R-L | L234Y/G237D/ P238D/P271G/ K326D/A330R | 5.20E−08 | 5.70E−07 | 2.40E−06 | 3.30E−08 | 3.60E−05 | 17.3 | 93.9 | 1.9 |
| IL6R-BP227/ IL6R-L | L234Y/G237D/ P238D/H268D/ P271G/K326D/ A330R | 2.70E−08 | 6.20E−07 | 2.90E−06 | 3.20E−08 | 2.60E−05 | 19.4 | 96.9 | 1.8 |
| IL6R-BP228/ IL6R-L | L234Y/G237D/ P238D/S267Q/ H268D/P271G/ K326D/A330R | 5.50E−09 | 4.20E−07 | 1.10E−05 | 4.00E−08 | 3.20E−05 | 10.5 | 77.5 | 2.6 |
| IL6R-BP229/ IL6R-L | E233D/L234Y/ P237D/P238D/ P271G/K326A/ A330R | 5.60E−08 | 8.10E−07 | 3.30E−06 | 4.20E−08 | 3.70E−05 | 19.3 | 73.8 | 1.4 |
| IL6R-BP230/ IL6R-L | E233D/G237D/ P238D/H268D/ P271G/Y296D/ A330R | 1.40E−08 | 5.70E−07 | 9.60E−06 | 2.10E−08 | 6.70E−05 | 27.1 | 147.6 | 1.9 |
| IL6R-BP231/ IL6R-L | G237D/P238D/ H268D/P271G/ Y296D/A330R | 9.40E−09 | 7.40E−07 | 1.10E−05 | 2.30E−08 | 4.00E−05 | 32.2 | 134.8 | 1.5 |
| IL6R-BP232/ IL6R-L | L234Y/G237D/ P238D/P271G/ K326A/A330K | 7.60E−08 | 8.40E−07 | 3.30E−06 | 5.60E−08 | 4.50E−05 | 15 | 55.4 | 1.3 |
| IL6R-BP233/ IL6R-L | L234Y/G237D/ P238D/P271G/ A330K | 7.00E−08 | 6.90E−07 | 2.80E−06 | 3.70E−08 | 5.10E−05 | 18.6 | 83.8 | 1.6 |
| IL6R-BP234/ IL6R-L | E233D/I234Y/ G237D/P238D/ | 6.50E−09 | 1.20E−06 | 2.00E−05 | 1.20E−07 | 3.10E−05 | 10 | 25.8 | 0.9 |

TABLE 20-continued

| VARIANT NAME | ALTERATION | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD (IIaR)/ KD (IIb) | KD (IIb) OF PARENT POLYPEPTIDE/ KD (IIb) OF ALTERED POLYPEPTIDE | KD (IIaR) OF PARENT POLYPEPTIDE/ KD (IIaR) OF ALTERED POLYPEPTIDE |
|---|---|---|---|---|---|---|---|---|---|
| IL6R-BP235/ IL6R-L | S267Q/H268D/ P271G/Y296D/ K326D/A330K E233D/I234Y/ G237D/P238D/ H268D/P271G/ Y296D/K326D/ A330R | 3.50E−09 | 6.80E−07 | 7.50E−06 | 4.40E−08 | 2.50E−05 | 15.5 | 70.5 | 1.6 |
| IL6R-BP236/ IL6R-L | E233D/L234Y/ G237D/P238D/ S267Q/H268D/ P271G/Y296D/ K326D/A330R | 7.70E−09 | 8.40E−07 | 1.90E−05 | 6.50E−08 | 3.90E−05 | 12.9 | 47.7 | 1.3 |
| IL6R-BP237/ IL6R-L | E233D/L234Y/ G237D/P238D/ S267Q/H268D/ P271G/Y296D/ K326A/A330K | 4.10E−09 | 1.10E−06 | 1.90E−05 | 1.00E−07 | 3.50E−05 | 11 | 31 | 1 |
| IL6R-BP238/ IL6R-L | E233D/I234Y/ G237D/P238D/ E268D/P271G/ Y296D/K326A/ A330R | 2.40E−09 | 6.40E−07 | 7.00E−06 | 3.60E−08 | 2.70E−05 | 17.8 | 86.1 | 1.7 |
| IL6R-BP239/ IL6R-L | E233D/L234Y/ G237D/P238D/ S267Q/H268D/ P271G/Y296D/ K326A/A330R | 7.60E−09 | 8.10E−07 | 1.70E−05 | 6.00E−08 | 4.80E−05 | 13.5 | 51.7 | 1.4 |
| IL6R-BP240/ IL6R-L | E233D/G237D/ P238D/S267Q/ H268D/P271G/ A330R | 7.60E−09 | 1.50E−06 | 2.60E−05 | 9.50E−08 | 5.20E−05 | 15.8 | 32.6 | 0.7 |
| IL6R-BP241/ IL6R-L | E233D/G237D/ P238D/H268D/ P271G/K326D/ A330R | 1.10E−09 | 6.80E−07 | 9.00E−06 | 4.50E−08 | 3.10E−05 | 15.1 | 68.9 | 1.6 |
| IL6R-BP242/ IL6R-L | E233D/G237D/ P238D/H268D/ P271G/K326A/ A330R | 1.90E−09 | 7.50E−07 | 8.60E−06 | 5.10E−08 | 2.90E−05 | 14.7 | 60.8 | 1.5 |
| IL6R-BP243/ IL6R-L | E233D/I234Y/ G237D/P238D/ H258D/P271G/ A330R | 3.00E−09 | 5.40E−07 | 6.00E−06 | 3.60E−08 | 2.50E−05 | 15 | 86.1 | 2 |
| IL6R-BP244/ IL6R-L | E233D/G237D/ P238D/S267Q/ H268D/P271G/ Y296D/A330R | 7.80E−09 | 1.80E−06 | 2.60E−05 | 1.10E−07 | 4.60E−05 | 16.4 | 28.2 | 0.6 |
| IL6R-BP245/ IL6R-L | E233D/G237D/ P238D/S267Q/ H268D/P271G/ Y296D/K325D/ A330R | 6.30E−09 | 1.40E−06 | 2.30E−05 | 8.30E−08 | 3.90E−05 | 16.9 | 37.3 | 0.8 |
| IL6R-BP246/ IL6R-L | E233D/G237D/ P238D/S267Q/ H268D/P271G/ Y296D/K325A/ A330R | 8.00E−09 | 1.60E−06 | 2.30E−05 | 9.20E−08 | 4.40E−05 | 17.4 | 33.7 | 0.7 |
| IL6R-BP247/ IL6R-L | E233D/G237D/ P238D/H268D/ P271G/Y296D/ K326D/A330R | 7.50E−09 | 8.10E−07 | 1.20E−05 | 3.70E−08 | 4.40E−05 | 21.9 | 83.8 | 1.4 |
| IL6R-BP248/ IL6R-L | E233D/G237D/ P238D/H268D/ P271G/Y296D/ K326A/A330R | 1.70E−09 | 8.20E−07 | 1.10E−05 | 3.50E−08 | 4.40E−05 | 23.4 | 88.6 | 1.3 |
| IL6R-BP249/ IL6R-L | E233D/L234Y/ G237D/P238D/ H258D/P271G/ Y296D/A330R | 7.00E−09 | 6.20E−07 | 7.20E−06 | 3.70E−08 | 2.80E−05 | 16.8 | 83.8 | 1.8 |

When taking the binding to each FcγR by IL6R-B3/IL6R-L resulting from introducing the K439E alteration into the IL6R-G1d/IL6R-L containing the sequence of native human IgG1 as 1, the binding of IL6R-G1d/IL6R-L to FcγRIa as 1.3 times; the binding of IL6R-G1d/IL6R-L to FcγRIIaR was 1.1 times; the binding of IL6R-G1d/IL6R-L to FcγRIIaH was 1.1 times, the binding of IL6R-G1d/IL6R-L to FcγRIIb binding was 1.2 times, and the binding of IL6R-G1d/IL6R-L to FcγRIIIaV was 0.9 times. Thus, for any given FcγR type, the binding of IL6R-B3/IL6R-L to FcγR was comparable to the binding of IL6R-G1d/IL6R-L to FcγR. Thus, the comparison of the binding of each variant to each FcγR with that of IL6R-B3/IL6R-L prior to introduction of the alteration is assumed to be equivalent to the comparison of the binding of each variant to each FcγR with the binding to each FcγR by IL6R-G1d/IL6R-L containing the sequence of native human IgG1. For this reason, in the subsequent Examples below, the binding activity of each variant to each FcγR will be compared to that to each FcγR by IL6R-B3/IL6R-L prior to introduction of the alteration. Table 20 shows that all the variants have increased FcγRIIb binding activity as compared to IL6R-B3 prior to introduction of the alteration. The binding activity of IL6R-BF648/IL6R-L, which was the lowest, was increased by 2.6 times, while the binding activity of IL6R-BP230/IL6R-L, which is the highest, was increased by 147.6 times. Regarding the value of KD (IIaR)/KD (IIb) that represents the selectivity, the value for IL6R-BP234/IL6R-L, which was the lowest, was 10.0, while the value for IL6R-BP231/IL6R-L, which was the highest, was 32.2. Compared to 0.3 for IL6R-B3/IL6R-L prior to introduction of the alteration, these values imply that all the variants have improved selectivity. All the variants showed lower binding activity to FcγRIa, FcγRIIaH, and FcγRIIIaV than that of IL6R-B3/IL6R-L prior to introduction of the alteration.

[Example 14] X-Ray Crystal Structure Analysis of the Complexes of FcγRIIb Extracellular Region or FcγRIIaR Extracellular Region and Fc Region with Enhanced FcγRIIb Binding As shown in Example 13, the FcγRIIb binding of variant IL6R-BP230/IL6R-L, whose FcγRIIb binding was enhanced most, was enhanced to about 150 times as compared to IL6R-B3/IL6R-L prior to introduction of the alteration, while the enhancement of its FcγRIIaR binding was suppressed to an extent of about 1.9 times. Thus, IL6R-BP230/IL6R-L is a variant excellent in both FcγRIIb binding and selectivity. However, the present inventors sought a possibility to create more preferable variants with further enhanced FcγRIIb binding while suppressing the FcγRIIaR binding as possible.

As shown in FIG. 25 described in Example 10, in the Fc region with alteration P238D, Asp at position 270 (EU numbering) in its CH2 domain B forms a tight electrostatic interaction with Arg at position 131 in FcγRIIb. This amino acid residue at position 131 is His in FcγRIIIa and FcγRIIaH, while it is Arg in FcγRIIaR like in FcγRIIb. Thus, there is no difference between FcγRIIaR and FcγRIIb in terms of the interaction of the amino acid residue at position 131 with Asp at position 270 (EU numbering) in the CH2 domain B.

This is assumed to be a major factor for the poor selectivity between the FcγRIIb binding and FcγRIIaR binding of the Fc region.

On the other hand, the extracellular regions of FcγRIIa and FcγRIIb are 93% identical in amino acid sequence, and thus they have very high homology. Based on the crystal structure analysis of the complex of the Fc region of native IgG1 (hereinafter abbreviated as Fc (WT)) and the extracellular region of FcγRIIaR (J. Imunol. (2011) 187, 3208-3217), a difference found around the interface between the two interacting with each other was only three amino acids (Gln127, Leu132, Phe160) between FcγRIIaR and FcγRIIb. Thus, the present inventors predicted that it was extremely difficult to improve the selectivity of the Fc region between the FcγRIIb binding and FcγRIIaR binding.

In this context, the present inventors conceived that, in order to further enhance the FcγRIIb-binding activity of the Fc region, and to improve the selectivity of the Fc regions between the binding to FcγRIIb and FcγRIIaR binding, it was important to clarify subtle differences between Fc region-FcγRIIb interaction and Fc region-FcγRIIaR interaction by analyzing not only the three-dimensional structure of the complex of the Fc region with enhanced FcγRIIb binding and the extracellular region of FcγRIIb but also the three-dimensional structure of the complex of the Fc region with enhanced FcγRIIb binding and the extracellular region of FcγRIIaR. First, the present inventors analyzed the X-ray crystal structure of the complex of the extracellular region of FcγRIIb or FcγRIIaR and Fc (P208) resulting from eliminating the K439E alteration from the Fc region of IL6R-BP208/IL6R-L created as described in Example 12, which was the variant used as the base in producing IL6R-BP230/IL6R-L.

(14-1) X-Ray Crystal Structure Analysis of the Complex of Fc (P208) and the Extracellular Region of FcγRIIb
[Expression and Purification of Fc (P208)]

Fc (P208) was prepared as described below. First, IL6R-P208 was produced by substituting Lys for Glu at position 439 (EU numbering) in IL6R-BP208, as is in the case of the sequence of native human IgG1. Then, the gene sequence of Fc (P208), which was cloned by PCR from Glu at position 216 (EU numbering) to the C terminus using as a template a DNA encoding a variant with a substitution of Ser for Cys at position 220 (EU numbering), was cloned. Expression vector construction, expression, and purification were achieved according to the method described in Reference Example 1. Meanwhile, Cys at position 220 (EU numbering) in ordinary IgG1 forms a disulfide bond to a Cys in the L chain. When preparing the Fc region alone, the L chain is not co-expressed. Thus, Cys at position 220 was substituted by Ser to avoid unnecessary disulfide bond formation.
[Expression and Purification of the Extracellular Region of FcγRIIb]

The extracellular region of FcγRIIb was prepared according to the method described in Reference Example 2.
[Purification of the Fc (P208)/FcγRIIb Extracellular Region Complex]

0.15 mg of the purified product of Endo F1 (Protein Science (1996) 5, 2617-2622) expressed in E. coli as a fusion protein with glutathione S-transferase was added 1.5 mg of a crystallization sample of the extracellular region of FcγRIIb. This added sample in 0.1 M Bis-Tris buffer (pH 6.5) was allowed to stand at room temperature for three days to cleave off N-type sugar chains except N-acetylglucosamine directly linked to the Asn in the sample of the extracellular region of FcγRIIb. Then, the sample of the extracellular region of FcγRIIb subjected to the sugar chain cleavage treatment was concentrated with a 5000 MWCO ultrafiltration filter, and purified by chromatography with a gel filtration column (Superdex200 10/300) equilibrated with 20 mM HEPES (pH7.5)/0.1 M NaCl. Furthermore, to the purified FcγRIIb extracellular region fraction with its sugar chains cleaved, Fc (P208) was added so that the molar ratio of the FcγRIIb extracellular region would be present in slight excess. The mixture concentrated by ultrafiltration with 10,000 MWCO was purified by chromatography with a gel filtration column (Superdex200 10/300) equilibrated with 25 mM HEPES (pH 7.5), 0.1 M NaCl. The purified fraction prepared as described above was used as a sample of Fc (P208)/FcγRIIb extracellular region complex in the subsequent assessment.

[Crystallization of the Complex of Fc (P208)/FcγRIIb Extracellular Region]

A sample of Fc (P208)/FcγRIIb extracellular region complex concentrated to about 10 mg/ml with a 10000 MWCO ultrafiltration filter was crystallized using the hanging drop vapor diffusion method in combination with the seeding method. VDXm plate (Hampton Research) was used for crystallization. Using a reservoir solution of 0.1 M Bis-Tris (pH 6.5), 19% (w/v) PEG3350, 0.2 M potassium phosphate dibasic, crystallization drops were prepared at a mixing ratio of reservoir solution:crystallization sample=0.85 μl:0.85 μl. Crystals of the complex obtained under the similar condition were crushed with Seed Bead (Hampton Research) to prepare a seed crystal solution. The crystallization drops were added with 0.15 μl of a diluted solution prepared from the seed solution and allowed to stand at 20° C. in sealed reservoir wells. This yielded plate-like crystals.

[X-Ray Diffraction Data Measurements from an Fc (P208)/FcγRIIb Extracellular Region Complex Crystal]

A single crystal of Fc (P208)/FcγRIIb extracellular region complex prepared as described above was soaked into a solution of 0.1 M Bis-Tris (pH 6.5), 24% (w/v) PEG3350, 0.2 M potassium phosphate dibasic, 20% (v/v) ethylene glycol. Then, the single crystal was fished out of the solution using a pin with attached tiny nylon loop, and frozen in liquid nitrogen. X-ray diffraction data of the single crystal was collected at Spring-8 BL32XU. During the measurement, the crystal was constantly placed in a nitrogen stream at −178° C. to maintain in a frozen state. A total of 300 X-ray diffraction images from the single crystal were collected using CCD detector MX-225HE (RAYONIX) attached to a beam line with rotating the single crystal 0.6° at a time. Based on the obtained diffraction images, lattice constant determination, diffraction spot indexing, and diffraction data processing were performed using programs Xia2 (J. Appl. Cryst. (2010) 43, 186-190), XDS Package (Acta Cryst. (2010) D66, 125-132) and Scala (Acta Cryst. (2006) D62, 72-82). Finally, the diffraction intensity data of the single crystal up to 2.81 Å resolution was obtained. The crystal belongs to the space group $C222_1$ with lattice constant a=156.69 Å, b=260.17 Å, c=56.85 Å, α=90°, β=90°, and γ=90°.

[X-Ray Crystal Structure Analysis of Fc (P208)/FcγRIIb Extracellular Region Complex]

The structure of Fc (P208)/FcγRIIb extracellular region complex was determined by a molecular replacement method using program Phaser (J. Appl. Cryst. (2007) 40, 658-674). The number of complexes in an asymmetrical unit was estimated to be one from the size of the obtained crystal lattice and the molecular weight of Fc (P208)/FcγRIIb extracellular region complex. The amino acid residue portions of the A chain positions 239-340 and the B chain positions 239-340, which were taken out as a separate coordinate from the structural coordinate of PDB code: 3SGJ for the crystal structure of Fc (WT)/FcγRIIIa extracellular region complex, were used respectively as models for searching the CH2 domain of the Fc region. Likewise, the amino acid residue portions of the A chain positions 341-444 and the B chain positions 341-443, which were taken out as a single coordinate from the structural coordinate of PDB code: 3 SGJ, were used as a model for searching the CH3 domain of the Fc region. Finally, the amino acid residue portions of the A chain positions 6-178, which were taken out from the structural coordinate of PDB code: 2FCB for the crystal structure of the extracellular region of FcγRIIb, were used as a model for searching Fc (P208). The present inventors tried to determine the orientations and positions of the respective search models of the CH3 domain of the Fc region, the extracellular region of FcγRIIb, and the CH2 domain of the Fc region in the crystal lattices based on the rotation function and translation function, but failed to determine the position of one of the CH2 domains. Then, with reference to the crystal structure of the complex of Fc (WT)/FcγRIIIa extracellular region, the position of the last CH2 domain A was determined based on an electron density map that was calculated based on the phase determined from the remaining three parts. Thus, the present inventors obtained an initial model for the crystal structure of the complex of Fc (P208)/FcγRIIb extracellular region. The crystallographic reliability factor R value of the structural model for the data of diffracted intensity at 25 to 3.0 Å was 42.6% and Free R value was 43.7% after rigid body refinement of the obtained initial structural model which moves the two CH2 domains and two CH3 domains of the Fc region, and the extracellular region of FcγRIIb. Then, structural model refinement was achieved by repeating structural refinement using program REFMAC5 (Acta Cryst. (2011) D67, 355-367) followed by revision of the structural model performed using program Coot (Acta Cryst. (2010) D66, 486-501) with reference to the electron density maps where the coefficients 2Fo-Fc and Fo-Fc were calculated using experimentally determined structural factor Fo, structural factor Fc region calculated according to the structural model, and the phases calculated according to the structural model. Finally, as a result of incorporation of water molecules into the model based on the electron density maps which use 2Fo-Fc or Fo-Fc as the coefficient, and the following refinement, the crystallographic reliability factor, R values and the Free R value of the model containing 4786 non-hydrogen atoms became 24.5% and 28.2% to 27259 diffraction intensity data from 25 Å to 2.81 Å resolution, respectively.

Figure 30:
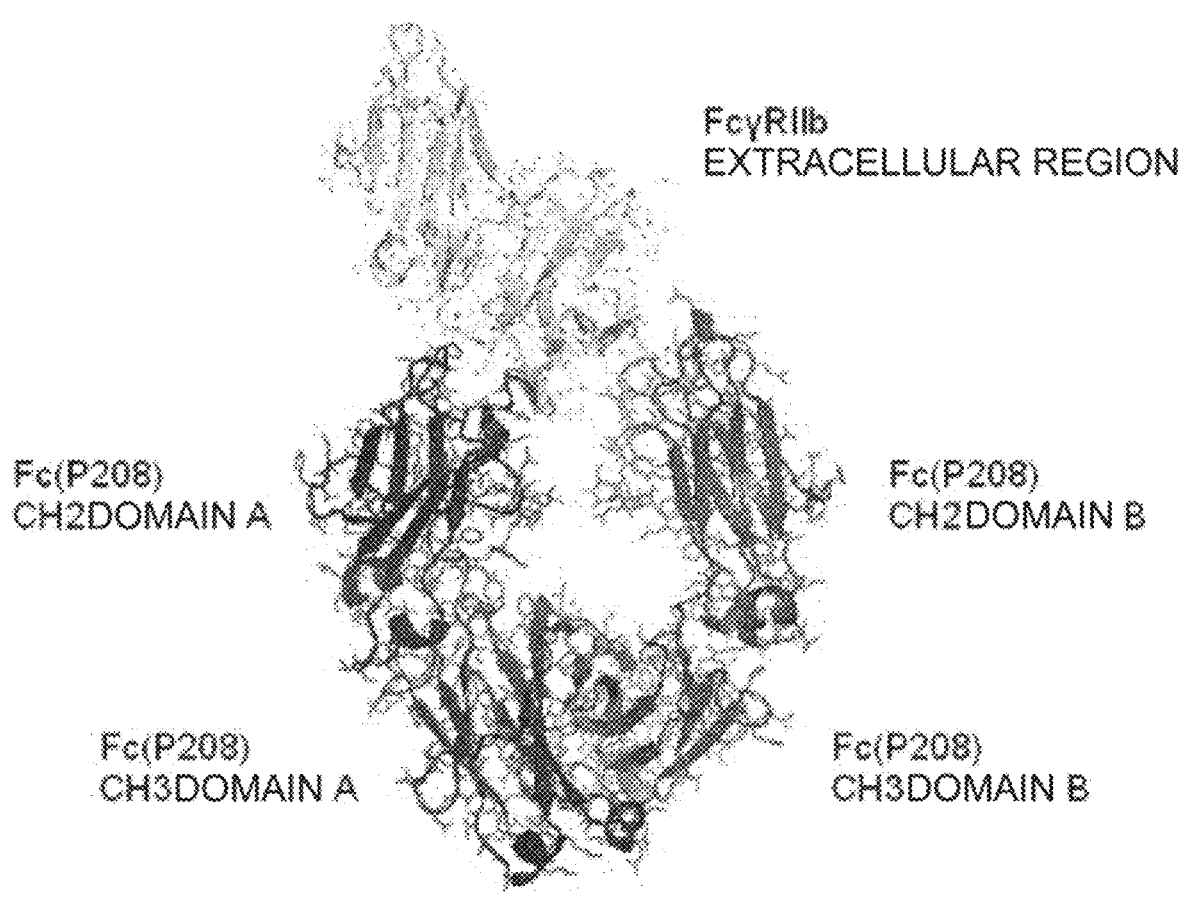
FIG. 30 shows an image of the Fc (P208)/FcγRIIb extracellular region complex determined by X-ray crystal structure analysis. For each of the CH2 and CH3 domains in the Fc portion, those on the left side are referred to as domain A and those on the right side are referred to as domain B.

The three-dimensional structure of the complex of Fc (P208)/FcγRIIb extracellular region was determined at a resolution of 2.81 Å by structure analysis. The structure obtained by the analysis is shown in FIG. 30. FcγRIIb extracellular region was revealed to be bound between the two CH2 domains of the Fc region, which resembles the three-dimensional structures of the previously analyzed complexes of Fc (WT), which is the Fc of native IgG, and each of the extracellular regions of FcγRIIIa (Proc. Natl. Acad. Sci. USA (2011) 108, 12669-126674), FcγRIIIb (Nature (2000) 400, 267-273; J. Biol. Chem. (2011) 276, 16469-16477), and FcγRIIa (J. Immunol. (2011) 187 (6), 3208-3217).

Figure 31:
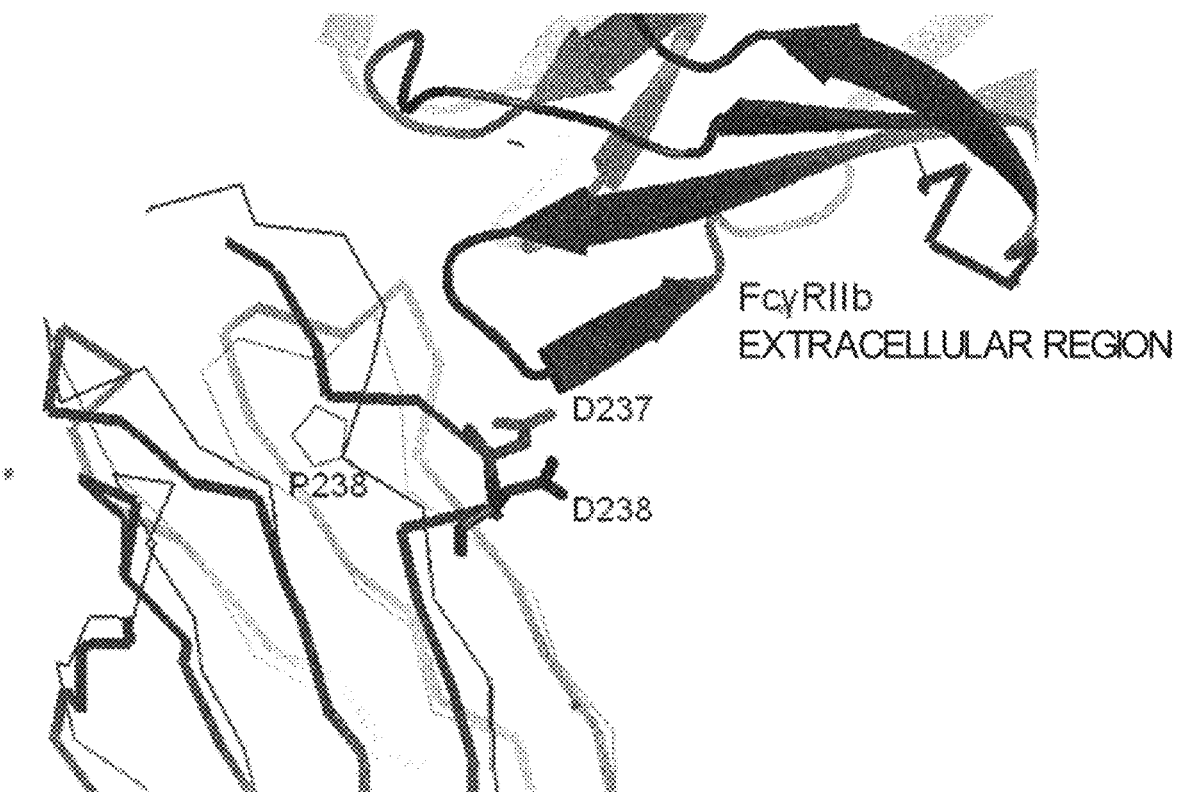
FIG. 31 shows comparison after superimposing the structures of Fc (P208)/FcγRIIb extracellular region complex and Fc (WT)/FcγRIIa extracellular region complex (PDB code: 3RY6) determined by X-ray crystal structure analysis with respect to the CH2 domain A of the Fc portion by the least squares fitting based on the Cα atom pair distances. In the diagram, the structure drawn with heavy line shows the Fc (P208)/FcγRIIb extracellular region complex, while the structure drawn with thin line indicates the structure of Fc (WT)/FcγRIIa extracellular region complex. Only the CH2 domain A of the Fc portion is drawn for the Fc (WT)/FcγRIIa extracellular region complex.
Figure 32:
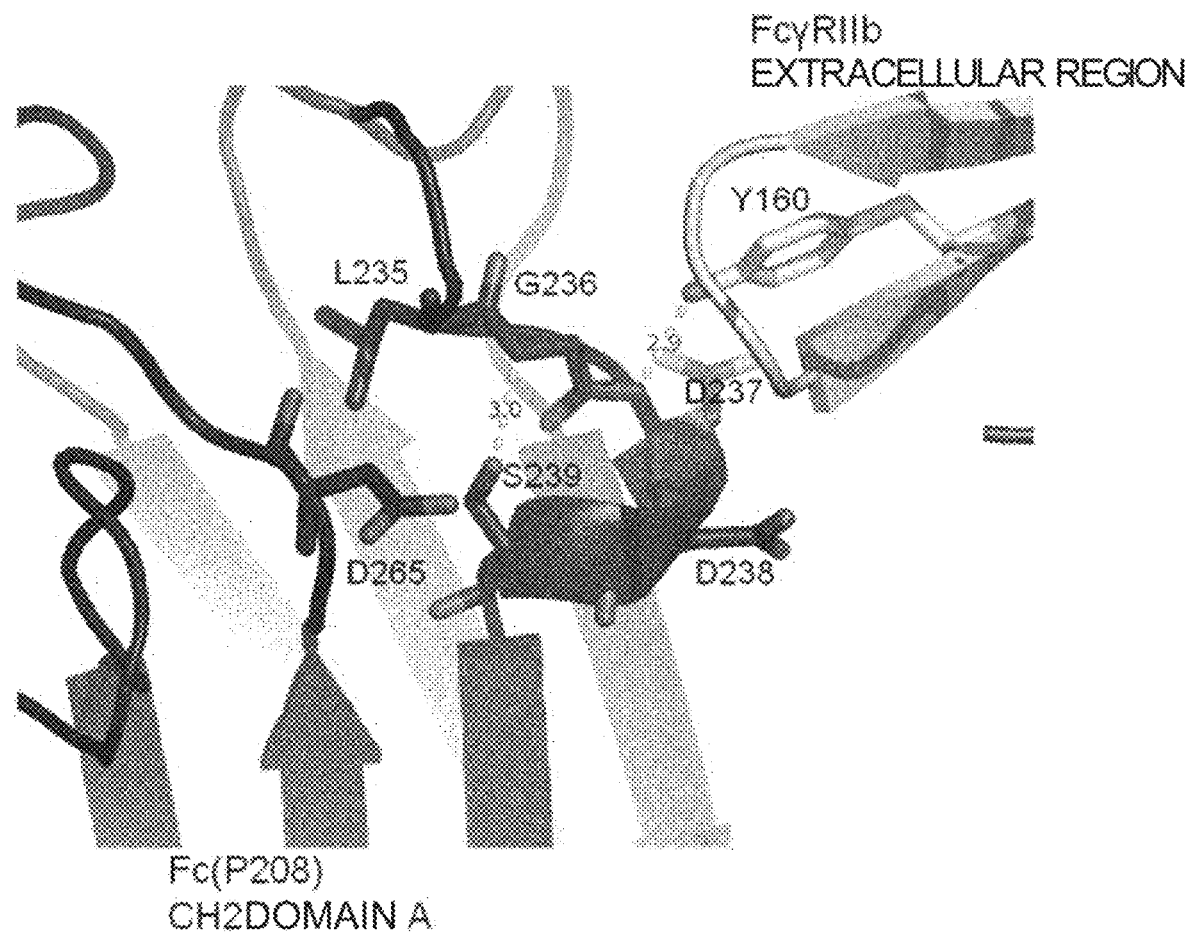
FIG. 32 shows in the X-ray crystal structure of the Fc (P208)/FcγRIIb extracellular region complex, a detailed structure around Asp at position 237 (EU numbering) in the CH2 domain A of the Fc portion, which forms a hydrogen bond with Tyr at position 160 in FcγRIIb at the main chain moiety.

A close observation of the complex of Fc (P208)/FcγRIIb extracellular region revealed a change in the loop structure at positions 233 to 239 (EU numbering) following the hinge region in the CH2 domain A of the Fc region due to an influence of the introduced the G237D and P238D alterations as compared to the complex of Fc (WT)/FcγRIIaR extracellular region (FIG. 31). This leads to that the main chain of Asp at position 237 (EU numbering) in Fc (P208) formed a tight hydrogen bond to the side chain of Tyr at position 160 in FcγRIIb (FIG. 32). In both FcγRIIaH and FcγRIIaR, the amino acid residue at position 160 is Phe, which is incapable of forming such a hydrogen bond. This suggests that the above described hydrogen bond has important contribution to the enhancement of the FcγRIIb binding and the acquisition of the selectivity against FcγRIIa binding of Fc (P208), i.e., improvement of the FcγRIIb-binding activity and reduction of FcγRIIa-binding activity of Fc (P208).

Figure 33:
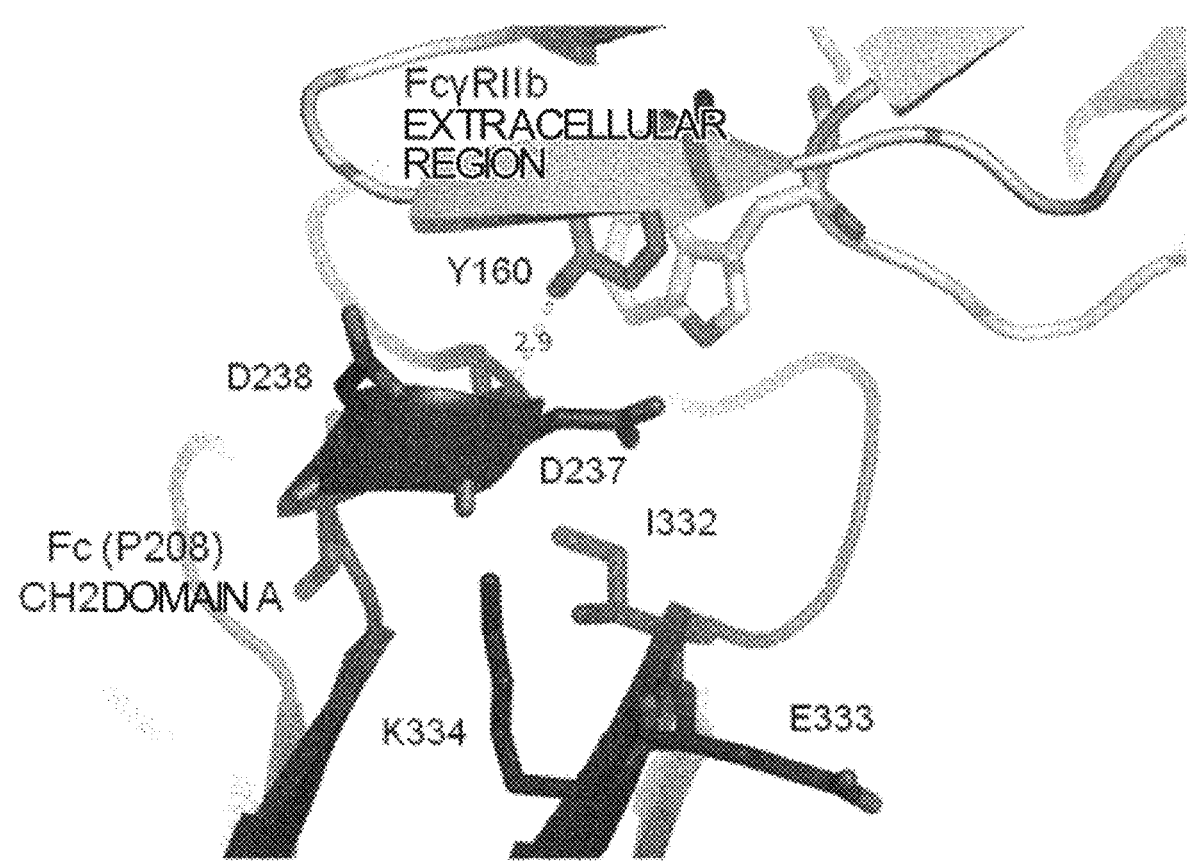
FIG. 33 shows in the X-ray crystal structure of the Fc (P208)/FcγRIIb extracellular region complex, the structure of amino acid residues around Asp at position 237 (EU numbering) in the CH2 domain A of the Fc portion, which forms a hydrogen bond with Tyr at position 160 in FcγRIIb at the main chain moiety.

On the other hand, the side chain of Asp at position 237 (EU numbering) in Fc (P208) forms neither particularly significant interaction in the FcγRIIb binding nor interaction with other residues within the Fc region. Ile at position 332, Glu at position 333, and Lys at position 334 (EU numbering) in the Fc region are located close to Asp at position 237 (EU numbering) (FIG. 33). When the amino acid residues of these positions are substituted by hydrophilic residues to form an interaction with the side chain of Asp at position 237 (EU numbering) in Fc (P208) and the loop structure can be stabilized by the interaction, this can lead to reduction of the entropic energy loss due to the hydrogen bonding between the Fc region and Tyr at position 160 in FcγRIIb and thereby to an increase in the binding free energy, i.e., an increase in the binding activity.

Figure 34:
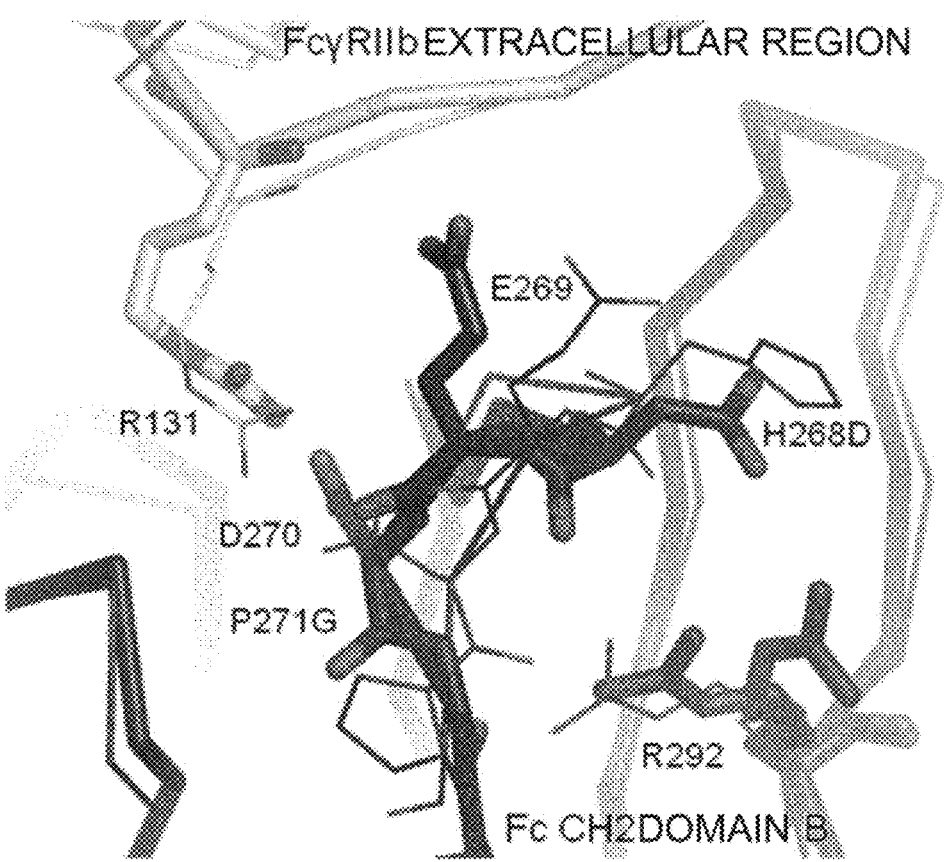
FIG. 34 shows comparison around the loop at positions 266 to 271 (EU numbering) after superimposing the X-ray crystal structures of the Fc (P238D)/FcγRIIb extracellular region complex shown in Example 10 and the Fc (P208)/FcγRIIb extracellular region complex with respect to the CH2 domain B of the Fc portion by the least squares fitting based on the Cα atom pair distances. When compared to Fc (P238D), Fc (P208) has the H268D alteration at position 268 (EU numbering) and the P271G alteration at position 271 (EU numbering) in the loop.

When the X-ray crystal structure of the complex of Fc (P238D) with the P238D alteration and FcγRIIb extracellular region described in Example 10 is compared to the X-ray crystal structure of the complex of Fc (P208) and FcγRIIb extracellular region, alterations are observed at five portions in Fc (P208) as compared to Fc (P238D) and most of the changes are seen only at the side chain level. Meanwhile, a positional deviation at the main chain level due to the Pro-to-Gly alteration at position 271 (EU numbering) is also observed in the CH2 domain B of the Fc region, and in addition there is a structural change in the loop at positions 266 to 270 (EU numbering) (FIG. 34). As described in Example 11, it is suggested that, when Asp at position 270 (EU numbering) in Fc (P238D) forms a tight electrostatic interaction with Arg at position 131 in FcγRIIb, the interaction can induce stereochemical stress at Pro at position 271 (EU numbering). The experiment described herein suggests that the structural change observed with the alteration to Gly for the amino acid at position 271 (EU numbering) is assumed to be a result of elimination of the structural distortion accumulated at Pro prior to the alteration and the elimination results in an increase in the free energy for the FcγRIIb binding, i.e., an increase in the binding activity.

Furthermore, it was demonstrated that, due to the change of the loop structure at positions 266 to 271 (EU numbering), Arg at position 292 (EU numbering) underwent a structural change with two states. In this case, it is suggested that the electrostatic interaction (FIG. 34) formed between Arg at position 292 (EU numbering) and Asp at position 268 (EU numbering) which is an altered residue in Fc (P208) can contribute to the stabilization of the loop structure. Since the electrostatic interaction formed between Asp at position 270 (EU numbering) in the loop and Arg at position 131 in FcγRIIb largely contribute to the binding activity of Fc (P208) to FcγRIIb, the stabilization of the loop structure in the binding conformation was likely to reduce the entropic energy loss upon binding. Thus, the alteration is expected to result in an increase in the binding free energy, i.e., an increase in the binding activity.

Figure 35:
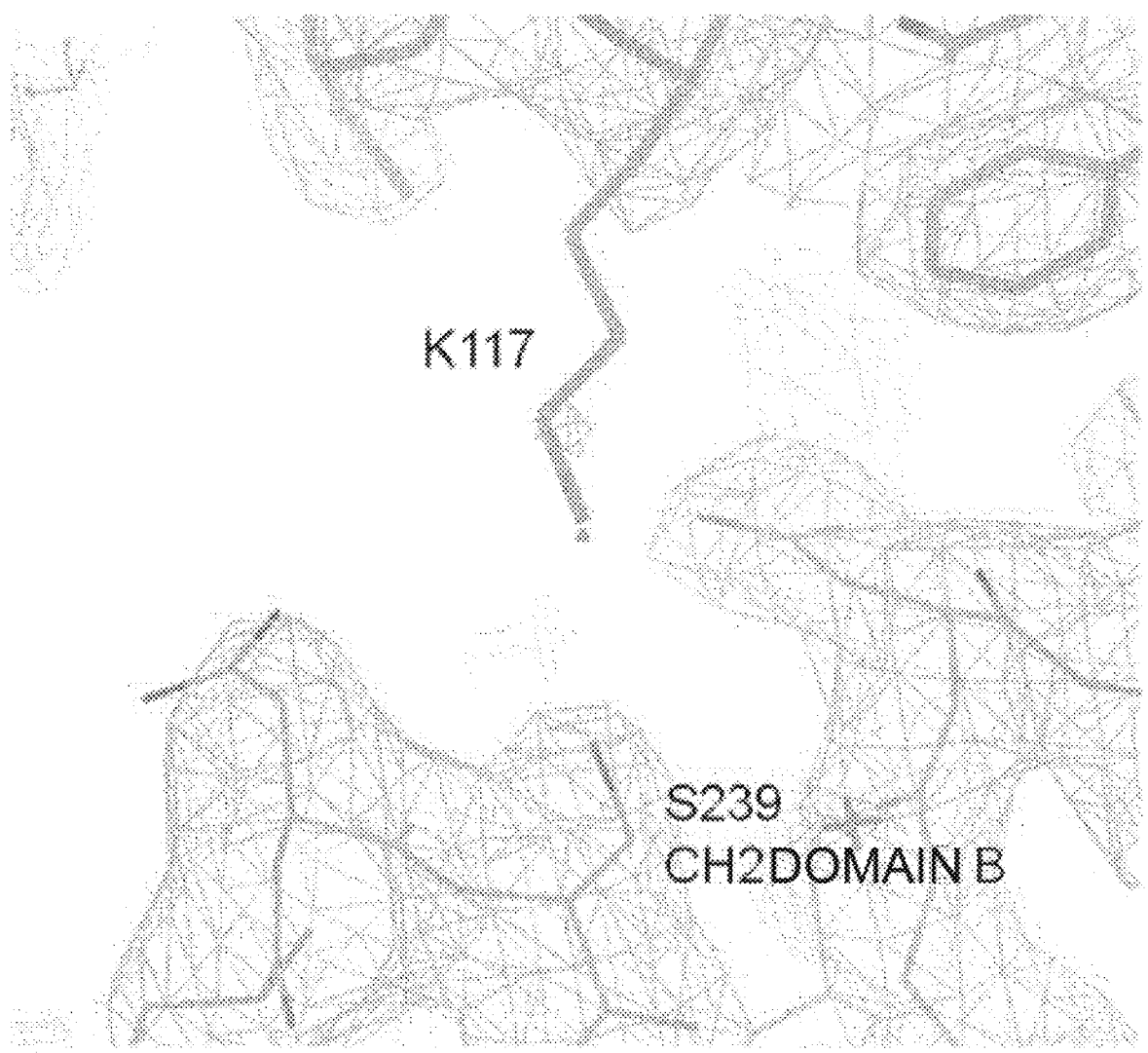
FIG. 35 is a diagram showing the structure around Ser239 in the CH2 domain B of the Fc portion in the X-ray crystal structure of the Fc (P208)/FcγRIIb extracellular region complex, along with the electron density with 2Fo-Fc coefficient determined by X-ray crystal structure analysis.

Moreover, the possibility of alteration to increase the activity was scrutinized based on the result of structural analysis. Ser at position 239 (EU numbering) was found as a candidate for the site to introduce alteration. As shown in FIG. 35, Ser at position 239 (EU numbering) in the CH2 domain B is present at the position toward which Lys at position 117 in FcγRIIb extends most naturally in structure. However, since the electron density was not observed for Lys at position 117 in FcγRIIb by the analysis described above, the Lys has no definite structure. In this situation, Lys117 is likely to have only a limited effect on the interaction with Fc (P208). When Ser at position 239 (EU numbering) in the CH2 domain B is substituted with negatively charged Asp or Glu, such an alteration is expected to cause an electrostatic interaction with the positively charged Lys at position 117 in FcγRIIb, thereby resulting in improved FcγRIIb-binding activity.

On the other hand, an observation of the structure of Ser at position 239 (EU numbering) in the CH2 domain A revealed that, by forming a hydrogen bond to the main chain of Gly at position 236 (EU numbering), the side chain of this Ser stabilized the loop structure at positions 233 to 239, including Asp at position 237 (EU numbering) that forms a hydrogen bond to the side chain of Tyr at position 160 in FcγRIIb, following the hinge region (FIG. 32). The stabilization of the loop structure in the binding conformation can reduce the entropic energy loss upon binding, and result in an increase in the binding free energy, i.e., an improvement of the binding activity. Meanwhile, when Ser at position 239 (EU numbering) in the CH2 domain A is substituted with Asp or Glu, the loop structure may become unstable due to loss of the hydrogen bond to the main chain of Gly at position 236 (EU numbering). In addition, the alteration may result in electrostatic repulsion to Asp at position 265 (EU numbering) in close proximity, leading to further destabilization of the loop structure. The energy for the destabilization corresponds to loss of free energy for the FcγRIIb binding, which may result in reduction in the binding activity.

(14-2) X-Ray Crystal Structure Analysis of the Complex of Fc (P208) and FcγRIIaR Extracellular Region
[Expression and Purification of the Extracellular Region of FcγRIIaR]

The extracellular region of FcγRIIaR was prepared according to the method described in Reference Example 2.
[Purification of the Complex of Fc (P208)/FcγRIIaR Type Extracellular Region]

1.5 mg of purified sample of the extracellular region of FcγRIIaR was added with 0.15 mg of the purified product of Endo F1 (Protein Science (1996) 5, 2617-2622) expressed in E. coli as a fusion protein with S-transferase, 20 µl of 5 U/ml Endo F2 (QA-bio), and 20 µl of 5 U/ml Endo F3 (QA-bio). After 9 days of incubation at room temperature in 0.1 M Na acetate buffer (pH 4.5), the sample was further added with 0.07 mg of the above-described Endo F1, 7.5 µl of the above-described Endo F2, and 7.5 µl of the above-described Endo F3, and was incubated for three days to cleave off N-type sugar chains except N-acetylglucosamine directly linked to the Asn in the sample of the extracellular region of FcγRIIaR. Then, the sample of the extracellular region of FcγRIIaR concentrated with a 10000 MWCO ultrafiltration filter and subjected to the above-described sugar chain cleavage treatment was purified by chromatography with a gel filtration column (Superdex200 10/300) equilibrated with 25 mM HEPES (pH 7), 0.1 M NaCl. Next, to the purified FcγRIIaR extracellular region fraction with its sugar chains cleaved, Fc (P208) was added so that the molar ratio of the FcγRIIb extracellular region would be present in slight excess. The mixture concentrated by ultrafiltration with 10,000 MWCO was purified by chromatography with a gel filtration column (Superdex200 10/300) equilibrated with 25 mM HEPES (pH 7), 0.1 M NaCl. The purified fraction prepared as described above was used as a sample of Fc (P208)/FcγRIIaR type extracellular region complex in the subsequent assessment.

[Crystallization of the Complex of Fc (P208)/FcγRIIaR Type Extracellular Region]

A sample of Fc (P208)/FcγRIIa R type extracellular region complex concentrated to about 10 mg/ml with a 10000 MWCO ultrafiltration filter was crystallized using the sitting drop vapor diffusion method. Using a reservoir solution of 0.1 M Bis-Tris (pH 7.5), 26% (w/v) PEG3350, 0.2 M ammonium sulfate, crystallization drops were prepared at a mixing ratio of reservoir solution:

crystallization sample=0.8 μl:1.0 μl. The drops were tight sealed and allowed to stand at 20° C. This yielded plate-like crystals.

[X-Ray Diffraction Data Measurement from Fc (P208)/FcγRIIaR Extracellular Region Complex Crystal]

A single crystal of Fc (P208)/FcγRIIaR extracellular region complex prepared as described above was soaked into a solution of 0.1 M Bis-Tris (pH 7.5)), 27.5% (w/v) PEG3350, 0.2 M ammonium sulfate, 20% (v/v) glycerol. Then, the crystal was fished out of the solution using a pin with attached tiny nylon loop, and frozen in liquid nitrogen. X-ray diffraction data of the single crystal was collected at synchrotron radiation facility Photon Factory BL-17A in the High Energy Accelerator Research Organization. The crystal was constantly placed in a nitrogen stream at −178° C. to maintain in a frozen state during the measurement. A total of 225 X-ray diffraction images from the single crystal were collected using CCD detector Quantum 315r (ADSC) equipped to the beam line with rotating the single crystal at 0.6° at a time. Based on the obtained diffraction images, lattice constant determination, diffraction spot indexing, and diffraction data processing were performed using programs Xia2 (J. Appl. Cryst. (2010) 43, 186-190), XDS Package (Acta Cryst. (2010) D66, 125-132), and Scala (Acta Cryst. (2006) D62, 72-82). Finally, diffraction intensity data up to 2.87 Å resolution was obtained. The crystal belongs to the space group C222₁ with lattice constant a=154.31 Å, b=257.61 Å, c=56.19 Å, α=90°, β=90°, and γ=90°.

[X-Ray Crystal Structure Analysis of Fc (P208)/FcγRIIaR Type Extracellular Region Complex]

The structure of Fc (P208)/FcγRIIaR type extracellular region complex was determined by a molecular replacement method using program Phaser (J. Appl. Cryst. (2007) 40, 658-674). The number of complexes in an asymmetrical unit was estimated to be one from the size of the obtained crystal lattice and the molecular weight of Fc (P208)/FcγRIIaR extracellular region complex. Using, as a search model, the crystallographic structure of Fc (P208)/FcγRIIb extracellular region complex obtained as described in Example (14-1), the orientation and position of Fc (P208)/FcγRIIaR extracellular region complex in the crystal lattices were determined based on the rotation function and translation function. The crystallographic reliability factor R value of the structural model for the data of diffracted intensity at 25 to 3.0 Å was 38.4% and Free R value was 30.0% after rigid body refinement of the obtained initial structural model which moves the two CH2 domains and two CH3 domains of the Fc region, and the extracellular region of FcγRIIaR. Then, structural model refinement was achieved by repeating structural refinement using program REFMAC5 (Acta Cryst. (2011) D67, 355-367) followed by revision of the structural model performed using program Coot (Acta Cryst. (2010) D66, 486-501) with reference to the electron density maps where the coefficients Fo-Fc and 2Fo-Fc were calculated using experimentally determined structural factor Fo, structural factor Fc calculated according to the model, and the phases calculated according to the model. Finally, as a result of incorporation of water molecules into the model based on the electron density maps which use 2Fo-Fc or Fo-Fc as the coefficient, and the following refinement, the crystallographic reliability factor, R values and the Free R value of the model containing 4758 non-hydrogen atoms became 26.3% and 38.0% to 24838 diffraction intensity data from 25 Å to 2.87 Å resolution, respectively.

Figure 36:
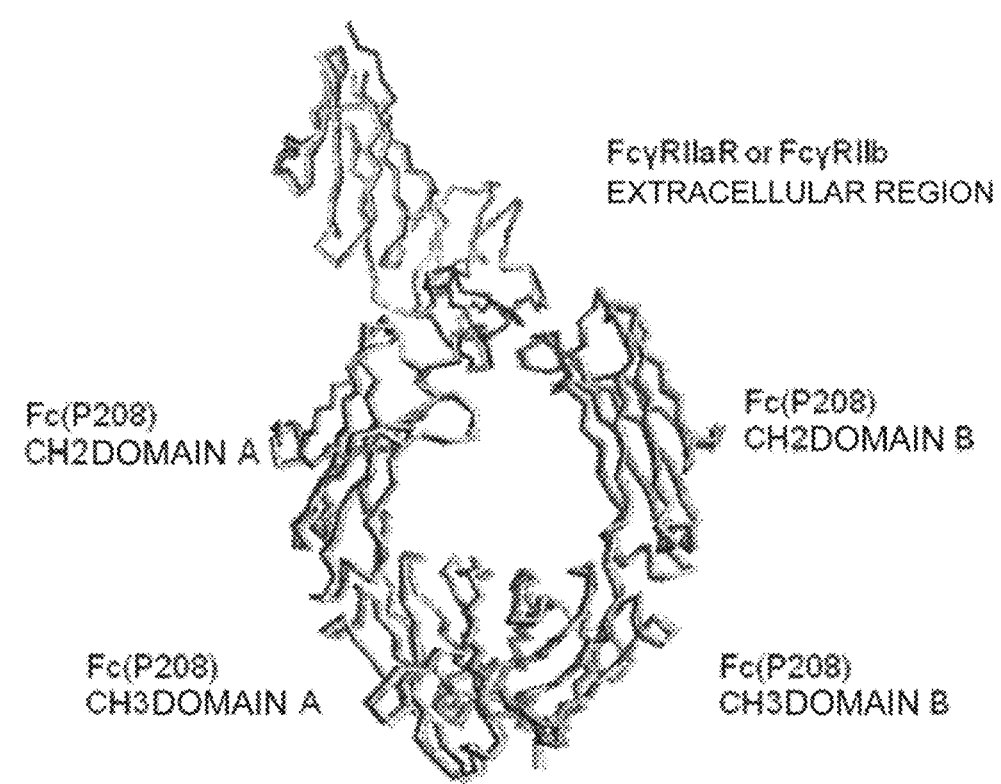
FIG. 36 shows comparison after superimposing the three-dimensional structures of the Fc (P208)/FcγRIIaR extracellular region complex and Fc (P208)/FcγRIIb extracellular region complex determined by X-ray crystal structure analysis by the least squares fitting based on the Cα atom pair distances.

The three-dimensional structure of the complex of Fc (P208)/FcγRIIaR extracellular region was determined at a resolution of 2.87 Å by structure analysis. A comparison of the crystal structure between the complex of Fc (P208)/FcγRIIaR type extracellular region and the complex of Fc (P208)/FcγRIIb extracellular region described in Example (14-1) detected almost no difference at the level of overall structure (FIG. 36), reflecting the very high amino acid identity between the two Fcγ receptors.

Figure 37:
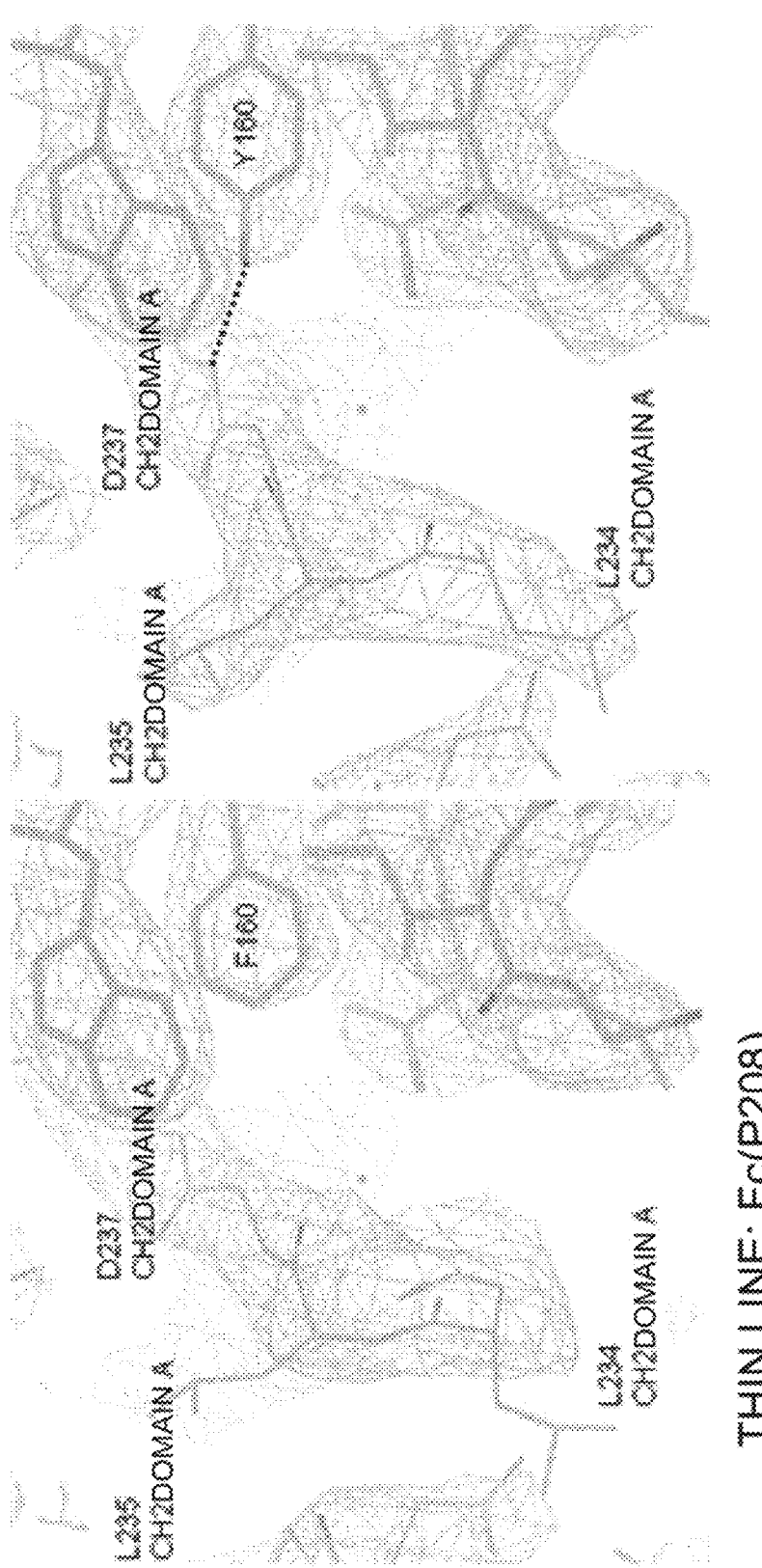
FIG. 37 shows comparison around Asp at position 237 (EU numbering) in the CH2 domain A of the Fc portion between the X-ray crystal structures of the Fc (P208)/FcγRIIaR extracellular region complex and the Fc (P208)/FcγRIIb extracellular region complex, along with the electron density with 2Fo-Fc coefficient determined by X-ray crystal structure analysis.
Figure 38:
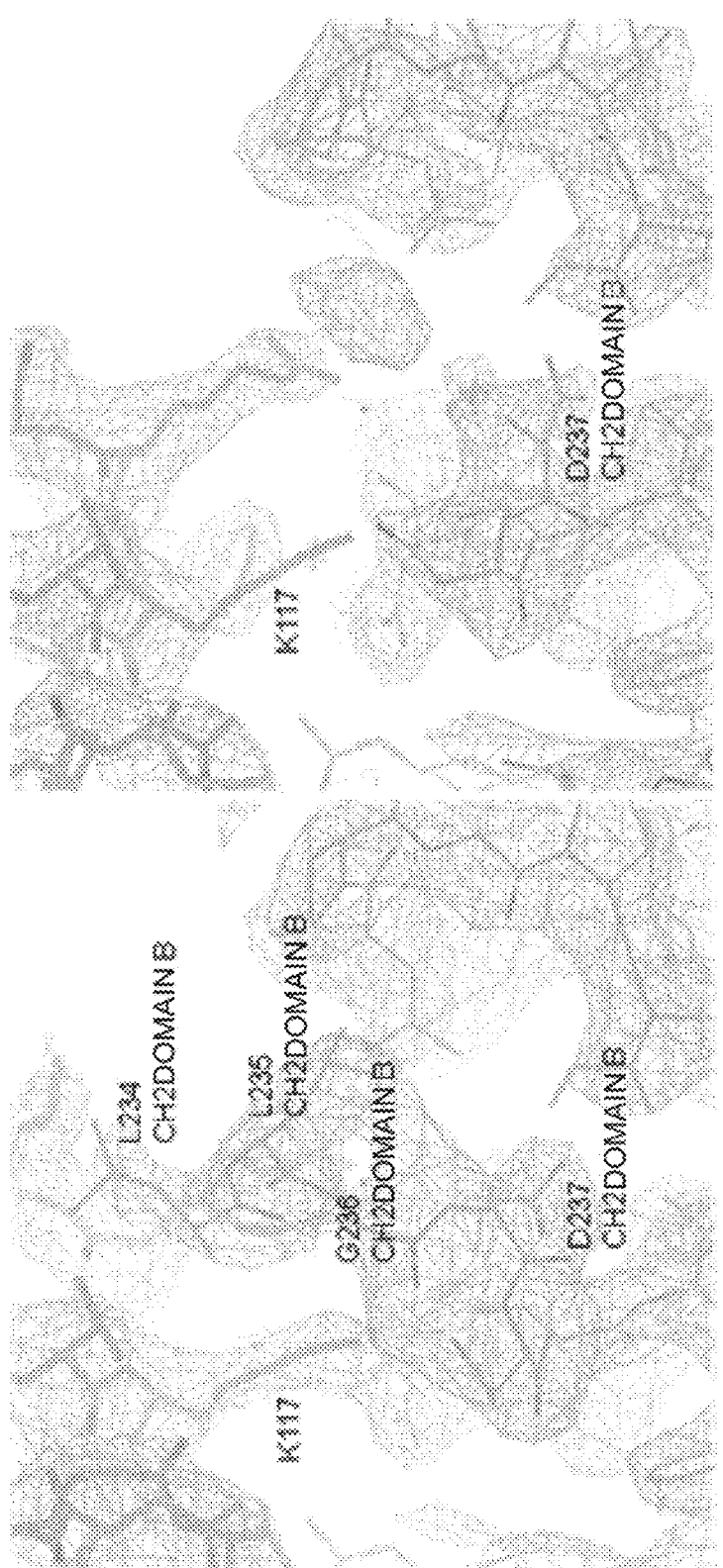
FIG. 38 shows comparison around Asp at position 237 (EU numbering) in the CH2 domain B of the Fc portion between the X-ray crystal structures of the Fc (P208)/ FcγRIIaR extracellular region complex and the Fc (P208)/ FcγRIIb extracellular region complex, along with the electron density with 2Fo-Fc coefficient determined by X-ray crystal structure analysis.

However, a precise observation of the structures at the electron density level detected some differences that can lead to improvement of the selectivity between the FcγRIIb binding and the FcγRIIaR binding of the Fc region. The amino acid residue at position 160 in FcγRIIaR is not Tyr but Phe. As shown in FIG. 37, the hydrogen bond between the main chain of the amino acid residue at position 237 (EU numbering) in the CH2 domain A of the Fc region and Tyr at position 160 in FcγRIIb, though formed upon binding between FcγRIIb and the Fc region with alteration P238D, is expected not to be formed upon binding between FcγRIIaR and the Fc region with alteration P238D. The absence of the hydrogen bond formation can be a major factor for improving the selectivity between the FcγRIIb binding and the FcγRIIaR binding of the Fc region introduced with alteration P238D. Further comparison at the electron density level showed that, in the Fc region/FcγRIIb complex, electron density was clearly observable for the side chains of Leu at positions 235 (EU numbering) and 234 (EU numbering), whereas the electron density of the side chains was unclear in the Fc region/FcγRIIaR complex. This suggests that the loop near position 237 (EU numbering) becomes flexible due to the reduced interaction with FcgRI-IaR around this position. Meanwhile, a structural comparison of the CH2 domain B of the Fc region (FIG. 38) in same region revealed that, in the complex of the Fc region and FcγRIIb, electron density was observable up to Asp at position 237 (EU numbering), whereas, in the complex structure of the Fc region and FcγRIIaR, electron density was observable up to three residues prior to Asp at position 237 (EU numbering), i.e., up to around Leu at position 234 (EU numbering), suggesting that FcγRIIaR binding forms an interaction over a larger region as compared to the FcgRIIb binding. The finding described above suggests the possibility that, in the CH2 domain A of the Fc region, the region from position 234 to 238 (EU numbering) has a large contribution to the binding between the Fc region and FcγRIIb, while in the CH2 domain B of the Fc region the region from position 234 to 238 (EU numbering) has a large contribution to the binding between the Fc region and FcγRIIaR.

[Example 15] Fc Variants for Which Alteration Sites were Determined Based on Crystal Structure As described in Example 14, Asp at position 268 (EU numbering) was suggested to electrostatically interact with Arg at position 292 (EU numbering) (FIG. 34) as a result of the local structural change due to introduction of the alteration P271G in domain B of the variant with enhanced FcγRIIb binding (P208). There is a possibility that the loop structure at positions 266 to 271 (EU numbering) is stabilized by the formation of the interaction, resulting in enhancement of the FcγRIIb binding. Thus, the present inventors assessed whether the FcγRIIb binding of the variant could be enhanced by additional stabilization of its loop structure due to enhancement of the electrostatic interaction by substituting Glu for Asp at position 268 (EU numbering) in the variant. On the other hand, as shown in FIG. 33, Tyr at position 160 (EU numbering) in FcγRIIb interacts with the main chain of Asp at position 237 (EU numbering) in domain A of P208. Meanwhile, the side chain of Asp at position 237 (EU numbering) is located close to Ile at position 332, Glu at position 333, and Lys at position 334

FcγRIIb by the KD value of each variant for FcγRIIb. Meanwhile, KD (IIaR) of parent polypeptide/KD (IIaR) of altered polypeptide shows the value obtained by dividing the KD value of IL6R-B3/IL6R-L for FcγR IIaR by the KD value of each variant for FcγR IIaR. KD (IIaR)/KD (IIb) shows the value obtained by dividing the KD of each variant for FcγRIIaR by the KD of the variant for FcγRIIb. The greater the value, the higher the selectivity to FcγRIIb. In Table 21, the binding of FcγR to IgG was concluded in some cases to be too weak to analyze correctly by kinetic analysis, and thus the values in the last thirteen rows of the fifth column (KD against FcγRIIaH) and the last thirteen rows of the seventh column (KD against FcγRIIIaV) were calculated using:

$$KD=C \cdot R_{max}/(R_{eq}-RI)-C \qquad \text{[Equation 2]}$$

described in Reference Example 2.

TABLE 21

| VARIANT NAME | ALTERATION INTRODUCED INTO IL6R-BP230 | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD (IIaR)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|
| IL6R-G1d/IL6R-L | | 3.20E−10 | 1.00E−06 | 6.70E−07 | 2.60E−06 | 3.50E−07 | 0.4 | 1.1 | 1.2 |
| IL6R-B3/IL6R-L | * | 4.20E−10 | 1.10E−06 | 7.70E−07 | 3.10E−06 | 3.30E−07 | 0.3 | 1 | 1 |
| IL6R-BP230/IL6R-L | | 1.40E−08 | 5.70E−07 | 9.60E−06 | 2.10E−08 | 6.70E−05 | 27.5 | 1.9 | 149 |
| IL6R-BP264/IL6R-L | H268E | 6.50E−09 | 4.80E−07 | 9.20E−06 | 1.20E−08 | 5.20E−05 | 40.6 | 2.3 | 265 |
| IL6R-BP384/IL6R-L | K334R | 3.00E−09 | 1.30E−06 | 1.80E−05 | 7.10E−08 | 4.50E−05 | 17.7 | 0.9 | 43.5 |
| IL6R-BP390/IL6R-L | I332S | 1.60E−09 | 4.90E−07 | 7.30E−06 | 2.10E−08 | 2.90E−05 | 22.9 | 2.2 | 144.9 |
| IL6R-BP391/IL6R-L | I332T | 9.60E−10 | 3.40E−07 | 4.40E−06 | 1.30E−08 | 1.90E−05 | 26.6 | 3.2 | 242.2 |
| IL6R-BP392/IL6R-L | I332K | 7.90E−09 | 7.30E−06 | 2.80E−05 | 9.90E−07 | 2.90E−05 | 7.3 | 0.2 | 3.1 |
| IL6R-BP393/IL6R-L | I332R | 1.10E−08 | 3.90E−06 | 4.60E−05 | 2.70E−06 | 4.80E−05 | 1.4 | 0.3 | 1.2 |
| IL6R-BP465/IL6R-L | E333K | 1.60E−08 | 6.10E−07 | 1.50E−05 | 2.10E−08 | 6.70E−05 | 29.8 | 1.8 | 151,2 |
| IL6R-BP466/IL6R-L | E333R | 1.50E−08 | 5.20E−07 | 1.10E−05 | 1.70E−08 | 2.90E−05 | 30.4 | 2.1 | 181.3 |
| IL6R-BP467/IL6R-L | K334S | 8.90E−10 | 1.10E−06 | 1.20E−05 | 4.10E−08 | 3.20E−05 | 25.8 | 1 | 75.4 |
| IL6R-BP468/IL6R-L | K334T | 9.70E−10 | 1.10E−06 | 9.70E−06 | 4.00E−08 | 2.70E−05 | 26.3 | 1 | 77.7 |
| IL6R-BP469/IL6R-L | E333S | 1.30E−08 | 6.00E−07 | 1.20E−05 | 2.30E−08 | 3.70E−05 | 26.4 | 1.8 | 136.6 |
| IL6R-BP470/IL6R-L | E333T | 1.50E−08 | 4.90E−07 | 1.00E−05 | 1.60E−08 | 3.70E−05 | 30.6 | 2.2 | 192.5 |

(EU numbering) in the molecule without forming any particularly significant interaction. Thus, the present inventors also assessed whether the interaction with Tyr at position 160 in FcγRIIb can be enhanced through stabilization of the loop structure at positions 266 to 271 (EU numbering) due to increased interaction with the side chain of Asp at position 237 (EU numbering) by substituting hydrophilic amino acid residues at the positions described above.

Variants of IL6R-BP230/IL6R-L prepared as described in Example 13 were produced by introducing with each of the alterations H268E, I332T, I332S, I332E, I332K, E333K, E333R, E333S, E333T, K334S, K334T, and K334E. IL6R-L (SEQ ID NO: 56) was used as the antibody L chain. Antibodies containing the light chain of IL6R-L and the above-described heavy chain variants were expressed and purified according to the method described in Reference Example 1. The purified antibodies were assessed for their binding to each FcγR (FcγRIa, FcγRIIaH, FcγRIIaR, FcgRIIb, or FcgRIIIaV) by the method described in Reference Example 2.

The KD of each variant to each FcγR is shown in Table 21. In the table, "alteration" refers to an alteration introduced into IL6R-BP3 (SEQ ID NO: 63). IL6R-B3/IL6R-L which is used as the template to produce IL6R-BP230 is indicated by asterisk (*). KD (IIb) of parent polypeptide/KD (IIb) of altered polypeptide in the table shows the value obtained by dividing the KD value of IL6R-B3/IL6R-L for Both FcγRIIb-binding activity and FcγRIIb selectivity of IL6R-BP264/IL6R-L, IL6R-BP465/IL6R-L, IL6R-BP466/IL6R-L, and IL6R-BP470, resulting from introducing alterations H268E, E333K, E333R, and E333T, respectively, into IL6R-BP230/IL6R-L were increased as compared to those of IL6R-BP230/IL6R-L. The FcγRIIb selectivity of IL6R-BP391/IL6R-L introduced with the I332T alteration was reduced while its FcγRIIb-binding activity was increased as compared to IL6R-BP230/IL6R-L.

[Example 16] Comprehensive Introduction of Alterations at Amino Acid Residues Around Position 271 (EU Numbering)

In the structural comparison between Fc (P208) and FcγRIIb and Fc (P238D)/FcγRIIb, the most significant difference is found in the structure around position 271 (EU numbering) in the CH2 domain B of the Fc region (FIG. 33). As described in Example 11, it is suggested that, when, in Fc (P238D), Asp at position 270 (EU numbering) forms a tight electrostatic interaction with Arg at position 131 in FcγRIIb, the interaction can induce stereochemical stress at Pro at position 271 (EU numbering). In the structure of Fc (P208)/FcγRIIb, due to the substitution of Gly for Pro at position 271 (EU numbering), a positional deviation occurred at the main chain level so as to eliminate the structural distortion, resulting in a large structural change around position 271.

There is a possibility that additional stabilization of the changed structure around position 271 further reduces the entropic energy loss caused by the binding upon formation of an electrostatic interaction with Arg at position 131 in FcγRIIb. Thus, alterations that enhance the FcγRIIb binding or increase the FcγRIIb selectivity of the Fc region were sought by comprehensive introduction of alterations at amino acid residues around position 271 (EU numbering).

IL6R-BP267 was constructed as a template in comprehensive introduction of alterations by introducing alterations E233D, G237D, P238D, H268E, and P271G into IL6R-B3 (SEQ ID NO: 63). IL6R-L (SEQ ID NO: 56) was used as the antibody L chain. Antibodies containing the light chain of IL6R-L and the above-described heavy chain variants were expressed and purified according to the method described in Reference Example 1. The purified antibodies were assessed for their binding to each FcγR (FcγRIa, FcγRIIaH, FcγRIIaR, FcgRIIb, or FcgRIIIaV) by the method described in Reference Example 2. The amino acids at positions 264, 265, 266, 267, 269, and 272 (EU numbering) in IL6R-BP267 were substituted with each of 18 types of amino acids, except Cys and the amino acid prior to substitution. IL6R-L (SEQ ID NO: 56) was used as the antibody L chain. Antibodies containing the light chain of IL6R-L and the above-described heavy chain variants were expressed and purified according to the method described in Reference Example 1. The purified antibodies were assessed for their binding to each FcγR (FcγRIa, FcγRIIaH, FcγRIIaR, FcγRIIb, or FcγRIIIaV) by the method described in Reference Example 2. Variants whose FcγRIIb binding has been enhanced or FcγRIIb selectivity has been increased as compared to the FcγRIIb binding or FcγIIb selectivity of IL6R-BP267/IL6R-L prior to introduction of the alterations are shown in Table 22.

peptide/KD (IIaR) of altered polypeptide shows the value obtained by dividing the KD of IL6R-B3/IL6R-L for FcγRIIaR by the KD of each variant for FcγR IIaR. KD (IIaR)/KD (IIb) shows the value obtained by dividing the KD value of each variant for FcγRIIaR by the KD value of the variant for FcγRIIb. The greater the value, the higher the selectivity to FcγRIIb. In Table 22, the binding of FcγR to IgG in some cases was concluded to be too weak to analyze correctly by kinetic analysis, and thus the values in the last sixteen rows of the fifth column (KD against FcγRIIaH) and the last sixteen rows of the seventh column (KD against FcγRIIaV) were calculated using:

$$KD = C \cdot R_{max}/(R_{eq} - RI) - C \qquad \text{[Equation 2]}$$

described in Reference Example 2.

All the binding activities of variants shown in Table 22 to FcγRIa, FcγRIIaH, and FcγRIIIaV were comparable or reduced as compared to that of IL6R-B3/IL6R-L. Meanwhile, the FcγRIIb-binding activity of variants resulting from adding alterations S267A, V264I, E269D, S267E, V266F, S267G, and V266M, respectively, to IL6R-BP267/IL6R-L were increased as compared to that of IL6R-BP267/IL6R-L prior to addition of alteration. Meanwhile, the KD (IIaR)/KD (IIb) values of variants resulting from adding the S267A, S267G, E272M, E272Q, D265E, E272D, E272N, V266L, E272I, and E272F alterations, respectively, to IL6R-BP267/IL6R-L were increased as compared to that of IL6R-BP267/IL6R-L prior to addition of alteration. This demonstrates that the S267A, S267G, E272M, E272Q, D265E, E272D, E272N, V266L, E272I, and E272F alterations produce the effect to improve the FcγRIIb selectivity.

TABLE 22

| VARIANT NAME | ALTERATION INTRODUCED INTO IL6R-BP267 | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD (IIaR)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|
| IL6R-B3/IL6R-L | * | 3.20E-10 | 1.00E-06 | 6.70E-07 | 2.60E-06 | 3.50E-07 | 0.4 | 1 | 1 |
| IL6R-BP267/IL6R-L | | 4.00E-09 | 1.70E-06 | 1.90E-05 | 1.30E-07 | 5.30E-05 | 13 | 0.6 | 20.5 |
| IL6R-BP348/IL6R-L | S267A | 5.50E-10 | 7.00E-07 | 2.20E-05 | 4.60E-08 | 2.70E-05 | 15.3 | 1.4 | 56.9 |
| IL6R-BP300/IL6R-L | V264I | 9.60E-09 | 6.90E-07 | 2.20E-05 | 5.80E-08 | 5.60E-05 | 11.9 | 1.4 | 44.8 |
| ILSR-BP367/IL6R-L | E269D | 3.10E-09 | 1.20E-06 | 4.60E-05 | 1.00E-07 | 5.30E-05 | 11.7 | 0.8 | 25.7 |
| ILSR-BP350/IL6R-L | S267E | 8.90E-10 | 1.50E-07 | 8.30E-05 | 1.00E-07 | 8.90E-05 | 1.5 | 6.5 | 25.2 |
| IL6R-BP333/IL6R-L | V266F | 9.10E-09 | 1.50E-06 | 3.40E-05 | 1.20E-07 | 5.90E-05 | 12.5 | 0.7 | 22.2 |
| IL6R-BP352/IL6R-L | S267G | 1.80E-09 | 1.90E-06 | 2.80E-05 | 1.20E-07 | 4.30E-05 | 15.7 | 0.5 | 21.3 |
| IL6R-BP339/IL6R-L | V266M | 4.60E-09 | 1.40E-06 | 1.80E-05 | 1.30E-07 | 2.40E-05 | 11.3 | 0.7 | 20.6 |
| IL6R-BP520/IL6R-L | E272M | 3.90E-09 | 3.00E-06 | 3.10E-05 | 1.70E-07 | 4.70E-05 | 17.5 | 0.3 | 14.9 |
| IL6R-BP523/IL6R-L | E272Q | 3.70E-09 | 2.70E-06 | 2.90E-05 | 1.70E-07 | 4.10E-05 | 15.9 | 0.4 | 15.5 |
| IL6R-BP313/IL6R-L | D265E | 2.60E-08 | 1.30E-05 | 4.70E-05 | 8.40E-07 | 3.80E-05 | 15.6 | 0.1 | 3.1 |
| IL6R-BP513/IL6R-L | E272D | 3.80E-09 | 1.70E-06 | 3.60E-05 | 1.10E-07 | 7.50E-05 | 15.4 | 0.6 | 23.6 |
| IL6R-BP521/IL6R-L | E272N | 3.60E-09 | 2.90E-06 | 4.40E-05 | 1.90E-07 | 9.90E-05 | 15.2 | 0.3 | 13.5 |
| IL6R-BP338/IL6R-L | V266L | 1.50E-08 | 2.20E-06 | 2.20E-05 | 1.50E-07 | 2.50E-05 | 15 | 0.5 | 17.9 |
| ILSR-BP517/IL6R-L | E272I | 3.20E-09 | 2.10E-06 | 2.20E-05 | 1.40E-07 | 3.50E-05 | 14.7 | 0.5 | 18.1 |
| IL6R-BP514/IL6R-L | E272F | 4.30E-09 | 3.00E-06 | 6.40E-05 | 2.10E-07 | 9.10E-05 | 14 | 0.3 | 12.3 |

The KD value of each variant to each FcγR is shown in Table 22. In the table, "alteration" refers to an alteration introduced into IL6R-B3, which was used as a template. IL6R-B3/IL6R-L which is used as the template to produce IL6R-BP267 is indicated by asterisk (*). In the table, KD (IIb) of parent polypeptide/KD (IIb) of altered polypeptide shows the value obtained by dividing the KD value of IL6R-B3/IL6R-L for FcγRIIb by the KD value of each variant for FcγRIIb. Meanwhile, KD (IIaR) of parent poly-

[Example 17] Enhancement of the FcγRIIb Binding by Introduction of Alterations into CH3 Region A substitution alteration of Leu for Pro at position 396 (EU numbering) has been reported to enhance the FcγRIIb binding (Cancer Res. (2007) 67, 8882-8890). The amino acid at position 396 (EU numbering) is present at a position which is not directly involved in the interaction with FcγR. However, the amino acid can be assumed to have an effect on the interaction with FcγR by changing the antibody structure. Thus, the present inventors assessed whether the FcγRIIb binding of the Fc region is enhanced or its FcγRIIb selectivity is increased by comprehensive introduction of amino acid alterations at position 396 (EU numbering) in the Fc region.

IL6R-BP423 was constructed as a template in comprehensive introduction of alterations by introducing alterations E233D, G237D, P238D, S267A, H268E, P271G, and A330R into IL6R-B3 (SEQ ID NO: 63). Variants, in which the amino acid at position 396 (EU numbering) in IL6R-BP423 was substituted with each of 18 types of amino acids, except cysteine and the amino acid prior to substitution, were constructed. IL6R-L (SEQ ID NO: 56) was used as the antibody L chain. Antibodies containing the light chain of IL6R-L and the above-described heavy chain variants were expressed and purified according to the method described in Reference Example 1. The purified antibodies were assessed for their binding to each FcγR (FcγRIa, FcγRIIaH, FcγRIIaR, FcγRIIb, or FcγRIIIaV) by the method described in Reference Example 2. The binding of the resulting variants to each FcγR is shown in Table 23.

and the last nineteen rows of the seventh column (KD against FcγRIIIaV) were calculated using:

$$KD = C \cdot R_{max}/(R_{eq}-RI)-C \qquad \text{[Equation 2]}$$

described in Reference Example 2.

The result shown in Table 23 demonstrates that: the FcγRIIb-binding activity of IL6R-BP456/IL6R-L resulting from introducing alteration P396M into IL6R-BP423/IL6R-L, IL6R-BP455/IL6R-L resulting from introducing alteration P396L into IL6R-BP423/IL6R-L, IL6R-BP464/IL6R-L resulting from introducing alteration P396Y into IL6R-BP423/IL6R-L, IL6R-BP450/IL6R-L resulting from introducing alteration P396F into IL6R-BP423/IL6R-L, IL6R-BP448/IL6R-L resulting from introducing alteration P396D into IL6R-BP423/IL6R-L, IL6R-BP458/IL6R-L resulting from introducing alteration P396Q into IL6R-BP423/IL6R-L, IL6R-BP453/IL6R-L resulting from introducing alteration P396I into IL6R-BP423/IL6R-L, IL6R-BP449/IL6R-L resulting from introducing alteration P396E into IL6R-BP423/IL6R-L, IL6R-BP454/IL6R-L resulting from introducing alteration P396K into IL6R-BP423/IL6R-L, and IL6R-BP459/IL6R-L resulting from introducing alteration

TABLE 23

| VARIANT NAME | ALTERATION INTRODUCED INTO IL6R-BP423 | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD (IIaR)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|
| IL6R-G1d/IL6R-L | | 3.20E−10 | 1.00E−06 | 6.70E−07 | 2.60E−06 | 3.50E−07 | 0.4 | 1.1 | 1.2 |
| IL6R-B3/IL6R-L | * | 4.20E−10 | 1.10E−06 | 7.70E−07 | 3.10E−06 | 3.30E−07 | 0.3 | 1 | 1 |
| IL6R-BP423/IL6R-L | | 7.70E−10 | 1.80E−07 | 2.00E−06 | 5.10E−09 | 1.60E−05 | 34.2 | 6.3 | 604 |
| IL6R-BP447/IL6R-L | P396A | 9.00E−10 | 1.60E−07 | 2.00E−06 | 5.30E−09 | 2.50E−05 | 29.7 | 7 | 584 |
| IL6R-BP448/IL6R-L | P396D | 7.50E−10 | 1.30E−07 | 1.40E−06 | 4.10E−09 | 9.70E−06 | 31.7 | 8.5 | 759 |
| IL6R-BP449/IL6R-L | P396E | 9.10E−10 | 1.40E−07 | 1.50E−06 | 4.60E−09 | 1.20E−05 | 29.8 | 8 | 667 |
| IL6R-BP450/IL6R-L | P396F | 8.40E−10 | 1.20E−07 | 1.30E−06 | 4.10E−09 | 9.60E−06 | 29.4 | 9.2 | 763 |
| IL6R-BP451/IL6R-L | P396G | 9.80E−10 | 1.80E−07 | 2.00E−06 | 6.20E−09 | 1.20E−05 | 29.2 | 6.1 | 499 |
| IL6R-BP452/IL6R-L | P396H | 7.50E−10 | 1.30E−07 | 1.50E−06 | 5.10E−09 | 1.10E−05 | 25.9 | 8.3 | 602 |
| IL6R-BP453/IL6R-L | P396I | 7.50E−10 | 1.20E−07 | 9.30E−07 | 4.60E−09 | 7.40E−06 | 25.5 | 9.4 | 675 |
| IL6R-BP454/IL6R-L | P396K | 8.20E−09 | 1.30E−07 | 1.40E−06 | 4.80E−09 | 9.10E−06 | 27.5 | 8.4 | 649 |
| IL6R-BP455/IL6R-L | P396L | 7.50E−10 | 1.30E−07 | 1.60E−06 | 4.00E−09 | 8.50E−06 | 31.8 | 8.6 | 767 |
| IL6R-BP456/IL6R-L | P396M | 6.00E−10 | 1.20E−07 | 2.00E−06 | 3.50E−09 | 9.20E−06 | 35.3 | 8.9 | 888 |
| IL6R-BP457/IL6R-L | P396N | 9.10E−10 | 1.50E−07 | 2.60E−06 | 5.20E−09 | 1.30E−05 | 28.9 | 7.3 | 591 |
| IL6R-BP458/IL6R-L | P396Q | 7.80E−10 | 1.40E−07 | 1.40E−06 | 4.50E−09 | 1.10E−05 | 31.1 | 7.9 | 687 |
| IL6R-BP459/IL6R-L | P396R | 1.10E−09 | 1.50E−07 | 1.40E−06 | 5.10E−09 | 1.20E−05 | 28.9 | 7.5 | 607 |
| IL6R-BP460/IL6R-L | P396S | 8.70E−10 | 1.60E−07 | 3.20E−06 | 6.50E−09 | 1.40E−05 | 25.2 | 6.7 | 478 |
| IL6R-BP461/IL6R-L | P396T | 1.30E−09 | 1.30E−07 | 1.50E−06 | 5.10E−09 | 9.90E−06 | 24.4 | 8.8 | 602 |
| IL6R-BP462/IL6R-L | P396V | 9.70E−10 | 1.30E−07 | 1.40E−06 | 5.20E−09 | 9.00E−06 | 25 | 8.5 | 593 |
| IL6R-BP463/IL6R-L | P396W | 1.30E−09 | 1.60E−07 | 1.90E−06 | 5.60E−09 | 1.20E−05 | 28.1 | 7 | 554 |
| IL6R-BP464/IL6R-L | P396Y | 1.10E−09 | 1.30E−07 | 2.10E−06 | 4.00E−09 | 9.90E−06 | 31.5 | 8.7 | 773 |

In the table, "alteration introduced into IL6R-BP423" refers to an alteration introduced into IL6R-BP423, which was used as a template. IL6R-B3/IL6R-L which is used as the template to produce IL6R-BP423 is indicated by asterisk (*). In the table, KD (IIb) of parent polypeptide/KD (IIb) of altered polypeptide shows the value obtained by dividing the KD value of IL6R-B3/IL6R-L for FcγRIIb by the KD value of each variant for FcγRIIb. Meanwhile, KD (IIaR) of parent polypeptide/KD (IIaR) of altered polypeptide shows the value obtained by dividing the KD value of IL6R-B3/IL6R-L for FcgR IIaR by the KD value of each variant for FcγR IIaR. KD (IIaR)/KD (IIb) shows the value obtained by dividing the KD of each variant for FcγRIIaR by the KD of the variant for FcγRIIb. The greater the value, the higher the selectivity to FcγRIIb. In Table 23, the binding of FcγR to IgG in some cases was concluded to be too weak to analyze correctly by kinetic analysis, and thus the values in the last nineteen rows of the fifth column (KD against FcγRIIaH)

P396R into IL6R-BP423/IL6R-L was all increased as compared to that of IL6R-BP423/IL6R-L prior to introduction of the alterations. Meanwhile, the KD (IIaR)/KD (IIb) value of IL6R-BP456/IL6R-L resulting from introducing alteration P396M into IL6R-BP423/IL6R-L was larger as compared to that of IL6R-BP423/IL6R-L prior to introduction of the alteration, demonstrating the improved FcγRIIb selectivity. As seen in Table 23, the binding activity of the prepared variants to FcγRIa, FcγRIIaH, and FcγRIIIaV was all lower than that of IL6R-B3/IL6R-L, which was the parent polypeptide.

[Example 18] Preparation of Variants with Enhanced FcγRIIb Binding Using Subclass Sequences The FcγR binding profile varies depending on the subclass of human IgG. The present inventors assessed whether the difference in the binding activity to each FcγR between IgG1 and IgG4 could be utilized to increase the FcγRIIb-binding activity and/or improve the selectivity. First, IgG1 and IgG4 were analyzed for their binding activity to each FcγR. IL6R-G4d (SEQ ID NO: 64) containing G4d was con- structed as the antibody H chain. G4d is an Fc region that lacks the C-terminal Gly and Lys and contains a substitution of Pro for Ser at position 228 (EU numbering) in human IgG4. IL6R-L (SEQ ID NO: 56) was used as the antibody L chain. Antibodies containing the light chain of IL6R-L and IL6R-G1d/IL6R-L or IL6R-G4d/IL6R-L were expressed and purified according to the method described in Reference Example 1. The purified antibodies were assessed for their binding to each FcγR (FcγRIa, FcγRIIaH, FcγRIIaR, FcγRIIb, or FcγRIIIaV) by the method described in Refer- ence Example 2. The binding of the resulting variants to each FcgR is summarized in Table 24.

TABLE 24

| VARIANT NAME | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) |
|---|---|---|---|---|---|
| IL6R-G1d/ IL6R-L | 1.20E−10 | 9.70E−07 | 6.50E−07 | 3.90E−06 | 4.20E−07 |
| IL6R-G4d/ IL6R-L | 6.60E−10 | 2.10E−06 | 3.40E−06 | 2.60E−06 | 3.40E−06 |

It was demonstrated that the FcγRIIb binding of IL6R-G4d/IL6R-L was 1.5 times stronger than that of IL6R-G1d/IL6R-L whereas the FcγRIIaR binding of IL6R-G4d/IL6R-L was 2.2 times weaker than that of IL6R-G1d/IL6R-L. Mean- while, the binding activity of IL6R-G4d/IL6R-L to FcγRIa, FcγRIIaH, and FcγRIIIaV was lower than that of IL6R-G1d/IL6R-L. The result described above revealed that IL6R-G4d had preferable characteristics as compared to IL6R-G1d in terms of both FcgRIIb-binding activity and selectivity.

Figure 39:
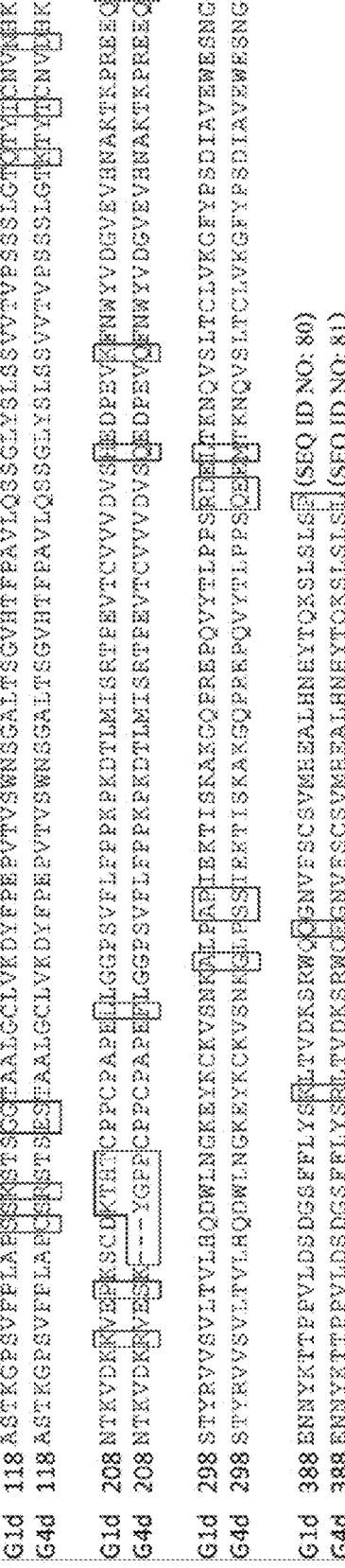
FIG. 39 shows comparison between the constant-region sequences of G1d and G4d. In the diagram, the amino acids boxed with thick-frame indicate positions with different amino acid residues between G1d and G4d.

FIG. 39 is an alignment to compare the CH1 sequences of G1d and G4d up to the C terminus (positions 118 to 445 (EU numbering)). In FIG. 39, amino acid residues that are different between G1d and G4d are filled with black. The present inventors assessed whether the FcγRIIb binding could be further increased and/or the FcγRIIb selectivity could be further improved by selecting, from the above-described different amino acids, some portions that are predicted to be involved in the interaction with FcγR, and grafting at least one amino acid residue or more of the G4d sequence, which confers a property preferable from the viewpoint of both FcγRIIb-binding activity and selectivity, to a variant with enhanced FcγRIIb binding.

Specifically, the present inventors produced:
IL6R-BP473 resulting from introducing alteration A327G into IL6R-BP230;
IL6R-BP472 resulting from introducing alteration A330S into IL6R-BP230;

IL6R-BP471 resulting from introducing alteration P331S into IL6R-BP230;

IL6R-BP474 resulting from introducing alterations A330S and P331S into IL6R-BP230;

IL6R-BP475 resulting from introducing alterations A327G and A330S into IL6R-BP230;

IL6R-BP476 resulting from introducing alterations A327G, A330S, and P331S into IL6R-BP230;

IL6R-BP477 resulting from introducing alterations A327G and P331S into IL6R-BP230.

Furthermore, to construct IL6R-BP478, the amino acids from Ala at position 118 to Thr at position 225 (EU numbering) in IL6R-BP230 was substituted with the amino acids of the G4d sequence from Ala at position 118 to Pro at position 222 (EU numbering). IL6R-L (SEQ ID NO: 56) was used as the antibody L chain. Antibodies containing the light chain of IL6R-L and the heavy chain variants described above were purified according to the method described in Reference Example 1. The purified antibodies were assessed for their binding activity to each FcγR (FcγRIa, FcγRIIaH, FcγRIIaR, FcγRIIb, or FcγRIIIaV) by the method described in Reference Example 2.

The KD value of each variant to each FcγR is shown in Table 25. "KD (IIb) of parent polypeptide/KD (IIb) of altered polypeptide" in the table shows the value obtained by dividing the KD value of IL6R-B3/IL6R-L for FcγRIIb by the KD value of each variant for FcγRIIb. In the table, "alteration introduced into IL6R-BP230" refers to an altera- tion introduced into IL6R-BP230. IL6R-B3/IL6R-L used as the template to produce IL6R-BP230 is indicated by *1. Meanwhile, IL6R-BP478, in which the G4d sequence from Ala at position 118 up to Pro at position 222 (EU numbering) has been substituted for the segment from Ala at position 118 up to Thr at position 225 (EU numbering) in IL6R-BP230, is indicated by *2. "KD (IIaR) of parent polypep- tide/KD (IIaR) of altered polypeptide" shows the value obtained by dividing the KD value of IL6R-B3/IL6R-L for FcγR IIaR by the KD value of the variant for FcγR IIaR. KD (IIaR)/KD (IIb) shows the value obtained by dividing the KD of each variant for FcγRIIaR by the KD of the variant for FcγRIIb. The greater the value, the higher the selectivity to FcγRIIb. In Table 25, the binding of FcγR to IgG in some cases was concluded to be too weak to analyze correctly by kinetic analysis, and thus the values in the last nine rows of the fifth column (KD against FcγRIIaH) and the last nine rows of the seventh column (KD against FcγRIIIaV) were calculated using:

$$KD = C \cdot R_{max}/(R_{eq}-RI)-C \qquad \text{[Equation 2]}$$

described in Reference Example 2.

TABLE 25

| VARIANT NAME | ALTERATION INTRODUCED INTO IL6R-BP230 | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD (IIaR)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|
| IL6R-G1d/IL6R-L | | 3.20E−10 | 1.00E−06 | 6.70E−07 | 2.60E−06 | 3.50E−07 | 0.4 | 1.1 | 1.2 |
| IL6R-B3/IL6R-L | *1 | 4.20E−10 | 1.10E−06 | 7.70E−07 | 3.10E−06 | 3.30E−07 | 0.3 | 1 | 1 |
| IL6R-BP230/IL6R-L | | 1.40E−08 | 5.70E−07 | 9.60E−06 | 2.10E−08 | 6.70E−05 | 27.5 | 1.9 | 149 |

TABLE 25-continued

| VARIANT NAME | ALTERATION INTRODUCED INTO IL6R-BP230 | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD (IIaR)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|
| IL6R-BP471/IL6R-L | P331S | 7.30E−09 | 8.00E−07 | 1.20E−05 | 3.50E−08 | 7.10E−05 | 22.7 | 1.4 | 88.1 |
| IL6R-BP472/IL6R-L | A330S | 5.20E−09 | 3.30E−06 | 2.40E−05 | 1.50E−07 | 3.80E−05 | 21.5 | 0.3 | 20.3 |
| IL6R-BP473/IL6R-L | A327G | 6.20E−09 | 3.80E−07 | 4.80E−06 | 1.80E−08 | 3.60E−05 | 21.1 | 2.9 | 172.2 |
| IL6R-BP474/IL6R-L | A330S/P331S | 4.10E−09 | 3.00E−06 | 3.70E−05 | 1.80E−07 | 5.50E−05 | 16.6 | 0.4 | 16.9 |
| IL6R-BP475/IL6R-L | A327G/A330S | 4.90E−09 | 1.00E−06 | 1.50E−05 | 1.10E−07 | 4.60E−05 | 9.7 | 1.1 | 29.2 |
| IL6R-BP476/IL6R-L | A327G/A330S/ P331S | 5.90E−09 | 1.30E−06 | 1.90E−05 | 1.30E−07 | 4.90E−05 | 9.7 | 0.9 | 23.7 |
| IL6R-BP477/IL6R-L | A327G/P331S | 9.20E−09 | 5.10E−07 | 7.60E−06 | 3.70E−08 | 5.80E−05 | 14 | 2.2 | 84.9 |
| IL6R-BP478/IL6R-L | *2 | 7.70E−09 | 5.40E−07 | 6.70E−06 | 1.90E−08 | 3.50E−05 | 28 | 2 | 160.6 |

Of the variants shown in Table 25, IL6R-BP473/IL6R-L introduced with the alteration A327G showed FcγRIIb binding increased by 1.2 times compared to that of IL6R-BP230/ IL6R-L. IL6R-BP478/IL6R-L produced by substituting the amino acids from Ala at position 118 to Thr at position 225 (EU numbering) of IL6R-BP230 with the amino acids from Ala at position 118 to Pro at position 222 (EU numbering) of G4d sequence, has 1.1 times enhanced binding to FcγRIIb than that of IL6R-BP230/IL6R-L, and binding of IL6R-BP478/IL6R-L to FcγRIIaR is decreased to 0.9 times that of IL6R-BP230/IL6R-L. Binding activities of all variants to FcγRIa, FcγRIIaH, and FcγRIIIaV were lower than those of the parent polypeptide IL6R-B3/IL6R-L.

In the examination carried out so far, introducing the A327G alteration, which substitutes the amino acid in the human IgG4 sequence for the amino acid at position 327 (EU numbering) in variant IL6R-BP230/IL6R-L, was shown to enhance FcγRIIb-binding activity. A further examination was performed for amino acids that do not match between the IgG4 and IgG1 sequences and those other than the amino acid at position 327 (EU numbering). Specifically, variants were produced by introducing the following alterations into IL6R-BP230, which was used as the antibody H chain: K274Q was introduced to produce IL6R-BP541; Y296F was introduced to produce IL6R-BP542; H268Q was introduced to produce IL6R-BP543; R355Q was introduced to produce IL6R-BP544; D356E was introduced to produce IL6R-BP545; L358M was introduced to produce IL6R-BP546; K409R was introduced to produce IL6R-BP547; and Q419E was introduced to produce IL6R-BP548, as indicated by EU numbering respectively. Meanwhile, IL6R-L was used as the common antibody L chain. Antibodies that contain the above heavy chain variant and the light chain IL6R-L were purified according to the methods described in Reference Example 1. The purified antibodies were assessed for their binding to each FcγR (FcγRIa, FcγRIIaH, FcγRIIaR, FcγRIIb, or FcγRIIIaV) by the method of Reference Example 2.

The KD of each variant to each FcγR is shown in Table 26. In the table, "KD (IIb) of the parent polypeptide/KD (IIb) of the altered polypeptide" represents the value obtained by dividing the KD value of IL6R-B3/IL6R-L to FcγRIIb by the KD value of each variant to FcγRIIb. In the table, "alteration of IL6R-BP230" refers to an alteration introduced into IL6R-BP230. IL6R-B3/IL6R-L used as the template to produce IL6R-BP230 is indicated with *1. "KD (IIaR) of the parent polypeptide/KD (IIaR) of the altered polypeptide" represents the value obtained by dividing the KD value of IL6R-B3/IL6R-L to FcγRIIaR by the KD value of the same variant to FcγRIIaR. KD (IIaR)/KD (IIb) represents the value obtained by dividing KD of each variant to FcγRIIaR by KD of the same variant to FcγRIIb. The greater the value, the higher the selectivity for FcγRIIb. It was found that, in some cases, the binding of FcγR to IgG was so weak that the analysis could not be correctly performed by kinetic analysis. Thus, the values in the last nine rows of the fifth column (KD against FcγRIIaH) and the last nine rows of the seventh column (KD against FcγRIIIaV) of Table 26 were calculated using:

$$KD = C \cdot R_{max}/(R_{eq} - RI) - C \qquad \text{[Equation 2]}$$

described in Reference Example 2.

TABLE 26

| VARIANT NAME | ALTERATION INTRODUCED INTO IL6R-BP230 | KD AGAINST FcgRIa (mol/L) | KD AGAINST FcgRIIaR (mol/L) | KD AGAINST FcgRIIaH (mol/L) | KD AGAINST FcgRIIb (mol/L) | KD AGAINST FcgRIIIaV (mol/L) | KD (IIaR)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|
| IL6R-G1d/IL6R-L | | 3.2E−10 | 1.0E−06 | 6.7E−07 | 2.6E−06 | 3.5E−07 | 0.4 | 1.1 | 1.2 |
| IL6R-B3/IL6R-L | *1 | 4.2E−10 | 1.1E−06 | 7.7E−07 | 3.1E−06 | 3.3E−07 | 0.3 | 1.0 | 1.0 |
| IL6R-BP230/IL6R-L | | 1.0E−08 | 4.9E−07 | 9.7E−06 | 1.8E−08 | 3.9E−05 | 28.0 | 2.2 | 175.6 |
| IL6R-BP541/IL6R-L | K274Q | 1.1E−08 | 4.5E−07 | 9.3E−06 | 1.6E−08 | 4.1E−05 | 27.8 | 2.4 | 189.6 |
| IL6R-BP542/IL6R-L | Y296F | 1.3E−08 | 4.9E−07 | 9.7E−06 | 2.0E−08 | 4.3E−05 | 24.4 | 2.2 | 153.7 |
| IL6R-BP543/IL6R-L | H268Q | 2.3E−08 | 5.6E−07 | 7.4E−06 | 2.0E−08 | 4.6E−05 | 27.3 | 1.9 | 151.5 |
| IL6R-BP544/IL6R-L | R355Q | 9.8E−09 | 4.8E−07 | 1.2E−05 | 1.7E−08 | 4.5E−05 | 28.8 | 2.2 | 183.9 |
| IL6R-BP545/IL6R-L | D356E | 9.9E−09 | 5.7E−07 | 9.1E−06 | 1.7E−08 | 4.5E−05 | 32.7 | 1.9 | 178.6 |
| IL6R-BP546/IL6R-L | L358M | 9.0E−09 | 5.0E−07 | 1.0E−05 | 1.5E−08 | 3.7E−05 | 32.8 | 2.2 | 204.6 |
| IL6R-BP547/IL6R-L | K409R | 1.2E−08 | 4.9E−07 | 7.5E−06 | 1.9E−08 | 3.5E−05 | 25.5 | 2.2 | 162.6 |
| IL6R-BP548/IL6R-L | Q419E | 1.2E−08 | 5.0E−07 | 9.4E−06 | 1.9E−08 | 3.4E−05 | 26.2 | 2.2 | 161.8 |

As shown in Table 26, IL6R-BP541/IL6R-L resulting from introducing K274Q (each represented by EU numbering) into IL6R-BP230/IL6R-L, IL6R-BP544/IL6R-L resulting from introducing R355Q into IL6R-BP230/IL6R-L, IL6R-BP545/IL6R-L resulting from introducing D356E into IL6R-BP230/IL6R-L, and IL6R-BP546/IL6R-L resulting from introducing L358M into IL6R-BP230/IL6R-L, showed enhanced FcγRIIb binding as compared to IL6R-BP230/IL6R-L prior to the introduction of alteration. Of them, IL6R-BP544/IL6R-L resulting from introducing R355Q (each represented by EU numbering) into IL6R-BP230/IL6R-L, IL6R-BP545/IL6R-L resulting from introducing D356E into IL6R-BP230/IL6R-L, and IL6R-BP546/IL6R-L resulting from introducing L358M into IL6R-BP230/IL6R-L, were shown to have an increased KD(IIaR)/KD(IIb) value and improved selectivity to FcγRIIb, as compared to IL6R-BP230/IL6R-L prior to the introduction of alteration.

[Example 19] Assessment of Combinations of Alterations that Enhance the FcγRIIb Binding or Improve the FcγRIIb Selectivity Additional combinations of the alterations which had been found by the evaluation described above to improve the FcγRIIb binding or FcγRIIb selectivity were assessed. Specifically, the alterations that had been assessed to be effective in enhancing the FcγRIIb binding and/or improving the FcγRIIb selectivity were introduced in combination into IL6R-B3 (SEQ ID NO: 63). Furthermore, existing alterations S267E and L328F that enhance the FcγRIIb binding (Seung et al., (Mol. Immunol. (2008) 45, 3926-3933)) were introduced into IL6R-B3 to produce IL6R-BP253 as a comparison control. IL6R-L (SEQ ID NO: 56) was used as the antibody L chain. Antibodies containing the light chain of IL6R-L and the above-described heavy chain variants were expressed and purified according to the method as described in Reference Example 1. The purified antibodies were assessed for their binding to each FcγR (FcγRIa, FcγRIIaH, FcγRIIaR, FcγRIIb, or FcγRIIIaV) by the method described in Reference Example 2.

The KD of each variant to each FcγR is shown in Tables 27-1 and 27-2. In these tables, "alteration" refers to an alteration introduced into IL6R-B3 (SEQ ID NO: 63). IL6R-B3/IL6R-L which is used as the template to produce each variant is indicated by asterisk (*). KD (IIb) of parent polypeptide/KD (IIb) of altered polypeptide shows the value obtained by dividing the KD value of IL6R-B3/IL6R-L for FcγRIIb by the KD value of each variant for FcγRIIb. Meanwhile, KD (IIaR) of parent polypeptide/KD (IIaR) of altered polypeptide shows the value obtained by dividing the KD value of IL6R-B3/IL6R-L for FcγR IIaR by the KD of the variant for FcγRIIaR. KD (IIaR)/KD (IIb) shows the value obtained by dividing the KD of each variant for FcγRIIaR by the KD of the variant for FcγRIIb. The greater the value, the higher the selectivity to FcγRIIb as compared to FcγRIIaR. Meanwhile, KD (IIaH)/KD (IIb) shows the value obtained by dividing the KD of each variant for FcγRIIaH by the KD of the variant for FcγRIIb. The greater the value, the higher the selectivity to FcγRIIb as compared to FcγRIIaH. For Tables 27-1 and 27-2, it was found that, in some cases, the binding of FcγR to IgG was too weak to analyze correctly by kinetic analysis. Thus, in Table 27-1, the values in the fifth column (KD against FcγRIIaH) for Fc variants BP262, BP264, BP265, BP266, BP268, BP269, BP423, BP425, BP426, BP428, BP429, BP430, BP431, BP433, BP434, BP435, BP437, BP439, BP440, BP441, BP442, BP443, BP479, BP480, BP481, BP483, BP484, BP492, BP493, BP494, and BP495 and the values in the last forty-three rows of the seventh column (KD against FcγRIIIaV), and in Table 27-2, the values in the fifth column (KD against FcγRIIaH) for Fc variants BP500, BP501, BP503, BP504, BP507, BP508, BP549, BP557, BP559, BP560, BP562, BP564, BP567, and BP568 and all values in the seventh column (KD against FcγRIIIaV) were calculated using:

$$KD = C \cdot R_{max}/(R_{eq} - RI) - C \qquad \text{[Equation 2]}$$

described in Reference Example 2.

TABLE 27-1

| VARIANT NAME | ALTERATION | KD AGAINST FcgRIa (mol/L) | KD AGAINST FcgRIIaR (mol/L) | KD AGAINST FcgRIIaH (mol/L) | KD AGAINST FcgRIIb (mol/L) | KD AGAINST FcgRIIIaV (mol/L) | KD (IIaR)/ KD (IIb) | KD (IIaH)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|---|
| G1d | | 3.2E−10 | 1.0E−06 | 6.7E−07 | 2.6E−08 | 3.5E−07 | 0.4 | 0.3 | 1.1 | 1.2 |
| B3 | * | 4.2E−10 | 1.1E−08 | 7.7E−07 | 3.1E−08 | 3.3E−07 | 0.3 | 0.2 | 1.0 | 1.0 |
| BP253 | S267E/L328F | 6.7E−11 | 2.1E−09 | 1.2E−06 | 1.1E−08 | 3.8E−06 | 0.2 | 107.1 | 528.8 | 276.8 |
| BP262 | G237D/P238D/ H268E/P271G | 1.0E−08 | 2.0E−06 | 4.5E−05 | 1.2E−07 | 5.6E−05 | 17.0 | 375.0 | 0.5 | 25.8 |
| BP264 | E233D/G237D/ P238D/H268E/ P271G/Y296D/ A330R | 7.4E−09 | 3.5E−07 | 2.8E−06 | 1.2E−08 | 2.6E−05 | 20.3 | 227.6 | 3.2 | 252.0 |
| BP265 | G237D/P238D/ H268E/P271G/ Y296D/A330R | 2.3E−08 | 8.3E−07 | 1.2E−05 | 1.5E−08 | 9.6E−05 | 41.2 | 789.5 | 1.8 | 203.9 |
| BP266 | E233D/G237D/ P236D/H268E/ P271G/A330R | 1.4E−06 | 3.2E−07 | 1.1E−05 | 1.8E−08 | 4.0E−05 | 10.0 | 621.5 | 3.4 | 175.1 |
| BP268 | E233D/G237D/ P238D/H268E/ P271G/Y296D | 4.5E−09 | 1.3E−06 | 2.1E−05 | 9.2E−08 | 2.8E−05 | 19.6 | 228.3 | 0.6 | 33.7 |
| BP269 | G237D/P236D/ H268E/P271G/ Y296D | 1.4E−06 | 2.2E−06 | 7.2E−05 | 1.1E−07 | 1.4E−04 | 19.6 | 637.2 | 0.5 | 27.4 |
| BP423 | E233D/G237D/ P238D/S207A/ | 7.7E−10 | 1.8E−07 | 2.0E−06 | 5.1E−09 | 1.6E−05 | 34.2 | 380.6 | 6.3 | 605.5 |

TABLE 27-1-continued

| VARIANT NAME | ALTERATION | KD AGAINST FcgRIa (mol/L) | KD AGAINST FcgRIIaR (mol/L) | KD AGAINST FcgRIIaH (mol/L) | KD AGAINST FcgRIIb (mol/L) | KD AGAINST FcgRIIIaV (mol/L) | KD (IIaR)/ KD (IIb) | KD (IIaH)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|---|
| | H268E/P271G/ A330R | | | | | | | | | |
| BP425 | E233D/G237D/ P238D/V266L/ S267A/H268E/ P271G/A330R | 4.1E−09 | 2.2E−07 | 1.5E−05 | 0.1E−09 | 4.2E−05 | 23.6 | 1644.7 | 5.1 | 339.9 |
| BP426 | E233D/GZSTD/ P238D/S267A/ H268E/E26BD/ P271G/A330R | 1.0E−09 | 1.6E−07 | 4.9E−05 | 5.8E−09 | 4.1E−05 | 27.6 | 8361.8 | 6.8 | 528.0 |
| BP428 | E233D/G287D/ P238D/S267G/ H268E/P271G/ A330R | 4.9E−09 | 3.9E−07 | 4.2E−05 | 1.4E−08 | 3.6E−05 | 28.0 | 3000.0 | 2.8 | 221.4 |
| BP429 | E233D/G237D/ P238D/V264I/ S267G/H268E/ P271G/A330R | 6.2E−09 | 1.7E−07 | 3.5E−06 | 5.4E−09 | 6.8E−05 | 31.5 | 640.1 | 6.5 | 574.1 |
| BP430 | E233D/G287D/ P238D/V266L/ S267G/H268E/ P271G/A330R | 1.7E−08 | 2.2E−07 | 1.1E−05 | 1.2E−08 | 3.5E−05 | 18.5 | 809.1 | 4.9 | 256.2 |
| BP431 | E233D/G237D/ P238D/S267G/ H268E/E269D/ P271G/A330R | 3.6E−09 | 4.1E−07 | 7.6E−06 | 1.2E−09 | 3.2E−05 | 34.6 | 649.6 | 2.7 | 265.0 |
| BP433 | E23SD/G287D/ P238D/H268D/ P271G/Y296D/ A330K/I332T | 7.5E−10 | 6.8E−07 | 7.3E−06 | 3.4E−08 | 2.6E−05 | 20.0 | 216.0 | 1.6 | 91.7 |
| BP434 | E238D/G287D/ P288D/H268D/ P271G/Y296D/ K326D/A330R/ I332T | 5.5E−10 | 3.4E−07 | 4.1E−06 | 1.2E−08 | 2.5E−05 | 27.2 | 333.3 | 3.3 | 252.0 |
| BP435 | E233D/G237D/ P238D/H268D/ P271G/Y296D/ K326NA330R/ I332T | 1.0E−09 | 1.2E−07 | 3.4E−06 | 1.6E−08 | 2.2E−05 | 27.1 | 217.8 | 2.6 | 198.7 |
| BP436 | E23SD/G237D/ P238D/S267A/ H268E/P271G/ Y296D/A330R/ I332T | 2.6E−10 | 2.2E−07 | 2.1E−06 | 5.1E−08 | 1.3E−05 | 43.8 | 411.0 | 4.9 | 606.7 |
| BP437 | G237D/P238D/ S267A/H268E/ P271G/Y296D/ AS30R/I332T | 7.5E−10 | 2.2E−07 | 1.4E−06 | 5.9E−09 | 1.1E−05 | 37.7 | 236.5 | 4.9 | 523.6 |
| BP438 | E233D/G237D/ P238D/S267A/ H268E/P271G/ A330R/I332T | 2.1E−10 | 1.3E−07 | 1.6E−06 | 5.5E−09 | 6.8E−06 | 32.7 | 293.6 | 8.2 | 568.8 |
| BP439 | E233D/G237D/ P238D/V264I/ V266L/3267A/ H266E/P271G/ A330R | 8.7E−09 | 1.3E−07 | 2.8E−06 | 6.1E−09 | 6.6E−05 | 20.9 | 460.5 | 8.7 | 509.9 |
| BP440 | E233D/G237D/ P238D/V264I/ H268E/P271G/ A330R | 8.7E−09 | 1.3E−07 | 1.5E−06 | 5.2E−09 | 2.8E−05 | 24.0 | 307.1 | 8.8 | 595.0 |
| BP441 | E233D/G237D/ P238D/V266L/ H260E/P271G/ A330R | 1.7E−00 | 3.6E−07 | 0.3E−08 | 1.5E−08 | 3.7E−05 | 24.0 | 502.0 | 3.0 | 205.3 |
| BP442 | E233D/G237D/ P238D/H268E/ E269D/P271G/ A330R | 4.5E−09 | 3.8E−07 | 4.7E−06 | 1.2E−08 | 2.5E−05 | 30.6 | 379.0 | 2.9 | 250.0 |

TABLE 27-1-continued

| VARIANT NAME | ALTERATION | KD AGAINST FcgRIa (mol/L) | KD AGAINST FcgRIIaR (mol/L) | KD AGAINST FcgRIIaH (mol/L) | KD AGAINST FcgRIIb (mol/L) | KD AGAINST FcgRIIIaV (mol/L) | KD (IIaR)/ KD (IIb) | KD (IIaH)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|---|
| BP443 | E233D/G237D/ P238D/V266L/ H268E/E269D/ P271G/A330R | 1.8E−08 | 5.1E−07 | 9.5E−06 | 2.3E−05 | 2.3E−05 | 21.7 | 406.0 | 2.2 | 132.5 |
| BP445 | E233D/G237D/ P238D/V264I/ S267A/H268E/ P271G/A330R | 2.0E−09 | 8.0E−08 | 1.5E−06 | 2.6E−09 | 2.4E−05 | 31.0 | 581.4 | 13.8 | 1201.6 |
| BP479 | E233D/G237D/ P238D/V264I/ V266L/S267A/ H268E/P271G | 5.3E−09 | 9.0E−07 | 1.5E−05 | 5.6E−06 | 4.0E−05 | 16.1 | 26S.3 | 1.2 | 55.5 |
| BP480 | E233D/G237D/ P238D/V266L/ H268E/E269D/ P271G | 1.3E−08 | 6.3E−06 | 2.1E−05 | 2.0E−07 | 4.0E−05 | 32.1 | 107.7 | 0.2 | 15.9 |
| BP481 | E233D/G237D/ P238D/V264I/ S267A/H268E/ P271G | 1.0E−09 | 4.0E−07 | 8.3E−06 | 1.9E−08 | 2.4E−05 | 20.5 | 350.5 | 2.8 | 159.8 |
| BP483 | E233D/G237D/ P23BD/V266L/ S267A/H268E/ P271G | 1.3E−09 | 1.3E−08 | 1.8E−05 | 7.8E−08 | 2.5E−05 | 16.0 | 230.0 | 0.8 | 39.7 |
| BP484 | E233D/G237D/ P238D/S267A/ H268E/E26BD/ P271G | 8.2E−10 | 7.8E−07 | 1.1E−05 | 4.6E−08 | 2.5E−05 | 17.1 | 240.7 | 1.4 | 67.8 |
| BP487 | E233D/G237D/ P238D/V264I/ S267A/H268E/ P271G/A330R/ P396M | 1.2E−09 | 3.9E−08 | 0.4E−07 | 1.2E−09 | 1.0E−05 | 33.3 | 730.4 | 28.3 | 2695.7 |
| BP488 | E233D/G237D/ P238D/V264I/ S267A/H268E/ P271G/Y296D/ A330R | 2.2E−09 | 7.4E−08 | 1.8E−06 | 1.9E−09 | 2.0E−05 | 40.1 | 864.8 | 14.8 | 1675.7 |
| BP489 | E233D/G237D/ P238D/V264I/ S267A/H268E/ P271G/Y296D/ A330R/P396M | 1.3E−09 | 4.3E−08 | 8.7E−07 | 1.0E−09 | 1.2E−05 | 42.3 | 870.0 | 25.7 | 3100.0 |
| BP490 | G237D/P238D/ V264I/S267A/ H268E/P271G/ A330R | 4.5E−09 | 1.1E−07 | 2.4E−06 | 2.4E−09 | 2.3E−05 | 46.7 | 1000.0 | 9.8 | 1281.7 |
| BP491 | G237D/P238D/ V264I/S267A/ H268E/P271G/ Y296D/A330R | 5.3E−09 | 1.2E−07 | 2.2E−06 | 3.0E−09 | 2.1E−05 | 38.3 | 723.7 | 9.3 | 1018.7 |
| BP492 | P238D/V264I/ S267A/H268E/ P271G | 7.9E−10 | 9.2E−07 | 1.5E−05 | 2.4E−08 | 3.0E−05 | 30.3 | 670.0 | 1.2 | 131.4 |
| BP493 | P238D/V264I/ S207A/H268E/ P271G/Y296D | 8.2E−10 | 1.1E−08 | 1.3E−05 | 2.1E−08 | 3.5E−05 | 52.1 | 900.5 | 1.0 | 146.9 |
| BP494 | G237D/P238D/ S267A/H268E/ P271G/Y296D/ A330R | 3.9E−09 | 2.5E−07 | 5.4E−06 | 6.6E−09 | 4.0E−05 | 38.6 | 820.7 | 4.3 | 471.1 |
| BP495 | G287D/P238D/ S267G/H268E/ P271G/Y296D/ A330R | 8.3E−09 | 4.9E−07 | 1.2E−05 | 9.7E−09 | 3.3E−05 | 50.9 | 1243.5 | 2.2 | 321.2 |
| BP496 | E233D/G237D/ P238D/V264I/ S267A/H268E/ P271G/Y296D | 1.2E−09 | 4.7E−07 | 3.7E−06 | 1.8E−08 | 3.0E−05 | 25.5 | 201.1 | 2.3 | 166.5 |
| BP497 | E233D/G287D/ P238D/V264I/ S267A/H268E/ | 2.1E−09 | 3.5E−08 | 8.5E−07 | 4.1E−09 | 2.E−05 | 21.0 | 236.5 | 12.9 | 763.5 |

TABLE 27-1-continued

| VARIANT NAME | ALTERATION | KD AGAINST FcgRIa (mol/L) | KD AGAINST FcgRIIaR (mol/L) | KD AGAINST FcgRIIaH (mol/L) | KD AGAINST FcgRIIb (mol/L) | KD AGAINST FcgRIIIaV (mol/L) | KD (IIaR)/ KD (IIb) | KD (IIaH)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|---|
| | P271G/N327G/ A330R | | | | | | | | | |
| BP498 | E233D/G237D/ P238D/V264I/ S267A/H268E/ P271G/A330R/ P396L | 1.3E−09 | 5.1E−08 | 9.3E−07 | 1.7E−09 | 1.0E−05 | 30.3 | 563.6 | 21.7 | 1870.8 |
| BP499 | E233D/G237D/ P2380/V264I/ S267A/H268E/ P271G/Y296D/ A330R/P396L | 1.2E−09 | 4.9E−08 | 1.0E−06 | 1.5E−09 | 1.2E−05 | 38.3 | 684.9 | 22.3 | 2123.3 |

TABLE 27-2

| VARIANT NAME | ALTERATION | KD AGAINST FcgRIa (mol/L) | KD AGAINST FcgRIIaR (mol/L) | KD AGAINST FcgRIIaH (mol/L) | KD AGAINST FcgRIIb (mol/L) |
|---|---|---|---|---|---|
| BP500 | G237D/P238D/V264I/ S267A/H268E/P271G/ Y286D | 2.3E−09 | 7.2E−07 | 25E−05 | 2.4E−08 |
| BP501 | G287D/P298D/V264I/ S267A/H268E/P271G | 2.1E−09 | 6.3E−07 | 1.4E−05 | 2.5E−08 |
| BP502 | E233D/G237D/P238D/ V264I/S267A/H268E/ P271G/Y296D/A327G/ A330R | 2.1E−09 | 1.1E−07 | 1.3E−06 | 3.7E−09 |
| BP503 | E233D/G237D/P238D/ V264I/S267A/H268E/ P271G/Y296D/A327G/ A830R/P396M | 1.2E−09 | 5.7E−08 | 8.6E−07 | 1.7E−09 |
| BP504 | E233D/G237D/P238D/ V264I/8267A/H268E/ P271G/E272P | 1.4E−09 | 4.5E−07 | 1.6E−05 | 2.4E−08 |
| BP505 | E233D/G237D/P238D/ V264I/5267A/H268E/ P271G/E272D | 1.1E−09 | 4.3E−07 | 1.1E−05 | 2.1E−06 |
| BP506 | E233D/G237D/P238D/ V264I/S267A/H268E/ P271G/E272P/Y296D/ A330R | 3.1E−09 | 1.2E−07 | 2.5E−06 | 3.4E−09 |
| BP507 | E233D/G237D/P238D/ V264I/S267A/H268E/ P271G/E272P/A330R | 2.6E−09 | 1.0E−07 | 1.8E−06 | 2.9E−09 |
| BP508 | E233D/G287D/P238D/ V264I/S267A/H268E/ P271G/E272P/Y296D | 1.4E−09 | 5.4E−07 | 2.0E−05 | 2.1E−08 |
| BP509 | E233D/G237D/P238D/ V264I/S267A/H268E/ P271G/E272D/Y296D | 1.1E−09 | 5.2E−07 | 7.9E−06 | 1.8E−08 |
| BP510 | G237D/P238D/V264I/ S267A/H268E/P271G/ E272P/A330R | 6.0E−09 | 1.7E−07 | 4.0E−06 | 3.8E−09 |
| BP511 | G237D/P238D/V264I/ S267A/H268E/P271G/ E272P/Y296D/A330R | 6.0E−09 | 1.8E−07 | 4.3E−06 | 3.5E−09 |
| BP531 | E233D/G237D/P238D/ V264I/S267G/H268E/ P271G/Y296D/A330R/ P396M | 9.4E−09 | 1.2E−07 | 3.5E−06 | 3.8E−09 |
| BP532 | E233D/G237D/P238D/ V264I/H268E/P271G/ Y296D/A330R/P396M | 1.2E−08 | 9.4E−08 | 1.9E−06 | 3.2E−09 |
| BP533 | E233D/G237D/P238D/ V264I/S267G/H268E/ P271G/Y296D/A330R/ P896L | 7.7E−09 | 1.2E−07 | 2.6E−06 | 4.1E−09 |

TABLE 27-2-continued

| | | | | | |
|---|---|---|---|---|---|
| BP534 | E233D/G287D/P238D/ V264I/H268E/P271G/ Y296D/A330R/P396L | 9.3E−09 | 9.1E−08 | 1.8E−06 | 3.0E−09 |
| BP535 | E233D/G237D/P238D/ V264I/S267G/H268E/ P271G/Y296D/A327G/ A330R/P396M | 1.1E−09 | 9.2E−08 | 3.2E−06 | 4.0E−09 |
| BP536 | E233D/G237D/P238D/ V264I/H268E/P271G/ Y296D/A327G/A330R/ P386M | 8.9E−09 | 7.9E−08 | 1.3E−06 | 3.0E−09 |
| BP537 | G237D/P238D/V264I/ S267G/H268E/P271G/ A330R | 2.9E−08 | 2.7E−07 | 3.1E−06 | 6.9E−09 |
| BP538 | G237D/P230D/V264I/ H266E/P271G/A330R | 5.5E−08 | 2.0E−07 | 3.0E−06 | 5.3E−09 |
| BP539 | G287D/P238D/V264I/ S267G/H268E/P271G/ E272P/Y296D/A330R | 6.4E−08 | 3.3E−07 | 5.6E−06 | 8.4E−09 |
| BP540 | C287D/P238D/V264I/ H268E/P271G/E272P/ Y296D/A330R | 9.6E−08 | 2.1E−07 | 4.8E−06 | 5.7E−09 |
| BP549 | G237D/P238D/S267G/ H268E/P271G/A330R | 1.8E−06 | 5.7E−07 | 1.1E−05 | 1.6E−08 |
| BP550 | G287D/P238D/V264I/ S267G/H268E/P271G/ E272D/Y296D/A330R | 2.5E−08 | 3.4E−07 | 5.0E−06 | 7.6E−09 |
| BP551 | G237D/P238D/V264I/ H268E/P271G/E272D/ Y296D/A330R | 3.2E−08 | 2.5E−07 | 2.8E−06 | 6.4E−09 |
| BP552 | E233D/G237D/P238D/ V264I/S267A/H268E/ P271G/E272D/Y296D/ A330R | 3.2E−09 | 9.7E−08 | 1.9E−06 | 2.6E−09 |
| BP553 | E233D/G237D/P238D/ V264I/S267A/H268E/ P271G/E272D/A330R | 3.4E−09 | 8.6E−08 | 1.4E−06 | 3.1E−09 |
| BP554 | G287D/P238D/V264I/ S267A/H268E/P271G/ E272D/A330R | 8.0E−09 | 1.5E−07 | 2.3E−06 | 4.4E−09 |
| BP555 | G287D/P298D/V264I/ S267A/H268E/P271G/ B272D/Y296D/A330R | 9.4E−09 | 1.6E−07 | 3.2E−06 | 4.1E−09 |
| BP556 | G287D/P238D/V264I/ S267G/H268E/P271G/ Y296D/A330R | 4.9E−08 | 3.0E−07 | 5.8E−06 | 8.4E−09 |
| BP557 | G237D/P238D/S267G/ H268D/P271G/Y296D/ A330R | 1.3E−08 | 8.5E−07 | 1.5E−05 | 2.0E−08 |
| BP558 | G237D/P238D/V264I/ S267G/H268E/P271G/ E272D/A330R | 1.3E−08 | 3.3E−07 | 4.9E−06 | 9.0E−09 |
| BP559 | P238D/V264I/S267AV/ H268E/P271G/E272D/ Y296D | 1.1E−09 | 1.6E−08 | 2.0E−05 | 2.8E−08 |
| BP560 | P238D/S267G/H268E/ P271G/Y296D/A330R | 5.6E−09 | 4.2E−06 | 3.1E−05 | 1.8E−07 |
| BP561 | E233D/G237D/P238D/ H268D/P271G/E272D/ Y2P6D/A330R | 9.4E−09 | 5.1E−07 | 5.3E−06 | 1.8E−08 |
| BP562 | G287D/P288D/H268D/ P271G/E272D/Y296D/ A330R | 2.5E−08 | 6.8E−07 | 1.1E−05 | 2.4E−08 |
| BP563 | E233D/G237D/P238D/ H268E/P271G/E272D/ Y296D/A330R | 1.2E−08 | 4.6E−07 | 8.3E−06 | 1.6E−08 |
| BP564 | G237D/P238D/H268E/ P271G/E272D/Y296D/ A330R | 3.1E−08 | 5.8E−07 | 1.0E−05 | 2.2E−09 |
| BP565 | E233D/G237D/P238D/ S267A/H268E/P271G/ Y2P6D/A330R | 2.4E−09 | 2.3E−07 | 4.7E−06 | 5.5E−09 |
| BP567 | E233D/P238D/V264I/ S267A/H268E/P271G/ Y296D | 2.1E−10 | 8.9E−07 | 1.7E−05 | 1.4E−08 |
| BP568 | E233D/P238D/V264I/ S267A/H268E/P271G | 1.9E−10 | 6.8E−07 | 1.1E−05 | 1.5E−08 |

TABLE 27-2-continued

| VARIANT NAME | KD AGAINST FcgRIIIaV (mol/L) | KD (IIaR)/ KD (IIb) | KD (IIaH)/ KD (IIb) | KD (IIaR) OF PARENT POLYPEPTIDE/ KD (IIaR) OF ALTERED POLYPEPTIDE | KD (Ib) OF PARENT POLYPEPTIDE/ KD (Ib) OF ALTERED POLYPEPTIDE |
|---|---|---|---|---|---|
| BP500 | 3.9E−05 | 28.9 | 1033.1 | 1.5 | 128.1 |
| BP501 | 1.9E−05 | 25.1 | 555.6 | 1.7 | 123.0 |
| BP502 | 2.4E−05 | 28.5 | 352.3 | 10.1 | 840.1 |
| BP503 | 2.1E−05 | 33.2 | 502.9 | 19.4 | 1812.9 |
| BP504 | 3.4E−05 | 18.5 | 658.4 | 2.4 | 127.6 |
| BP505 | 3.8E−05 | 20.0 | 514.0 | 2.6 | 144.9 |
| BP506 | 5.5E−05 | 35.1 | 731.0 | 9.2 | 806.4 |
| BP507 | 2.6E−05 | 34.2 | 618.6 | 11.1 | 1065.3 |
| BP508 | 6.1E−05 | 26.0 | 961.5 | 2.0 | 149.0 |
| BP509 | 2.3E−05 | 29.2 | 443.8 | 2.1 | 174.2 |
| BP510 | 2.5E−05 | 43.5 | 1041.7 | 6.6 | 807.3 |
| BP511 | 7.1E−05 | 50.6 | 1235.6 | 6.3 | 890.8 |
| BP531 | 2.7E−05 | 33.1 | 933.3 | 8.9 | 826.7 |
| BP532 | 2.6E−05 | 29.3 | 593.8 | 11.7 | 968.8 |
| BP533 | 2.7E−05 | 28.3 | 684.1 | 9.2 | 756.1 |
| BP534 | 2.5E−05 | 30.7 | 606.1 | 12.1 | 1043.8 |
| BP535 | 3.3E−05 | 23.2 | 606.0 | 11.9 | 780.9 |
| BP536 | 2.3E−05 | 26.6 | 437.7 | 13.9 | 1043.8 |
| BP537 | 3.6E−05 | 39.1 | 447.3 | 4.1 | 447.3 |
| BP538 | 3.3E−05 | 30.6 | 566.2 | 5.4 | 507.1 |
| BP539 | 3.4E−05 | 38.0 | 666.7 | 3.4 | 369.0 |
| BP540 | 3.9E−05 | 36.8 | 802.8 | 5.2 | 541.0 |
| BP549 | 2.4E−05 | 35.9 | 696.2 | 1.9 | 196.2 |
| BP550 | 4.8E−05 | 44.2 | 655.3 | 3.3 | 406.3 |
| BP551 | 4.8E−05 | 38.1 | 435.5 | 4.5 | 482.1 |
| BP552 | 3.0E−05 | 37.3 | 733.6 | 11.4 | 1196.9 |
| BP553 | 2.0E−05 | 27.8 | 453.1 | 12.8 | 1003.2 |
| BP554 | 2.4E−05 | 32.7 | 518.0 | 7.6 | 698.2 |
| BP555 | 3.0E−05 | 39.7 | 778.6 | 6.7 | 754.9 |
| BP556 | 6.0E−05 | 35.4 | 692.1 | 3.7 | 369.9 |
| BP557 | 2.9E−05 | 42.0 | 746.3 | 1.3 | 154.2 |
| BP558 | 3.6E−05 | 36.4 | 543.2 | 3.4 | 343.7 |
| BP559 | 4.4E−05 | 58.4 | 711.7 | 0.7 | 110.3 |
| BP560 | 4.1E−05 | 22.8 | 168.5 | 0.3 | 16.8 |
| BP561 | 3.7E−05 | 28.0 | 291.2 | 2.2 | 170.3 |
| BP562 | 5.3E−05 | 20.0 | 466.1 | 1.6 | 131.4 |
| BP563 | 3.8E−05 | 29.1 | 525.3 | 2.4 | 196.2 |
| BP564 | 4.9E−05 | 26.2 | 454.5 | 1.9 | 140.9 |
| BP565 | 2.1E−05 | 41.5 | 856.1 | 4.8 | 564.7 |
| BP567 | 3.9E−05 | 64.4 | 1231.9 | 1.2 | 224.6 |
| BP568 | 2.5E−05 | 46.1 | 748.3 | 1.6 | 210.9 |

Of the variants shown in Tables 27-1 and 27-2, IL6R-BP253/IL6R-L added with the existing alterations that enhance the FcγRIIb binding exhibited FcγRIIb- and FcγRIIaR-binding activities increased to 277 times and 529 times those of IL6R-B3/IL6R-L prior to introduction of the alterations, respectively. Furthermore, the FcγRIa-binding activity of IL6R-BP253/IL6R-L was also greater than that of IL6R-B3/IL6R-L. Meanwhile, the FcγRIIaH binding and FcγRIIIaV binding of IL6R-BP253/IL6R-L were reduced as compared to those of IL6R-B3/IL6R-L. Among other variants, IL6R-BP436/IL6R-L and IL6R-BP438/IL6R-L showed an FcγRIa binding slightly enhanced as compared to that of IL6R-B3/IL6R-L prior to introduction of the alterations. All other variants showed a reduced FcγRIa binding. In addition, all the variants exhibited reduced FcγRIIaH binding and FcγRIIIaV binding as compared to those of IL6R-B3/IL6R-L.

Regarding IL6R-BP489/IL6R-L, IL6R-BP487/IL6R-L, IL6R-BP499/IL6R-L, IL6R-BP498/IL6R-L, IL6R-BP503/IL6R-L, IL6R-BP488/IL6R-L, IL6R-BP490/IL6R-L, IL6R-BP445/IL6R-L, IL6R-BP552/IL6R-L, IL6R-BP507/IL6R-L, IL6R-BP536/IL6R-L, IL6R-BP534/IL6R-L, IL6R-491/IL6R-L, IL6R-BP553/IL6R-L, IL6R-BP532/IL6R-L, IL6R-BP506/IL6R-L, IL6R-BP511/IL6R-L, IL6R-BP502/IL6R-L, IL6R-BP531/IL6R-L, IL6R-BP510/IL6R-L, IL6R-BP535/IL6R-L, IL6R-BP497/IL6R-L, IL6R-BP533/IL6R-L, IL6R-BP555/IL6R-L, IL6R-BP554/IL6R-L, IL6R-BP436/IL6R-L, IL6R-BP423/IL6R-L, IL6R-BP440/IL6R-L, IL6R-BP538/IL6R-L, IL6R-BP429/IL6R-L, IL6R-BP438/IL6R-L, IL6R-BP565/IL6R-L, IL6R-BP540/IL6R-L, IL6R-BP426/IL6R-L, IL6R-BP437/IL6R-L, IL6R-BP439/IL6R-L, IL6R-BP551/IL6R-L, IL6R-BP494/IL6R-L, IL6R-BP537/IL6R-L, IL6R-BP550/IL6R-L, IL6R-BP556/IL6R-L, IL6R-BP539/IL6R-L, IL6R-BP558/IL6R-L, IL6R-BP425/IL6R-L, and IL6R-BP495/IL6R-L, their FcγRIIb binding was higher than that of IL6R-BP253/IL6R-L added with the existing alteration that enhances the FcγRIIb binding. Of the above, the enhancement of the FcγRIIb binding ranges from 321 times (lowest) to 3100 times (highest), compared to the binding of IL6R-B3/IL6R-L (which is defined to be 1), from IL6R-BP495/IL6R-L to IL6R-BP489/IL6R-L, respectively. Thus, it can be said that these variants are superior in both of the level and selectivity of enhancement of the FcγRIIb binding activity compared to the prior art.

Comparison of variants produced in this examination with the existing variant IL6R-BP253/IL6R-L having enhanced FcγRIIb binding showed that the value of KD (IIaR)/KD (IIb) is 16.1 for IL6R-BP479/IL6R-L which showed the lowest value and is 64.4 for IL6R-BP567/IL6R-L which showed the highest value, and the values for all variants were higher than 0.2 for IL6R-BP253/IL6R-L. Furthermore, the value of KD (IIaH)/KD (IIb) is 107.7 for IL6R-BP480/IL6R-L which showed the lowest value and is 8362 for IL6R-BP426/IL6R-L which showed the highest value, and the values for all variants were higher than 107.1 for IL6R-BP253/IL6R-L. From these results, all of the variants shown in Table 27 have been shown to be variants with improved selectivity to FcγRIIb as compared to the known variant into which alteration(s) to enhance FcγRIIb binding is introduced. In particular, IL6R-BP559/IL6R-L, IL6R-BP493/IL6R-L, IL6R-BP557/IL6R-L, IL6R-BP492/IL6R-L, and IL6R-BP500/IL6R-L all have FcγRIIaR binding maintained at not more than 1.5 times that of IL6R-B3/IL6R-L, and at the same time FcγRIIb-binding activity enhanced by 100 times; therefore, these variants were expected to show effects yielded by enhanced binding to FcγRIIb while avoiding side effects caused by enhanced binding to FcγRIIaR. Accordingly, these variants can be considered to have better properties in terms of both binding activities and selectivity to FcγRIIb than antibodies produced by existing techniques.

Without being bound by a particular theory, variants IL6R-BP568/IL6R-L and IL6R-BP492/IL6R-L which have conserved Tregitope sequence having higher Treg-inducing ability (De Groot et al. (Blood (2008) 112, 3303-3311)) and thus considered to have high Treg-inducing activity than the variants having Y296D, IL6R-BP567/IL6R-L and IL6R-BP493/IL6R-L, may be more effective. Regarding the binding activity and selectivity of these variants for FcγRIIb, comparison with the native type shows that FcγRIIaR binding is 1.6 times and FcγRIIb binding is 211 times that of the native type for IL6R-BP568/IL6R-L, and FcγRIIaR binding is 1.2 times and FcγRIIb binding is 131 times that of the native type for IL6R-BP492/IL6R-L, and these variants were found to have high binding activity and selectivity to FcγRIIb.

[Example 20] Preparation of Antibodies that Bind to Human IgA in a Calcium-Dependent Manner (20-1) Preparation of Human IgA (hIgA)

Examples 2 to 4 show that molecules that have enhanced mouse FcγR binding and which bind in a pH-dependent manner to human IL-6 receptor as an antigen, can significantly reduce the concentration of the antigen in plasma. Then, an additional test was carried out using antibodies to human IgA as an antigen, in order to assess the presence of a similar effect of eliminating soluble antigens from plasma in a living organism administered with antibodies that have enhanced mouse FcγR binding and which bind in a pH-dependent manner to antigens other than human IL-6 receptor. The antigen, human IgA (hereinafter also referred to as hIgA) (its variable region is from an anti-human IL6R antibody) was prepared using the following recombination technique. hIgA was expressed by culturing host cells containing a recombinant vectors carrying H (WT)-IgA1 (SEQ ID NO: 65) and L (WT)-CK (SEQ ID NO: 42), and purified by a method known to those skilled in the art using ion-exchange chromatography and gel filtration chromatography.

(20-2) Expression and Purification of an Antibody that Binds to hIgA

GA2-IgG1 (heavy chain, SEQ ID NO: 66; light chain, SEQ ID NO: 67) is an antibody that binds to hIgA. A DNA sequence encoding GA2-IgG1 (heavy chain, SEQ ID NO: 66; light chain, SEQ ID NO: 67) was inserted into an animal cell expression plasmid by a method known to those skilled in the art. The antibody was expressed and purified by the method described below. Cells of the human fetal kidney cell-derived FreeStyle 293-F line (Invitrogen) were suspended in FreeStyle 293 Expression Medium (Invitrogen). The cell suspension was plated at a cell density of $1.33 \times 10^6$ cells/ml in 3 ml to each well of a 6-well plate. Then, the prepared plasmid was introduced into cells by the lipofection method. The cells were cultured in a $CO_2$ incubator (37° C., 8% $CO_2$, 90 rpm) for 4 days. From the isolated culture supernatant, the antibody was purified by a method known to those skilled in the art using rProtein A Sepharose™ Fast Flow (Amersham Biosciences). The absorbance (wavelength: 280 nm) of the solution of the purified antibody was measured using a spectrophotometer. The antibody concentration was determined using the extinction coefficient calculated from the measured value by the PACE method (Protein Science (1995) 4, 2411-2423).

(20-3) Assessment of the Isolated Antibody for its Calcium-Dependent hIgA-Binding Ability The antibody isolated as described in Example (20-2) was assessed for its hIgA-binding activity (dissociation constant, KD (M)) using Biacore T200 (GE Healthcare). The binding activity was measured using as a running buffer, 0.05% tween20, 20 mmol/l ACES, 150 mmol/l NaCl (pH 7.4 or pH 5.8) containing 3 μM or 1.2 mM $CaCl_2$. An appropriate amount of recombinant Protein A/G (Thermo Scientific) was immobilized onto a Sensor chip CM5 (GE Healthcare) by an amino coupling method, and the antibody was allowed to bind thereto. Then, an appropriate concentration of hIgA (described in (A1-1)) was injected as an analyte and allowed to interact with the antibody on the sensor chip. The measurement was carried out at 37° C. After measurement, 10 mmol/L glycine-HCl (pH 1.5) was injected to regenerate the sensor chip. From the measurement result, the dissociation constant KD (M) was calculated by curve fitting analysis and equilibrium analysis using Biacore T200 Evaluation Software (GE Healthcare). The result is shown in Table 28. GA2-IgG1 strongly bound to hIgA at a $Ca^{2+}$ concentration of 1.2 mM, and weakly bound to hIgA at a $Ca^{2+}$ concentration of 3 μM. Meanwhile, at a $Ca^{2+}$ concentration of 1.2 mM, GA2-IgG1 strongly bound to human IgA at pH 7.4, and weakly bound to human IgA at pH 5.8. In summary, GA2-IgG1 was demonstrated to bind to human IgA in a pH- and calcium-dependent manner.

TABLE 28

| Antibody name | Condition | Fit | ka | kd | KD [M] |
|---|---|---|---|---|---|
| GA2-IgG1 | pH 7.4, 1.2 mM Ca | 1:1binding model | 4.0E+05 | 1.6E−02 | 3.9E−08 |
| | pH 7.4, 3 μM Ca | Steady State Affinity | — | — | 6.7E−06 |
| | pH 5.8, 1.2 mM Ca | Steady State Affinity | — | — | 4.0E−06 |
| | pH 5.8, 3 μM Ca | Steady State Affinity | — | — | 5.0E−06 |

[Example 21] Preparation of Antibody Variants that
Bind to hIgA in a Calcium-Dependent Manner Next, to further accelerate antigen (hIgA) elimination
from plasma, GA2-F1087 (heavy chain, SEQ ID NO: 68)
was produced by substituting Tyr for Leu at position 328
(EU numbering) in GA2-IgG1 for enhancing the mouse
FcγR binding of GA2-IgG1 that binds to hIgA in a calcium-
dependent manner. A DNA sequence encoding GA2-F1087
(heavy chain, SEQ ID NO: 68; light chain, SEQ ID NO: 67)
was inserted into an animal expression plasmid by a method
known to those skilled in the art. Antibody variants were
expressed by the above-described method using the plasmid.
The concentrations of the variants were measured after
purification. Antibodies comprising the above alteration
exhibited significantly increased mouse FcγR binding, as
shown in Example (4-3).

[Example 22] Assessment of the Effect on the
Plasma Antigen Retention in Normal Mice
Administered with Ca-Dependent hIgA-Binding
Antibodies (22-1) In Vivo Tests Using Normal Mice hIgA (human IgA, prepared as described in Example
(20-1)) was administered alone or in combination with an
anti-hIgA antibody to normal mice (C57BL/6J mouse,
Charles River Japan). After administration, the in vivo
dynamics of hIgA and anti-hIgA antibodies was assessed.
An hIgA solution (80 μg/ml) or a mixed solution of hIgA and
an anti-hIgA antibody was administered once at a dose of 10
ml/kg into the caudal vein. The anti-hIgA antibodies used
were GA2-IgG1 and GA2-F1087 described above.

In all of the mixed solutions, the concentration of hIgA
was 80 μg/ml, and the concentration of anti-hIgA antibody
was 2.69 mg/ml. In this experiment, the anti-hIgA antibodies
were present significantly in excess over hIgA, and thus
most of hIgA was thought to bind to the antibodies. In the
group administered with GA-hIgG1, from the mice, the
blood was collected five minutes, seven hours, one day, two
days, three days, and seven days after administration. Mean-
while, in the group administered with GA-F1087, from the
mice, the blood was collected five minutes, 30 minutes, one
hour, two hours, one day, three days, and seven days after
administration. The collected blood was immediately cen-
trifuged at 12,000 rpm and 4° C. for 15 minutes to isolate the
plasma. The isolated plasma was stored in a freezer at −20°
C. or below until use.

Figure 40:
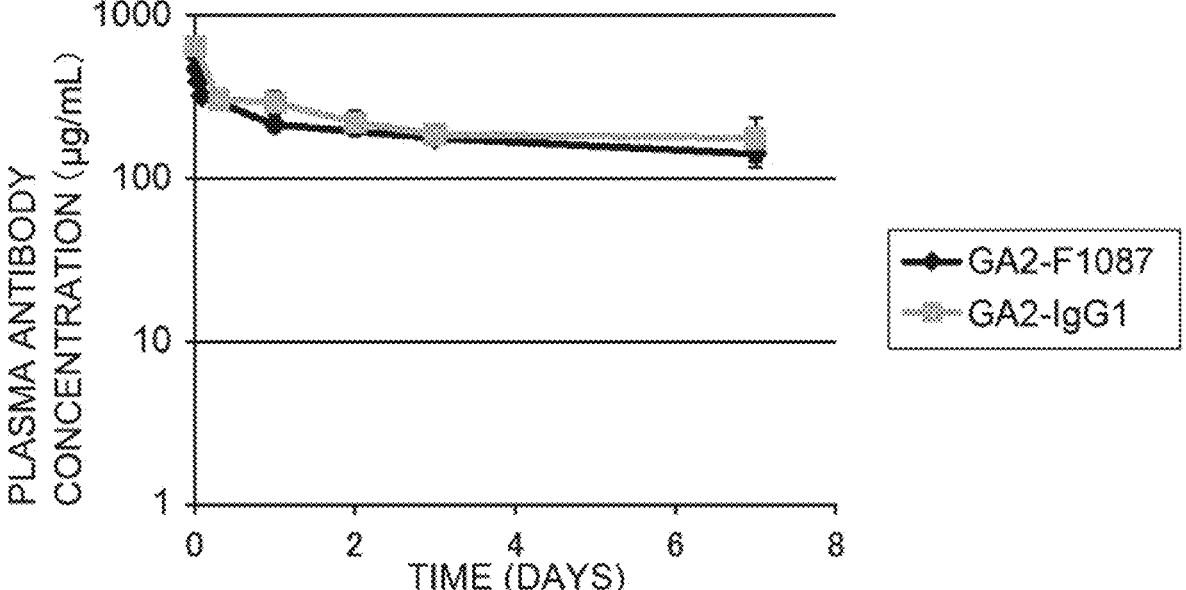
FIG. 40 shows the change in plasma antibody concentration of GA2-IgG1 and GA2-F1087 in normal mice.

(22-2) Determination of the Plasma Anti-hIgA Antibody
Concentration in Normal Mice by the ELISA Method Anti-hIgA antibody concentrations in mouse plasma were
measured by the ELISA method. First, to prepare an anti-
human IgG-immobilized plate, Anti-Human IgG (γ-chain
specific) F(ab')2 Fragment of Antibody (SIGMA) was ali-
quoted to each well of a Nunc-Immuno Plate, MaxiSorp
(Nalge nunc International), and the plate was allowed to
stand at 4° C. overnight. Calibration curve samples of
anti-hIgA antibody prepared as standard solutions for the
plasma concentration (0.5, 0.25, 0.125, 0.0625, 0.03125,
0.01563, and 0.007813 μg/ml) and assay samples of mouse
plasma diluted 100 times or more, were aliquoted to the
above-mentioned anti-human IgG-immobilized plate. After
one hour of incubation of the plate at 25° C., Goat Anti-
Human IgG (γ chain specific) Biotin (BIOT) Conjugate
(Southern Biotechnology Associates Inc.) was aliquoted to
each well of the plate. Then, the plate was incubated at 25°
C. for one hour. Next, Streptavidin-PolyHRP80 (Stereospecific Detection Technologies) was aliquoted to each well of
the plate. Then, the plate was incubated at 25° C. for one
hour. Chromogenic reaction was performed using as a
substrate TMB One Component HRP Microwell Substrate
(BioFX Laboratories). After terminating the reaction with 1
N sulfuric acid (Showa Chemical), the absorbance of the
reaction solution in each well was measured at 450 nm with
a microplate reader. Anti-hIgA antibody concentrations in
mouse plasma were determined based on the absorbance of
the standard curve using the analysis software SOFTmax
PRO (Molecular Devices). A time course of the antibody
concentrations of GA2-IgG1 and GA2-F1087 in the plasma
of normal mice after intravenous administration, which were
measured by the method described above, is shown in FIG.
40. The results demonstrate that, with respect to the clone
GA2-IgG1 that has pH-dependent, strong hIgA-binding
activity, the plasma concentration of the antibody is not
significantly reduced even if the FcγR binding is enhanced.

Figure 41:
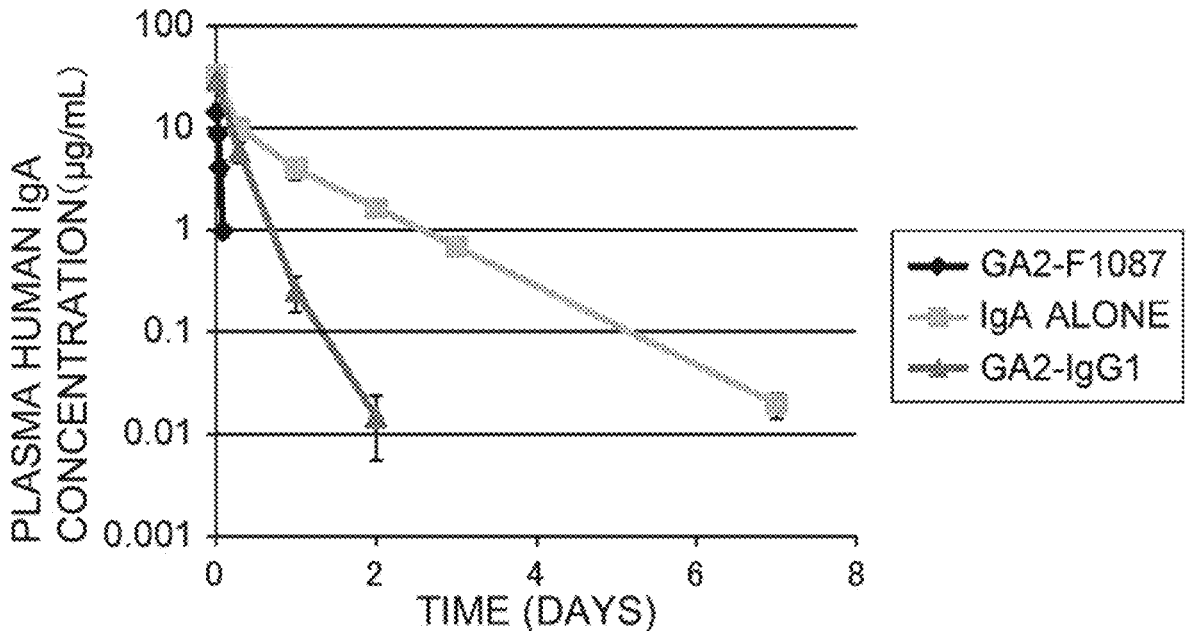
FIG. 41 shows the change in plasma hIgA concentration in normal mice administered with GA2-IgG1 and GA2-F1087.

(22-3) Determination of the Plasma hIgA Concentration by
the ELISA Method hIgA concentrations in mouse plasma were measured by
the ELISA method. First, to prepare an anti-human IgA-
immobilized plate, Goat anti-Human IgA Antibody
(BETHYL) was aliquoted to each well of a Nunc-Immuno
Plate, MaxiSoup (Nalge nunc International), and the plate
was allowed to stand at 4° C. overnight. Calibration curve
samples of hIgA were prepared as standard solutions for the
plasma concentration (0.4, 0.2, 0.1, 0.05, 0.025, 0.0125, and
0.00625 μg/ml), and used. 100 μl each of the calibration
curve samples and assay samples of mouse plasma diluted
100 times or more, was combined with 200 μl of 500 ng/ml
hsL6R. This was mixed and incubated at room temperature
for one hour. Then, 100 μl of the mixtures was aliquoted to
the anti-human IgA-immobilized plate. The plate was
allowed to stand at room temperature for one hour. Next,
Biotinylated Anti-human IL-6 R Antibody (R&D) was ali-
quoted to each well of the plate. After one hour of incubation
at room temperature, Streptavidin-PolyHRP80 (Stereospe-
cific Detection Technologies) was aliquoted to each well of
the plate. The plate was incubated at room temperature for
one hour. Chromogenic reaction was performed using as a
substrate TMB One Component HRP Microwell Substrate
(BioFX Laboratories). After terminating the reaction with 1
N sulfuric acid (Showa Chemical), the absorbance of the
reaction solution in each well was measured at 450 nm with
a microplate reader. The concentrations in mouse plasma
were determined based on the absorbance of the standard
curve using the analysis software SOFTmax PRO (Molecu-
lar Devices). A time course of the hIgA concentration in the
plasma of normal mice after intravenous administration,
which was measured by the above method, is shown in FIG.
41.

The result showed that, in mice administered with hIgA in
combination with GA2-IgG1 having a Ca-dependent hIgA-
binding activity of 100 times or more greater, hIgA elimi-
nation was accelerated compared to the administration of
hIgA alone. Meanwhile, in the plasma of mice administered
with GA2-F1087 with enhanced binding to hIgA and FcγR,
the concentration of hIgA was reduced below the measur-
able range (0.006 μg/ml or more) one day after administra-
tion, and thus the hIgA elimination was significantly accel-
erated compared to the plasma of mice administered with
GA-IgG1. The findings described in Examples 2 to 7 above
demonstrate the increased antigen elimination effect of
antibodies with enhanced FcγR binding in mice adminis-
tered with IL6R and anti-IL6R antibody. Likewise, a similar
effect was also demonstrated to be achieved in mice administered with the hIgA antigen and anti-hIgA antibody. From the results obtained so far in the Examples, antigen elimination in this case may also be mediated by FcγRIIb.

[Example 23] Preparation of a pH-Dependent Anti-IgE Antibody (23-1) Preparation of an Anti-Human IgE Antibody In order to prepare a pH-dependent anti-human IgE antibody, human IgE (heavy chain, SEQ ID NO: 69; light chain, SEQ ID NO: 70) (its variable region is from an anti-human glypican 3 antibody) was expressed as an antigen using FreeStyle293 (Life Technologies). The expressed human IgE was prepared and purified by a general chromatographic method known to those skilled in the art. An antibody that binds to human IgE in a pH-dependent manner was selected from many antibodies isolated. The heavy chain and light chain variable regions of the selected anti-human IgE antibody were fused with a human IgG1 heavy streptavidin affinity. An appropriate concentration of human IgE was injected and captured by the biotinylated GPC3 peptide to immobilize human IgE on the chip. An appropriate concentration of 278-IgG1 was injected as an analyte, and allowed to interact with human IgE on the sensor chip. Then, 10 mmol/L glycine-HCl (pH 1.5) was injected to regenerate the sensor chip. All of the assay for the interaction was performed at 37° C. Using Biacore T200 Evaluation Software (GE Healthcare), the assay results were analyzed by curve fitting to determine the binding rate constant ka (1/Ms) and dissociation rate constant kd (1/s). Dissociation constant KD (M) was calculated from the above constants. Then, the pH-dependent binding was assessed by calculating the KD ratio of each antibody between the conditions of pH 5.8/1.2 mM Ca and pH 7.4/1.2 mM Ca. The pH/Ca-dependent binding was assessed by calculating the KD ratio of each antibody between the conditions of pH 5.8/3 μM Ca and pH 7.4/1.2 mM Ca. The results are shown in Table 29.

TABLE 29

| Antibody name (abbreviated) | Buffer condition | ka (1/Ms) | kd (1/s) | KD (M) | pH dependency KD (pH 5.8, 1.2 mM Ca)/ KD (pH 7.4, 1.2 mM Ca) | pH/Ca dependency KD (pH 5.8, 3 μM Ca)/ KD (pH 7.4, 1.2 mM Ca) |
|---|---|---|---|---|---|---|
| Clone 278 | pH 7.4, 1.2 mM Ca | 1.5E+06 | 3.6E−03 | 2.4E−09 | 842.5 | 1636.5 |
| | pH 5.8, 1.2 mM Ca | 1.2E+05 | 2.3E−01 | 2.0E−06 | | |
| | pH 5.8, 3 μM Ca | 6.2E+04 | 2.4E−01 | 3.9E−06 | | |
| Xolair | pH 7.4, 1.2 mM Ca | 2.5E+06 | 1.1E−02 | 4.4E−09 | 2.3 | 2.9 |
| | pH 5.8, 1.2 mM Ca | 2.4E+06 | 2.4E−02 | 9.9E−09 | | |
| | pH 5.8, 3 μM Ca | 1.4E+06 | 1.7E−02 | 1.3E−08 | | | chain constant region and a human light chain constant region, and the resulting antibody gene was inserted into a vector. Using the vector, a recombinant anti-human IgE antibody was expressed and purified. The prepared antibody was named clone 278 (hereinafter referred to as 278-IgG1; heavy chain, SEQ ID NO: 71, light chain, SEQ ID NO: 72).

(23-2) Assessment of the Anti-Human IgE Antibody for the Human IgE-Binding Activity and pH-Dependent Binding Activity Antibodies capable of dissociating antigens in the endosome can be produced in such a way that they bind to antigens not only in a pH-dependent manner but also in a Ca-dependent manner. Thus, 278-IgG1 and the control human IgG1 antibody Xolair (omalizumab, Novartis) without pH/Ca-dependent IgE-binding ability were assessed for the pH-dependent binding ability and pH/Ca-dependent binding ability to human IgE (hIgE). Specifically, 278-IgG1 and Xolair were assessed for their hIgE-binding activity (dissociation constant, KD (M)) using Biacore T200 (GE Healthcare). Measurements were carried out using the following three types of running buffers:

1.2 mmol/l CaCl$_2$, 0.05% tween20, 20 mmol/l ACES, 150 mmol/l NaCl, pH 7.4
1.2 mmol/l CaCl$_2$, 0.05% tween20, 20 mmol/l ACES, 150 mmol/l NaCl, pH 5.8
3 μmol/l CaCl$_2$, 0.05% tween20, 20 mmol/l ACES, 150 mmol/l NaCl, pH 5.8

An appropriate amount of a peptide (hereinafter referred to as "biotinylated GPC3 peptide") resulting from adding biotin to the C-terminal Lys of a chemically synthesized sequence derived from human glypican 3 protein (SEQ ID NO: 73) was loaded on a Sensor chip SA (GE Healthcare), and immobilized on the Sensor chip SA based on biotin/

[Example 24] Preparation of an Antibody Variant that Binds to Human IgE in a pH-Dependent Manner Next, for further accelerating the elimination of antigen (human IgE) from plasma, a DNA sequence encoding 278-F1087 (heavy chain, SEQ ID NO: 74; light chain, SEQ ID NO: 72) with a substitution of Tyr for Leu at position 328 (EU numbering) in 278-IgG1 was inserted into an animal expression plasmid by a method known to those skilled in the art, in order to enhance the mouse FcγR binding of 278-IgG1 that binds to human IgE in a pH-dependent manner. The antibody variants were expressed by the above-mentioned method using animal cells introduced with the plasmid. The concentrations of the antibody variants were determined after purification.

[Example 25] In Vivo Assessment of 278-IgG1

(25-1) Preparation of Human IgE (hIgE (Asp6)) for In Vivo Assessment hIgE (Asp6) (its variable region is from an anti-human glypican 3 antibody), which is a human IgE for in vivo assessment, consisting of the heavy chain (SEQ ID NO: 75) and light chain (SEQ ID NO: 70), was prepared by the same method as described in Example (23-1). hIgE (Asp6) is a molecule in which asparagine has been replaced with aspartic acid in the six N-glycosylation sites in human IgE, so that time-dependent changes in the concentration of human IgE as an antigen in the plasma does not affect the heterogeneity of N-linked sugar chains of human IgE.

(25-2) Assessment of the Effect of Accelerating Human IgE Elimination from the Plasma of Normal Mice Administered with Clone 278

As described in Examples 2 to 4, and 22, the antigen concentration was demonstrated to be significantly reduced in the plasma of mice administered with the molecules that bind in a pH-dependent manner to human IL-6 receptor or human IgA as an antigen, and whose binding to mouse FcγR has been enhanced. An additional test was carried out using antibodies to human IgE as an antigen to assess whether a similar effect of eliminating soluble antigens from the plasma of a living organism administered with antibodies with enhanced mouse FcγR binding that bind in a pH-dependent manner to antigens other than human IL-6 receptor and human IgA, when the binding to mouse FcγR is enhanced.

hIgE (Asp6) and anti-human IgE antibodies were assessed for their in vivo dynamics after administration of hIgE (Asp6) alone, or hIgE (Asp6) in combination with the anti-hIgE antibodies (278-IgG1 and 278-F1087) to C57BL/6J mice (Charles river Japan). hIgE (Asp6) (20 µg/ml) or a mixture of hIgE (Asp6) and an anti-human IgE antibody was administered once at 10 mL/kg into the caudal vein (as described in Table 30, all antibodies were prepared at the same concentration). In this case, each antibody was present significantly in excess over hIgE (Asp6), and thus almost all of hIgE (Asp6) was thought to bind to the antibody. In the group administered with clone 278 (278-IgG1), from the mice, the blood was collected five minutes, two hours, seven hours, one day, two days, four days, five days, seven days, 14 days, and 21 days after administration. In the group administered with 278-F1087, from the mice, the blood was collected five minutes, 30 minutes, one hour, two hours, one day, three days, seven days, 14 days, and 21 days after administration. The collected blood was immediately centrifuged at 15,000 rpm and 4° C. for 5 minutes to isolate the plasma. The isolated plasma was stored in a freezer at –20° C. or below until use.

TABLE 30

| Anti-hIgE antibody | hIgE (Asp6) concentration in administered solution (µg/mL) | Anti-hIgE antibody concentration in administered solution (µg/mL) |
| --- | --- | --- |
| 278-IgG1 | 20 | 100 |
| 278-F1087 | 20 | 100 |

Figure 42:
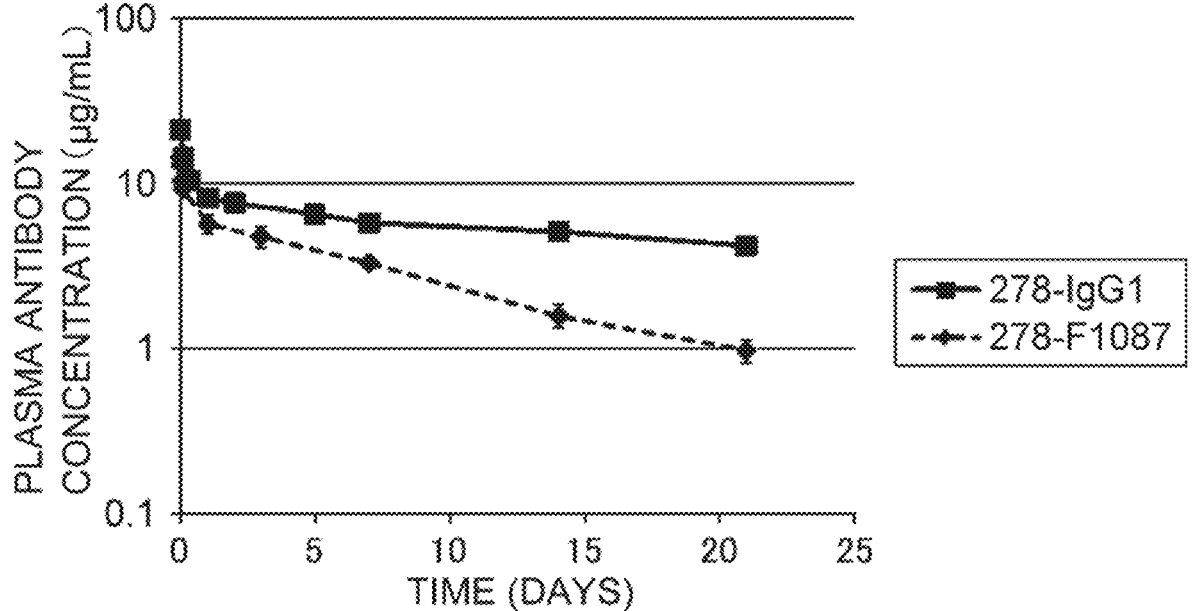
FIG. 42 shows the change in plasma antibody concentration of 278-IgG1 and 278-F1087 in normal mice.

(25-3) Determination of the Plasma Anti-Human IgE Antibody Concentration in Normal Mice Anti-hIgE antibody concentrations in mouse plasma were measured by the ELISA method. Standard curve samples were prepared at 0.4, 0.2, 0.1, 0.05, 0.025, 0.0125, and 0.00625 µg/ml for plasma concentrations. To secure the homogeneity of the immune complex between hIgE (Asp6) and anti-hIgE antibody, hIgE (Asp6) was added at 1 µg/ml to the standard curve samples and assay samples of mouse plasma. The samples of the 278-hIgG1 administration group and the corresponding standard curve samples were allowed to stand at room temperature for 30 minutes. Meanwhile, the samples of the 278-F1087 administration group and corresponding standard curve samples were stirred at 37° C. overnight. After incubation or stirring, the standard curve samples and assay samples of mouse plasma were aliquoted to an immunoplate (Nunc-Immuno Plate, MaxiSorp (Nalge nunc International)) immobilized with Anti-Human Kappa Light Chain Antibody (Bethyl Laboratories), and this was allowed to stand/stirred at room temperature for two hours (the samples of the 278-F1087 administration group and the standard curve samples of 278-F1087), or allowed to stand at 4° C. overnight (the samples of the 278-hIgG1 administration group and the standard curve samples of 278-hIgG1). Then, Rabbit anti-Human IgG (Fc) Secondary antibody, Biotin conjugate (Pierce Biotechnology) and Streptavidin-Poly HRP80 (Stereospecific Detection Technologies) were each reacted in succession for one hour. Chromogenic reaction was performed using as a substrate TMB One Component HRP Microwell Substrate (BioFX Laboratories). After terminating the reaction with 1 N sulfuric acid (Showa Chemical), the concentrations in mouse plasma were determined based on the color development by a method for measuring the absorbance at 450 nm with a microplate reader. The concentrations in mouse plasma were determined based on the absorbance of the standard curve using the analysis software SOFTmax PRO (Molecular Devices). A time course of antibody concentrations in plasma after intravenous administration, which were determined by the above method, is shown in FIG. 42. The result demonstrates that, in mice administered with the variants resulting from enhancing the FcγR binding of 278-IgG1 with pH-dependent, strong human IgE-binding activity, the antibody concentration in the plasma of the mice was not significantly reduced as compared to that of 278-IgG1.

Figure 43:
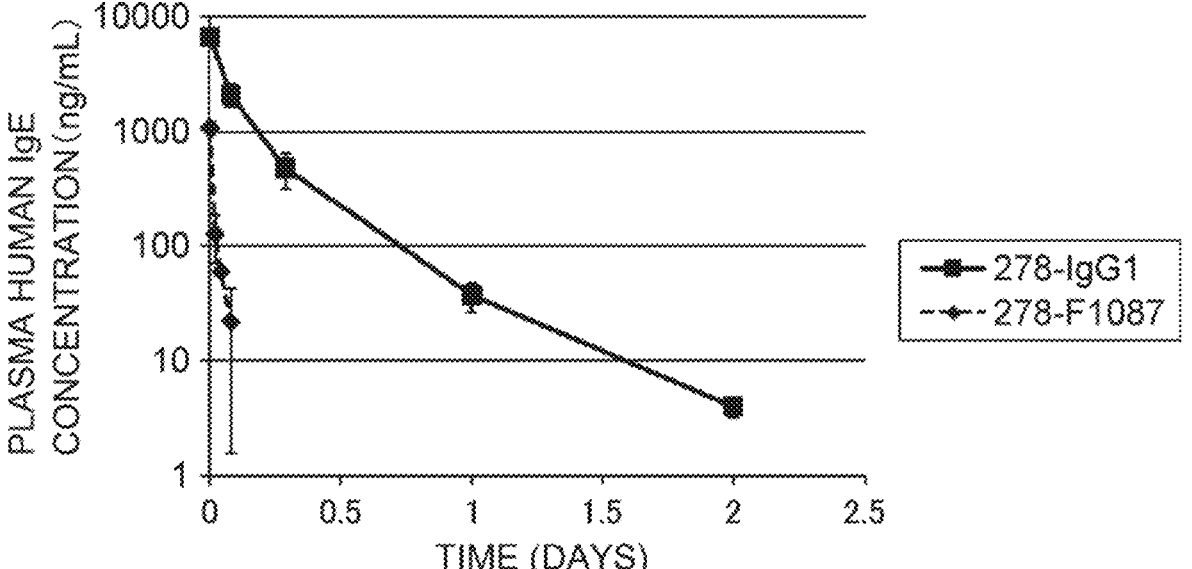
FIG. 43 shows the change in plasma hIgE (Asp6) concentration in C57BL/6J mice administered with 278-IgG1 and 278-F1087.

(25-4) Determination of the Plasma hIgE (Asp6) Concentration in Normal Mice hIgE (Asp6) concentrations in mouse plasma were measured by the ELISA method. Calibration curve samples were prepared at 192, 96, 48, 24, 12, 6, and 3 ng/ml for plasma concentrations. To secure the homogeneity of the immune complex between hIgE (Asp6) and anti-hIgE antibody, in the group administrated with 278-hIgG1, Xolair (Novartis) was added at 10 µg/ml to the standard curve and assay samples of mouse plasma, and the mixtures were allowed to stand at room temperature for 30 munities. In the group administrated with 278-F1087, 278-F1022 (heavy chain, SEQ ID NO: 76; light chain, SEQ ID NO: 72; prepared in the same manner as Example 24) or 278-F760 (heavy chain, SEQ ID NO: 77; light chain, SEQ ID NO: 72; prepared in the same manner as Example A5) was added at 20 µg/ml, and the mixtures were stirred at 37° C. for 60 hours. The assay samples of mouse plasma were aliquoted to an immunoplate (MABTECH) immobilized with anti-human IgE, or an immunoplate (Nunc F96 MicroWell Plate (Nalge nunc International)) immobilized with anti-human IgE (clone 107, MABTECH), and this was allowed to stand or stirred at room temperature for two hours, or allowed to stand at 4° C. overnight. Then, the human GPC3 core protein (SEQ ID NO: 78), anti-GPC3 antibody (in-house preparation) biotinylated with NHS-PEG4-Biotin (Thermo Fisher Scientific), and Sterptavidin-PolyHRP80 (Stereospecific Detection Technologies) were each reacted in succession for one hour. Chromogenic reaction was performed using as a substrate TMB One Component HRP Microwell Substrate (BioFX Laboratories). After terminating the reaction with 1 N sulfuric acid (Showa Chemical), the concentrations in mouse plasma were determined based on the color development by a method for measuring the absorbance at 450 nm with a microplate reader. Alternatively, chromogenic reaction was performed using as a substrate SuperSignal(r) ELISA Pico Chemiluminescent Substrate (Thermo Fisher Scientific), and the concentrations in mouse plasma were determined by a method for measuring the luminescence intensity with a microplate reader. The concentrations in mouse plasma were determined based on the absorbance or luminescence intensity of the standard curve using the analysis software SOFTmax PRO (Molecular Devices). A time course of hIgE (Asp6) concentrations in plasma after intravenous administration, which were determined by the above method, is shown in FIG. 43.

Regarding the elimination of human IgE alone, the result demonstrates that, in mice administered with human IgE in combination with 278-IgG1 having the strong pH-dependent binding activity, the elimination of human IgE was accelerated as compared to the administration of human IgE alone. Furthermore, in mice administered with human IgE in combination with 278-F1087 resulting from enhancing FcγR binding of 278-IgG1, the elimination of human IgE was demonstrated to be significantly accelerated as compared to the mice administered with human IgE alone, or human IgE in combination with 278-IgG1. That is, it was shown that the antigen elimination was accelerated not only in mice administered with the above-mentioned anti-IL6R antibody and anti-IgA antibody with enhanced FcγR binding, but also in mice administered with the anti-IgE antibody with enhanced FcγR binding. From the results obtained so far in the Examples, antigen elimination in this case may also be mainly mediated by FcγRIIb.

[Example 26] Effects of Eliminating Antigens from Plasma for Antigen-Binding Molecules with FcγRIIb-Binding Activity Higher Than that of an Fc Region of Native Mouse IgG (26-1) Antigen Elimination Effect of Mouse Antibodies with Selectively Enhanced FcγRIIb-Binding Activity In Examples 5 to 7, a group of normal mice administered with an antigen-binding molecule produced by enhancing the mouse FcγR-binding activity of an antigen-binding molecule having a mouse antibody Fc region and having pH-dependent human IL-6 receptor-binding properties, and a group of Fc receptor γ chain-deficient mice and a group of FcγRIII-deficient mice which simulates the condition where an antibody with selectively enhanced mouse FcγRIIb-binding activity is administered were examined. From these results, antigen-binding molecules exhibiting pH-dependent binding to soluble antigens and having selectively enhanced FcγRIIb-binding activity were shown to be able to efficiently eliminate soluble antigens in plasma when administered in vivo. Whether this effect will be seen in normal mice administered with an antigen-binding molecule comprising a mouse Fc region with selectively enhanced mouse FcγRIIb-binding activity and having pH-dependent human IL-6 receptor-binding properties was examined as indicated below.

(26-2) Production of Mouse Antibodies with Selectively Enhanced FcγRIIb-Binding Activity VH3-mIgG1 (SEQ ID NO: 49) and VL3-mk1 (SEQ ID NO: 50) were produced as the heavy chain and light chain, respectively, of a mouse IgG1 antibody having pH-dependent human IL-6 receptor-binding properties using the method of Reference Example 1. Furthermore, to enhance the mouse FcγRIIb-binding activity of VH3-mIgG1, substitutions of Glu for Thr at position 230, Ala for Val at position 231, Asn for Pro at position 232, Glu for Ser at position 238, and Asp for Ser at position 239 as indicated by EU numbering were carried out to produce VH3-mIgG1-MB367 (SEQ ID NO: 79). Fv4-mIgG1 or Fv4-mIgG1-MB367 comprising VL3-mk1 as the light chain and VH3-mIgG1 or VH3-mIgG1-MB367, respectively, as the heavy chain was expressed and purified using the method of Reference Example 1.

(26-3) Confirmation of Mouse FcγR-Binding Activity

VH3/L(WT)-mIgG1 or VH3/L(WT)mIgG1-MB367 comprising L(WT)-CK (SEQ ID NO: 42) as the light chain and VH3-mIgG1 or VH3-mIgG1-MB367, respectively, as the heavy chain was expressed and purified using the method of Reference Example 1. Mouse FcγR-binding activities of these antibodies were assessed by the method of Reference Example 2, and the results are shown in Table 31. Furthermore, how much the mouse FcγR-binding activity of each variant is enhanced as compared to mIgG1 before the alteration is shown in Table 32.

TABLE 31

| | KD (M) | |
|---|---|---|
| VARIANT NAME | mFc γ RIIb | mFc γ RIII |
| VH3/L (WT)-mIgG1 | 2.10E−07 | 2.82E−07 |
| VH3/L (WT)-mIgG1-MB367 | 1.32E−09 | 4.54E−08 |

TABLE 32

| | BINDING RATIO TO mIgG1 | |
|---|---|---|
| VARIANT NAME | mFc γ RIIb | mFc γ RIII |
| VH3/L (WT)-mIgG1 | 1.0 | 1.0 |
| VH3/L (WT)-mIgG1-MB367 | 158.6 | 6.2 |

According to the results shown in Table 32, VH3/L(WT)-mIgG1-MB367 produced by introducing the five above-mentioned alterations into VH3/L(WT)-mIgG1 had mouse FcγRIIb-binding activity that was enhanced approximately 160 times and mouse FcγRIII-binding activity that was enhanced 6.2 times as compared to before alteration. That is, VH3/L(WT)-mIgG1-MB367 showed selective and enhanced mouse FcγRIIb-binding activity.

(26-4) Confirmation of Effects of Reducing the Concentration of Soluble Human IL-6 Receptor in Plasma Using Normal Mice Effects of elimination of soluble human IL-6 receptor in plasma of normal mice administered with Fv4-mIgG1 or Fv4-mIgG1-MB367 as the anti-human IL-6 receptor antibody were examined as described below.

(26-4-1) In Vivo Test Using Normal Mice

Normal mice (C57BL/6J mouse; Charles River Japan) were co-administered with soluble human IL-6 receptor and anti-human IL-6 receptor mouse antibody, and then assessed for their in vivo dynamics. A mixed solution of soluble human IL-6 receptor and an anti-human IL-6 receptor mouse antibody was administered once at a dose of 10 mL/kg into the tail vein. In this case, the soluble human IL-6 receptor and the anti-human IL-6 receptor mouse antibody were administered at a dose of 50 μg/kg and 1 mg/kg, respectively. The above-mentioned Fv4-mIgG1 or Fv4-mIgG1-MB367 was used as an anti-human IL-6 receptor mouse antibody. Blood was collected from the mice 5 minutes, 7 hours, 1 day, 2 days, 3 days, 7 days, 14 days, 21 days, and 28 days after administration of the anti-human IL-6 receptor mouse antibody. The collected blood samples were immediately centrifuged at 4° C. and 15,000 rpm for 15 minutes to obtain the plasma. The separated plasma was stored in a freezer at −20° C. or below until measurement.

(26-4-2) ELISA Determination of the Anti-Human IL-6 Receptor Mouse Antibody Concentration in Plasma The anti-human IL-6 receptor mouse antibody concentration in mouse plasma was determined by ELISA. First, soluble human IL-6 receptor was aliquoted into a Nunc-Immuno Plate, MaxiSoup (Nalge nunc International) and allowed to stand overnight at 4° C. to prepare a soluble human IL-6 receptor-immobilized plate. Calibration curve samples containing an anti-human IL-6 receptor mouse antibody were prepared at plasma concentrations of 2.50, 1.25, 0.625, 0.313, 0.156, 0.078, and 0.039 μg/mL, and mouse plasma assay samples diluted 100 times or higher were prepared. 100 μL of these calibration curve samples and plasma assay samples were aliquoted into each well of the soluble human IL-6 receptor-immobilized plate, and this was stirred at room temperature for two hours. Subsequently, color development reaction of a reaction solution which was allowed to react at room temperature for two hours with Anti-mouse IgG-peroxidase antibody (SIGMA) was carried out using TMB One Component HRP Microwell Substrate (BioFX Laboratories) as a substrate. After stopping the reaction by adding 1 N Sulfuric acid (Showa Chemical), absorbance of the reaction solution in each well at 450 nm was measured by a microplate reader. The antibody concentration in mouse plasma was calculated based on the absorbance from the calibration curve using the analytical software SOFTmax PRO (Molecular Devices). The results are shown in FIG. 44.

Figure 45:
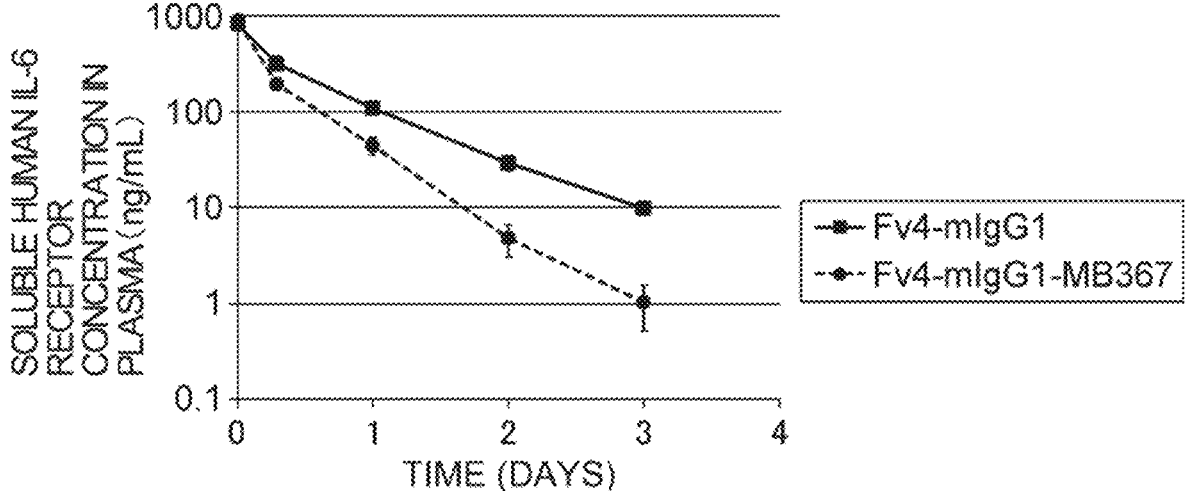
FIG. 45 shows a time course of soluble human IL-6 receptor concentration in the plasma of normal mice administered with Fv4-mIgG1 and Fv4-mIgG1-MB367 which is an Fv4-mIgG1 variant with enhanced mouse FcγRIIb binding.

(26-4-3) Determination of Soluble Human IL-6 Receptor Concentration in Plasma by an Electrochemiluminescent Method An hsIL-6R concentration in mouse plasma was determined by an electrochemiluminescent method. Calibration curve samples of hsIL-6R were prepared at plasma concentrations of 12.5, 6.25, 3.13, 1.56, 0.781, 0.391, and 0.195 ng/mL. Mouse plasma assay samples were prepared by 50 times or higher dilution. Monoclonal Anti-human IL-6R Antibody (R&D) which has been ruthenium-labeled using SULFO-TAG NETS Ester (Meso Scale Discovery), Biotinylated Anti-human IL-6 R Antibody (R&D), and tocilizumab solution (Chugai Pharmaceutical Co. Ltd.) were mixed in and was allowed to react overnight at 37° C. Then, a Streptavidin Gold Multi-ARRAY Plate (Meso Scale Discovery) was blocked with a PBS-Tween solution containing 0.5% BSA (w/v) at 5° C. overnight, and the mixed solution was aliquoted into the plate. After further reacting the plate for two hours at room temperature, the plate was washed. Then, Read Buffer T (×2) (Meso Scale Discovery) was aliquoted into the plate and measurements were performed immediately using SECTOR Imager 2400 (Meso Scale Discovery). hSIL-6R concentrations were calculated based on the response from the calibration curve using the analytical software SOFTmax PRO (Molecular Devices). The results are shown in FIG. 45.

Figure 44:
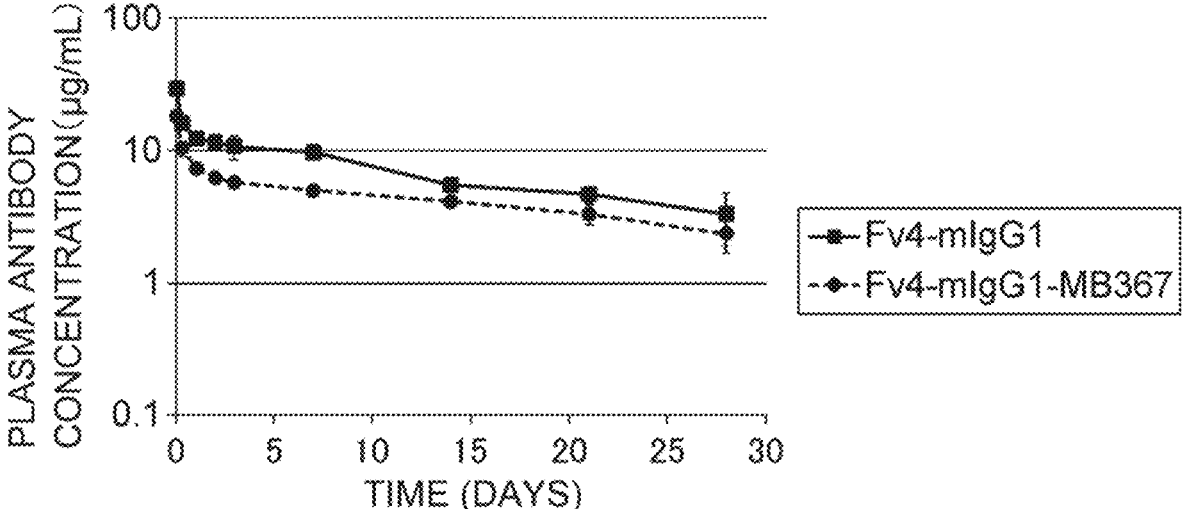
FIG. 44 shows a time course of anti-human IL-6 receptor mouse antibody concentration in the plasma of normal mice administered with Fv4-mIgG1 and Fv4-mIgG1-MB367 which is an Fv4-mIgG1 variant with enhanced mouse FcγRIIb binding.

As shown in FIG. 44, in the group administered with Fv4-mIgG1-MB367 having selectively enhanced mouse FcγRIIb-binding activity, while the time-course change in plasma antibody concentration was equivalent to that in the group administered with Fv4-mIgG1, decrease in plasma retention of antibody due to enhancement of mouse FcγRIIb-binding activity was not observed. Meanwhile, as shown in FIG. 45, in the group administered with Fv4-mIgG1-MB367 having selectively enhanced mouse FcγRIIb-binding activity, plasma concentration of the soluble IL-6 receptor was remarkably decreased as compared to that of the Fv4-mIgG1-administered group.

The above showed that when administered in vivo, an antigen-binding molecule which binds to a soluble antigen in a pH-dependent manner and has selectively enhanced FcγRIIb-binding activity can efficiently eliminate soluble antigens in plasma in normal mice as well. Without being restricted to a particular theory, the phenomena observed here may be explained as follows.

When an antibody that binds to a soluble antigen in a pH-dependent manner and has enhanced FcγRIIb-binding activity is administered to a mouse, the antibody is actively taken up mainly by cells expressing FcγRIIb on its cell membrane. The internalized antibody dissociates from the soluble antigen under the acidic pH condition in the endosome, and is then recycled to the plasma via FcRn. Therefore, one of the elements that brings about an effect of eliminating soluble antigens in plasma due to such antibody may include the strength of FcγRIIb-binding activity of the antibody. That is, a stronger FcγRIIb-binding activity leads to a more active internalization into FcγRIIb-expressing cells, and soluble antigens in the plasma can be eliminated quickly. Furthermore, such effects can be verified in a similar manner regardless of whether the Fc region included in the antibody is derived from a human IgG1 or a mouse IgG1, as long as FcγRIIb-binding activity is enhanced. More specifically, verification can be carried out using the Fc region of any animal species, such as from human IgG1, human IgG2, human IgG3, human IgG4, mouse IgG1, mouse IgG2a, mouse IgG2b, mouse IgG3, rat IgG, monkey IgG, or rabbit IgG as long as binding activity is enhanced for FcγRIIb of the animal species to which it is administered.

[Reference Example 1] Construction of Antibody Expression Vectors; and Expression and Purification of Antibodies Synthesis of full-length genes encoding the nucleotide sequences of the H chain and L chain of the antibody variable regions was carried out by production methods known to those skilled in the art using Assemble PCR and such. Introduction of amino acid substitutions was carried out by methods known to those skilled in the art using PCR or such. The obtained plasmid fragment was inserted into an animal cell expression vector, and the H-chain expression vector and L-chain expression vector were produced. The nucleotide sequence of the obtained expression vector was determined by methods known to those skilled in the art. The produced plasmids were introduced transiently into the HEK293H cell line derived from human embryonic kidney cancer cells (Invitrogen) or into FreeStyle293 cells (Invitrogen) for antibody expression. The obtained culture supernatant was collected, and then passed through a 0.22 μm MILLEX(R)-GV filter (Millipore), or through a 0.45 μm MILLEX(R)-GV filter (Millipore) to obtain the culture supernatant. Antibodies were purified from the obtained culture supernatant by methods known to those skilled in the art using rProtein A Sepharose Fast Flow (GE Healthcare) or Protein G Sepharose 4 Fast Flow (GE Healthcare). For the concentration of the purified antibodies, their absorbance at 280 nm was measured using a spectrophotometer. From the obtained value, the extinction coefficient calculated by the methods such as PACE was used to calculate the antibody concentration (Protein Science 1995; 4: 2411-2423).

[Reference Example 2] Method for Preparing FcγR and Method for Analyzing the Interaction Between an Altered Antibody and FcγR Extracellular domains of FcγRs were prepared by the following method. First, a gene of the extracellular domain of FcγR was synthesized by a method well known to those skilled in the art. At that time, the sequence of each FcγR was produced based on the information registered at NCBI. Specifically, FcγRI was produced based on the sequence of NCBI Accession No. NM_000566 (Version No. NM_000566.3), FcγRIIa was produced based on the sequence of NCBI Accession No. NM_001136219 (Version No. NM_001136219.1), FcγRIIb was produced based on the sequence of NCBI Accession No. NM_004001 (Version No. NM_004001.3), FcγRIIIa was produced based on the sequence of NCBI Accession No. NM_001127593 (Version No. NM_001127593.1), and FcγRIIIb was produced based on the sequence of NCBI Accession No. NM_000570 (Version No. NM_000570.3), and a His tag was attached to the C terminus. Furthermore, the existence of polymorphism is known for FcγRIIa, FcγRIIIa, and FcγRIIIb, and the polymorphic sites were produced by referring to Warmerdam et al. (J. Exp. Med., 1990, 172: 19-25) for FcγRIIa; Wu et al. (J. Clin. Invest., 1997, 100 (5): 1059-1070) for FcγRIIIa; and Ory et al. (J. Clin. Invest., 1989, 84, 1688-1691) for FcγRIIIb.

The obtained gene fragments were inserted into an animal cell expression vector, and expression vectors were produced. The produced expression vectors were introduced transiently into human embryonic kidney cancer cell line-derived FreeStyle293 cells (Invitrogen) to express the proteins of interest. Regarding FcγRIIb used for crystallographic analysis, the protein of interest was expressed in the presence of Kifunesine at a final concentration of 10 μg/mL, so that the sugar chain added to FcγRIIb will be the high-mannose type. Cells were cultured, and after collection of the obtained culture supernatant, this was passed through a 0.22 μm filter to obtain the culture supernatant. In principle, the obtained culture supernatants were purified in the following four steps. The steps carried out were, cation exchange column chromatography (SP Sepharose FF) in step 1, affinity column chromatography (HisTrap HP) for His tag in step 2, gel filtration column chromatography (Superdex200) in step 3, and aseptic chromatography in step 4. However, for FcγRI, anion exchange column chromatography using Q sepharose FF was performed as step 1. The purified proteins were subjected to absorbance measurements at 280 nm using a spectrophotometer; and from the obtained values, the concentrations of the purified proteins were calculated using the absorption coefficient calculated using methods such as PACE (Protein Science 1995; 4: 2411-2423).

Analysis of interaction between each altered antibody and the Fcγ receptor prepared as mentioned above was carried out using Biacore T100 (GE Healthcare), Biacore T200 (GE Healthcare), Biacore A100, and Biacore 4000. HBS-EP+ (GE Healthcare) was used as the running buffer, and the measurement temperature was set to 25° C. Chips produced by immobilizing the antigen peptide, Protein A (Thermo Scientific), Protein A/G (Thermo Scientific), and Protein L (ACTIGEN or BioVision) by the amine coupling method to a Series S sensor Chip CM5 (GE Healthcare) or Series S sensor Chip CM4 (GE Healthcare), or alternatively, chips produced by allowing preliminarily biotinylated antigen peptides to interact with and immobilize onto a Series S Sensor Chip SA (certified) (GE Healthcare) were used.

After capturing of antibodies of interest onto these sensor chips, an Fcγ receptor diluted with the running buffer was allowed to interact, the amount bound to an antibody was measured, and the antibodies were compared. However, since the amount of Fcγ receptor bound depends on the amount of the captured antibodies, the amount of Fcγ receptor bound was divided by the amount of each antibody captured to obtain corrected values, and these values were compared. Furthermore, antibodies captured onto the chips were washed by reaction with 10 mM glycine-HCl, pH 1.5, and the chips were regenerated and used repeatedly.

Kinetic analyses for calculating the KD values of each altered antibody for FcγR were performed according to the following method. First, antibodies of interest were captured onto the above-mentioned sensor chips, and an Fcγ receptor diluted with the running buffer was allowed to interact. The Biacore Evaluation Software was used to globally fit the measured results to the obtained sensorgram using the 1:1 Langmuir binding model, and the association rate constant ka (L/mol/s) and the dissociation rate constant kd (1/s) were calculated; and from those values the dissociation constants KD (mol/L) were calculated.

When the interaction between each of the altered antibodies and FcγR was weak, and correct analysis was determined to be impossible by the above-mentioned kinetic analysis, the KD for such interactions were calculated using the following 1:1 binding model equation described in the Biacore T100 Software Handbook BR1006-48 Edition AE.

The behavior of interacting molecules according to the 1:1 binding model on Biacore can be described by Equation 3 shown below.

$$R_{eq} = C \cdot R_{max}/(KD+C)+RI \qquad \text{[Equation 3]}$$

Req: a plot of steady-state binding levels against analyte concentration

C: concentration

RI: bulk refractive index contribution in the sample

Rmax: analyte binding capacity of the surface

When this equation is rearranged, KD can be expressed as Equation 2 shown below.

$$KD = C \cdot R_{max}/(R_{eq}-RI)-C \qquad \text{[Equation 2]}$$

KD can be calculated by substituting the values of Rmax, RI, and C into this equation. The values of RI and C can be determined from the sensorgram of the measurement results and measurement conditions. Rmax was calculated according to the following method. As a target of comparison, for antibodies that had sufficiently strong interactions as evaluated simultaneously in the same round of measurement, the Rmax value was obtained through global fitting using the 1:1 Langmuir binding model, and then it was divided by the amount of the comparison antibody captured onto the sensor chip, and multiplied by the captured amount of an altered antibody to be evaluated.

---

The invention claimed is:

1. A pharmaceutical composition comprising an antibody comprising a heavy chain constant region comprising SEQ ID NO: 14 with at least the following substitutions: L234Y/P238D/A330K, wherein all position numbers are by EU numbering.

2. The pharmaceutical composition of claim 1, wherein the heavy chain constant region further comprises a V264I substitution, by EU numbering.

3. The pharmaceutical composition of claim 1, wherein the heavy chain constant region further comprises a K439E substitution, by EU numbering.

4. The pharmaceutical composition of claim 2, wherein the heavy chain constant region further comprises a K439E substitution, by EU numbering.

5. The pharmaceutical composition of claim 1, wherein the antibody further comprises a human or humanized heavy chain variable domain, a human or humanized light chain variable domain, and a human light chain constant region.

6. The pharmaceutical composition of claim 2, wherein the antibody further comprises a human or humanized heavy chain variable domain, a human or humanized light chain variable domain, and a human light chain constant region.

7. A pharmaceutical composition comprising an antibody comprising a heavy chain constant region comprising SEQ ID NO: 14 with at least the following substitutions: L234Y/P238D/A330K, and with a deletion of the two carboxy-terminal amino acids, wherein all position numbers are by EU numbering.

8. The pharmaceutical composition of claim 7, wherein the heavy chain constant region further comprises a V264I substitution, by EU numbering.

9. The pharmaceutical composition of claim 7, wherein the heavy chain constant region further comprises a K439E substitution, by EU numbering.

10. The pharmaceutical composition of claim 8, wherein the heavy chain constant region further comprises a K439E substitution, by EU numbering.

11. The pharmaceutical composition of claim 7, wherein the antibody further comprises a human or humanized heavy chain variable domain, a human or humanized light chain variable domain, and a human light chain constant region.

12. The pharmaceutical composition of claim 8, wherein the antibody further comprises a human or humanized heavy chain variable domain, a human or humanized light chain variable domain, and a human light chain constant region.

* * * * *

SEQUENCE LISTING

<160> NUMBER OF SEQ ID NOS: 81

<210> SEQ ID NO 1
<211> LENGTH: 468
<212> TYPE: PRT

<213> ORGANISM: Homo sapiens

<400> SEQUENCE: 1

```
Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
        50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
        130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Pro Ala Asn Ile Thr Val
        210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
        290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Ser Val Pro Leu Pro Thr Phe Leu
            355                 360                 365

Val Ala Gly Gly Ser Leu Ala Phe Gly Thr Leu Leu Cys Ile Ala Ile
        370                 375                 380

Val Leu Arg Phe Lys Lys Thr Trp Lys Leu Arg Ala Leu Lys Glu Gly
385                 390                 395                 400
```

```
Lys Thr Ser Met His Pro Pro Tyr Ser Leu Gly Gln Leu Val Pro Glu
            405             410             415

Arg Pro Arg Pro Thr Pro Val Leu Val Pro Leu Ile Ser Pro Pro Val
            420             425             430

Ser Pro Ser Ser Leu Gly Ser Asp Asn Thr Ser Ser His Asn Arg Pro
            435             440             445

Asp Ala Arg Asp Pro Arg Ser Pro Tyr Asp Ile Ser Asn Thr Asp Tyr
        450             455             460

Phe Phe Pro Arg
465
```

```
<210> SEQ ID NO 2
<211> LENGTH: 1407
<212> TYPE: DNA
<213> ORGANISM: Homo sapiens

<400> SEQUENCE: 2
atgctggccg tcggctgcgc gctgctggct gccctgctgg ccgcgccggg agcggcgctg      60
gccccaaggc gctgccctgc gcaggaggtg gcgagaggcg tgctgaccag tctgccagga     120
gacagcgtga ctctgacctg cccgggggta gagccggaag acaatgccac tgttcactgg     180
gtgctcagga agccggctgc aggctcccac cccagcagat gggctggcat gggaaggagg     240
ctgctgctga ggtcggtgca gctccacgac tctggaaact attcatgcta ccgggccggc     300
cgcccagctg ggactgtgca cttgctggtg gatgttcccc ccgaggagcc ccagctctcc     360
tgcttccgga gagccccct cagcaatgtt gtttgtgagt ggggtcctcg gagcacccca     420
tccctgacga caaaggctgt gctcttggtg aggaagtttc agaacagtcc ggccgaagac     480
ttccaggagc cgtgccagta ttcccaggag tcccagaagt ctcctgcca gttagcagtc      540 ccggagggag acagctcttt ctacatagtg tccatgtgcg tcgccagtag tgtcgggagc     600
aagttcagca aaactcaaac ctttcagggt tgtggaatct tgcagcctga tccgcctgcc     660
aacatcacag tcactgccgt ggccagaaac ccccgctggc tcagtgtcac ctggcaagac     720
ccccactcct ggaactcatc tttctacaga ctacggtttg agctcagata tcgggctgaa     780
cggtcaaaga cattcacaac atggatggtc aaggacctcc agcatcactg tgtcatccac     840
gacgcctgga gcggcctgag gcacgtggtg cagcttcgtg cccaggagga gttcgggcaa     900
ggcgagtgga gcgagtggag cccggaggcc atgggcacgc cttggacaga tccaggagt     960 cctccagctg agaacgaggt gtccacccc atgcaggcac ttactactaa taaagacgat    1020
gataatattc tcttcagaga ttctgcaaat gcgacaagcc tcccagtgca agattcttct    1080
tcagtaccac tgcccacatt cctggttgct ggagggagcc tggccttcgg aacgctcctc    1140
tgcattgcca ttgttctgag gttcaagaag acgtggaagc tgcgggctct gaaggaaggc    1200
aagacaagca tgcatccgcc gtactctttg gggcagctgg tcccggagag gcctcgaccc    1260
accccagtgc ttgttcctct catctcccca ccggtgtccc ccagcagcct ggggtctgac    1320
aatacctcga gccacaaccg accagatgcc agggaccac ggagcccta tgacatcagc     1380 aatacagact acttcttccc cagatag                                       1407
```

```
<210> SEQ ID NO 3
<211> LENGTH: 107
<212> TYPE: PRT
<213> ORGANISM: Homo sapiens

<400> SEQUENCE: 3
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105
```

```
<210> SEQ ID NO 4
<211> LENGTH: 19
<212> TYPE: PRT
<213> ORGANISM: Artificial Sequence
<220> FEATURE:
<223> OTHER INFORMATION: An artificially synthesized sequence

<400> SEQUENCE: 4
```

```
Met Gly Trp Ser Cys Ile Ile Leu Phe Leu Val Ala Thr Ala Thr Gly
1               5                   10                  15

Val His Ser
```

```
<210> SEQ ID NO 5
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 5
```

```
Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Ser Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys
            100                 105
```

```
<210> SEQ ID NO 6
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 6
```

```
Asp Ile Gln Met Thr Gln Ser Pro Ser Ser Leu Ser Ala Ser Val Gly
1               5                   10                  15
```

-continued

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 7
<211> LENGTH: 112
<212> TYPE: PRT
<213> ORGANISM: Artificial Sequence
<220> FEATURE:
<223> OTHER INFORMATION: An artificially synthesized sequence

<400> SEQUENCE: 7

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asp Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu Arg Asn Pro Leu Thr Phe Gly Gly Gly Thr Lys Val Glu Ile Gln
            100                 105                 110

<210> SEQ ID NO 8
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 8

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 9
<211> LENGTH: 112
<212> TYPE: PRT
<213> ORGANISM: Artificial Sequence

<400> SEQUENCE: 9

Asp Ile Val Met Thr Gln Ser Pro Glu Ser Leu Val Leu Ser Leu Gly
1               5                   10                  15

Gly Thr Ala Thr Ile Asn Cys Arg Ser Ser Gln Ser Val Leu Tyr Ser
            20                  25                  30

Ser Asn Asn Lys Asn Tyr Leu Thr Trp Tyr Gln Gln Lys Pro Gly Gln
        35                  40                  45

Pro Pro Thr Leu Leu Phe Ser Trp Ala Ser Ile Arg Asp Ser Gly Val
    50                  55                  60

Pro Asp Arg Phe Ser Ala Ser Gly Ser Gly Thr Glu Phe Thr Leu Thr
65                  70                  75                  80

Ile Ser Asp Leu Gln Ala Glu Asp Ala Ala Val Tyr Tyr Cys Gln Gln
            85                  90                  95

Tyr Tyr Arg Ala Pro Ser Phe Gly Gln Gly Thr Lys Leu Gln Ile Lys
            100                 105                 110

<210> SEQ ID NO 10
<211> LENGTH: 121
<212> TYPE: PRT
<213> ORGANISM: Artificial Sequence
<220> FEATURE:
<223> OTHER INFORMATION: An artificially synthesized sequence

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Asp Asp Pro Gly Gly Gly Glu Tyr Tyr Phe Asp Tyr Trp Gly
            100                 105                 110

Gln Gly Thr Leu Val Thr Val Ser Ser
        115                 120

<210> SEQ ID NO 11
<211> LENGTH: 126
<212> TYPE: PRT
<213> ORGANISM: Artificial Sequence
<220> FEATURE:
<223> OTHER INFORMATION: An artificially synthesized sequence

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser
        115                 120                 125

<210> SEQ ID NO 12
<211> LENGTH: 365
<212> TYPE: PRT
<213> ORGANISM: Homo sapiens

<400> SEQUENCE: 12

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Leu Val Val Gly Ile Val
    290                 295                 300

Ile Gly Val Leu Leu Leu Thr Ala Ala Ala Val Gly Gly Ala Leu Leu
```

```
305              310              315              320

Trp Arg Arg Met Arg Ser Gly Leu Pro Ala Pro Trp Ile Ser Leu Arg
                325              330              335

Gly Asp Asp Thr Gly Val Leu Leu Pro Thr Pro Gly Glu Ala Gln Asp
            340              345              350

Ala Asp Leu Lys Asp Val Asn Val Ile Pro Ala Thr Ala
        355              360              365
```

<210> SEQ ID NO 13
<211> LENGTH: 119
<212> TYPE: PRT
<213> ORGANISM: Homo sapiens

<400> SEQUENCE: 13

```
Met Ser Arg Ser Val Ala Leu Ala Val Leu Ala Leu Leu Ser Leu Ser
1               5               10              15

Gly Leu Glu Ala Ile Gln Arg Thr Pro Lys Ile Gln Val Tyr Ser Arg
            20              25              30

His Pro Ala Glu Asn Gly Lys Ser Asn Phe Leu Asn Cys Tyr Val Ser
        35              40              45

Gly Phe His Pro Ser Asp Ile Glu Val Asp Leu Leu Lys Asn Gly Glu
    50              55              60

Arg Ile Glu Lys Val Glu His Ser Asp Leu Ser Phe Ser Lys Asp Trp
65              70              75              80

Ser Phe Tyr Leu Leu Tyr Tyr Thr Glu Phe Thr Pro Thr Glu Lys Asp
            85              90              95

Glu Tyr Ala Cys Arg Val Asn His Val Thr Leu Ser Gln Pro Lys Ile
        100             105             110

Val Lys Trp Asp Arg Asp Met
        115
```

<210> SEQ ID NO 14
<211> LENGTH: 330
<212> TYPE: PRT
<213> ORGANISM: Artificial Sequence
<220> FEATURE:
<223> OTHER INFORMATION: An artificially synthesized sequence

<400> SEQUENCE: 14

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
            85              90              95

Lys Val Glu Pro Lys Ser Cys Asp Lys Thr His Thr Cys Pro Pro Cys
        100             105             110

Pro Ala Pro Glu Leu Leu Gly Gly Pro Ser Val Phe Leu Phe Pro Pro
        115             120             125

Lys Pro Lys Asp Thr Leu Met Ile Ser Arg Thr Pro Glu Val Thr Cys
        130             135             140
```

-continued

```
Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
        275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330
```

```
<210> SEQ ID NO 15
<211> LENGTH: 326
<212> TYPE: PRT
<213> ORGANISM: Artificial Sequence
<220> FEATURE:
<223> OTHER INFORMATION: An artificially synthesized sequence

<400> SEQUENCE: 15
```

```
Ala Ser Thr Lys Gly Pro Ser Val Phe Pro Leu Ala Pro Cys Ser Arg
1               5               10              15

Ser Thr Ser Glu Ser Thr Ala Ala Leu Gly Cys Leu Val Lys Asp Tyr
                20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Asn Phe Gly Thr Gln Thr
65              70              75              80

Tyr Thr Cys Asn Val Asp His Lys Pro Ser Asn Thr Lys Val Asp Lys
                85              90              95

Thr Val Glu Arg Lys Cys Cys Val Glu Cys Pro Pro Cys Pro Ala Pro
            100             105             110

Pro Val Ala Gly Pro Ser Val Phe Leu Phe Pro Pro Lys Pro Lys Asp
        115             120             125

Thr Leu Met Ile Ser Arg Thr Pro Glu Val Thr Cys Val Val Val Asp
    130             135             140

Val Ser His Glu Asp Pro Glu Val Gln Phe Asn Trp Tyr Val Asp Gly
145             150             155             160

Val Glu Val His Asn Ala Lys Thr Lys Pro Arg Glu Glu Gln Phe Asn
                165             170             175
```

-continued

```
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325
```

```
<210> SEQ ID NO 16
<211> LENGTH: 377
<212> TYPE: PRT
<213> ORGANISM: Homo sapiens

<400> SEQUENCE: 16
```

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
```

```
            210                215                  220
Gln Tyr Asn Ser Thr Phe Arg Val Val Ser Val Leu Thr Val Leu His
225                     230                  235                  240

Gln Asp Trp Leu Asn Gly Lys Glu Tyr Lys Cys Lys Val Ser Asn Lys
                245                  250                  255

Ala Leu Pro Ala Pro Ile Glu Lys Thr Ile Ser Lys Thr Lys Gly Gln
                260                  265                  270

Pro Arg Glu Pro Gln Val Tyr Thr Leu Pro Pro Ser Arg Glu Glu Met
            275                  280                  285

Thr Lys Asn Gln Val Ser Leu Thr Cys Leu Val Lys Gly Phe Tyr Pro
        290                  295                  300

Ser Asp Ile Ala Val Glu Trp Glu Ser Ser Gly Gln Pro Glu Asn Asn
305                  310                  315                  320

Tyr Asn Thr Thr Pro Pro Met Leu Asp Ser Asp Gly Ser Phe Phe Leu
                325                  330                  335

Tyr Ser Lys Leu Thr Val Asp Lys Ser Arg Trp Gln Gln Gly Asn Ile
            340                  345                  350

Phe Ser Cys Ser Val Met His Glu Ala Leu His Asn Arg Phe Thr Gln
            355                  360                  365

Lys Ser Leu Ser Leu Ser Pro Gly Lys
        370                  375
```

```
<210> SEQ ID NO 17
<211> LENGTH: 327
<212> TYPE: PRT
<213> ORGANISM: Artificial Sequence
<220> FEATURE:
<223> OTHER INFORMATION: An artificially synthesized sequence

<400> SEQUENCE: 17

Ala Ser Thr Lys Gly Pro Ser Val Phe Pro Leu Ala Pro Cys Ser Arg
1                   5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

-continued

```
               195                 200                 205
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 18
<211> LENGTH: 1125
<212> TYPE: DNA
<213> ORGANISM: Homo sapiens

<400> SEQUENCE: 18
atgtggttct tgacaactct gctcctttgg gttccagttg atgggcaagt ggacaccaca      60
aaggcagtga tcactttgca gcctccatgg gtcagcgtgt ccaagagga aaccgtaacc     120 ttgcactgtg aggtgctcca tctgcctggg agcagctcta cacagtggtt tctcaatggc     180
acagccactc agacctcgac ccccagctac agaatcacct ctgccagtgt caatgacagt     240
ggtgaataca ggtgccagag aggtctctca gggcgaagtg accccataca gctggaaatc     300
cacagaggct ggctactact gcaggtctcc agcagagtct tcacggaagg agaacctctg     360
gccttgaggt gtcatgcgtg gaaggataag ctggtgtaca atgtgcttta ctatcgaaat     420
ggcaaagcct ttaagttttt ccactggaat tctaacctca ccattctgaa aaccaacata     480
agtcacaatg gcacctacca ttgctcaggc atgggaaagc atcgctacac atcagcagga     540
atatctgtca ctgtgaaaga gctatttcca gctccagtgc tgaatgcatc tgtgacatcc     600
ccactcctgg aggggaatct ggtcaccctg agctgtgaaa caaagttgct cttgcagagg     660
cctggtttgc agctttactt ctccttctac atgggcagca agaccctgcg aggcaggaac     720
acatcctctg aataccaaat actaactgct agaagagaag actctgggtt atactggtgc     780
gaggctgcca cagaggatgg aaatgtcctt aagcgcagcc ctgagttgga gcttcaagtg     840
cttggcctcc agttaccaac tcctgtctgg tttcatgtcc ttttctatct ggcagtggga     900
ataatgtttt tagtgaacac tgttctctgg gtgacaatac gtaaagaact gaaaagaaag     960
aaaaagtggg atttagaaat ctctttggat tctggtcatg agaagaaggt aatttccagc    1020
cttcaagaag acagacattt agaagaagag ctgaaatgtc aggaacaaaa agaagaacag    1080
ctgcaggaag gggtgcaccg gaaggagccc caggggggca cgtag                     1125
```

```
<210> SEQ ID NO 19
<211> LENGTH: 374
<212> TYPE: PRT
<213> ORGANISM: Homo sapiens

<400> SEQUENCE: 19
```

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
                180                 185                 190

Val Leu Asn Ala Ser Val Thr Ser Pro Leu Leu Glu Gly Asn Leu Val
            195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
            275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
            325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
            355                 360                 365

Glu Pro Gln Gly Ala Thr
    370
```

<210> SEQ ID NO 20
<211> LENGTH: 951
<212> TYPE: DNA
<213> ORGANISM: Homo sapiens

<400> SEQUENCE: 20
atgactatgg agacccaaat gtctcagaat gtatgtccca gaaacctgtg gctgcttcaa      60
ccattgacag ttttgctgct gctggcttct gcagacagtc aagctgctcc cccaaaggct     120
gtgctgaaac ttgagccccc gtggatcaac gtgctccagg aggactctgt gactctgaca     180 tgccagggg ctcgcagccc tgagagcgac tccattcagt ggttccacaa tgggaatctc      240
attcccaccc acacgcagcc cagctacagg ttcaaggcca acaacaatga cagcgggggag    300 tacacgtgcc agactggcca gaccagcctc agcgaccctg tgcatctgac tgtgctttcc     360
gaatggctgg tgctccagac ccctcacctg gagttccagg agggagaaac catcatgctg     420
aggtgccaca gctggaagga caagcctctg gtcaaggtca cattcttcca gaatggaaaa     480
tcccagaaat ctcccatt ggatcccacc ttctccatcc cacaagcaaa ccacagtcac       540
agtggtgatt accactgcac aggaaacata ggctacacgc tgttctcatc caagcctgtg     600
accatcactg tccaagtgcc cagcatgggc agctcttcac caatggggt cattgtggct      660 gtggtcattg cgactgctgt agcagccatt gttgctgctg tagtggcctt gatctactgc     720
aggaaaaagc ggatttcagc caattccact gatcctgtga aggctgccca atttgagcca     780
cctggacgtc aaatgattgc catcagaaag agacaacttg aagaaccaa caatgactat       840 gaaacagctg acggcggcta catgactctg aaccccaggg cacctactga cgatgataaa     900
aacatctacc tgactcttcc tcccaacgac catgtcaaca gtaataacta a             951

<210> SEQ ID NO 21
<211> LENGTH: 316
<212> TYPE: PRT
<213> ORGANISM: Homo sapiens

<400> SEQUENCE: 21

```
Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Gln Gly Ala
    50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
```

-continued

```
            195                 200                 205
Met Gly Ser Ser Ser Pro Met Gly Val Ile Val Ala Val Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
            275                 280                 285

Thr Leu Asn Pro Arg Ala Pro Thr Asp Asp Asp Lys Asn Ile Tyr Leu
    290                 295                 300

Thr Leu Pro Pro Asn Asp His Val Asn Ser Asn Asn
305                 310                 315
```

<210> SEQ ID NO 22
<211> LENGTH: 876
<212> TYPE: DNA
<213> ORGANISM: Homo sapiens

<400> SEQUENCE: 22

```
atgggaatcc tgtcattctt acctgtcctt gccactgaga gtgactgggc tgactgcaag     60
tccccccagc cttgggggtca tatgcttctg tggacagctg tgctattcct ggctcctgtt    120
gctgggacac ctgcagctcc cccaaaggct gtgctgaaac tcgagcccca gtggatcaac    180
gtgctccagg aggactctgt gactctgaca tgccggggga ctcacagccc tgagagcgac    240
tccattcagt ggttccacaa tgggaatctc attcccaccc acacgcagcc cagctacagg    300
ttcaaggcca acaacaatga cagcgggggag tacacgtgcc agactggcca gaccagcctc    360
agcgaccctg tgcatctgac tgtgcttctt gagtggctgg tgctccagac ccctcacctg    420
gagttccagg agggagaaac catcgtgctg aggtgccaca gctggaagga caagcctctg    480
gtcaaggtca cattcttcca gaatggaaaa tccaagaaat tttcccgttc ggatcccaac    540
ttctccatcc cacaagcaaa ccacagtcac agtggtgatt accactgcac aggaaacata    600
ggctacacgc tgtactcatc caagcctgtg accatcactg tccaagctcc cagctcttca    660
ccgatgggga tcattgtggc tgtggtcact gggattgctg tagcggccat tgttgctgct    720
gtagtggcct tgatctactg caggaaaaag cggatttcag ccaatcccac taatcctgat    780
gaggctgaca agttggggc tgagaacaca atcacctatt cacttctcat gcacccggat    840
gctctggaag agcctgatga ccagaaccgt atttag                              876
```

<210> SEQ ID NO 23
<211> LENGTH: 291
<212> TYPE: PRT
<213> ORGANISM: Homo sapiens

<400> SEQUENCE: 23

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
                20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
```

```
            50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
                100                 105                 110

Cys Gln Thr Gly Gln Thr Ser Leu Ser Asp Pro Val His Leu Thr Val
            115                 120                 125

Leu Ser Glu Trp Leu Val Leu Gln Thr Pro His Leu Glu Phe Gln Glu
        130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
                180                 185                 190

Asp Tyr His Cys Thr Gly Asn Ile Gly Tyr Thr Leu Tyr Ser Ser Lys
            195                 200                 205

Pro Val Thr Ile Thr Val Gln Ala Pro Ser Ser Ser Pro Met Gly Ile
        210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
                260                 265                 270

Tyr Ser Leu Leu Met His Pro Asp Ala Leu Glu Glu Pro Asp Asp Gln
                275                 280                 285

Asn Arg Ile
    290

<210> SEQ ID NO 24
<211> LENGTH: 765
<212> TYPE: DNA
<213> ORGANISM: Homo sapiens

<400> SEQUENCE: 24
atgtggcagc tgctcctccc aactgctctg ctacttctag tttcagctgg catgcggact      60
gaagatctcc caaaggctgt ggtgttcctg gagcctcaat ggtacagggt gctcgagaag     120
gacagtgtga ctctgaagtg ccagggagcc tactcccctg aggacaattc cacacagtgg     180
tttcacaatg agagcctcat ctcaagccag gcctcgagct acttcattga cgctgccaca     240
gttgacgaca gtggagagta caggtgccag acaaacctct ccaccctcag tgacccggtg     300
cagctagaag tccatatcgg ctggctgttg ctccaggccc ctcggtgggt gttcaaggag     360
gaagaccgta ttcacctgag gtgtcacagc tggaagaaca ctgctctgca taaggtcaca     420
tatttacaga tggcaaagg caggaagtat tttcatcata attctgactt ctacattcca     480
aaagccacac tcaaagacag cggctcctac ttctgcaggg ggcttgttgg gagtaaaaat     540
gtgtcttcag agactgtgaa catcaccatc actcaaggtt tgtcagtgtc aaccatctca     600
tcattctttc cacctgggta ccaagtctct ttctgcttgg tgatggtact ccttttttgca     660 gtggacacag gactatattt ctctgtgaag acaaacattc gaagctcaac aagagactgg     720
```

```
aaggaccata aatttaaatg gagaaaggac cctcaagaca aatga              765
```

<210> SEQ ID NO 25
<211> LENGTH: 254
<212> TYPE: PRT
<213> ORGANISM: Homo sapiens

<400> SEQUENCE: 25

```
Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ser Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 26
<211> LENGTH: 702
<212> TYPE: DNA
<213> ORGANISM: Homo sapiens

<400> SEQUENCE: 26

```
atgtggcagc tgctcctccc aactgctctg ctacttctag tttcagctgg catgcggact    60
gaagatctcc caaaggctgt ggtgttcctg gagcctcaat ggtacagcgt gcttgagaag   120
gacagtgtga ctctgaagtg ccagggagcc tactcccctg aggacaattc cacacagtgg   180
tttcacaatg agagcctcat ctcaagccag gcctcgagct acttcattga cgctgccaca   240
gtcaacgaca gtggagagta caggtgccag acaaacctct ccaccctcag tgacccggtg   300
cagctagaag tccatatcgg ctggctgttg ctccaggccc ctcggtgggt gttcaaggag   360 gaagaccta ttcacctgag gtgtcacagc tggaagaaca ctgctctgca taaggtcaca   420
```

```
tatttacaga atggcaaaga caggaagtat tttcatcata attctgactt ccacattcca      480
aaagccacac tcaaagatag cggctcctac ttctgcaggg ggcttgttgg gagtaaaaat      540
gtgtcttcag agactgtgaa catcaccatc actcaaggtt tggcagtgtc aaccatctca      600
tcattctctc cacctgggta ccaagtctct ttctgcttgg tgatggtact ccttttttgca     660 gtggacacag gactatattt ctctgtgaag acaaacattt ga                         702
```

```
<210> SEQ ID NO 27
<211> LENGTH: 233
<212> TYPE: PRT
<213> ORGANISM: Homo sapiens

<400> SEQUENCE: 27

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230
```

```
<210> SEQ ID NO 28
<211> LENGTH: 4
<212> TYPE: PRT
<213> ORGANISM: Artificial Sequence
<220> FEATURE:
<223> OTHER INFORMATION: An artificially synthesized sequence

<400> SEQUENCE: 28

Gly Gly Gly Ser
1
```

```
<210> SEQ ID NO 29
```

```
<211> LENGTH: 4
<212> TYPE: PRT
<213> ORGANISM: Artificial Sequence
<220> FEATURE:
<223> OTHER INFORMATION: An artificially synthesized sequence

<400> SEQUENCE: 29

Ser Gly Gly Gly
1

<210> SEQ ID NO 30
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 30

Gly Gly Gly Gly Ser
1               5

<210> SEQ ID NO 31
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 31

Ser Gly Gly Gly Gly
1               5

<210> SEQ ID NO 32
<211> LENGTH: 6
<212> TYPE: PRT
<213> ORGANISM: Artificial Sequence
<220> FEATURE:
<223> OTHER INFORMATION: An artificially synthesized sequence

<400> SEQUENCE: 32

Gly Gly Gly Gly Gly Ser
1               5

<210> SEQ ID NO 33
<211> LENGTH: 6
<212> TYPE: PRT
<213> ORGANISM: Artificial Sequence
<220> FEATURE:
<223> OTHER INFORMATION: An artificially synthesized sequence

<400> SEQUENCE: 33

Ser Gly Gly Gly Gly Gly
1               5

<210> SEQ ID NO 34
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 34

Gly Gly Gly Gly Gly Gly Ser
1               5

<210> SEQ ID NO 35
<211> LENGTH: 7
```

```
<212> TYPE: PRT
<213> ORGANISM: Artificial Sequence
<220> FEATURE:
<223> OTHER INFORMATION: An artificially synthesized sequence

<400> SEQUENCE: 35

Ser Gly Gly Gly Gly Gly Gly
1               5

<210> SEQ ID NO 36
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 36

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320
```

-continued

```
Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445
```

```
<210> SEQ ID NO 37
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 37
```

```
Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
                20                  25                  30

Leu Asn Trp Tyr Gln Gln Lys Pro Gly Lys Ala Pro Glu Leu Leu Ile
            35                  40                  45

Tyr Tyr Gly Ser Glu Leu His Ser Gly Val Pro Ser Arg Phe Ser Gly
        50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 38
```

```
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
        50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380
```

-continued

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 39
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 39

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
                20                  25                  30

Leu Asn Trp Tyr Gln Gln Lys Pro Gly Lys Ala Pro Glu Leu Leu Ile
            35                  40                  45

Tyr Tyr Gly Ser His Leu Leu Ser Gly Val Pro Ser Arg Phe Ser Gly
        50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
```

-continued

```
              20              25              30
His Ala Trp Ser Trp Val Arg Gln Pro Pro Gly Glu Gly Leu Glu Trp
         35              40              45
Ile Gly Phe Ile Ser Tyr Ser Gly Ile Thr Asn Tyr Asn Pro Ser Leu
     50              55              60
Gln Gly Arg Val Thr Ile Ser Arg Asp Asn Ser Lys Asn Thr Leu Tyr
65              70              75              80
Leu Gln Met Asn Ser Leu Arg Ala Glu Asp Thr Ala Val Tyr Tyr Cys
             85              90              95
Ala Arg Ser Leu Ala Arg Thr Thr Ala Met Asp Tyr Trp Gly Glu Gly
            100             105             110
Thr Leu Val Thr Val Ser Ser Ala Ser Thr Lys Gly Pro Ser Val Phe
        115             120             125
Pro Leu Ala Pro Ser Ser Lys Ser Thr Ser Gly Gly Thr Ala Ala Leu
    130             135             140
Gly Cys Leu Val Lys Asp Tyr Phe Pro Glu Pro Val Thr Val Ser Trp
145             150             155             160
Asn Ser Gly Ala Leu Thr Ser Gly Val His Thr Phe Pro Ala Val Leu
            165             170             175
Gln Ser Ser Gly Leu Tyr Ser Leu Ser Ser Val Val Thr Val Pro Ser
        180             185             190
Ser Ser Leu Gly Thr Gln Thr Tyr Ile Cys Asn Val Asn His Lys Pro
        195             200             205
Ser Asn Thr Lys Val Asp Lys Lys Val Glu Pro Lys Ser Cys Asp Lys
    210             215             220
Thr His Thr Cys Pro Pro Cys Pro Ala Pro Glu Leu Leu Gly Gly Pro
225             230             235             240
Ser Val Phe Leu Phe Pro Pro Lys Pro Lys Asp Thr Leu Met Ile Ser
            245             250             255
Arg Thr Pro Glu Val Thr Cys Val Val Val Asp Val Ser His Glu Asp
        260             265             270
Pro Glu Val Lys Phe Asn Trp Tyr Val Asp Gly Val Glu Val His Asn
        275             280             285
Ala Lys Thr Lys Pro Arg Glu Glu Gln Tyr Asn Ser Thr Tyr Arg Val
    290             295             300
Val Ser Val Leu Thr Val Leu His Gln Asp Trp Leu Asn Gly Lys Glu
305             310             315             320
Tyr Lys Cys Lys Val Ser Asn Asp Ala Tyr Pro Ala Pro Ile Glu Lys
            325             330             335
Thr Ile Ser Lys Ala Lys Gly Gln Pro Arg Glu Pro Gln Val Tyr Thr
        340             345             350
Leu Pro Pro Ser Arg Asp Glu Leu Thr Lys Asn Gln Val Ser Leu Thr
        355             360             365
Cys Leu Val Lys Gly Phe Tyr Pro Ser Asp Ile Ala Val Glu Trp Glu
    370             375             380
Ser Asn Gly Gln Pro Glu Asn Asn Tyr Lys Thr Thr Pro Pro Val Leu
385             390             395             400
Asp Ser Asp Gly Ser Phe Phe Leu Tyr Ser Lys Leu Thr Val Asp Lys
            405             410             415
Ser Arg Trp Gln Gln Gly Asn Val Phe Ser Cys Ser Val Met His Glu
        420             425             430
Ala Leu His Asn His Tyr Thr Gln Lys Ser Leu Ser Leu Ser Pro
        435             440             445
```

-continued

<210> SEQ ID NO 41
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Arg Gly Gly Pro
225                 230                 235                 240

Lys Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

-continued

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
        435                 440                 445
```

```
<210> SEQ ID NO 42
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 42
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 43
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 43
```

```
Gln Val Gln Leu Gln Glu Ser Gly Pro Gly Leu Val Lys Pro Ser Glu
```

-continued

```
1                   5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Tyr Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
            420                 425                 430
```

-continued

Ala Leu His Ser His Tyr Thr Gln Lys Ser Leu Ser Leu Ser Pro
        435                 440                 445

<210> SEQ ID NO 44
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
        20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Tyr Pro Ala Pro Ile Glu Lys
            325                 330                 335

Thr Ile Ser Lys Ala Lys Gly Gln Pro Arg Glu Pro Gln Val Tyr Thr
        340                 345                 350

-continued

```
Leu Pro Pro Ser Arg Asp Glu Leu Thr Lys Asn Gln Val Ser Leu Thr
        355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro
        435             440             445

<210> SEQ ID NO 45
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 45

Gln Val Gln Leu Gln Glu Ser Gly Pro Gly Leu Val Lys Pro Ser Glu
1               5               10              15

Thr Leu Ser Leu Thr Cys Ala Val Ser Gly His Ser Ile Ser His Asp
            20              25              30

His Ala Trp Ser Trp Val Arg Gln Pro Pro Gly Glu Gly Leu Glu Trp
        35              40              45

Ile Gly Phe Ile Ser Tyr Ser Gly Ile Thr Asn Tyr Asn Pro Ser Leu
    50              55              60

Gln Gly Arg Val Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Ser Leu Ala Arg Thr Thr Ala Met Asp Tyr Trp Gly Glu Gly
            100             105             110

Thr Leu Val Thr Val Ser Ser Ala Ser Thr Lys Gly Pro Ser Val Phe
            115             120             125

Pro Leu Ala Pro Ser Ser Lys Ser Thr Ser Gly Gly Thr Ala Ala Leu
        130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
            180             185             190

Ser Ser Leu Gly Thr Gln Thr Tyr Ile Cys Asn Val Asn His Lys Pro
            195             200             205

Ser Asn Thr Lys Val Asp Lys Lys Val Glu Pro Lys Ser Cys Asp Lys
        210             215             220

Thr His Thr Cys Pro Pro Cys Pro Ala Pro Glu Leu Leu Gly Gly Pro
225             230             235             240

Asp Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270
```

-continued

```
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Glu Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
        435                 440                 445
```

```
<210> SEQ ID NO 46
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 46
```

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
        20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
        50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
        100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
        180                 185                 190
```

-continued

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Tyr Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
                420                 425                 430

Ala Leu His Ser His Tyr Thr Gln Lys Ser Leu Ser Leu Ser Pro
                435                 440                 445

<210> SEQ ID NO 47
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 47

Gln Val Gln Leu Gln Glu Ser Gly Pro Gly Leu Val Lys Pro Ser Glu
1                   5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110
```

-continued

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Asp Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Glu Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Ser His Tyr Thr Gln Lys Ser Leu Ser Leu Ser Pro
        435                 440                 445

<210> SEQ ID NO 48
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
        20                  25                  30
```

-continued

```
His Ala Trp Ser Trp Val Arg Gln Pro Pro Gly Glu Gly Leu Glu Trp
    35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Tyr Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Ala His Tyr Thr Gln Lys Ser Leu Ser Leu Ser Pro
    435                 440                 445
```

```
<210> SEQ ID NO 49
<211> LENGTH: 443
<212> TYPE: PRT
<213> ORGANISM: Mus musculus

<400> SEQUENCE: 49

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
            245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
    370                 375                 380
```

-continued

```
Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr Glu Lys Ser Leu Ser His Ser Pro Gly Lys
            435                 440

<210> SEQ ID NO 50
<211> LENGTH: 214
<212> TYPE: PRT
<213> ORGANISM: Mus musculus

<400> SEQUENCE: 50

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
                20                  25                  30

Leu Asn Trp Tyr Gln Gln Lys Pro Gly Lys Ala Pro Glu Leu Leu Ile
            35                  40                  45

Tyr Tyr Gly Ser His Leu Leu Ser Gly Val Pro Ser Arg Phe Ser Gly
        50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Ala Asp Ala Ala
                100                 105                 110

Pro Thr Val Ser Ile Phe Pro Pro Ser Ser Glu Gln Leu Thr Ser Gly
                115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
    210

<210> SEQ ID NO 51
<211> LENGTH: 443
<212> TYPE: PRT
<213> ORGANISM: Artificial Sequence
<220> FEATURE:
<223> OTHER INFORMATION: An artificially synthesized sequence

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30
```

His Ala Trp Ser Trp Val Arg Gln Pro Pro Gly Glu Gly Leu Glu Trp
        35                      40                      45

Ile Gly Phe Ile Ser Tyr Ser Gly Ile Thr Asn Tyr Asn Pro Ser Leu
    50                      55                      60

Gln Gly Arg Val Thr Ile Ser Arg Asp Asn Ser Lys Asn Thr Leu Tyr
65                      70                      75                      80

Leu Gln Met Asn Ser Leu Arg Ala Glu Asp Thr Ala Val Tyr Tyr Cys
                85                      90                      95

Ala Arg Ser Leu Ala Arg Thr Thr Ala Met Asp Tyr Trp Gly Glu Gly
            100                     105                     110

Thr Leu Val Thr Val Ser Ser Ala Lys Thr Thr Pro Pro Ser Val Tyr
            115                     120                     125

Pro Leu Ala Pro Gly Ser Ala Ala Gln Thr Asn Ser Met Val Thr Leu
    130                     135                     140

Gly Cys Leu Val Lys Gly Tyr Phe Pro Glu Pro Val Thr Val Thr Trp
145                     150                     155                     160

Asn Ser Gly Ser Leu Ser Ser Gly Val His Thr Phe Pro Ala Val Leu
                165                     170                     175

Gln Ser Asp Leu Tyr Thr Leu Ser Ser Ser Val Thr Val Pro Ser Ser
            180                     185                     190

Thr Trp Pro Ser Glu Thr Val Thr Cys Asn Val Ala His Pro Ala Ser
            195                     200                     205

Ser Thr Lys Val Asp Lys Lys Ile Val Pro Arg Asp Cys Gly Cys Lys
    210                     215                     220

Pro Cys Ile Cys Thr Val Pro Glu Val Ser Ser Val Phe Ile Phe Pro
225                     230                     235                     240

Pro Lys Pro Lys Asp Val Leu Thr Ile Thr Leu Thr Pro Lys Val Thr
            245                     250                     255

Cys Val Val Val Asp Ile Ser Lys Asp Asp Pro Glu Val Gln Phe Ser
            260                     265                     270

Trp Phe Val Asp Asp Val Glu Val His Thr Ala Gln Thr Gln Pro Arg
            275                     280                     285

Glu Glu Gln Phe Asn Ser Thr Phe Arg Ser Val Ser Glu Leu Pro Ile
    290                     295                     300

Met His Gln Asp Trp Leu Asn Gly Lys Glu Phe Lys Cys Arg Val Asn
305                     310                     315                     320

Ser Ala Asp Phe Pro Ala Pro Ile Glu Lys Thr Ile Ser Lys Thr Lys
                325                     330                     335

Gly Arg Pro Lys Ala Pro Gln Val Tyr Thr Ile Pro Pro Pro Lys Glu
            340                     345                     350

Gln Met Ala Lys Asp Lys Val Ser Leu Thr Cys Met Ile Thr Asp Phe
            355                     360                     365

Phe Pro Glu Asp Ile Thr Val Glu Trp Gln Trp Asn Gly Gln Pro Ala
    370                     375                     380

Glu Asn Tyr Lys Asn Thr Gln Pro Ile Met Asp Thr Asp Gly Ser Tyr
385                     390                     395                     400

Phe Val Tyr Ser Lys Leu Asn Val Gln Lys Ser Asn Trp Glu Ala Gly
                405                     410                     415

Asn Thr Phe Thr Cys Ser Val Leu His Glu Gly Leu His Asn His His
                420                     425                     430

Thr Glu Lys Ser Leu Ser His Ser Pro Gly Lys
            435                     440

<210> SEQ ID NO 52
<211> LENGTH: 443
<212> TYPE: PRT
<213> ORGANISM: Artificial Sequence
<220> FEATURE:
<223> OTHER INFORMATION: An artificially synthesized sequence

<400> SEQUENCE: 52

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
        130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
        210                 215                 220

Pro Cys Ile Cys Thr Val Pro Glu Val Ser Asp Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
        290                 295                 300

Met His Gln Asp Trp Leu Asn Gly Lys Glu Phe Lys Cys Arg Val Asn
305                 310                 315                 320

Ser Ala Asp Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala

-continued

```
            370              375              380
Glu Asn Tyr Lys Asn Thr Gln Pro Ile Met Asp Thr Asp Gly Ser Tyr
385              390              395              400

Phe Val Tyr Ser Lys Leu Asn Val Gln Lys Ser Asn Trp Glu Ala Gly
                405              410              415

Asn Thr Phe Thr Cys Ser Val Leu His Glu Gly Leu His Asn His His
                420              425              430

Thr Glu Lys Ser Leu Ser His Ser Pro Gly Lys
        435              440
```

<210> SEQ ID NO 53
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 53

```
Gln Val Gln Leu Gln Glu Ser Gly Pro Gly Leu Val Lys Pro Ser Glu
1               5               10              15

Thr Leu Ser Leu Thr Cys Ala Val Ser Gly His Ser Ile Ser His Asp
                20              25              30

His Ala Trp Ser Trp Val Arg Gln Pro Pro Gly Glu Gly Leu Glu Trp
        35              40              45

Ile Gly Phe Ile Ser Tyr Ser Gly Ile Thr Asn Tyr Asn Pro Ser Leu
    50              55              60

Gln Gly Arg Val Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Ser Leu Ala Arg Thr Thr Ala Met Asp Tyr Trp Gly Glu Gly
        100             105             110

Thr Leu Val Thr Val Ser Ser
        115
```

<210> SEQ ID NO 54
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 54

```
Gln Val Gln Leu Gln Glu Ser Gly Pro Gly Leu Val Lys Pro Ser Glu
1               5               10              15

Thr Leu Ser Leu Thr Cys Ala Val Ser Gly His Ser Ile Ser His Asp
                20              25              30

His Ala Trp Ser Trp Val Arg Gln Pro Pro Gly Glu Gly Leu Glu Trp
        35              40              45

Ile Gly Phe Ile Ser Tyr Ser Gly Ile Thr Asn Tyr Asn Pro Ser Leu
    50              55              60

Gln Gly Arg Val Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Ser Leu Ala Arg Thr Thr Ala Met Asp Tyr Trp Gly Glu Gly
        100             105             110
```

-continued

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
        435                 440                 445
```

```
<210> SEQ ID NO 55
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30
```

```
His Ala Trp Ser Trp Val Arg Gln Pro Pro Gly Glu Gly Leu Glu Trp
        35              40              45
Ile Gly Phe Ile Ser Tyr Ser Gly Ile Thr Asn Tyr Asn Pro Ser Leu
    50              55              60
Gln Gly Arg Val Thr Ile Ser Arg Asp Asn Ser Lys Asn Thr Leu Tyr
65              70              75              80
Leu Gln Met Asn Ser Leu Arg Ala Glu Asp Thr Ala Val Tyr Tyr Cys
                85              90              95
Ala Arg Ser Leu Ala Arg Thr Thr Ala Met Asp Tyr Trp Gly Glu Gly
                100             105             110
Thr Leu Val Thr Val Ser Ser Ala Ser Thr Lys Gly Pro Ser Val Phe
                115             120             125
Pro Leu Ala Pro Ser Ser Lys Ser Thr Ser Gly Gly Thr Ala Ala Leu
    130             135             140
Gly Cys Leu Val Lys Asp Tyr Phe Pro Glu Pro Val Thr Val Ser Trp
145             150             155             160
Asn Ser Gly Ala Leu Thr Ser Gly Val His Thr Phe Pro Ala Val Leu
                165             170             175
Gln Ser Ser Gly Leu Tyr Ser Leu Ser Ser Val Val Thr Val Pro Ser
                180             185             190
Ser Ser Leu Gly Thr Gln Thr Tyr Ile Cys Asn Val Asn His Lys Pro
                195             200             205
Ser Asn Thr Lys Val Asp Lys Lys Val Glu Pro Lys Ser Cys Asp Lys
    210             215             220
Thr His Thr Cys Pro Pro Cys Pro Ala Pro Glu Leu Leu Gly Gly Pro
225             230             235             240
Ser Val Phe Leu Phe Pro Pro Lys Pro Lys Asp Thr Leu Met Ile Ser
                245             250             255
Arg Thr Pro Glu Val Thr Cys Val Val Val Asp Val Glu His Glu Asp
                260             265             270
Pro Glu Val Lys Phe Asn Trp Tyr Val Asp Gly Val Glu Val His Asn
                275             280             285
Ala Lys Thr Lys Pro Arg Glu Glu Gln Tyr Asn Ser Thr Tyr Arg Val
    290             295             300
Val Ser Val Leu Thr Val Leu His Gln Asp Trp Leu Asn Gly Lys Glu
305             310             315             320
Tyr Lys Cys Lys Val Ser Asn Lys Ala Phe Pro Ala Pro Ile Glu Lys
                325             330             335
Thr Ile Ser Lys Ala Lys Gly Gln Pro Arg Glu Pro Gln Val Tyr Thr
                340             345             350
Leu Pro Pro Ser Arg Asp Glu Leu Thr Lys Asn Gln Val Ser Leu Thr
                355             360             365
Cys Leu Val Lys Gly Phe Tyr Pro Ser Asp Ile Ala Val Glu Trp Glu
    370             375             380
Ser Asn Gly Gln Pro Glu Asn Asn Tyr Lys Thr Thr Pro Pro Val Leu
385             390             395             400
Asp Ser Asp Gly Ser Phe Phe Leu Tyr Ser Lys Leu Thr Val Asp Lys
                405             410             415
Ser Arg Trp Gln Gln Gly Asn Val Phe Ser Cys Ser Val Met His Glu
                420             425             430
Ala Leu His Asn His Tyr Thr Gln Lys Ser Leu Ser Leu Ser Pro
                435             440             445
```

-continued

```
<210> SEQ ID NO 56
<211> LENGTH: 214
<212> TYPE: PRT
<213> ORGANISM: Homo sapiens

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 57
<211> LENGTH: 449
<212> TYPE: PRT
<213> ORGANISM: Artificial Sequence
<220> FEATURE:
<223> OTHER INFORMATION: An artificially synthesized sequence

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
                20                  25                  30

Tyr Ser Trp Asn Trp Ile Arg Gln Ala Pro Gly Lys Gly Leu Glu Trp
            35                  40                  45

Val Ala Ser Ile Thr Tyr Asp Gly Ser Thr Asn Tyr Asn Pro Ser Val
        50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
                100                 105                 110
```

-continued

```
Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro
```

```
<210> SEQ ID NO 58
<211> LENGTH: 218
<212> TYPE: PRT
<213> ORGANISM: Artificial Sequence
<220> FEATURE:
<223> OTHER INFORMATION: An artificially synthesized sequence

<400> SEQUENCE: 58

Asp Ile Gln Leu Thr Gln Ser Pro Ser Ser Leu Ser Ala Ser Val Gly
1               5                   10                  15
```

-continued

```
Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215
```

```
<210> SEQ ID NO 59
<211> LENGTH: 449
<212> TYPE: PRT
<213> ORGANISM: Artificial Sequence
<220> FEATURE:
<223> OTHER INFORMATION: An artificially synthesized sequence

<400> SEQUENCE: 59
```

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
            35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

-continued

Ser Trp Asn Ser Gly Ala Leu Thr Ser Gly Val His Thr Phe Pro Ala
              165                 170                 175

Val Leu Gln Ser Ser Gly Leu Tyr Ser Leu Ser Ser Val Val Thr Val
          180                 185                 190

Pro Ser Ser Ser Leu Gly Thr Gln Thr Tyr Ile Cys Asn Val Asn His
          195                 200                 205

Lys Pro Ser Asn Thr Lys Val Asp Lys Lys Val Glu Pro Lys Ser Cys
      210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
              245                 250                 255

Ile Ser Arg Thr Pro Glu Val Thr Cys Val Val Val Asp Val Glu His
              260                 265                 270

Glu Asp Pro Glu Val Lys Phe Asn Trp Tyr Val Asp Gly Val Glu Val
          275                 280                 285

His Asn Ala Lys Thr Lys Pro Arg Glu Glu Gln Tyr Asn Ser Thr Tyr
          290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Phe Pro Ala Pro Ile
              325                 330                 335

Glu Lys Thr Ile Ser Lys Ala Lys Gly Gln Pro Arg Glu Pro Gln Val
              340                 345                 350

Tyr Thr Leu Pro Pro Ser Arg Asp Glu Leu Thr Lys Asn Gln Val Ser
          355                 360                 365

Leu Thr Cys Leu Val Lys Gly Phe Tyr Pro Ser Asp Ile Ala Val Glu
      370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
              405                 410                 415

Asp Lys Ser Arg Trp Gln Gln Gly Asn Val Phe Ser Cys Ser Val Met
              420                 425                 430

His Glu Ala Leu His Asn His Tyr Thr Gln Lys Ser Leu Ser Leu Ser
          435                 440                 445

Pro

<210> SEQ ID NO 60
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 60

Gln Val Gln Leu Gln Glu Ser Gly Pro Gly Leu Val Lys Pro Ser Glu
1                 5                 10                 15

Thr Leu Ser Leu Thr Cys Ala Val Ser Gly His Ser Ile Ser His Asp
          20                 25                 30

His Ala Trp Ser Trp Val Arg Gln Pro Pro Gly Glu Gly Leu Glu Trp
          35                 40                 45

Ile Gly Phe Ile Ser Tyr Ser Gly Ile Thr Asn Tyr Asn Pro Ser Leu
      50                 55                 60

Gln Gly Arg Val Thr Ile Ser Arg Asp Asn Ser Lys Asn Thr Leu Tyr

```
65                    70                    75                    80
Leu Gln Met Asn Ser Leu Arg Ala Glu Asp Thr Ala Val Tyr Tyr Cys
                85                    90                    95

Ala Arg Ser Leu Ala Arg Thr Thr Ala Met Asp Tyr Trp Gly Glu Gly
                100                   105                   110

Thr Leu Val Thr Val Ser Ser Ala Ser Thr Lys Gly Pro Ser Val Phe
                115                   120                   125

Pro Leu Ala Pro Ser Ser Lys Ser Thr Ser Gly Gly Thr Ala Ala Leu
    130                   135                   140

Gly Cys Leu Val Lys Asp Tyr Phe Pro Glu Pro Val Thr Val Ser Trp
145                   150                   155                   160

Asn Ser Gly Ala Leu Thr Ser Gly Val His Thr Phe Pro Ala Val Leu
                165                   170                   175

Gln Ser Ser Gly Leu Tyr Ser Leu Ser Ser Val Val Thr Val Pro Ser
                180                   185                   190

Ser Ser Leu Gly Thr Gln Thr Tyr Ile Cys Asn Val Asn His Lys Pro
                195                   200                   205

Ser Asn Thr Lys Val Asp Lys Lys Val Glu Pro Lys Ser Cys Asp Lys
    210                   215                   220

Thr His Thr Cys Pro Pro Cys Pro Ala Pro Glu Leu Leu Gly Gly Pro
225                   230                   235                   240

Ser Val Phe Leu Phe Pro Pro Lys Pro Lys Asp Thr Leu Tyr Ile Ser
                245                   250                   255

Arg Thr Pro Glu Val Thr Cys Val Val Val Asp Val Ser His Glu Asp
                260                   265                   270

Pro Glu Val Lys Phe Asn Trp Tyr Val Asp Gly Val Glu Val His Asn
                275                   280                   285

Ala Lys Thr Lys Pro Arg Glu Glu Gln Tyr Asn Ser Thr Tyr Arg Val
                290                   295                   300

Val Ser Val Leu Thr Val Leu His Gln Asp Trp Leu Asn Gly Lys Glu
305                   310                   315                   320

Tyr Lys Cys Lys Val Ser Asn Lys Ala Leu Pro Ala Pro Ile Glu Lys
                325                   330                   335

Thr Ile Ser Lys Ala Lys Gly Gln Pro Arg Glu Pro Gln Val Tyr Thr
                340                   345                   350

Leu Pro Pro Ser Arg Asp Glu Leu Thr Lys Asn Gln Val Ser Leu Thr
                355                   360                   365

Cys Leu Val Lys Gly Phe Tyr Pro Ser Asp Ile Ala Val Glu Trp Glu
    370                   375                   380

Ser Asn Gly Gln Pro Glu Asn Asn Tyr Lys Thr Thr Pro Pro Val Leu
385                   390                   395                   400

Asp Ser Asp Gly Ser Phe Phe Leu Tyr Ser Lys Leu Thr Val Asp Lys
                405                   410                   415

Ser Arg Trp Gln Gln Gly Asn Val Phe Ser Cys Ser Val Met His Glu
                420                   425                   430

Ala Leu His Tyr His Tyr Thr Gln Lys Ser Leu Ser Leu Ser Pro
                435                   440                   445
```

<210> SEQ ID NO 61
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 61

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
            435                 440                 445

<210> SEQ ID NO 62
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 62

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
            50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

```
Thr Ile Ser Lys Ala Lys Gly Gln Pro Arg Glu Pro Gln Val Tyr Thr
        340             345             350

Leu Pro Pro Ser Arg Asp Glu Leu Thr Lys Asn Gln Val Ser Leu Thr
        355             360             365

Cys Leu Val Lys Gly Phe Tyr Pro Ser Asp Ile Ala Val Glu Trp Glu
        370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
                405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro
        435             440             445
```

<210> SEQ ID NO 63
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 63

```
Gln Val Gln Leu Gln Glu Ser Gly Pro Gly Leu Val Lys Pro Ser Glu
1               5               10              15

Thr Leu Ser Leu Thr Cys Ala Val Ser Gly His Ser Ile Ser His Asp
        20              25              30

His Ala Trp Ser Trp Val Arg Gln Pro Pro Gly Glu Gly Leu Glu Trp
        35              40              45

Ile Gly Phe Ile Ser Tyr Ser Gly Ile Thr Asn Tyr Asn Pro Ser Leu
    50              55              60

Gln Gly Arg Val Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Ser Leu Ala Arg Thr Thr Ala Met Asp Tyr Trp Gly Glu Gly
        100             105             110

Thr Leu Val Thr Val Ser Ser Ala Ser Thr Lys Gly Pro Ser Val Phe
        115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
        180             185             190

Ser Ser Leu Gly Thr Gln Thr Tyr Ile Cys Asn Val Asn His Lys Pro
        195             200             205

Ser Asn Thr Lys Val Asp Lys Lys Val Glu Pro Lys Ser Cys Asp Lys
    210             215             220

Thr His Thr Cys Pro Pro Cys Pro Ala Pro Glu Leu Leu Gly Gly Pro
225             230             235             240

Ser Val Phe Leu Phe Pro Pro Lys Pro Lys Asp Thr Leu Met Ile Ser
            245             250             255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Glu Ser Leu Ser Leu Ser Pro
            435                 440                 445
```

<210> SEQ ID NO 64
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 64

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
        180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
        260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu
                435                 440

<210> SEQ ID NO 65
<211> LENGTH: 464
<212> TYPE: PRT
<213> ORGANISM: Artificial sequence
<220> FEATURE:
<223> OTHER INFORMATION: An artificially synthesized sequence

<400> SEQUENCE: 65

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95
```

-continued

```
Ala Arg Ser Leu Ala Arg Thr Thr Ala Met Asp Tyr Trp Gly Gln Gly
            100                 105                 110

Ser Leu Val Thr Val Ser Ser Ala Ser Pro Thr Ser Pro Lys Val Phe
            115                 120                 125

Pro Leu Ser Leu Cys Ser Thr Gln Pro Asp Gly Asn Val Val Ile Ala
            130                 135                 140

Cys Leu Val Gln Gly Phe Phe Pro Gln Glu Pro Leu Ser Val Thr Trp
145                 150                 155                 160

Ser Glu Ser Gly Gln Gly Val Thr Ala Arg Asn Phe Pro Pro Ser Gln
                165                 170                 175

Asp Ala Ser Gly Asp Leu Tyr Thr Thr Ser Ser Gln Leu Thr Leu Pro
            180                 185                 190

Ala Thr Gln Cys Leu Ala Gly Lys Ser Val Thr Cys His Val Lys His
            195                 200                 205

Tyr Thr Asn Pro Ser Gln Asp Val Thr Val Pro Cys Pro Val Pro Ser
    210                 215                 220

Thr Pro Pro Thr Pro Ser Pro Ser Thr Pro Pro Thr Pro Ser Pro Ser
225                 230                 235                 240

Cys Cys His Pro Arg Leu Ser Leu His Arg Pro Ala Leu Glu Asp Leu
                245                 250                 255

Leu Leu Gly Ser Glu Ala Asn Leu Thr Cys Thr Leu Thr Gly Leu Arg
                260                 265                 270

Asp Ala Ser Gly Val Thr Phe Thr Trp Thr Pro Ser Ser Gly Lys Ser
            275                 280                 285

Ala Val Gln Gly Pro Pro Glu Arg Asp Leu Cys Gly Cys Tyr Ser Val
    290                 295                 300

Ser Ser Val Leu Pro Gly Cys Ala Glu Pro Trp Asn His Gly Lys Thr
305                 310                 315                 320

Phe Thr Cys Thr Ala Ala Tyr Pro Glu Ser Lys Thr Pro Leu Thr Ala
                325                 330                 335

Thr Leu Ser Lys Ser Gly Asn Thr Phe Arg Pro Glu Val His Leu Leu
            340                 345                 350

Pro Pro Pro Ser Glu Glu Leu Ala Leu Asn Glu Leu Val Thr Leu Thr
            355                 360                 365

Cys Leu Ala Arg Gly Phe Ser Pro Lys Asp Val Leu Val Arg Trp Leu
    370                 375                 380

Gln Gly Ser Gln Glu Leu Pro Arg Glu Lys Tyr Leu Thr Trp Ala Ser
385                 390                 395                 400

Arg Gln Glu Pro Ser Gln Gly Thr Thr Thr Phe Ala Val Thr Ser Ile
                405                 410                 415

Leu Arg Val Ala Ala Glu Asp Trp Lys Lys Gly Asp Thr Phe Ser Cys
            420                 425                 430

Met Val Gly His Glu Ala Leu Pro Leu Ala Phe Thr Gln Lys Thr Ile
            435                 440                 445

Asp Arg Leu Ala Gly Lys Glu Gln Lys Leu Ile Ser Glu Glu Asp Leu
    450                 455                 460
```

<210> SEQ ID NO 66
<211> LENGTH: 451
<212> TYPE: PRT
<213> ORGANISM: Artificial sequence
<220> FEATURE:
<223> OTHER INFORMATION: An artificially synthesized sequence

<400> SEQUENCE: 66

-continued

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Pro Arg Trp Glu Thr Ala Ile Ser Ser Asp Ala Phe Asp Ile
        100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415
```

-continued

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro
    450

<210> SEQ ID NO 67
<211> LENGTH: 214
<212> TYPE: PRT
<213> ORGANISM: Artificial sequence
<220> FEATURE:
<223> OTHER INFORMATION: An artificially synthesized sequence

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
            20                  25                  30

Leu Asn Trp Tyr Gln Gln Lys Pro Gly Lys Ala Pro Lys Leu Leu Ile
            35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Ser Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 68
<211> LENGTH: 451
<212> TYPE: PRT
<213> ORGANISM: Artificial sequence
<220> FEATURE:
<223> OTHER INFORMATION: An artificially synthesized sequence

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

-continued

```
Gly Gly Ile Ile Pro Ile Phe Gly Thr Ala Asn Tyr Ala Gln Lys Phe
    50              55              60

Gln Gly Arg Val Thr Ile Thr Ala Asp Glu Ser Thr Ser Thr Ala Tyr
65              70              75              80

Met Glu Leu Ser Ser Leu Arg Ser Glu Asp Thr Ala Val Tyr Tyr Cys
                85              90              95

Ala Arg Pro Arg Trp Glu Thr Ala Ile Ser Ser Asp Ala Phe Asp Ile
            100             105             110

Trp Gly Gln Gly Thr Met Val Thr Val Ser Ser Ala Ser Thr Lys Gly
            115             120             125

Pro Ser Val Phe Pro Leu Ala Pro Ser Ser Lys Ser Thr Ser Gly Gly
    130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
                165             170             175

Pro Ala Val Leu Gln Ser Ser Gly Leu Tyr Ser Leu Ser Ser Val Val
            180             185             190

Thr Val Pro Ser Ser Ser Leu Gly Thr Gln Thr Tyr Ile Cys Asn Val
            195             200             205

Asn His Lys Pro Ser Asn Thr Lys Val Asp Lys Lys Val Glu Pro Lys
    210             215             220

Ser Cys Asp Lys Thr His Thr Cys Pro Pro Cys Pro Ala Pro Glu Leu
225             230             235             240

Leu Gly Gly Pro Ser Val Phe Leu Phe Pro Pro Lys Pro Lys Asp Thr
            245             250             255

Leu Met Ile Ser Arg Thr Pro Glu Val Thr Cys Val Val Val Asp Val
            260             265             270

Ser His Glu Asp Pro Glu Val Lys Phe Asn Trp Tyr Val Asp Gly Val
            275             280             285

Glu Val His Asn Ala Lys Thr Lys Pro Arg Glu Glu Gln Tyr Asn Ser
    290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Ala Tyr Pro Ala
            325             330             335

Pro Ile Glu Lys Thr Ile Ser Lys Ala Lys Gly Gln Pro Arg Glu Pro
            340             345             350

Gln Val Tyr Thr Leu Pro Pro Ser Arg Asp Glu Leu Thr Lys Asn Gln
            355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
            435             440             445

Leu Ser Pro
    450
```

-continued

```
<210> SEQ ID NO 69
<211> LENGTH: 543
<212> TYPE: PRT
<213> ORGANISM: Artificial sequence
<220> FEATURE:
<223> OTHER INFORMATION: An artificially synthesized sequence

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser Ala Ser Thr Gln Ser Pro Ser Val Phe Pro Leu Thr Arg
        115                 120                 125

Cys Cys Lys Asn Ile Pro Ser Asn Ala Thr Ser Val Thr Leu Gly Cys
    130                 135                 140

Leu Ala Thr Gly Tyr Phe Pro Glu Pro Val Met Val Thr Trp Asp Thr
145                 150                 155                 160

Gly Ser Leu Asn Gly Thr Thr Met Thr Leu Pro Ala Thr Thr Leu Thr
                165                 170                 175

Leu Ser Gly His Tyr Ala Thr Ile Ser Leu Leu Thr Val Ser Gly Ala
            180                 185                 190

Trp Ala Lys Gln Met Phe Thr Cys Arg Val Ala His Thr Pro Ser Ser
            195                 200                 205

Thr Asp Trp Val Asp Asn Lys Thr Phe Ser Val Cys Ser Arg Asp Phe
    210                 215                 220

Thr Pro Pro Thr Val Lys Ile Leu Gln Ser Ser Cys Asp Gly Gly Gly
225                 230                 235                 240

His Phe Pro Pro Thr Ile Gln Leu Leu Cys Leu Val Ser Gly Tyr Thr
            245                 250                 255

Pro Gly Thr Ile Asn Ile Thr Trp Leu Glu Asp Gly Gln Val Met Asp
            260                 265                 270

Val Asp Leu Ser Thr Ala Ser Thr Thr Gln Glu Gly Glu Leu Ala Ser
        275                 280                 285

Thr Gln Ser Glu Leu Thr Leu Ser Gln Lys His Trp Leu Ser Asp Arg
    290                 295                 300

Thr Tyr Thr Cys Gln Val Thr Tyr Gln Gly His Thr Phe Glu Asp Ser
305                 310                 315                 320

Thr Lys Lys Cys Ala Asp Ser Asn Pro Arg Gly Val Ser Ala Tyr Leu
            325                 330                 335

Ser Arg Pro Ser Pro Phe Asp Leu Phe Ile Arg Lys Ser Pro Thr Ile
            340                 345                 350

Thr Cys Leu Val Val Asp Leu Ala Pro Ser Lys Gly Thr Val Asn Leu
        355                 360                 365
```

-continued

```
Thr Trp Ser Arg Ala Ser Gly Lys Pro Val Asn His Ser Thr Arg Lys
    370             375             380

Glu Glu Lys Gln Arg Asn Gly Thr Leu Thr Val Thr Ser Thr Leu Pro
385             390             395             400

Val Gly Thr Arg Asp Trp Ile Glu Gly Glu Thr Tyr Gln Cys Arg Val
            405             410             415

Thr His Pro His Leu Pro Arg Ala Leu Met Arg Ser Thr Thr Lys Thr
            420             425             430

Ser Gly Pro Arg Ala Ala Pro Glu Val Tyr Ala Phe Ala Thr Pro Glu
            435             440             445

Trp Pro Gly Ser Arg Asp Lys Arg Thr Leu Ala Cys Leu Ile Gln Asn
    450             455             460

Phe Met Pro Glu Asp Ile Ser Val Gln Trp Leu His Asn Glu Val Gln
465             470             475             480

Leu Pro Asp Ala Arg His Ser Thr Thr Gln Pro Arg Lys Thr Lys Gly
            485             490             495

Ser Gly Phe Phe Val Phe Ser Arg Leu Glu Val Thr Arg Ala Glu Trp
            500             505             510

Glu Gln Lys Asp Glu Phe Ile Cys Arg Ala Val His Glu Ala Ala Ser
            515             520             525

Pro Ser Gln Thr Val Gln Arg Ala Val Ser Val Asn Pro Gly Lys
    530             535             540

<210> SEQ ID NO 70
<211> LENGTH: 219
<212> TYPE: PRT
<213> ORGANISM: Artificial sequence
<220> FEATURE:
<223> OTHER INFORMATION: An artificially synthesized sequence

<400> SEQUENCE: 70

Asp Val Val Met Thr Gln Ser Pro Leu Ser Leu Pro Val Thr Pro Gly
1               5               10              15

Glu Pro Ala Ser Ile Ser Cys Arg Ser Ser Gln Ser Leu Val His Ser
            20              25              30

Asn Arg Asn Thr Tyr Leu His Trp Tyr Leu Gln Lys Pro Gly Gln Ser
        35              40              45

Pro Gln Leu Leu Ile Tyr Lys Val Ser Asn Arg Phe Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Ser Gln Asn
            85              90              95

Thr His Val Pro Pro Thr Phe Gly Gln Gly Thr Lys Leu Glu Ile Lys
            100             105             110

Arg Thr Val Ala Ala Pro Ser Val Phe Ile Phe Pro Pro Ser Asp Glu
            115             120             125

Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
            165             170             175

Thr Tyr Ser Leu Ser Ser Thr Leu Thr Leu Ser Lys Ala Asp Tyr Glu
            180             185             190
```

-continued

```
Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 71
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 71

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
        20                  25                  30

Met Ser Trp Val Arg Gln Ala Pro Gly Lys Gly Leu Glu Trp Ile Gly
        35                  40                  45

Val Ile Asn Ser Ala Gly Asn Thr Tyr Tyr Ala Ser Trp Ala Lys Gly
        50                  55                  60

Arg Phe Thr Val Ser Lys Thr Ser Thr Thr Val Asp Leu Asn Leu Thr
65                  70                  75                  80

Ser Leu Thr Thr Glu Asp Thr Ala Thr Tyr Phe Cys Ala Arg Tyr Val
            85                  90                  95

Phe Ser Ser Gly Ser His Asp Ile Trp Gly Pro Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335
```

```
Ala Lys Gly Gln Pro Arg Glu Pro Gln Val Tyr Thr Leu Pro Pro Ser
        340             345             350

Arg Glu Glu Met Thr Lys Asn Gln Val Ser Leu Thr Cys Leu Val Lys
        355             360             365

Gly Phe Tyr Pro Ser Asp Ile Ala Val Glu Trp Glu Ser Asn Gly Gln
        370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
                405             410             415

Gln Gly Asn Val Phe Ser Cys Ser Val Met His Glu Ala Leu His Asn
            420             425             430

His Tyr Thr Gln Lys Ser Leu Ser Leu Ser Pro
        435             440
```

<210> SEQ ID NO 72
<211> LENGTH: 217
<212> TYPE: PRT
<213> ORGANISM: Artificial sequence
<220> FEATURE:
<223> OTHER INFORMATION: An artificially synthesized sequence

<400> SEQUENCE: 72

```
Ala Tyr Asp Met Thr Gln Thr Pro Ala Ser Val Glu Val Ala Val Gly
1               5               10              15

Gly Thr Val Thr Ile Lys Cys Gln Ala Ser Gln Ser Ile Gly Ser Trp
            20              25              30

Leu Ala Trp Tyr Gln Gln Lys Pro Gly Gln Pro Pro Lys Glu Leu Ile
        35              40              45

Tyr Gly Thr Ser Thr Leu Glu Ser Gly Val Pro Ser Arg Phe Ile Gly
    50              55              60

Ser Gly Ser Gly Thr Glu Phe Thr Leu Thr Ile Ser Gly Val Glu Cys
65              70              75              80

Ala Asp Ala Ala Thr Tyr Tyr Cys Gln Gln Gly Tyr Ser Glu Asp Asn
            85              90              95

Ile Asp Asn Ala Phe Gly Gly Gly Thr Glu Val Val Val Lys Arg Thr
            100             105             110

Val Ala Ala Pro Ser Val Phe Ile Phe Pro Pro Ser Asp Glu Gln Leu
        115             120             125

Lys Ser Gly Thr Ala Ser Val Val Cys Leu Leu Asn Asn Phe Tyr Pro
    130             135             140

Arg Glu Ala Lys Val Gln Trp Lys Val Asp Asn Ala Leu Gln Ser Gly
145             150             155             160

Asn Ser Gln Glu Ser Val Thr Glu Gln Asp Ser Lys Asp Ser Thr Tyr
            165             170             175

Ser Leu Ser Ser Thr Leu Thr Leu Ser Lys Ala Asp Tyr Glu Lys His
            180             185             190

Lys Val Tyr Ala Cys Glu Val Thr His Gln Gly Leu Ser Ser Pro Val
        195             200             205

Thr Lys Ser Phe Asn Arg Gly Glu Cys
    210             215
```

<210> SEQ ID NO 73
<211> LENGTH: 32
<212> TYPE: PRT
<213> ORGANISM: Artificial sequence
<220> FEATURE:

-continued

<223> OTHER INFORMATION: An artificially synthesized sequence

<400> SEQUENCE: 73

```
Val Asp Asp Ala Pro Gly Asn Ser Gln Gln Ala Thr Pro Lys Asp Asn
1               5                   10                  15

Glu Ile Ser Thr Phe His Asn Leu Gly Asn Val His Ser Pro Leu Lys
            20                  25                  30
```

<210> SEQ ID NO 74
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 74

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
            20                  25                  30

Met Ser Trp Val Arg Gln Ala Pro Gly Lys Gly Leu Glu Trp Ile Gly
        35                  40                  45

Val Ile Asn Ser Ala Gly Asn Thr Tyr Tyr Ala Ser Trp Ala Lys Gly
    50                  55                  60

Arg Phe Thr Val Ser Lys Thr Ser Thr Thr Val Asp Leu Asn Leu Thr
65                  70                  75                  80

Ser Leu Thr Thr Glu Asp Thr Ala Thr Tyr Phe Cys Ala Arg Tyr Val
                85                  90                  95

Phe Ser Ser Gly Ser His Asp Ile Trp Gly Pro Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320
```

-continued

```
Val Ser Asn Lys Ala Tyr Pro Ala Pro Ile Glu Lys Thr Ile Ser Lys
                325             330             335

Ala Lys Gly Gln Pro Arg Glu Pro Gln Val Tyr Thr Leu Pro Pro Ser
            340             345             350

Arg Asp Glu Leu Thr Lys Asn Gln Val Ser Leu Thr Cys Leu Val Lys
            355             360             365

Gly Phe Tyr Pro Ser Asp Ile Ala Val Glu Trp Glu Ser Asn Gly Gln
        370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
            405             410             415

Gln Gly Asn Val Phe Ser Cys Ser Val Met His Glu Ala Leu His Asn
            420             425             430

His Tyr Thr Gln Lys Ser Leu Ser Leu Ser Pro
            435             440
```

```
<210> SEQ ID NO 75
<211> LENGTH: 543
<212> TYPE: PRT
<213> ORGANISM: Artificial sequence
<220> FEATURE:
<223> OTHER INFORMATION: An artificially synthesized sequence

<400> SEQUENCE: 75
```

```
Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Asp Tyr
            20              25              30

Glu Met His Trp Val Arg Gln Ala Pro Gly Gln Gly Leu Glu Trp Met
        35              40              45

Gly Ala Leu Asp Pro Lys Thr Gly Asp Thr Ala Tyr Ser Gln Lys Phe
    50              55              60

Lys Gly Arg Val Thr Leu Thr Ala Asp Lys Ser Thr Ser Thr Ala Tyr
65              70              75              80

Met Glu Leu Ser Ser Leu Thr Ser Glu Asp Thr Ala Val Tyr Tyr Cys
            85              90              95

Thr Arg Phe Tyr Ser Tyr Thr Tyr Trp Gly Gln Gly Thr Leu Val Thr
            100             105             110

Val Ser Ser Ala Ser Thr Gln Ser Pro Ser Val Phe Pro Leu Thr Arg
            115             120             125

Cys Cys Lys Asn Ile Pro Ser Asp Ala Thr Ser Val Thr Leu Gly Cys
        130             135             140

Leu Ala Thr Gly Tyr Phe Pro Glu Pro Val Met Val Thr Trp Asp Thr
145             150             155             160

Gly Ser Leu Asp Gly Thr Thr Met Thr Leu Pro Ala Thr Thr Leu Thr
            165             170             175

Leu Ser Gly His Tyr Ala Thr Ile Ser Leu Leu Thr Val Ser Gly Ala
            180             185             190

Trp Ala Lys Gln Met Phe Thr Cys Arg Val Ala His Thr Pro Ser Ser
            195             200             205

Thr Asp Trp Val Asp Asp Lys Thr Phe Ser Val Cys Ser Arg Asp Phe
        210             215             220

Thr Pro Pro Thr Val Lys Ile Leu Gln Ser Ser Cys Asp Gly Gly Gly
225             230             235             240
```

-continued

```
His Phe Pro Pro Thr Ile Gln Leu Leu Cys Leu Val Ser Gly Tyr Thr
                245                 250                 255

Pro Gly Thr Ile Asp Ile Thr Trp Leu Glu Asp Gly Gln Val Met Asp
                260                 265                 270

Val Asp Leu Ser Thr Ala Ser Thr Thr Gln Glu Gly Glu Leu Ala Ser
                275                 280                 285

Thr Gln Ser Glu Leu Thr Leu Ser Gln Lys His Trp Leu Ser Asp Arg
        290                 295                 300

Thr Tyr Thr Cys Gln Val Thr Tyr Gln Gly His Thr Phe Glu Asp Ser
305                 310                 315                 320

Thr Lys Lys Cys Ala Asp Ser Asn Pro Arg Gly Val Ser Ala Tyr Leu
                325                 330                 335

Ser Arg Pro Ser Pro Phe Asp Leu Phe Ile Arg Lys Ser Pro Thr Ile
                340                 345                 350

Thr Cys Leu Val Val Asp Leu Ala Pro Ser Lys Gly Thr Val Asp Leu
                355                 360                 365

Thr Trp Ser Arg Ala Ser Gly Lys Pro Val Asp His Ser Thr Arg Lys
        370                 375                 380

Glu Glu Lys Gln Arg Asn Gly Thr Leu Thr Val Thr Ser Thr Leu Pro
385                 390                 395                 400

Val Gly Thr Arg Asp Trp Ile Glu Gly Glu Thr Tyr Gln Cys Arg Val
                405                 410                 415

Thr His Pro His Leu Pro Arg Ala Leu Met Arg Ser Thr Thr Lys Thr
                420                 425                 430

Ser Gly Pro Arg Ala Ala Pro Glu Val Tyr Ala Phe Ala Thr Pro Glu
                435                 440                 445

Trp Pro Gly Ser Arg Asp Lys Arg Thr Leu Ala Cys Leu Ile Gln Asn
        450                 455                 460

Phe Met Pro Glu Asp Ile Ser Val Gln Trp Leu His Asn Glu Val Gln
465                 470                 475                 480

Leu Pro Asp Ala Arg His Ser Thr Thr Gln Pro Arg Lys Thr Lys Gly
                485                 490                 495

Ser Gly Phe Phe Val Phe Ser Arg Leu Glu Val Thr Arg Ala Glu Trp
                500                 505                 510

Glu Gln Lys Asp Glu Phe Ile Cys Arg Ala Val His Glu Ala Ala Ser
        515                 520                 525

Pro Ser Gln Thr Val Gln Arg Ala Val Ser Val Asn Pro Gly Lys
        530                 535                 540
```

```
<210> SEQ ID NO 76
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 76
```

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
                20                  25                  30

Met Ser Trp Val Arg Gln Ala Pro Gly Lys Gly Leu Glu Trp Ile Gly
        35                  40                  45

Val Ile Asn Ser Ala Gly Asn Thr Tyr Tyr Ala Ser Trp Ala Lys Gly
        50                  55                  60
```

-continued

```
Arg Phe Thr Val Ser Lys Thr Ser Thr Thr Val Asp Leu Asn Leu Thr
65                  70                  75                  80

Ser Leu Thr Thr Glu Asp Thr Ala Thr Tyr Phe Cys Ala Arg Tyr Val
                85                  90                  95

Phe Ser Ser Gly Ser His Asp Ile Trp Gly Pro Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Asp Ala Tyr Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
            435                 440
```

<210> SEQ ID NO 77
<211> LENGTH: 443
<212> TYPE: PRT
<213> ORGANISM: Artificial sequence
<220> FEATURE:

-continued

<223> OTHER INFORMATION: An artificially synthesized sequence

<400> SEQUENCE: 77

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
            20                  25                  30

Met Ser Trp Val Arg Gln Ala Pro Gly Lys Gly Leu Glu Trp Ile Gly
        35                  40                  45

Val Ile Asn Ser Ala Gly Asn Thr Tyr Tyr Ala Ser Trp Ala Lys Gly
    50                  55                  60

Arg Phe Thr Val Ser Lys Thr Ser Thr Thr Val Asp Leu Asn Leu Thr
65                  70                  75                  80

Ser Leu Thr Thr Glu Asp Thr Ala Thr Tyr Phe Cys Ala Arg Tyr Val
                85                  90                  95

Phe Ser Ser Gly Ser His Asp Ile Trp Gly Pro Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
    210                 215                 220

Pro Pro Cys Pro Ala Pro Glu Leu Arg Gly Gly Pro Lys Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400
```

-continued

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 78
<211> LENGTH: 545
<212> TYPE: PRT
<213> ORGANISM: Homo sapiens

<400> SEQUENCE: 78

Gln Pro Pro Pro Pro Pro Asp Ala Thr Cys His Gln Val Arg Ser
1               5                   10                  15

Phe Phe Gln Arg Leu Gln Pro Gly Leu Lys Trp Val Pro Glu Thr Pro
            20                  25                  30

Val Pro Gly Ser Asp Leu Gln Val Cys Leu Pro Lys Gly Pro Thr Cys
        35                  40                  45

Cys Ser Arg Lys Met Glu Glu Lys Tyr Gln Leu Thr Ala Arg Leu Asn
    50                  55                  60

Met Glu Gln Leu Leu Gln Ser Ala Ser Met Glu Leu Lys Phe Leu Ile
65                  70                  75                  80

Ile Gln Asn Ala Ala Val Phe Gln Glu Ala Phe Glu Ile Val Val Arg
                85                  90                  95

His Ala Lys Asn Tyr Thr Asn Ala Met Phe Lys Asn Asn Tyr Pro Ser
            100                 105                 110

Leu Thr Pro Gln Ala Phe Glu Phe Val Gly Glu Phe Phe Thr Asp Val
            115                 120                 125

Ser Leu Tyr Ile Leu Gly Ser Asp Ile Asn Val Asp Asp Met Val Asn
    130                 135                 140

Glu Leu Phe Asp Ser Leu Phe Pro Val Ile Tyr Thr Gln Leu Met Asn
145                 150                 155                 160

Pro Gly Leu Pro Asp Ser Ala Leu Asp Ile Asn Glu Cys Leu Arg Gly
            165                 170                 175

Ala Arg Arg Asp Leu Lys Val Phe Gly Asn Phe Pro Lys Leu Ile Met
            180                 185                 190

Thr Gln Val Ser Lys Ser Leu Gln Val Thr Arg Ile Phe Leu Gln Ala
        195                 200                 205

Leu Asn Leu Gly Ile Glu Val Ile Asn Thr Thr Asp His Leu Lys Phe
    210                 215                 220

Ser Lys Asp Cys Gly Arg Met Leu Thr Arg Met Trp Tyr Cys Ser Tyr
225                 230                 235                 240

Cys Gln Gly Leu Met Met Val Lys Pro Cys Gly Gly Tyr Cys Asn Val
            245                 250                 255

Val Met Gln Gly Cys Met Ala Gly Val Val Glu Ile Asp Lys Tyr Trp
            260                 265                 270

Arg Glu Tyr Ile Leu Ser Leu Glu Glu Leu Val Asn Gly Met Tyr Arg
        275                 280                 285

Ile Tyr Asp Met Glu Asn Val Leu Leu Gly Leu Phe Ser Thr Ile His
    290                 295                 300

Asp Ser Ile Gln Tyr Val Gln Lys Asn Ala Gly Lys Leu Thr Thr Thr
305                 310                 315                 320

Ile Gly Lys Leu Cys Ala His Ser Gln Gln Arg Gln Tyr Arg Ser Ala
            325                 330                 335

-continued

```
Tyr Tyr Pro Glu Asp Leu Phe Ile Asp Lys Lys Val Leu Lys Val Ala
            340                 345                 350

His Val Glu His Glu Glu Thr Leu Ser Ser Arg Arg Arg Glu Leu Ile
            355                 360                 365

Gln Lys Leu Lys Ser Phe Ile Ser Phe Tyr Ser Ala Leu Pro Gly Tyr
            370                 375                 380

Ile Cys Ser His Ser Pro Val Ala Glu Asn Asp Thr Leu Cys Trp Asn
385                 390                 395                 400

Gly Gln Glu Leu Val Glu Arg Tyr Ser Gln Lys Ala Ala Arg Asn Gly
                405                 410                 415

Met Lys Asn Gln Phe Asn Leu His Glu Leu Lys Met Lys Gly Pro Glu
            420                 425                 430

Pro Val Val Ser Gln Ile Ile Asp Lys Leu Lys His Ile Asn Gln Leu
            435                 440                 445

Leu Arg Thr Met Ser Met Pro Lys Gly Arg Val Leu Asp Lys Asn Leu
            450                 455                 460

Asp Glu Glu Gly Phe Glu Ala Gly Asp Cys Gly Asp Asp Glu Asp Glu
465                 470                 475                 480

Cys Ile Gly Gly Ala Gly Asp Gly Met Ile Lys Val Lys Asn Gln Leu
                485                 490                 495

Arg Phe Leu Ala Glu Leu Ala Tyr Asp Leu Asp Val Asp Asp Ala Pro
                500                 505                 510

Gly Asn Ser Gln Gln Ala Thr Pro Lys Asp Asn Glu Ile Ser Thr Phe
            515                 520                 525

His Asn Leu Gly Asn Val His Ser Pro Leu Lys His His His His His
            530                 535                 540

His
545
```

<210> SEQ ID NO 79
<211> LENGTH: 433
<212> TYPE: PRT
<213> ORGANISM: Artificial sequence
<220> FEATURE:
<223> OTHER INFORMATION: An artificially synthesized sequence

<400> SEQUENCE: 79

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
            50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
            130                 135                 140
```

-continued

```
Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
        210                 215                 220

Pro Cys Ile Cys Glu Ala Asn Glu Val Glu Asp Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
        290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
        370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr
```

```
<210> SEQ ID NO 80
<211> LENGTH: 328
<212> TYPE: PRT
<213> ORGANISM: Artificial sequence
<220> FEATURE:
<223> OTHER INFORMATION: An artificially synthesized sequence

<400> SEQUENCE: 80
```

```
Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

-continued

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

```
<210> SEQ ID NO 81
<211> LENGTH: 325
<212> TYPE: PRT
<213> ORGANISM: Artificial sequence
<220> FEATURE:
<223> OTHER INFORMATION: An artificially synthesized sequence

<400> SEQUENCE: 81
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

-continued

```
Arg Val Glu Ser Lys Tyr Gly Pro Pro Cys Pro Pro Cys Pro Ala Pro
            100             105             110

Glu Phe Leu Gly Gly Pro Ser Val Phe Leu Phe Pro Pro Lys Pro Lys
        115             120             125

Asp Thr Leu Met Ile Ser Arg Thr Pro Glu Val Thr Cys Val Val Val
    130             135             140

Asp Val Ser Gln Glu Asp Pro Glu Val Gln Phe Asn Trp Tyr Val Asp
145             150             155             160

Gly Val Glu Val His Asn Ala Lys Thr Lys Pro Arg Glu Glu Gln Phe
            165             170             175

Asn Ser Thr Tyr Arg Val Val Ser Val Leu Thr Val Leu His Gln Asp
            180             185             190

Trp Leu Asn Gly Lys Glu Tyr Lys Cys Lys Val Ser Asn Lys Gly Leu
        195             200             205

Pro Ser Ser Ile Glu Lys Thr Ile Ser Lys Ala Lys Gly Gln Pro Arg
    210             215             220

Glu Pro Gln Val Tyr Thr Leu Pro Pro Ser Gln Glu Glu Met Thr Lys
225             230             235             240

Asn Gln Val Ser Leu Thr Cys Leu Val Lys Gly Phe Tyr Pro Ser Asp
            245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
        275             280             285

Arg Leu Thr Val Asp Lys Ser Arg Trp Gln Glu Gly Asn Val Phe Ser
    290             295             300

Cys Ser Val Met His Glu Ala Leu His Asn His Tyr Thr Gln Lys Ser
305             310             315             320

Leu Ser Leu Ser Leu
            325
```